United States Patent
Han et al.

(10) Patent No.: US 10,711,032 B2
(45) Date of Patent: Jul. 14, 2020

(54) STEROIDS AND PROTEIN-CONJUGATES THEREOF

(71) Applicant: Regeneron Pharmaceuticals, Inc., Tarrytown, NY (US)

(72) Inventors: Amy Han, Hockessin, DE (US); Andrew J. Murphy, Croton-on-Hudson, NY (US); William Olson, Yorktown Heights, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/806,197

(22) Filed: Nov. 7, 2017

(65) Prior Publication Data
US 2018/0155389 A1 Jun. 7, 2018

Related U.S. Application Data

(60) Provisional application No. 62/508,317, filed on May 18, 2017, provisional application No. 62/419,365, filed on Nov. 8, 2016.

(51) Int. Cl.
| | |
|---|---|
| C07J 71/00 | (2006.01) |
| C07J 41/00 | (2006.01) |
| A61K 47/68 | (2017.01) |
| A61K 31/566 | (2006.01) |
| A61P 29/00 | (2006.01) |
| A61K 31/58 | (2006.01) |
| A61K 47/61 | (2017.01) |
| A61K 47/69 | (2017.01) |

(52) U.S. Cl.
CPC ......... *C07J 71/0026* (2013.01); *A61K 31/566* (2013.01); *A61K 31/58* (2013.01); *A61K 47/61* (2017.08); *A61K 47/6801* (2017.08); *A61K 47/6803* (2017.08); *A61K 47/6849* (2017.08); *A61K 47/6889* (2017.08); *A61K 47/6951* (2017.08); *A61P 29/00* (2018.01); *C07J 41/005* (2013.01); *C07J 41/0088* (2013.01); *C07J 71/0031* (2013.01)

(58) Field of Classification Search
None
See application file for complete search history.

(56) References Cited

U.S. PATENT DOCUMENTS

| | | |
|---|---|---|
| 3,020,275 A | 2/1962 | Marx et al. |
| 3,033,873 A | 5/1962 | Pinson et al. |
| 3,033,874 A | 5/1962 | Pinson et al. |
| 3,197,469 A | 7/1965 | Fried |
| 3,798,216 A | 3/1974 | Boissier et al. |
| 3,886,145 A | 5/1975 | Diamanti |
| 3,928,326 A | 12/1975 | Brattsand et al. |
| 3,929,768 A | 12/1975 | Brattsand et al. |
| 4,925,933 A | 5/1990 | Jakupovic et al. |
| 5,116,829 A | 5/1992 | Hori et al. |
| 5,183,815 A | 2/1993 | Saari et al. |
| 5,208,020 A | 5/1993 | Chari et al. |
| 5,500,362 A | 3/1996 | Robinson et al. |
| 5,714,586 A | 2/1998 | Kunstmann et al. |
| 5,821,337 A | 10/1998 | Carter et al. |
| 5,837,698 A | 11/1998 | Tjoeng et al. |
| 5,908,833 A | 6/1999 | Brattsand et al. |
| 6,596,541 B2 | 7/2003 | Murphy et al. |
| 7,750,116 B1 | 7/2010 | Doronina et al. |
| 8,524,697 B2 | 9/2013 | Anthes et al. |
| 2003/0199529 A1 | 10/2003 | Garvey et al. |
| 2004/0157810 A1 | 8/2004 | Teicher et al. |
| 2004/0192778 A1 | 9/2004 | Jardien et al. |
| 2005/0009798 A1 | 1/2005 | Currie et al. |
| 2005/0192257 A1 | 9/2005 | Peyman |
| 2006/0046967 A1 | 3/2006 | Satyam |
| 2007/0258987 A1 | 11/2007 | Francisco et al. |
| 2008/0305497 A1 | 12/2008 | Kosmeder et al. |
| 2009/0318396 A1 | 12/2009 | Baker et al. |
| 2010/0041633 A1 | 2/2010 | Benedini et al. |
| 2010/0093685 A1 | 4/2010 | Benedini et al. |
| 2010/0129314 A1 | 5/2010 | Singh et al. |
| 2010/0323973 A1 | 12/2010 | Leamon et al. |
| 2012/0058892 A1 | 3/2012 | Braun et al. |
| 2012/0059158 A1 | 3/2012 | Ishii |
| 2012/0096572 A1 | 4/2012 | Macdonald et al. |
| 2012/0258107 A1 | 10/2012 | Graversen et al. |
| 2013/0101546 A1 | 4/2013 | Yurkovetskiy et al. |
| 2015/0152187 A1 | 6/2015 | Sun et al. |
| 2015/0290337 A1 | 10/2015 | Vetter et al. |
| 2016/0279054 A1 | 9/2016 | Rangaramanujam et al. |
| 2018/0126000 A1 | 5/2018 | Mcpherson et al. |
| 2018/0155389 A1 | 6/2018 | Han et al. |
| 2018/0333504 A1 | 11/2018 | Han et al. |

(Continued)

FOREIGN PATENT DOCUMENTS

| | | |
|---|---|---|
| CN | 1414008 A | 4/2003 |
| CN | 101397328 A | 4/2009 |

(Continued)

OTHER PUBLICATIONS

CAS RN 57-86-3 (entered into STN Nov. 16, 1984) (Year: 1984).*
CAS RN 2341-08-4 (entered into STN Nov. 16, 1984) (Year: 1984).*
CAS RN 3859-14-1 (entered into STN Nov. 16, 1984) (Year: 1984).*
Invitation to Pay Additional Fees and, Where Applicable, Protest Fee dated Feb. 13, 2018 for PCT/US2017/060434 filed Nov. 7, 2017, 21 page.
Agarwal et al., "A Pictet-Spengler ligation for protein chemical modification", PNAS, Jan. 2, 2013, vol. 110, No. 1, pp. 46-51.
Angal et al., "A Single Amino Acid Substitution Abolishes the Heterogeneity of Chimeric Mouse/Human (IgG4) Antibody", Molecular Immunology, Jan. 1993, vol. 30, No. 1, pp. 105-108.

(Continued)

*Primary Examiner* — Craig D Ricci
(74) *Attorney, Agent, or Firm* — Squire Patton Boggs (US) LLP

(57) ABSTRACT

Described herein protein steroid conjugates that are useful, for example, for the target-specific delivery of glucocorticoids (GCs) to cells.

33 Claims, 40 Drawing Sheets

(56) References Cited

U.S. PATENT DOCUMENTS

| | | | |
|---|---|---|---|
| 2018/0360979 | A1 | 12/2018 | Mejia Oneto et al. |
| 2019/0030171 | A1 | 1/2019 | Garbaccio et al. |

FOREIGN PATENT DOCUMENTS

| | | | |
|---|---|---|---|
| DE | 1165595 | B | 3/1964 |
| EP | 1625854 | A1 | 2/2006 |
| ES | 544825 | A1 | 7/1985 |
| GB | 889766 | A | 2/1962 |
| GB | 898295 | A | 6/1962 |
| GB | 1428416 | | 3/1976 |
| IL | 73337 | A | 9/1988 |
| WO | WO 94/22898 | A1 | 10/1994 |
| WO | WO 97/41144 | A1 | 11/1997 |
| WO | WO 2000/049993 | A2 | 8/2000 |
| WO | WO 2005/089808 | | 9/2005 |
| WO | WO 2008/122039 | | 10/2008 |
| WO | WO 2009/085879 | A2 | 7/2009 |
| WO | WO 2009/085880 | A2 | 7/2009 |
| WO | WO 2010/010324 | | 1/2010 |
| WO | WO 2010/126953 | A1 | 11/2010 |
| WO | WO 2010/132743 | A1 | 11/2010 |
| WO | WO 2011/018611 | | 2/2011 |
| WO | WO 2011/039511 | A2 | 4/2011 |
| WO | WO 2011/081937 | A1 | 7/2011 |
| WO | WO 2011/130598 | | 10/2011 |
| WO | WO2012/058592 | | 5/2012 |
| WO | WO 2012/166559 | | 12/2012 |
| WO | WO 2013/053872 | | 4/2013 |
| WO | WO 2013/053873 | | 4/2013 |
| WO | WO 2013/055990 | | 4/2013 |
| WO | WO 2013/055993 | | 4/2013 |
| WO | WO 2013/068874 | | 5/2013 |
| WO | WO 2013/085925 | | 6/2013 |
| WO | WO 2013/093465 | A2 | 6/2013 |
| WO | WO 2014/065661 | | 5/2014 |
| WO | WO 2014/197854 | | 12/2014 |
| WO | WO 2015/153401 | A1 | 10/2015 |
| WO | WO 2017/062271 | A1 | 4/2017 |
| WO | WO 2017/132103 | A2 | 8/2017 |
| WO | WO/2017/147542 | | 8/2017 |
| WO | WO 2017/210471 | A1 | 12/2017 |
| WO | WO 2018/089373 | A9 | 5/2018 |
| WO | WO 2018/213077 | A1 | 11/2018 |

OTHER PUBLICATIONS

Baskin et al., "Copper-free click chemistry for dynamic in vivo imaging", PNAS, Oct. 23, 2007, vol. 104, No. 43, pp. 16793-16797.

Berge et al., "Pharmaceutical Salts", Review Article, Jan. 1977, vol. 66, No. 1, pp. 1-19.

Carrico et al., "Introducing genetically enclosed aldehydes into proteins", Nature Chemical Biology, Jun. 2007, vol. 3, No. 6, pp. 321-322.

Casati et al., "Unraveling Unidirectional Threading of α-Cyclodextrin in a [2]Rotaxane through Spin Labeling Approach", Journal of the American Chemical Society, Oct. 29, 2012, vol. 134, pp. 19108-19117.

Cho et al., "Regioselective Synthesis of Heterocycles Containing Nitrogen Neighboring an Aromatic Ring by Reductive Ring Expansion Using Diisobutylaluminum Hydride and Studies on the Reaction Mechanism", J. Org. Chem., 2010, vol. 75, pp. 627-636; published online Dec. 29, 2009.

Dennler et al., "Transglutaminase-Based Chemo-Enzymatic Conjugation Approach Yields Homogeneous Antibody-Drug Conjugates", Bioconjugate Chem., Feb. 3, 2014, vol. 25, pp. 569-578.

Hamasaki et al., "Fluorescent sensors of molecular recognition. Modified cyclodextrins capable of exhibiting guest-responsive twisted intramolecular charge transfer fluorescence", J. Am. Chem. Soc., Jun. 1993, vol. 115, No. 12, pp. 5035-5040.

Hofer et al., "An engineered selenocysteine defines a unique class of antibody derivatives", PNAS, Aug. 26, 2008, vol. 105, No. 34, pp. 12451-12456.

Hollander et al., "Selection of Reaction Additives Used in the Preparetion of Monomeric Antibody-Calicheamicin Conjugates", Bioconjugate Chem., 2008, vol. 19, pp. 358-361; published on online Nov. 10, 2007.

Clynes et al., "Fc receptors are required in passive and active immunity to melanoma", Proc. Natl. Acad. Sci. USA, Jan. 1998, vol. 95, pp. 652-656.

Lichtenecker R. J., "Synthesis of aromatic $^{13}C/^2H$-α-ketoacid precursors to be used in selective phenylalanine and tyrosine protein labelling", Organic & Biomolecular Chemistry, Jul. 31, 2014, vol. 12, pp. 7551-7560.

Lu et al., "Linkers Having a Crucial Role in Antibody—Drug Conjugates", Int. J. Mol. Sci., Apr. 14, 2016, vol. 17, No. 561, 22 pages.

McCombs et al., "Antibody Drug Conjugates: Design and Selection of Linker, Payload and Conjugation Chemistry", The AAPS Journal, Mar. 2015, vol. 17, No. 2, pp. 339-351.

Papachristos et al., "Antibody-drug conjugates: a mini-review. The synopsis of two approved medicines", Drug Delivery, 2016, vol. 23, No. 5, pp. 1662-1666; published online Jan. 27, 2015.

Rabuka et al., "Site-specific chemical protein conjugation using genetically encoded aldehyde tags", Nat Protoc., vol. 7, No. 6, pp. 1052-1067, Dec. 1, 2012, doi:10.1038/nprot.2012.04.

Reggelin et al., "Asymmetric Synthesis of Highly Substituted Azapolycyclic Compounds via 2-Alkenyl Sulfoximines: Potential Scaffolds for Peptide Mimetics", J. American Chemical Society, Mar. 8, 2006, vol. 128, pp. 4023-4034.

Ryan et al., "Polyclonal Antibody Production Against Chito-Oligosaccharides", Food and Agricultural Immunology, 2001, vol. 13, pp. 127-130.

Samal et al., "The First Synthesis of Water-Soluble Cyclodextrinazafullerenes", Synthetic Communications, 2002, vol. 32, No. 21, pp. 3367-3372.

Shaunak et al., "Site-specific PEGylation of native disulfide bonds in therapeutic proteins", Nature Chemical Biology, Jun. 2006, vol. 2, No. 6, pp. 312-313.

Taylor et al., "A transgenic mouse that expresses a diversity of human sequence heavy and light chain immunoglobulins", Nucleic Acids Research, 1992, vol. 20, No. 23, pp. 6287-6295.

Uekama et al., "$6^A$-O-[(4-Biphenylyl)acetyl]-α-, -β-, and -γ-cyclodextrins and 6 $^A$-Deoxy-6 $^A$-[[(4-biphenylyl)acetyl]amino]-α-, -β-, and -γ-cyclodextrins: Potential Prodrugs for Colon-Specific Delivery", J. Med. Chem., 1997, vol. 40, pp. 2755-2761.

Beck et al., "Strategies and challenges for the next generation of antibody—drug conjugates", Nature Reviews/Drug Discovery, vol. 16, May 2017, pp. 315-337.

Berlin M., "Recent advances in the development of novel glucocorticoid receptor modulators", Review, Expert Opinion on Therapeutic Patents (2010) 20(7), pp. 855-873; DOI: 10.1517/13543776.2010.493876.

Dubois-Camacho et al., "Glucocorticosteroid therapy in inflammatory bowel diseases: From clinical practice to molecular biology", World J Gastroenterol, Sep. 28, 2017, vol. 23(36), pp. 6628-6638; DOI: 10.3748/wjg.v23.i36.6628.

International Search Report of PCT/US2017/060434 dated May 18, 2018, along with updated Written Opinion; 27 pages.

Krajcsi et al., "Novel Synthesis of 21-Aminopregnanes", J. Chem. Research (S), Nov. 1987, issue 11, pp. 382-383.

Paul-Clark et al., "Glucocorticoid Receptor Nitration Leads to Enhanced Anti-Inflammatory Effects of Novel Steroid Ligands", The Journal of Immunology, 2003, vol. 171, pp. 3245-3252; doi: 10.4049/jimmunol.171.6.3245.

Toth et al., "Amino-derivatives of 11,17,21-Trihydroxy-3,20-Dioxo-1,4-Pregnadiene", Nature 191, Aug. 5, 1961, p. 607.

Biju et al., "Synthesis of novel anti-inflammatory steroidal macrocycles using ring closing metathesis reaction", Tetrahedron Letters, Jan. 2015, vol. 56, issue 4, pp. 636-638.

Fellier et al., "Bindung von Cortisol, Fluocortolon und Difluocortolon a Humanplasmaproteine", J. Clin. Chem. Clin. Biochem., 1977, vol. 15, pp. 545-548.

Ferraboschi et al., "Estimation and characterisation of budesonide tablets impurities", Journal of Pharmaceutical and Biomedical Analysis, 2008, 47(3), pp. 636-640.

(56) References Cited

OTHER PUBLICATIONS

Kapp et al., "Studies on the Pharmacology of 6alpha,9-difluoro-11beta-hydroxy-16alpha-methyl-21-valeryloxy-1,4-pregnadiene-3,20-dione", Arzneimittel-Forschung Drug Reserch. 1976;26(7b):1463-1475; with an English abstract.

Muck et al., "High pressure liquid chromatography of some triamcinolone derivatives", Bollettino chimico farmaceutica, Italy, Apr. 1981, 120(4), pp. 240-247; with an English abstract.

Sehgal et al., "Desownethasone: a new topical corticosteroid", International Journal of Dermatology, Dec. 1976, vol. 15, pp. 770-773; with an English abstract.

Thalen et al., "Epimers of budesonide and related corticosteroids. I. Preparative resolution by chromatography on Sephadex LH-20", Acta Pharmaceutica Suecica, 1982, 19(4), pp. 247-266.

Thalen et al., "Synthesis and pharmacological properties of some 16α, 17α-acetals of 16α hydroxyhydrocortisone, 16α-hydroxyprednisolone and fluorinated 16α-hydroxyprednisolones", Acta Pharmaceutica Suecica, 1984, 21(2), pp. 109-124.

Thalen, "Epimers of budesonide and related corticosteroids. II. Structure elucidation by mass spectrometry", Acta Pharmaceutica Suecica, 1982, 19(5), pp. 327-354.

Wikby et al., "Separation of epimers of budesonide and related corticosteroids by high-performance liquid chromatography. A comparison between straight- and reversed-phase systems", Journal of Chromatography, 1978, 157(1), pp. 65-74.

Wikby et al., "Separation of epimers of budesonide and related corticosteroids by reversed bonded-phase liquid chromatography", Journal of Chromatography, 1978, 157(1), pp. 51-64.

Compounds retrieved on Nov. 18, 2017 from SciFinder, Set 1; 4 pages.

Compounds retrieved on Nov. 18, 2017 from SciFinder, Set 2; 1 page.

Compounds retrieved on Nov. 18, 2017 from SciFinder, Set 3; 3 pages.

Compounds from CAS Registry database, accessed May 20, 2019; 16 pages.

CAS Registry Compounds, accessed Jul. 16, 2019; 355 pages.

Aherne et al., "A sensitive radioimmunoassay for budesonide in plasma", Journal of Steroid Biochemistry, vol. 17, No. 5, Nov. 1982, pp. 559-565.

Graversen et al., "Targeting the Hemoglobin Scavenger receptor CD163 in Macrophages Highly Increases the Anti-inflammatory Potency of Dexamethasone", Molecular Therapy, vol. 20, No. 8, Aug. 2012, pp. 1550-1558.

Kern et al., "Discovery of Pyrophosphate Diesters as Tunable, Soluble, and Bioorthogonal Linkers for Site-Specific Antibody—Drug Conjugates", J. Am. Chem. Soc. (JACS), Jan. 25, 2016, vol. 138, No. 4, pp. 1430-1445.

Kern et al., "Novel Phosphate Modified Cathepsin B Linkers: Improving Aqueous Solubility and Enhancing Payload Scope of ADCs", Bioconjugate Chem. Bioconjugate Chem., Jul. 28, 2016, vol. 27, No. 9, pp. 2081-2088.

Kronkvist et al., "Determination of Drugs in Biosamples at Picomolar Concentrations Using Competitive Elisa With Electrochemical Detection: Application to Steroids", Journal of Pharmaceutical and Biomedical Analysis, vol. 11, No. 6, 1993, pp. 459-463.

Svendsen et al., "Antibody-Directed Glucocorticoid Targeting to CD163 M2-type Macrophages Attenuates Fructose-Induced Liver Inflammatory Changes", Molecular Therapy—Methods & Clinical Develop, vol. 4, Mar. 2017, pp. 50-61.

\* cited by examiner

FIG. 23
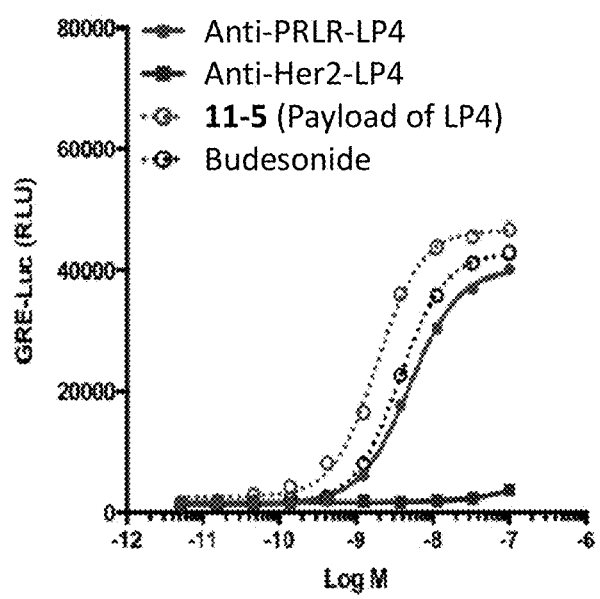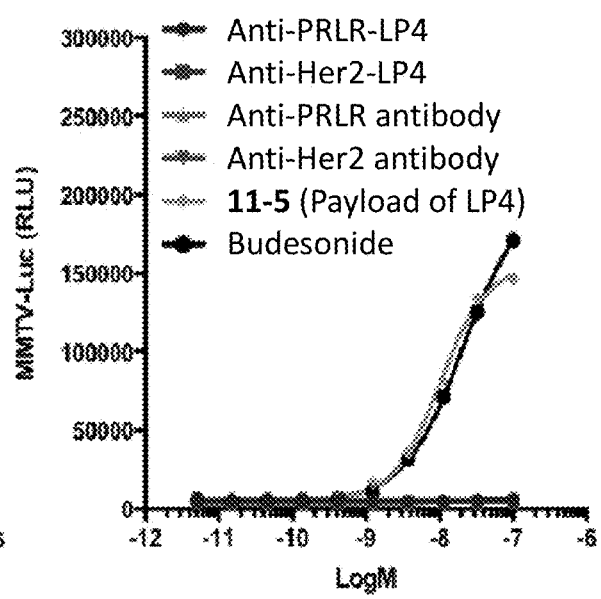
FIG. 23A
FIG. 23B

FIG. 25
FIG. 25A
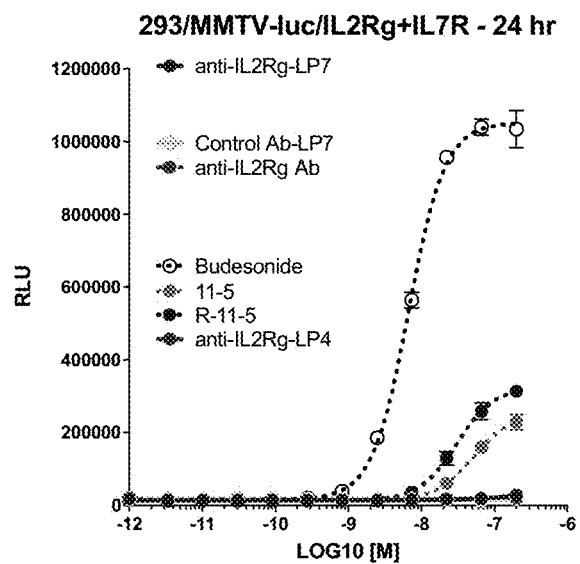
FIG. 25B
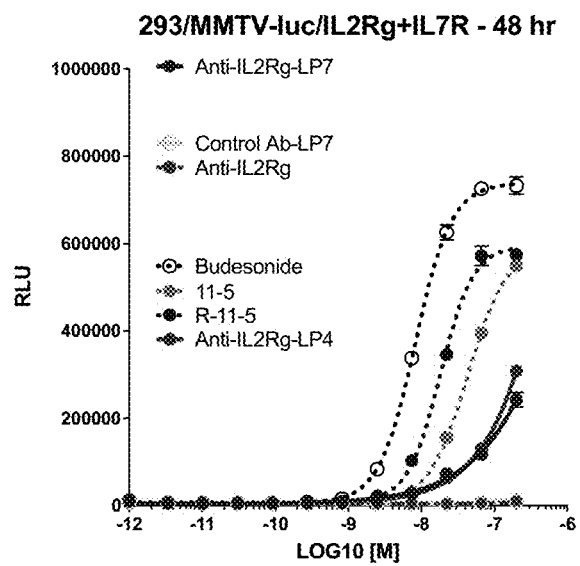

Mean blood concentration-time profiles of testing samples at 1 mg/kg in male C57BL/6 mice (N=4)

— Dexamethasone, IP-1mg/kg
— 4b, IP-1mg/kg
— 6-I, IP-1mg/kg

| PK parameters | Unit | Dexamethasone (IP, 1mg/Kg in male C57BL/6 mice) | | | 4b (IP, 1mg/Kg in male C57BL/6 mice) | | | 6-I (IP, 1mg/Kg in male C57BL/6 mice) | | |
|---|---|---|---|---|---|---|---|---|---|---|
| | | Mean | SD | CV(%) | Mean | SD | CV(%) | Mean | SD | CV(%) |
| $T_{max}$ | hr | 0.625 | 0.433 | 69.3 | 0.438 | 0.375 | 85.7 | 0.250 | 0.00 | 0.00 |
| $C_{max}$ | ng/mL | 231 | 7.97 | 3.45 | 39.4 | 1.75 | 4.43 | 44.8 | 4.77 | 10.6 |
| Terminal $t_{1/2}$ | hr | 1.64 | 0.187 | 11.4 | 1.69 | 0.620 | 36.7 | 1.91 | 0.210 | 11.0 |
| $AUC_{last}$ | hr*ng/mL | 545 | 60.6 | 11.1 | 84.6 | 7.71 | 9.12 | 107 | 13.6 | 12.7 |
| $AUC_{INF}$ | hr*ng/mL | 562 | 67.2 | 11.9 | 89.2 | 8.20 | 9.19 | 113 | 14.1 | 12.5 |

STEROIDS AND PROTEIN-CONJUGATES THEREOF

CROSS-REFERENCE TO RELATED APPLICATIONS

This application claims priority to and the benefit of U.S. Provisional Patent Application No. 62/508,317 filed on May 18, 2017, and also U.S. Provisional Patent Application No. 62/419,365, filed on Nov. 8, 2016, the entire contents of each of which are herein incorporated in their entirety for all purposes.

FIELD

Provided herein are novel steroids, protein conjugates thereof, and methods for treating diseases, disorders, and conditions comprising administering the steroids and conjugates.

BACKGROUND

Antibody-drug conjugates (ADCs) are antibodies that are covalently linked to biologically active small molecule drugs, thus combining the targeting specificity of antibodies with the mode-of-action and potency of small molecule drugs. The therapeutic utility of ADC(s) has been validated in cancer treatment and is a major ongoing focus of study. ADCETRIS® (brentuximab vedotin) and KADCYLA® (ado-trastuzumab emtansine) are ADCs approved for the treatment of certain cancer types, and at least forty ADCs are currently in clinical development.

Glucocorticoids (GCs) are small molecule steroids that bind to glucocorticoid receptors (GRs) and are utilized in anti-inflammatory and immunosuppressive therapies. However, due to the ubiquitous expression of glucocorticoid receptors in many cell types, glucocorticoid treatments are compromised by toxicities to most organ systems. Thus, there is need for both novel glucocorticoids as well as novel therapies that minimize the side effects arising from glucocorticoid administration, particularly those arising from activating glucocorticoid receptors in non-target cells. The instant disclosure provides solutions to the aforementioned needs as well as other unmet needs in the field to which the instant disclosure pertains. Included in the instant disclosure are antibody-drug conjugates comprising glucocorticoid payloads.

SUMMARY

Provided herein are compounds and methods useful for the treatment of various diseases, disorders, or conditions. In certain aspects, the compounds have the structure of Formula (A):

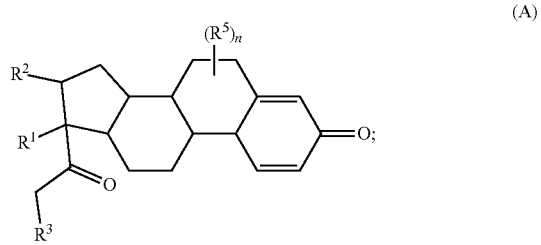

or a pharmaceutically acceptable salt, solvate, stereoisomer, or derivative thereof, wherein:

$R^1$ and $R^2$ are, independently, —H, alkyl, alkyl-C(O)—O—, —OH, or halo; or $R^1$ and $R^2$ together form

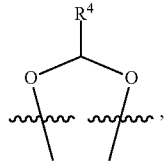

wherein $R^4$ is alkyl, aryl, arylalkyl, or an N-containing heterocycloalkyl, wherein the alkyl, aryl, arylalkyl, and N-containing heterocycloalkyl are, independently in each instance, optionally substituted with —$NR^aR^b$;

$R^3$ is —OH, $R^Z$—C(O)—X—, heteroalkyl, piperidinyl, —$NR^aR^b$, -oxyaryl-$NR^aR^b$ or —Z-A($R^P$)$_t$;

$R^5$ is, independently in each instance, —OH, halo, alkyl, or arylalkyl;

$R^Z$ is alkyl;

X is O or $NR^a$;

Z is S, S(O), S(O)$_2$, SO$_2R^a$, O, C(O)$NR^a$, C(O), or $NR^a$;

A is aryl, arylalkyl, or heteroaryl;

$R^P$ is, independently in each instance, halo, optionally substituted alkyl, —OH, or —$NR^aR^b$;

$R^a$ and $R^b$ are, independently in each instance, —H, optionally substituted alkyl, or optionally substituted aryl;

n is an integer from 0-19; and t is an integer from 1-3;

with the proviso that:

(1) $R^3$ is not —OH (a) when $R^1$ is —OH or (b) when $R^1$ and $R^2$ together form

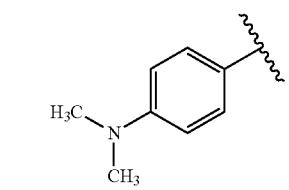

wherein $R^4$ is $C_{1-9}$alkyl or

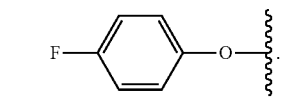

and (2) $R^3$ is not

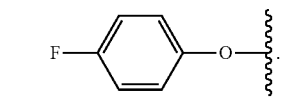

In certain aspects, the compounds are protein-drug conjugates, e.g., antibody-drug conjugates, comprising an antigen-binding protein, e.g., antibody and a compound of Formula (A).

In certain aspects, the compounds are protein-drug conjugates, e.g., antibody-drug conjugates, comprising an antigen-binding protein, e.g., antibody, a compound of Formula (A), and a cyclodextrin moiety.

BRIEF DESCRIPTIONS OF THE DRAWINGS

FIG. 1. shows a sequence for synthesizing the certain steroids described herein.

FIG. 2. shows a sequence for modifying the primary alcohol position of budesonide.

FIG. 3. shows a sequence for modifying the primary alcohol position of Flumethasone.

FIG. 4. shows a sequence for modifying the primary alcohol position of dexamethasone.

FIG. 23 shows selective GR activation in 293/PRLR/GRE-Luc cells (FIG. 23A) and 293/MMTV-Luc cells (FIG. 23B) by steroid ADCs and budesonide control as described in Example 64.

DETAILED DESCRIPTION

A. Definitions

Figure 1:
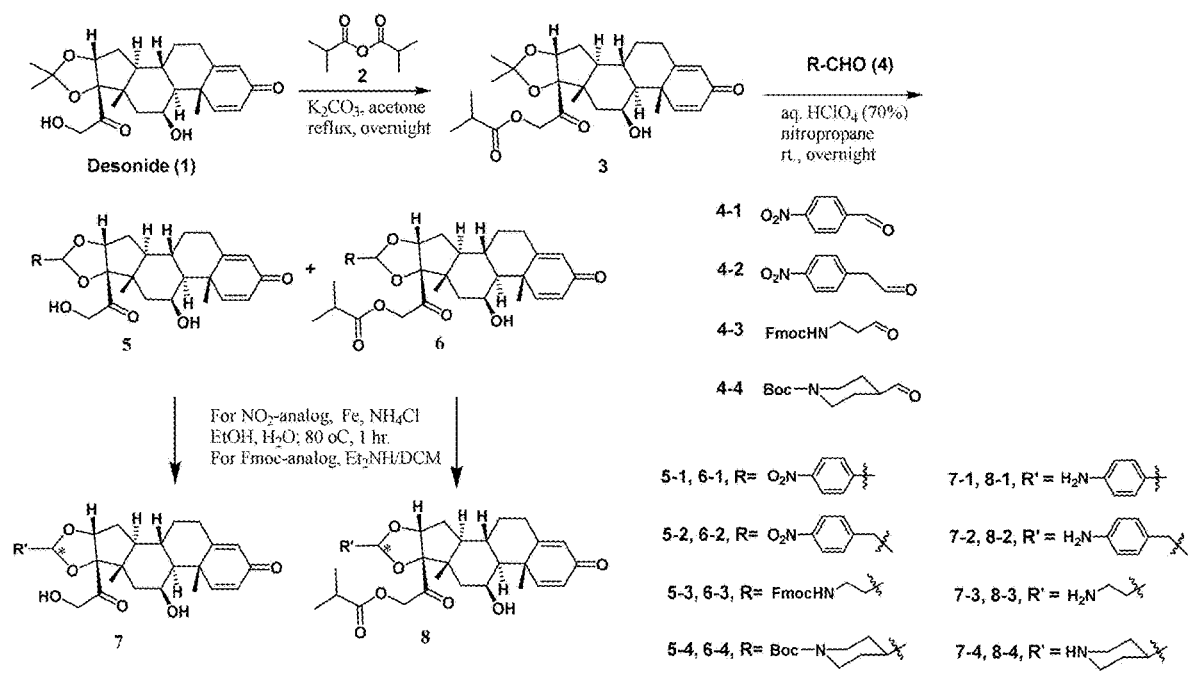

As used herein, "alkyl" refers to a monovalent and saturated hydrocarbon radical moiety. Alkyl is optionally substituted and can be linear, branched, or cyclic, i.e., cycloalkyl. Alkyl includes, but is not limited to, those having 1-20 carbon atoms, i.e., $C_{1-20}$ alkyl; 1-12 carbon atoms, i.e., $C_{1-12}$ alkyl; 1-8 carbon atoms, i.e., $C_{1-8}$ alkyl; 1-6 carbon atoms, i.e., $C_{1-6}$ alkyl; and 1-3 carbon atoms, i.e., $C_{1-3}$ alkyl. Examples of alkyl moieties include, but are not limited to methyl, ethyl, n-propyl, i-propyl, n-butyl, s-butyl, t-butyl, i-butyl, a pentyl moiety, a hexyl moiety, cyclopropyl, cyclobutyl, cyclopentyl, and cyclohexyl. "Alkylene" is divalent alkyl.

As used herein, "haloalkyl" refers to alkyl, as defined above, wherein the alkyl includes at least one substituent selected from a halogen, e.g., F, Cl, Br, or I.

As used herein, "alkenyl" refers to a monovalent hydrocarbon radical moiety containing at least two carbon atoms and one or more nonaromatic carbon-carbon double bonds. Alkenyl is optionally substituted and can be linear, branched, or cyclic. Alkenyl includes, but is not limited to, those having 2-20 carbon atoms, i.e., $C_{2-20}$ alkenyl; 2-12 carbon atoms, i.e., $C_{2-12}$ carbon atoms, i.e., $C_{2-8}$alkenyl; 2-6 carbon atoms, i.e., $C_{2-6}$ alkenyl; and 2-4 carbon atoms, i.e., $C_{2-4}$ alkenyl. Examples of alkenyl moieties include, but are not limited to vinyl, propenyl, butenyl, and cyclohexenyl. "Alkenylene" is divalent alkenyl.

As used herein, "alkynyl" refers to a monovalent hydrocarbon radical moiety containing at least two carbon atoms and one or more carbon-carbon triple bonds. Alkynyl is optionally substituted and can be linear, branched, or cyclic. Alkynyl includes, but is not limited to, those having 2-20 carbon atoms, i.e., $C_{2-20}$ alkynyl; 2-12 carbon atoms, i.e., $C_{2-12}$ alkynyl; 2-8 carbon atoms, i.e., $C_{2-8}$ alkynyl; 2-6 carbon atoms, i.e., $C_{2-6}$ alkynyl; and 2-4 carbon atoms, i.e., $C_{2-4}$ alkynyl. Examples of alkynyl moieties include, but are not limited to ethynyl, propynyl, and butynyl. "Alkynylene" is divalent alkynyl.

As used herein, "alkoxy" refers to a monovalent and saturated hydrocarbon radical moiety wherein the hydrocarbon includes a single bond to an oxygen atom and wherein the radical is localized on the oxygen atom, e.g., $CH_3CH_2$—O— for ethoxy. Alkoxy substituents bond to the compound which they substitute through this oxygen atom of the alkoxy substituent. Alkoxy is optionally substituted and can be linear, branched, or cyclic, i.e., cycloalkoxy. Alkoxy includes, but is not limited to, those having 1-20 carbon atoms, i.e., $C_{1-20}$ alkoxy; 1-12 carbon atoms, i.e., $C_{1-12}$ alkoxy; 1-8 carbon atoms, i.e., $C_{1-8}$ alkoxy; 1-6 carbon atoms, i.e., $C_{1-6}$ alkoxy; and 1-3 carbon atoms, i.e., $C_{1-3}$ alkoxy. Examples of alkoxy moieties include, but are not limited to methoxy, ethoxy, n-propoxy, i-propoxy, n-butoxy, s-butoxy, t-butoxy, i-butoxy, a pentoxy moiety, a hexoxy moiety, cyclopropoxy, cyclobutoxy, cyclopentoxy, and cyclohexoxy.

As used herein, "haloalkoxy" refers to alkoxy, as defined above, wherein the alkoxy includes at least one substituent selected from a halogen, e.g., F, Cl, Br, or I.

As used herein, "aryl" refers to a monovalent moiety that is a radical of an aromatic compound wherein the ring atoms are carbon atoms. Aryl is optionally substituted and can be monocyclic or polycyclic, e.g., bicyclic or tricyclic. Examples of aryl moieties include, but are not limited to those having 6 to 20 ring carbon atoms, i.e., $C_{6-20}$ aryl; 6 to 15 ring carbon atoms, i.e., $C_{6-15}$ aryl, and 6 to 10 ring carbon atoms, i.e., $C_{6-10}$ aryl. Examples of aryl moieties include, but are limited to phenyl, naphthyl, fluorenyl, azulenyl, anthryl, phenanthryl, and pyrenyl.

As used herein, "arylalkyl" refers to an monovalent moiety that is a radical of an alkyl compound, wherein the alkyl compound is substituted with an aromatic substituent, i.e., the aromatic compound includes a single bond to an alkyl group and wherein the radical is localized on the alkyl group. An arylalkyl group bonds to the illustrated chemical structure via the alkyl group. An arylalkyl can be represented by the structure, e.g.,

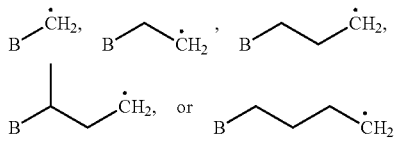

wherein B is an aromatic moiety, e.g., phenyl. Arylalkyl is optionally substituted, i.e., the aryl group and/or the alkyl group, can be substituted as disclosed herein. Examples of arylalkyl include, but are not limited to, benzyl.

As used herein, "aryloxy" refers to a monovalent moiety that is a radical of an aromatic compound wherein the ring atoms are carbon atoms and wherein the ring is substituted with an oxygen radical, i.e., the aromatic compound includes a single bond to an oxygen atom and wherein the radical is localized on the oxygen atom, e.g.

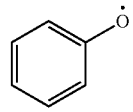

for phenoxy. Aryloxy substituents bond to the compound which they substitute through this oxygen atom. Aryloxy is optionally substituted. Aryloxy includes, but is not limited to those having 6 to 20 ring carbon atoms, i.e., $C_{6-20}$ aryloxy; 6 to 15 ring carbon atoms, i.e., $C_{6-15}$ aryloxy, and 6 to 10 ring carbon atoms, i.e., $C_{6-10}$ aryloxy. Examples of aryloxy moieties include, but are not limited to phenoxy, naphthoxy, and anthroxy.

As used herein, "$R^aR^bN$-aryloxy" refers to a monovalent moiety that is a radical of an aromatic compound wherein the ring atoms are carbon atoms and wherein the ring is substituted with an $R^aR^bN$-substituent and an oxygen radical, i.e., the aromatic compound includes a single bond to an $R^aR^bN$-substituent and a single bond to an oxygen atom and wherein the radical is localized on the oxygen atom, e.g.

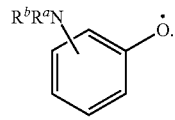

$R^aR^bN$-aryloxy substituents bond to the compound which they substitute through this oxygen atom. $R^aR^bN$-aryloxy is optionally substituted. $R^aR^bN$-aryloxy includes, but is not limited to those having 6 to 20 ring carbon atoms, 6 to 15 ring carbon atoms; and 6 to 10 ring carbon atoms. An example of an $R^aR^bN$-aryloxy moiety includes, but is not limited to 4-(dimethyl-amino)-phenoxy,

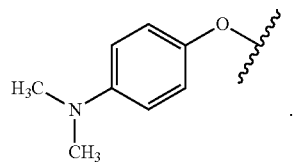 [SMILES: *Oc1ccc(N(C)C)cc1]

As used herein, "arylene" refers to a divalent moiety of an aromatic compound wherein the ring atoms are only carbon atoms. Arylene is optionally substituted and can be monocyclic or polycyclic, e.g., bicyclic or tricyclic. Examples of arylene moieties include, but are not limited to those having 6 to 20 ring carbon atoms, i.e., $C_{6-20}$ arylene; 6 to 15 ring carbon atoms, i.e., $C_{6-15}$ arylene, and 6 to 10 ring carbon atoms, i.e., $C_{6-10}$ arylene.

As used herein, "heteroalkyl" refers to an alkyl in which one or more carbon atoms are replaced by heteroatoms. As used herein, "heteroalkenyl" refers to an alkenyl in which one or more carbon atoms are replaced by heteroatoms. As used herein, "heteroalkynyl" refers to an alkynyl in which one or more carbon atoms are replaced by heteroatoms. Suitable heteroatoms include, but are not limited to, nitrogen, oxygen, and sulfur atoms. Heteroalkyl is optionally substituted. Examples of heteroalkyl moieties include, but are not limited to, aminoalkyl, sulfonylalkyl, sulfinylalkyl. Examples of heteroalkyl moieties also include, but are not limited to, methylamino, methylsulfonyl, and methylsulfinyl.

As used herein, "heteroaryl" refers to a monovalent moiety that is a radical of an aromatic compound wherein the ring atoms contain carbon atoms and at least one oxygen, sulfur, nitrogen, or phosphorus atom. Examples of heteroaryl moieties include, but are not limited to those having 5 to 20 ring atoms; 5 to 15 ring atoms; and 5 to 10 ring atoms. Heteroaryl is optionally substituted.

As used herein, "heteroarylene" refers to an arylene in which one or more ring atoms of the aromatic ring are replaced with an oxygen, sulfur, nitrogen, or phosphorus atom. Heteroarylene is optionally substituted.

As used herein, "heterocycloalkyl" refers to a cycloalkyl in which one or more carbon atoms are replaced by heteroatoms. Suitable heteroatoms include, but are not limited to, nitrogen, oxygen, and sulfur atoms. Heterocycloalkyl is optionally substituted. Examples of heterocycloalkyl moieties include, but are not limited to, morpholinyl, piperidinyl, tetrahydropyranyl, pyrrolidinyl, imidazolidinyl, oxazolidinyl, thiazolidinyl, dioxolanyl, dithiolanyl, oxanyl, or thianyl.

As used herein, "N-containing heterocycloalkyl," refers to a cycloalkyl in which one or more carbon atoms are replaced by heteroatoms and wherein at least one heteroatom is a nitrogen atom. Suitable heteroatoms in addition to nitrogen, include, but are not limited to oxygen and sulfur atoms. N-containing heterocycloalkyl is optionally substituted. Examples of N-containing heterocycloalkyl moieties include, but are not limited to, morpholinyl, piperidinyl, pyrrolidinyl, imidazolidinyl, oxazolidinyl, or thiazolidinyl.

As used herein, "optionally substituted," when used to describe a radical moiety, e.g., optionally substituted alkyl, means that such moiety is optionally bonded to one or more substituents. Examples of such substituents include, but are not limited to halo, cyano, nitro, haloalkyl, azido, epoxy, optionally substituted heteroaryl, optionally substituted heterocycloalkyl,

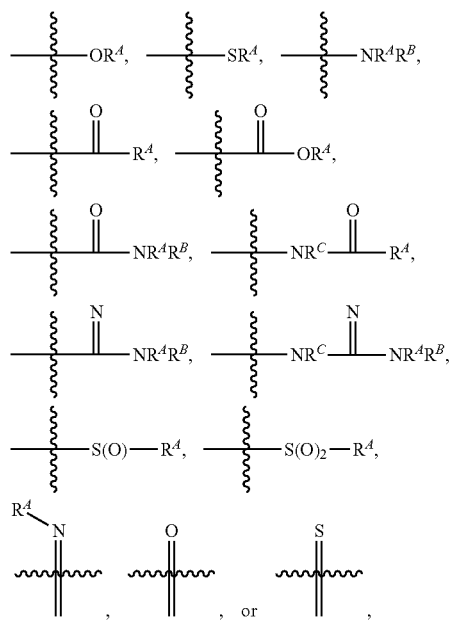

wherein $R^A$, $R^B$, and $R^C$ are, independently at each occurrence, a hydrogen atom, alkyl, alkenyl, alkynyl, aryl, alkylaryl, arylalkyl, heteroalkyl, heteroaryl, or heterocycloalkyl, or $R^A$ and $R^B$, together with the atoms to which they are bonded, form a saturated or unsaturated carbocyclic ring, wherein the ring is optionally substituted and wherein one or more ring atoms is optionally replaced with a heteroatom. In certain embodiments, when a radical moiety is optionally substituted with an optionally substituted heteroaryl, optionally substituted heterocycloalkyl, or optionally substituted saturated or unsaturated carbocyclic ring, the substituents on the optionally substituted heteroaryl, optionally substituted heterocycloalkyl, or optionally substituted saturated or unsaturated carbocyclic ring, if they are substituted, are not substituted with substituents which are further optionally substituted with additional substituents. In some embodiments, when a group described herein is optionally substituted, the substituent bonded to the group is unsubstituted unless otherwise specified.

As used herein, "binding agent" refers to any molecule capable of binding with specificity to a given binding partner. In some embodiments, the binding agent is an antibody, or an antigen binding fragment thereof.

As used herein, "linker" refers to a divalent moiety that covalently links the binding agent to the steroid described herein.

As used herein, "amide synthesis conditions" refers to reaction conditions suitable facilitate the formation of an amide, e.g., by the reaction of a carboxylic acid, activated carboxylic acid, or acyl halide with an amine. In some examples, "amide synthesis conditions" refers to reaction conditions suitable to facilitate the formation of an amide bond between a carboxylic acid and an amine. In some of these examples, the carboxylic acid is first converted to an activated carboxylic acid before the activated carboxylic acid reacts with an amine to form an amide. Suitable conditions to effect the formation of an amide include, but are not limited to, those utilizing reagents to effect the reaction between a carboxylic acid an amine, including, but not limited to, dicyclohexylcarbodiimide (DCC), diisopropylcarbodiimide (DIC), (benzotriazol-1-yloxy)tris(dimethylamino)phosphonium hexafluorophosphate (BOP), (benzotriazol-1-yloxy)tripyrrolidinophosphonium hexafluorophosphate (PyBOP), (7-azabenzotriazol-1-yloxy) tripyrrolidinophosphonium hexafluorophosphate (PyAOP), bromotripyrrolidinophosphonium hexafluorophosphate (PyBrOP), O-(benzotriazol-1-yl)-N,N,N',N'-tetramethyluronium hexafluorophosphate (HBTU), O-(benzotriazol-1-yl)-N,N,N',N'-tetramethyluronium tetrafluoroborate (TBTU), 1-[Bis(dimethylamino)methylene]1H-1,2,3-triazolo[4,5-b] pyridinium 3-oxid hexafluorophosphate (HATU), 2-Ethoxy-1-ethoxycarbonyl-1,2-dihydroquinoline (EEDQ), 1-Ethyl-3-(3-dimethylaminopropyl)carbodiimide (EDC), 2-Chloro-1,3-dimethylimidazolidinium hexafluorophosphate (CIP), 2-chloro-4,6-dimethoxy-1,3,5-triazine (CDMT), and carbonyldiimidazole (CDI). In some examples, a carboxylic acid is first converted to an activated carboxylic ester before reacting with an amine to form an amide bond. In certain embodiments, the carboxylic acid is reacted with a reagent. The reagent activates the carboxylic acid by deprotonating the carboxylic acid and then forming a product complex with the deprotonated carboxylic acid as a result of nucleophilic attack by the deprotonated carboxylic acid onto the protonated reagent. For certain carboxylic acids, this activated ester is more susceptible subsequently to nucleophilic attack by an amine than the carboxylic acid is before it is converted. This results in amide bond formation. As such, the carboxylic acid is described as activated. Exemplary reagents include DCC and DIC.

As used herein, "therapeutically effective amount" refers to an amount (of a compound) that is sufficient to provide a therapeutic benefit to a patient in the treatment or management of a disease or disorder, or to delay or minimize one or more symptoms associated with the disease or disorder.

As used herein, "pharmaceutically acceptable derivative" refers to any form, e.g., ester or prodrug of a compound, which provides said compound upon administration to a patient.

As used herein, "pharmaceutically acceptable salt" refers to any salt suitable for administration to a patient. Suitable salts include, but are not limited to, those disclosed in Berge et al., "Pharmaceutical Salts", *J. Pharm. Sci.,* 1977, 66:1, incorporated herein by reference. Examples of salts include, but are not limited to, acid-derived, base-derived, organic, inorganic, amine, and alkali or alkaline earth metal salts, including but not limited to calcium salts, magnesium salts, potassium salts, sodium salts, salts of hydrochloric acid, hydrobromic acid, sulfuric acid, nitric acid, phosphoric acid, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, and salicylic acid, and the like.

Certain groups, moieties, substituents, and atoms are depicted with a wiggly line that intersects or caps a bond or bonds to indicate the atom through which the groups, moieties, substituents, atoms are bonded. For example, a phenyl group that is substituted with a propyl group depicted as:

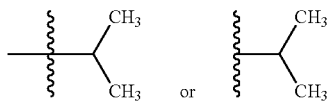

has the following structure:

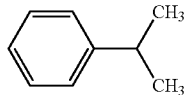

As used herein, illustrations showing substituents bonded to a cyclic group (e.g., aromatic, heteroaromatic, fused ring, and saturated or unsaturated cycloalkyl or heterocycloalkyl) through a bond between ring atoms are meant to indicate, unless specified otherwise, that the cyclic group may be substituted with that substituent at any ring position in the cyclic group or on any ring in the fused ring group, according to techniques set forth herein or which are known in the field to which the instant disclosure pertains. For example, the group,

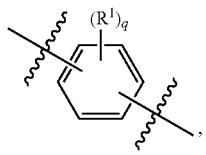

wherein subscript q is an integer from 0 to 4 and in which the positions of substituent $R^1$ are described generically, i.e., not directly attached to any vertex of the bond line structure, i.e., specific ring carbon atom, includes the following, non-limiting examples of, groups in which the substituent $R^1$ is bonded to a specific ring carbon atom:

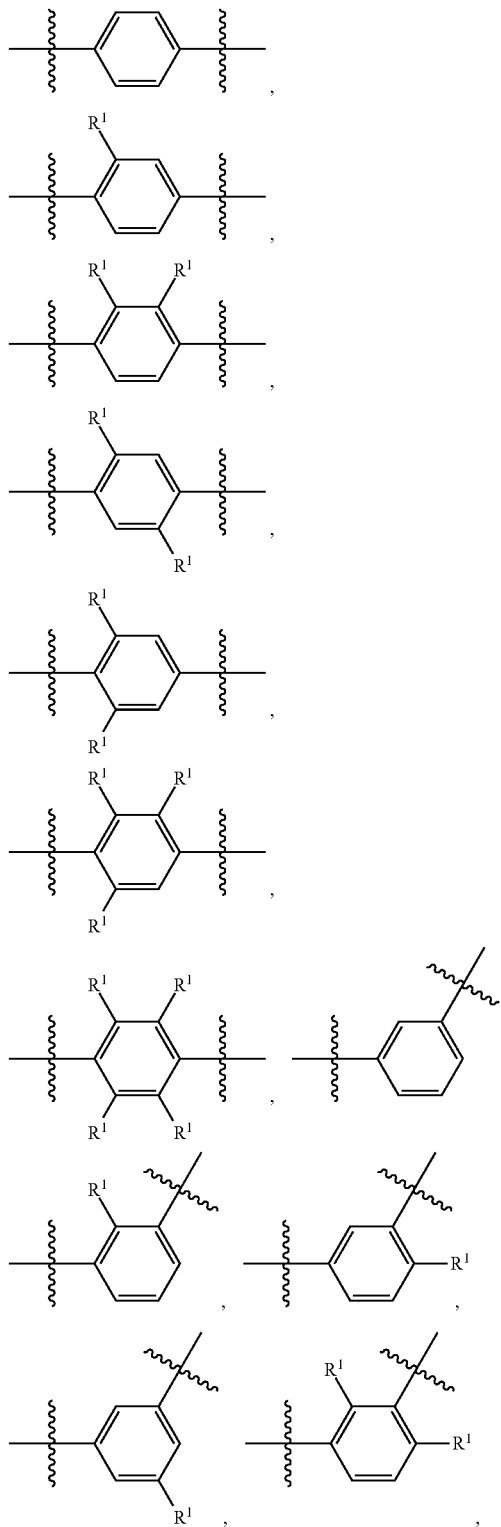

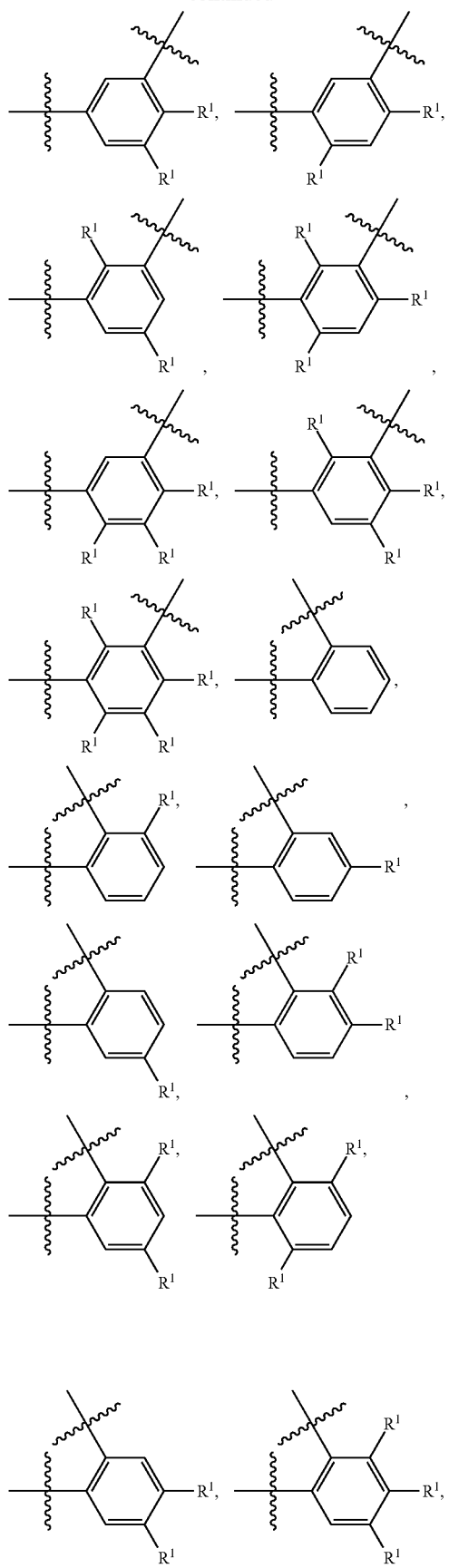
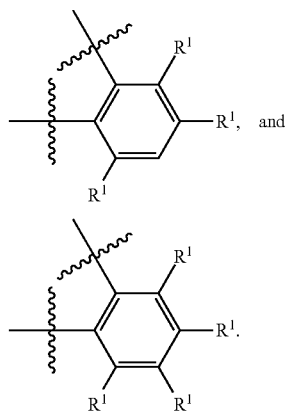
Also, for example, the group,
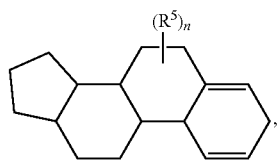
wherein subscript n is an integer from 0 to 19 and in which the positions of substituent $R^5$ are described generically, i.e., depicted as not directly attached to any vertex of the bond line structure, includes the following, non-limiting examples of, groups in which the substituent $R^5$ is bonded to a specific ring carbon atom:
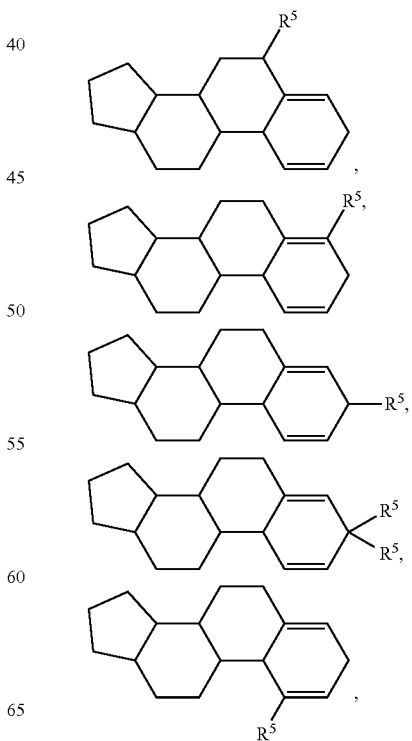

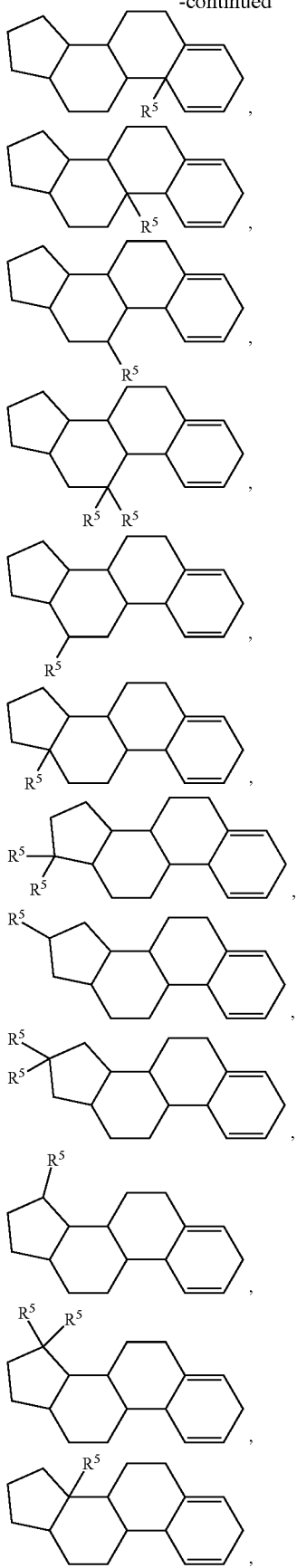

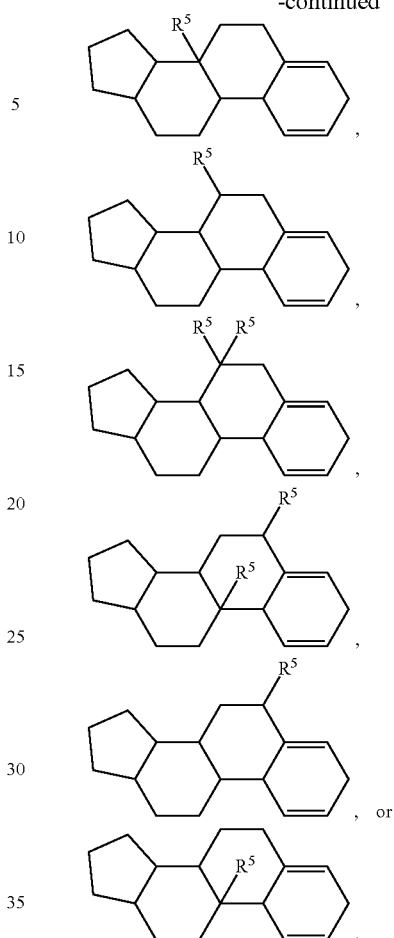

As used herein, the phrase "reactive linker," or the abbreviation "RL" refers to a monovalent group that comprises a reactive group and linking group, depicted as

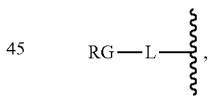

wherein RG is the reactive group and L is the linking group. The linking group is any divalent moiety that bridges the reactive group to a payload. The reactive linkers (RL), together with the payloads to which they are bonded, comprise intermediates ("linker-payloads") useful as synthetic precursors for the preparation of the antibody steroid conjugates described herein. The reactive linker contains a reactive group ("RG"), which is a functional group or moiety that reacts with a reactive portion of an antibody, modified antibody, or antigen binding fragment thereof. The moiety resulting from the reaction of the reactive group with the antibody, modified antibody, or antigen binding fragment thereof, together with the linking group, comprise the "binding agent linker" ("BL") portion of the conjugate, described herein. In certain embodiments, the "reactive group" is a functional group or moiety (e.g., maleimide or NHS ester) that reacts with a cysteine or lysine residue of an antibody or antigen-binding fragment thereof. In certain embodiments, the "reactive group" is a functional group or moiety that is capable of undergoing a click chemistry reaction. In some embodiments of said click chemistry reaction, the reactive group is an alkyne that is capable of undergoing a 1,3 cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3 cycloaddition reactions with azides in the absence of copper catalysts. Suitable alkynes also include, but are not limited to, DIBAC, DIBO, BARAC, DIFO, substituted, e.g., fluorinated alkynes, aza-cycloalkynes, BCN, and derivatives thereof. Linker-payloads comprising such reactive groups are useful for conjugating antibodies that have been functionalized with azido groups. Such functionalized antibodies include antibodies functionalized with azido-polyethylene glycol groups. In certain embodiments, such functionalized antibody is derived by reacting an antibody comprising at least one glutamine residue, e.g., heavy chain Q295 (EU numbering), with a compound according to the formula H$_2$N-LL-N$_3$, wherein LL is a divalent polyethylene glycol group, in the presence of the enzyme transglutaminase.

In some examples, the reactive group is an alkyne, e.g.,

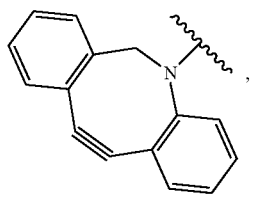 [SMILES: *N1Cc2ccccc2C#Cc2ccccc21]

which can react via click chemistry with an azide, e.g.,

to form a click chemistry product, e.g.

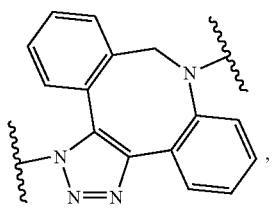 [SMILES: *N1Cc2ccccc2-c2c(nnn2*)-c2ccccc21]

its regioisomer, or mixture thereof. In some examples, reactive group is an alkyne, e.g.,

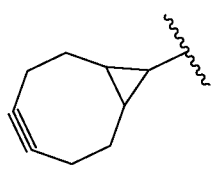 or 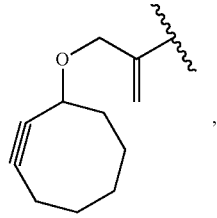

which can react via click chemistry with an azide, e.g.,

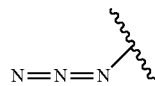

to form a click chemistry product, e.g.,

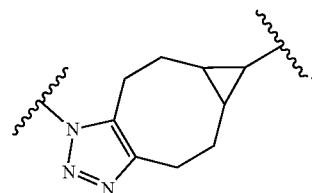

In some examples, the reactive group is an alkyne, e.g.,

which can react via click chemistry with an azide, e.g.,

to form a click chemistry product, e.g.,

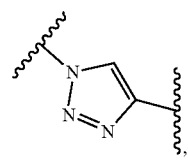 [SMILES: *c1cn(*)nn1]

its regioisomer, or mixture thereof. In some examples, the reactive group is a functional group, e.g.,

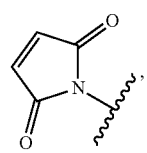

which reacts with a cysteine residue on an antibody or antigen-binding fragment thereof, to form a bond thereto, e.g.,

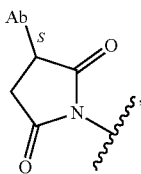

wherein Ab refers to an antibody or antigen-binding fragment thereof and S refers to the S atom on a cysteine residue through which the functional group bonds to the Ab. In some examples, the reactive group is a functional group, e.g.,

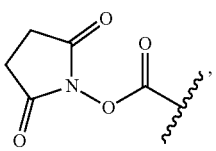 [SMILES: *C(=O)ON1C(=O)CCC1=O]

which reacts with a lysine residue on an antibody or antigen-binding fragment thereof, to form a bond thereto, e.g.,

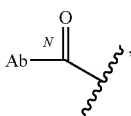

wherein Ab refers to an antibody or antigen-binding fragment thereof and N refers to the N atom on a lysine residue through which the functional group bonds to the Ab.

As used herein, the phrase "binding agent linker," or "BL" refers to any divalent group or moiety that links, connects, or bonds a binding agent (e.g., an antibody or an antigen binding fragment thereof) with a payload compound set forth herein (e.g., steroid). Generally, suitable binding agent linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers are linkers that are cleaved by intracellular metabolism following internalization, e.g., cleavage via hydrolysis, reduction, or enzymatic reaction. Non-cleavable linkers are linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise glucuronides, succinimide-thioethers, polyethylene glycol (PEG) units, hydrazones, mal-caproyl units, disulfide units (e.g., —S—S—, —S—C($R^1R^2$)—, wherein $R^1$ and $R^2$ are independently hydrogen or hydrocarbyl), carbamate units, para-amino-benzyl units (PAB), phosphate units, e.g., mono-, bis-, or tris-phosphate units, and peptide units, e.g., peptide units containing two, three four, five, six, seven, eight, or more amino acids, including but not limited to valine-citrulline and units. In some embodiments, the binding agent linker (BL) comprises a moiety that is formed by the reaction of the reactive group (RG) of a reactive linker (RL) and reactive portion of the binding agent, e.g., antibody, modified antibody, or antigen binding fragment thereof.

In some examples, the BL comprises the following moiety:

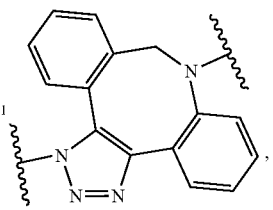 [SMILES: *N1Cc2ccccc2-c2c(nnn2*)-c2ccccc21]

its regioisomer, or mixture thereof, wherein ⅰ is the bond to the binding agent. In some examples, the BL comprises the following moiety:

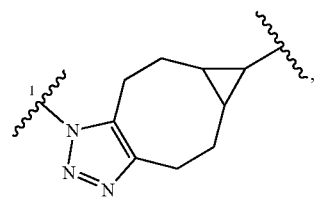 [SMILES: *C1C2CCc3nnn(*)c3CCC12]

its regioisomer, or mixture thereof, wherein ⅰ is the bond to the binding agent. In some examples, the BL comprises the following moiety:

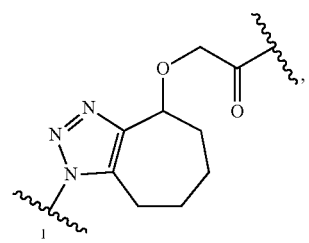 [SMILES: *C(=O)COC1CCCCc2c1nnn2*]

its regioisomer, or mixture thereof, wherein ⅰ is the bond to the binding agent. In some examples, the BL comprises the following moiety:

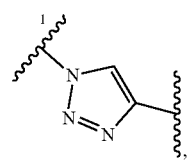 [SMILES: *c1cn(*)nn1]

its regioisomer, or mixture thereof, wherein ⅰ is the bond to the binding agent. In some examples, the BL comprises the following moiety:

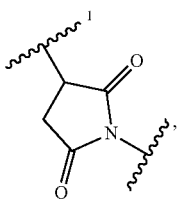 [SMILES: *C1CC(=O)N(*)C1=O]

wherein ⁞ is the bond to the cysteine of the antibody or antigen-binding fragment thereof. In some examples, the BL comprises the following moiety:

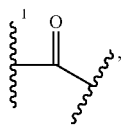

wherein ⁞ is the bond to the lysine of the antibody or antigen-binding fragment thereof. In these examples, the bond to the binding agent is direct or via a linker. In particular embodiments, the binding agent is modified with an azide to facilitate linkage to BL. Examples are described below.

B. Steroids

Provided herein are compounds having the structure of Formula (A):

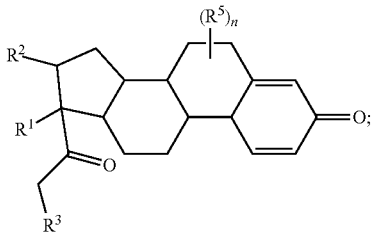

or a pharmaceutically acceptable salt, solvate, stereoisomer, or derivative thereof, wherein:

$R^1$ and $R^2$ are, independently, —H, alkyl, alkylene-C(O)—O—, —OH, or halo; or $R^1$ and $R^2$ together form

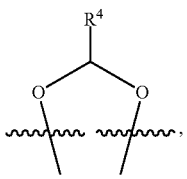

wherein $R^4$ is alkyl, aryl, arylalkyl, or an N-containing heterocycloalkyl, wherein the alkyl, aryl, arylalkyl, and N-containing heterocycloalkyl are, independently in each instance, optionally substituted with —$NR^aR^b$;

$R^3$ is —OH, $R^Z$—C(O)—X—, heteroalkyl, piperidinyl, —$NR^aR^b$, -oxyaryl-$NR^aR^b$, or —Z-A($R^P$)$_t$;

$R^5$ is, independently in each instance, —OH, halo, alkyl, or arylalkyl;

$R^Z$ is alkyl;

X is O or $NR^a$;

Z is S, S(O), S(O)$_2$, SO$_2NR^a$, O, C(O)$NR^a$, C(O), or $NR^a$;

A is aryl or heteroaryl;

$R^P$ is, independently in each instance, halo, optionally substituted alkyl, —OH, or —$NR^aR^b$;

$R^a$ and $R^b$ are, independently in each instance, —H or optionally substituted alkyl;

n is an integer from 0-19; and t is an integer from 1-3;

with the proviso that (1) $R^3$ is not —OH (a) when $R^1$ is —OH or (b) when $R^1$ and $R^2$ together form

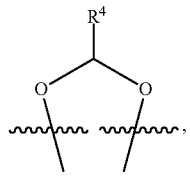

wherein $R^4$ is $C_{1-9}$alkyl or

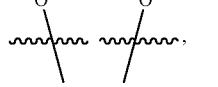

and (2) $R^3$ is not

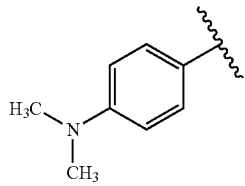

In some embodiments, the compound of Formula (A) has the structure of Formula ($A^1$):

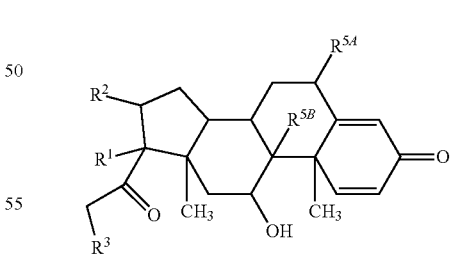

wherein $R^1$-$R^3$ are as defined above and $R^{5A}$ and $R^{5B}$ are each, independently, halo or a hydrogen atom.

In some embodiments of the compound of Formula ($A^1$), $R^{5A}$ and $R^{5B}$ are hydrogen atoms. In some embodiments of the compound of Formula ($A^1$), $R^{5A}$ and $R^{5B}$ are fluoro. In some embodiments of the compound of Formula ($A^1$), $R^{5A}$ is a hydrogen atom and $R^{5B}$ is fluoro.

In some embodiments of the compound of Formula ($A^1$), $R^1$ is alkylene-C(O)—O— or —OH and $R^2$ is alkyl.

In some embodiments of the compound of Formula (A¹), R¹ and R² together form

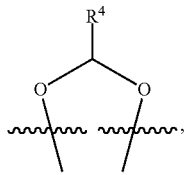

wherein R⁴ is aryl, arylalkyl, or alkyl, wherein the aryl, arylalkyl, and alkyl are optionally substituted with —NR$^a$R$^b$. In some embodiments, R⁴ is -aryl-NR$^a$R$^b$. In some embodiments, R⁴ is -phenyl-NR$^a$R$^b$.

In some embodiments of the compound of Formula (A¹), R¹ and R² together form

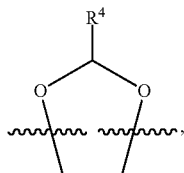

wherein R⁴ is

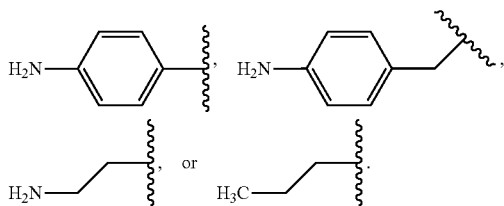

In some embodiments of the compound of Formula (A¹), R³ is —OH, —NR$^a$R$^b$, R$^Z$—C(O)—X—, or

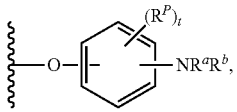

wherein R$^P$ is halo, t is an integer from 0 to 2, R$^a$ is H, R$^b$ is H or alkyl, X is O or NH, and R$^Z$ is alkyl.

In some embodiments of the compound of Formula (A¹), R³ is —OH, —NH₂, —NHCH₃, —N(CH₃)₂,

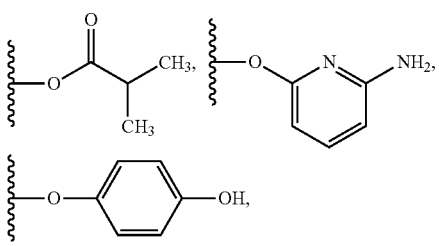

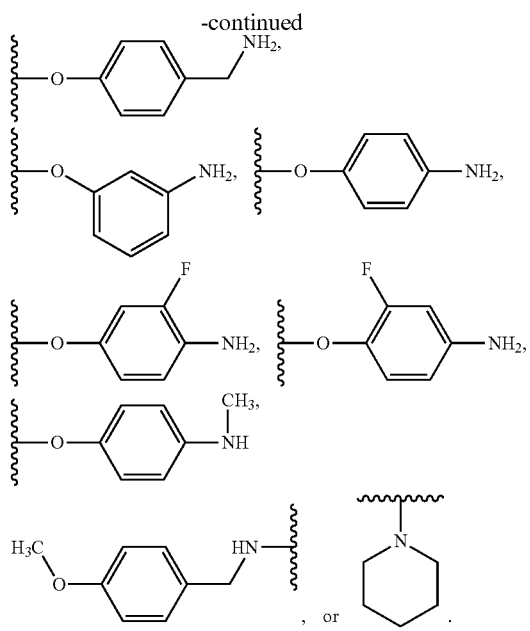

In some embodiments of the compound of Formula (A¹), R¹ and R² together form

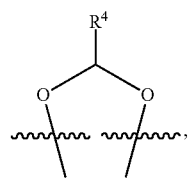

wherein R⁴ is aryl, arylalkyl, or alkyl, wherein the aryl, arylalkyl, and alkyl are optionally substituted with —NR$^a$R$^b$; R³ is —OH, —NR$^a$R$^b$, R$^Z$—C(O)—X—, or

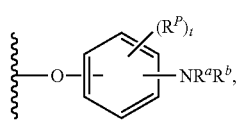

wherein R$^P$ is halo, t is an integer from 0 to 2, R$^a$ is H, R$^b$ is H or alkyl, X is O or NH, and R$^Z$ is alkyl; and R⁵, independently at each occurrence, is fluoro or a hydrogen atom.

Set forth are also compounds of Formula (A²):

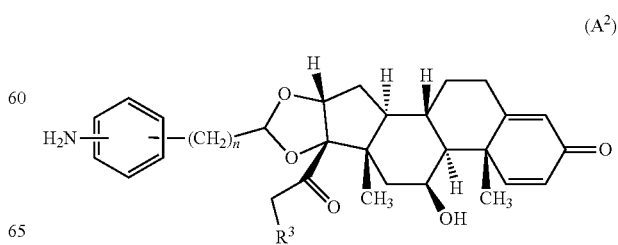

(A²)

wherein n is an integer from 0 to 4 and R³ is —OH or R^Z—C(O)—O—; wherein R^Z is alkyl. In certain embodiments, n is 0 or 1.

Set forth are also compounds of Formula (A³):

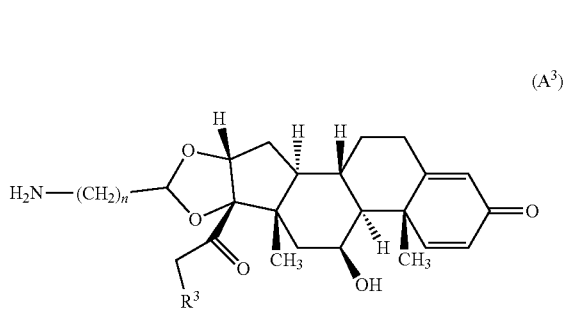

(A³)

wherein n is an integer from 1-4 and R³ is —OH or R^Z—C(O)—O—; wherein R^Z is alkyl. In certain embodiments, n is 2.

Set forth are also compounds of Formula (A⁴):

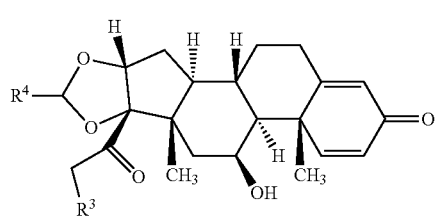

(A⁴)

wherein R³ is —NR^aR^b and R⁴ is alkyl, wherein R^a and R^b are each, independently, a hydrogen atom or alkyl, or R^a and R^b, taken together form a 3-7 membered ring. In certain embodiments, R⁴ is C_{1-4} alkyl. In some embodiments, R⁴ is propyl. In certain embodiments, R³ is —NH₂, —NHCH₃, or —N(CH₃)₂.

Set forth are also compounds of Formula (A⁵):

(A⁵)

wherein R⁴ is alkyl, R^{P1} is halo or a hydrogen atom, and R^{P2} is —NR^aR^b or —OH, wherein R^a and R^b are each, independently, a hydrogen atom or alkyl. In some embodiments, R⁴ is C_{1-4} alkyl and R^{P2} is —NH₂.

Set forth are also compounds of Formula (A⁶):

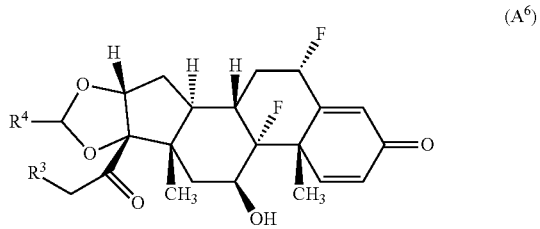

(A⁶)

wherein R³ is

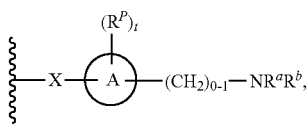

R^ZC(O)X—,

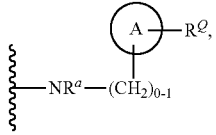

or NR^aR^b, wherein X is O or NR^a,

is aryl or heteroaryl, R^P is halo, t is an integer from 0-2, R^a and R^b are each, independently, a hydrogen atom or alkyl, R^Z is alkyl, and R^Q is alkoxy, and R⁴ is alkyl. In some embodiments, R³ is

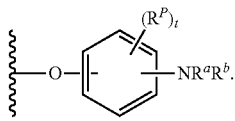

Set forth herein are also compounds of Formula (A⁷)

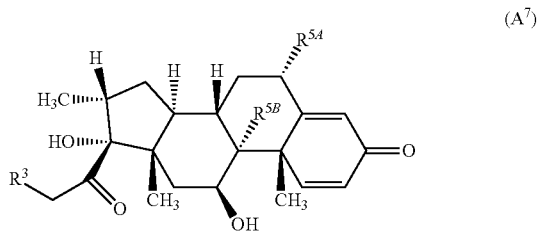

(A⁷)

wherein $R^3$ is

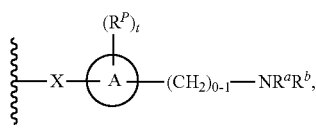

wherein X is O or $NR^a$,

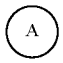

is aryl or heteroaryl, $R^P$ is halo, t is an integer from 0-2, $R^a$ and $R^b$ are each, independently, a hydrogen atom or alkyl, $R^{5A}$ is a hydrogen atom or fluoro, and $R^{5B}$ is fluoro. In some embodiments, $R^3$ is

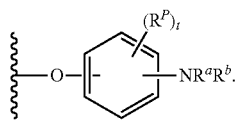

In some examples, set forth herein is a compound having the structure of Formula (I):

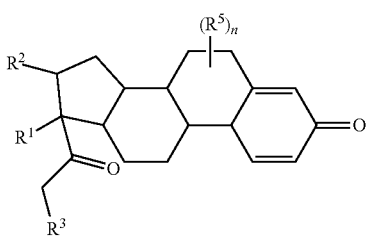

or a pharmaceutically acceptable salt, solvate, stereoisomer, or derivative thereof, wherein:
$R^1$ and $R^2$ are, independently, —H, alkyl, alkyl-C(O)—O—, —OH, or halo; or $R^1$ and $R^2$ together form

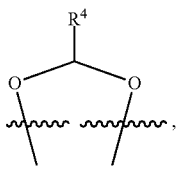

wherein $R^4$ is alkyl, aryl, arylalkyl, or an N-containing heterocycloalkyl, wherein the alkyl, aryl, arylalkyl, and N-containing heterocycloalkyl are, independently in each instance, optionally substituted with —$NR^aR^b$;
$R^3$ is —OH, alkyl-C(O)—O—, heteroalkyl, —$NR^aR^b$, —$NR^aR^b$-aryloxy, or $R^aR^bN$-aryloxy-, wherein the alkyl-C(O)—O—, heteroalkyl, —$NR^aR^b$, and $R^aR^bN$-aryloxy- are optionally substituted with halo;
$R^5$ is, independently in each instance, —OH, halo, alkyl, or arylalkyl;

$R^a$ and $R^b$ are, independently in each instance, H or alkyl; and
n is an integer from 0-19;
with the proviso that $R^3$ is not —OH when either (a) or (b): (a) $R^1$ is —OH or (b) $R^1$ and $R^2$ together form

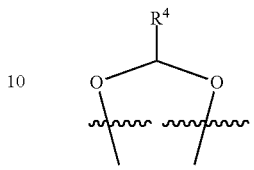

and $R^4$ is a $C_{1-9}$alkyl or

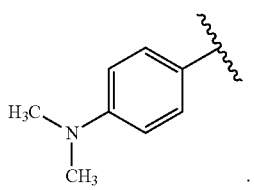

In some of these examples, $R^1$ and $R^2$ are, independently, selected from —H, alkyl, alkyl-C(O)—O—, —OH, and halo. In some other examples, $R^1$ and $R^2$ together form

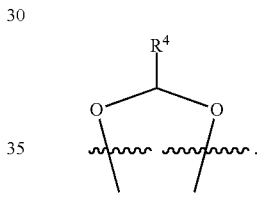

In certain examples, $R^1$ is —H. In certain other examples, $R^1$ is alkyl. In some examples, $R^1$ is alkyl-C(O)—O—. In some other examples, $R^1$ is —OH. In certain examples, $R^1$ is halo. In certain other examples, $R^1$ is —F. In some examples, $R^1$ is —Cl. In some other examples, $R^1$ is —Br. In certain examples, $R^1$ is —I. In certain other examples, $R^2$ is —OH. In some examples, $R^2$ is halo. In some other examples, $R^2$ is —F. In certain examples, $R^2$ is —Cl. In certain other examples, $R^2$ is —Br. In some examples, $R^2$ is —I.

In some examples, in Formula (I), $R^5$ is —OH. In some examples, $R^5$ is halo such as but not limited to —F, —Cl, —Br, or —I. In some examples, $R^5$ is —F. In some examples, $R^5$ is —Cl. In some examples, $R^5$ is —Br. In some examples, $R^5$ is —I. In some examples, $R^5$ is alkyl such as, but not limited to, methyl, ethyl, propyl, butyl, pentyl, hexyl, heptyl, octyl, or nonyl. In some examples, $R^5$ is benzyl.

In some examples, in Formula (I), $R^3$ is selected from —OH, alkyl-C(O)—O—, and $R^aR^bN$-aryloxy. In some of these examples, alkyl-C(O)—O— or $R^aR^bN$-aryloxy is optionally substituted with halo. In some examples, $R^3$ is —OH. In some examples, $R^3$ is alkyl-C(O)—O—. In some examples, $R^3$ is $R^aR^bN$-aryloxy. In some examples, $R^3$ is

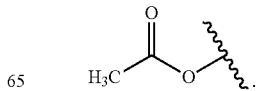

In some examples, R³ is

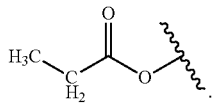

In some examples, R³ is

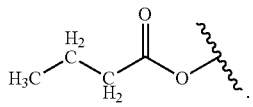

In some examples, R³ is

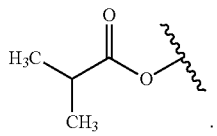

In some examples, R³ is

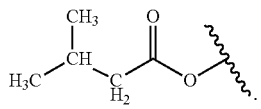

In some examples of Formula (I), R³ is —OH, alkyl-C(O)—O—, heteroalkyl, —NR$^a$R$^b$, or R$^a$R$^b$N-aryloxy, wherein alkyl-C(O)—O—, heteroalkyl, —NR$^a$R$^b$, or R$^a$R$^b$N-aryloxy is optionally substituted with halo. R$^a$ and R$^b$ are, independently in each instance, —H or alkyl.

In some examples, R³ is R$^a$R$^b$N-aryloxy, wherein R$^a$ and R$^b$ are, independently in each instance, —H or alkyl.

In some examples, R³ is

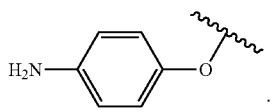

In some examples, R³ is

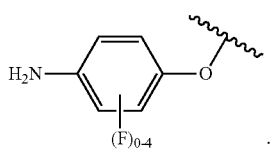

In some examples, R³ is

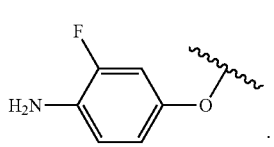

In some examples, R³ is

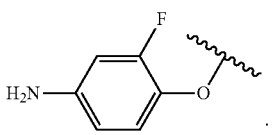

In some examples, R³ is

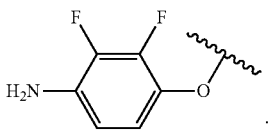

In some examples, R³ is

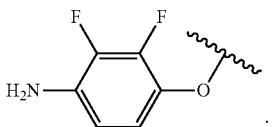

In some examples, R³ is

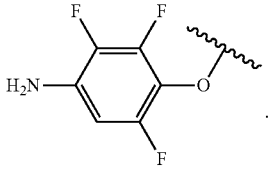

In some examples, R³ is

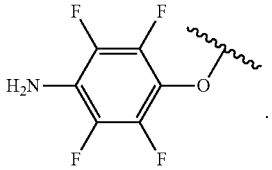

In some examples, R³ is

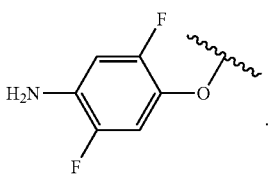

In some examples, $R^3$ is

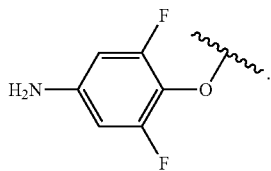

In some examples, $R^3$ is

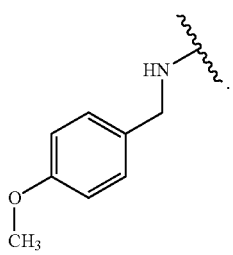 [SMILES: *NCc1ccc(OC)cc1]

In some examples, $R^3$ is $R^aR^bN$-aryloxy, wherein $R^a$ and $R^b$ are, independently in each instance, —H or alkyl.

In some examples, in Formula (I), $R^4$ is selected from the group consisting of alkyl, aryl, arylalkyl, and an N-containing heterocycloalkyl. In some of these examples, alkyl, aryl, arylalkyl, or N-containing heterocycloalkyl are optionally substituted with —$NR^aR^b$. In some examples, $R^4$ is alkyl such as, but not limited to, methyl, ethyl, propyl, butyl, pentyl, hexyl, heptyl, octyl, or nonyl. In some examples, $R^4$ is methyl. In some examples, $R^4$ is ethyl. In some examples, $R^4$ is n-propyl. In some examples, $R^4$ is i-propyl. In some examples, $R^4$ is n-butyl. In some examples, $R^4$ is i-butyl. In some examples, $R^4$ is t-butyl. In some examples, $R^4$ is sec-butyl. In some examples, $R^4$ is pentyl. In some examples, $R^4$ is hexyl. In some examples, $R^4$ is heptyl. In some examples, $R^4$ is octyl, or nonyl. In some examples, $R^4$ is aryl such as but not limited to phenyl or naphthyl. In some examples, $R^4$ is phenyl. In some examples, $R^4$ is naphthyl. In some examples, $R^4$ is arylalkyl—such as but not limited to benzyl. In some examples, $R^4$ is N-containing heterocycloalkyl such as but not limited to piperidinyl. In some examples, $R^4$ is 4-amino-phenyl. In some examples, $R^4$ is 4-aminophenyl optionally substituted with halo.

In some examples, $R^4$ is

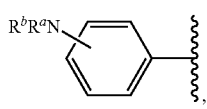

wherein $R^a$ and $R^b$ are, independently in each instance, H or alkyl.

In some examples, $R^4$ is

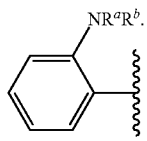

In some examples, $R^4$ is

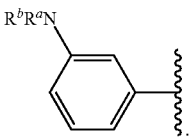

In some examples, $R^4$ is

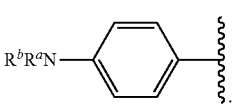

In some examples, $R^4$ is

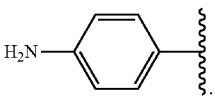

In some examples, $R^4$ is

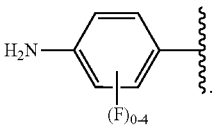

In some examples, $R^4$ is

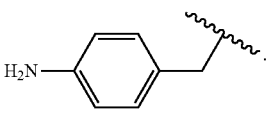

In some examples, $R^4$ is

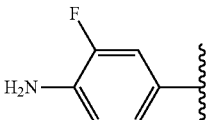

In some examples, $R^4$ is

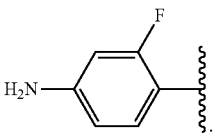 [SMILES: *c1ccc(N)cc1F]

In some examples, $R^4$ is
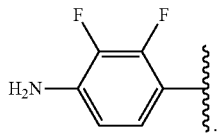
In some examples, $R^4$ is
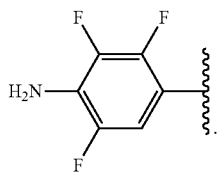
In some examples, $R^4$ is
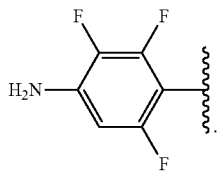
In some examples, $R^4$ is
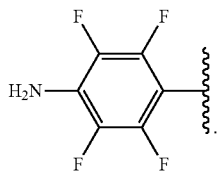
In some examples, $R^4$ is
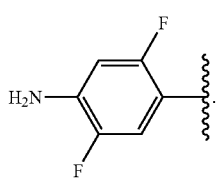
In some examples, $R^4$ is
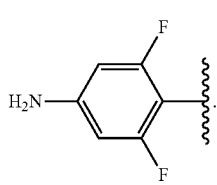
In some examples, $R^4$ is
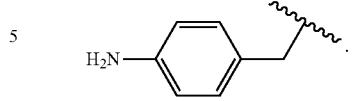
In some examples, $R^4$ is
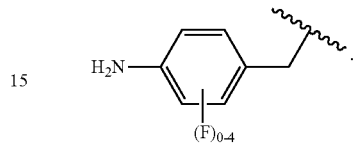
In some examples, $R^4$ is
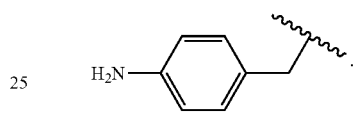
In some examples, $R^4$ is
In some examples, $R^4$ is
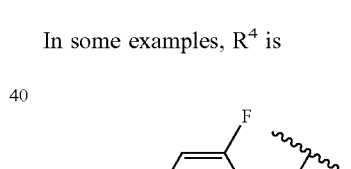
In some examples, $R^4$ is
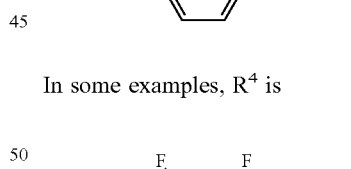
In some examples, $R^4$ is
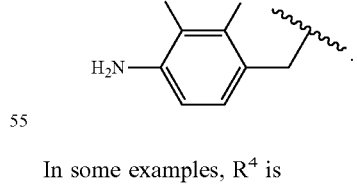
In some examples, $R^4$ is
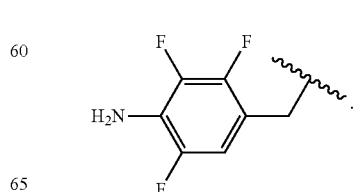

In some examples, $R^4$ is
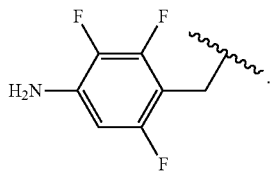
In some examples, $R^4$ is
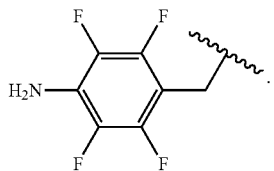
In some examples, $R^4$ is
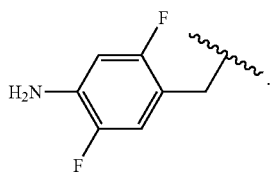
In some examples, $R^4$ is
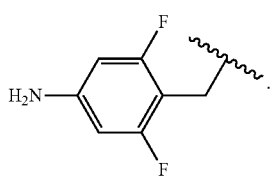 [SMILES: *Cc1c(F)cc(N)cc1F]
In some examples, $R^4$ is
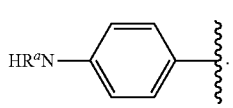
In some examples, $R^4$ is
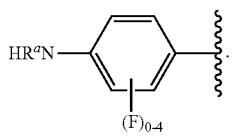
In some examples, $R^4$ is
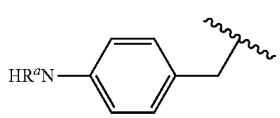
In some examples, $R^4$ is
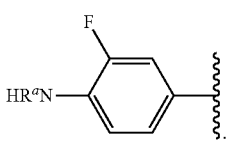
In some examples, $R^4$ is
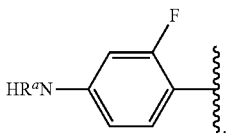
In some examples, $R^4$ is
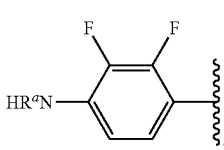
In some examples, $R^4$ is
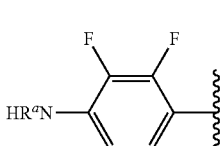
In some examples, $R^4$ is
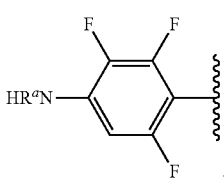
In some examples, $R^4$ is
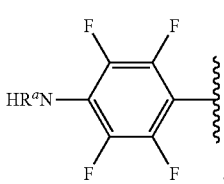

In some examples, R⁴ is

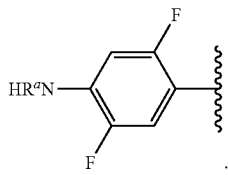

In some examples, R⁴ is

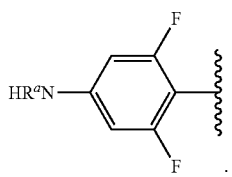

In some examples, R⁴ is

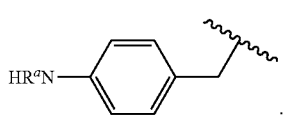

In some examples, R⁴ is

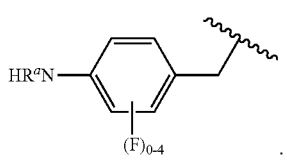

In some examples, R⁴ is

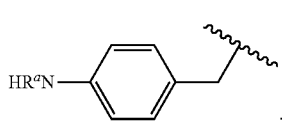

In some examples, R⁴ is

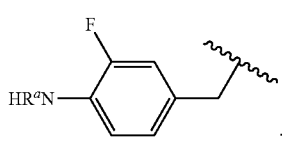

In some examples, R⁴ is

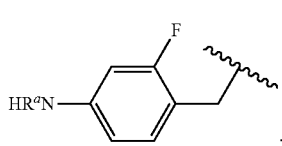

In some examples, R⁴ is

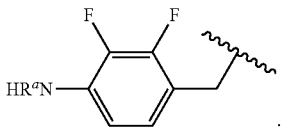

In some examples, R⁴ is

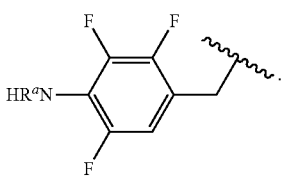

In some examples, R⁴ is

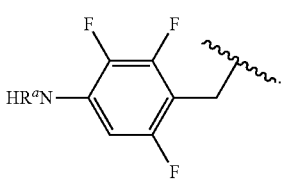

In some examples, R⁴ is

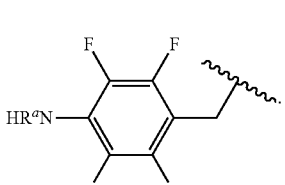

In some examples, R⁴ is

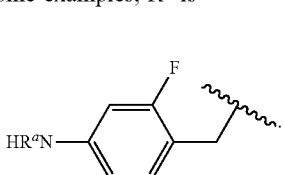

In some examples, R⁴ is

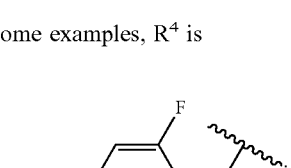

In some examples, R⁴ is

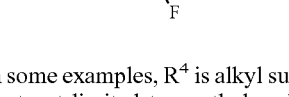

In some examples, R⁴ is alkyl substituted with amino such as, but not limited to, methyl-amino, ethyl-amino, propyl-amino, butyl-amino, pentyl-amino, hexyl-amino, heptyl-amino, octyl-amino, or nonyl-amino. In some examples, R⁴ is methyl-amino. In some examples, $R^4$ is ethyl-amino. In some examples, $R^4$ is n-propyl-amino. In some examples, $R^4$ is i-propyl-amino. In some examples, $R^4$ is n-butyl-amino. In some examples, $R^4$ is i-butyl-amino. In some examples, $R^4$ is t-butyl-amino. In some examples, $R^4$ is pentyl-amino. In some examples, $R^4$ is hexyl-amino. In some examples, $R^4$ is heptyl-amino. In some examples, $R^4$ is octyl-amino. In some examples, $R^4$ is nonyl-amino.

In some examples, $R^4$ is

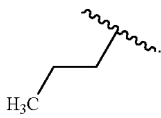

In some examples, $R^4$ is

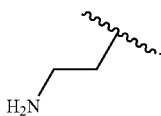

In some examples, $R^4$ is

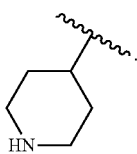 [SMILES: *C1CCNCC1]

In some examples, $R^4$ is

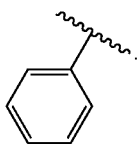 [SMILES: *c1ccccc1]

In some examples, herein, $R^a$ and $R^b$ are, independently in each instance, selected from H and alkyl. In some examples, both $R^a$ and $R^b$ are H. In some examples, both $R^a$ and $R^b$ are methyl. In some examples, both $R^a$ and $R^b$ are ethyl. In some examples, both $R^a$ and $R^b$ are propyl. In some examples, one of $R^a$ or $R^b$ is —H and the other is alkyl. In some examples, one of $R^a$ or $R^b$ is —H and the other is methyl. In some examples, one of $R^a$ or $R^b$ is —H and the other is ethyl. In some examples, one of $R^a$ or $R^b$ is —H and the other is propyl.

In some examples, n is an integer from 0-19. In some examples, n is 0. In some other examples, n is 1. In certain examples, n is 2. In some other examples, n is 3. In certain examples, n is 4. In some examples, n is 5. In some other examples, n is 6. In certain examples, n is 7. In some other examples, n is 8. In certain examples, n is 9. In some examples, n is 10. In some other examples, n is 11. In certain examples, n is 12. In some other examples, n is 13. In certain examples, n is 14. In some examples, n is 15. In some other examples, n is 16. In certain examples, n is 17. In some other examples, n is 18. In certain examples, n is 19.

In some examples, in Formula (I), $R^3$ is not —OH when $R^1$ is —OH.

In some examples, in Formula (I), $R^3$ is not —OH when $R^1$ and $R^2$ together form

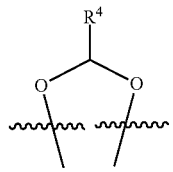

wherein $R^4$ is a $C_{1-9}$alkyl or 4-(dimethyl-amino)-phenyl.

In some examples, set forth herein is a compound of Formula (I), wherein $R^1$ and $R^2$ together form

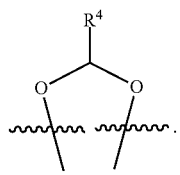

In some of these examples, $R^4$ is alkyl, aryl, arylalkyl, or a N-containing heterocycloalkyl. In certain examples, alkyl, aryl, heteroaryl, arylalkyl, or N-containing heterocycloalkyl are optionally substituted with —$NR^aR^b$. In some of these examples, $R^4$ is alkyl. In some of these examples, $R^4$ is aryl. In some of these examples, $R^4$ is arylalkyl. In some of these examples, $R^4$ is N-containing heterocycloalkyl. In some examples, $R^4$ is alkyl such as, but not limited to, methyl, ethyl, propyl, butyl, pentyl, hexyl, heptyl, octyl, or nonyl. In some examples, $R^4$ is methyl. In some examples, $R^4$ is ethyl. In some examples, $R^4$ is n-propyl. In some examples, $R^4$ is i-propyl. In some examples, $R^4$ is n-butyl. In some examples, $R^4$ is i-butyl. In some examples, $R^4$ is t-butyl. In some examples, $R^4$ is sec-butyl. In some examples, $R^4$ is pentyl. In some examples, $R^4$ is hexyl. In some examples, $R^4$ is heptyl. In some examples, $R^4$ is octyl, or nonyl. In some examples, $R^4$ is aryl such as but not limited to phenyl or naphthyl. In some examples, $R^4$ is phenyl. In some examples, $R^4$ is naphthyl. In some examples, $R^4$ is heteroaryl—such as but not limited to thiophene or phenol. In some examples, $R^4$ is arylalkyl—such as but not limited to benzyl. In some examples, $R^4$ is N-containing heterocycloalkyl such as but not limited to piperidinyl. In some examples, $R^4$ is 4-amino-phenyl. In some examples, $R^4$ is 4-amino-phenyl optionally substituted with halo.

In some examples, set forth herein is a compound of Formula (I), wherein $R^1$ and $R^2$ together form

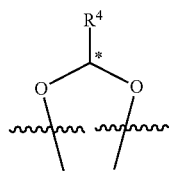

wherein $R^4$ is selected from the group consisting of alkyl, aryl, arylalkyl, and a N-containing heterocycloalkyl; and wherein alkyl, aryl, arylalkyl, or N-containing heterocycloalkyl are optionally substituted with —$NR^aR^b$; and wherein the stereochemistry of the carbon indicated by * is the R configuration.

In some examples, set forth herein is a compound of Formula (I), wherein $R^1$ and $R^2$ together form

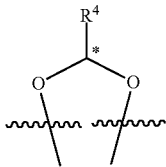

wherein $R^4$ is selected from the group consisting of alkyl, aryl, arylalkyl, and a N-containing heterocycloalkyl; and wherein alkyl, aryl, arylalkyl, or N-containing heterocycloalkyl are optionally substituted with —$NR^aR^b$; and wherein the stereochemistry of the carbon indicated by * is the S configuration.

In some examples, set forth herein is a compound of Formula (I), wherein the compound has the structure of Formula (PIa):

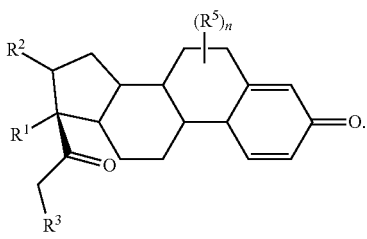

(PIa)

In some of these examples, $R^1$ and $R^2$ are, independently, selected from —H, alkyl, alkyl-C(O)—O—, —OH, and halo. In some other examples, $R^1$ and $R^2$ together form

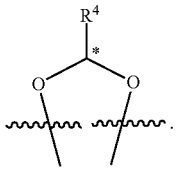

In certain examples, $R^1$ is —H. In certain other examples, $R^1$ is alkyl. In some examples, $R^1$ is alkyl-C(O)—O—. In some other examples, $R^1$ is —OH. In certain examples, $R^1$ is halo. In certain other examples, $R^1$ is —F. In some examples, $R^1$ is —Cl. In some other examples, $R^1$ is —Br. In certain examples, $R^1$ is —I. In certain other examples, $R^2$ is —OH. In some examples, $R^2$ is halo. In some other examples, $R^2$ is —F. In certain examples, $R^2$ is —Cl. In certain other examples, $R^2$ is —Br. In some examples, $R^2$ is —I.

In some examples in Formula (PIa), $R^5$ is —OH. In some examples, $R^5$ is halo such as but not limited to —F, —Cl, —Br, or —I. In some examples, $R^5$ is —F. In some examples, $R^5$ is —Cl. In some examples, $R^5$ is —Br. In some examples, $R^5$ is —I. In some examples, $R^5$ is alkyl such as, but not limited to, methyl, ethyl, propyl, butyl, pentyl, hexyl, heptyl, octyl, or nonyl.

In some examples, in Formula (PIa), $R^3$ is selected from —OH, alkyl-C(O)—O—, and $R^aR^bN$-aryloxy. In some of these examples, alkyl-C(O)—O— or $R^aR^bN$-aryloxy is optionally substituted with halo. In some examples, $R^3$ is —OH. In some examples, $R^3$ is alkyl-C(O)—O—. In some examples, $R^3$ is $R^aR^bN$-aryloxy. In some examples, $R^3$ is

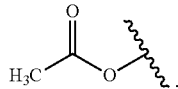

In some examples, $R^3$ is

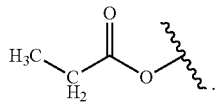

In some examples, $R^3$ is

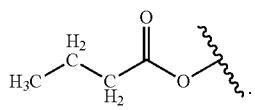

In some examples, $R^3$ is

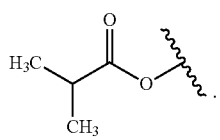

In some examples, $R^3$ is

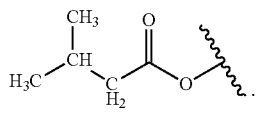

In some examples, $R^3$ is $R^aR^bN$-aryloxy. In some examples, $R^3$ is —$NR^aR^b$-aryloxy.

In some examples, in Formula (PIa), $R^4$ is selected from the group consisting of alkyl, aryl, arylalkyl, and an N-containing heterocycloalkyl. In some of these examples, alkyl, aryl, arylalkyl, or N-containing heterocycloalkyl are optionally substituted with —$NR^aR^b$. In some examples, $R^4$ is alkyl such as, but not limited to, methyl, ethyl, propyl, butyl, pentyl, hexyl, heptyl, octyl, or nonyl. In some examples, $R^4$ is methyl. In some examples, $R^4$ is ethyl. In some examples, $R^4$ is n-propyl. In some examples, $R^4$ is i-propyl. In some examples, $R^4$ is n-butyl. In some examples, $R^4$ is i-butyl. In some examples, $R^4$ is t-butyl. In some examples, $R^4$ is pentyl. In some examples, $R^4$ is hexyl. In some examples, $R^4$ is heptyl. In some examples, $R^4$ is octyl, or nonyl. In some examples, $R^4$ is aryl such as but not limited to phenyl or naphthyl. In some examples, $R^4$ is phenyl. In some examples, $R^4$ is naphthyl. In some examples, $R^4$ is arylalkyl such as but not limited to benzyl. In some examples, $R^4$ is N containing heterocycloalkyl such as but not limited to piperidinyl. In some examples, $R^4$ is 4-amino-phenyl. In some examples, $R^4$ is 4-amino-phenyl optionally substituted with halo.

In some examples, R⁴ is
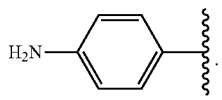
In some examples, R⁴ is
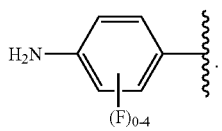
In some examples, R⁴ is
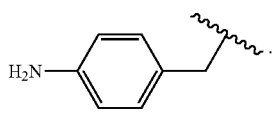
In some examples, R⁴ is
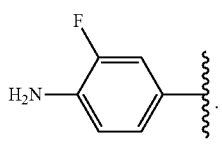
In some examples, R⁴ is
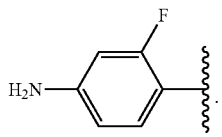
In some examples, R⁴ is
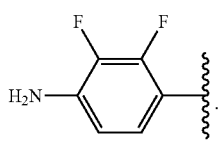
In some examples, R⁴ is
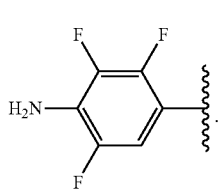
In some examples, R⁴ is
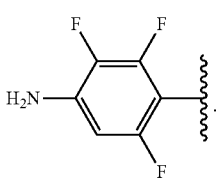
In some examples, R⁴ is
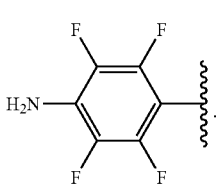
In some examples, R⁴ is
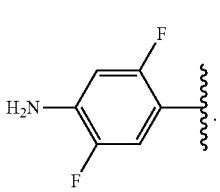
In some examples, R⁴ is
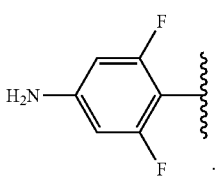
In some examples, R⁴ is
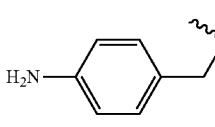
In some examples, R⁴ is
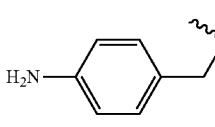
In some examples, R⁴ is
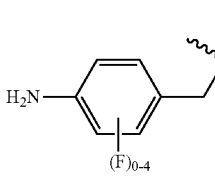

In some examples, R⁴ is
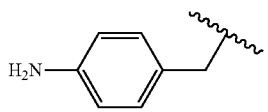
In some examples, R⁴ is
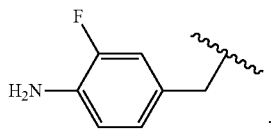
In some examples, R⁴ is
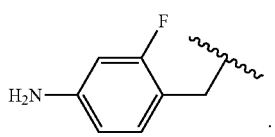
In some examples, R⁴ is
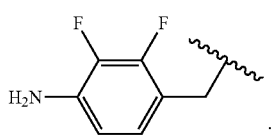
In some examples, R⁴ is
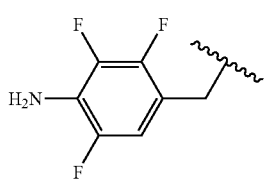
In some examples, R⁴ is
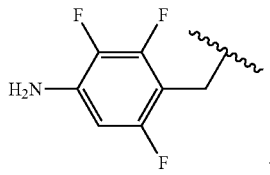
In some examples, R⁴ is
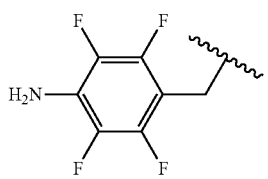
In some examples, R⁴ is
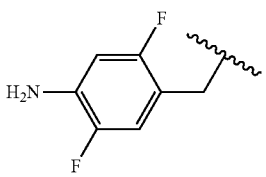
In some examples, R⁴ is
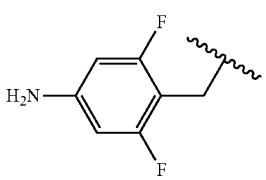
In some examples, R⁴ is
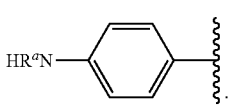
In some examples, R⁴ is
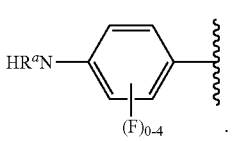
In some examples, R⁴ is
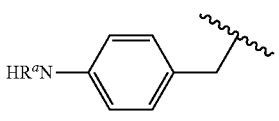
In some examples, R⁴ is
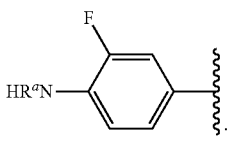
In some examples, R⁴ is
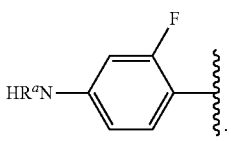
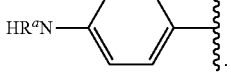

In some examples, $R^4$ is
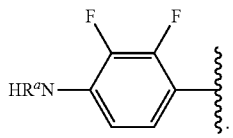
In some examples, $R^4$ is
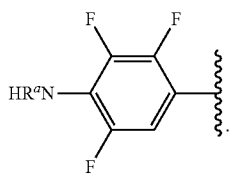
In some examples, $R^4$ is
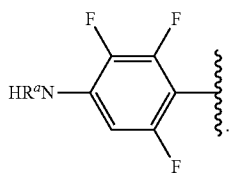
In some examples, $R^4$ is
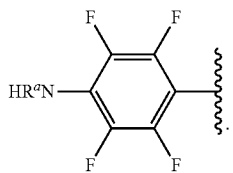
In some examples, $R^4$ is
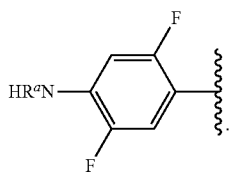
In some examples, $R^4$ is
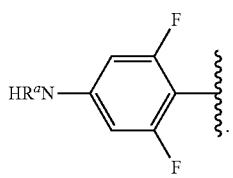
In some examples, $R^4$ is
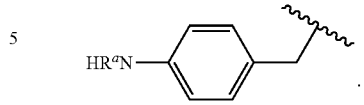
In some examples, $R^4$ is
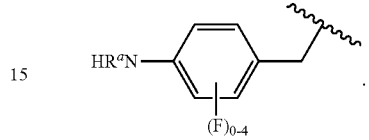
In some examples, $R^4$ is
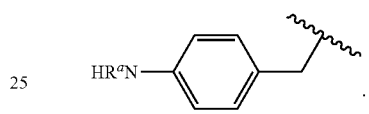
In some examples, $R^4$ is
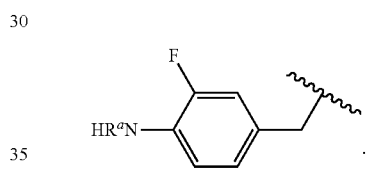
In some examples, $R^4$ is
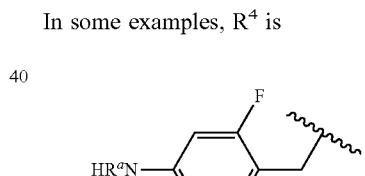
In some examples, $R^4$ is
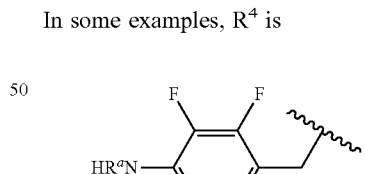
In some examples, $R^4$ is
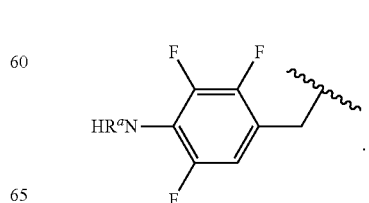

In some examples, $R^4$ is

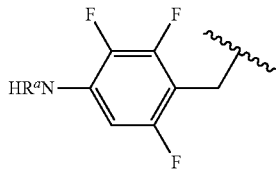

In some examples, $R^4$ is

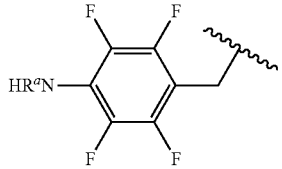

In some examples, $R^4$ is

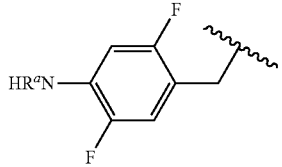

In some examples, $R^4$ is

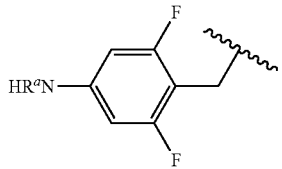

In some examples, $R^4$ is alkyl substituted with amino such as, but not limited to, methyl-amino, ethyl-amino, propyl-amino, butyl-amino, pentyl-amino, hexyl-amino, heptyl-amino, octyl-amino, or nonyl-amino. In some examples, $R^4$ is methyl-amino. In some examples, $R^4$ is ethyl-amino. In some examples, $R^4$ is n-propyl-amino. In some examples, $R^4$ is i-propyl-amino. In some examples, $R^4$ is n-butyl-amino. In some examples, $R^4$ is i-butyl-amino. In some examples, $R^4$ is t-butyl-amino. In some examples, $R^4$ is pentyl-amino. In some examples, $R^4$ is hexyl-amino. In some examples, $R^4$ is heptyl-amino. In some examples, $R^4$ is octyl-amino. In some examples, $R^4$ is nonyl-amino.

In some examples, $R^4$ is

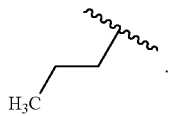

In some examples, $R^4$ is

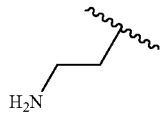

In some examples, $R^4$ is

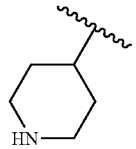

In some examples, herein, $R^a$ and $R^b$ are, independently in each instance, selected from —H or alkyl. In some examples, both $R^a$ and $R^b$ are —H. In some examples, both $R^a$ and $R^b$ are methyl. In some examples, both $R^a$ and $R^b$ are ethyl. In some examples, both $R^a$ and $R^b$ are propyl. In some examples, one of $R^a$ or $R^b$ is H and the other is alkyl. In some examples, one of $R^a$ or $R^b$ is —H and the other is methyl. In some examples, one of $R^a$ or $R^b$ is —H and the other is ethyl. In some examples, one of $R^a$ or $R^b$ is —H and the other is propyl.

In some examples, in Formula (PIa), n is an integer from 0-19. In some examples, n is 0. In some other examples, n is 1. In certain examples, n is 2. In some other examples, n is 3. In certain examples, n is 4. In some examples, n is 5. In some other examples, n is 6. In certain examples, n is 7. In some other examples, n is 8. In certain examples, n is 9. In some examples, n is 10. In some other examples, n is 11. In certain examples, n is 12. In some other examples, n is 13. In certain examples, n is 14. In some examples, n is 15. In some other examples, n is 16. In certain examples, n is 17. In some other examples, n is 18. In certain examples, n is 19.

In some examples, in Formula (PIa), $R^3$ is not —OH when $R^1$ is —OH.

In some examples, in Formula (PIa), $R^3$ is not —OH when $R^1$ and $R^2$ together form

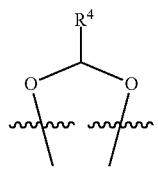

wherein $R^4$ is a $C_{1-9}$alkyl or 4-(dimethyl-amino)-phenyl. In some examples, $R^4$ is

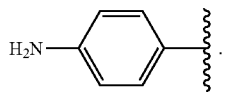

In some examples, R⁴ is

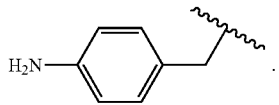

In some examples, set forth herein is a compound of Formula (PIa), wherein the compound has the structure of Formula (PIb-1) or (PIb-2):

(PIb-1)

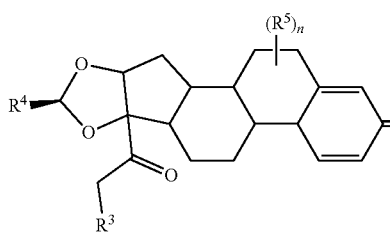

or (PIb-2)

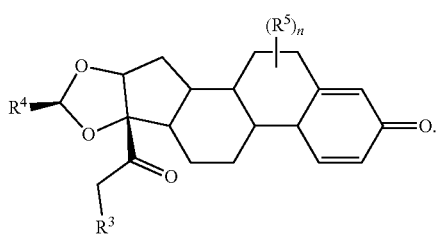

In some examples, set forth herein is a compound of Formula (PIa), wherein the compound has the structure of Formula (PIc-1) or (PIc-2):

(PIc-1)

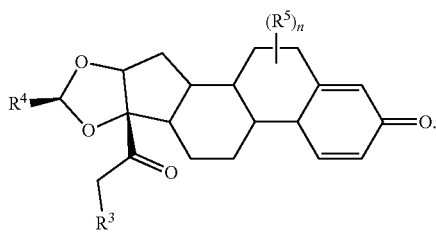

or (PIc-2)

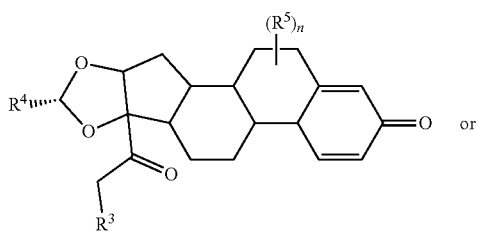

In some examples, set forth herein is a compound of Formula (PIa), wherein the compound has the structure of Formula (PId-1) or (PId-2):

(PId-1)

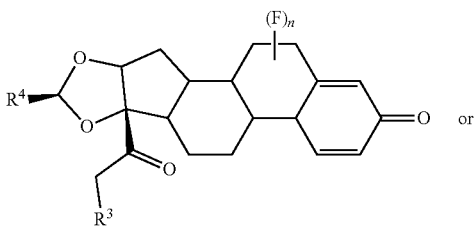

or (PId-2)

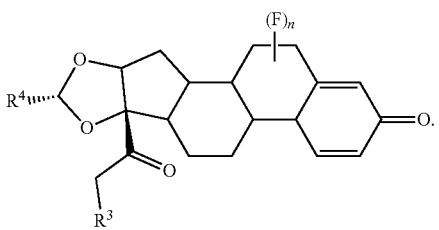

In some examples, n is 0. In some examples, n is 1. In some examples, n is 2.

In some examples, set forth herein is a compound of Formula (I), wherein the compound has the structure of Formula (PIe-1) or (PIe-2):

(PIe-1)

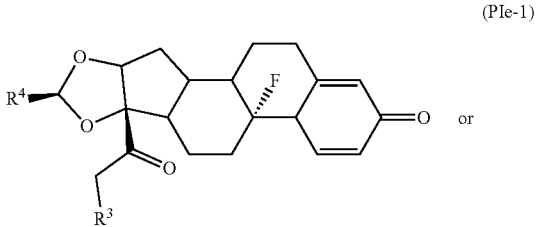

or (PIe-2)

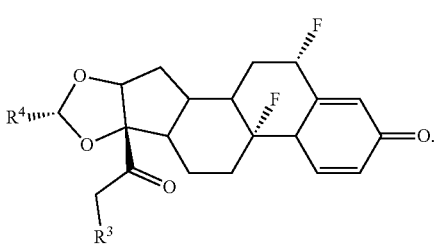

In some examples, set forth herein is a compound of Formula (PIa), (PIb-1), (PIb-2), (PIc-1), (PIc-2), (PId-1), (PId-2), (PIe-1), or (PIe-2) wherein R³ is selected from alkyl-C(O)—O— or RᵃRᵇN-aryloxy-; wherein alkyl-C(O)—O—, or RᵃRᵇN-aryloxy- are optionally substituted with halo.

In some examples, set forth herein is a compound of Formula (PIa), (PIb-1), (PIb-2), (PIc-1), (PIc-2), (PId-1), (PId-2), (PIe-1), or (PIe-2), wherein R³ is alkyl-C(O)—O— optionally substituted with halo.

In some examples, set forth herein is a compound of Formula (PIa), (PIb-1), (PIb-2), (PIc-1), (PIc-2), (PId-1), (PId-2), (PIe-1), or (PIe-2), wherein R³ is In some examples, $R^4$ is

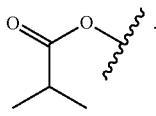

In some examples, set forth herein is a compound of Formula (PIa), (PIb-1), (PIb-2), (PIc-1), (PIc-2), (PId-1), (PId-2), (PIe-1), or (PIe-2), wherein $R^3$ is $R^aR^bN$-aryloxy- optionally substituted with halo.

In some examples, set forth herein is a compound of Formula (PIa), (PIb-1), (PIb-2), (PIc-1), (PIc-2), (PId-1), (PId-2), (PIe-1), or (PIe-2), wherein $R^3$ is

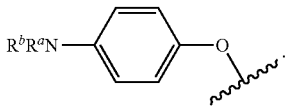

In some examples, set forth herein is a compound of Formula (PIa), (PIb-1), (PIb-2), (PIc-1), (PIc-2), (PId-1), (PId-2), (PIe-1), or (PIe-2), wherein $R^3$ is

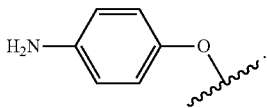

In some examples, set forth herein is a compound of Formula (PIa), (PIb-1), (PIb-2), (PIc-1), (PIc-2), (PId-1), (PId-2), (PIe-1), or (PIe-2), wherein $R^3$ is selected from —OH, alkyl-C(O)—O—, and $R^aR^bN$-aryloxy-. In some of these examples, alkyl-C(O)—O— or $R^aR^bN$-aryloxy- is optionally substituted with halo. In some examples, $R^3$ is —OH. In some examples, $R^3$ is alkyl-C(O)—O—. In some examples, $R^3$ is $R^aR^bN$-aryloxy-. In some examples, $R^3$ is

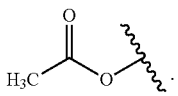

In some examples, $R^3$ is

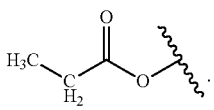

In some examples, $R^3$ is

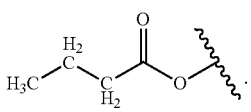

In some examples, $R^3$ is

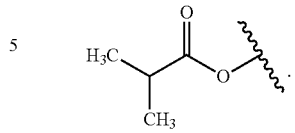

In some examples, $R^3$ is

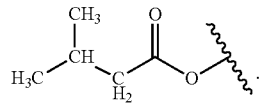

In some examples, $R^3$ is $R^aR^bN$-aryloxy-. In some examples, $R^3$ is —$NR^aR^b$-aryloxy.

In some examples, set forth herein is a compound of Formula (PIa), (PIb-1), (PIb-2), (PIc-1), (PIc-2), (PId-1), (PId-2), (PIe-1), or (PIe-2), wherein $R^3$ is $R^aR^bN$-aryloxy-, wherein $R^a$ and $R^b$ are, independently in each instance, H or alkyl.

In some examples, set forth herein is a compound of Formula (PIa), (PIb-1), (PIb-2), (PIc-1), (PIc-2), (PId-1), (PId-2), (PIe-1), or (PIe-2), wherein $R^4$ is selected from the group consisting of alkyl, aryl, arylalkyl, and an N-containing heterocycloalkyl. In some of these examples, alkyl, aryl, arylalkyl, or N-containing heterocycloalkyl are optionally substituted with —$NR^aR^b$. In some examples, $R^4$ is alkyl such as, but not limited to, methyl, ethyl, propyl, butyl, pentyl, hexyl, heptyl, octyl, or nonyl. In some examples, $R^4$ is methyl. In some examples, $R^4$ is ethyl. In some examples, $R^4$ is n-propyl. In some examples, $R^4$ is propyl. In some examples, $R^4$ is n-butyl. In some examples, $R^4$ is i-butyl. In some examples, $R^4$ is t-butyl. In some examples, $R^4$ is pentyl. In some examples, $R^4$ is hexyl. In some examples, $R^4$ is heptyl. In some examples, $R^4$ is octyl, or nonyl. In some examples, $R^4$ is aryl such as but not limited to phenyl or naphthyl. In some examples, $R^4$ is phenyl. In some examples, $R^4$ is naphthyl. In some examples, $R^4$ is arylalkyl—such as but not limited to benzyl. In some examples, $R^4$ is N-containing heterocycloalkyl such as but not limited to piperidinyl. In some examples, $R^4$ is 4-amino-phenyl. In some examples, $R^4$ is 4-amino-phenyl optionally substituted with halo.

In some examples, $R^4$ is

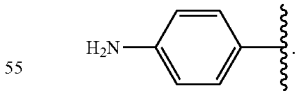

In some examples, $R^4$ is

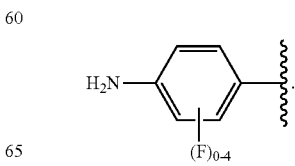

In some examples, $R^4$ is

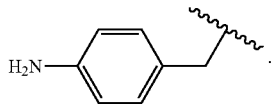

In some examples, $R^4$ is

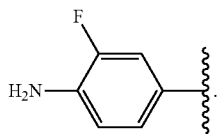 [SMILES: *c1ccc(N)c(F)c1]

In some examples, $R^4$ is

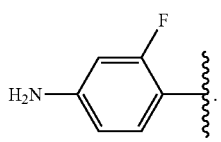 [SMILES: *c1ccc(N)cc1F]

In some examples, $R^4$ is

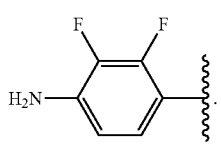 [SMILES: *c1ccc(N)c(F)c1F]

In some examples, $R^4$ is

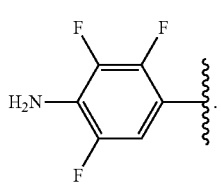

In some examples, $R^4$ is

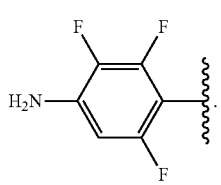

In some examples, $R^4$ is

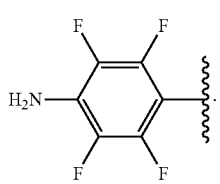

In some examples, $R^4$ is

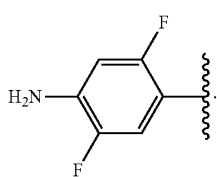

In some examples, $R^4$ is

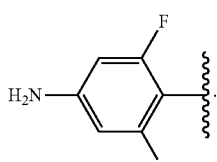

In some examples, $R^4$ is

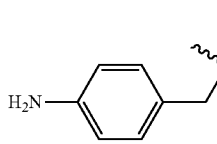

In some examples, $R^4$ is

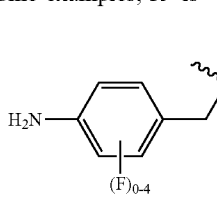

In some examples, $R^4$ is

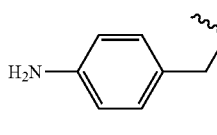

In some examples, $R^4$ is

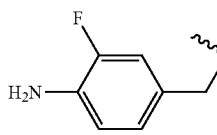

In some examples, $R^4$ is

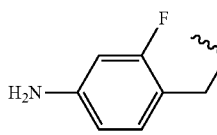

In some examples, $R^4$ is

In some examples, R⁴ is
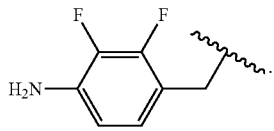
In some examples, R⁴ is
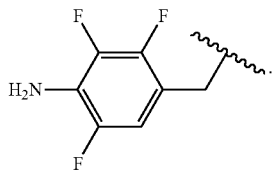
In some examples, R⁴ is
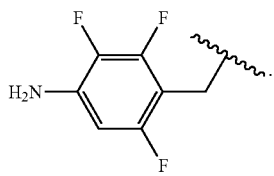
In some examples, R⁴ is
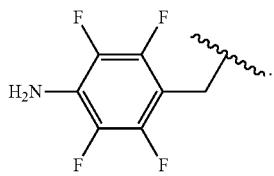
In some examples, R⁴ is
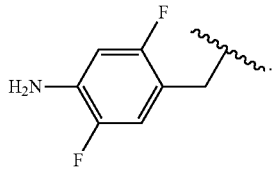
In some examples, R⁴ is
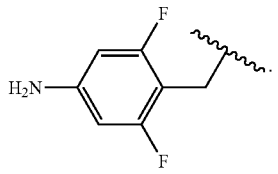
In some examples, R⁴ is
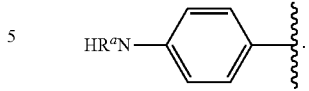
In some examples, R⁴ is
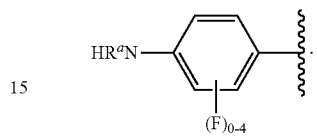
In some examples, R⁴ is
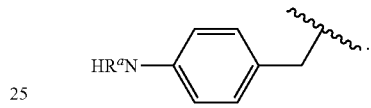
In some examples, R⁴ is
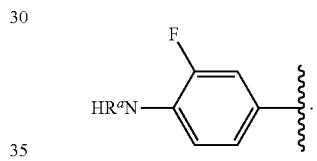
In some examples, R⁴ is
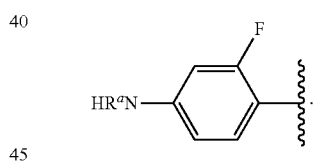
In some examples, R⁴ is
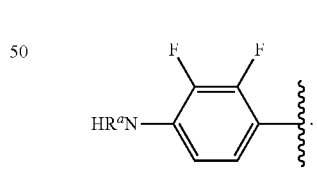
In some examples, R⁴ is
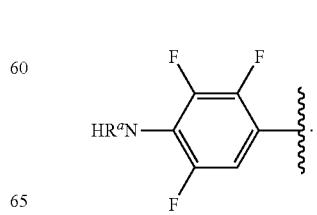

In some examples, R⁴ is
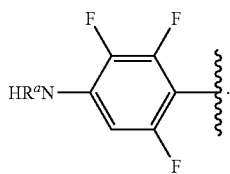
In some examples, R⁴ is
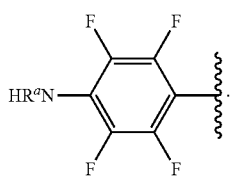
In some examples, R⁴ is
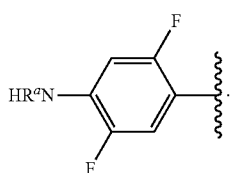
In some examples, R⁴ is
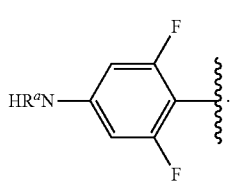
In some examples, R⁴ is
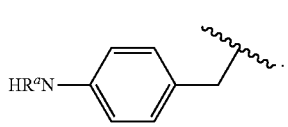
In some examples, R⁴ is
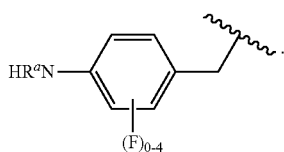
In some examples, R⁴ is
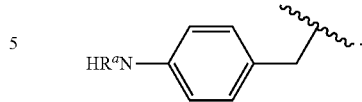
In some examples, R⁴ is
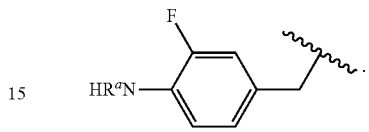
In some examples, R⁴ is
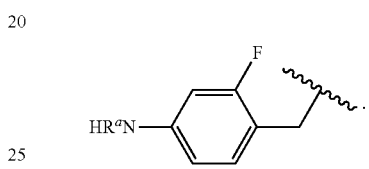
In some examples, R⁴ is
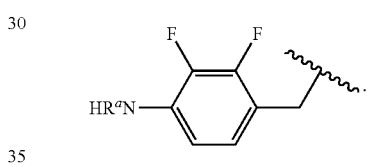
In some examples, R⁴ is
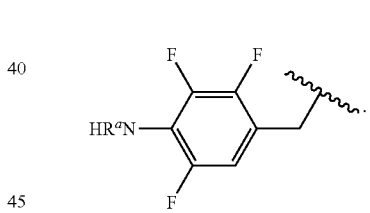
In some examples, R⁴ is
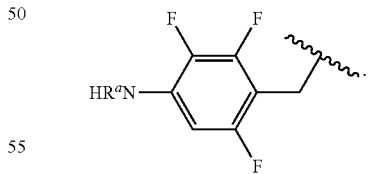
In some examples, R⁴ is
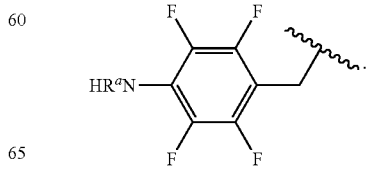

In some examples, $R^4$ is

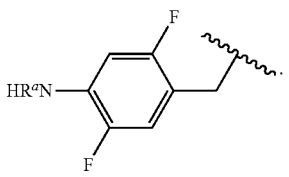

In some examples, $R^4$ is

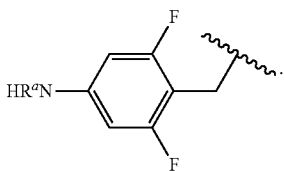

In some examples, set forth herein is a compound of Formula (PIa), (PIb-1), (PIb-2), (PIc-1), (PIc-2), (PId-1), (PId-2), (PIe-1), or (PIe-2), wherein $R^4$ is alkyl substituted with amino such as, but not limited to, methyl-amino, ethyl-amino, propyl-amino, butyl-amino, pentyl-amino, hexyl-amino, heptyl-amino, octyl-amino, or nonyl-amino. In some examples, $R^4$ is methyl-amino. In some examples, $R^4$ is ethyl-amino. In some examples, $R^4$ is n-propyl-amino. In some examples, $R^4$ is i-propyl-amino. In some examples, $R^4$ is n-butyl-amino. In some examples, $R^4$ is i-butyl-amino. In some examples, $R^4$ is t-butyl-amino. In some examples, $R^4$ is pentyl-amino. In some examples, $R^4$ is hexyl-amino. In some examples, $R^4$ is heptyl-amino. In some examples, $R^4$ is octyl-amino. In some examples, $R^4$ is nonyl-amino.

In some examples, $R^4$ is

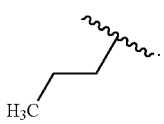

In some examples, $R^4$ is

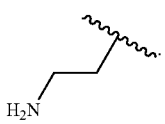

In some examples, $R^4$ is

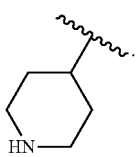

The compound of Formula (I) is not one of the following compounds:

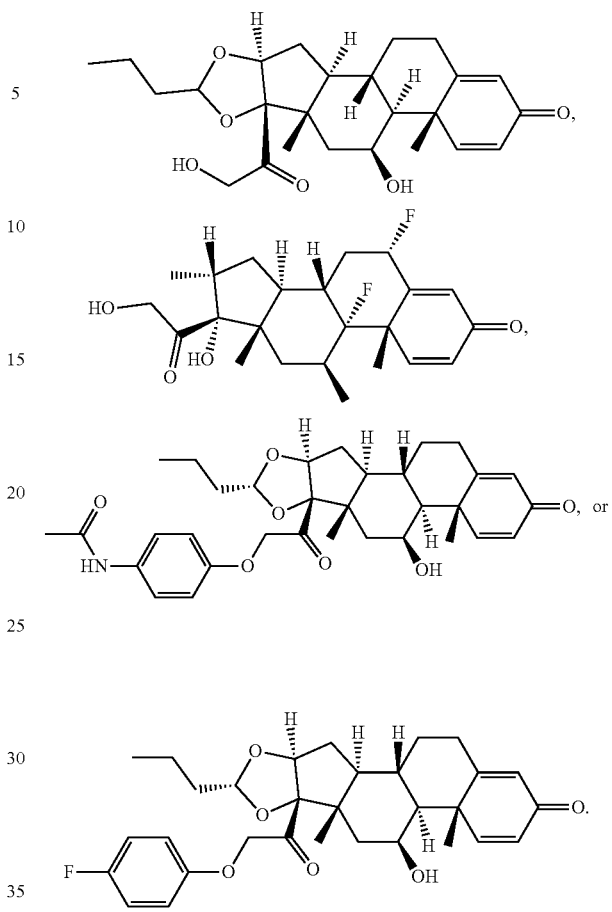

In some examples, set forth herein is a compound of Formula (I), wherein the compound has the structure of Formula (PII):

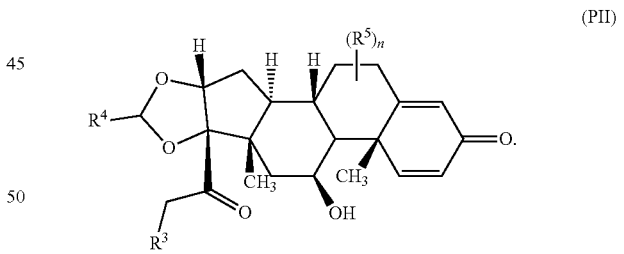

In Formula (PII), $R^3$ is selected from —OH, alkyl-C(O)—O—, or $R^aR^bN$-aryloxy. In some of these examples, alkyl-C(O)—O— or $R^aR^bN$-aryloxy is optionally substituted with halo. In some examples, $R^3$ is —OH. In some examples, $R^3$ is alkyl-C(O)—O—. In some examples, $R^3$ is $R^aR^bN$-aryloxy-. In some examples, $R^3$ is

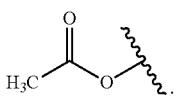

In some examples, $R^3$ is

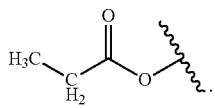

In some examples, $R^3$ is

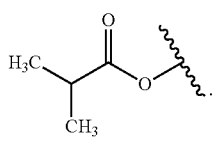

In some examples, $R^3$ is

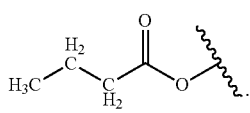

In some examples, $R^3$ is

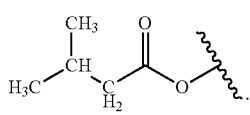

In some examples, $R^3$ is $R^aR^b$N-aryloxy-.

In some examples, in Formula (PII), $R^4$ is selected from the group consisting of alkyl, aryl, arylalkyl, and an N-containing heterocycloalkyl. In some of these examples, alkyl, aryl, arylalkyl, or N-containing heterocycloalkyl are optionally substituted with —$NR^aR^b$. In some examples, $R^4$ is alkyl such as, but not limited to, methyl, ethyl, propyl, butyl, pentyl, hexyl, heptyl, octyl, or nonyl. In examples, $R^4$ is methyl. In some examples, $R^4$ is ethyl. In some examples, $R^4$ is n-propyl. In some examples, $R^4$ is i-propyl. In some examples, $R^4$ is n-butyl. In some examples, $R^4$ is i-butyl. In some examples, $R^4$ is t-butyl. In some examples, $R^4$ is sec-butyl. In some examples, $R^4$ is pentyl. In some examples, $R^4$ is hexyl. In some examples, $R^4$ is heptyl. In some examples, $R^4$ is octyl, or nonyl. In some examples, $R^4$ is aryl such as but not limited to phenyl or naphthyl. In some examples, $R^4$ is phenyl. In some examples, $R^4$ is naphthyl. In some examples, $R^4$ is arylalkyl—such as but not limited to benzyl. In some examples, $R^4$ is N-containing heterocycloalkyl such as but not limited to piperidinyl. In some examples, $R^4$ is 4-amino-phenyl. In some examples, $R^4$ is 4-aminophenyl optionally substituted with halo.

In some examples, $R^4$ is

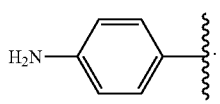

In some examples, $R^4$ is

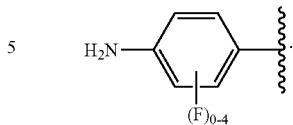

In some examples, $R^4$ is

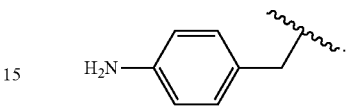

In some examples, $R^4$ is

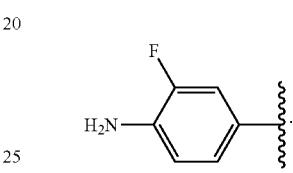

In some examples, $R^4$ is

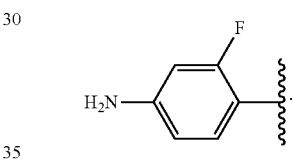

In some examples, $R^4$ is

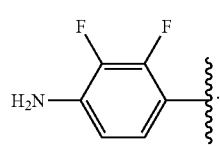

In some examples, $R^4$ is

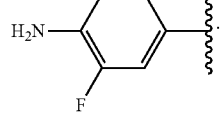

In some examples, $R^4$ is

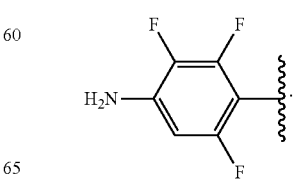

In some examples, $R^4$ is

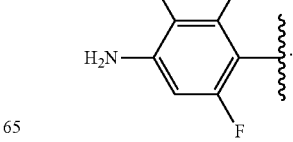

In some examples, $R^4$ is
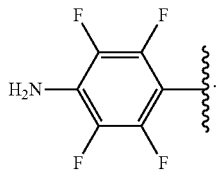 [SMILES: *c1c(F)c(F)c(N)c(F)c1F]
In some examples, $R^4$ is
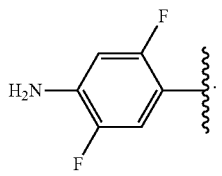
In some examples, $R^4$ is
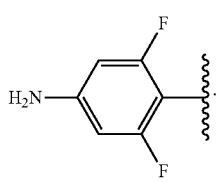 [SMILES: *c1c(F)cc(N)cc1F]
In some examples, $R^4$ is
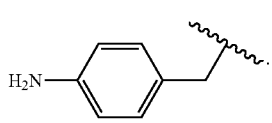
In some examples, $R^4$ is
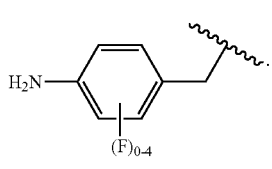
In some examples, $R^4$ is
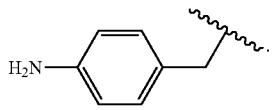 [SMILES: *Cc1ccc(N)cc1]
In some examples, $R^4$ is
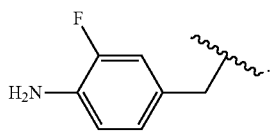
In some examples, $R^4$ is
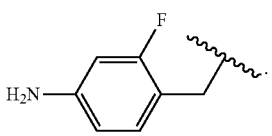 [SMILES: *Cc1ccc(N)cc1F]
In some examples, $R^4$ is
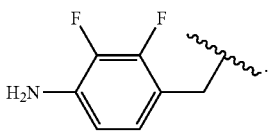 [SMILES: *Cc1ccc(N)c(F)c1F]
In some examples, $R^4$ is
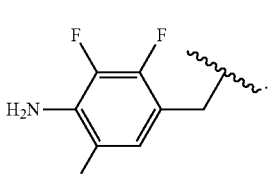
In some examples, $R^4$ is
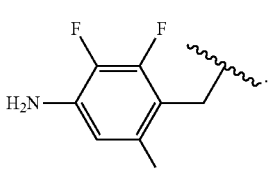
In some examples, $R^4$ is
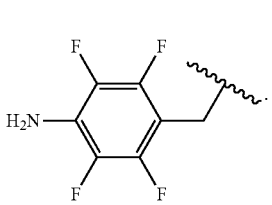 [SMILES: *Cc1c(F)c(F)c(N)c(F)c1F]
In some examples, $R^4$ is
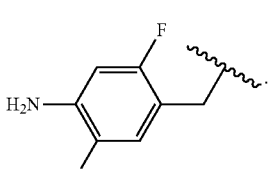

In some examples, R⁴ is
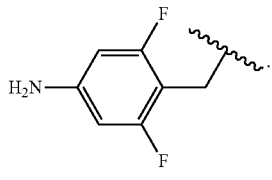 [SMILES: *Cc1c(F)cc(N)cc1F]
In some examples, R⁴ is
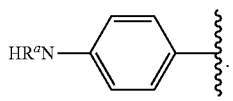
In some examples, R⁴ is
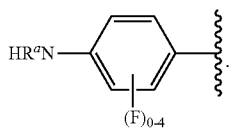
In some examples, R⁴ is
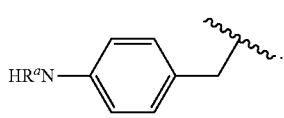
In some examples, R⁴ is
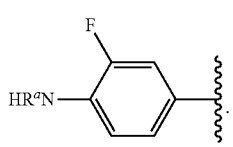
In some examples, R⁴ is
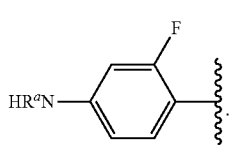
In some examples, R⁴ is
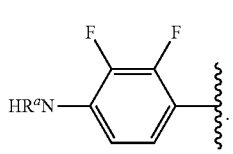
In some examples, R⁴ is
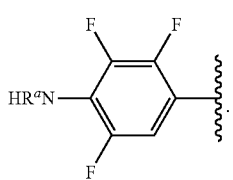
In some examples, R⁴ is
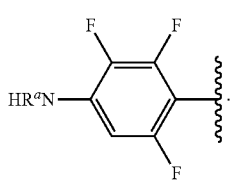
In some examples, R⁴ is
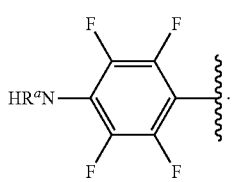
In some examples, R⁴ is
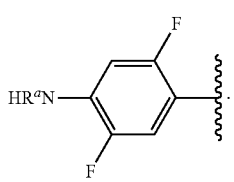
In some examples, R⁴ is
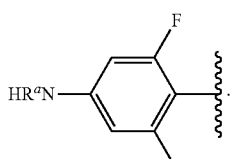
In some examples, R⁴ is
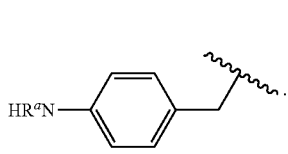

In some examples, $R^4$ is

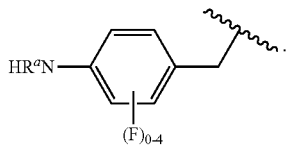

In some examples, $R^4$ is

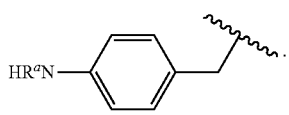

In some examples, $R^4$ is

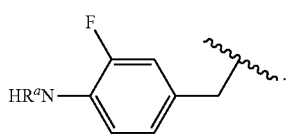

In some examples, $R^4$ is

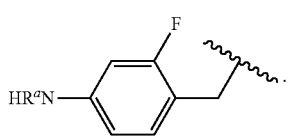

In some examples, $R^4$ is

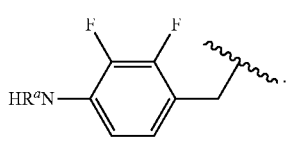

In some examples, $R^4$ is

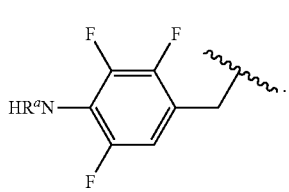

In some examples, $R^4$ is

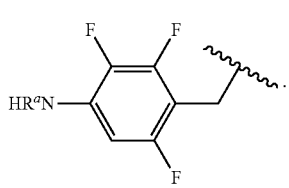

In some examples, $R^4$ is

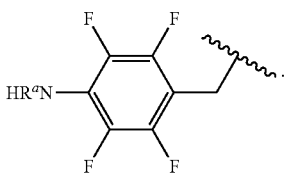

In some examples, $R^4$ is

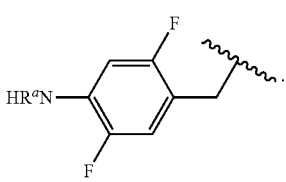

In some examples, $R^4$ is

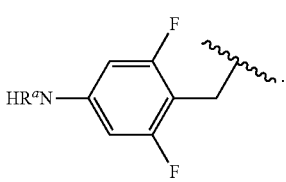

In some examples, $R^4$ is alkyl substituted with amino such as, but not limited to, methyl-amino, ethyl-amino, propyl-amino, butyl-amino, pentyl-amino, hexyl-amino, heptyl-amino, octyl-amino, or nonyl-amino. In some examples, $R^4$ is methyl-amino. In some examples, $R^4$ is ethyl-amino. In some examples, $R^4$ is n-propyl-amino. In some examples, $R^4$ is i-propyl-amino. In some examples, $R^4$ is n-butyl-amino. In some examples, $R^4$ is i-butyl-amino. In some examples, $R^4$ is t-butyl-amino. In some examples, $R^4$ is pentyl-amino. In some examples, $R^4$ is hexyl-amino. In some examples, $R^4$ is heptyl-amino. In some examples, $R^4$ is octyl-amino. In some examples, $R^4$ is nonyl-amino.

In some examples, $R^4$ is

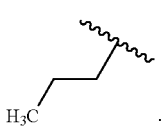

In some examples, $R^4$ is

In some examples, R⁴ is

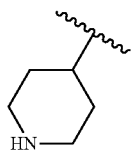

In some examples, herein, $R^a$ and $R^b$ are, independently in each instance, selected from H or alkyl. In some examples, both $R^a$ and $R^b$ are —H. In some examples, both $R^a$ and $R^b$ are methyl. In some examples, both $R^a$ and $R^b$ are ethyl. In some examples, both $R^a$ and $R^b$ are propyl. In some examples, one of $R^a$ or $R^b$ is H and the other is alkyl. In some examples, one of $R^a$ or $R^b$ is —H and the other is methyl. In some examples, one of $R^a$ or $R^b$ is —H and the other is ethyl. In some examples, one of $R^a$ or $R^b$ is —H and the other is propyl.

In some examples, in Formula (PII), n is an integer from 0-19. In some examples, n is 0. In some other examples, n is 1. In certain examples, n is 2. In some other examples, n is 3. In certain examples, n is 4. In some examples, n is 5. In some other examples, n is 6. In certain examples, n is 7. In some other examples, n is 8. In certain examples, n is 9. In some examples, n is 10. In some other examples, n is 11. In certain examples, n is 12. In some other examples, n is 13. In certain examples, n is 14. In some examples, n is 15. In some other examples, n is 16. In certain examples, n is 17. In some other examples, n is 18. In certain examples, n is 19.

In some examples, set forth herein is a compound of Formula (I), wherein the compound has the structure of Formula (PIIa) or (PIIb):

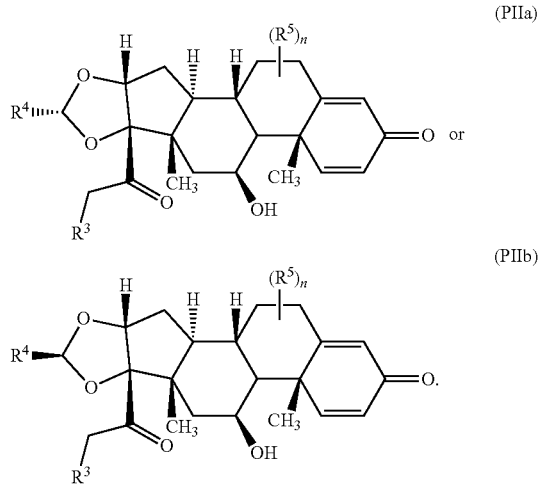

In some examples, set forth herein is a compound of Formula (PIIa) or (PIIb), wherein R⁴ is selected from 4-amino-phenyl, 4-amino-1-methyl-phenyl, 2-amino-ethyl, piperidinyl, or propyl. In some examples, R⁴ is 4-amino-phenyl. In some examples, R⁴ is 4-amino-1-methyl-phenyl. In some examples, R⁴ is 2-amino-ethyl. In some examples, R⁴ is piperidinyl. In some examples, R⁴ is propyl. In some examples, R⁴ is n-propyl. In some examples, R⁴ is i-propyl.

In some examples, set forth herein is a compound of Formula (PIIa) or (PIIb), wherein R³ is selected from alkyl-C(O)—O— or $R^aR^bN$-aryloxy; wherein alkyl-C(O)—O—, or $R^aR^bN$-aryloxy are optionally substituted with halo.

In some examples, set forth herein is a compound of Formula (PIIa) or (PIIb), wherein R³ is

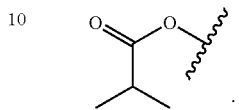

In some examples, set forth herein is a compound of Formula (PIIa) or (PIIb), wherein R³ is

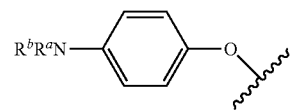

In some examples, set forth herein is a compound of Formula (PIIa) or (PIIb), wherein R³ is

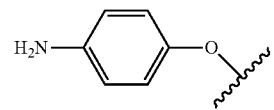

In some examples, set forth herein is a compound of Formula (PIIa) or (PIIb), wherein the compound has the structure of Formula (PIII):

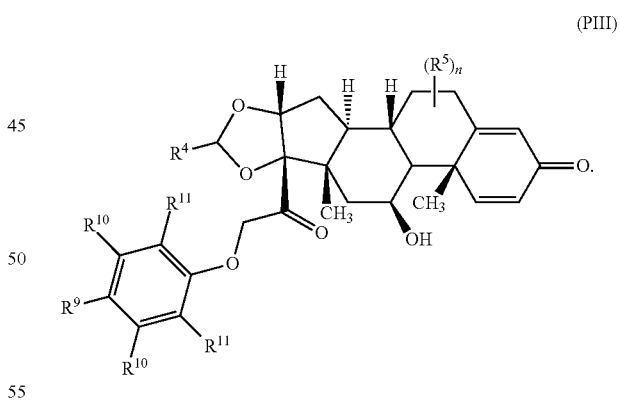

In Formula (PIII), R⁹ is selected from H or —$NR^aR^b$. In some examples, R⁹ is H. In some other examples, R⁹ is —$NR^aR^b$. R⁴, R⁴, and subscript n are defined as in Formula I and noted above.

In Formula (PIII), R¹⁰ and R¹¹, are each, independently in each instance, selected from H, F, or —$NR^aR^b$.

In some examples, set forth herein is a compound of Formula (III), wherein the compound has the structure of Formula (PIIIa) or (PIIIb):

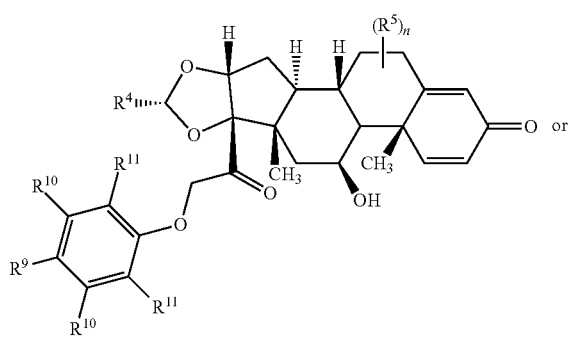

(PIIIa)

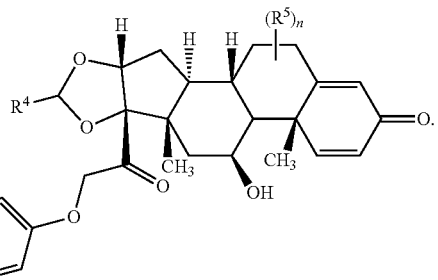

(PV)

In Formula (PV), $R^4$, $R^4$, and subscript n are defined as in Formula I and noted above.

In some examples, set forth herein is a compound of Formula (PV), wherein the compound has the structure of Formula (PVa) or (PVb):

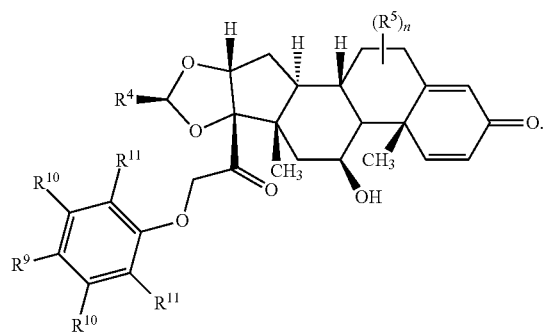

(PIIIb)

(PVa)

(PVb)

In some examples, set forth herein is a compound of Formula (I), wherein the compound has the structure of Formula (PIV):

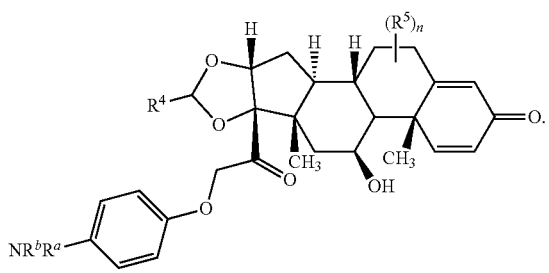

(PIV)

In some examples, set forth herein is a compound of Formula (I), wherein the compound has the structure of Formula (PVI):

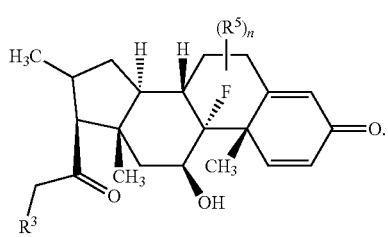

(PVI)

In Formula (PIV), —$NR^aR^b$, $R^4$, $R^5$, and subscript n are defined as in Formula I and noted above.

In some examples, set forth herein is a compound of Formula (I), wherein the compound has the structure of Formula (PV):

In Formula (PVI) $R^3$ is selected from alkyl-C(O)—O— or $R^aR^b$N-aryloxy, wherein alkyl-C(O)—O—, or —$NR^aR^b$-aryloxy are optionally substituted with halo.

In some examples, in Formula (PVI), $R^4$ is selected from —H, —OH, halo, or alkyl. In some examples, $R^4$ is halo such as but not limited to —F, —Cl, —Br, or —I. In some examples, R⁴ is —F. In some examples, R⁴ is —Cl. In some examples, R⁴ is —Br. In some examples, R⁴ is —I. In some examples, R⁴ is alkyl such as, but not limited to, methyl, ethyl, propyl, butyl, pentyl, hexyl, heptyl, octyl, or nonyl. Subscript n is an integer from 0-19. In some examples, n is 0. In some other examples, n is 1. In certain examples, n is 2. In some other examples, n is 3. In certain examples, n is 4. In some examples, n is 5. In some other examples, n is 6. In certain examples, n is 7. In some other examples, n is 8. In certain examples, n is 9. In some examples, n is 10. In some other examples, n is 11. In certain examples, n is 12. In some other examples, n is 13. In certain examples, n is 14. In some examples, n is 15. In some other examples, n is 16. In certain examples, n is 17. In some other examples, n is 18. In certain examples, n is 19.

In some examples, in Formula (PVI), R³ is selected from —OH, alkyl-C(O)—O—, —NR$^a$R$^b$, or NR$^a$R$^b$-aryloxy. In some of these examples, alkyl-C(O)—O— or R$^a$R$^b$N-aryloxy is optionally substituted with halo. In some examples, R³ is —OH. In some examples, R³ is alkyl C(O)—O—. In some examples, R³ is R$^a$R$^b$N-aryloxy.

In some examples, R³ is —NR$^a$R$^b$. In some examples, R³ is —NH₂. In some examples, R³ is —NH(CH₃).

In some examples, R³ is R$^a$R$^b$N-aryloxy.

In some examples, R³ is

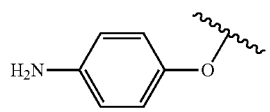

In some examples, R³ is

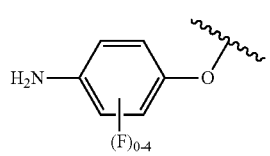

In some examples, R³ is

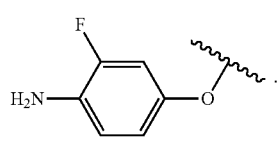

In some examples, R³ is

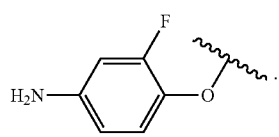

In some examples, R³ is

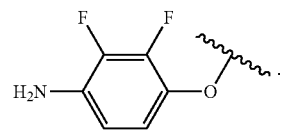

In some examples, R³ is

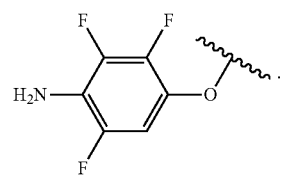

In some examples, R³ is

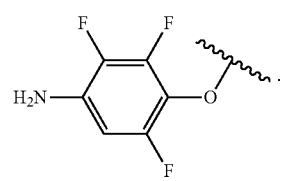

In some examples, R³ is

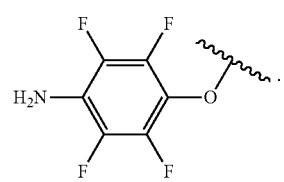

In some examples, R³ is

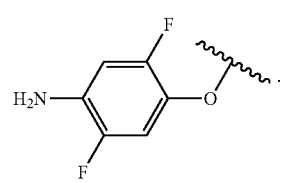 [SMILES: *Oc1cc(F)c(N)cc1F]

In some examples, R³ is

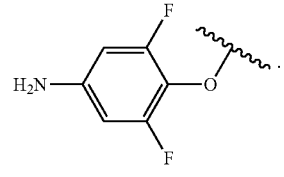 [SMILES: *Oc1c(F)cc(N)cc1F]

In some examples, $R^3$ is

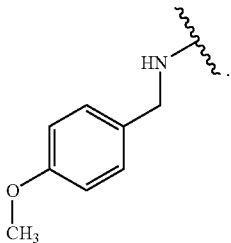 [SMILES: *NCc1ccc(OC)cc1]

In some examples, set forth herein is a compound of Formula (I), wherein the compound has the structure of Formula (PVII):

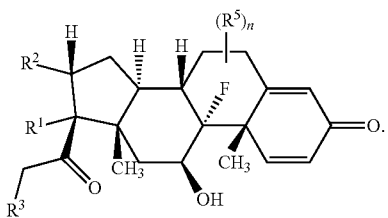

(PVII)

In Formula (PVII) $R^3$ is selected from alkyl-C(O)—O— or $R^aR^bN$-aryloxy, wherein alkyl-C(O)—O—, or $R^aR^bN$-aryloxy are optionally substituted with halo.

In some examples, in Formula (PVII), $R^4$ is selected from —H, —OH, halo, or alkyl. In some examples, $R^4$ is halo such as but not limited to —F, —Cl, —Br, or —I. In some examples, $R^4$ is —F. In some examples, $R^4$ is —Cl. In some examples, $R^4$ is —Br. In some examples, $R^4$ is —I. In some examples, $R^4$ is alkyl such as, but not limited to, methyl, ethyl, propyl, butyl, pentyl, hexyl, heptyl, octyl, or nonyl. Subscript n is an integer from 0-19. In some examples, n is 0. In some other examples, n is 1. In certain examples, n is 2. In some other examples, n is 3. In certain examples, n is 4. In some examples, n is 5. In some other examples, n is 6. In certain examples, n is 7. In some other examples, n is 8. In certain examples, n is 9. In some examples, n is 10. In some other examples, n is 11. In certain examples, n is 12. In some other examples, n is 13. In certain examples, n is 14. In some examples, n is 15. In some other examples, n is 16. In certain examples, n is 17. In some other examples, n is 18. In certain examples, n is 19. In some examples, in Formula (PVII), $R^3$ is selected from —OH, alkyl-C(O)—O—, —$NR^aR^b$, or $R^aR^bN$-aryloxy. In some of these examples, alkyl-C(O)—O— or $NR^aR^b$-aryloxy is optionally substituted with halo. In some examples, $R^3$ is —OH. In some examples, $R^3$ is alkyl-C(O)—O—. In some examples, $R^3$ is $R^aR^bN$-aryloxy.

In some examples, $R^3$ is —$NR^aR^b$. In some examples, $R^3$ is —$NH_2$. In some examples, $R^3$ is —$NH(CH_3)$.

In some examples, $R^3$ is $R^aR^bN$-aryloxy-.

In some examples, $R^3$ is

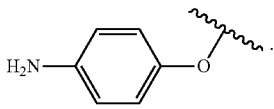

In some examples, $R^3$ is

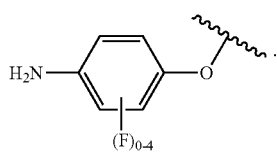

In some examples, $R^3$ is

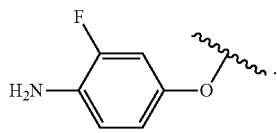

In some examples, $R^3$ is

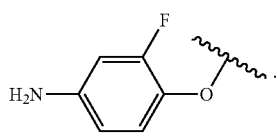

In some examples, $R^3$ is

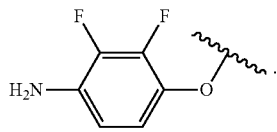

In some examples, $R^3$ is

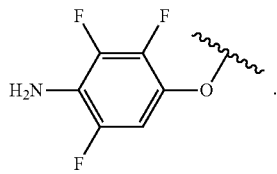 [SMILES: *Oc1cc(F)c(N)c(F)c1F]

In some examples, $R^3$ is

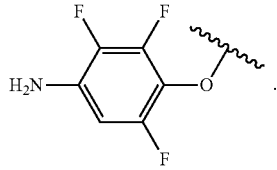 [SMILES: *Oc1c(F)cc(N)c(F)c1F]

In some examples, R³ is

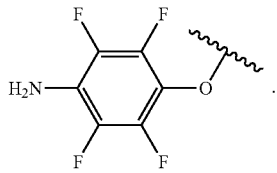

In some examples, R³ is

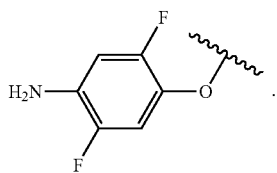

In some examples, R³ is

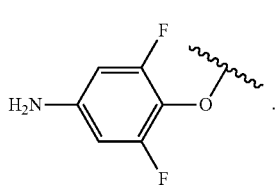 [SMILES: *Oc1c(F)cc(N)cc1F]

In some examples, R³ is

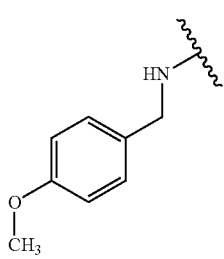

In some examples, set forth herein is a compound of Formula (PVII), wherein the compound has the structure of Formula (PVIIa):

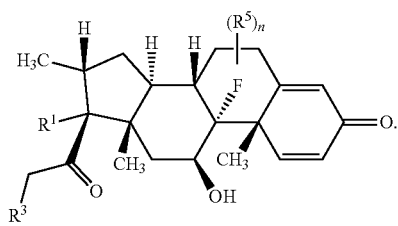
(PVIIa)

In some examples, set forth herein is a compound of Formula (PVII), wherein the compound has the structure of Formula (PVIIb):

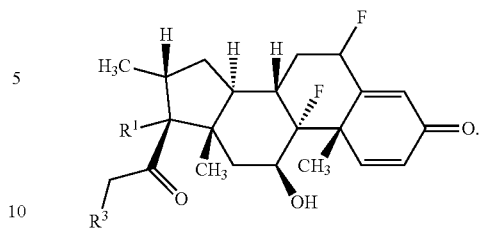
(PVIIb)

In some examples, set forth herein is a compound of Formula (PVII), (PVIIa), or (PVIIb), wherein R³ is

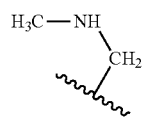

or $R^aR^bN$-aryloxy- optionally substituted with halo.

In some examples, set forth herein is a compound of Formula (PVII), (PVIIa), or (PVIIb), wherein R³ is

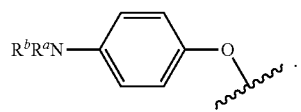

In some examples, set forth herein is a compound of Formula (PVII), (PVIIa), or (PVIIb), wherein R³ is

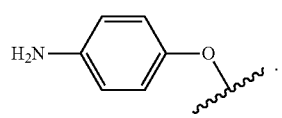

In some examples, set forth herein is a compound of Formula (PVII), wherein the compound has the structure of Formula (PVIIb-1) or (PVIIb-2):

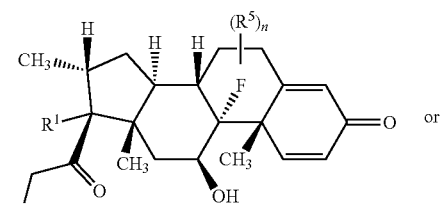
(PVIIb-1)

or

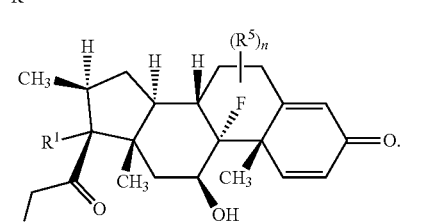
(PVIIb-2)

In some examples, set forth herein is a compound of Formula (PVII), (PVIIa), (PVIIb), (PVIIb-1), or (PVIIb-2), wherein $R^3$ is alkyl-C(O)—O— or $R^aR^b$N-aryloxy.

In some examples, set forth herein is a compound of Formula (I), wherein the compound has the structure of Formula (PVIII):

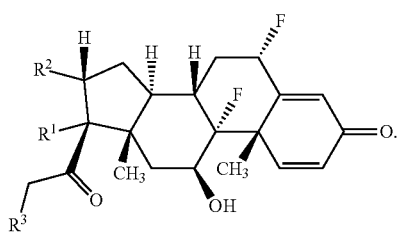

(PVIII)

In some examples, of any of the Formula (PI), (PIa), (PIb-1), (PIb-2), (PIc-1), (PIc-2), (PId-1), (PId-2), (PIe-1), (PIe-2), (PII), (PIIa), (PIIb), (PIIIa), (PIIIb), (PIV), (PV), (PVa), (PVb), (PVI), (PVII), (PVIIa), (PVIIb), (PVIIb-1), or (PVIIb-2), wherein halo, when present, is fluoro.

In some examples of the compound of Formula (I), $R^1$ and $R^2$ are, independently, selected from —H, alkyl, alkyl-C(O)—O—, —OH, or halo. In some other examples, $R^1$ and $R^2$ together form

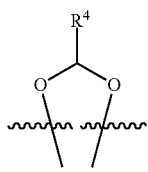

In certain examples, $R^1$ is —H. In certain other examples, $R^1$ is alkyl. In some examples, $R^1$ is alkyl-C(O)—O—. In some other examples, $R^1$ is —OH. In certain examples, $R^1$ is halo. In certain other examples, $R^1$ is —F. In some examples, $R^1$ is —Cl. In some other examples, $R^1$ is —Br. In certain examples, $R^1$ is —I. In certain other examples, $R^2$ is —OH. In some examples, $R^2$ is halo. In some other examples, $R^2$ is —F. In certain examples, $R^2$ is —Cl. In certain other examples, $R^2$ is —Br. In some examples, $R^2$ is —I.

In some examples, in Formula (I), $R^5$ is, independently in each instance, selected from —OH, halo, alkyl, or arylalkyl. In some examples, $R^5$ is —OH. In some examples, $R^5$ is halo such as but not limited to —F, —Cl, —Br, or —I. In some examples, $R^5$ is —F. In some examples, $R^5$ is —Cl. In some examples, $R^5$ is —Br. In some examples, $R^5$ is —I. In some examples, $R^5$ is alkyl such as, but not limited to, methyl, ethyl, propyl, butyl, pentyl, hexyl, heptyl, octyl, or nonyl. In some examples, $R^5$ is benzyl.

In some examples, in Formula (I), $R^4$ is selected from the group consisting of alkyl, aryl, arylalkyl, and an N-containing heterocycloalkyl. In some of these examples, alkyl, aryl, arylalkyl, or N-containing heterocycloalkyl are optionally substituted with —$NR^aR^b$. In some examples, $R^4$ is alkyl such as, but not limited to, methyl, ethyl, propyl, butyl, pentyl, hexyl, heptyl, octyl, or nonyl. In some examples, $R^4$ is methyl. In some examples, $R^4$ is ethyl. In some examples, $R^4$ is n-propyl. In some examples, $R^4$ is i-propyl. In some examples, $R^4$ is n-butyl. In some examples, $R^4$ is i-butyl. In some examples, $R^4$ is t-butyl. In some examples, $R^4$ is sec-butyl. In some examples, $R^4$ is pentyl. In some examples, $R^4$ is hexyl. In some examples, $R^4$ is heptyl. In some examples, $R^4$ is octyl, or nonyl. In some examples, $R^4$ is aryl such as but not limited to phenyl or naphthyl. In some examples, $R^4$ is phenyl. In some examples, $R^4$ is naphthyl. In some examples, $R^4$ is arylalkyl—such as but not limited to benzyl. In some examples, $R^4$ is N-containing heterocycloalkyl such as but not limited to piperidinyl. In some examples, $R^4$ is 4-amino-phenyl. In some examples, $R^4$ is 4-aminophenyl optionally substituted with halo.

In some examples, $R^4$ is

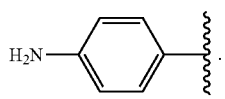

In some examples, $R^4$ is

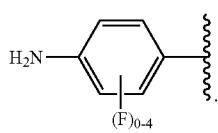

In some examples, $R^4$ is

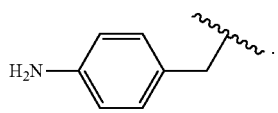

In some examples, $R^4$ is

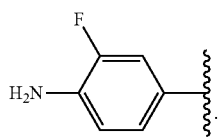 [SMILES: *c1ccc(N)c(F)c1]

In some examples, $R^4$ is

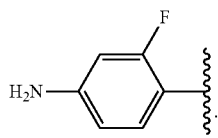 [SMILES: *c1ccc(N)cc1F]

In some examples, $R^4$ is

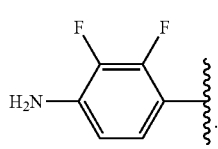 [SMILES: *c1ccc(N)c(F)c1F]

In some examples, R⁴ is
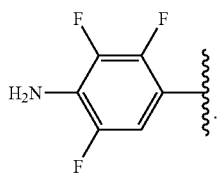
In some examples, R⁴ is
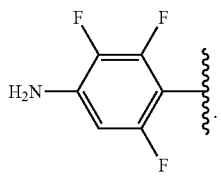
In some examples, R⁴ is
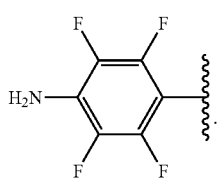
In some examples, R⁴ is
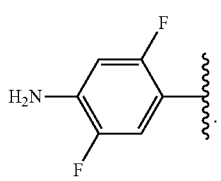
In some examples, R⁴ is
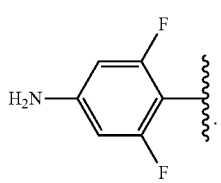
In some examples, R⁴ is
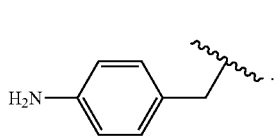 [SMILES: *Cc1ccc(N)cc1]
In some examples, R⁴ is
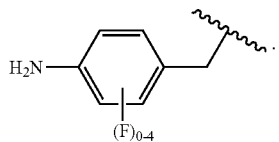
In some examples, R⁴ is
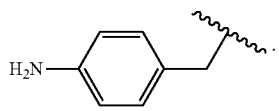
In some examples, R⁴ is
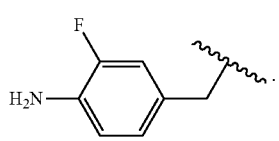 [SMILES: *Cc1ccc(N)c(F)c1]
In some examples, R⁴ is
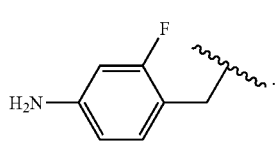
In some examples, R⁴ is
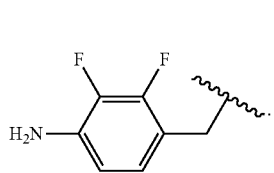
In some examples, R⁴ is
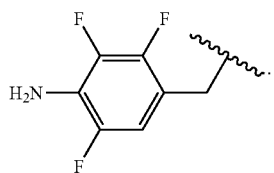
In some examples, R⁴ is
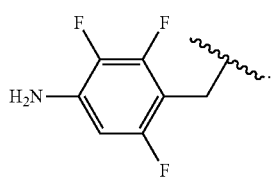

In some examples, $R^4$ is

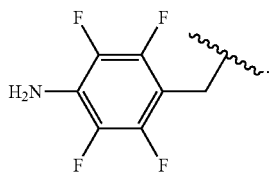 [SMILES: *Cc1c(F)c(F)c(N)c(F)c1F]

In some examples, $R^4$ is

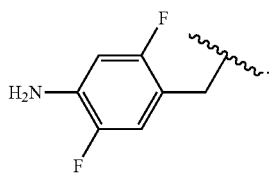

In some examples, $R^4$ is

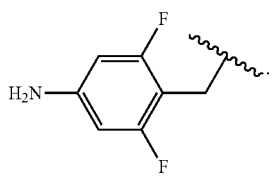

In some examples, $R^4$ is alkyl substituted with amino such as, but not limited to, methyl-amino, ethyl-amino, propyl-amino, butyl-amino, pentyl-amino, hexyl-amino, heptyl-amino, octyl-amino, or nonyl-amino. In some examples, $R^4$ is methyl-amino. In some examples, $R^4$ is ethyl-amino. In some examples, $R^4$ is n-propyl-amino. In some examples, $R^4$ is i-propyl-amino. In some examples, $R^4$ is n-butyl-amino. In some examples, $R^4$ is i-butyl-amino. In some examples, $R^4$ is t-butyl-amino. In some examples, $R^4$ is sec-butyl. In some examples, $R^4$ is pentyl-amino. In some examples, $R^4$ is hexyl-amino. In some examples, $R^4$ is heptyl-amino. In some examples, $R^4$ is octyl-amino. In some examples, $R^4$ is nonyl-amino.

In some examples, $R^4$ is

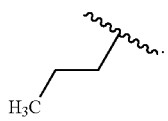

In some examples, $R^4$ is

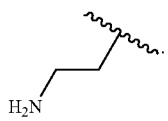

In some examples, $R^4$ is

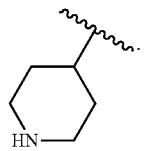

In some examples, herein, $R^a$ and $R^b$ are, independently in each instance, selected from H or alkyl. In some examples, both $R^a$ and $R^b$ are H. In some examples, both $R^a$ and $R^b$ are methyl. In some examples, both $R^a$ and $R^b$ are ethyl. In some examples, both $R^a$ and $R^b$ are propyl. In some examples, one of $R^a$ or $R^b$ is H and the other is alkyl. In some examples, one of $R^a$ or $R^b$ is H and the other is methyl. In some examples, one of $R^a$ or $R^b$ is H and the other is ethyl. In some examples, one of $R^a$ or $R^b$ is H and the other is propyl.

In some examples, in Formula (I), n is an integer from 0-19. In some examples, n is 0. In some other examples, n is 1. In certain examples, n is 2. In some other examples, n is 3. In certain examples, n is 4. In some examples, n is 5. In some other examples, n is 6. In certain examples, n is 7. In some other examples, n is 8. In certain examples, n is 9. In some examples, n is 10. In some other examples, n is 11. In certain examples, n is 12. In some other examples, n is 13. In certain examples, n is 14. In some examples, n is 15. In some other examples, n is 16. In certain examples, n is 17. In some other examples, n is 18. In certain examples, n is 19.

In some examples, in Formula (I), $R^3$ is not —OH when $R^1$ is —OH.

In some examples, in Formula (I), $R^3$ is not —OH when $R^1$ and $R^2$ together form

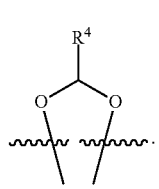

wherein $R^4$ is a $C_{1-9}$alkyl or 4-(dimethyl-amino)-phenyl.

In some examples, set forth herein is a compound of Formula (I), wherein $R^1$ and $R^2$ together form

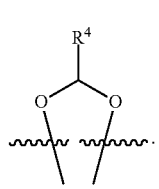

In some of these examples, $R^4$ is alkyl, aryl, arylalkyl, or a N-containing heterocycloalkyl. In certain examples, alkyl, aryl, arylalkyl, or N-containing heterocycloalkyl are optionally substituted with —$NR^aR^b$. In some of these examples, $R^4$ is alkyl. In some of these examples, $R^4$ is aryl. In some of these examples, $R^4$ is arylalkyl. In some of these examples, $R^4$ is N-containing heterocycloalkyl. In some examples, $R^4$ is alkyl such as, but not limited to, methyl, ethyl, propyl, butyl, pentyl, hexyl, heptyl, octyl, or nonyl. In some examples, $R^4$ is methyl. In some examples, $R^4$ is ethyl. In some examples, $R^4$ is n propyl. In some examples, $R^4$ is i-propyl. In some examples, $R^4$ is n-butyl. In some examples, $R^4$ is i-butyl. In some examples, $R^4$ is t-butyl. In some examples, $R^4$ is sec-butyl. In some examples, $R^4$ is pentyl. In some examples, $R^4$ is hexyl. In some examples, $R^4$ is heptyl. In some examples, $R^4$ is octyl. In some examples, $R^4$ is nonyl. In some examples, $R^4$ is aryl such as but not limited to phenyl or naphthyl. In some examples, $R^4$ is phenyl. In some examples, $R^4$ is naphthyl. In some examples, $R^4$ is arylalkyl—such as but not limited to benzyl. In some examples, $R^4$ is N-containing heterocycloalkyl such as but not limited to piperidinyl. In some examples, $R^4$ is 4-amino-phenyl. In some examples, $R^4$ is 4-amino-phenyl optionally substituted with halo.

In some examples, set forth herein is a compound of Formula (I), wherein $R^1$ and $R^2$ together form

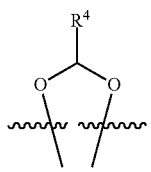

wherein $R^4$ is selected from the group consisting of alkyl, aryl, arylalkyl, and a N-containing heterocycloalkyl; and wherein alkyl, aryl, arylalkyl, or N-containing heterocycloalkyl are optionally substituted with —$NR^aR^b$; and wherein the stereochemistry of the carbon indicated by * is R.

In some examples, set forth herein is a compound of Formula (I), wherein $R^1$ and $R^2$ together form

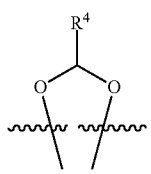

wherein $R^4$ is selected from the group consisting of alkyl, aryl, arylalkyl, and a N-containing heterocycloalkyl; and wherein alkyl, aryl, arylalkyl, or N-containing heterocycloalkyl are optionally substituted with —$NR^aR^b$; and wherein the stereochemistry of the carbon indicated by * is S.

In Formula (I), $R^3$ is not —OH when $R^1$ is —OH or when $R^1$ and $R^2$ together form

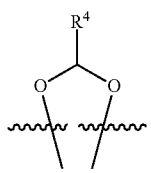

wherein $R^4$ is a $C_{1-9}$alkyl or 4-(dimethyl-amino)-phenyl.

In some examples, the payload set forth herein is a derivative or analog of budesonide or diflorasone. In certain examples, the derivative is an amine or aniline containing molecule which is related in structure to budesonide or diflorasone. As set forth herein, the payloads set forth herein as well as other steroids can be conjugated to an antibody or an antigen-binding fragment thereof based on the methods set forth herein. As set forth herein, the payloads set forth herein as well as other steroids can be conjugated to an antibody, or an antigen-binding fragment thereof, and also to a cyclodextrin moiety based on the methods set forth herein. As taught herein, stable linker-payloads can be use with these methods of conjugation to produce antibody-steroid-conjugates. In some examples, the antibody-steroid conjugates also include a cyclodextrin moiety.

In some embodiments, provided herein are compounds of Formula (V):

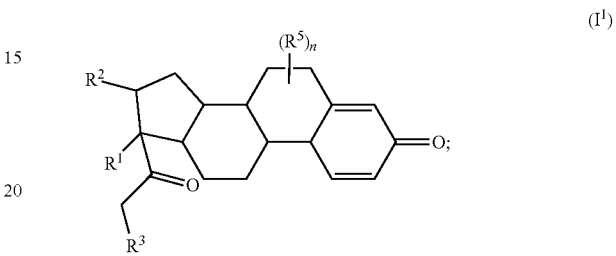

or pharmaceutically acceptable salt, solvate, stereoisomer, or derivative thereof, wherein:

$R^1$ and $R^2$ are, independently, —H, alkyl, alkyl-C(O)—O—, —OH, or halo; or $R^1$ and $R^2$ together form

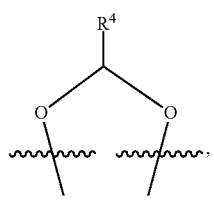

wherein $R^4$ is alkyl, aryl, arylalkyl, or an N-containing heterocycloalkyl, wherein the alkyl, aryl, arylalkyl, and N-containing heterocycloalkyl are, independently in each instance, optionally substituted with —$NR^aR^b$;

$R^5$ is, independently in each instance, —OH, halo, alkyl, or arylalkyl;

$R^3$ is —OH, alkyl-C(O)—O—, or —X-aryl-$NR^aR^b$, wherein X is selected from S, S(O), S(O)$_2$, SO$_2NR^a$, CONR$^a$, C(O), or NR$^a$, wherein the alkyl-C(O)—O— and —X-aryl-$NR^aR^b$ are optionally substituted with halo or prodrug.

$R^a$ and $R^b$ are, independently in each instance, H or alkyl, aryl;

$R^c$ is —H or alkyl; and n is an integer from 0-19;

with the proviso that $R^3$ is not —OH when either (a) or (b): (a) $R^1$ is —OH or (b) $R^1$ and $R^2$ together form

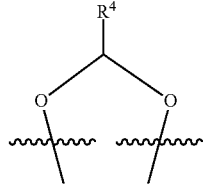

and $R^4$ is a $C_{1-9}$alkyl or

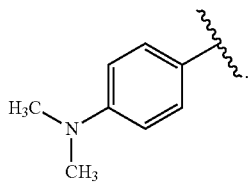

In some of these examples, alkyl-C(O)—O— or —X-aryl-NR$^a$R$^b$ is optionally substituted with halo. In some examples, $R^3$ is —OH. In some examples, $R^3$ is alkyl-C(O)—O—. In some examples, $R^3$ is R$^a$R$^b$N-aryloxy. In some examples, $R^3$ is

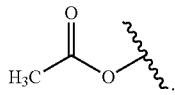

In some examples, $R^3$ is

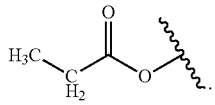

In some examples, $R^3$ is

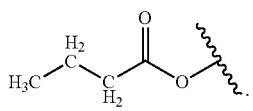

In some examples, $R^3$ is

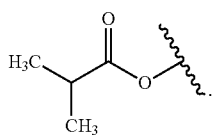

In some examples, $R^3$ is

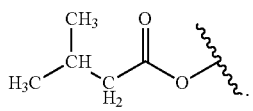

In some examples, $R^3$ is —X-aryl-NR$^a$R$^b$.
In some examples, $R^3$ is

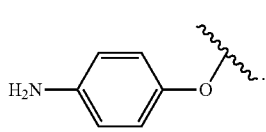

In some examples, $R^3$ is

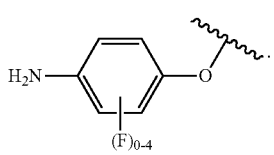

In some examples, $R^3$ is

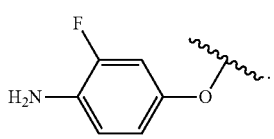 [SMILES: *Sc1ccc(N)c(F)c1]

In some examples, $R^3$ is

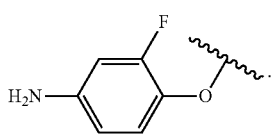

In some examples, $R^3$ is

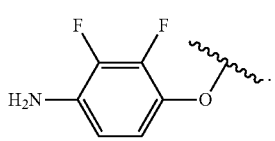

In some examples, $R^3$ is

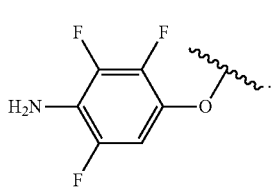

In some examples, $R^3$ is

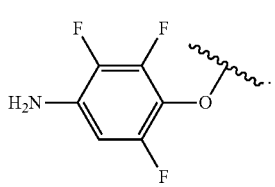

In some examples, $R^3$ is
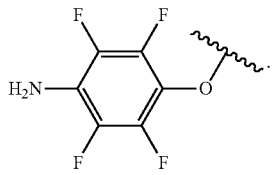
In some examples, $R^3$ is
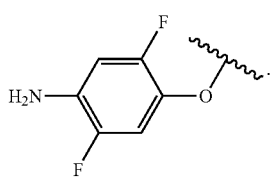
In some examples, $R^3$ is
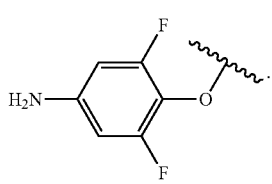
In some examples, $R^3$ is
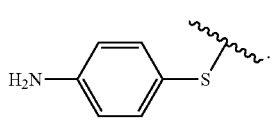
In some examples, $R^3$ is
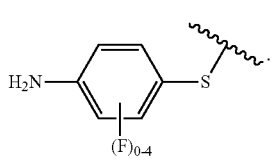
In some examples, $R^3$ is
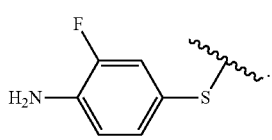
In some examples, $R^3$ is
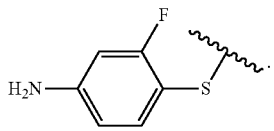
In some examples, $R^3$ is
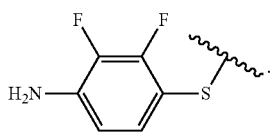
In some examples, $R^3$ is
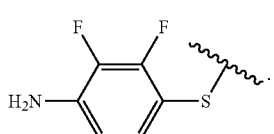
In some examples, $R^3$ is
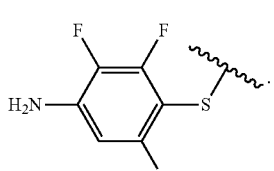
In some examples, $R^3$ is
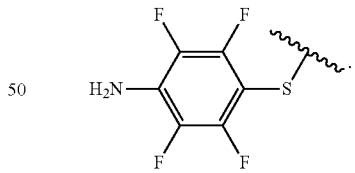
In some examples, $R^3$ is
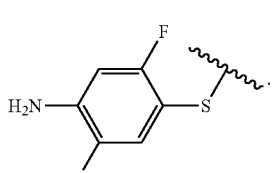

In some examples, R³ is
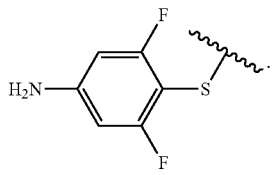
In some examples, R³ is
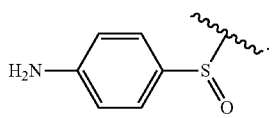 [SMILES: *S(=O)c1ccc(N)cc1]
In some examples, R³ is
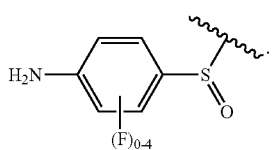
In some examples, R³ is
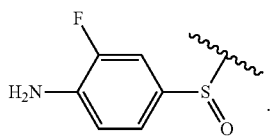
In some examples, R³ is
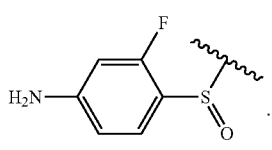
In some examples, R³ is
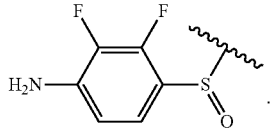
In some examples, R³ is
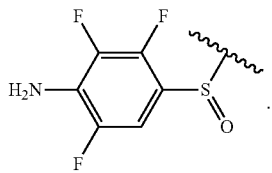 [SMILES: *S(=O)c1cc(F)c(N)c(F)c1F]
In some examples, R³ is
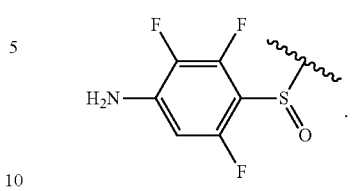
In some examples, R³ is
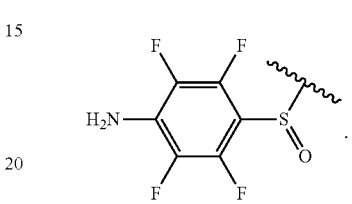
In some examples, R³ is
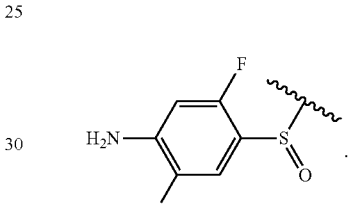
In some examples, R³ is
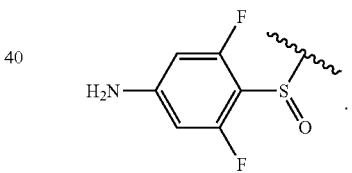
In some examples, R³ is
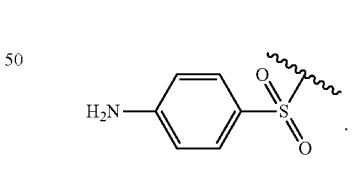
In some examples, R³ is
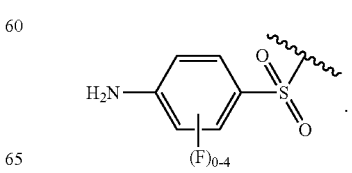

In some examples, R³ is
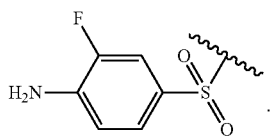
In some examples, R³ is
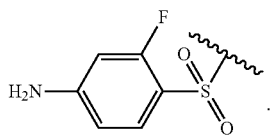
In some examples, R³ is
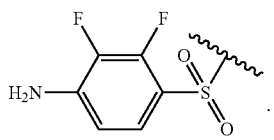
In some examples, R³ is
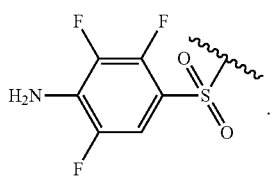
In some examples, R³ is
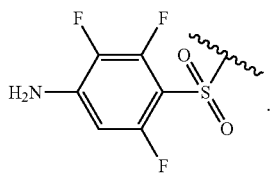
In some examples, R³ is
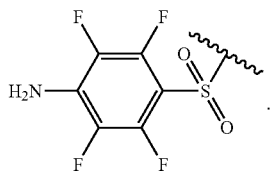
In some examples, R³ is
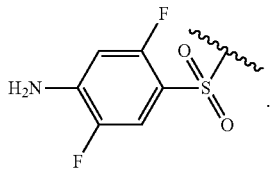 [SMILES: *S(=O)(=O)c1cc(F)c(N)cc1F]
In some examples, R³ is
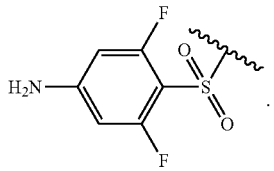 [SMILES: *S(=O)(=O)c1c(F)cc(N)cc1F]
In some examples, R³ is
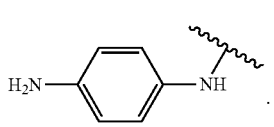
In some examples, R³ is
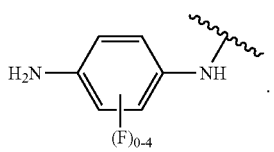
In some examples, R³ is
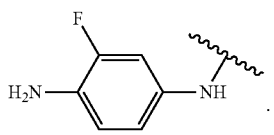 [SMILES: *Nc1ccc(N)c(F)c1]
In some examples, R³ is
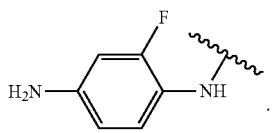 [SMILES: *Nc1ccc(N)cc1F]
In some examples, R³ is
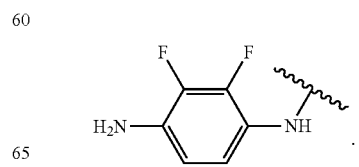

In some examples, R³ is

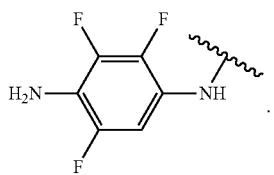.

In some examples, R³ is

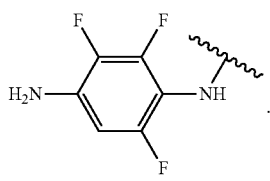.

In some examples, R³ is

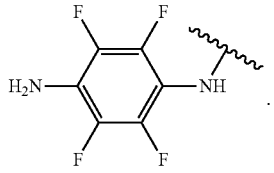.

In some examples, R³ is

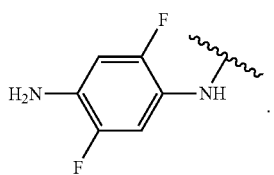 [SMILES: *Nc1cc(F)c(N)cc1F].

In some examples, R³ is

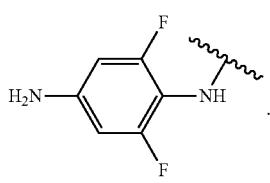.

In some examples, set forth herein is a compound of Formula (I), wherein R³ has a structure selected from one of the following structures:

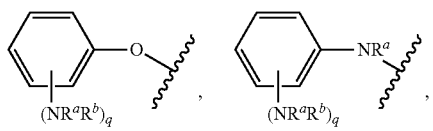,

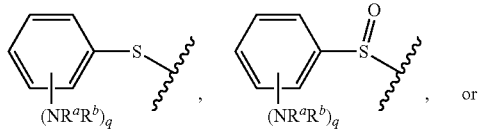, or

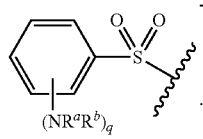.

In some examples, R³ is

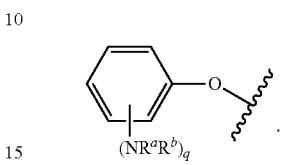.

In some examples, R³ is

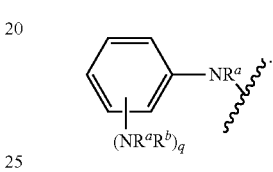.

In some examples, R³ is

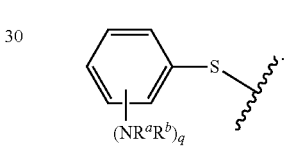.

In some examples, R³ is

.

In some examples, R³ is

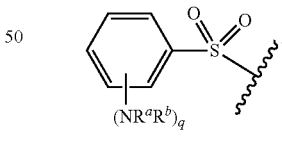.

In these examples, q is an integer from 0 to 5.

In some examples, set forth herein is a compound of Formula (I), wherein R³ has a structure selected from one of the following structures:

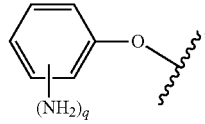, 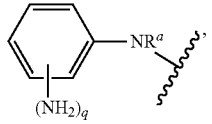,

-continued

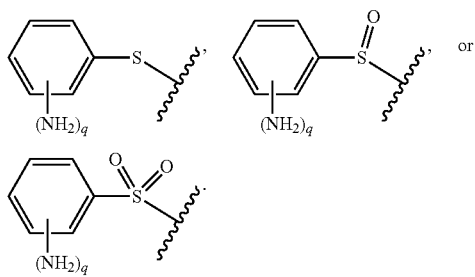

In some examples, R³ is

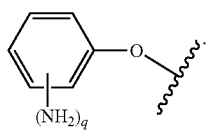

In some examples, R³ is

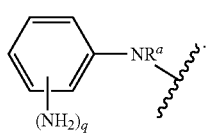

In some examples, R³ is

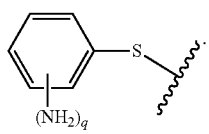

In some examples, R³ is

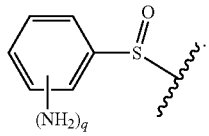

In some examples, R³ is

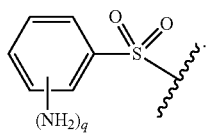

In these examples, q is an integer from 0 to 5.

In some examples, set forth herein is a compound of Formula (I), wherein R³ has a structure selected from one of the following structures:

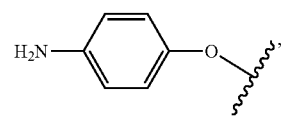

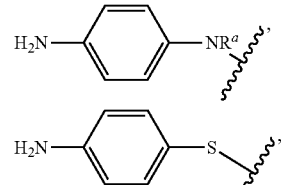

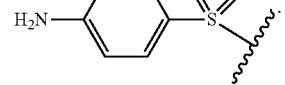

In some examples, R³ is

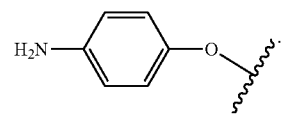 [SMILES: *Sc1ccc(N)cc1]

In some examples, R³ is

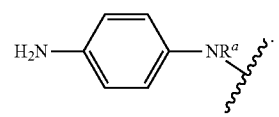

In some examples, R³ is

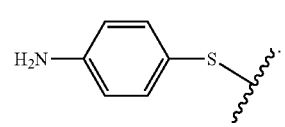

In some examples, R³ is

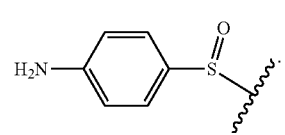 [SMILES: *S(=O)c1ccc(N)cc1]

In some examples, R³ is

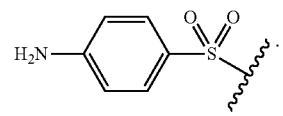

In some examples, set forth herein is a compound of Formula (I), wherein the compound has the structure of Formula 1000:

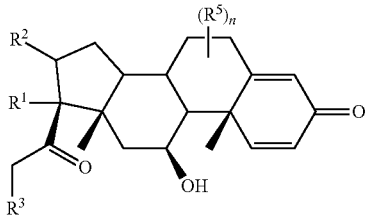

or a pharmaceutically acceptable salt, solvate, or stereoisomer thereof. In Formula 1000, $R^1$ and $R^2$ are, independently, selected from the group consisting of —H, —OH, alkyl, —O—C(O)-alkyl, and halo; or $R^1$ and $R^2$ together form

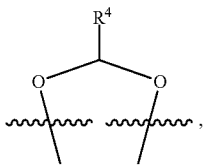

wherein $R^4$ is selected from the group consisting of alkyl, aryl, alkylaryl, arylalkyl, heteroaryl, -alkylene-$NR^aR^b$, —X-arylene-Y—$NR^aR^b$, —X-heteroarylene-Y—$NR^aR^b$, and N-containing heterocycloalkyl; wherein X is absent, —N—, —$CH_2$—, or —O—; wherein Y is absent or —$CH_2$—. $R^3$ is selected from the group consisting of —OH, —O—C(O)-alkyl, —O-aryl, —$NR^aR^b$, -alkylene-$NR^aR^b$, —X-arylene-Y—$NR^aR^b$, —X-heteroarylene-Y—$NR^aR^b$, and N-containing heterocycloalkyl; wherein X is absent, —N—, —$CH_2$—, or —O—; wherein Y is absent or —$CH_2$—. $R^5$ is, independently in each instance, selected from a substituent in the group consisting of —OH, halo, and alkyl; n is an integer from 0-19; and each $R^5$ is positioned on any ring atom. $R^a$ and $R^b$ are, independently in each instance, selected from the group consisting of —H and alkyl; or $R^a$ and $R^b$ cyclize to form cycloheteroalkyl with three to six ring atoms, including one hetero atom, which is the N to which they are attached. $R^a$ and $R^b$ are, independently in each instance, optionally substituted with at least one substituent selected from the group consisting of —OH, —$PO_4H$, $NH_2$, —C(O)OH, and —C(O)$CH_3$.

In certain embodiments, provided herein are compounds according to Formula 1000, wherein $R^3$ is selected from the group consisting of -alkylene-$NR^aR^b$, —X-arylene-Y—$NR^aR^b$, —X-heteroarylene-Y—$NR^aR^b$, and N-containing heterocycloalkyl; wherein X is absent, —N—, —$CH_2$—, or —O—; wherein Y is absent or —$CH_2$—; and $R^4$ is selected from the group consisting of alkyl, aryl, alkylaryl, arylalkyl, heteroaryl, -alkylene-$NR^aR^b$, —X-arylene-Y—$NR^aR^b$, —X-heteroarylene-Y—$NR^aR^b$, and N-containing heterocycloalkyl; wherein X is absent, —N—, —$CH_2$—, or —O—; wherein Y is absent or —$CH_2$—.

In certain embodiments, provided herein are compounds according to Formula 1000, wherein $R^3$ is selected from the group consisting of -alkylene-$NR^aR^b$, —X-arylene-Y—$NR^aR^b$, —X-heteroarylene-Y—$NR^aR^b$, and N-containing heterocycloalkyl; wherein X is absent, —N—, —$CH_2$—, or —O—; wherein Y is absent or —$CH_2$—.

In certain embodiments, provided herein are compounds according to Formula 1000, wherein $R^3$ is —$NR^aR^b$; and $R^4$ is alkyl. In certain embodiments, $R^3$ is —$NH_2$. In certain embodiments, $R^4$ is n-propyl. In certain embodiments, $R^3$ is —$NH_2$ and $R^4$ is n-propyl.

In certain embodiments, the compound of Formula 1000 is according to Formula 1010, 1020, 1030, or 1040:

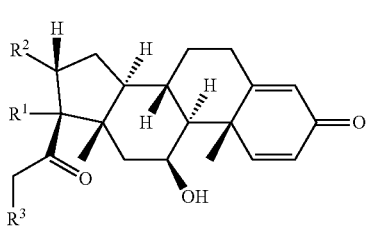

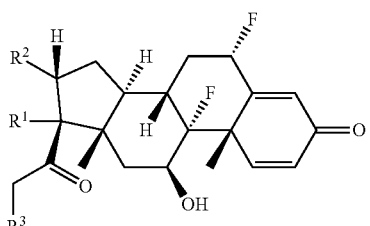

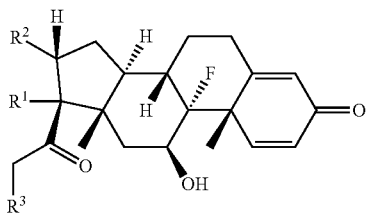

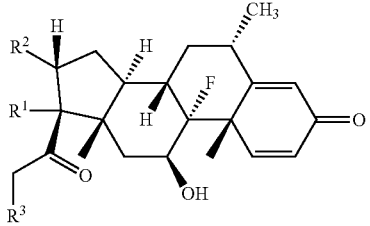

or a pharmaceutically acceptable salt, solvate, or stereoisomer thereof.

In certain embodiments, the compound of Formula 1000 is according to Formula 1110, 1120, 1130, or 1140:

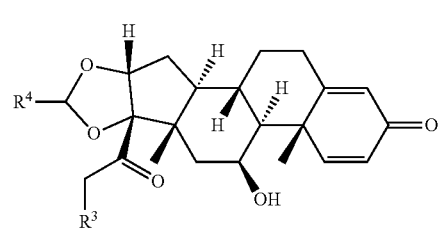

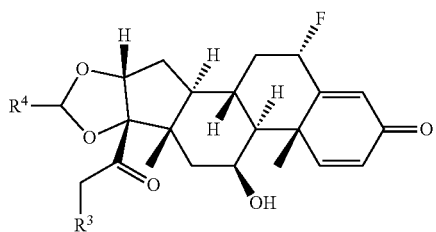

1120

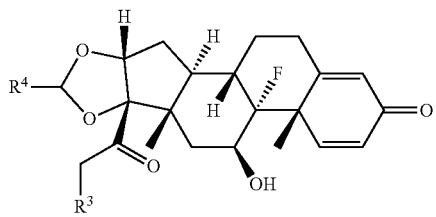

1130

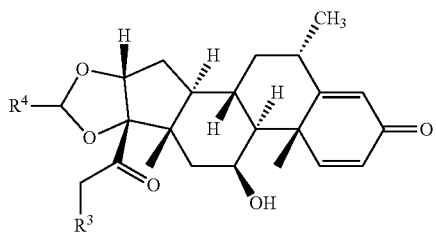

1140 or a pharmaceutically acceptable salt, solvate, or stereoisomer thereof.

In certain embodiments according to any of Formulas 1000-1140, $R^3$ is —OH or —O—C(O)-alkyl; and $R^4$ is -alkylene-NR$^a$R$^b$, —X-arylene-NR$^a$R$^b$, —X-heteroarylene-NR$^a$R$^b$, or N-containing heterocycloalkyl; wherein X is absent or —CH$_2$—. In certain embodiments, $R^4$ is -alkylene-NH$_2$, —C$_6$H$_5$—NH$_2$ or —CH$_2$—C$_6$H$_5$—NH$_2$.

In certain embodiments according to any of Formulas 1000-1140, $R^3$ is —O-aryl, —NR$^a$R$^b$, -alkylene-NR$^a$R$^b$, —X-arylene-Y—NR$^a$R$^b$, —X-heteroarylene-Y—NR$^a$R$^b$, or N-containing heterocycloalkyl; wherein X is absent, —N—, —CH$_2$—, or —O—; wherein Y is absent or —CH$_2$—; and $R^4$ is alkyl, aryl, alkylaryl, or arylalkyl. In certain embodiments, $R^3$ is —O-arylene-NR$^a$R$^b$, —O-heteroarylene-NR$^a$R$^b$; wherein aryl or heteroaryl is optionally substituted with halogen, deuterium, hydroxyl, or methoxyl. In certain embodiments, $R^3$ is —O-phenyl-NR$^a$R$^b$, —O-heteroarylene-NR$^a$R$^b$; wherein phenyl or heteroaryl is optionally substituted with halogen or deuterium. In certain embodiments according to this paragraph, $R^4$ is n-propyl.

In certain embodiments, provided herein are compounds according to any of Formulas 1000-1140, wherein $R^3$ is —NR$^a$R$^b$; and $R^4$ is alkyl. In certain embodiments, $R^3$ is —NH$_2$. In certain embodiments, $R^4$ is n-propyl. In certain embodiments, $R^3$ is NH$_2$ and $R^4$ is n-propyl.

In any of Formulas 1000-1140, $R^3$ can be any specific $R^3$ provided above. In particular embodiments, $R^3$ is —NH$_2$, —N(H)CH$_3$, —N(CH$_3$)$_2$, or

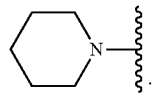

In particular embodiments, $R^3$ is

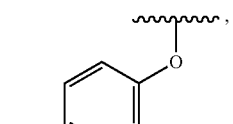

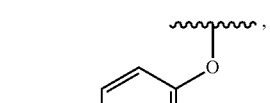

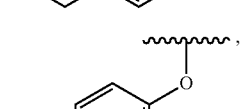

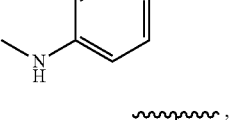

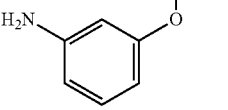

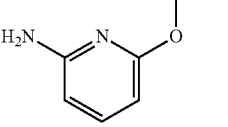 or

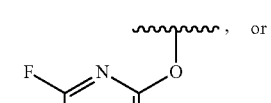

In particular embodiments, $R^3$ is

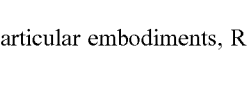 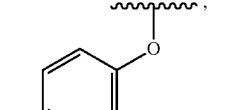 or

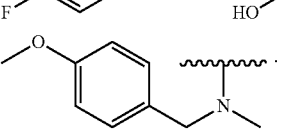

In particular embodiments, R³ is
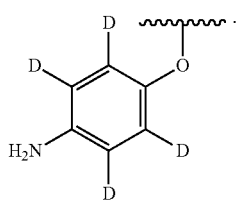
In any of Formulas 1000-1140, R⁴ can be any specific R⁴ provided above. In particular embodiments, R⁴ is selected from —CH₂—CH₂—NH₂,
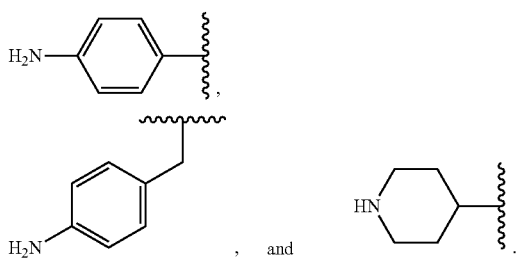
In particular embodiments, R⁴ is n-propyl.
Set forth herein are also compounds having the following structures:
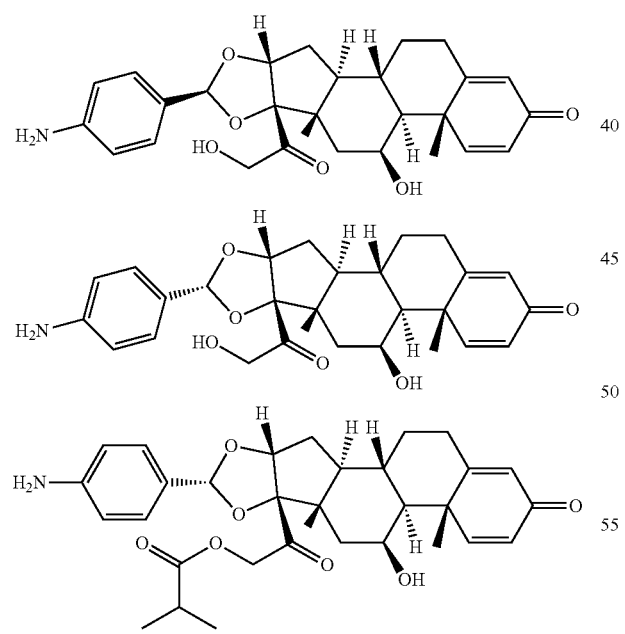
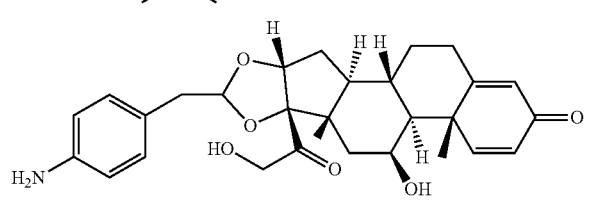
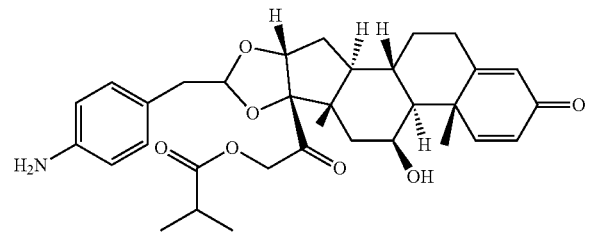
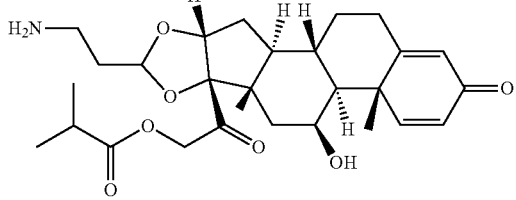
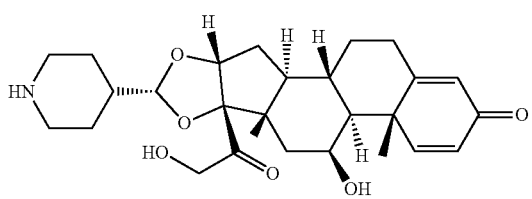
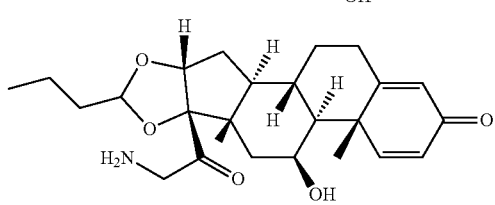
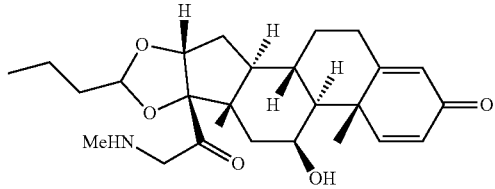
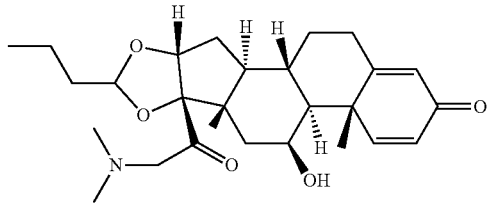
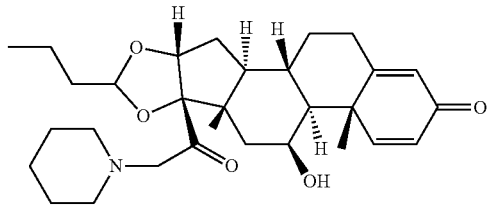
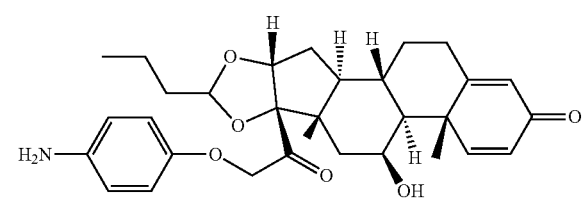

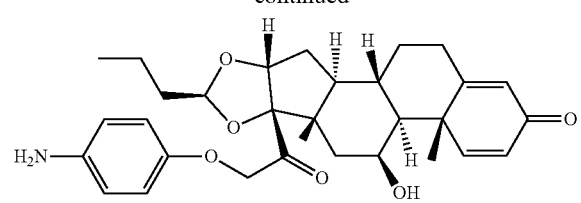
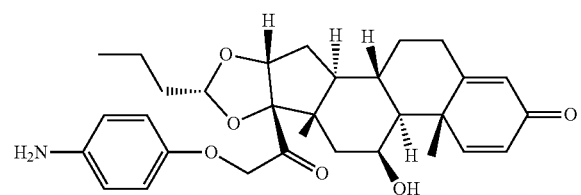
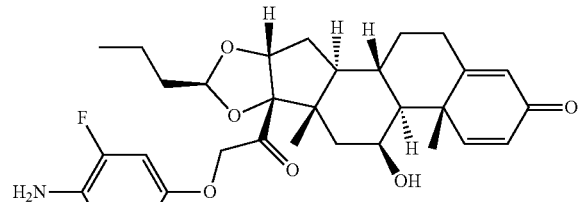
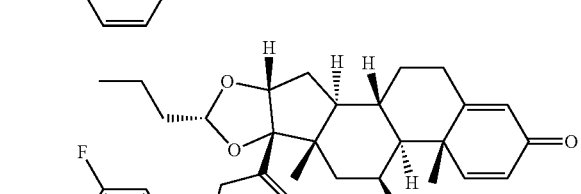
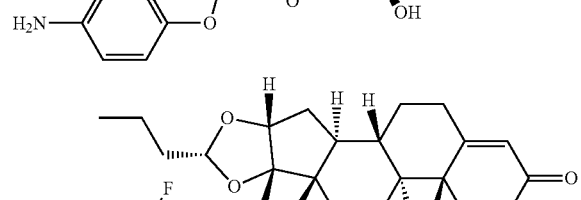
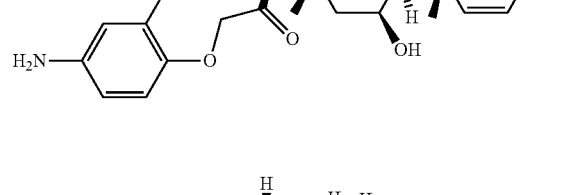
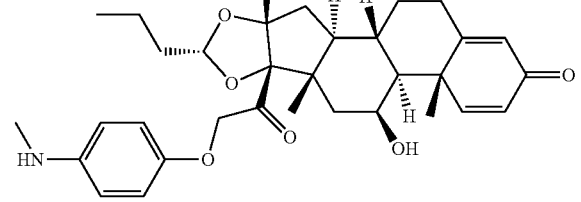
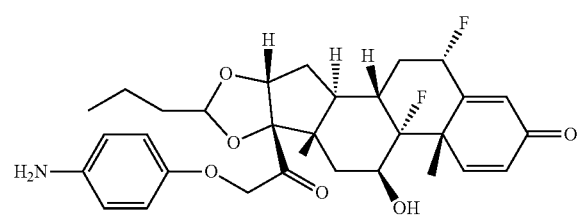
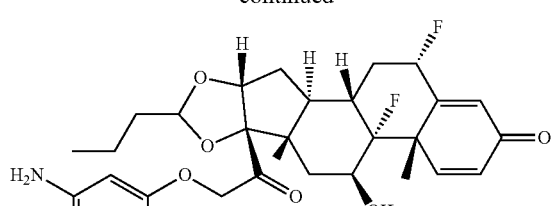
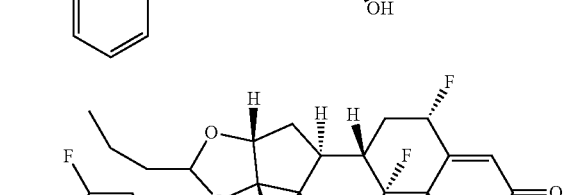
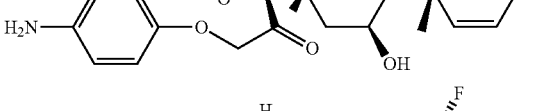
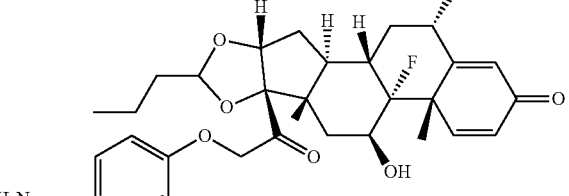
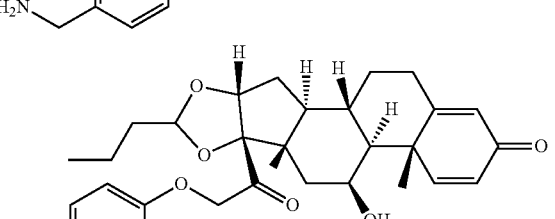
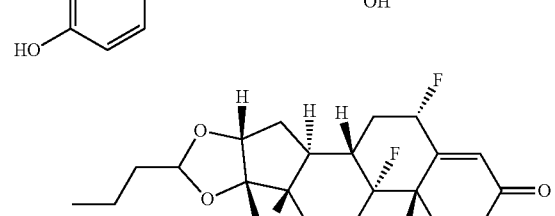
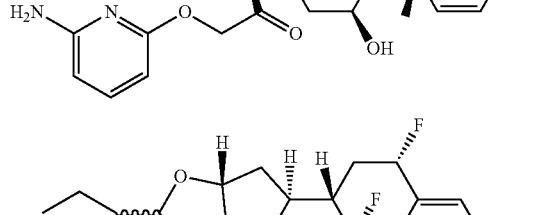
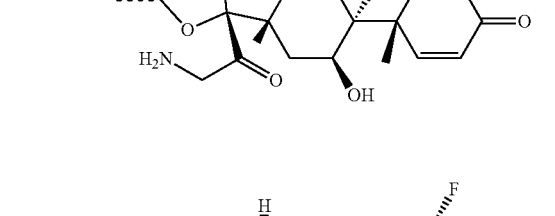
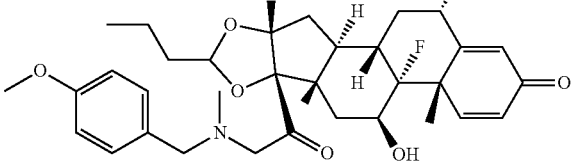

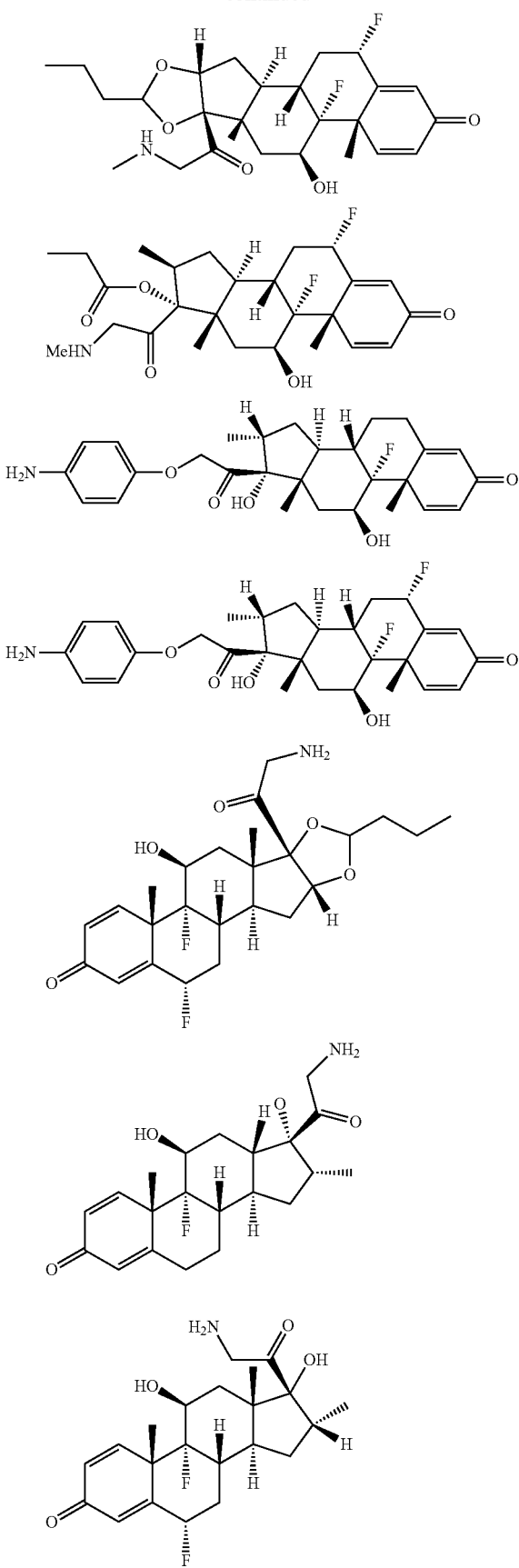
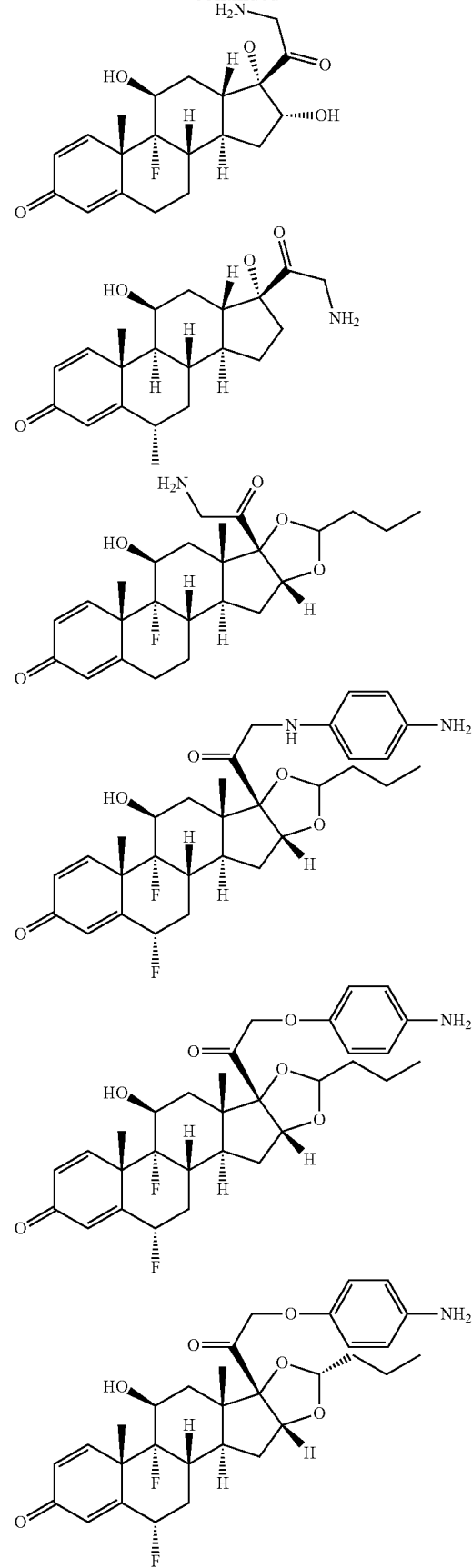

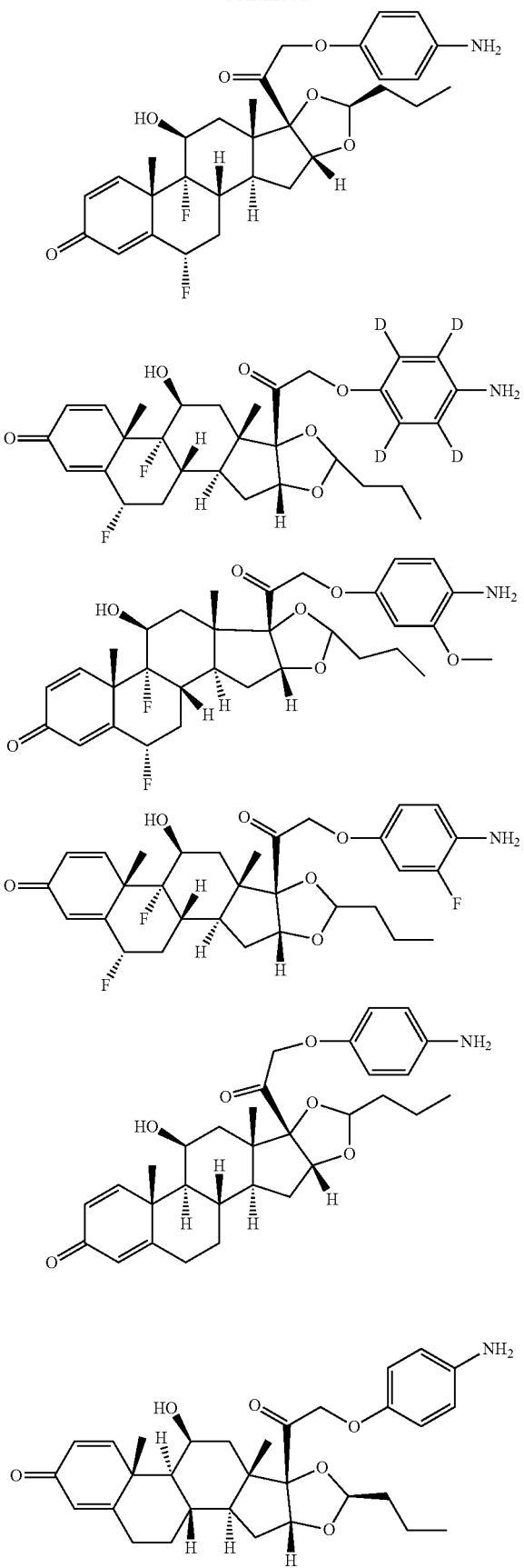

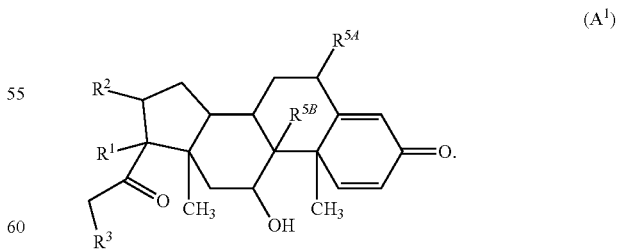

or a pharmaceutically acceptable salt, solvate, or stereoisomer thereof.

Included within the scope of this disclosure are pharmaceutically acceptable salts, solvates, crystalline forms, amorphous forms, polymorphic forms, regioisomers, stereoisomers, prodrugs, e.g., phosphatase-prodrugs, glucose-prodrugs, ester prodrugs, etc., metabolites, and physiological adducts of the steroid payloads described herein, including those of Formula (I), (I'), and (A$^1$)-(A$^7$).

C. Protein Steroid Conjugates

Provided herein are protein conjugates of the steroids described herein. Such conjugates include proteins, e.g., antibodies or antigen-binding fragments thereof, that are covalently linked, e.g., via the binding agent linkers described herein, to the compounds described in Section B above, e.g., the compounds of Formula (A), (A$^1$), (A$^2$), (A$^3$), (A$^4$), (A$^5$), (A$^6$), (A$^7$), (I), (I'), (PIa), (PIb-1), (PIb-2), PIc-1), (PIc-2), (PId-1), (PId-2), (PIe-1), (PIe-2), (PII), (PIIa), (PIIb), (PIII), (PIIIa), (PIIIb), (PINT), (PV), (PVa), (PVb), (PVI), (PVII), (PVIIa), (PVIIb), (PVIIb-1), (PVIIb-2), (PVIII), and (1000)-(1140).

The binding agent linker can be linked to a steroid described herein at any suitable moiety or position of the steroid, including e.g., through an amide, ether, ester, carbamate, or amine. For example, the binding agent linker can be attached to compounds through R$^1$, R$^3$, or R$^4$ or hydroxyl group depicted Formula (A$^1$):

In certain embodiments, the steroids described herein are attached to the binding agent linker by reacting an amino or hydroxyl group of the steroid with a suitable reactive group present on the linker. In some embodiments, the binding agent linker also includes a cyclodextrin moiety. For example, the cyclodextrin moiety may be bonded to the chemical backbone structure of the binding agent linker.

In certain embodiments, provided herein are compounds having the structure:

BA-(L-PAY)$_x$ wherein BA is a binding agent as described herein; L is an optional linker as described herein; PAY is a steroid compound as described herein; and x is an integer from 1-30. In particular embodiments, each PAY is a radical obtainable by removal of an atom, for example a hydrogen atom from a compound according to a Formula selected from the group consisting of Formulas (A), (A$^1$), (A$^2$), (A$^3$), (A$^4$), (A$^5$), (A$^6$), (A$^7$), (I), (I$^1$), (PIa), (PIb-1), (PIb-2), (PIc-1), (PIc-2), (PId-1), (PId-2), (PIe-1), (PIe-2), (PII), (PIIa), (PIIb), (PIII), (PIIIa), (PIIIb), (PIV), (PV), (PVa), (PVb), (PVI), (PVII), (PVIIa), (PVIIb), (PVIIb-1), (PVIIb-2), (PVIII), and (1000)-(1140). Examples of such compounds are described in detail below.

In certain embodiments, provided herein are compounds having the structure of Formula (III):

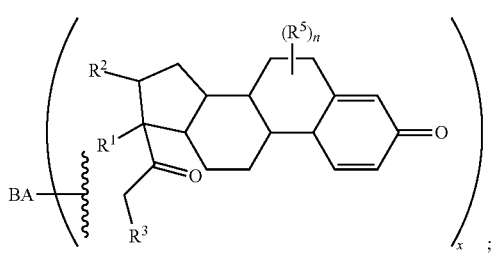
(III)

wherein either (a) or (b):
(a) R$^3$ is -BL-, -BL-X—, or

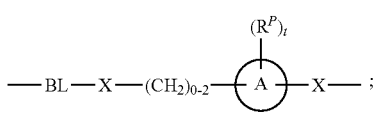

R$^1$ and R$^2$ are each, independently, —H, alkyl, alkyl-C(O)—O—, —OH, or halo; or R$^1$ and R$^2$ together form

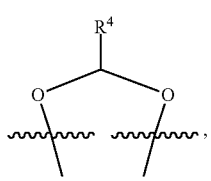

wherein R$^4$ is alkyl, aryl, arylalkyl, or an N-containing heterocycloalkyl; wherein the alkyl, aryl, arylalkyl, and N-containing heterocycloalkyl are optionally substituted with —NR$^a$R$^b$; or
(b) R$^3$ is —OH, alkyl-C(O)—O—, heteroalkyl, —NR$^a$R$^b$ or aryloxy, wherein the alkyl-C(O)—O—, heteroalkyl, or aryloxy is optionally substituted with —NR$^a$R$^b$, —NR$^a$R$^b$-aryloxy, or halo, and R$^1$ and R$^2$ together form

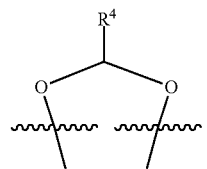

wherein R$^4$ is -BL-,

-BL-X—(CH$_2$)$_{1-4}$— or -BL-Y—, wherein Y is an N-containing divalent heterocycle;
-BL- is a divalent binding agent linker;
R$^5$ is, independently in each instance, —OH, halo, alkyl, or arylalkyl;
R$^a$ and R$^b$ are, independently in each instance, —H or alkyl;
R$^P$, independently in each instance, is halo;
BA is a binding agent bonded to -BL-;
X, independently in each instance, is NR$^a$ or O;

is aryl or heteroaryl;
t is an integer from 0-2;
x is an integer from 1-30; and
n is an integer from 0-19.

In some examples, subscript x is 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30. In some examples, subscript x is 0. In some examples, subscript x is 1. In some examples, subscript x is 2. In some examples, subscript x is 3. In some examples, subscript x is 4. In some examples, subscript x is 5. In some examples, subscript x is 6. In some examples, subscript x is 7. In some examples, subscript x is 8. In some examples, subscript x is 9. In some examples, subscript x is 10. In some examples, subscript x is 11. In some examples, subscript x is 12. In some examples, subscript x is 13. In some examples, subscript x is 14. In some examples, subscript x is 15. In some examples, subscript x is 16. In some examples, subscript x is 17. In some examples, subscript x is 18. In some examples, subscript x is 19. In some examples, subscript x is 20. In some examples, subscript x is 21. In some examples, subscript x is 22. In some examples, subscript x is 23. In some examples, subscript x is 24. In some examples, subscript x is 25. In some examples, subscript x is 26. In some examples, subscript x is 27. In some examples, subscript x is 28. In some examples, subscript x is 29. In some examples, subscript x is 30.

In some examples of Formula (III), R$^1$ and R$^2$ are, each, independently, —H, alkyl, or —OH. In some examples of Formula (III), one of R$^1$ or R$^2$ is —H, alkyl, or —OH. In some examples of Formula (III), both R$^1$ and R$^2$ are either —H, alkyl, or —OH.

In some examples of Formula (III), R$^1$ and R$^2$ together form

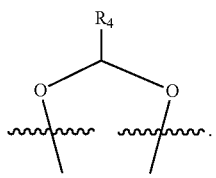

In some examples, $R^4$ is -RL. In some examples, $R^4$ is RL-$NR^a$-aryl. In some other examples, $R^4$ is alkyl. In certain examples, $R^4$ is arylalkyl, In some examples, $R^4$ is aryl. In other examples, $R^4$ is N-containing heterocycloalkyl. In some of these examples, the alkyl, aryl, arylalkyl, or N-containing heterocycloalkyl is optionally substituted.

In some examples of Formula (III), $R^5$ is —H or halo. In some examples of Formula (II), $R^5$ is —H or fluoro. In some examples of Formula (III), one of $R^5$ is —H or halo. In some examples of Formula (III), $R^5$ is —H or halo and n is 2. In some examples of Formula (III), $R^5$ is —F and n is 1. In some examples of Formula (II), $R^5$ is —F and n is 2.

In some examples of Formula (III), $R^3$ is BL. In some examples of Formula (III), $R^3$ is RL-$NR^a$-aryloxy-. In some other examples of Formula (III), $R^3$ is —OH. In some other examples of Formula (III), $R^3$ is alkyl-C(O)—O—. In some other examples of Formula (III), $R^3$ is heteroalkyl. In some other examples of Formula (III), $R^3$ is —$NR^aR^b$. In some other examples of Formula (III), $R^3$ is aryl. In some other examples of Formula (III), $R^3$ is aryloxy. In some other examples of Formula (III), alkyl-C(O)—O—, heteroalkyl, or aryloxy is optionally substituted with —$NR^aR^b$ or halo.

In some examples of Formula (II), $R^3$ is —OH. In some examples of Formula (III), $R^3$ is alkyl-C(O)—O—. In some examples $R^3$ is

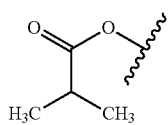

In some examples of Formula (III), $R^3$ is heteroalkyl. In some examples $R^3$ is

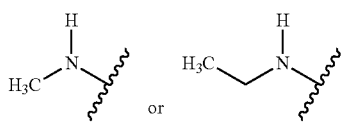

In some examples of Formula (III), $R^3$ is

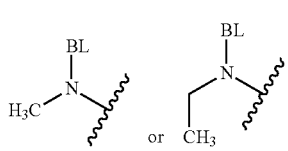

In some examples of Formula (III), $R^3$ is —$NR^aR^b$. In some examples, $R^3$ is —$NR^aR^b$-aryloxy. In some examples, $R^3$ is

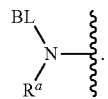

In some examples $R^3$ is

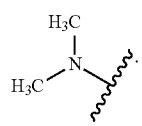

In some examples, $R^3$ is

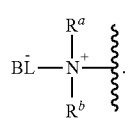

In some examples $R^3$ is aryloxy. In some examples $R^3$ is

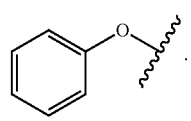 [SMILES: *Oc1ccccc1]

In some examples $R^3$ is

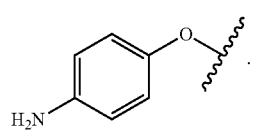

In some examples, $R^3$ is

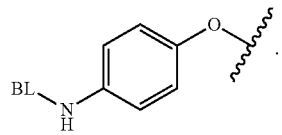

In some examples $R^3$ is

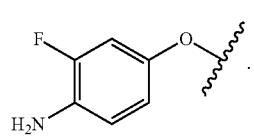

In some examples, R³ is

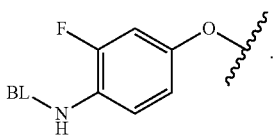

In some examples R³ is

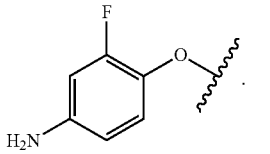

In some examples, R³ is

In some examples R³ is

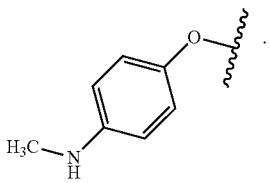

In some examples, R³ is

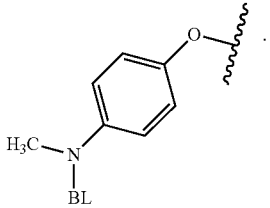

In some examples R³ is

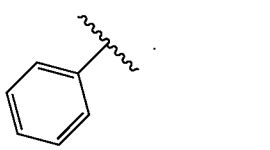 [SMILES: *c1ccccc1]

In some examples, R³ is

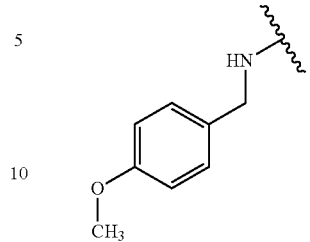

In Formula (III), subscript n is an integer from 0-19. In some examples, n is 0. In some other examples, n is 1. In certain examples, n is 2. In some other examples, n is 3. In certain examples, n is 4. In some examples, n is 5. In some other examples, n is 6. In certain examples, n is 7. In some other examples, n is 8. In certain examples, n is 9. In some examples, n is 10. In some other examples, n is 11. In certain examples, n is 12. In some other examples, n is 13. In certain examples, n is 14. In some examples, n is 15. In some other examples, n is 16. In certain examples, n is 17. In some other examples, n is 18. In certain examples, n is 19.

In some examples, set forth herein is a compound having the structure of Formula (IIIa):

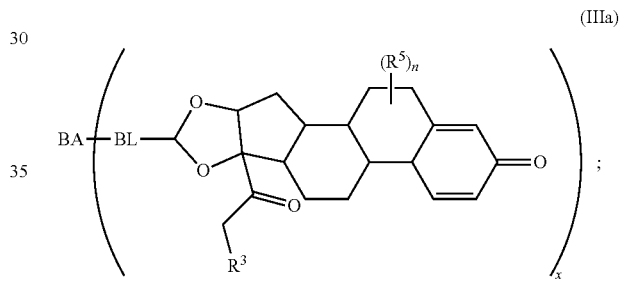

(IIIa)

wherein:
BA is a binding agent;
R⁵ is, independently in each instance, —OH, halo, or alkyl;
R³ is selected from —OH, alkyl-C(O)—O—, heteroalkyl, —NR$^a$R$^b$, —NR$^a$R$^b$-aryloxy, or aryloxy, wherein the alkyl-C(O)—O—, heteroalkyl, or aryloxy is optionally substituted with —NR$^a$R$^b$ or halo;
BL is a binding agent linker;
R$^a$ and R$^b$ are, independently in each instance, selected from H, alkyl, and alkyl-C(O);
n is an integer from 0 to 19; and
x is an integer from 1 to 30.

In some examples, set forth herein is a compound having the structure of Formula (IIIa2):

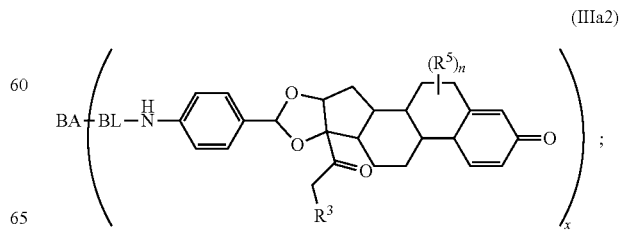

(IIIa2)

wherein:
  BA is a binding agent;
  $R^5$ is, independently in each instance, —OH, halo, or alkyl;
  $R^3$ is —OH, alkyl-C(O)—O—, heteroalkyl, —NR$^a$R$^b$, —NR$^a$R$^b$-aryloxy, or aryloxy, wherein the alkyl-C(O)—O—, heteroalkyl, or aryloxy is optionally substituted with —NR$^a$R$^b$ or halo;
  BL is a binding agent linker;
  $R^a$ and $R^b$ are, independently in each instance, selected from H, alkyl, or alkyl-C(O);
  n is an integer from 0 to 19; and
  x is an integer from 0 to 30.

In some examples of Formula (IIIa2), $R^3$ is —OH. In some examples of Formula (IIIa2), $R^3$ is alkyl-C(O)—O—. In some examples $R^3$ is

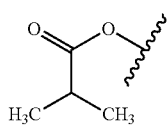

In some examples of Formula (IIIa2), $R^3$ is heteroalkyl. In some examples $R^3$ is

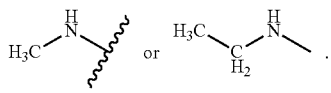

In some examples of Formula (IIIa2), $R^3$ is —NR$^a$R$^b$. In some examples $R^3$ is

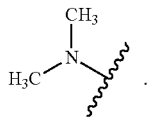

In some examples $R^3$ is aryloxy. In some examples $R^3$ is

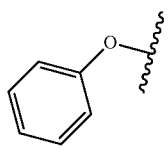

In some examples $R^3$ is

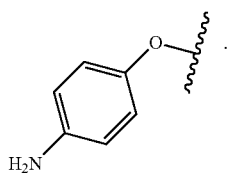

In some examples $R^3$ is

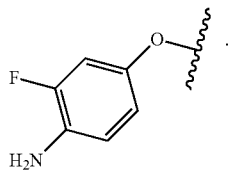 [SMILES: *Oc1ccc(N)c(F)c1]

In some examples $R^3$ is

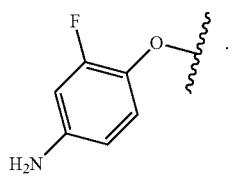

In some examples $R^3$ is

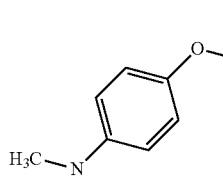

In some examples, $R^3$ is

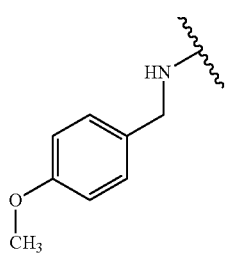

In some examples, the compound of Formula (IIIa2) has the following structure:

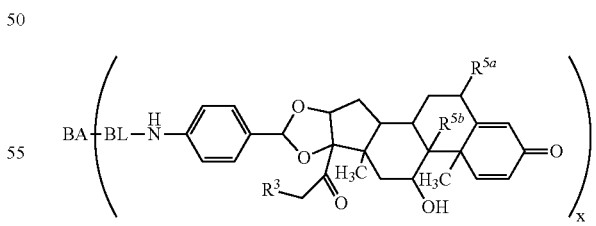

wherein:
  BA is a binding agent;
  $R^3$ is —OH or alkyl-C(O)—O—;
  $R^{5a}$ and $R^{5b}$ are each, independently, —F or H;
  BL is a binding agent linker; and
  x is an integer from 1 to 30.

In some examples, set forth herein is a compound having the structure of Formula (IIIb):

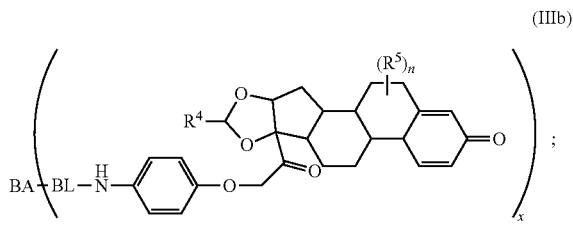

(IIIb)

wherein
BA is a binding agent;
R⁵ is, independently in each instance, —OH, halo, or alkyl;
R⁴ is selected from alkyl, aryl, arylalkyl, or an N-containing heterocycloalkyl, wherein the alkyl, aryl, arylalkyl, or N-containing heterocycloalkyl are optionally substituted with —NR$^a$R$^b$;
BL is a binding agent linker;
R$^a$ and R$^b$ are, independently in each instance, selected from H, alkyl, and alkyl-C(O);
n is an integer from 0 to 19; and
x is an integer from 0 to 30.

In some examples of Formula (IIIb), R⁵ is —H or halo. In some examples of Formula (IIIb), R⁵ is fluoro. In some examples of Formula (IIIb), n is at least 2, and two of R⁵ is halo. In some examples of Formula (IIIb), R⁵ is —F and n is 1. In some examples of Formula (IIIb), R⁵ is —F.

In some examples of Formula (IIIb), R⁴ is alkyl. In some examples of Formula (IIb), R⁴ is methyl, ethyl, n-propyl, i-propyl, n-butyl, s-butyl, t-butyl, i-butyl, a pentyl moiety, a hexyl moiety, cyclopropyl, cyclobutyl, cyclopentyl, or cyclohexyl. In some examples of Formula (IIIb), R⁴ is n-propyl.

In some examples, the compound of Formula (IIIb) has the following structure:

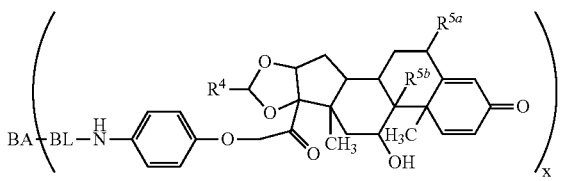

wherein:
BA is a binding agent;
R⁴ is alkyl;
R$^{5a}$ and R$^{5b}$ are each, independently, —F or H;
BL is a binding agent linker; and
x is an integer from 1 to 30.

In some examples, set forth herein is a compound having the structure of Formula (IIIc):

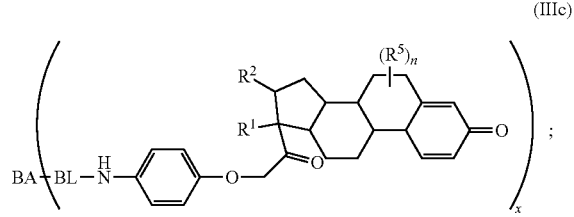

(IIIc)

wherein
BA is a binding agent;
R¹ and R² are, independently, —H, alkyl, alkyl-C(O)—O—, —OH, or halo;
R⁵ is, independently in each instance, selected from —OH, halo, or alkyl;
BL is a binding agent linker;
n is an integer from 0 to 19; and
x is an integer from 1 to 30.

In some examples of Formula (IIIc), R⁵ is halo. In some examples of Formula (IIIc), R⁵ is fluoro. In some examples of Formula (IIIc), one of R⁵ is halo. In some examples of Formula (IIIc), two of R⁵ is halo. In some examples of Formula (IIIc), R⁵ is —F and n is 2.

In some examples of Formula (IIIc), R¹ is CH₃.
In other examples of Formula (IIIc), R¹ is OH.
In some other examples of Formula (IIIc), R¹ is H.
In some examples of Formula (IIIc), R² is CH₃.
In other examples of Formula (IIIc), R² is OH.
In some other examples of Formula (IIIc), R² is H.
In some examples of Formula (IIIc), R¹ is CH₃ and R² is CH₃.
In other examples of Formula (IIIc), R¹ is CH₃ and R² is OH.
In some examples of Formula (IIIc), R¹ is CH₃ and R² is H.
In some other examples of Formula (IIIc), R¹ is OH and R² is CH₃.
In other examples of Formula (IIIc), R¹ is OH and R² is OH.
In some examples of Formula (IIIc), R¹ is H and R² is H.
In some other examples of Formula (IIIc), R¹ is H and R² is OH.
In other examples of Formula (IIIc), R¹ is H and R² is H.

In some embodiments, the compound of Formula (IIIc) has the following structure:

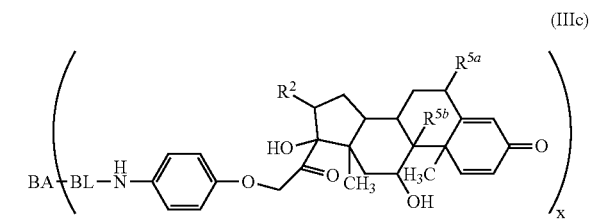

(IIIc)

wherein:
BA is a binding agent;
R² is methyl;
R$^{5a}$ and R$^{5b}$ are each, independently, —F or H;
BL is a binding agent linker; and
x is an integer from 0 to 30.

In some embodiments, the compound of Formula (IIIc) has the following structure:

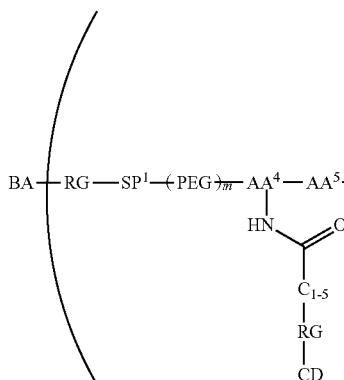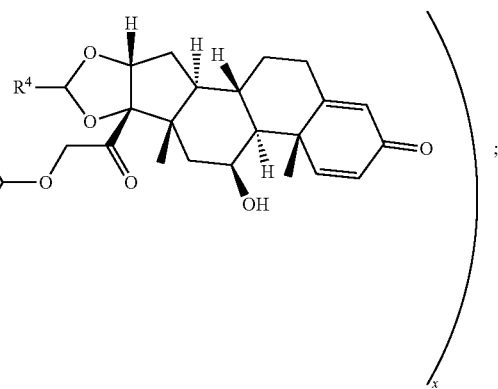

BA is a binding agent;
RG is a reactive group residue;
CD is a cyclodextrin;
$SP^1$ is a spacer group;
$AA^4$ is an amino acid residue;
$AA^5$ is a dipeptide residue;
PEG is polyethylene glycol;
m is an integer from 0 to 4;
x is an integer from 0 to 30;
$R^4$ is alkyl, aryl, arylalkyl, or an N-containing heterocycloalkyl; wherein the alkyl, aryl, arylalkyl, and N-containing heterocycloalkyl are optionally substituted with $-NR^aR^b$;
$R^a$ and $R^b$ are, independently in each instance, —H or alkyl;
BA is a binding agent bonded to -BL-;
$SP^1$ and $SP^2$ are each, independently in each instance, absent or a spacer group residue, and wherein $SP^1$ comprises a trivalent linker; $AA^4$ is a trivalent linker comprising an amino acid residue; $AA^5$ is a di-peptide residue; PEG is a polyethylene glycol residue; wherein the ⊀ indicates the atom through which the indicated chemical group is bonded to the adjacent groups in the formula, CD is, independently in each instance, absent or a cyclodextrin residue, wherein at least one CD is present, subscript m is an integer from 0 to 5; In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples, any one of $AA^4$ or $AA^5$ comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, $AA^4$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, $AA^4$ is lysine. In certain embodiments, $AA^4$ is lysine or a derivative of lysine. In certain embodiments, the $AA^5$ is valine-citrulline. In some embodiments, the $AA^5$ is citrulline-valine. In some embodiments, the $AA^5$ is valine-alanine. In some embodiments, the $AA^5$ is alanine-valine. In some embodiments, the $AA^5$ is valine-glycine. In some embodiments, the $AA^5$ is glycine-valine. In some embodiments, the $AA^5$ glutamate-valine-citrulline. In some embodiments, the $AA^5$ is glutamine-valine-citrulline. In some embodiments, the $AA^5$ is lysine-valine-alanine. In some embodiments, the $AA^5$ is lysine-valine-citrulline. In some embodiments, the $AA^5$ is glutamate-valine-citrulline. In some examples, $SP^1$ is independently in each instance, selected from the group consisting of $C_{1-6}$ alkylene, —NH—, —C(O)—, $(-CH_2-CH_2-O)_e$, $-NH-CH_2-CH_2-(-O-CH_2-CH_2)_e-C(O)-$, $-C(O)-(CH_2)_u-C(O)-$, $-C(O)-NH-(CH_2)_v-$, and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, $(-CH_2-CH_2-O)_e$, $-NH-CH_2-CH_2-(-O-CH_2-CH_2)_e-C(O)-$, $-C(O)-(CH_2)_u-C(O)-$, $-C(O)-NH-(CH_2)_v-$, and combinations thereof, wherein subscript e is an integer from 0 to 4, subscript u is an integer from 1 to 8, and subscript v is an integer from 1 to 8.

Set forth are also compounds of Formula ($B^2$):

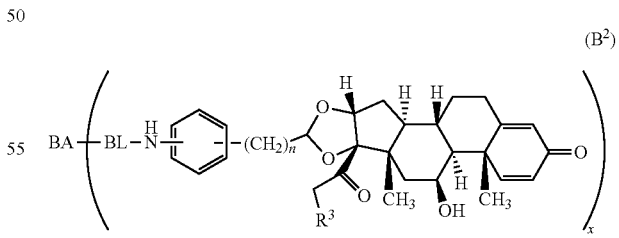

(B²)

wherein n is an integer from 0 to 4, $R^3$ is —OH or $R^Z$—C(O)—O—; wherein $R^Z$ is alkyl, BL is a binding agent linker, BA is a binding agent, and x is an integer from 1 to 30. In certain embodiments, n is 0 or 1 and x is an integer from 1-6. In certain embodiments, x is 4.

Set forth are also compounds of Formula (B³):

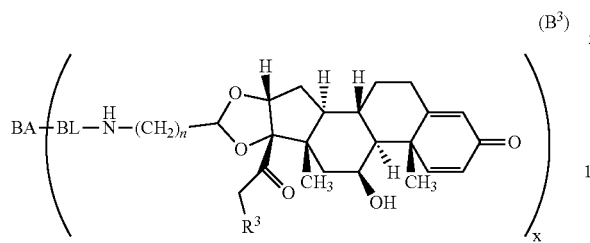

wherein n is an integer from 1-4, R³ is —OH or $R^Z$—C(O)—O—; wherein $R^Z$ is alkyl, BL is a binding agent linker, BA is a binding agent, and x is an integer from 1-30. In certain embodiments, n is 2 and x is an integer from 1-6. In certain embodiments, x is 4.

Set forth are also compounds of Formula (B⁴):

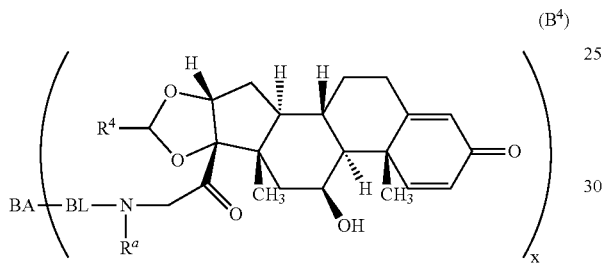

wherein R⁴ is alkyl, wherein $R^a$ is a hydrogen atom or alkyl, BL is a binding agent linker, and BA is a binding agent. In certain embodiments, R⁴ is $C_{1-4}$ alkyl. In some embodiments, R⁴ is propyl. In certain embodiments, R³ is —NH₂, —NHCH₃, or —N(CH₃)₂. In certain embodiments, x is an integer from 1-6. In certain embodiments, x is 4.

Set forth are also compounds of Formula (B⁵):

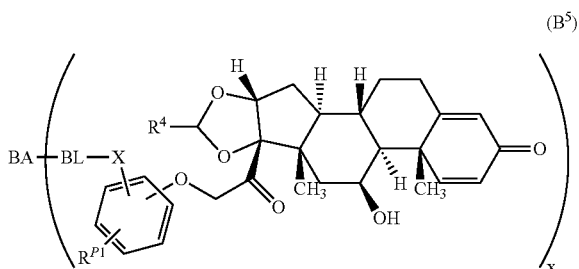

wherein R⁴ is alkyl, $R^{P1}$ is halo or a hydrogen atom, and X is $NR^a$ or O, wherein $R^a$ is a hydrogen atom or alkyl, BL is a binding agent linker, BA is a binding agent, and x is an integer from 1-30. In some embodiments, R⁴ is $C_{1-4}$ alkyl, X is NH, and x is an integer from 1-6. In certain embodiments, x is 4.

Set forth are also compounds of Formula ($B^{6A}$):

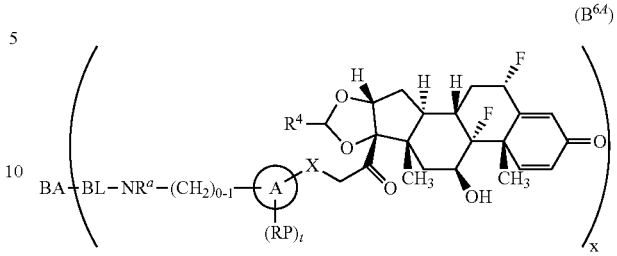

wherein X is O or $NR^a$,

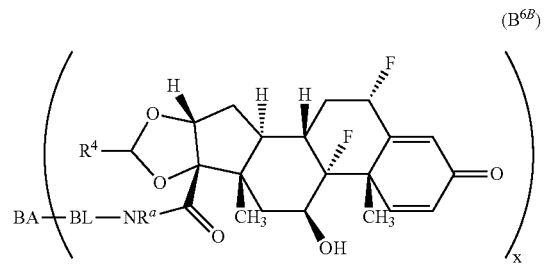

is aryl or heteroaryl, $R^P$ is halo, t is an integer from 0-2, $R^a$ is a hydrogen atom or alkyl, BL is a binding agent linker, BA is a binding agent, and x is an integer from 1-30, and R⁴ is alkyl. In some embodiments X is O, R⁴ is alkyl, and x is an integer from 1-6. In certain embodiments, x is 4.

Set forth herein are also compounds of Formula ($B^{6B}$)

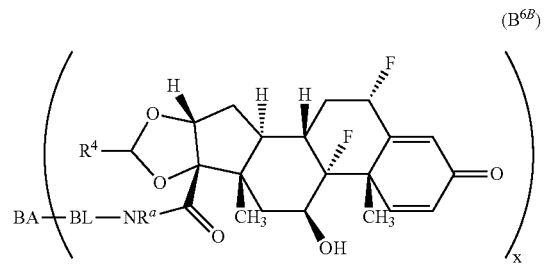

wherein $R^a$ is a hydrogen atom or alkyl, BL is a binding agent linker, BA is a binding agent, and x is an integer from 1-30. In some embodiments, x is an integer from 1-6. In some embodiments, x is 4.

As used herein, the phrase "binding agent linker," or "BL" refers to any divalent group or moiety that links, connects, or bonds a binding agent (e.g., an antibody or an antigen-binding fragment thereof) with a payload compound set forth herein (e.g., steroid). Generally, suitable binding agent linkers for the antibody conjugates described herein are those that are sufficiently stable to exploit the circulating half-life of the antibody and, at the same time, capable of releasing its payload after antigen-mediated internalization of the conjugate. Linkers can be cleavable or non-cleavable. Cleavable linkers are linkers that are cleaved by intracellular metabolism following internalization, e.g., cleavage via hydrolysis, reduction, or enzymatic reaction. Non-cleavable linkers are linkers that release an attached payload via lysosomal degradation of the antibody following internalization. Suitable linkers include, but are not limited to, acid-labile linkers, hydrolysis-labile linkers, enzymatically cleavable linkers, reduction labile linkers, self-immolative linkers, and non-cleavable linkers. Suitable linkers also include, but are not limited to, those that are or comprise glucuronides, succinimide-thioethers, polyethylene glycol (PEG) units, carbamates, hydrazones, mal-caproyl units, disulfide units (e.g., —S—S—, —S—S—C(R¹)(R²)—, wherein R¹ and R² are independently hydrogen or hydrocarbyl), para-amino-benzyl (PAB) units, phosphate units, e.g., mono-, bis-, and tris-phosphate units, peptides, e.g., peptide units containing two, three, four, five, six, seven, eight, or more amino acid units, including but not limited to valine citrulline units, valine-alanine units, valine-arginine units, valine-lysine units, -lysine-valine-citrulline units, and -lysine-valine-alanine units. In some embodiments, the binding agent linker group of the conjugates described herein are derived from the reaction of a "reactive linker" group of a linker-payload described herein with a reactive portion of an antibody. The reactive linker group (RL) refers to a monovalent group that comprises a reactive group and linking group, depicted as

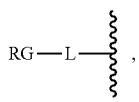

wherein RG is the reactive group, L is the linking group, and the wiggly line represents a bond to a payload. The linking group is any divalent moiety that bridges the reactive group to the payload. The linking group may also be any trivalent moiety that bridges the reactive group, the payload and a cyclodextrin moiety. In some examples, the linking group is trivalent and includes a cyclodextrin moiety bonded to a trivalent group (e.g., a lysine residue) in the linking group. The reactive linkers (RL), together with the payloads to which they are bonded, comprise intermediates ("linker-payloads") useful as synthetic precursors for the preparation of the antibody steroid conjugates described herein. The reactive linker contains a reactive group (RG), which is a functional group or moiety that reacts with a reactive portion of an antibody, modified antibody, or antigen binding fragment thereof. The moiety resulting from the reaction of the reactive group (RG) with the antibody, modified antibody, or antigen binding fragment thereof, together with the linking group (L), comprise the "binding agent linker" (BL) portion of the conjugate, described herein. Thus, in some embodiments, BL is has the following structure:

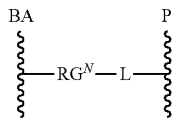

wherein ⸸ is the bond to the biding agent, $RG^N$ is the moiety resulting from the reaction of a reactive group of a linker-payload with a reactive portion of a binding agent, L is a linking group, and ⸸ is a bond to a payload.

In certain embodiments, $RG^N$ is derived from the reaction of RG with a cysteine or lysine residue of an antibody or antigen-binding fragment thereof. In certain embodiments, $RG^N$ is derived from a click chemistry reaction. In some embodiments of said click chemistry reaction, $RG^N$ is derived from a 1,3 cycloaddition reaction between an alkyne and an azide. Non-limiting examples of such $RG^N$s include those derived from strained alkynes, e.g., those suitable for strain-promoted alkyne-azide cycloadditions (SPAAC), cycloalkynes, e.g., cyclooctynes, benzannulated alkynes, and alkynes capable of undergoing 1,3 cycloaddition reactions with azides in the absence of copper catalysts. Suitable $RG^N$s also include, but are not limited to those derived from DIBAC, DIBO, BARAC, substituted, e.g., fluorinated alkynes, aza-cycloalkynes, BCN, and derivatives thereof. Conjugates containing such $RG^N$ groups can be derived from antibodies that have been functionalized with azido groups. Such functionalized antibodies include antibodies functionalized with azido-polyethylene glycol groups. In certain embodiments, such functionalized antibody is derived by reacting an antibody comprising at least one glutamine residue with a compound according to the formula $H_2N$-LL-$N_3$, wherein LL is a divalent polyethylene glycol group, in the presence of the enzyme transglutaminase, e.g., microbial transglutaminase. Suitable glutamine residues of an antibody include Q295, or those derived by insertion or mutation, e.g., N297Q mutation.

In some embodiments, BA of the conjugates described herein is an antibody or an antigen-binding fragment thereof. In some embodiments, the conjugates described herein are derived from azido-functionalized antibodies. In certain embodiments, BA of the conjugates described herein is:

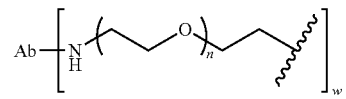

wherein Ab is an antibody or antigen-binding fragment thereof, n is an integer from 1 to 10, w is the number of linker payload moieties, and ⸸ is a bond to a single binding agent linker (BL), e.g., bond to a moiety derived from a 1,3-cycloaddition reaction between an alkyne and azide. In certain embodiments, w is 3. In certain embodiments, w is 2 or 4, i.e., the conjugate comprises 2 or 4 linker payload moieties.

In some embodiments, BL is a divalent moiety of Formula ($BL^A$);

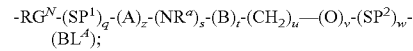

wherein $RG^N$ is as defined herein;
A is an amino acid or a peptide;
$R^a$ is H or alkyl;
B is aryl, heteroaryl, or heterocycloalkyl, wherein aryl, heteroaryl, or heterocycloalkyl is optionally substituted with alkyl, —OH, or —$NR^aR^b$;
$SP^1$ and $SP^2$ are, independently, a spacer groups; and q, z, s, t, u, v, and w are, independently in each instance, 0 or 1.

In some other embodiments, BL is a trivalent moiety of Formula ($BL^B$);

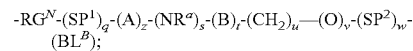

wherein $RG^N$ is as defined herein;
A is tripeptide, wherein at least one of the amino acids in the tripeptide is bonded directly or indirectly to a cyclodextrin moiety;
$R^a$ is H or alkyl;
B is aryl, heteroaryl, or heterocycloalkyl, wherein aryl, heteroaryl, or heterocycloalkyl is optionally substituted with alkyl, —OH, or —$NR^aR^b$;
$SP^1$ and $SP^2$ are, independently, a spacer groups; and q, z, s, t, u, v, and w are, independently in each instance, 0 or 1.

In some examples, the cyclodextrin (CD) is bonded directly to an amino acid residue, such as a lysine amino acid residue. This means that the CD is one bond position away from the lysine amino acid covalent linker. In some of these examples, the covalent linker is also bonded directly to a payload moiety. This means that the covalent linker is one bond position away from a payload such as, but not limited to a steroid payload set forth herein. In some of these examples, the covalent linker is also bonded directly to a CD moiety. This means that the covalent linker is one bond position away from a CD, such as the CD(s) set forth herein. In some of these examples, the covalent linker is a lysine amino acid or a derivative thereof.

In some examples, the CD is bonded indirectly to a covalent linker in a linking group (e.g., a BL). This means that the CD is more than one bond position away from the covalent linker. This also means that the CD is bonded through another moiety to the covalent linker. For example, the CD may be bonded to a maleimide group which is bonded to a polyethylene glycol group which is bonded to the covalent linker. In some of these examples, the covalent linker is also bonded indirectly to a payload moiety. This means that the covalent linker is more than one bond position away from a payload such as, but not limited to a steroid payload set forth herein. This also means that the covalent linker is bonded through another moiety to the payload. For example, the covalent linker may be bonded to a dipeptide, such as but not limited to Val-Ala or Val-Cit, which may be bonded to para-amino benzoyl which may be bonded to the payload. In some of these examples, the covalent linker is also bonded indirectly to a cyclodextrin moiety. This means that the covalent linker is more than one bond position away from a cyclodextrin, such as the cyclodextrins set forth herein. This also means that the covalent linker is bonded through another moiety to the cyclodextrin. For example, the covalent linker may be bonded to a polyethylene glycol group which may be bonded to reactive group which may be bonded to the cyclodextrin. In some of these examples, the covalent linker is a lysine amino acid or a derivative thereof.

In some embodiments, BL is —$RG^N$-$(SP^1)_q$-$(A)_z$-. In some embodiments, BL is —$RG^N$-$(SP^1)_q$-$(A)_2$-. In some embodiments, BL is a moiety of Formula ($BL^{A1}$)

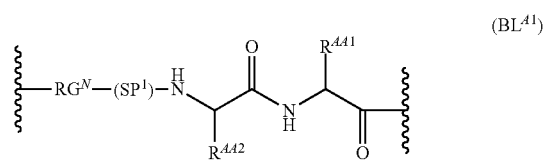

($BL^{A1}$)

wherein $R^{AA1}$ and $R^{AA2}$ are each, independently, amino acid side chains. In some examples of Formula $RL^{A1}$, $SP^1$ is a divalent polyethylene glycol group and $RG^N$ is a 1,3-cycloaddition reaction adduct of the reaction between an alkyne and an azide.

In some embodiments, BL is —$RG^N$-$(SP^1)_q$-$(A)_z$-. In some embodiments, BL is —$RG^N$-$(SP^1)_q$-$(A)_2$-. In some embodiments, BL is a moiety of Formula ($BL^{B1}$)

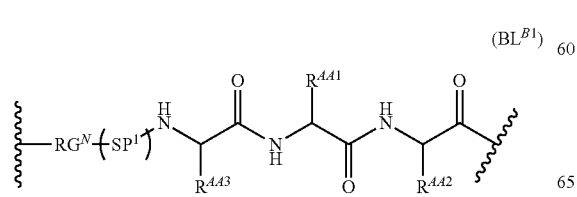

($BL^{B1}$)

wherein $R^{AA1}$ and $R^{AA2}$ are each, independently, amino acid side chains. $R^{AA3}$ is an amino acid side chain that is bonded directly or indirectly to a cyclodextrin moiety. In some examples of Formula $RL^{B1}$, $SP^1$ is a divalent polyethylene glycol group and $RG^N$ is a 1,3-cycloaddition reaction adduct of the reaction between an alkyne and an azide.

In some embodiments, BL has the following structure:

—$RG^N$-$(SP^1)$q-$Z^1$—$Z^2$—$Z^3_{0-1}$— wherein:

$RG^N$, $SP^1$, are as defined herein;

q is 0 or 1;

$Z^1$ is a polyethylene glycol or caproyl group;

$Z^2$ is a dipeptide or tripeptide; and $Z^3$ is a PAB group.

In certain embodiments, $RG^N$ is derived from a click-chemistry reactive group and $Z^1$ is a polyethylene glycol group. In certain embodiments, RGN-(SP1)q-Z1- is:

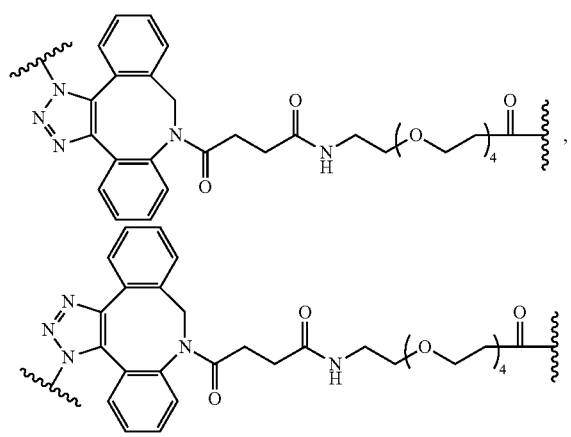

or mixture thereof; or

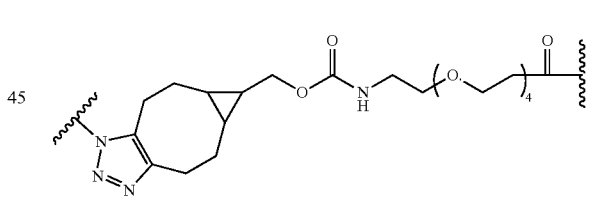

In some embodiments, the dipeptide is valine-citrulline or valine alanine.

In some embodiments, the BL is attached to the payload via tertiary amine. For example, if the steroid is the following compound,

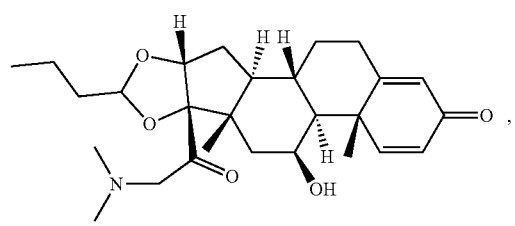 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CN(C)C)O1]

the RL can bond to the tertiary amine as follows:

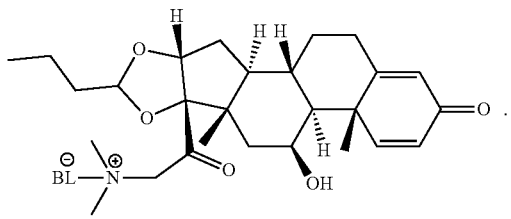

In some examples, set forth is a compound as follows:

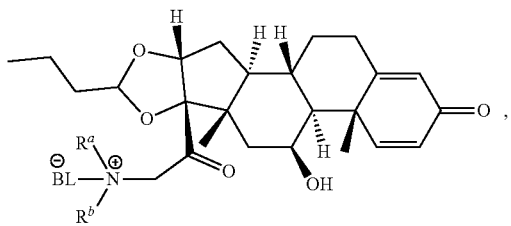

wherein:
BL is a binding agent linker as defined above;
$R^a$ and $R^b$ are, independently in each instance, —H or alkyl.

In some examples, herein $RG^N$ is derived from a click-chemistry reactive group. In some examples, $RG^N$ is:

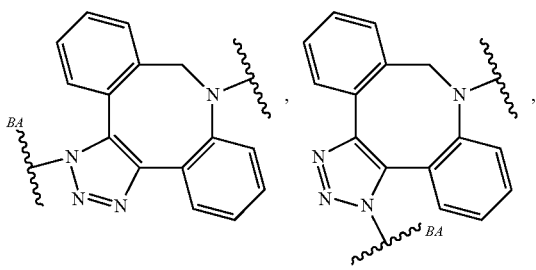 [SMILES: *N1Cc2ccccc2-c2c(nnn2*)-c2ccccc21 ; *N1Cc2ccccc2-c2nnn(*)c2-c2ccccc21]

or mixture thereof;

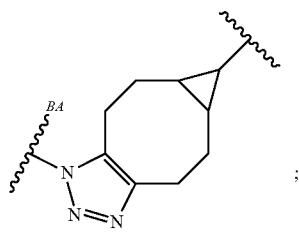 [SMILES: *C1C2CCc3nnn(*)c3CCC12]

or

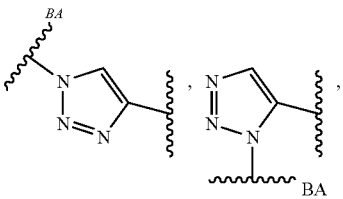

or mixture thereof; wherein is † a bonding to a binding agent.

In some other examples, herein $RG^N$ is selected from a group which reacts with a cysteine or lysine residue on an antibody or an antigen-binding fragment thereof. In some examples, $RG^N$ is

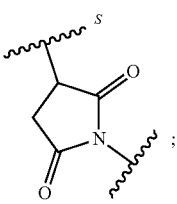

wherein † is a bond to cysteine of a binding agent, e.g., antibody. In some examples, $RG^N$ is

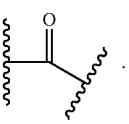

In some embodiments, $SP^1$ is selected from:

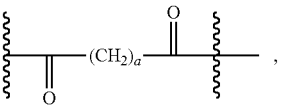

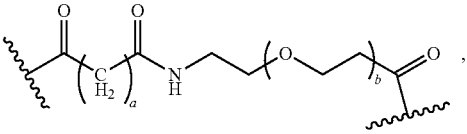

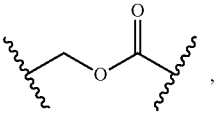

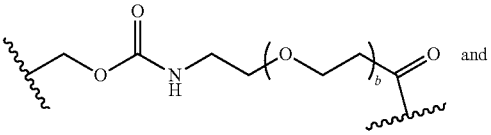 and

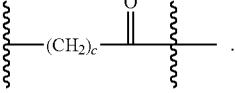

In some examples, SP¹ is

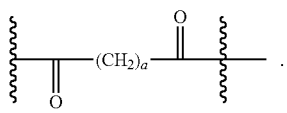

In some other examples, SP¹ is

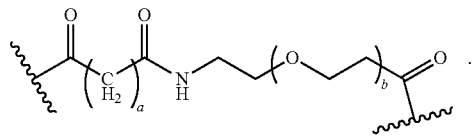

In other examples, SP¹ is

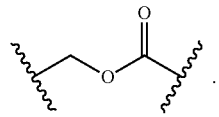 [SMILES: *COC(*)=O]

In still other examples, SP¹ is

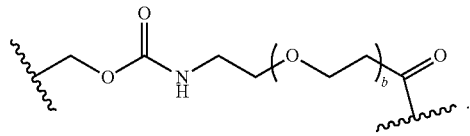

In some other examples, SP¹ is

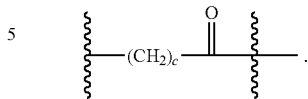

In any of the above examples, subscripts a, b, and c are independently, in each instance, an integer from 1 to 20.

In some embodiments, $R^{AA3}$ is selected from

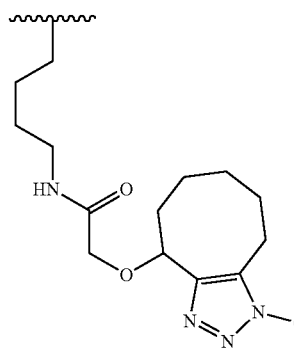

wherein CD is a cyclodextrin moiety. In some embodiments, $R^{AA3}$ is selected from

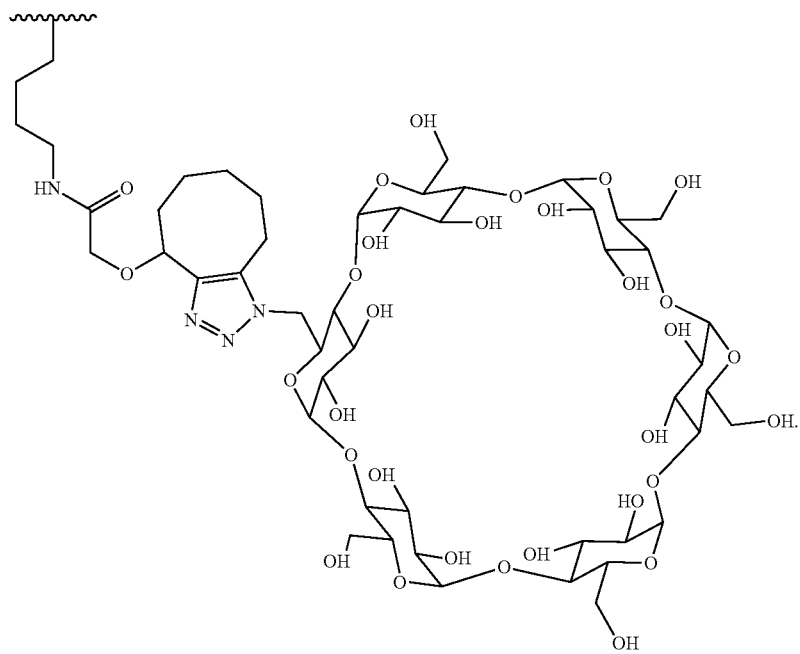 [SMILES: *CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O]

In any of the compounds of Formula (II), (IIa), (IIb), or (IIc), SP¹ is selected from:
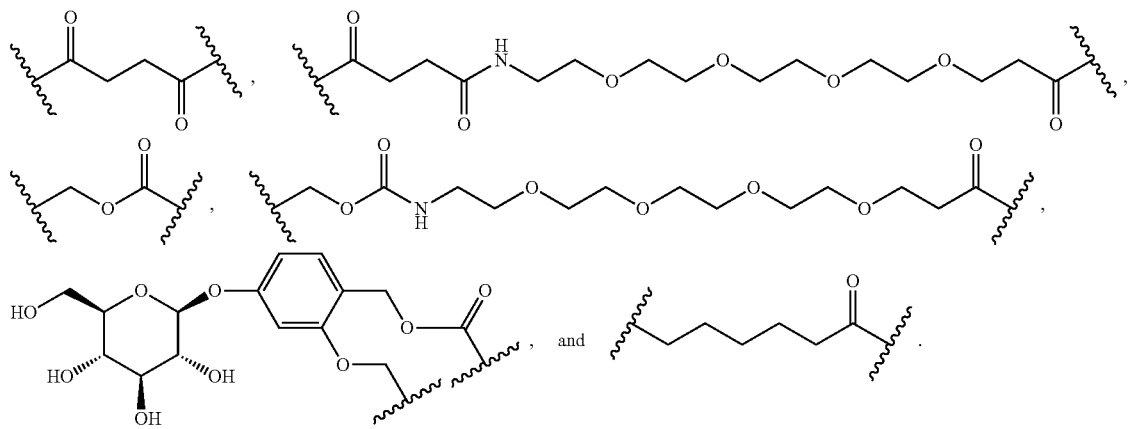
In some examples, SP¹ is
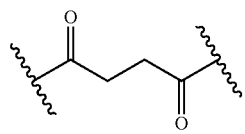
In some examples, SP¹ is
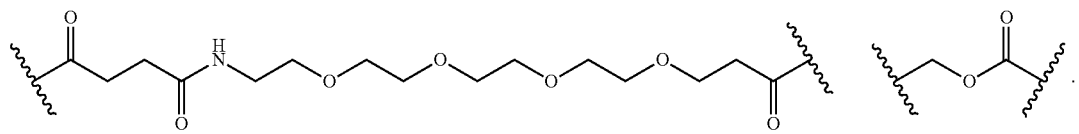 [SMILES: *C(=O)CCOCCOCCOCCOCCNC(=O)CCC(*)=O ; *COC(*)=O]
In some examples, SP¹ is
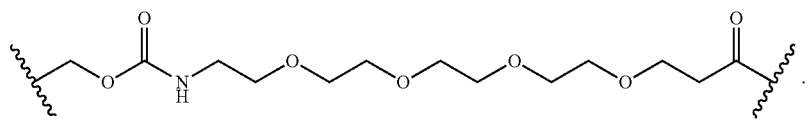 [SMILES: *COC(=O)NCCOCCOCCOCCOCCC(*)=O]
In some examples, SP¹ is
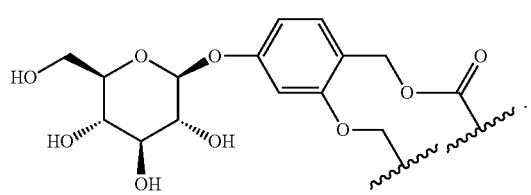 [SMILES: *COc1cc(O[C@@H]2O[C@H](CO)[C@@H](O)[C@H](O)[C@H]2O)ccc1COC(*)=O]
In some examples, SP¹ is
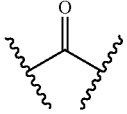
In some examples, SP¹ is
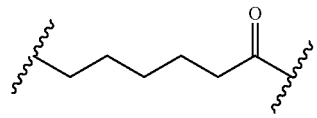
In some examples, SP¹ is
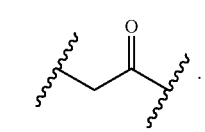 [SMILES: *CC(*)=O]

In some examples, SP¹ is
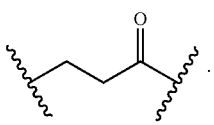 [SMILES: *CCC(*)=O]
In some examples, SP¹ is
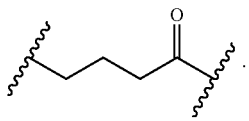 [SMILES: *CCCC(*)=O]
In some examples, SP¹ is
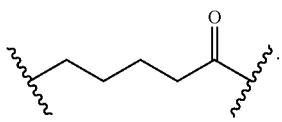 [SMILES: *CCCCC(*)=O]
In some examples, SP¹ is
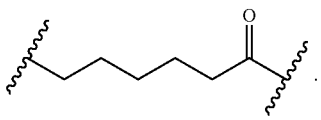 [SMILES: *CCCCCC(*)=O]
In some embodiments, BL-SP¹ is:
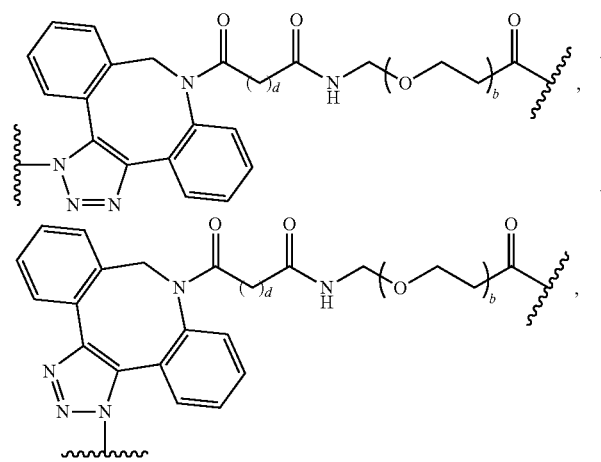
or mixture thereof;
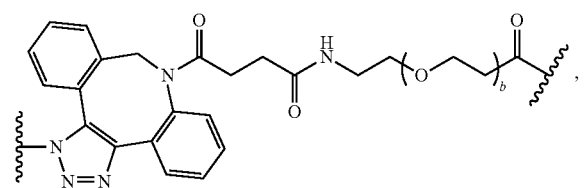
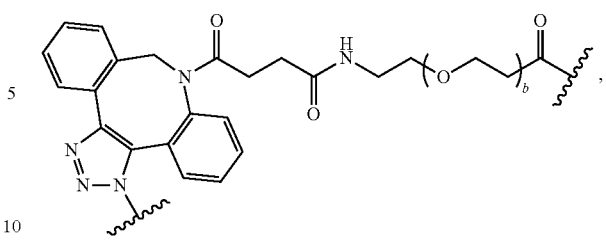
or mixture thereof;
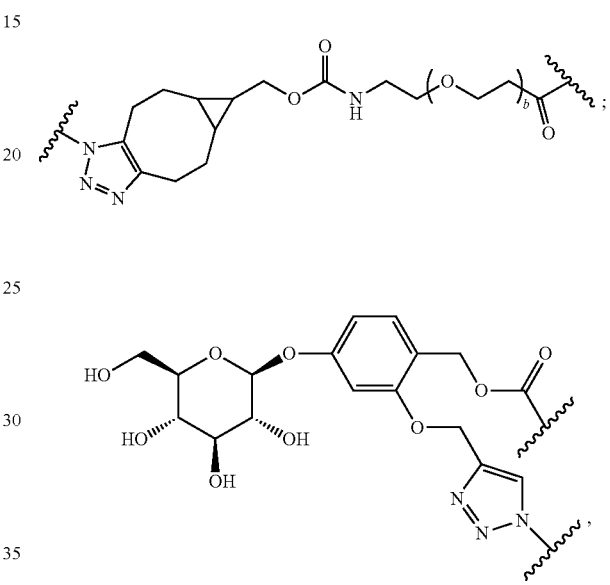
or mixture thereof; or
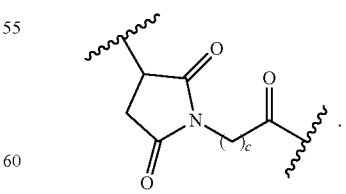
In some of these examples, subscripts b, c, and d are independently, in each instance, an integer from 1 to 20.
In any of the compounds of Formula (II), (IIa), (IIb), or (IIc), BL-SP¹ is selected from:

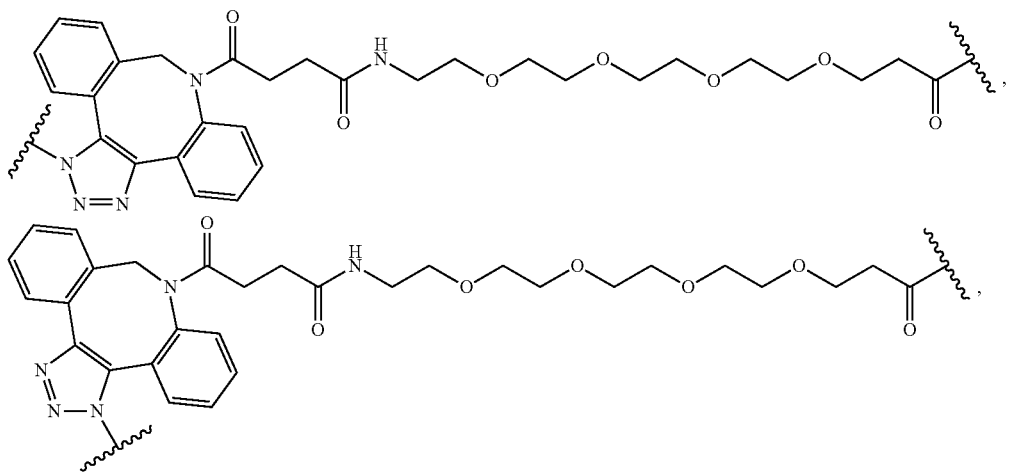

or mixture thereof;

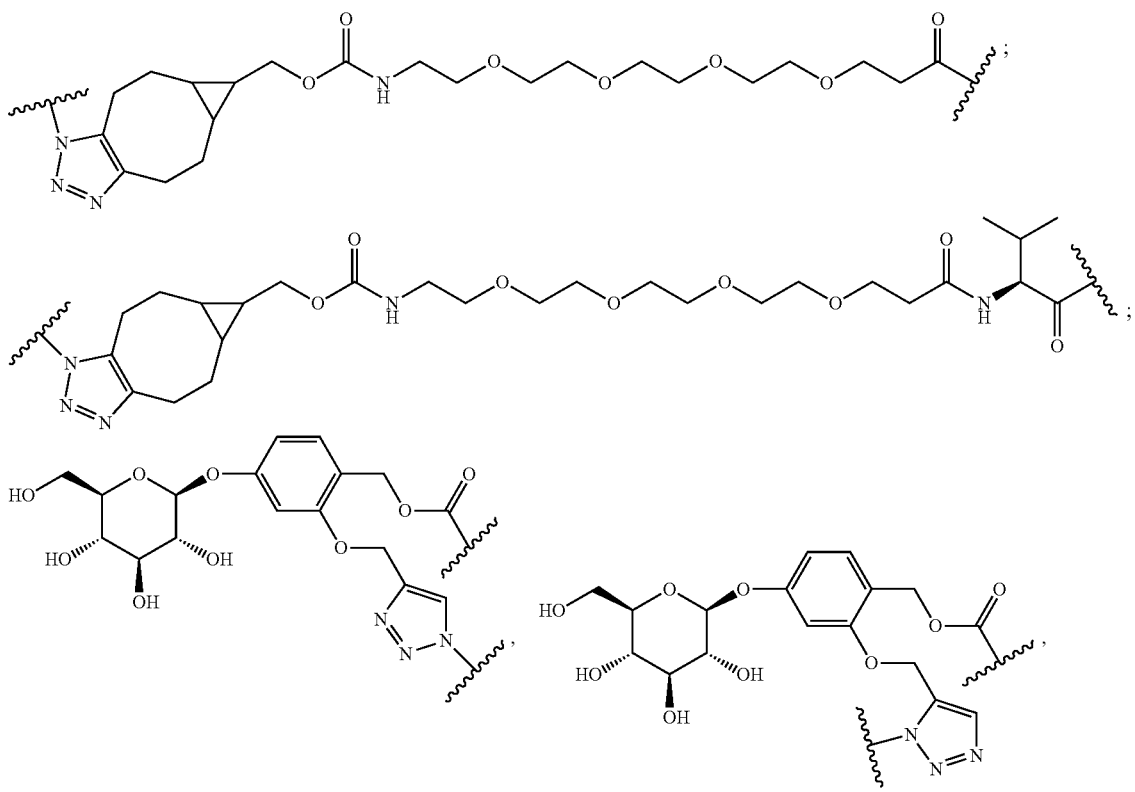

or mixture thereof; or

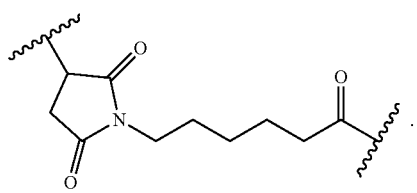 [SMILES: *C(=O)CCCCCN1C(=O)CC(*)C1=O]

In some embodiments, A is a peptide selected from valine-citrulline, citrulline-valine, lysine-phenylalanine, phenylalanine-lysine, valine-asparagine, asparagine-valine, threonine-asparagine, asparagine-threonine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, or asparagine-alanine.

In some examples, A is valine-citrulline or citrulline-valine.

In some examples, A is valine-alanine or alanine-valine.

In some examples, A is lysine-valine-alanine or alanine-valine-lysine.

In some examples, A is lysine-valine-citrulline or citrulline-valine-lysine.

In some examples, A is valine.

In some examples, A is alanine.

In some examples, A is citrulline.

In some examples, A is

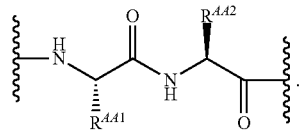

In some of these examples, $R^{AA1}$ is an amino acid side chain, and wherein $R^{AA2}$ is an amino acid side chain.

In some examples, A is

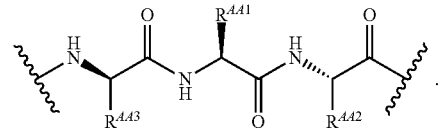

In some of these examples, $R^{AA1}$ is an amino acid side chain, $R^{AA2}$ is an amino acid side chain, and $R^{AA3}$ is an amino acid side chain that is bonded directly or indirectly to a cyclodextrin moiety.

In some examples, A is

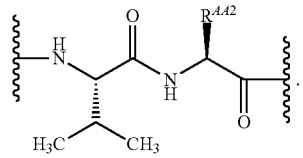

In some examples, A is

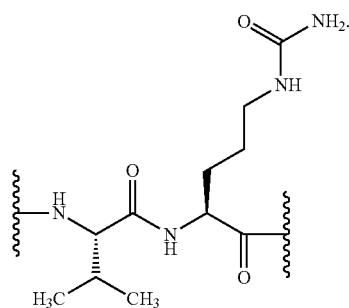 [SMILES: *N[C@H](C(=O)N[C@@H](CCCNC(N)=O)C(*)=O)C(C)C]

In some examples, A is

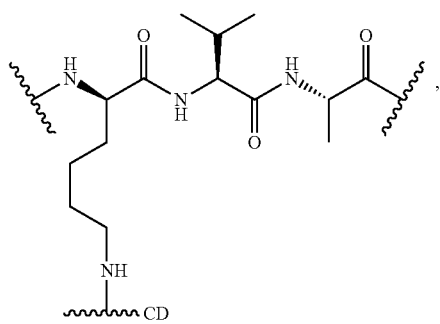

wherein ⁓CD represents a direct or indirect bond to a cyclodextrin moiety.

In some examples, including any of the foregoing, CD is, independently in each instance, selected from

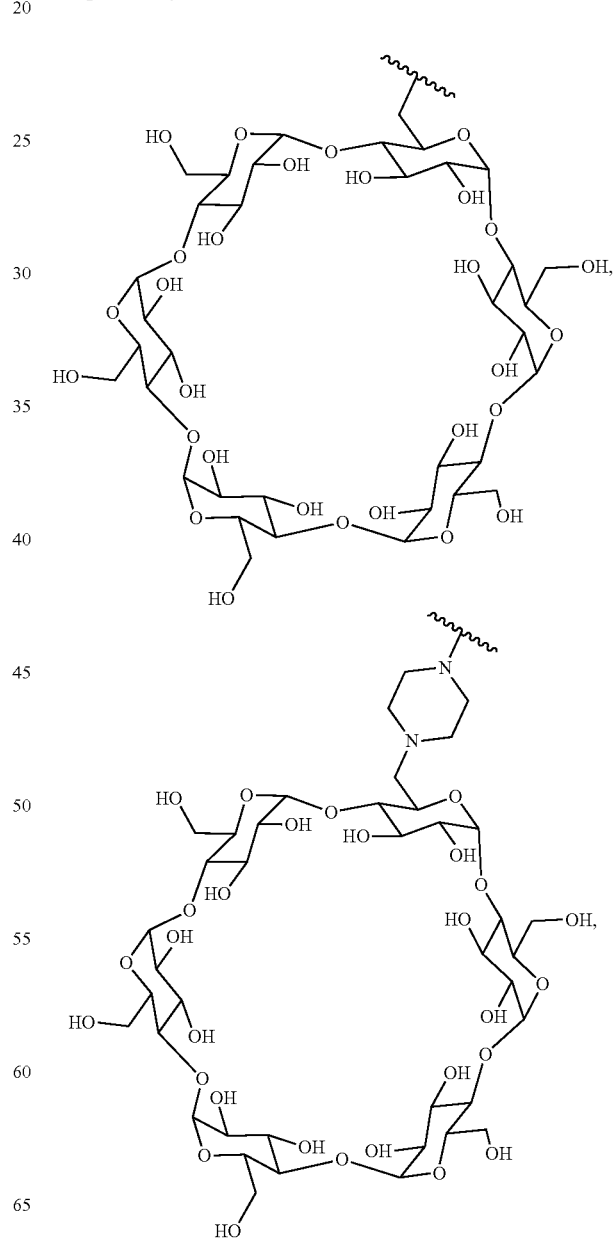

141
-continued
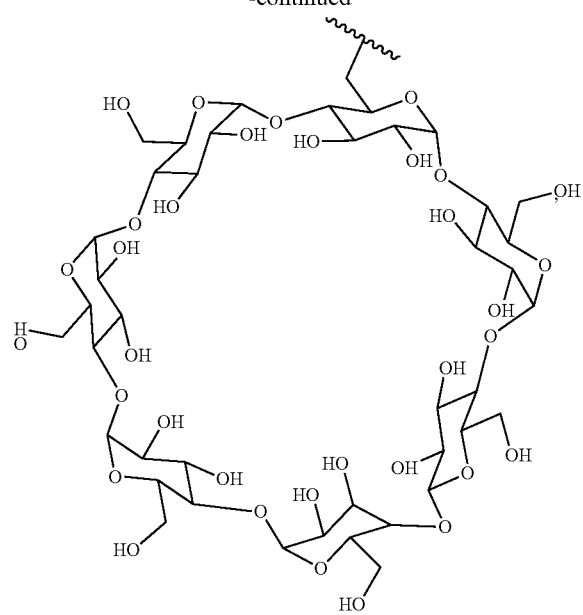
142
-continued
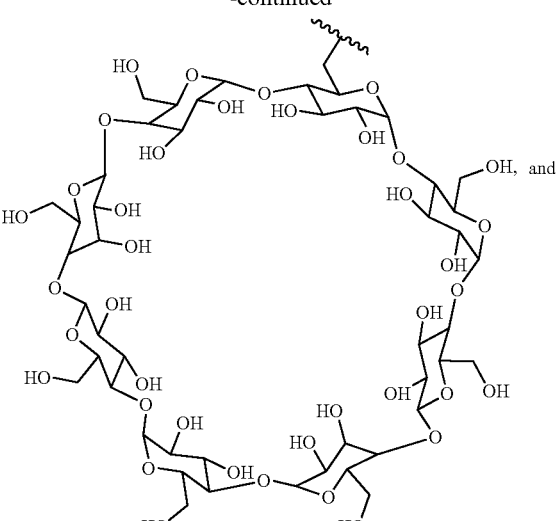
OH, and
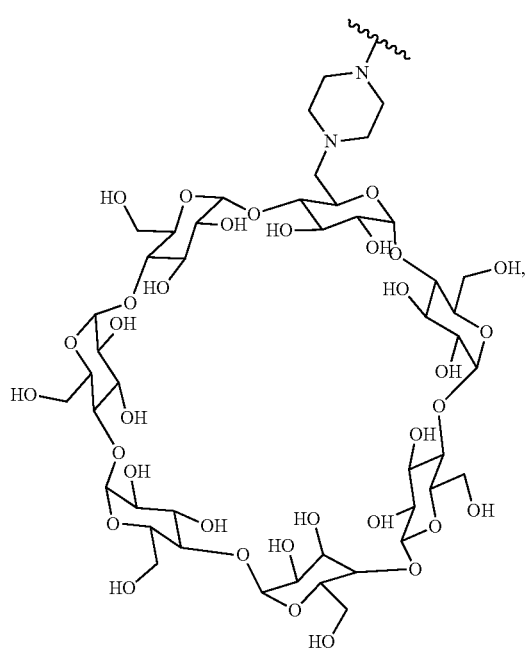
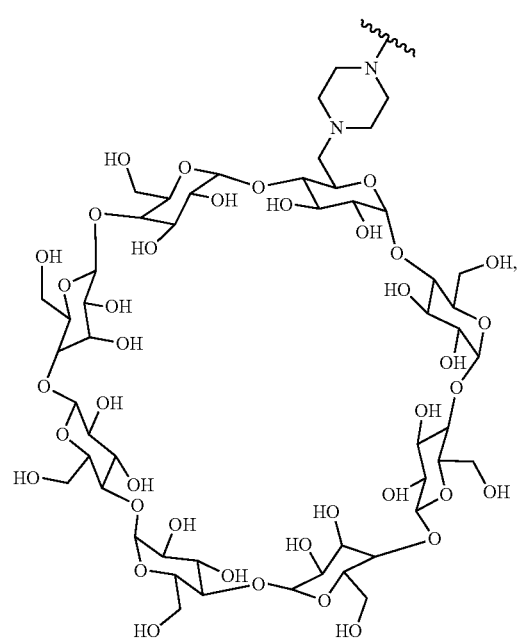

In some examples, the CD is
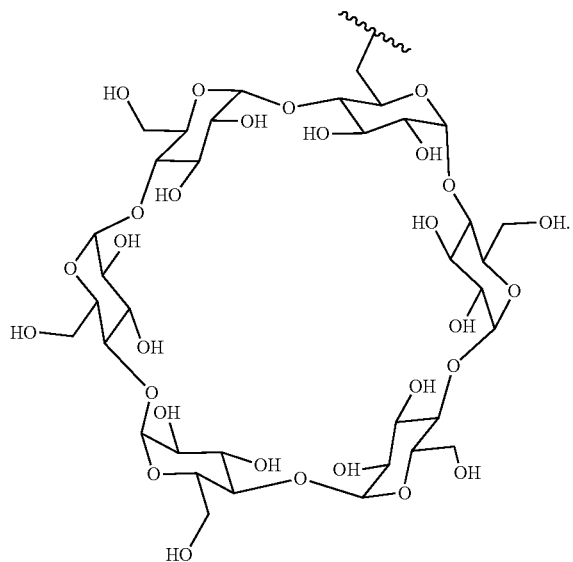 [SMILES: *CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O]
In some examples, the CD is
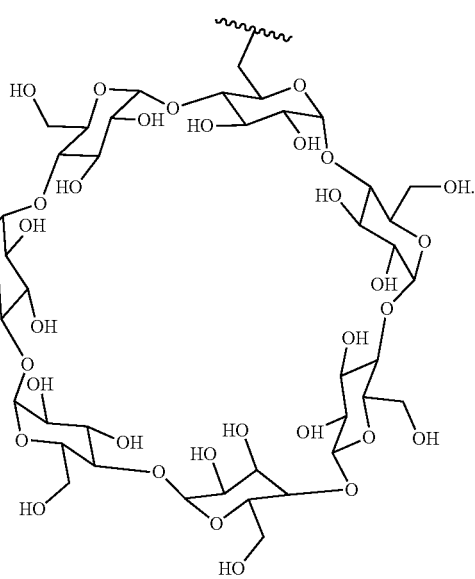
In some examples, the CD is
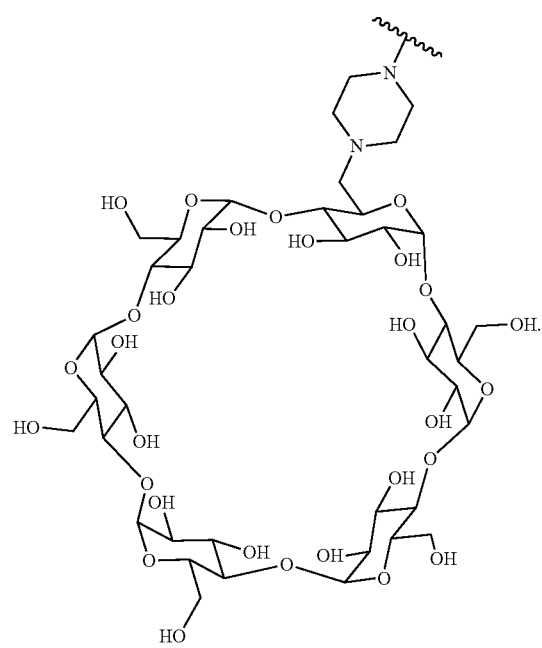 [SMILES: *N1CCN(CC2OC3OC4C(CO)OC(OC5C(CO)OC(OC6C(CO)OC(OC7C(CO)OC(OC8C(CO)OC(OC2C(O)C3O)C(O)C8O)C(O)C7O)C(O)C6O)C(O)C5O)C(O)C4O)CC1]
In some examples, the CD is
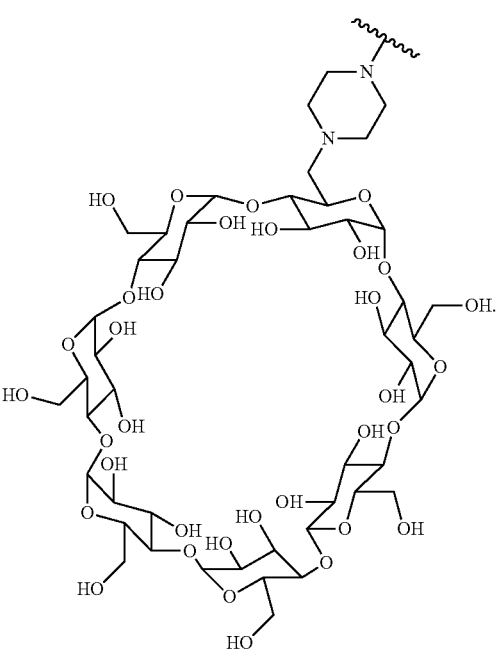 [SMILES: *N1CCN(CC2OC3OC4C(CO)OC(OC5C(CO)OC(OC6C(CO)OC(OC7C(CO)OC(OC8C(CO)OC(OC9C(CO)OC(OC2C(O)C3O)C(O)C9O)C(O)C8O)C(O)C7O)C(O)C6O)C(O)C5O)C(O)C4O)CC1]

In some examples, the CD is

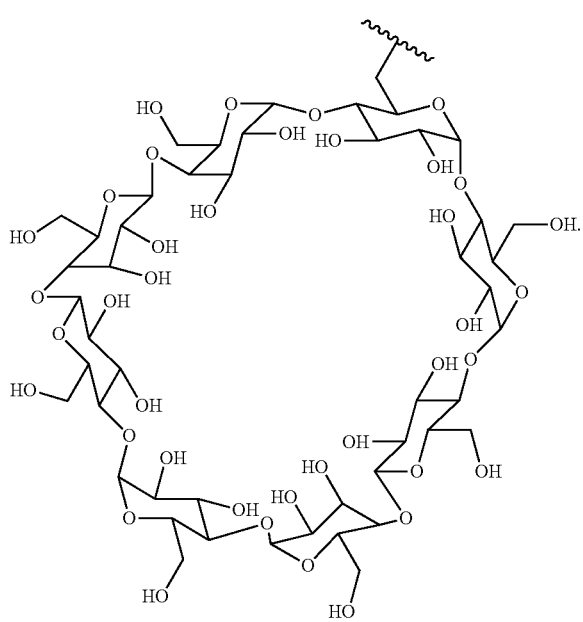 [SMILES: *CC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O]

In some examples, the CD is

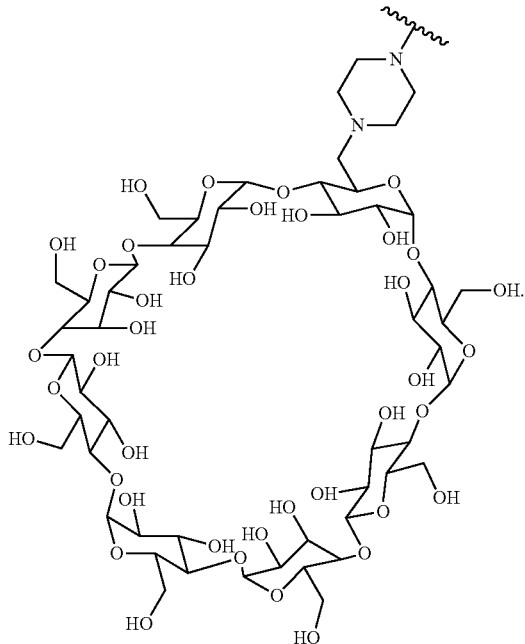 [SMILES: *N1CCN(CC2OC3OC4C(CO)OC(OC5C(CO)OC(OC6C(CO)OC(OC7C(CO)OC(OC8C(CO)OC(OC9C(CO)OC(OC%10C(CO)OC(OC2C(O)C3O)C(O)C%10O)C(O)C9O)C(O)C8O)C(O)C7O)C(O)C6O)C(O)C5O)C(O)C4O)CC1]

In some examples, A is

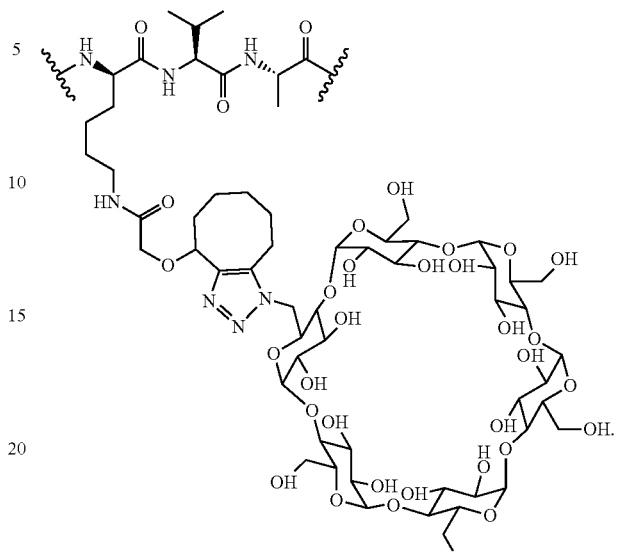

In some examples, $R^a$ is H.
In some examples, $R^a$ is alkyl.
In some examples, $R^a$ is methyl, ethyl, n-propyl, i-propyl, n-butyl, t-butyl, i-butyl, or pentyl.
In some embodiments, B is aryl.
In some examples, B is phenyl.
In some examples of compounds of Formula (II), (IIa), (IIb), or (IIc), B is phenyl or pyridinyl.
In some examples herein, B is:

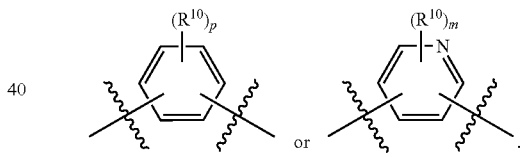

In these examples, $R^{10}$ is alkyl, alkenyl, alkynyl, alkoxy, aryl, alkylaryl, arylalkyl, halo, haloalkyl, haloalkoxy, heteroaryl, heterocycloalkyl, hydroxyl, cyano, nitro,

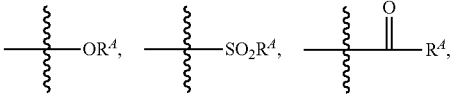

$NR^aR^b$, or azido. In these examples, subscripts p and m are independently, in each instance, selected from an integer from 0 to 4.
In some examples herein, B is:

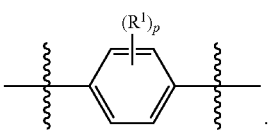

In these examples, p is 0, 1, 2, 3 or 4. In some of these examples, $R^1$ is, independently at each occurrence, alkyl, alkoxy, haloalkyl, or halo. In some examples, $R^1$ is alkyl. In some examples, $R^1$ is alkoxy. In some examples, $R^1$ is haloalkyl. In some examples, $R^1$ is halo.
In some embodiments of Formula (BL$^A$), the —(NR$^a$)$_s$—(B)$_t$—(CH$_2$)$_u$—(O)$_v$-(SP$^2$)$_w$ is:
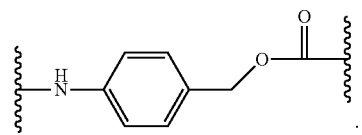 [SMILES: *Nc1ccc(COC(*)=O)cc1]
Set forth herein are antibody-steroid conjugates having the following formulas:
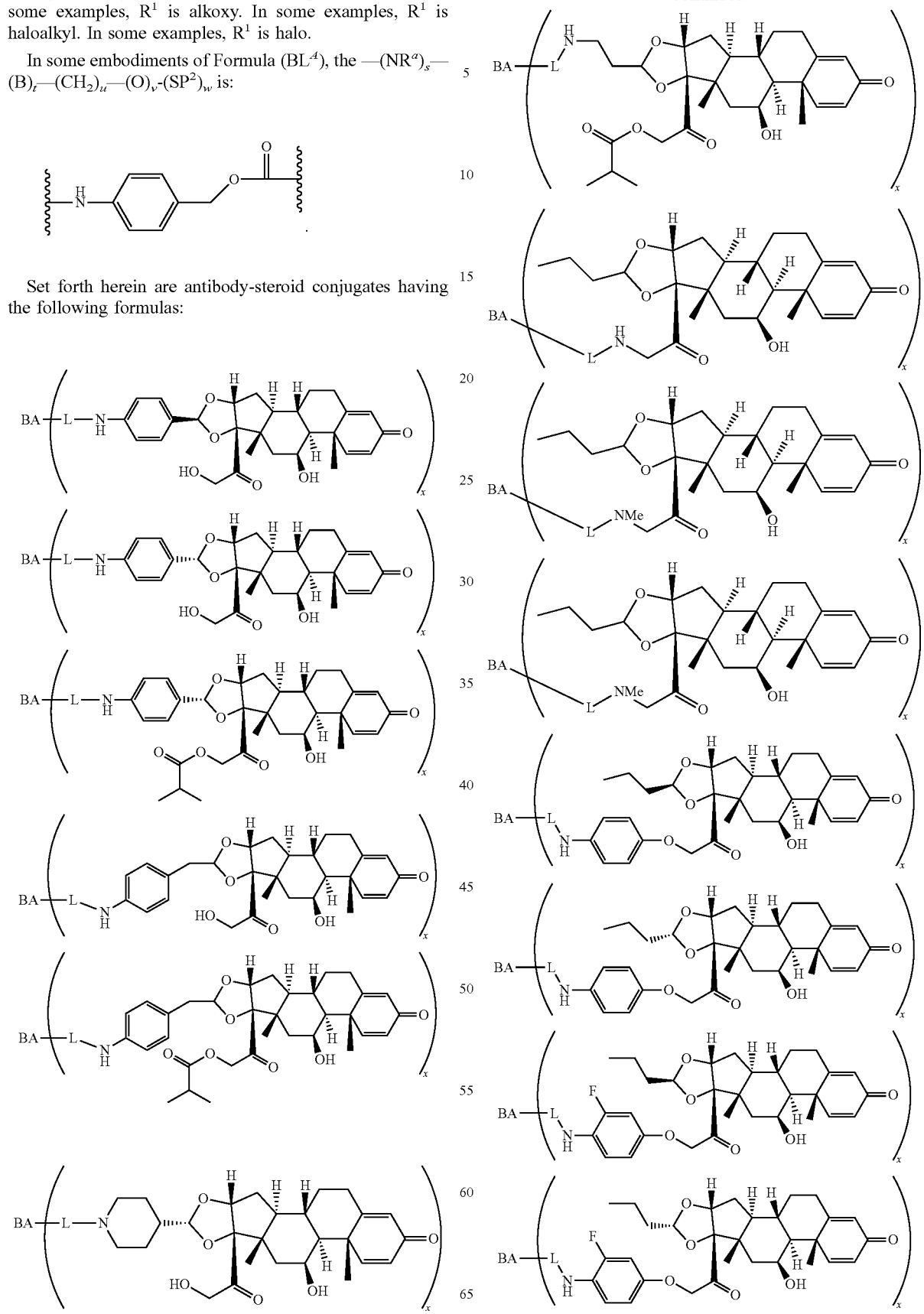

-continued
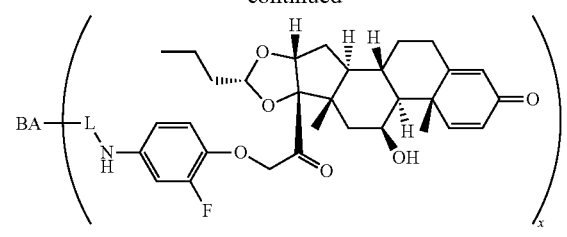
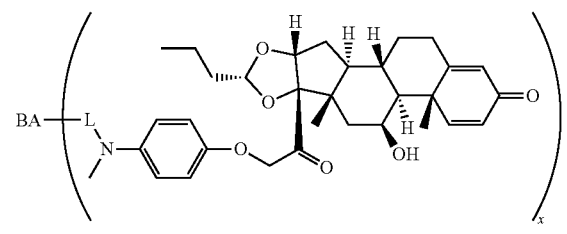
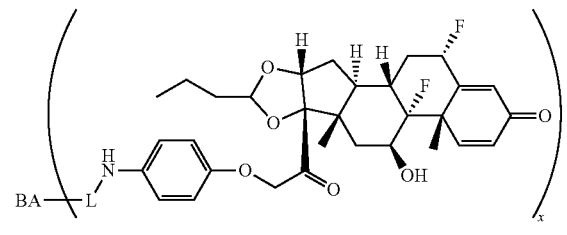
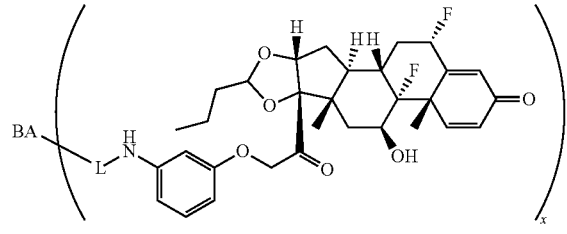
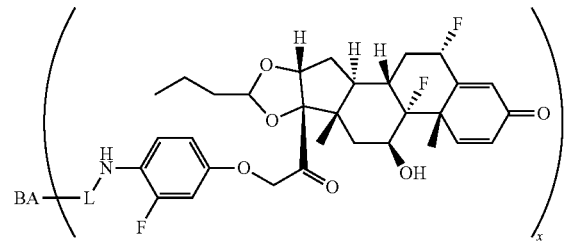
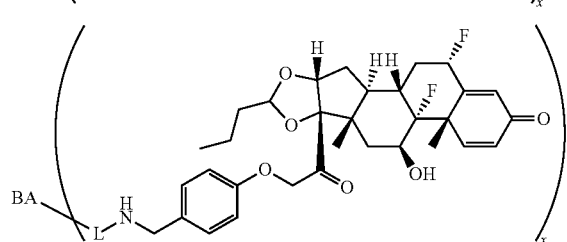
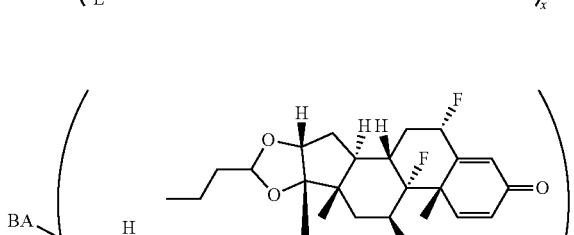
-continued
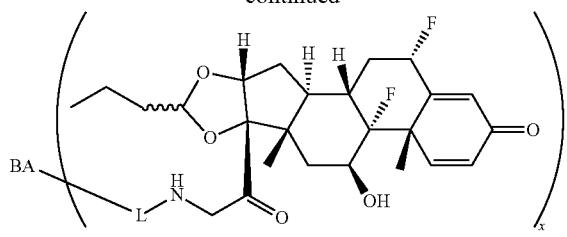
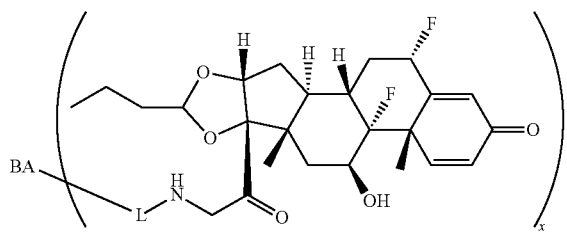
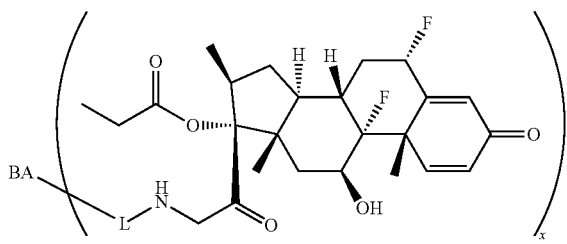
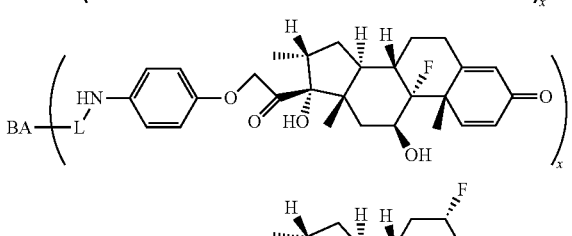
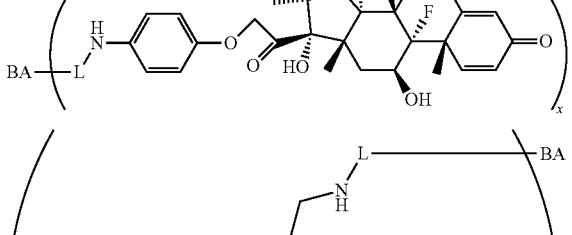
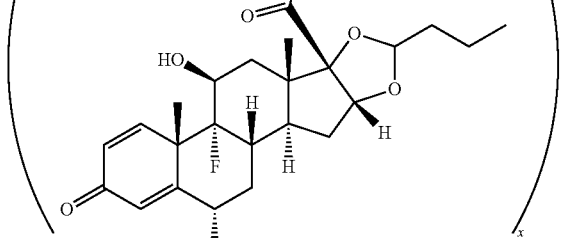
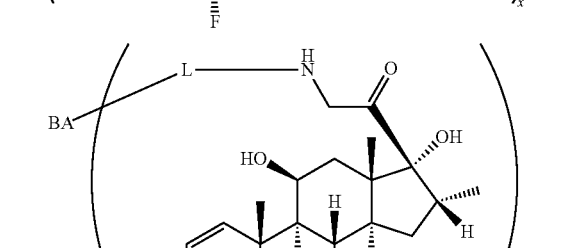

151
-continued
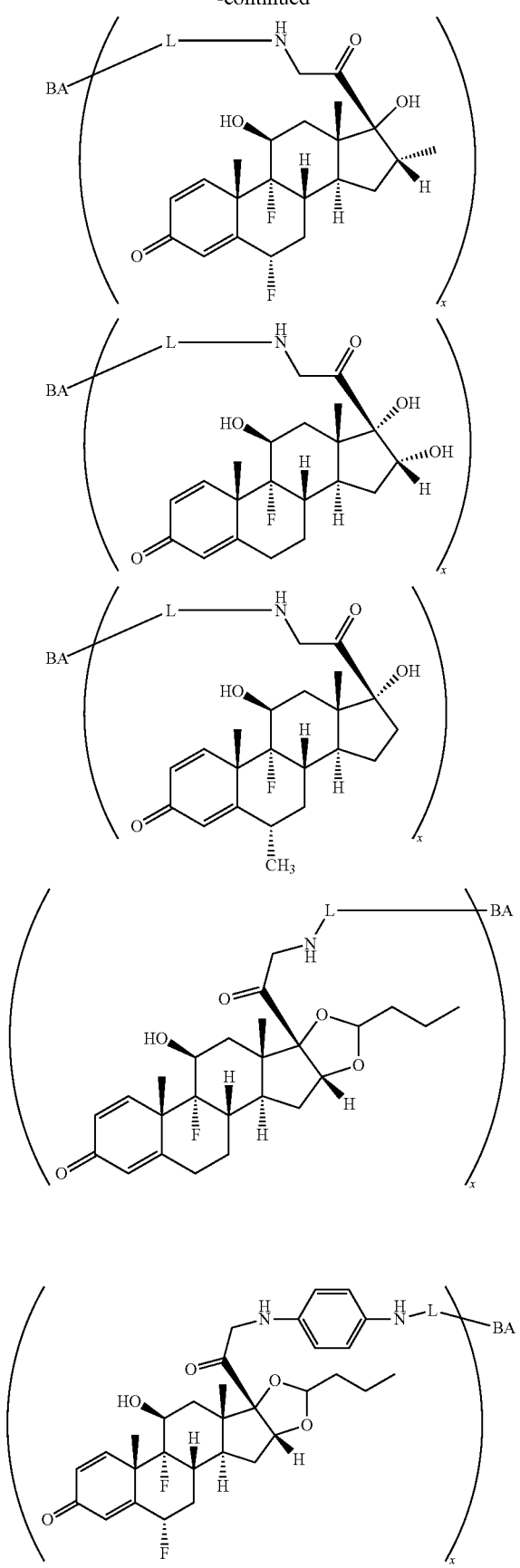
152
-continued
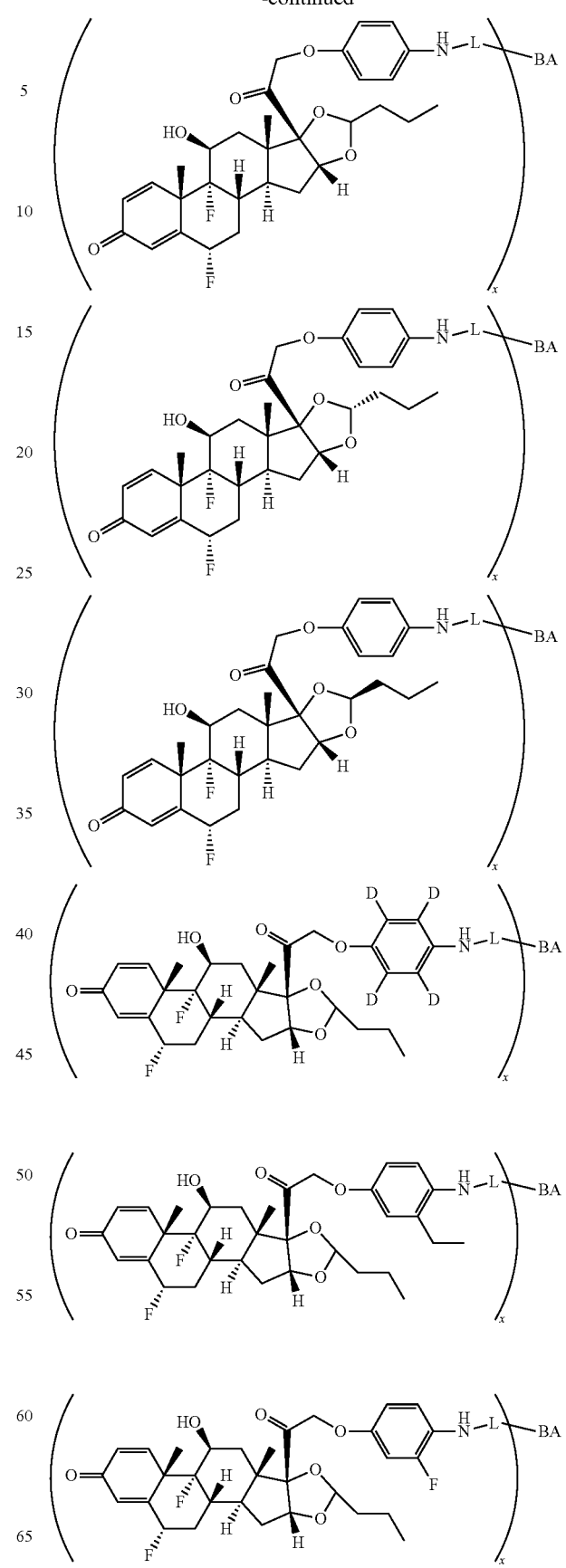

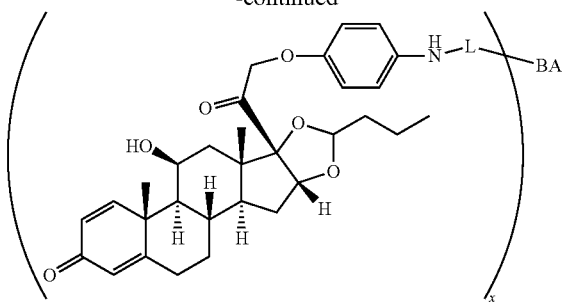

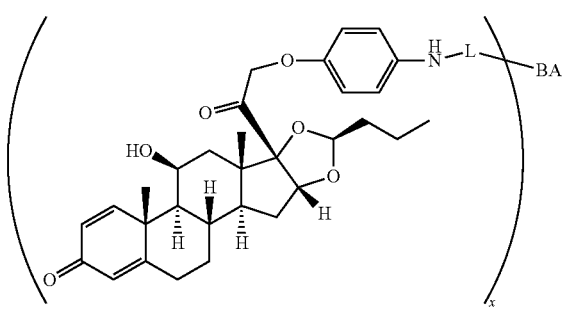

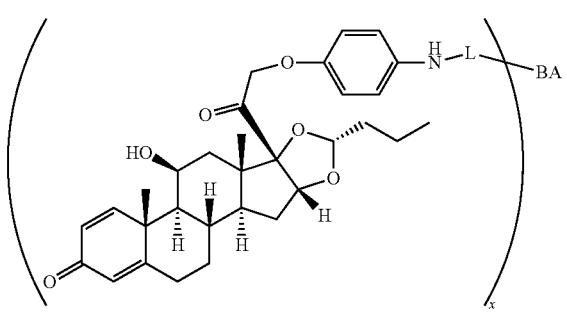

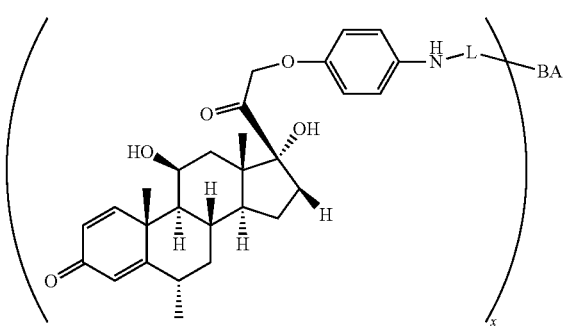

or a pharmaceutically acceptable salt or solvate thereof; wherein BA is a binding agent, and x is an integer from 1-30. In particular embodiments, BA is an antibody. In some embodiments, x is an integer from 1 to 4. In some embodiments, x is 4. In some embodiments, x is 2.

Set forth herein are antibody-steroid conjugates according to Formula 1200:

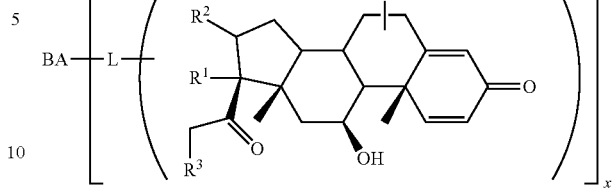

or a pharmaceutically acceptable salt, solvate, or stereoisomer thereof, wherein: BA is a binding agent; each L is an optional linker; BA or L is covalently bonded to $R^3$ or $R^4$; and x is an integer from 1 to 30. Those of skill will recognize that when L is present, L is bonded to $R^3$ or $R^4$; when L is not present, BA is bonded to $R^3$ or $R^4$. The groups $R^3$ or $R^4$ are described in detail below. In particular embodiments, BA is an antibody. In some embodiments, x is an integer from 1 to 4. In some embodiments, x is 4. In some embodiments, x is 2.

In certain embodiments of Formula 1200, $R^1$ and $R^2$ are, independently, selected from the group consisting of —H, —OH, alkyl, —O—C(O)-alkyl, and halo; or $R^1$ and $R^2$ together form

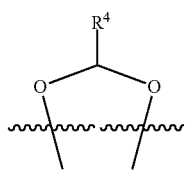

In certain embodiments, $R^3$ is selected from the group consisting of -alkylene-$NR^aR^b$, —X-arylene-Y—$NR^aR^b$, —X-heteroarylene-Y—$NR^aR^b$, and N-containing heterocycloalkyl; wherein X is absent, —N—, —$CH_2$—, or —O—; wherein Y is absent or —$CH_2$—; and $R^4$ is selected from the group consisting of alkyl, aryl, alkylaryl, arylalkyl, heteroaryl, -alkylene-$NR^aR^b$, —X-arylene-Y—$NR^aR^b$, —X-heteroarylene-Y—$NR^aR^b$, and N-containing heterocycloalkyl; wherein X is absent, —N—, —$CH_2$—, or —O—; wherein Y is absent or —$CH_2$—.

In certain embodiments of Formula 1200, $R^3$ is selected from the group consisting of —OH, —O—C(O)-alkyl, —O-aryl, —$NR^aR^b$, -alkylene-$NR^aR^b$, —X-arylene-Y—$NR^aR^b$, —X-heteroarylene-Y—$NR^aR^b$, and N-containing heterocycloalkyl; wherein X is absent, —N—, —$CH_2$—, or —O—; wherein Y is absent or —$CH_2$—; and $R^4$ is selected from the group consisting of -alkylene-$NR^aR^b$, —X-arylene-Y—$NR^aR^b$, —X-heteroarylene-Y—$NR^aR^b$, and N-containing heterocycloalkyl; wherein X is absent, —N—, —$CH_2$—, or —O—; wherein Y is absent or —$CH_2$—.

In certain embodiments of Formula 1200, $R^3$ is —$NR^aR^b$; and $R^4$ is alkyl.

In each embodiment of Formula 1200, BA or L is bonded to a functional group in $R^3$ or $R^4$. For instance, if $R^3$ or $R^4$ comprises a amino group, BA or L can be bonded to the amino group, substituting for a hydrogen atom. In each embodiment, $R^5$ is, independently in each instance, selected from a substituent in the group consisting of —OH, halo, and alkyl; n is an integer from 0-19; and each $R^5$ is positioned on any ring atom. In each embodiment, $R^a$ and $R^b$ are, independently in each instance, selected from the group consisting of —H and alkyl; or $R^a$ and $R^b$ cyclize to form cycloheteroalkyl with three to six ring atoms, including one hetero atom, which is the N to which they are attached. In particular embodiments, BA is an antibody. In some embodiments, x is an integer from 1 to 4. In some embodiments, x is 4. In some embodiments, x is 2.

Set forth herein are antibody-steroid conjugates according to according to Formula 1210, 1220, 1230, or 1240:

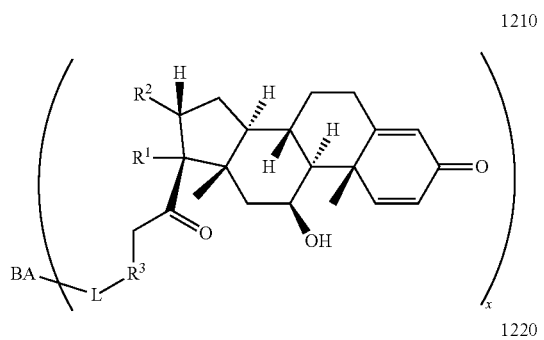

1210

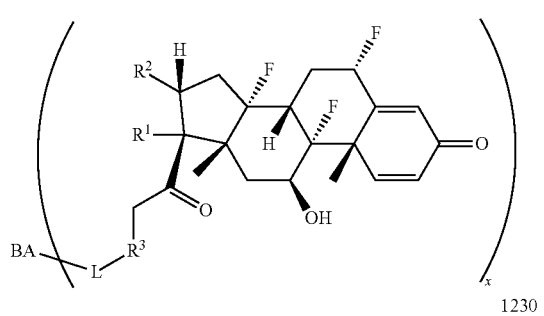

1220

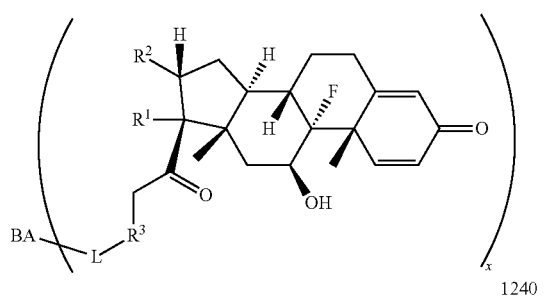

1230

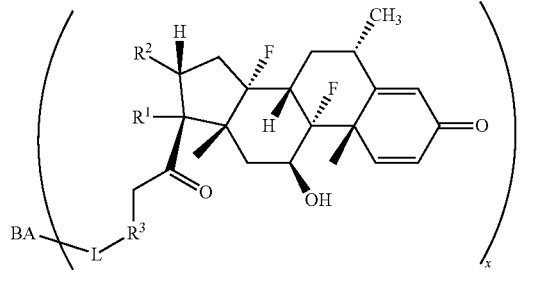

1240 or a pharmaceutically acceptable salt, solvate, or stereoisomer thereof; wherein $R^3$ is covalently bonded to L or BA.

In certain embodiments of Formula 1210, 1220, 1230, or 1240, $R^1$ and $R^2$ are, independently, selected from the group consisting of —H, —OH, alkyl, —O—C(O)-alkyl, and halo; or $R^1$ and $R^2$ together form

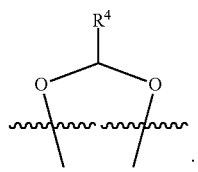

In certain embodiments, $R^3$ is selected from the group consisting of -alkylene-$NR^aR^b$, —X-arylene-Y—$NR^aR^b$, —X-heteroarylene-Y—$NR^aR^b$, and N-containing heterocycloalkyl; wherein X is absent, —N—, —$CH_2$—, or —O—; wherein Y is absent or —$CH_2$—; and $R^4$ is selected from the group consisting of alkyl, aryl, alkylaryl, arylalkyl, heteroaryl, -alkylene-$NR^aR^b$, —X-arylene-Y—$NR^aR^b$, —X-heteroarylene-Y—$NR^aR^b$, and N-containing heterocycloalkyl; wherein X is absent, —N—, —$CH_2$—, or —O—; wherein Y is absent or —$CH_2$—. In certain embodiments, $R^3$ is —$NR^aR^b$; and $R^4$ is alkyl. In each embodiment, BA or L is bonded to an amino group in $R^3$, for instance, substituting for a hydrogen atom. In each embodiment, $R^a$ and $R^b$ are, independently in each instance, selected from the group consisting of —H and alkyl; or $R^a$ and $R^b$ cyclize to form cycloheteroalkyl with three to six ring atoms, including one hetero atom, which is the N to which they are attached. In particular embodiments, BA is an antibody. In some embodiments, x is an integer from 1 to 4. In some embodiments, x is 4. In some embodiments, x is 2.

Set forth herein are antibody-steroid conjugates according to according to Formula 1310, 1320, 1330, or 1340:

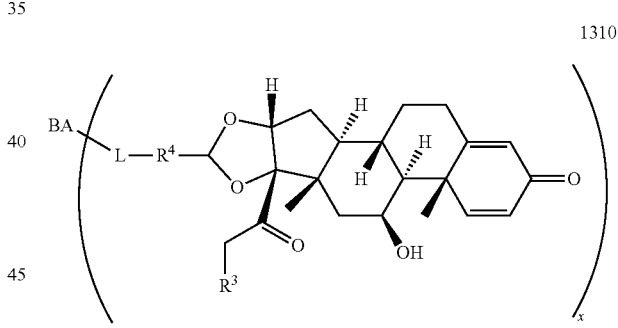

1310

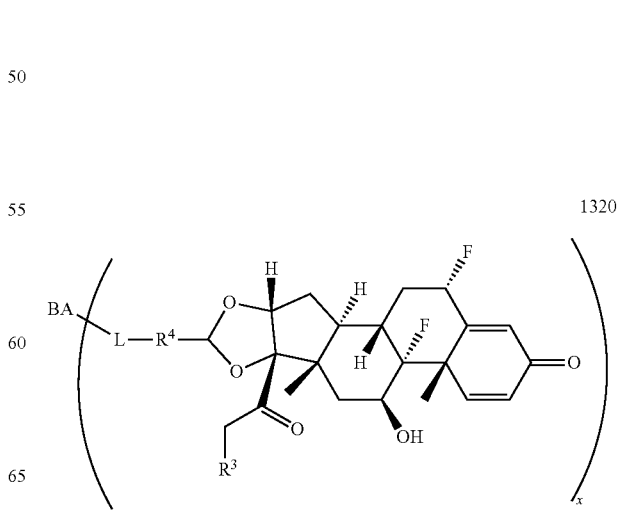

1320

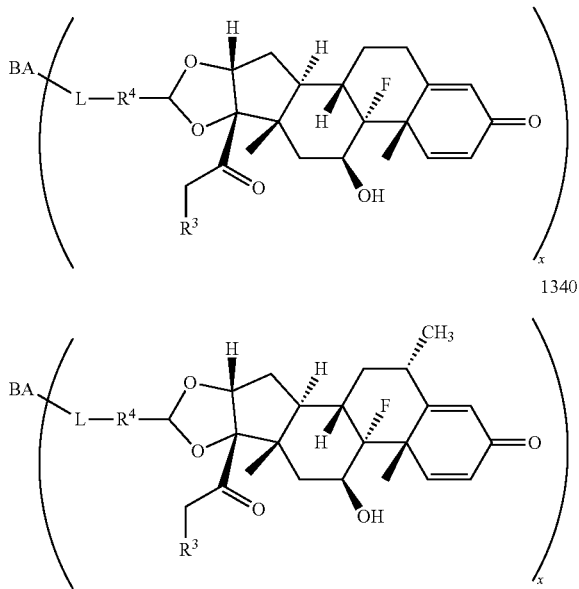

or a pharmaceutically acceptable salt, solvate, or stereoisomer thereof; wherein $R^4$ is covalently bonded to L or BA.

In certain embodiments of Formula 1310, 1320, 1330, or 1340, $R^3$ is selected from the group consisting of —OH, —O—C(O)-alkyl, —O-aryl, —NR$^a$R$^b$, -alkylene-NR$^a$R$^b$, —X-arylene-Y—NR$^a$R$^b$, —X-heteroarylene-Y—NR$^a$R$^b$, and N-containing heterocycloalkyl; wherein X is absent, —N—, —CH$_2$—, or —O—; wherein Y is absent or —CH$_2$—; and $R^4$ is selected from the group consisting of -alkylene-NR$^a$R$^b$, —X-arylene-Y—NR$^a$R$^b$, —X-heteroarylene-Y—NR$^a$R$^b$, and N-containing heterocycloalkyl; wherein X is absent, —N—, —CH$_2$—, or —O—; wherein Y is absent or —CH$_2$—. In each embodiment, BA or L is bonded to an amino group in $R^4$, for instance, substituting for a hydrogen atom. In each embodiment, $R^a$ and $R^b$ are, independently in each instance, selected from the group consisting of —H and alkyl; or $R^a$ and $R^b$ cyclize to form cycloheteroalkyl with three to six ring atoms, including one hetero atom, which is the N to which they are attached. In particular embodiments, BA is an antibody. In some embodiments, x is an integer from 1 to 4. In some embodiments, x is 4. In some embodiments, x is 2.

Set forth herein are also antibody-steroid conjugates having the following formulas:

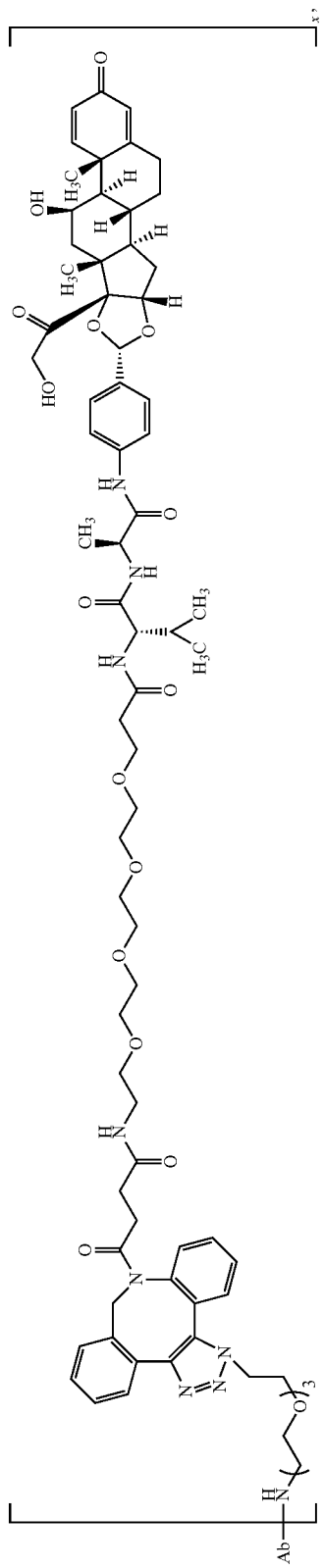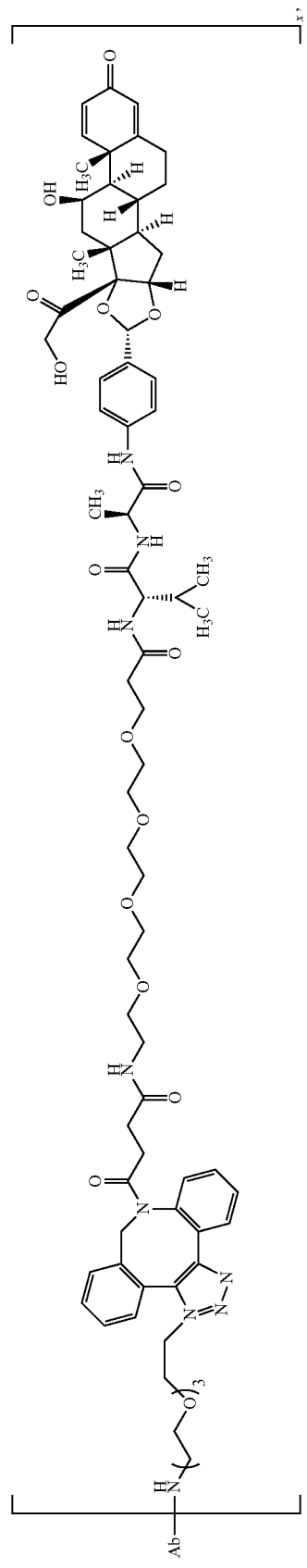

or mixture thereof;

163 164
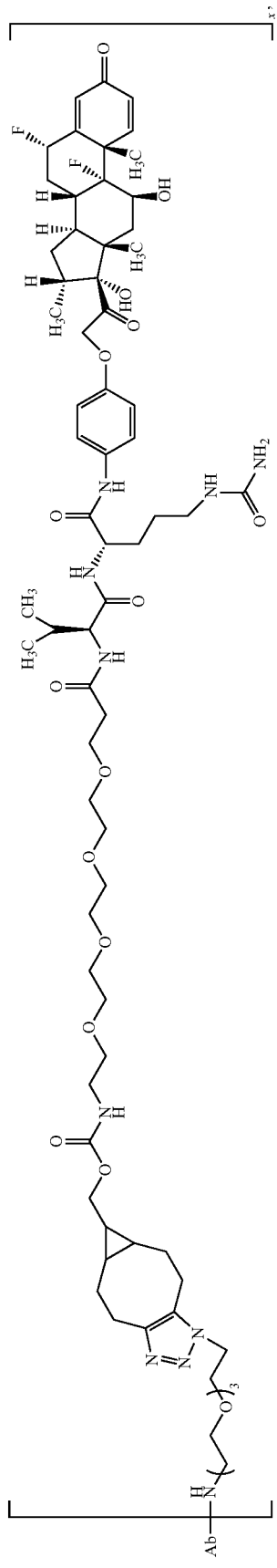
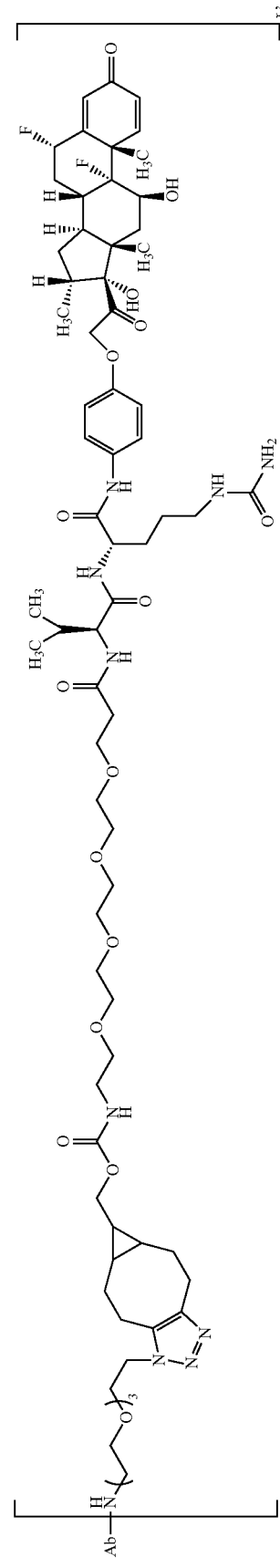

or mixture thereof;

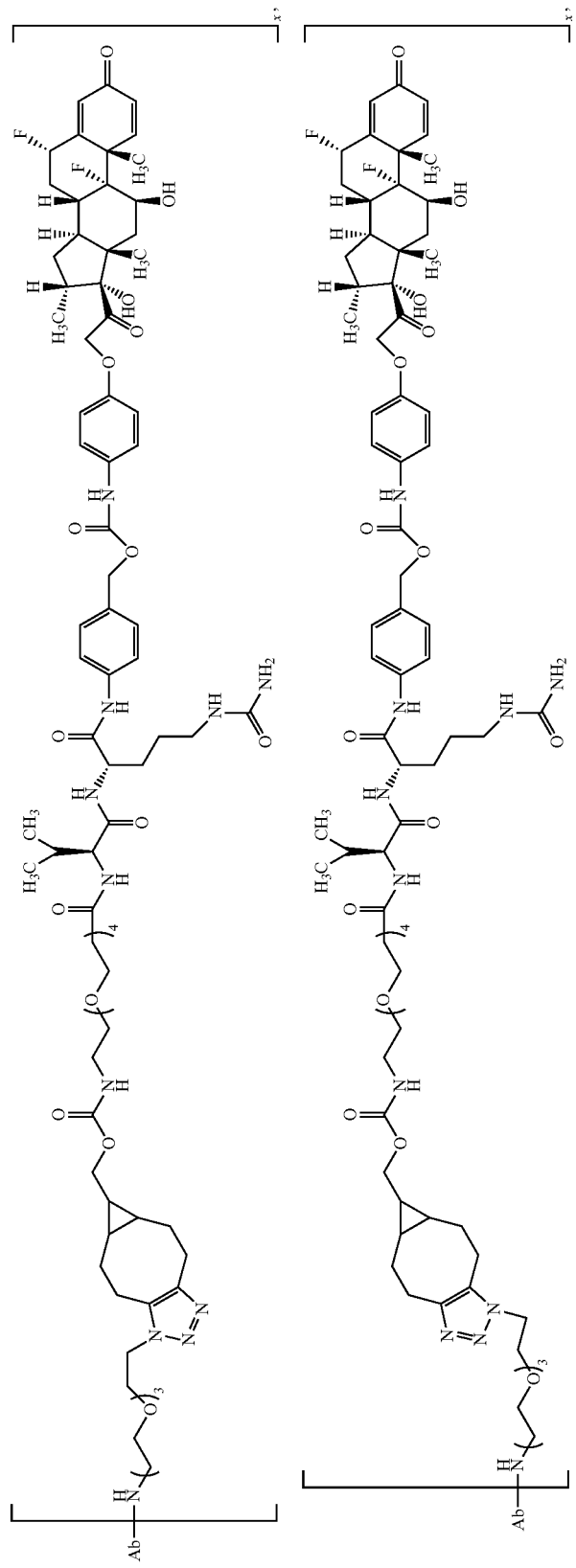

or mixture thereof;
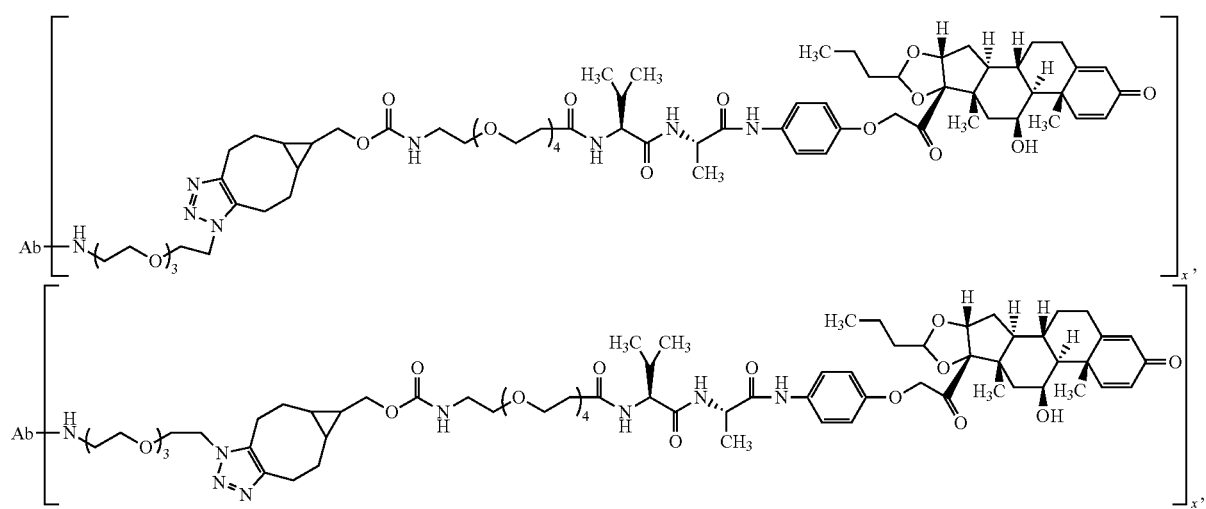
or mixture thereof;

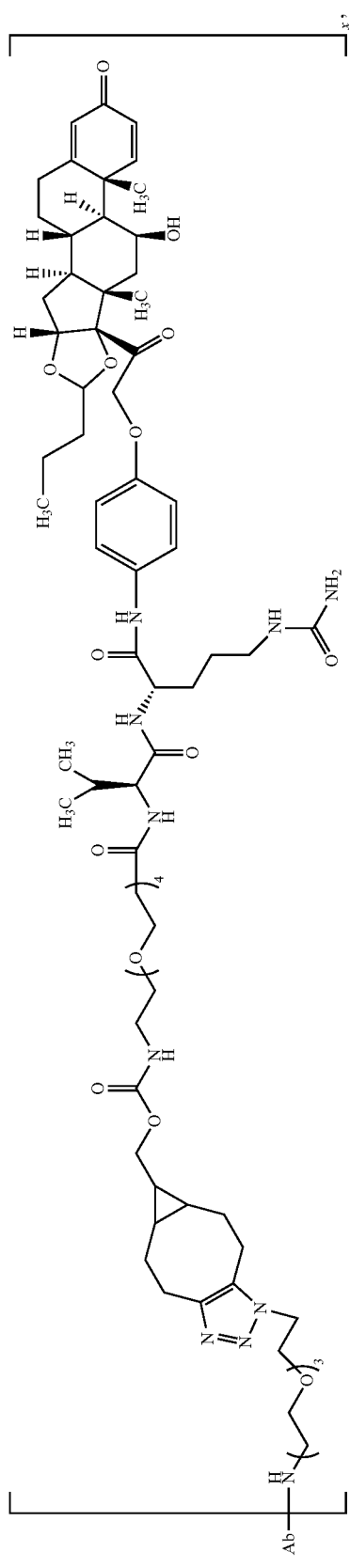 171
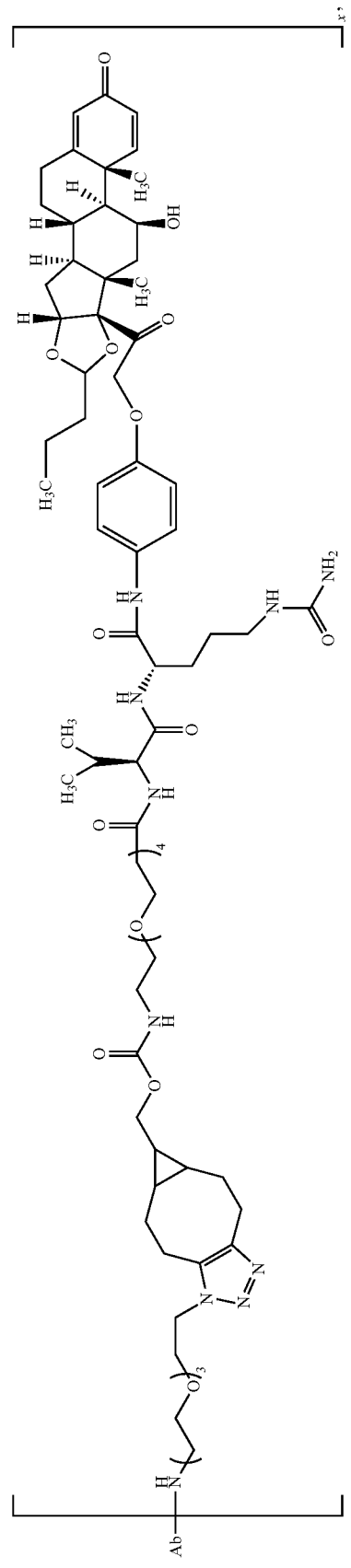 172 or mixture thereof;
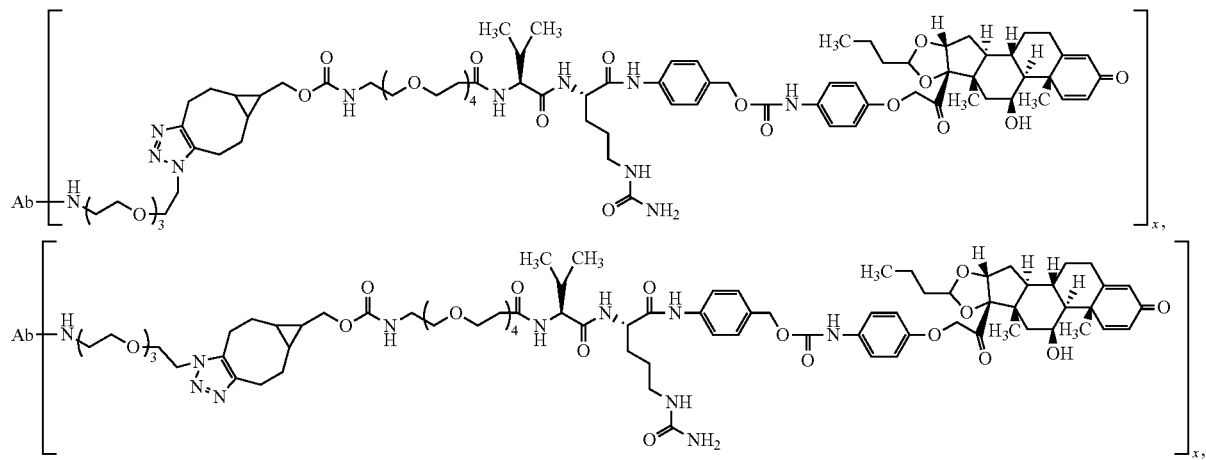
or mixture thereof;
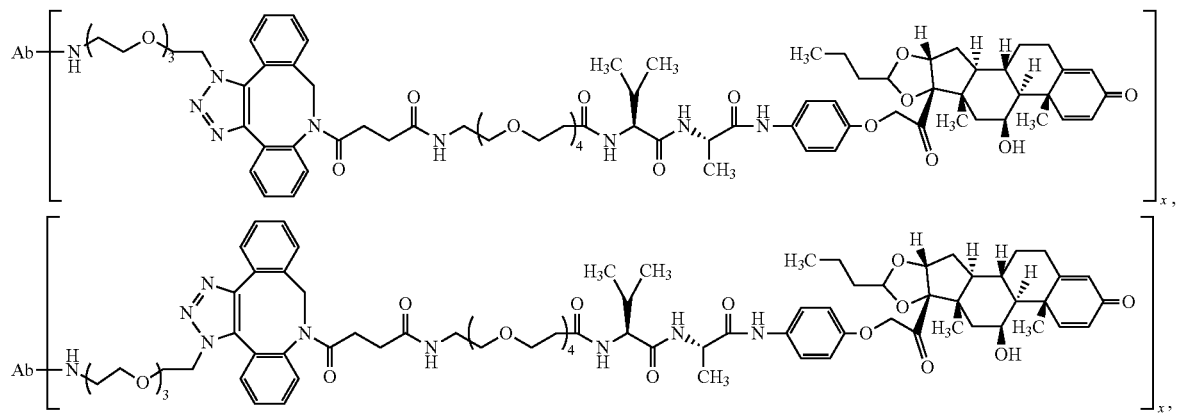
or mixture thereof;
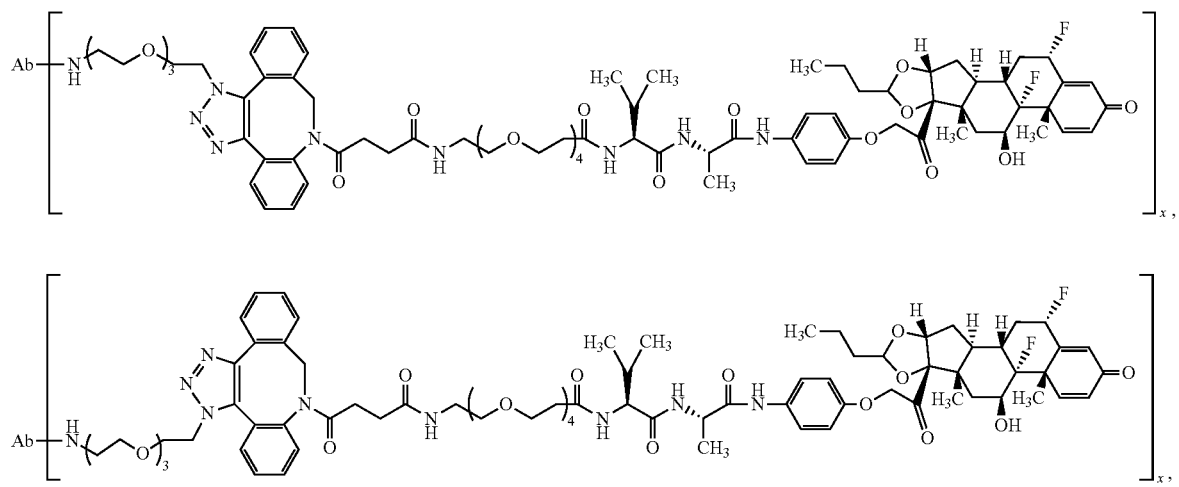
or mixture thereof;

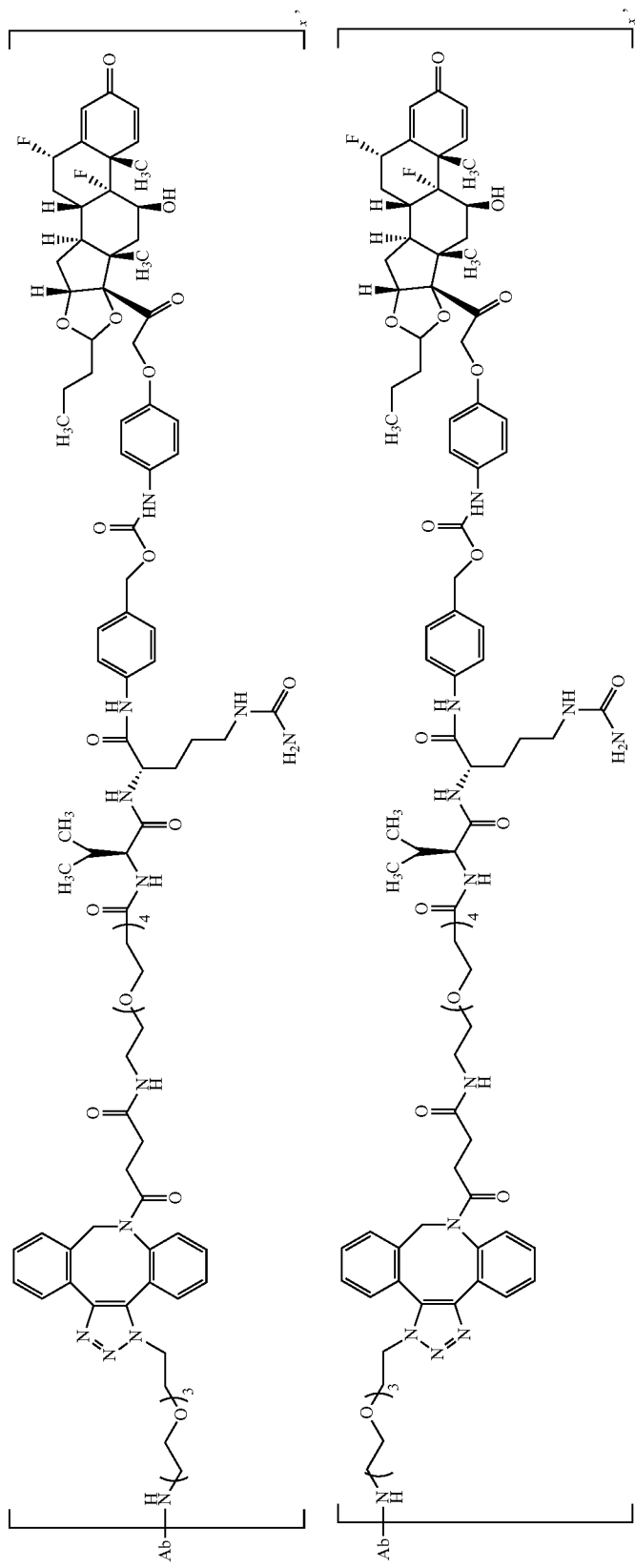

or mixture thereof;
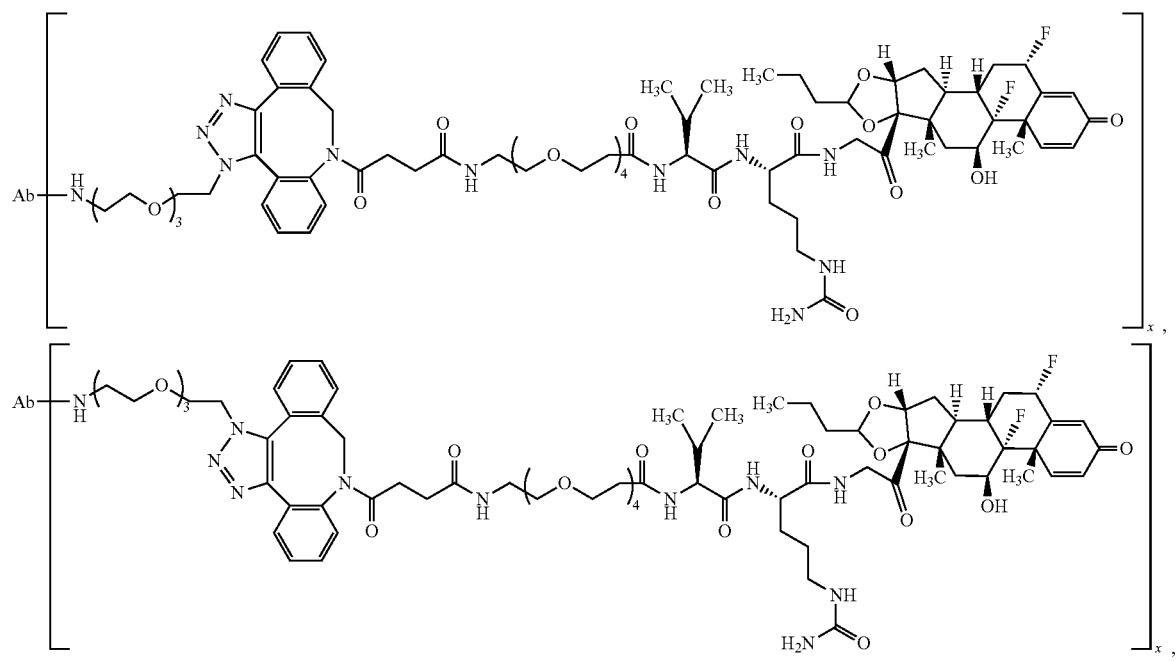
or mixture thereof;

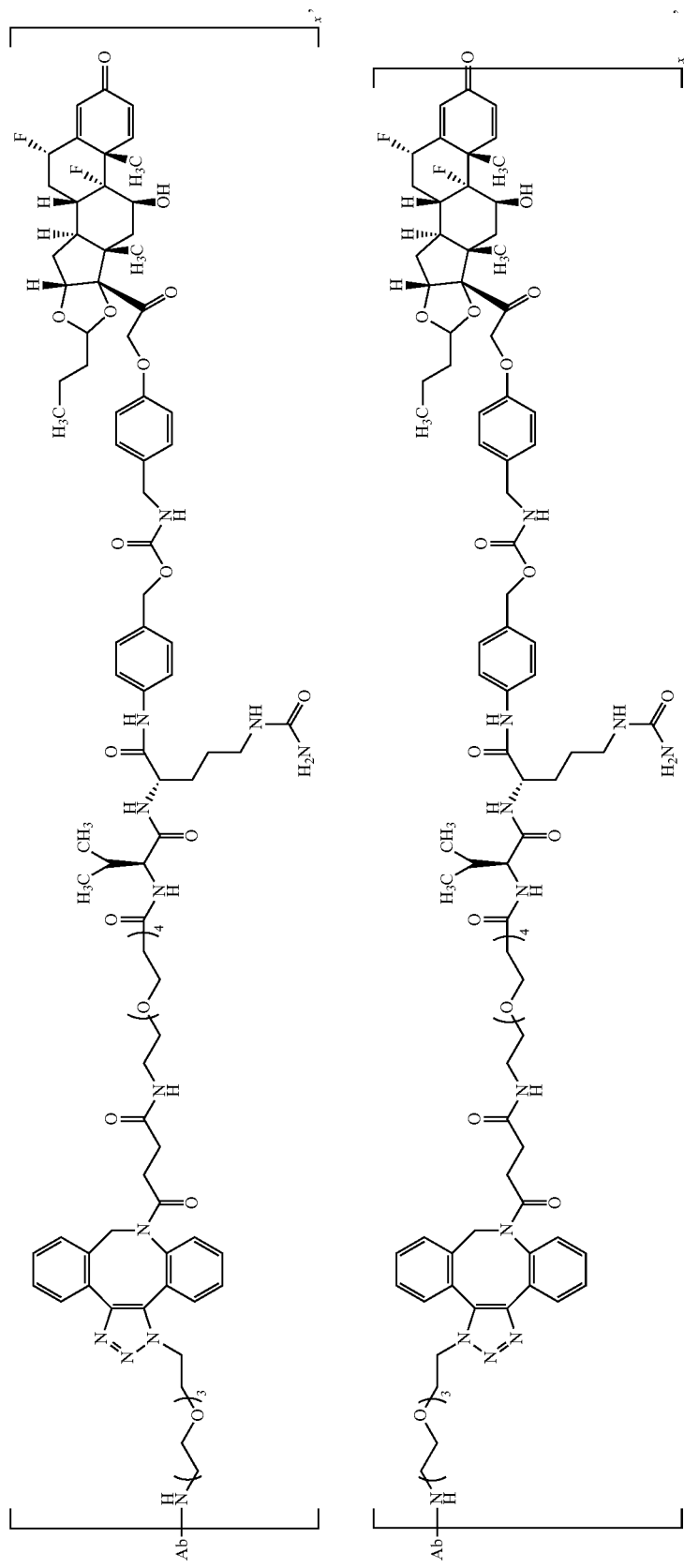

or mixture thereof; wherein Ab is an antibody and x is an integer from 1-30. In some embodiments, x is an integer from 1 to 4. In some embodiments, x is 4. In some embodiments, x is 2.

Set forth herein are also antibody-steroid conjugates having the following formulas:

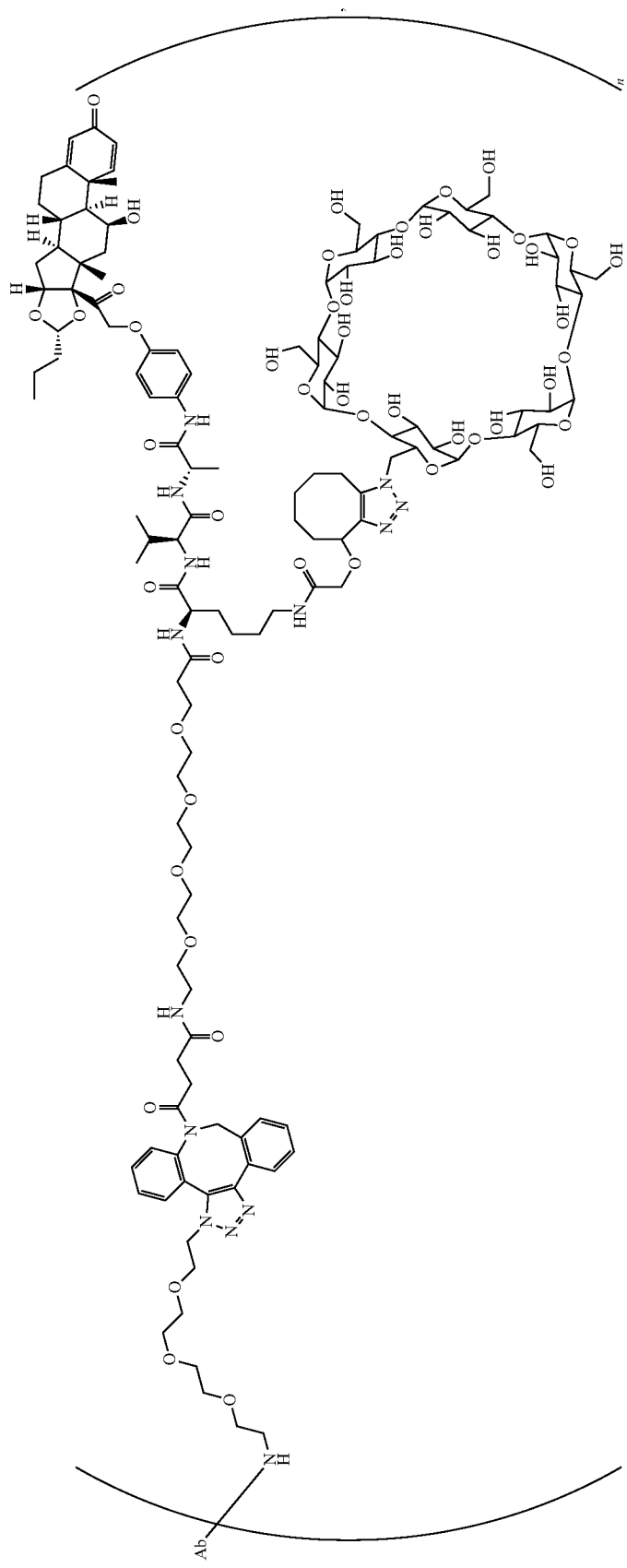

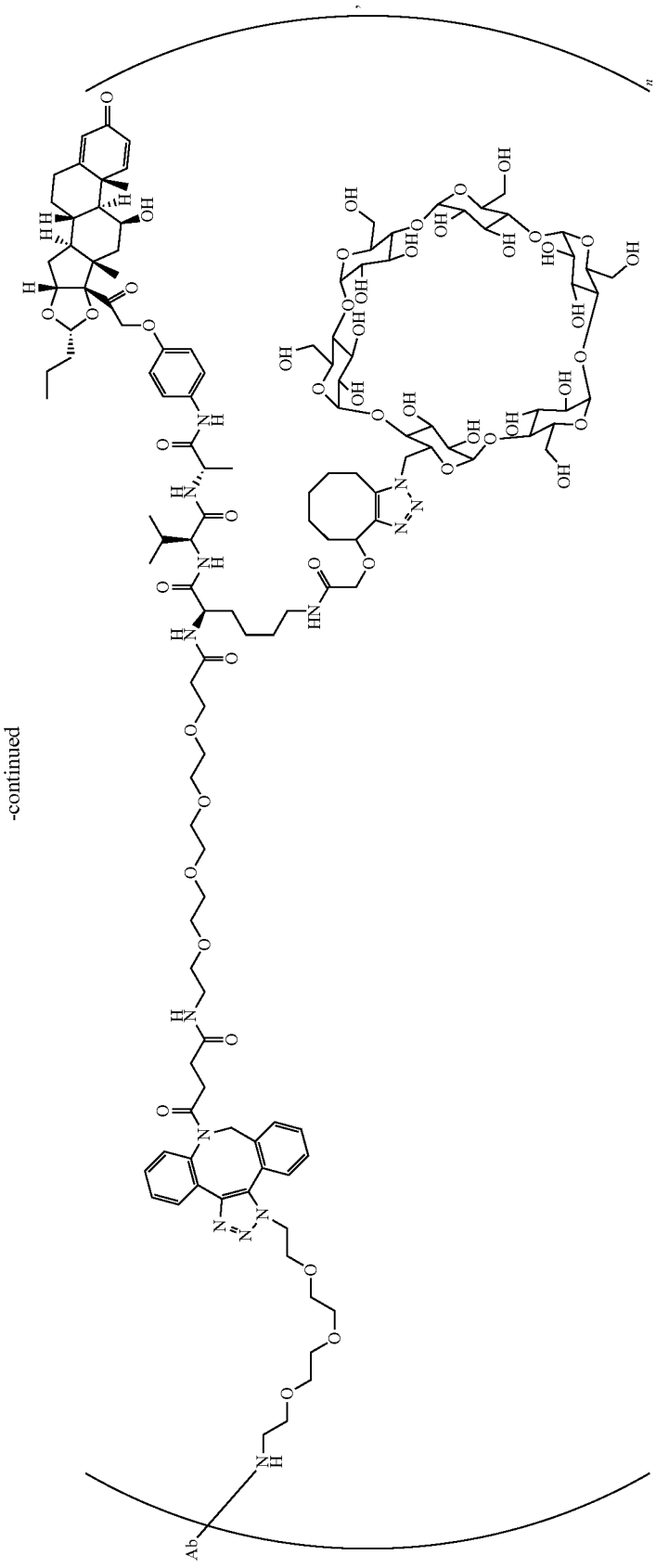

or mixtures thereof.

In particular embodiments, Ab is an antibody and x is an integer from 1-30. In some embodiments, x is an integer from 1 to 4. In some embodiments, x is 4. In some embodiments, x is 2.

Set forth herein are also antibody-steroid conjugates having the following formula:

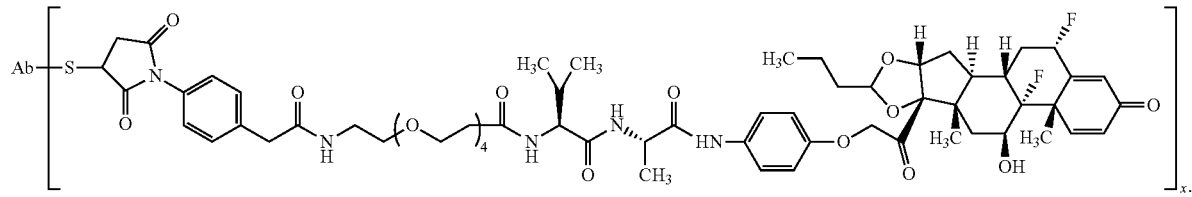

Set forth herein are also antibody-steroid conjugates having the following formulas:

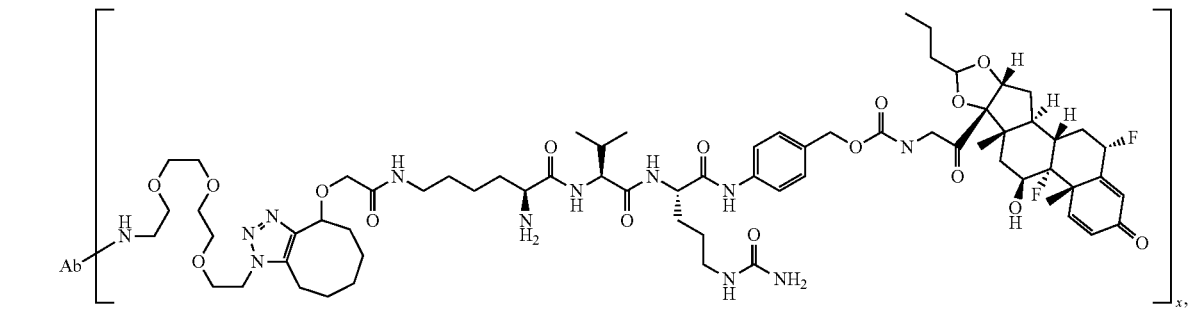

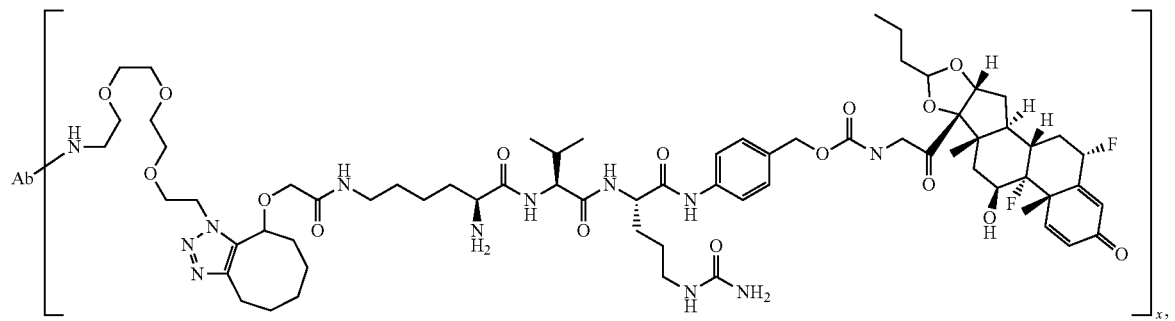

or mixtures thereof;

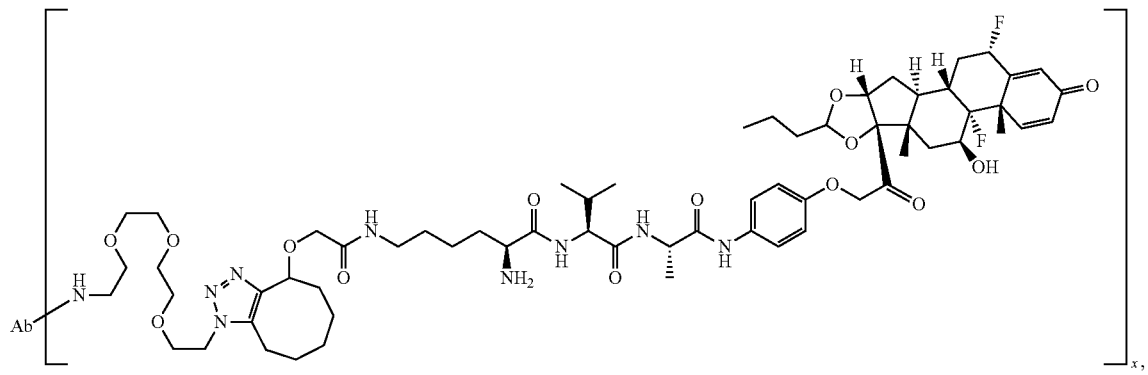

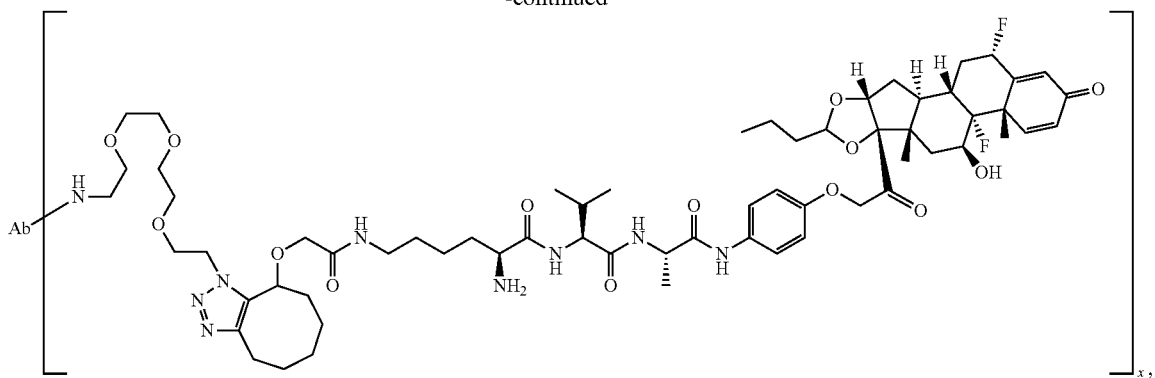
or mixtures thereof;
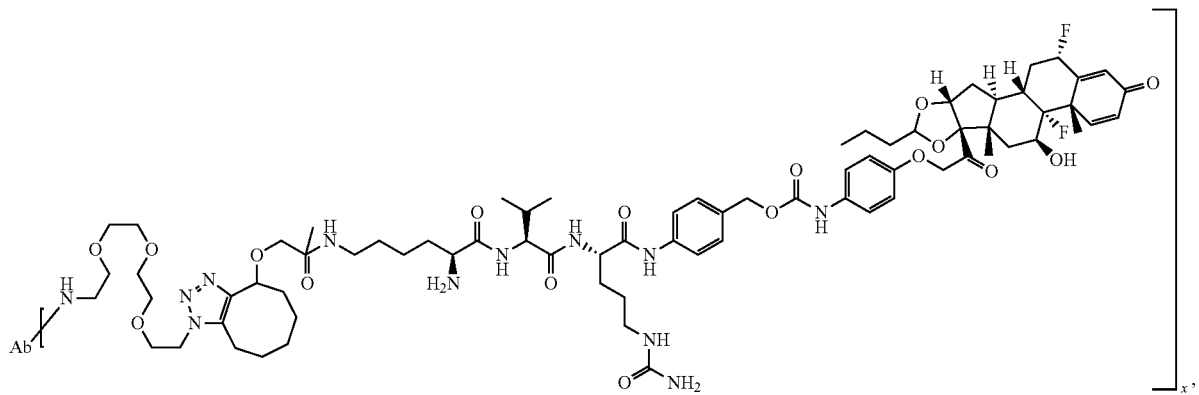
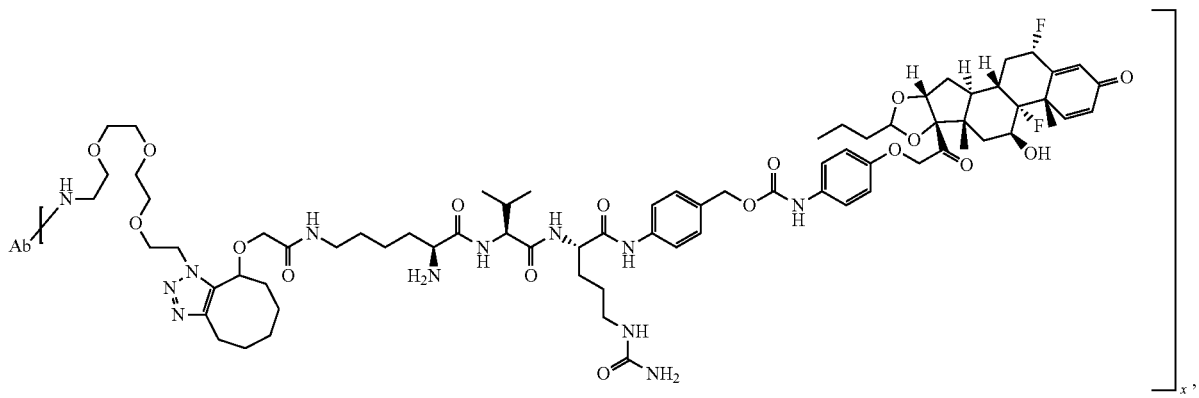
or mixtures thereof;

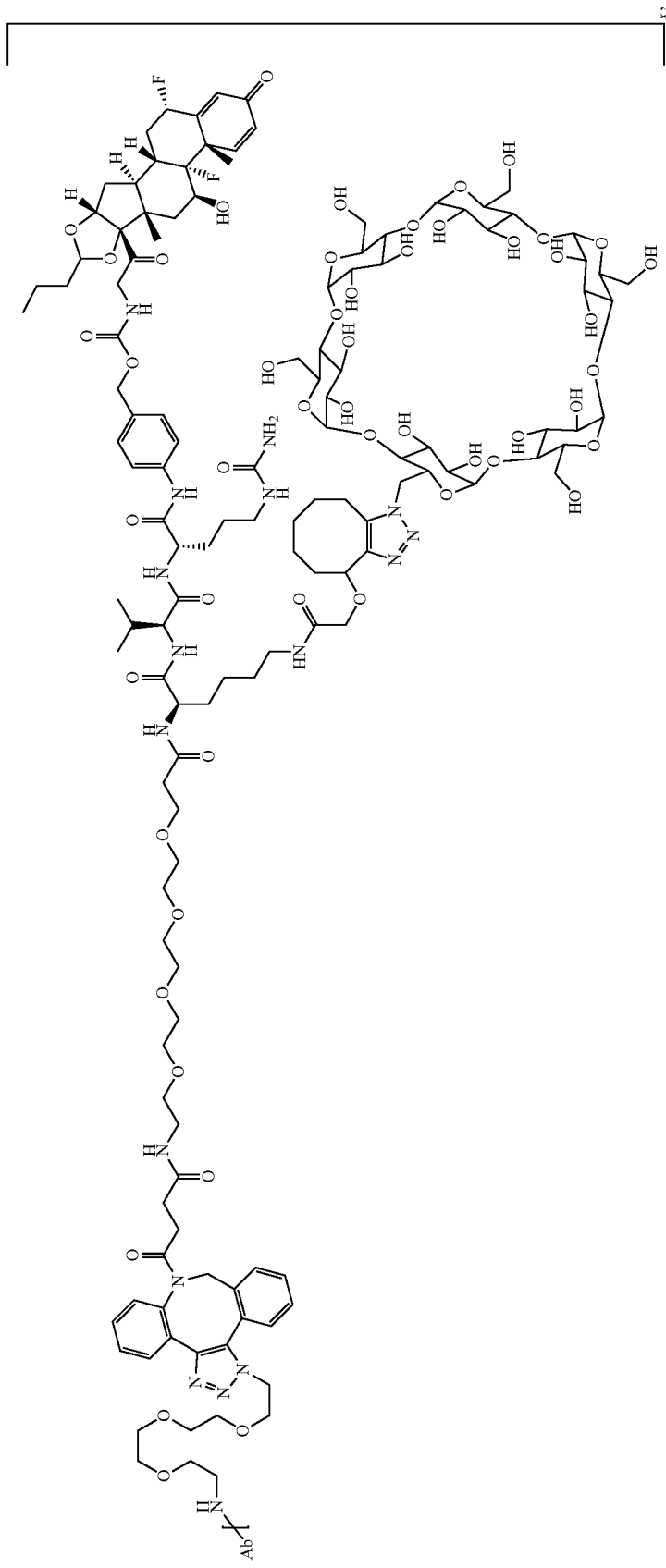

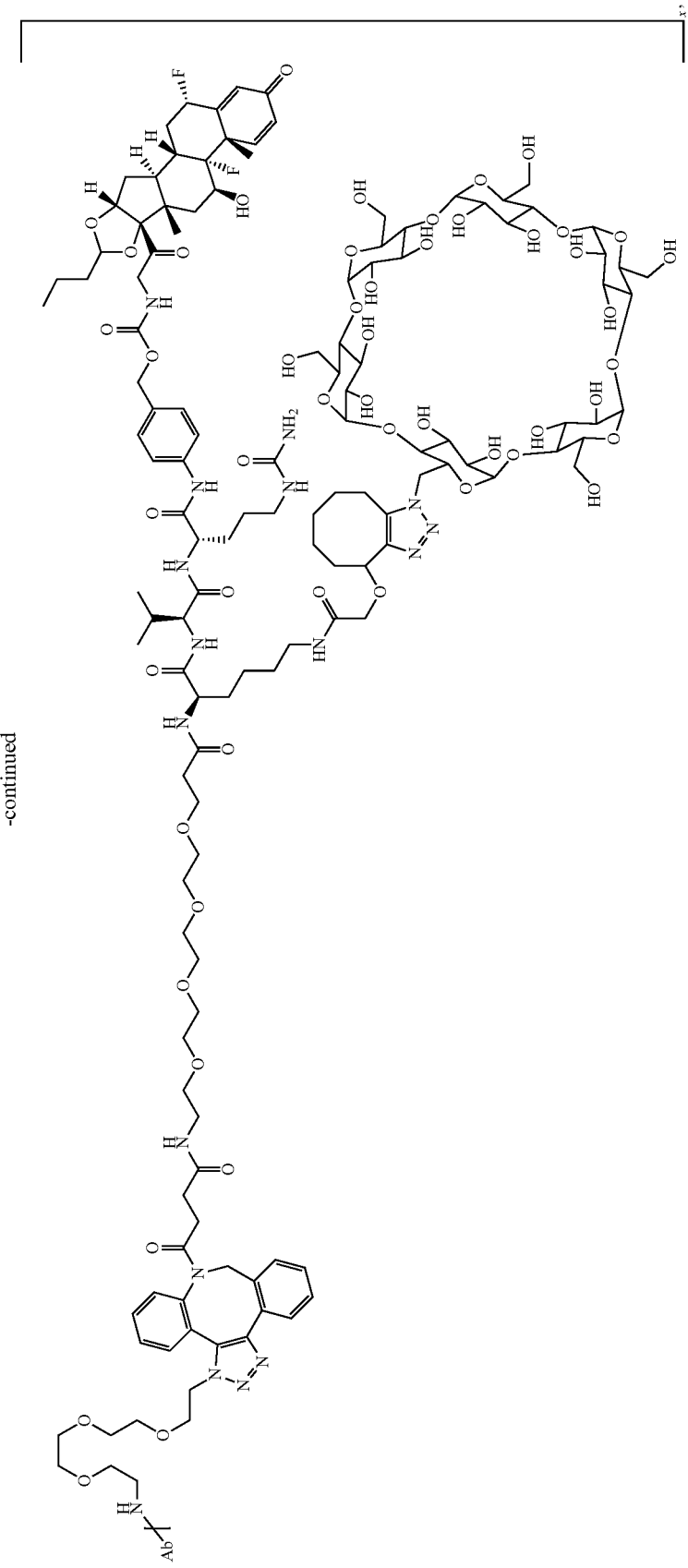

or mixtures thereof;

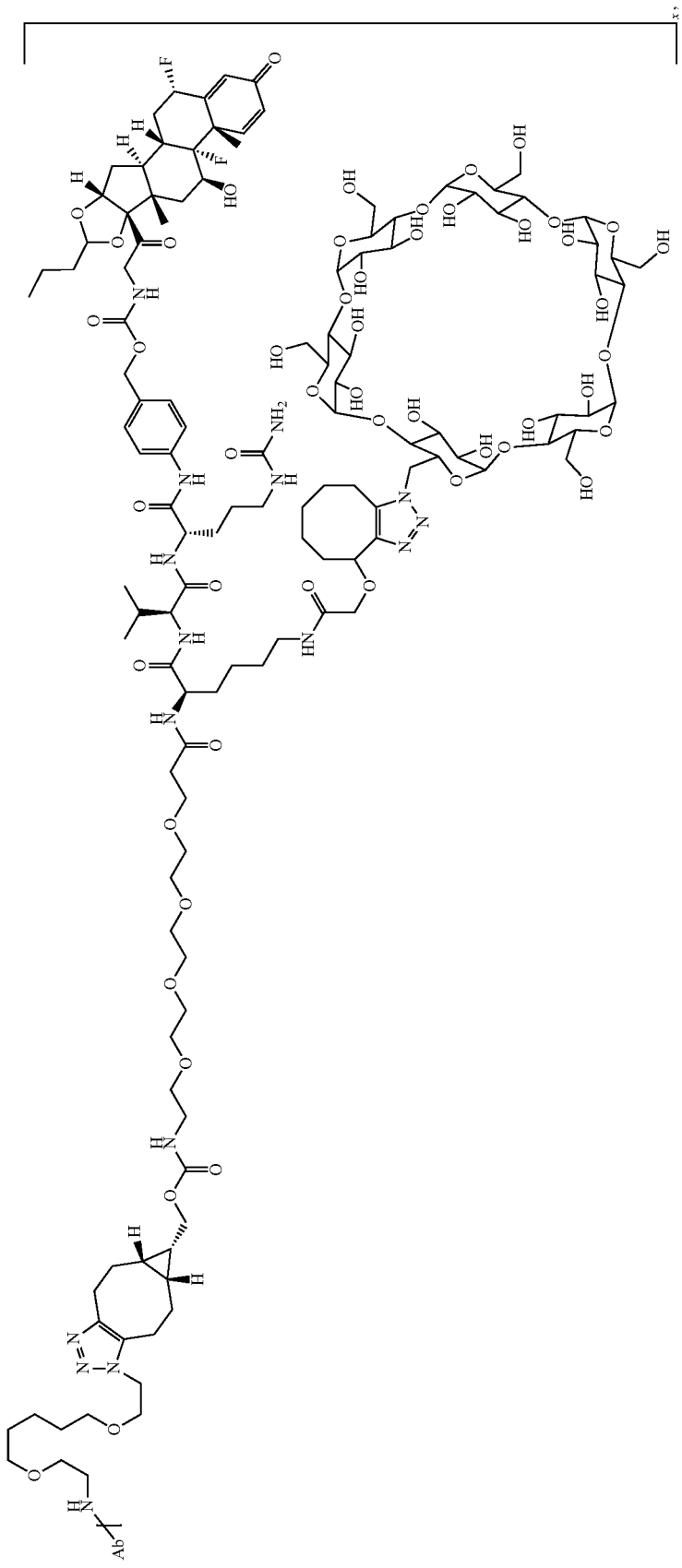

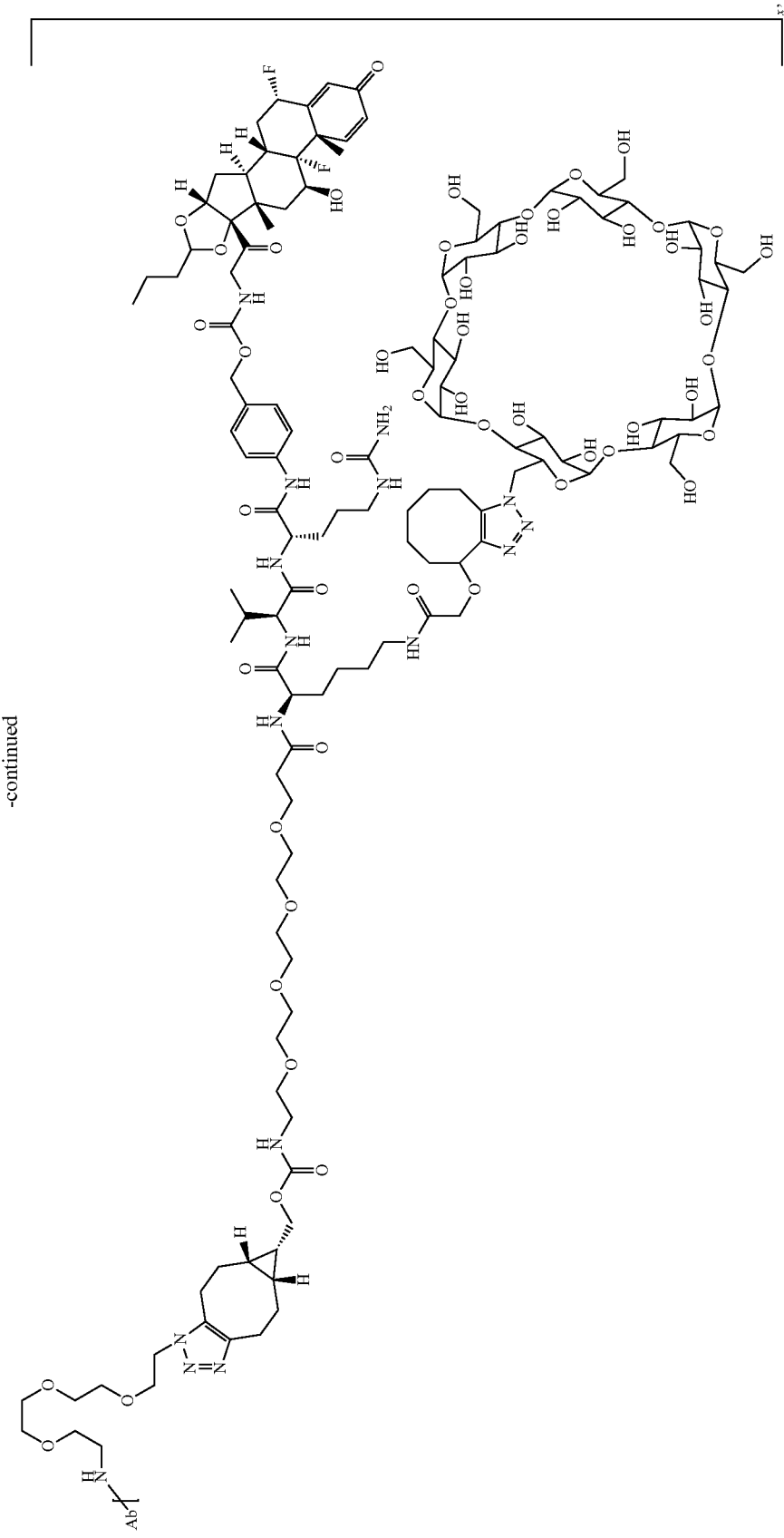

or mixtures thereof;

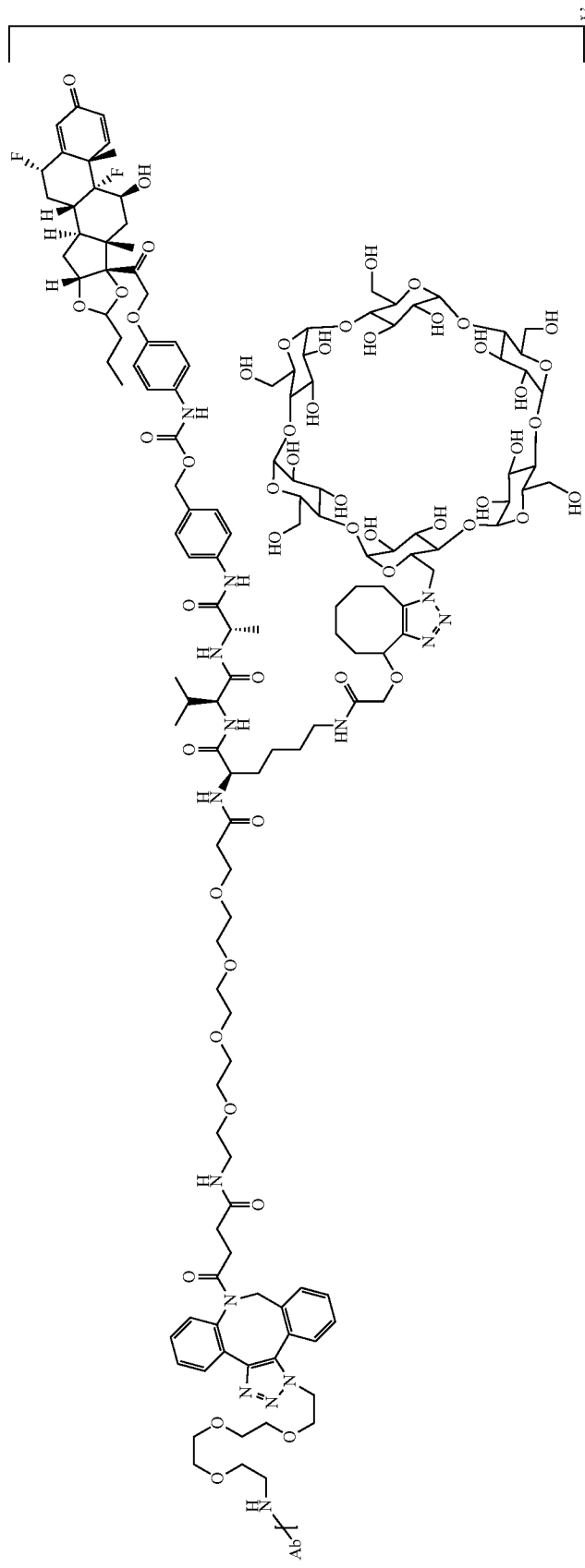

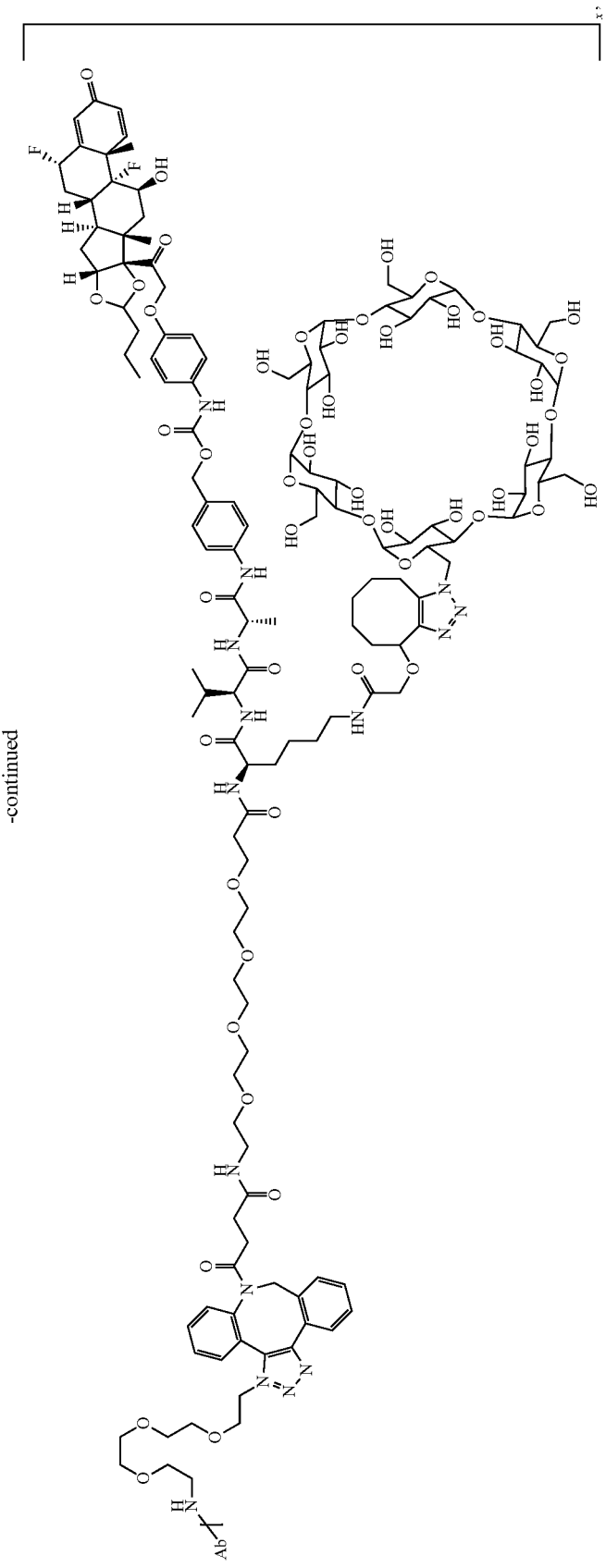

or mixtures thereof;

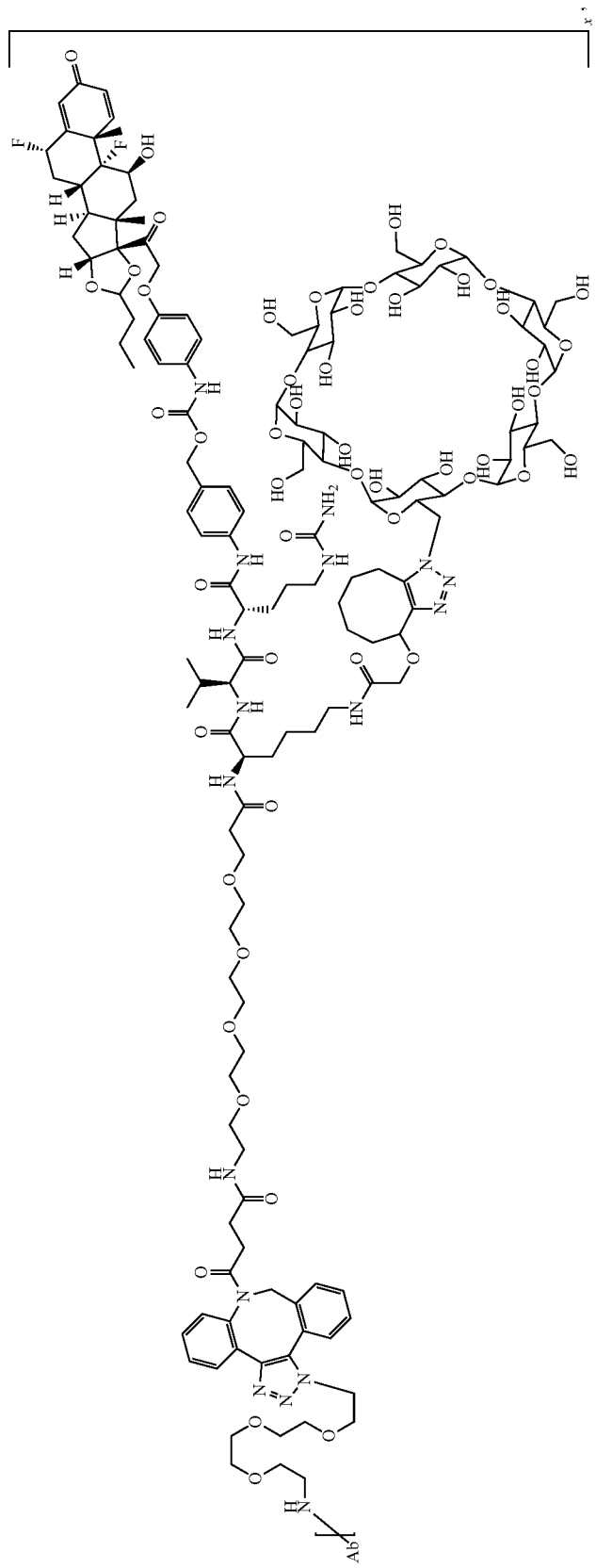

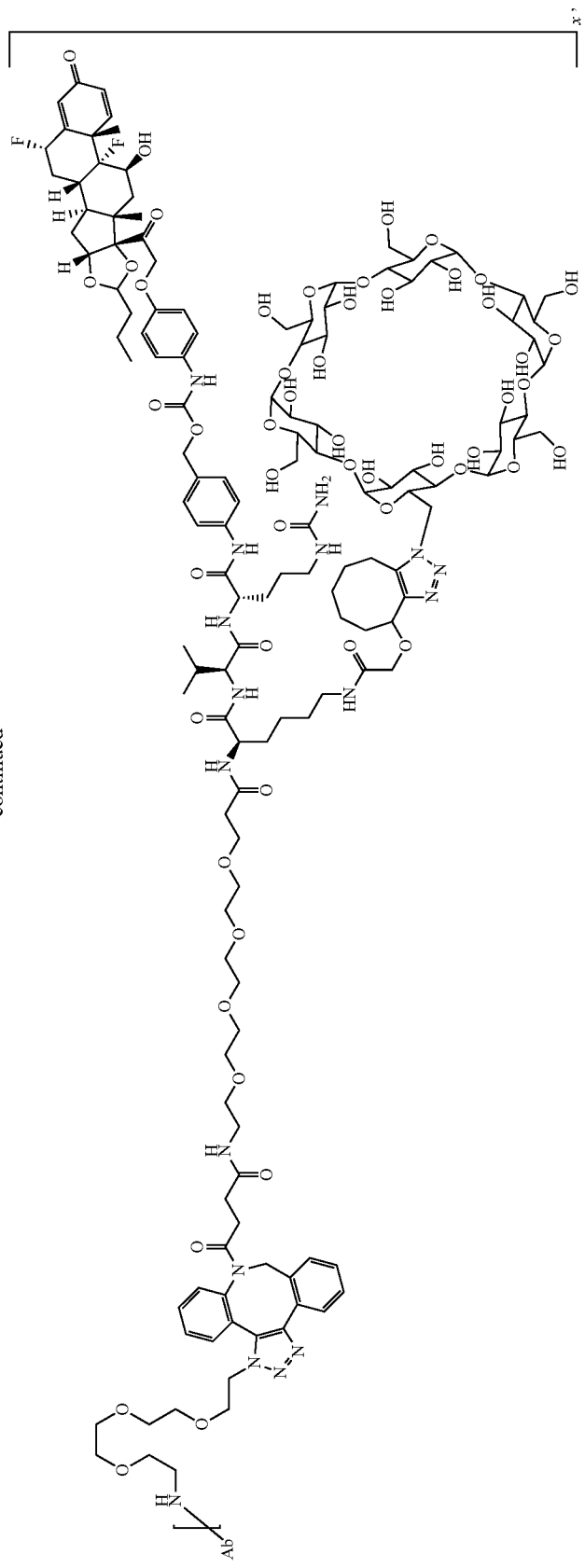

or mixtures thereof;
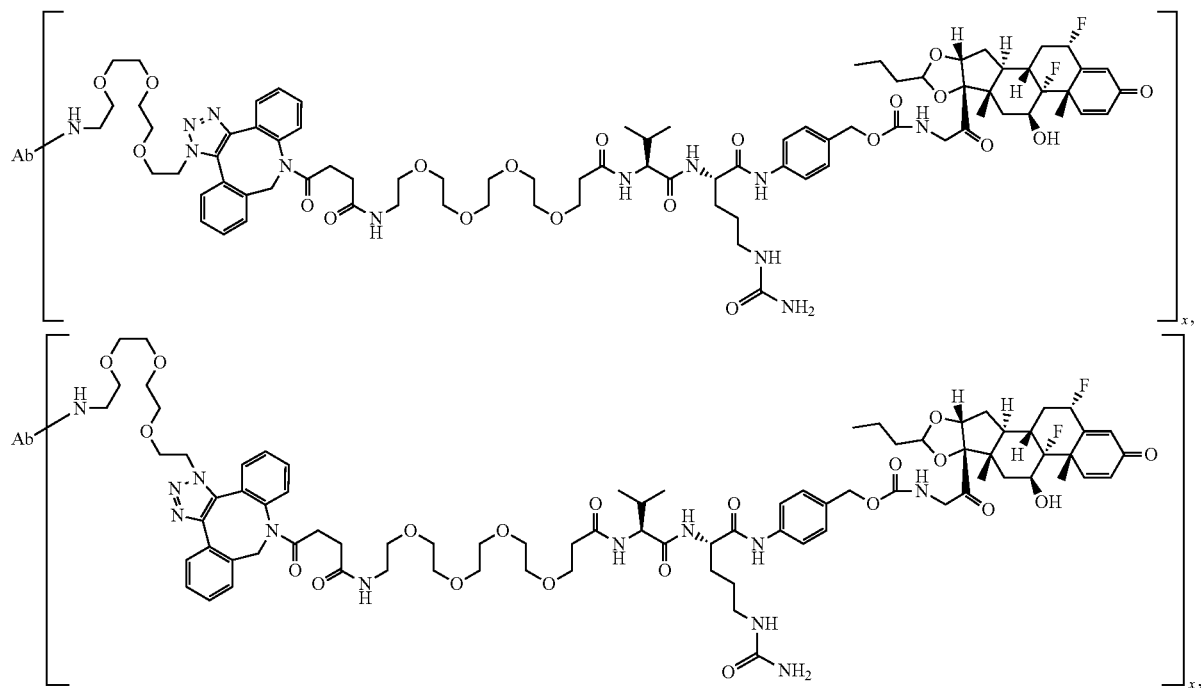
or mixtures thereof;
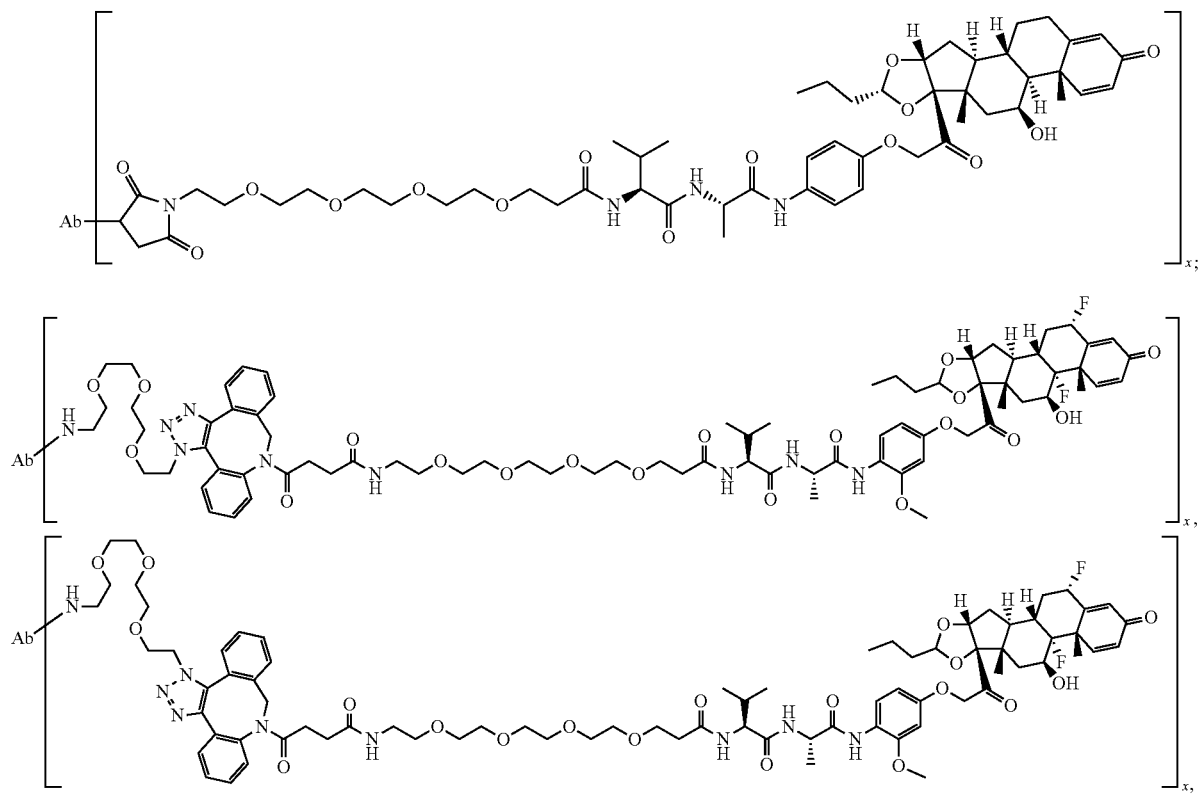
or mixtures thereof;

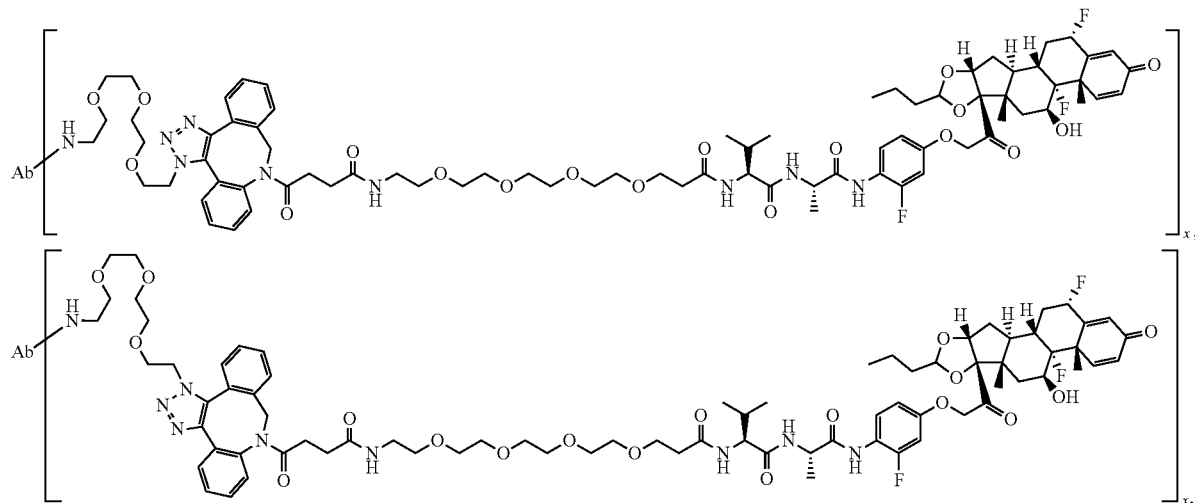

or mixtures thereof;

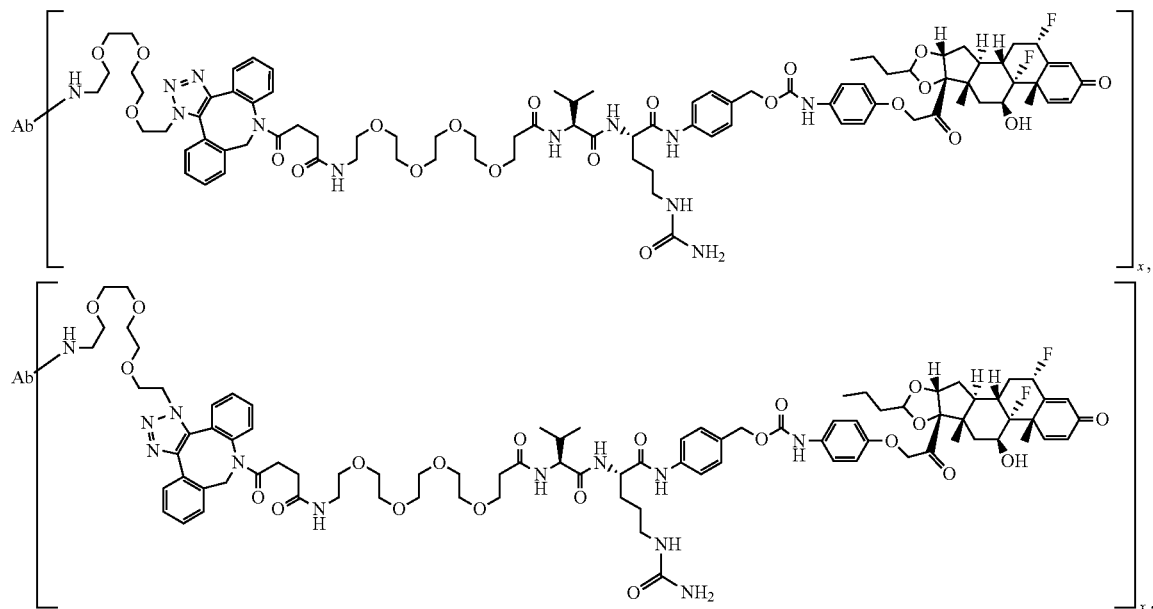

or mixtures thereof.

In particular embodiments, Ab is an antibody and x is an integer from 1-30. In some embodiments, x is an integer from 1 to 4. In some embodiments, x is 4. In some embodiments, x is 2.

Provided herein are also binding agent conjugates of budesonide or diflorasone.

Suitable binding agents for any of the conjugates provided in the instant disclosure include, but are not limited to, antibodies, lymphokines, hormones, growth factors, viral receptors, interleukins, or any other cell binding or peptide binding molecules or substances.

In some embodiments, the binding agent is an antibody. The term "antibody", as used herein, means any antigen-binding molecule or molecular complex comprising at least one complementarity determining region (CDR) that specifically binds to or interacts with a particular antigen. The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxyterminus in the following order: FR1, CDR1, FR2, CDR2, FR3, CDR3, FR4. In some embodiments, the FRs of the antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present disclosure include: (i) $V_H$-$C_H1$; (ii) $V_H$-$C_H2$; (iii) $V_H$-$C_H3$; (iv) $V_H$-$C_H1$-$C_H2$; (v) $V_H$-$C_H1$-$C_H2$-$C_H3$; (vi) $V_H$-$C_H2$-$C_H3$; (vii) $V_H$-$C_L$; (viii) $V_L$-$C_H1$; (ix) $V_L$-$C_H2$; (x) $V_L$-$C_H3$; (xi) $V_L$-$C_H1$-$C_H2$; (xii) $V_L$-$C_H1$-$C_H2$-$C_H3$; (xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present disclosure may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present disclosure using routine techniques available in the art.

The antibodies of the present disclosure may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the instant disclosure in the presence of complement. "Antibody-dependent cell-mediated cytotoxicity" (ADCC) refers to a cell-mediated reaction in which non-specific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The antibodies useful for the compounds herein include human antibodies. The term "human antibody", as used herein, is intended to include antibodies having variable and constant regions derived from human germline immunoglobulin sequences. The human antibodies can include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences. The term "human antibody" does not include naturally occurring molecules that normally exist without modification or human intervention/manipulation, in a naturally occurring, unmodified living organism.

The antibodies can, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via inter-chain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant disclosure encompasses antibodies having one or more mutations in the hinge, $C_H2$ or $C_H3$ region which may be desirable, for example, in production, to improve the yield of the desired antibody form.

The antibodies useful for the compounds herein can be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the instant disclosure. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The antibodies useful for the compounds disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present disclosure includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present disclosure may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc.

In some embodiments, the antibody is a monoclonal antibody, polyclonal antibody, antibody fragment (Fab, Fab', and F(ab)2, minibody, diabody, tribody, and the like), or bispecific antibody. Antibodies herein can be humanized using methods described in U.S. Pat. No. 6,596,541 and US Publication No. 2012/0096572, each incorporated by reference in their entirety.

Where the binding agent is an antibody, it binds to an antigen binding partner that is a polypeptide and may be a transmembrane molecule (e.g., receptor) or a growth factor that might be glycosylated or phosphorylated.

Suitable targets to which the binding agent binds include any target to which steroid delivery is desirable. In some embodiments, the binding agent is an antibody, modified antibody, or antigen binding fragment there of that binds a target selected from: AXL, BAFFR, BCMA, BCR-list components, BDCA2, BDCA4, BTLA, BTNL2 BTNL3, BTNL8, BTNL9, C10orf54, CCR1, CCR3, CCR4, CCR5, CCR6, CCR7, CCR9, CCR10, CD11c, CD137, CD138, CD14, CD168, CD177, CD19, CD20, CD209, CD209L, CD22, CD226, CD248, CD25, CD27, CD274, CD276, CD28, CD30, CD300A, CD33, CD37, CD38, CD4, CD40, CD44, CD45, CD46, CD47, CD48, CD5, CD52, CD55, CD56, CD59, CD62E, CD68, CD69, CD70, CD74, CD79a, CD79b, CD8, CD80, CD86, CD90.2, CD96, CLEC12A, CLEC12B, CLEC7A, CLEC9A, CR1, CR3, CRTAM, CSF1R, CTLA4, CXCR1/2, CXCR4, CXCR5, DDR1, DDR2, DEC-205, DLL4, DR6, FAP, FCamR, FCMR, FcR's, Fire, GITR, HHLA2, HLA class II, HVEM, ICOSLG, IFNLR1, IL10R1, IL10R2, IL12R, IL13RA1, IL13RA2, IL15R, IL17RA, IL17RB, IL17RC, IL17RE, IL20R1, IL20R2, IL21R, IL22R1, IL22RA, IL23R, IL27R, IL29R, IL2Rg, IL31R, IL36R, IL3RA, IL4R, IL6R, IL5R, IL7R, IL9R, Integrins, LAG3, LIFR, MAG/Siglec-4, MMR, MSR1, NCR3LG1, NKG2D, NKp30, NKp46, PDCD1, PROKR1, PVR, PVRIG, PVRL2, PVRL3, RELT, SIGIRR, Siglec-1, Siglec-10, Siglec-5, Siglec-6, Siglec-7, Siglec-8, Siglec-9, SIRPA, SLAMF7, TACI, TCR-list components/ assoc, PTCRA, TCRb, CD3z, CD3, TEK, TGFBR1, TGFBR2, TGFBR3, TIGIT, TLR2, TLR4, TROY, TSLPR, TYRO, VLDLR, VSIG4, and VTCN1.

The binding agent linkers can be bonded to the binding agent, e.g., antibody or antigen-binding molecule, through an attachment at a particular amino acid within the antibody or antigen-binding molecule. Exemplary amino acid attachments that can be used in the context of this aspect of the disclosure include, e.g., lysine (see, e.g., U.S. Pat. No. 5,208,020; US 2010/0129314; Hollander et al., *Bioconjugate Chem.*, 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., *Proc. Natl. Acad. Sci., USA*, 2008, 105:12451-12456), formyl glycine (see, e.g., Carrico et al., *Nat. Chem. Biol.*, 2007, 3:321-322; Agarwal et al., *Proc. Natl. Acad. Sci., USA*, 2013, 110:46-51, and Rabuka et al., *Nat. Protocols*, 2012, 10:1052-1067), non-natural amino acids (see, e.g., WO 2013/068874, and WO 2012/166559), and acidic amino acids (see, e.g., WO 2012/05982). Linkers can be conjugated via glutamine via transglutaminase-based chemoenzymatic conjugation (see, e.g., Dennler et al., *Bioconjugate Chem.* 2014, 25, 569-578). Linkers can also be conjugated to an antigen binding protein via attachment to carbohydrates (see, e.g., US 2008/0305497, WO 2014/065661, and Ryan et al., *Food & Agriculture Immunol.*, 2001, 13:127-130) and disulfide linkers (see, e.g., WO 2013/085925, WO 2010/010324, WO 2011/018611, WO 2014/197854, and Shaunak et al., *Nat. Chem. Biol.*, 2006, 2:312-313). In some examples, the binding agent is an antibody, and the antibody is bonded to the linker through a lysine residue. In some embodiments, the antibody is bonded to the linker through a cysteine residue.

D. Methods of Preparing Compounds

The conjugates described herein can be synthesized by coupling the linker-payloads described herein with a binding agent, e.g., antibody under standard conjugation conditions (see, e.g., *Drug Deliv.* 2016 June; 23(5):1662-6; *AAPS Journal*, Vol. 17, No. 2, March 2015; and *Int. J Mol. Sci.* 2016, 17, 561, the entireties of which are incorporated herein by reference). Linker-payloads are synthetic intermediates comprising the payload of interest and linking moiety that ultimately serves as the moiety (or portion thereof) that connects the binding agent with the payload. Linker-payloads comprise a reactive group that reacts with the binding agent to form the conjugates described herein. When the binding agent is an antibody, the antibody can be coupled to a linker-payload via one or more cysteine, lysine, or other residue of the antibody. Linker payloads can be coupled to cysteine residues, for example, by subjecting the antibody to a reducing agent, e.g., dithiothreitol, to cleave the disulfide bonds of the antibody, purifying the reduced antibody, e.g., by gel filtration, and subsequently reacting the antibody with a linker-payload containing a reactive moiety, e.g., a maleimido group. Suitable solvents include, but are not limited to water, DMA, DMF, and DMSO. Linker-payloads containing a reactive group, e.g., activated ester or acid halide group, can be coupled to lysine residues. Suitable solvents include, but are not limited to, water, DMA, DMF, and DMSO. Conjugates can be purified using known protein techniques, including, for example, size exclusion chromatography, dialysis, and ultrafiltration/diafiltration.

Binding agents, e.g., antibodies, can also be conjugated via click chemistry reaction. In some embodiments of said click chemistry reaction, the linker-payload comprises a reactive group, e.g., alkyne that is capable of undergoing a 1,3 cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3 cycloaddition reactions with azides in the absence of copper catalysts. Suitable alkynes also include, but are not limited to, DIBAC, DIBO, BARAC, DIFO, substituted, e.g., fluorinated alkynes, aza-cycloalkynes, BCN, and derivatives thereof. Linker-payloads comprising such reactive groups are useful for conjugating antibodies that have been functionalized with azido groups. Such functionalized antibodies include antibodies functionalized with azido-polyethylene glycol groups. In certain embodiments, such functionalized antibody is derived by reacting an antibody comprising at least one glutamine residue, e.g., heavy chain Q295, with a compound according to the formula $H_2N$-LL-$N_3$, wherein LL is a divalent polyethylene glycol group, in the presence of the enzyme transglutaminase. For convenience, in certain Formulas herein, the antibody Ab is a modified antibody with one or more covalently linked -LL-$N_3$ groups, or residues thereof. Preferably, each -LL-$N_3$ is covalently bonded to an amino acid side chain of a glutamine residue of the antibody. Also preferably, the -LL-$N_3$ is or can be reacted with a reactive group RG to form a covalent bond to a linker-payload. Again for convenience, in certain Formulas herein, the -LL-$N_3$ groups are expressly drawn.

Set forth here are methods of synthesizing the conjugates described herein comprising contacting a binding agent, e.g., antibody, with a linker-payload described herein. In certain embodiments, the linker-payload includes a cyclodextrin moiety.

In some embodiments, the linker payload is a compound of Formula (II):

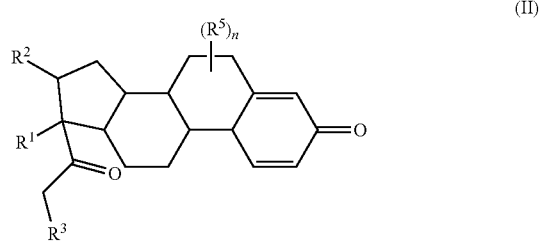

(II)

(a) $R^3$ is RL-, RL-X—, or

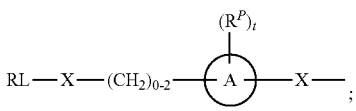

$R^1$ and $R^2$ are each, independently, —H, alkyl, alkyl-C(O)—O—, —OH, or halo; or $R^1$ and $R^2$ together form

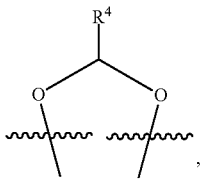

wherein $R^4$ is alkyl, aryl, arylalkyl, or an N-containing heterocycloalkyl; wherein the alkyl, aryl, arylalkyl, and N-containing heterocycloalkyl are optionally substituted with —NR$^a$R$^b$; or (b) $R^3$ is —OH, alkyl-C(O)—O—, heteroalkyl, —NR$^a$R$^b$ or aryloxy, wherein the alkyl-C(O)—O—, heteroalkyl, or aryloxy is optionally substituted with —NR$^a$R$^b$ or halo, and $R^1$ and $R^2$ together form

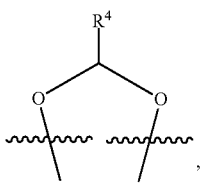

wherein $R^4$ is -RL-,

BL-X—(CH$_2$)$_{1-4}$— or RL-Y, where Y is an N-containing divalent heterocycle;
RL is a reactive linker;
$R^5$ is, independently in each instance, —OH, halo, alkyl, or arylalkyl;
$R^a$ and $R^b$ are, independently in each instance, —H or alkyl;
$R^P$, independently in each instance, is halo;
X, independently in each instance, is NR$^a$ or O;

is aryl or heteroaryl; and
n is an integer from 0-19.

Compounds of Formula (II) are linker-payloads that are useful as synthetic intermediates in the synthesis of the conjugates described herein. These linker-payloads comprise a reactive group that can react with an antibody to form the conjugates described herein.

In some examples of Formula (II), $R^1$ and $R^2$ are, each, independently, —H, alkyl, or —OH. In some examples of Formula (II), one of $R^1$ or $R^2$ is —H, alkyl, or —OH. In some examples of Formula (II), both $R^1$ and $R^2$ are either —H, alkyl, or —OH.

In some examples of Formula (II), $R^1$ and $R^2$ together form

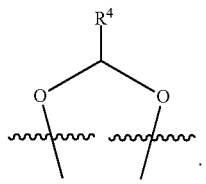

In some examples, $R^4$ is -RL. In some examples, $R^4$ is RL-NR$^a$-aryl. In some other examples, $R^4$ is alkyl. In certain examples, $R^4$ is arylalkyl, In some examples, $R^4$ is aryl. In other examples, $R^4$ is N-containing heterocycloalkyl. In some of these examples, the alkyl, aryl, arylalkyl, or N-containing heterocycloalkyl is optionally substituted.

In some examples of Formula (II), $R^5$ is halo. In some examples of Formula (II), $R^5$ is fluoro. In some examples of Formula (II), one of $R^5$ is halo. In some examples of Formula (II), $R^5$ is halo and n is 2. In some examples of Formula (II), $R^5$ is —F and n is 1. In some examples of Formula (II), $R^5$ is —F and n is 1.

In some examples of Formula (II), $R^3$ is RL. In some examples of Formula (II), $R^3$ is RL-NR$^a$-aryloxy. In some other examples of Formula (II), $R^3$ is —OH. In some other examples of Formula (II), $R^3$ is alkyl-C(O)—O—. In some other examples of Formula (II), $R^3$ is heteroalkyl. In some other examples of Formula (II), $R^3$ is NR$^a$R$^b$. In some other examples of Formula (II), $R^3$ is aryl. In some other examples of Formula (II), $R^3$ is aryloxy. In some other examples of Formula (II), alkyl-C(O)—O—, heteroalkyl, or aryloxy is optionally substituted with NR$^a$R$^b$ or halo.

In some examples of Formula (II), $R^3$ is —OH. In some examples of Formula (II), $R^3$ is alkyl-C(O)—O—. In some examples of Formula (II), $R^3$ is

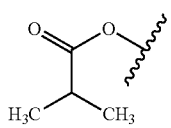

In some examples of Formula (II), $R^3$ is heteroalkyl. In some examples of Formula (II), $R^3$ is

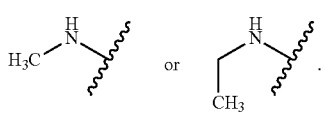

In some examples of Formula (II), $R^3$ is

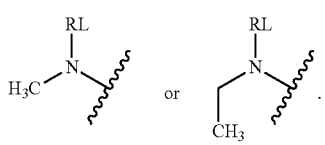

In some examples of Formula (II), $R^3$ is —$NR^aR^b$. In some examples of Formula (II), $R^3$ is

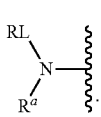

In some examples of Formula (II), $R^3$ is

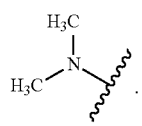

In some examples of Formula (II), $R^3$ is

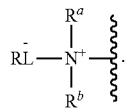

In some examples of Formula (II), $R^3$ is aryloxy. In some examples of Formula (II), $R^3$ is

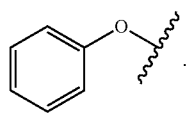

In some examples of Formula (II), $R^3$ is

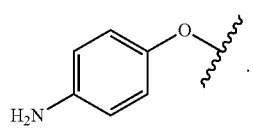

In some examples of Formula (II), $R^3$ is

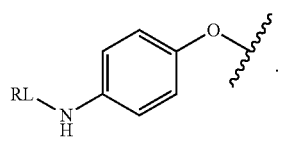

In some examples of Formula (II), $R^3$ is

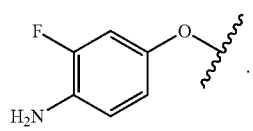

In some examples of Formula (II), $R^3$ is

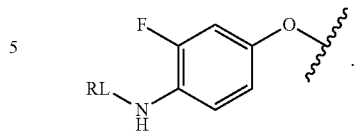

In some examples of Formula (II), $R^3$ is

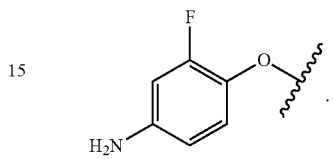

In some examples of Formula (II), $R^3$ is

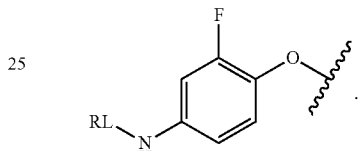

In some examples of Formula $R^3$ is

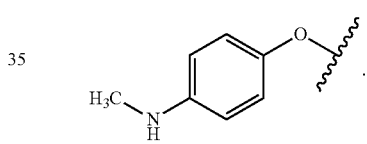

In some examples of Formula (II), $R^3$ is

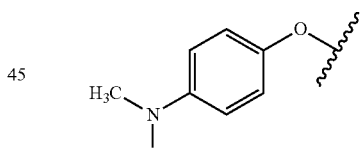

In some examples of Formula (II), $R^3$ is

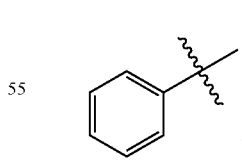

In Formula (II), subscript n is an integer from 0-19. In some examples, n is 0. In some other examples, n is 1. In certain examples, n is 2. In some other examples, n is 3. In certain examples, n is 4. In some examples, n is 5. In some other examples, n is 6. In certain examples, n is 7. In some other examples, n is 8. In certain examples, n is 9. In some examples, n is 10. In some other examples, n is 11. In certain examples, n is 12. In some other examples, n is 13. In certain examples, n is 14. In some examples, n is 15. In some other examples, n is 16. In certain examples, n is 17. In some other examples, n is 18. In certain examples, n is 19.

In some examples, set forth herein is a compound having the structure of Formula (IIa):

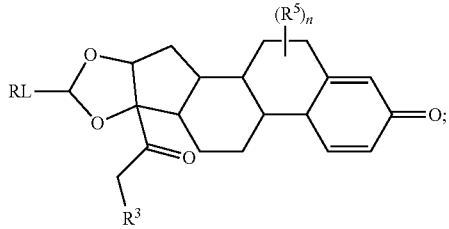

(IIa)

wherein:
R$^5$ is, independently in each instance, —OH, halo, or alkyl;
R$^3$ is selected from —OH, alkyl-C(O)—O—, heteroalkyl, —NR$^a$R$^b$ or aryloxy, wherein
the alkyl-C(O)—O—, heteroalkyl, or aryloxy is optionally substituted with NR$^a$R$^b$ or halo;
RL is a reactive linker;
R$^a$ and R$^b$ are, independently in each instance, selected from H, alkyl, and alkyl-C(O); and
n is an integer from 0-19.

In some examples, set forth herein is a compound having the structure of Formula (IIa2):

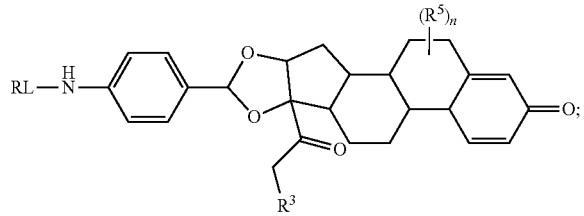

(IIa2)

wherein:
R$^5$ is, independently in each instance, —OH, halo, or alkyl;
R$^3$ is —OH, alkyl-C(O)—O—, heteroalkyl, —NR$^a$R$^b$ or aryloxy, wherein the alkyl-C(O)—O—, heteroalkyl, or aryloxy is optionally substituted with —NR$^a$R$^b$ or halo;
RL is a reactive linker;
R$^a$ and R$^b$ are, independently in each instance, selected from H, alkyl, or alkyl-C(O); and
n is an integer from 0-19.

In some examples of Formula (IIa2), R$^3$ is —OH. In some examples of Formula (IIa2), R$^3$ is alkyl-C(O)—O—. In some examples R$^3$ is

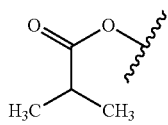

In some examples of Formula (IIa2), R$^3$ is heteroalkyl. In some examples R$^3$ is

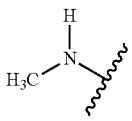

or. In some examples of Formula (IIa2), R$^3$ is —NR$^a$R$^b$. In some examples R$^3$ is

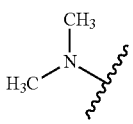

In some examples of Formula (IIa2), R$^3$ is aryloxy. In some examples of Formula (IIa2), R$^3$ is

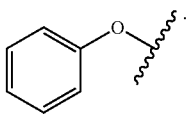 [SMILES: *Oc1ccccc1]

In some examples of Formula (IIa2), R$^3$ is

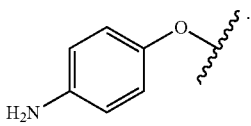

In some examples of Formula (IIa2), R$^3$ is

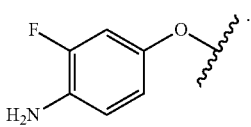

In some examples of Formula (IIa2), R$^3$ is

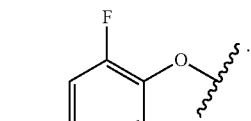

In some examples of Formula (IIa2), R$^3$ is

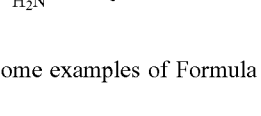

In some examples, the compound of Formula (IIa2) has the following structure:

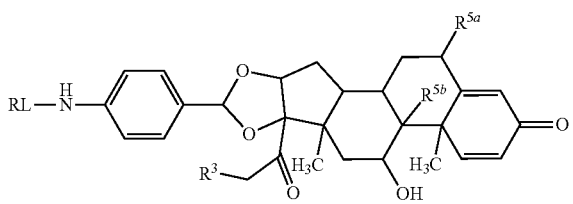

wherein:
R³ is —OH or alkyl-C(O)—O—;
R$^{5a}$ and R$^{5b}$ are each, independently, —F or H; and
RL is a reactive linker.

In some examples, set forth herein is a compound having the structure of Formula (IIb):

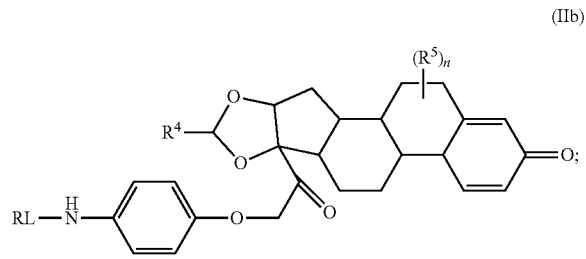

wherein
R$^5$ is, independently in each instance, —OH, halo, or alkyl;
R$^4$ is selected from alkyl, aryl, arylalkyl, or an N-containing heterocycloalkyl, wherein the alkyl, aryl, arylalkyl, or N-containing heterocycloalkyl are optionally substituted with —NR$^a$R$^b$;
RL is a reactive linker;
R$^a$ and R$^b$ are, independently in each instance, selected from H, alkyl, and alkyl-C(O); and
n is an integer from 0-19.

In some examples of Formula (IIb), R$^5$ is halo. In some examples of Formula (IIb), R$^5$ is fluoro. In some examples of Formula (IIb), n is at least 2, and two of R$^5$ is halo. In some examples of Formula (IIb), R$^5$ is —F and n is 1. In some examples of Formula (IIb), R$^5$ is —F.

In some examples of Formula (IIb), R$^4$ is alkyl. In some examples of Formula (IIb), R$^4$ is methyl, ethyl, n-propyl, i-propyl, n-butyl, s-butyl, t-butyl, i-butyl, a pentyl moiety, a hexyl moiety, cyclopropyl, cyclobutyl, cyclopentyl, or cyclohexyl. In some examples of Formula (IIb), R$^4$ is n-propyl.

In some examples, the compound of Formula (IIb) has the following structure:

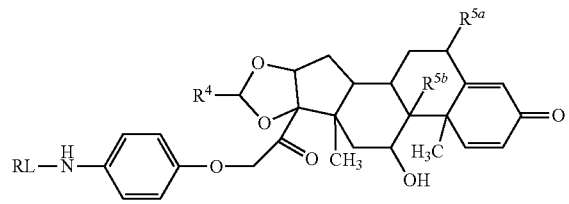

wherein:
R$^4$ is alkyl;
R$^{5a}$ and R$^{5b}$ are each, independently, —F or H; and
RL is a reactive linker.

In some examples, set forth herein is a compound having the structure of Formula (IIc):

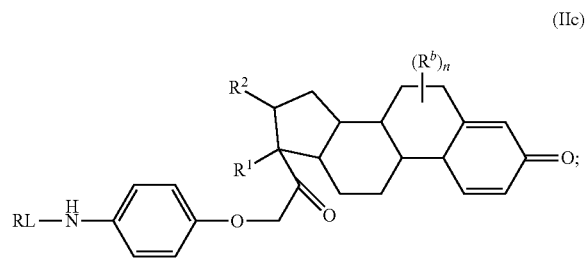

wherein
R¹ and R² are, independently, —H, alkyl, alkyl-C(O)—O—, —OH, or halo;
R$^5$ is, independently in each instance, selected from —OH, halo, or alkyl;
RL is a reactive linker; and
n is an integer from 0-19.

In some examples of Formula (IIc), R$^5$ is halo. In some examples of Formula (IIc), R$^5$ is fluoro. In some examples of Formula (IIc), one of R$^5$ is halo. In some examples of Formula (IIc), two of R$^5$ is halo. In some examples of Formula (IIc), R$^5$ is —F and n is 2.

In some examples of Formula (IIc), R¹ is CH₃.
In other examples of Formula (IIc), R¹ is OH.
In some other examples of Formula (IIc), R¹ is H.
In some examples of Formula (IIc), R² is CH₃.
In other examples of Formula (IIc), R² is OH.
In some other examples of Formula (IIc), R² is H.
In some examples of Formula (IIc), R¹ is CH₃ and R² is CH₃.
In other examples of Formula (IIc), R¹ is CH₃ and R² is OH.
In some examples of Formula (IIc), R¹ is CH₃ and R² is H.
In some other examples of Formula (IIc), R¹ is OH and R² is CH₃.
In other examples of Formula (IIc), R¹ is OH and R² is OH.
In some examples of Formula (IIc), R¹ is H and R² is H.
In some other examples of Formula (IIc), R¹ is H and R² is OH.
In other examples of Formula (IIc), R¹ is H and R² is H.

In some embodiments, the compound of Formula (IIc) has the following structure:

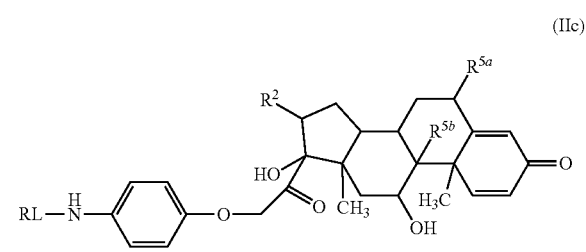

wherein:
R² is methyl;
R$^{5a}$ and R$^{5b}$ are each, independently, —F or H; and
RL is a reactive linker.

In certain embodiments, set forth herein is a compound having the structure of Formula (III-R):

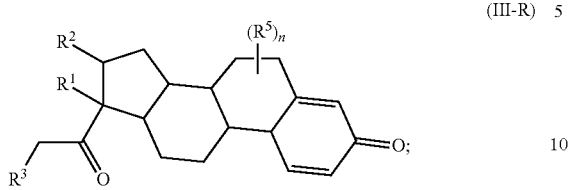

(III-R)

wherein:
R³ is

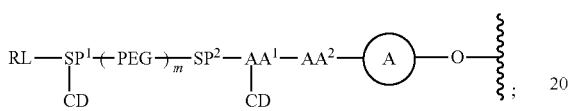

R¹ and R² are each, independently, —H, alkyl, alkyl-C(O)—O—, —OH, or halo; or R¹ and R² together form

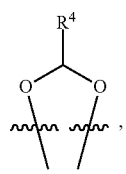

wherein R⁴ is alkyl, aryl, arylalkyl, or an N-containing heterocycloalkyl; wherein the alkyl, aryl, arylalkyl, and N-containing heterocycloalkyl are optionally substituted with —NR$^a$R$^b$;

R⁵ is, independently in each instance, —OH, halo, alkyl, or arylalkyl;

R$^a$ and R$^b$ are, independently in each instance, —H or alkyl;

R$^P$, independently in each instance, is halo;

is aryl or heteroaryl;

t is an integer from 0-2;

x is an integer from 1-30; and wherein

RL is a reactive linker, defined below; SP¹ and SP² are each, independently in each instance, absent or a spacer group residue, and wherein SP¹ comprises a trivalent linker; AA¹ is a trivalent linker comprising an amino acid residue; AA² is a di-peptide residue; PEG is a polyethylene glycol residue; wherein the ⌇ indicates the atom through which the indicated chemical group is bonded to the adjacent groups in the formula, CD is, independently in each instance, absent or a cyclodextrin residue, wherein at least one CD is present, subscript m is an integer from 0 to 5; In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples, any one of AA¹ or AA² comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, AA¹ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, AA¹ is lysine. In certain embodiments, AA¹ is lysine or a derivative of lysine. In certain embodiments, the AA² is valine-citrulline. In some embodiments, the AA² is citrulline-valine. In some embodiments, the AA² is valine-alanine. In some embodiments, the AA² is alanine-valine. In some embodiments, the AA² is valine-glycine. In some embodiments, the AA² is glycine-valine. In some embodiments, the AA² glutamate-valine-citrulline. In some embodiments, the AA² is glutamine-valine-citrulline. In some embodiments, the AA² is lysine-valine-alanine. In some embodiments, the AA² is lysine-valine-citrulline. In some embodiments, the AA² is glutamate-valine-citrulline. In some examples, SP¹ is independently in each instance, selected from the group consisting of $C_{1-6}$ alkylene, —NH—, —C(O)—, (—CH₂—CH₂—O)$_e$, —NH—CH₂—CH₂—(—O—CH₂—CH₂)$_e$—C(O)—, —C(O)—(CH₂)$_u$—C(O)—, —C(O)—NH—(CH₂)$_v$—, and combinations thereof, wherein subscript e is an integer from 0 to 4, subscript u is an integer from 1 to 8, and subscript v is an integer from 1 to 8. In some examples, SP² is independently in each instance, selected from the group consisting of $C_{1-6}$ alkylene, —NH—, —C(O)—, (—CH₂—CH₂—O)$_e$, —NH—CH₂—CH₂—(—O—CH₂—CH₂)$_e$—C(O)—, —C(O)—(CH₂)$_u$—C(O)—, —C(O)—NH—(CH₂)$_v$—, and combinations thereof, wherein subscript e is an integer from 0 to 4, subscript u is an integer from 1 to 8, and subscript v is an integer from 1 to 8.

In certain embodiments, set forth herein is a compound having the structure of Formula (IIIc-R):

Formula (IIIc-R)

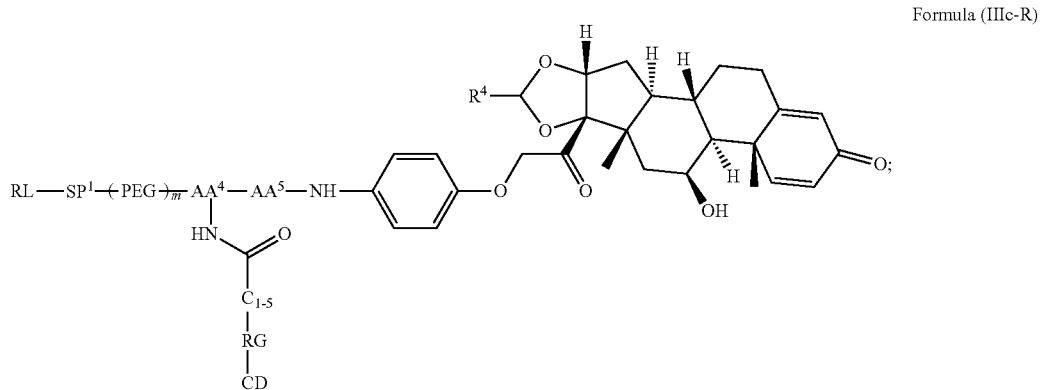

RL is a reactive linker;
CD is a cyclodextrin;
$SP^1$ is a spacer group;
$AA^4$ is an amino acid residue;
$AA^5$ is a dipeptide residue;
PEG is polyethylene glycol;
m is an integer from 0 to 4;
x is an integer from 0 to 30;
$R^4$ is alkyl, aryl, arylalkyl, or an N-containing heterocycloalkyl; wherein the alkyl, aryl, arylalkyl, and N-containing heterocycloalkyl are optionally substituted with $—NR^aR^b$;
$R^a$ and $R^b$ are, independently in each instance, —H or alkyl;
$SP^1$ and $SP^2$ are each, independently in each instance, absent or a spacer group residue, and wherein $SP^1$ comprises a trivalent linker; $AA^4$ is a trivalent linker comprising an amino acid residue; $AA^5$ is a di-peptide residue; PEG is a polyethylene glycol residue; wherein the ⟨ indicates the atom through which the indicated chemical group is bonded to the adjacent groups in the formula, CD is, independently in each instance, absent or a cyclodextrin residue, wherein at least one CD is present, subscript m is an integer from 0 to 5; In these examples, subscript m is 0, 1, 2, 3, 4, or 5. In some examples, subscript m is 0. In some examples, subscript m is 1. In some examples, subscript m is 2. In some examples, subscript m is 3. In some examples, subscript m is 4. In some examples, subscript m is 5. In some examples, any one of $AA^4$ or $AA^5$ comprises, independently in each instance, an amino acid selected from alanine, valine, leucine, isoleucine, methionine, tryptophan, phenylalanine, proline, serine, threonine, cysteine, tyrosine, asparagine, glutamine, aspartic acid, glutamic acid, lysine, arginine, histidine, or citrulline, a derivative thereof, or a combination thereof. In certain embodiments, $AA^4$ is an amino acid selected from alanine, valine, leucine, isoleucine, methionine, tryptophan, phenylalanine, proline, glycine, serine, threonine, cysteine, tyrosine, asparagine, glutamine, aspartic acid, glutamic acid, lysine, arginine, histidine, or citrulline, a derivative thereof, or a combination thereof. In certain embodiments, $AA^4$ is lysine. In certain embodiments, $AA^4$ is lysine or a derivative of lysine. In certain embodiments, the $AA^5$ is valine-citrulline. In some embodiments, the $AA^5$ is citrulline-valine. In some embodiments, the $AA^5$ is valine-alanine. In some embodiments, the $AA^5$ is alanine-valine. In some embodiments, the $AA^5$ is valine-glycine. In some embodiments, the $AA^5$ is glycine-valine. In some embodiments, the $AA^5$ glutamate-valine-citrulline. In some embodiments, the $AA^5$ is glutamine-valine-citrulline. In some embodiments, the $AA^5$ is lysine-valine-alanine. In some embodiments, the $AA^5$ is lysine-valine-citrulline. In some embodiments, the $AA^5$ is glutamate-valine-citrulline. In some examples, $SP^1$ is independently in each instance, selected from the group consisting of $C_{1-6}$ alkylene, —NH—, —C(O)—, $(—CH_2—CH_2—O)_e$, —NH—$CH_2$—$CH_2$—$(—O—CH_2—CH_2)_e$—C(O)—, —C(O)—$(CH_2)_u$—C(O)—, —C(O)—NH—$(CH_2)_v$—, and combinations thereof, wherein subscript e is an integer from 0 to 4, subscript u is an integer from 1 to 8, and subscript v is an integer from 1 to 8. In some examples, $SP^2$ is independently in each instance, selected from the group consisting of $C_{1-6}$ alkylene, —NH—, —C(O)—, $(—CH_2—CH_2—O)_e$, —NH—$CH_2$—$CH_2$—$(—O—CH_2—CH_2)_e$—C(O)—, —C(O)—$(CH_2)_u$—C(O)—, —C(O)—NH—$(CH_2)_v$—, and combinations thereof, wherein subscript e is an integer from 0 to 4, subscript u is an integer from 1 to 8, and subscript v is an integer from 1 to 8.

As used herein, the phrase "reactive linker," or the abbreviation "RL" refers to a monovalent group that comprises a reactive group and linking group, depicted as

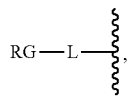

wherein RG is the reactive group and L is the linking group. The linking group is any divalent moiety that bridges the reactive group to a payload. The linking group also includes any trivalent moiety that bridges the reactive group, a cyclodextrin moiety, and a payload. The reactive linkers (RL), together with the payloads to which they are bonded, comprise intermediates ("linker-payloads") useful as synthetic precursors for the preparation of the antibody steroid conjugates described herein. The reactive linker contains a reactive group ("RG"), which is a functional group or moiety that reacts with a reactive portion of an antibody, modified antibody, or antigen binding fragment thereof. The moiety resulting from the reaction of the reactive group with the antibody, modified antibody, or antigen binding fragment thereof, together with the linking group, comprise the "binding agent linker" ("BL") portion of the conjugate, described herein. In certain embodiments, the "reactive group" is a functional group or moiety (e.g., maleimide or NHS ester) that reacts with a cysteine or lysine residue of an antibody or antigen-binding fragment thereof. In certain embodiments, the "reactive group" is a functional group or moiety that is capable of undergoing a click chemistry reaction. In some embodiments of said click chemistry reaction, the reactive group is an alkyne that is capable of undergoing a 1,3 cycloaddition reaction with an azide. Such suitable reactive groups include, but are not limited to, strained alkynes, e.g., those suitable for strain-promoted alkyne-azide cycloadditions (SPAAC), cycloalkynes, e.g., cyclooctynes, benzannulated alkynes, and alkynes capable of undergoing 1,3 cycloaddition reactions with alkynes in the absence of copper catalysts. Suitable alkynes also include, but are not limited to, DIBAC, DIBO, BARAC, substituted, e.g., fluorinated alkynes, aza-cycloalkynes, BCN, and derivatives thereof. Linker-payloads comprising such reactive groups are useful for conjugating antibodies that have been functionalized with azido groups. Such functionalized antibodies include antibodies functionalized with azidopolyethylene glycol groups. In certain embodiments, such functionalized antibody is derived by reacting an antibody comprising at least one glutamine residue, e.g., heavy chain Q295, with a compound according to the formula $H_2N$-LL-$N_3$, wherein LL is, for example, a divalent polyethylene glycol group, or wherein LL is a trivalent group which includes polyethylene glycol and a cyclodextrin moiety, in the presence of the enzyme transglutaminase. In some embodiments, the antibody is a functionalized antibody having the following structure:

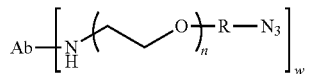

wherein Ab is an antibody, R is hydrocarbyl, n is an integer from 1 to 10, w is an integer from 1-10. In certain embodiments, R is ethylene. In certain embodiments, n is 3. In certain embodiments, w is 2 or 4.

In some examples, the reactive group is an alkyne, e.g.,

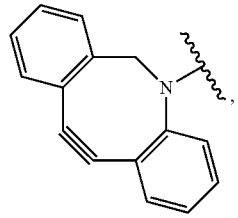 [SMILES: *N1Cc2ccccc2C#Cc2ccccc21]

which can react via click chemistry with an azide, e.g.,

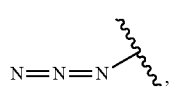

to form a click chemistry product, e.g.,

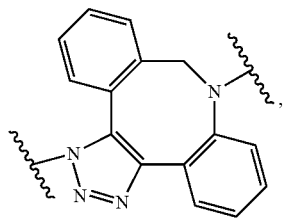 [SMILES: *N1Cc2ccccc2-c2c(nnn2*)-c2ccccc21]

its regioisomer, or a mixture thereof. In some examples, the reactive group is an alkyne, e.g.,

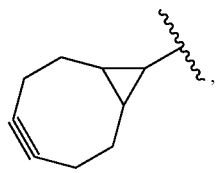 [SMILES: *C1C2CCC#CCCC12]

which can react via click chemistry with an azide, e.g.,

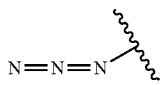

to form a click chemistry product, e.g.,

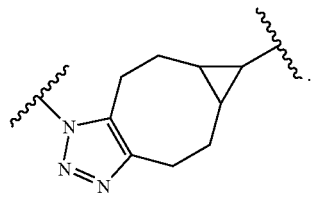 [SMILES: *C1C2CCc3nnn(*)c3CCC12]

In some examples, the reactive group is an alkyne, e.g.,

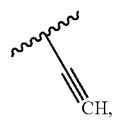

which can react via click chemistry with an azide, e.g.,

to form a click chemistry product, e.g., its regioisomer, or a mixture thereof. In some examples, the reactive group is a functional group, e.g., which reacts with a cysteine residue on an antibody or antigen-binding fragment thereof, to form a bond thereto, e.g., wherein Ab refers to an antibody or antigen-binding fragment thereof and S refers to the S atom on a cysteine residue through which the functional group bonds to the Ab. In some examples, the reactive group is a functional group, e.g., which reacts with a lysine residue on an antibody or antigen-binding fragment thereof, to form a bond thereto, e.g., wherein Ab refers to an antibody or antigen-binding fragment thereof and —NH— refers to the end of the lysine residue through which the functional group bonds to the Ab. In some examples, this N atom on a lysine residue through which the functional group bonds is indicated herein as the letter N above a bond, e.g., In some embodiments, RL is a monovalent moiety of Formula ($RL^A$);

$$RG\text{-}(SP^1)_q\text{-}(A)_z\text{-}(NR^a)_s\text{-}(B)_t\text{-}(CH_2)_u\text{-}(O)_v\text{-}(SP^2)_w\text{-} \quad (RL^A);$$

wherein RG is a reactive group;
A is an amino acid or a peptide;
$R^a$ is H or alkyl;
B is aryl, heteroaryl, or heterocycloalkyl, wherein aryl, heteroaryl, or heterocycloalkyl is optionally substituted with alkyl, —OH, or —$NR^aR^b$;
$SP^1$ and $SP^2$ are, independently, a spacer groups; and q, z, s, t, u, v, and w are, independently in each instance, 0 or 1.

In some embodiments, RL is $RG\text{-}(SP^1)_q\text{-}(A)_z\text{-}$. In some embodiments, RL is $RG\text{-}(SP^1)_q\text{-}(A)_2\text{-}$. In some embodiments, RL is a moiety of Formula ($RL^{A1}$)

($RL^{A1}$)

wherein $R^{AA1}$ and $R^{AA2}$ are each, independently, amino acid side chains. In some examples of Formula $RL^{A1}$, $SP^1$ is a divalent polyethylene glycol group and RG is a group comprising an alkyne that is capable of undergoing a 1,3-cycloaddition reaction with an azide.

In some embodiments, RL has the following structure:

$$RG\text{-}(SP^1)q\text{-}Z^1\text{—}Z^2\text{—}Z^3{}_{0\text{-}1}\text{—}$$

wherein:
RG, $SP^1$, and q are as defined herein;
$Z^1$ is a polyethylene glycol or caproyl group;
$Z^2$ is a dipeptide; and
$Z^3$ is a PAB group.

In some other embodiments, BL is a trivalent moiety of Formula ($BL^B$);

$$\text{-}RG^N\text{-}(SP^1)_q\text{-}(A)_z\text{-}(NR^a)_s\text{-}(B)_t\text{—}(CH_2)_u\text{—}(O)_v\text{-}(SP^2)_w\text{-}(BL^B);$$

wherein $RG^N$ is as defined herein;
A is tripeptide, wherein at least one of the amino acids in the tripeptide is bonded directly or indirectly to a cyclodextrin moiety;
$R^a$ is H or alkyl;
B is aryl, heteroaryl, or heterocycloalkyl, wherein aryl, heteroaryl, or heterocycloalkyl is optionally substituted with alkyl, —OH, or —$NR^aR^b$;
$SP^1$ and $SP^2$ are, independently, a spacer groups; and q, z, s, t, u, v, and w are, independently in each instance, 0 or 1.

In some examples, the cyclodextrin (CD) is bonded directly to an amino acid residue, such as a lysine amino acid residue. This means that the CD is one bond position away from the lysine amino acid covalent linker. In some of these examples, the covalent linker is also bonded directly to a payload moiety. This means that the covalent linker is one bond position away from a payload such as, but not limited to a steroid payload set forth herein. In some of these examples, the covalent linker is also bonded directly to a CD moiety. This means that the covalent linker is one bond position away from a CD, such as the CD(s) set forth herein.

In some of these examples, the covalent linker is a lysine amino acid or a derivative thereof.

In some examples, the CD is bonded indirectly to a covalent linker in a linking group (e.g., a BL). This means that the CD is more than one bond position away from the covalent linker. This also means that the CD is bonded through another moiety to the covalent linker. For example, the CD may be bonded to a maleimide group which is bonded to a polyethylene glycol group which is bonded to the covalent linker. In some of these examples, the covalent linker is also bonded indirectly to a payload moiety. This means that the covalent linker is more than one bond position away from a payload such as, but not limited to a steroid payload set forth herein. This also means that the covalent linker is bonded through another moiety to the payload. For example, the covalent linker may be bonded to a dipeptide, such as but not limited to Val-Ala or Val-Cit, which may be bonded to para-amino benzoyl which may be bonded to the payload. In some of these examples, the covalent linker is also bonded indirectly to a cyclodextrin moiety. This means that the covalent linker is more than one bond position away from a cyclodextrin, such as the cyclodextrins set forth herein. This also means that the covalent linker is bonded through another moiety to the cyclodextrin. For example, the covalent linker may be bonded to a polyethylene glycol group which may be bonded to reactive group which may be bonded to the cyclodextrin. In some of these examples, the covalent linker is a lysine amino acid or a derivative thereof.

In some embodiments, BL is $-RG^N-(SP^1)_q-(A)_z-$. In some embodiments, BL is $-RG^N-(SP^1)_q-(A)_2-$. In some embodiments, BL is a moiety of Formula ($BL^{B1}$)

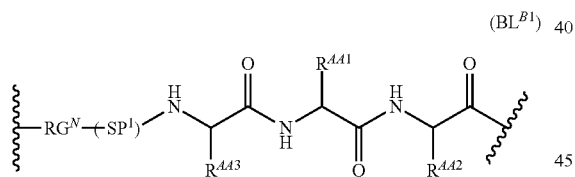

(BL$^{B1}$)

wherein $R^{AA1}$ and $R^{AA2}$ are each, independently, amino acid side chains. $R^{AA3}$ is an amino acid side chain that is bonded directly or indirectly to a cyclodextrin moiety. In some examples of Formula $RL^{B1}$, $SP^1$ is a divalent polyethylene glycol group and $RG^N$ is a 1,3-cycloaddition reaction adduct of the reaction between an alkyne and an azide.

In some examples, A is

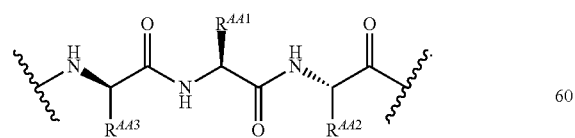

In some of these examples, $R^{AA1}$ is an amino acid side chain, $R^{AA2}$ is an amino acid side chain, and $R^{AA3}$ is an amino acid side chain that is bonded directly or indirectly to a cyclodextrin moiety.

In some examples, A is

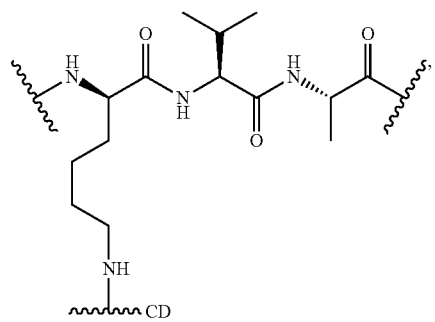

wherein ⌇CD represents a direct or indirect bond to a cyclodextrin moiety.

In some examples, including any of the foregoing, CD is, independently in each instance, selected from

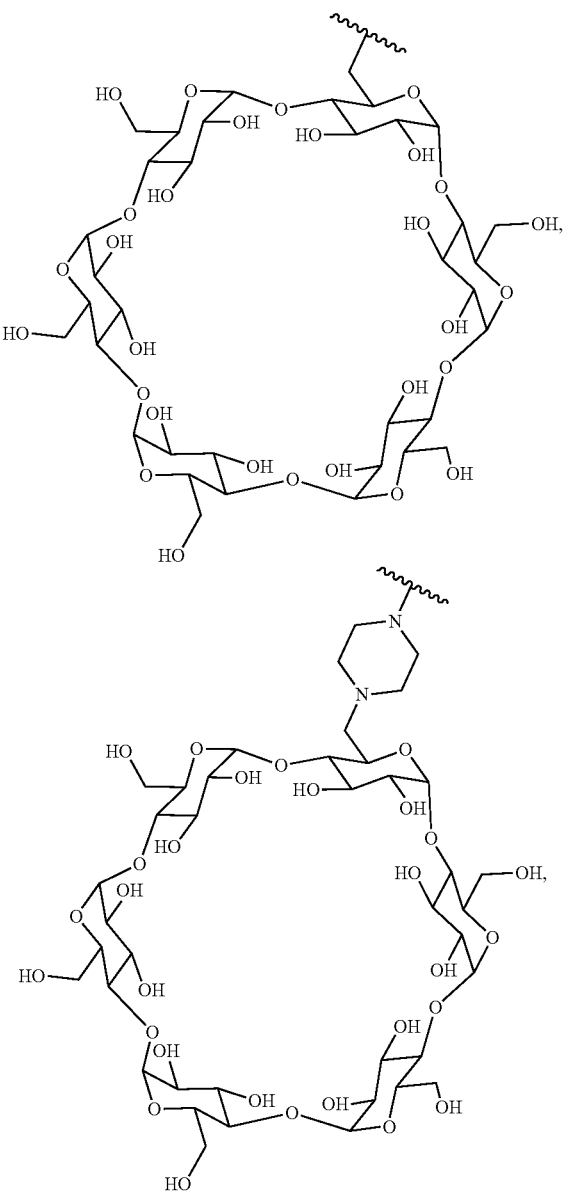

241
-continued
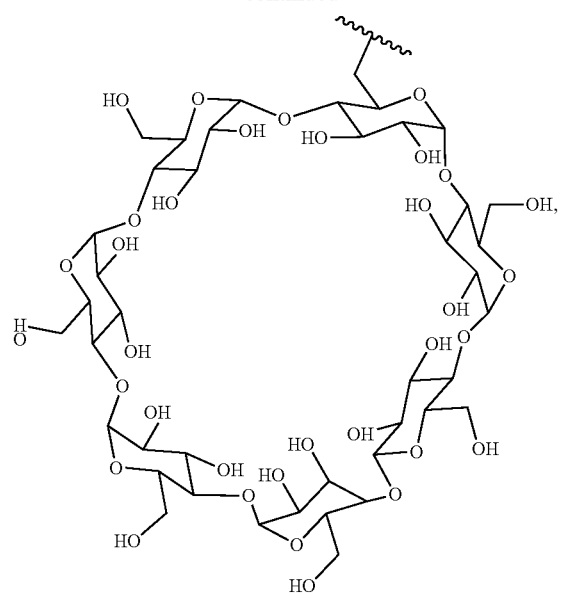
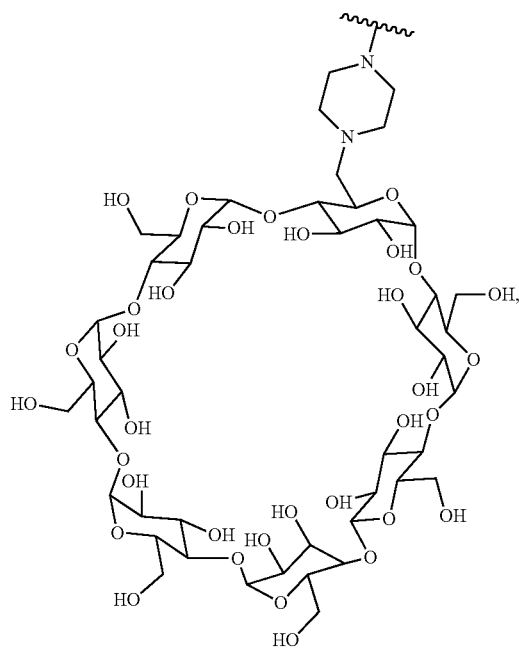
242
-continued
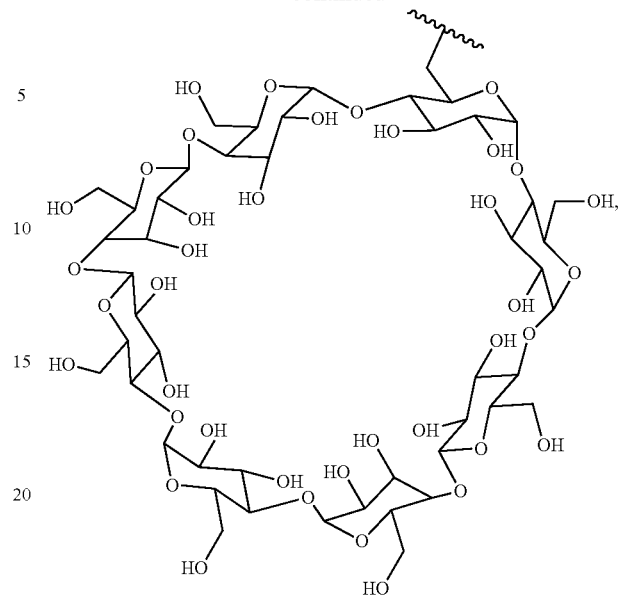
and
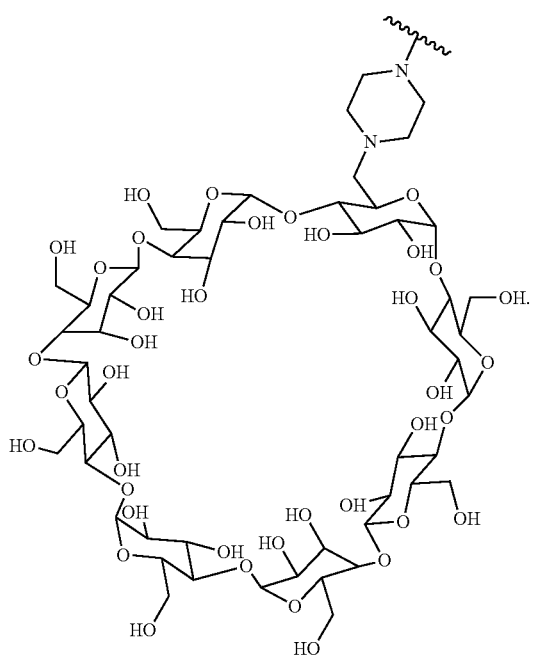

In some examples, the CD is
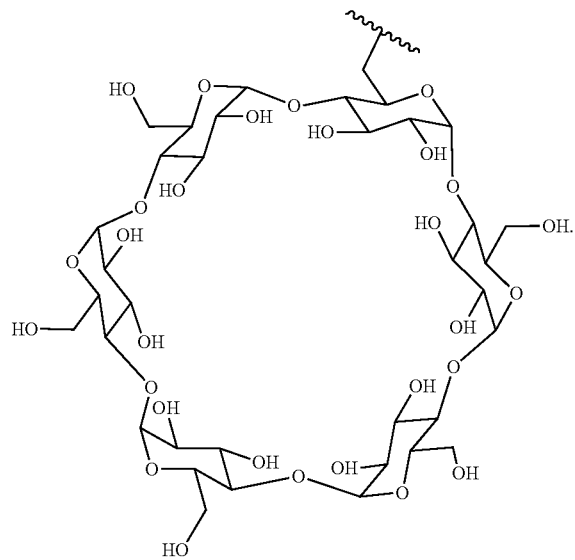 [SMILES: *CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O]
In some examples, the CD is
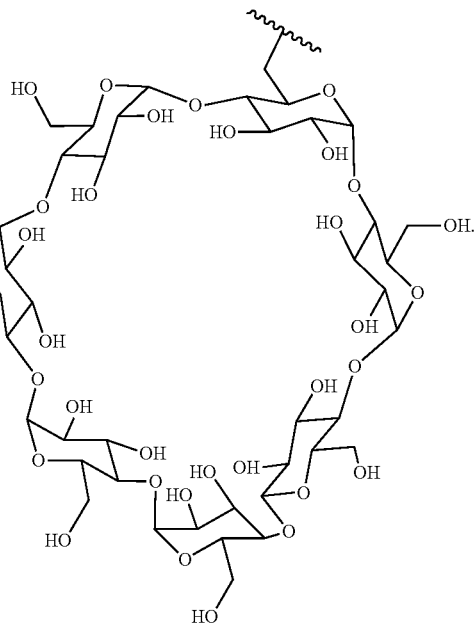
In some examples, the CD is
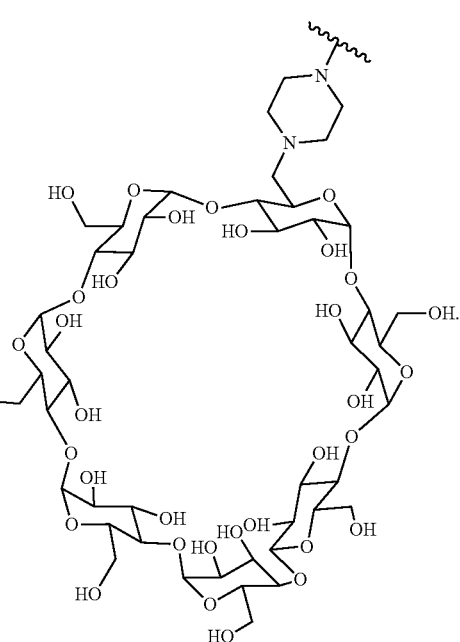
In some examples, the CD is
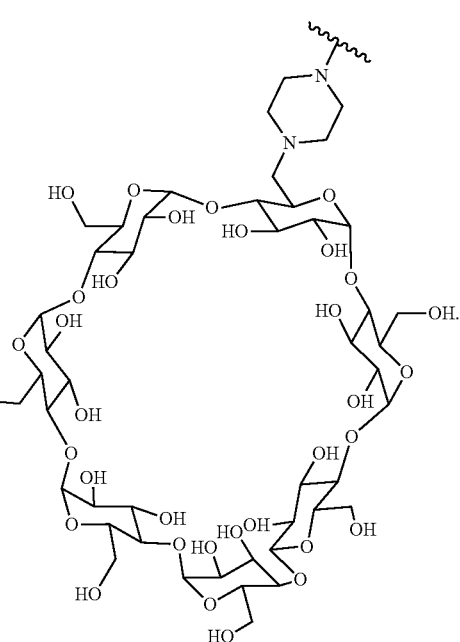

In some examples, the CD is
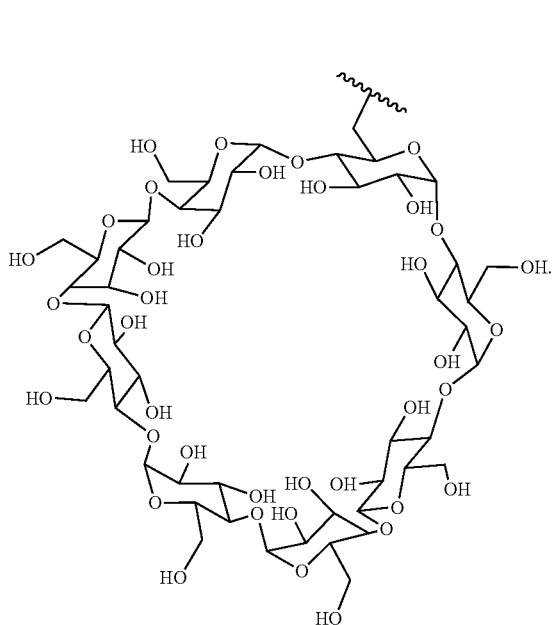 [SMILES: *CC1OC2OC3C(CO)OC(OC4C(CO)OC(OC5C(CO)OC(OC6C(CO)OC(OC7C(CO)OC(OC8C(CO)OC(OC9C(CO)OC(OC1C(O)C2O)C(O)C9O)C(O)C8O)C(O)C7O)C(O)C6O)C(O)C5O)C(O)C4O)C(O)C3O]
In some examples, the CD is
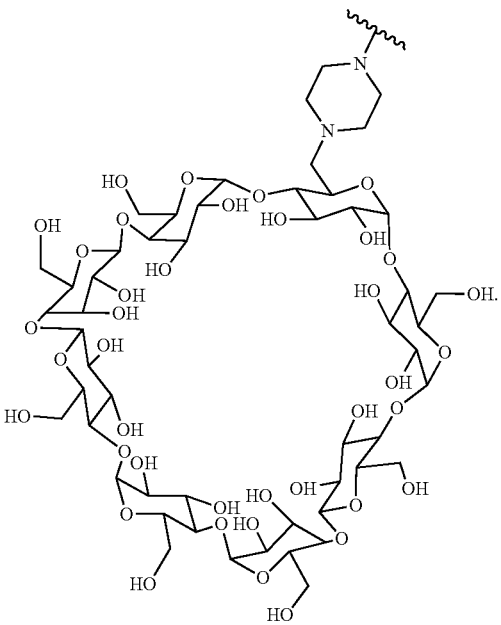 [SMILES: *N1CCN(CC2OC3OC4C(CO)OC(OC5C(CO)OC(OC6C(CO)OC(OC7C(CO)OC(OC8C(CO)OC(OC9C(CO)OC(OC%10C(CO)OC(OC2C(O)C3O)C(O)C%10O)C(O)C9O)C(O)C8O)C(O)C7O)C(O)C6O)C(O)C5O)C(O)C4O)CC1]
In some examples, A is
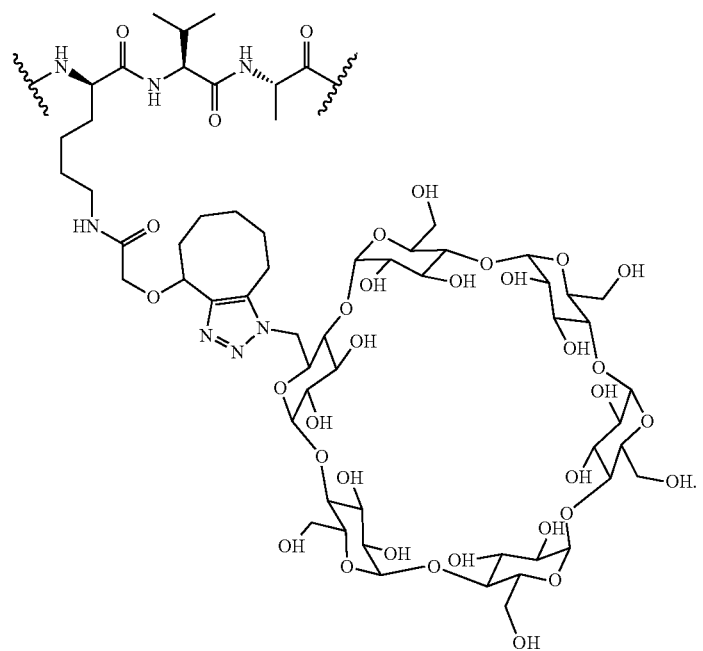 [SMILES: *N[C@H](CCCCNC(=O)COC1CCCCCc2c1nnn2CC1OC2OC3C(CO)OC(OC4C(CO)OC(OC5C(CO)OC(OC6C(CO)OC(OC7C(CO)OC(OC1C(O)C2O)C(O)C7O)C(O)C6O)C(O)C5O)C(O)C4O)C(O)C3O)C(=O)N[C@H](C(=O)N[C@@H](C)C(*)=O)C(C)C]

In some embodiments, the RL attaches to a tertiary amine. For example, if the steroid is the following compound,

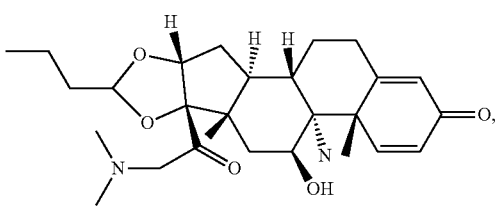 [SMILES: CCCC1O[C@@H]2C[C@H]3[C@@H]4CCC5=CC(=O)C=C[C@]5(C)[C@@]4(N)[C@@H](O)C[C@]3(C)[C@]2(C(=O)CN(C)C)O1]

the RL may bond to the tertiary amine as follows:

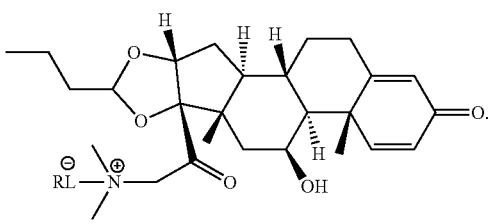

In some examples, set forth is a compound as follows:

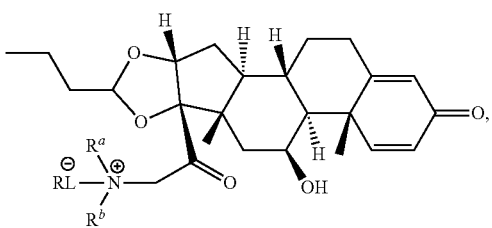

wherein:
RL is a reactive linker as defined above;
$R^a$ and $R^b$ are, independently in each instance, —H or alkyl.

In some examples, herein RG is selected from a click-chemistry reactive group.

In some other examples, herein RG is selected from a group which reacts with a cysteine or lysine residue on an antibody or an antigen-binding fragment thereof.

In some embodiments, RG is

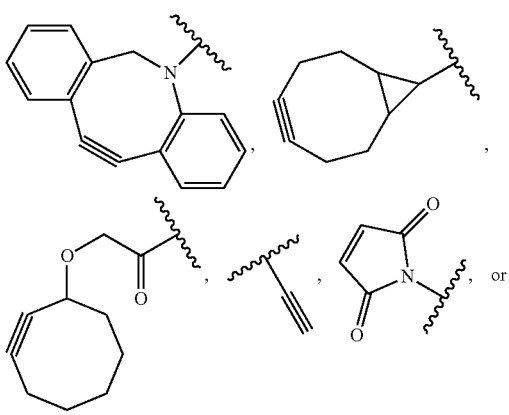

, or

In some examples, RG is

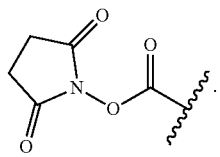

.

In some examples, RG is

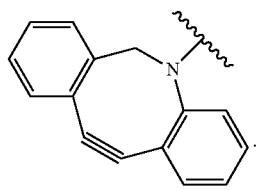 [SMILES: *N1Cc2ccccc2C#Cc2ccccc21]

.

In other examples, RG is

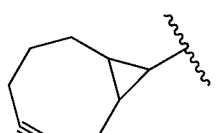

.

In some other examples, RG is

.

In some examples, RG is

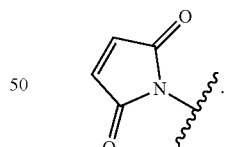

.

In other examples, RG is

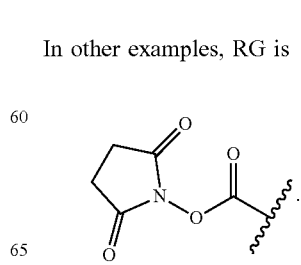

.

In other examples, RG is

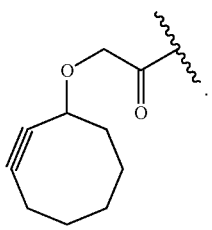 [SMILES: *C(=O)COC1C#CCCCCC1]

In some embodiments, SP¹ may be selected from:

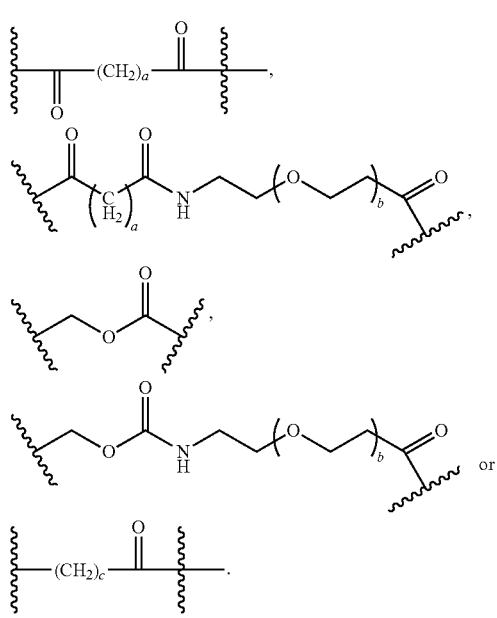

In some examples, SP¹ is

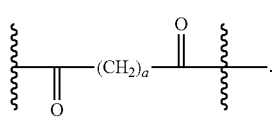

In some other examples, SP¹ is

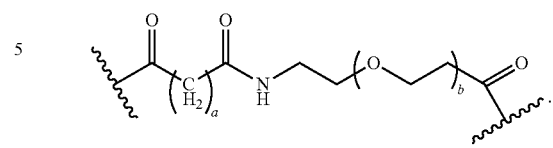

In other examples, SP¹ is

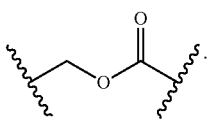 [SMILES: *COC(*)=O]

In still other examples, SP¹ is

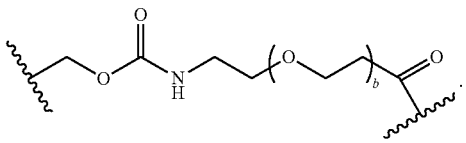

In some other examples, SP¹ is

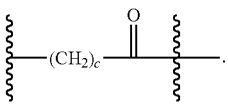

In any of the above examples, subscripts a, b, and c are independently, in each instance, an integer from 1 to 20.

In any of the compounds of Formula (II), (IIa), (IIb), or (IIc), SP¹ may be selected from:

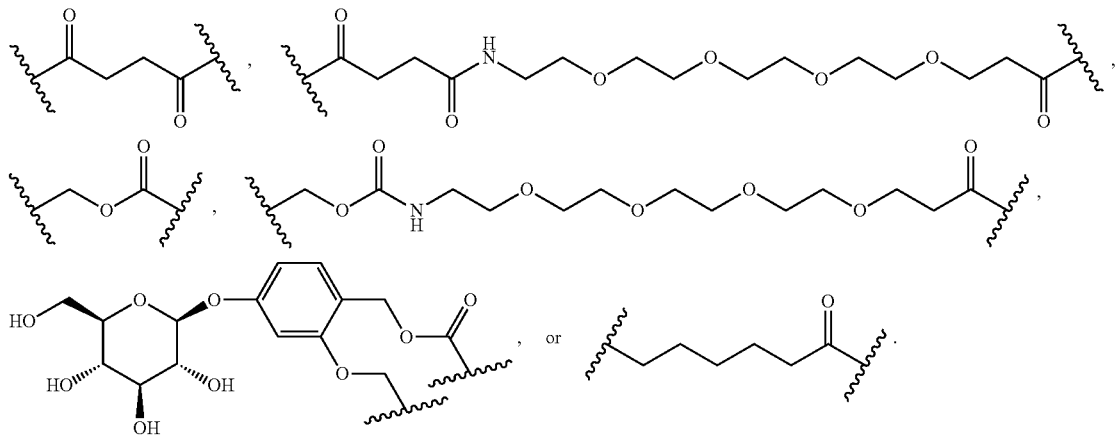

In some examples, SP¹ is

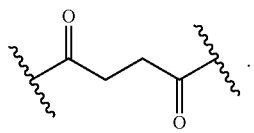 [SMILES: *C(=O)CCC(*)=O]

In some examples, SP¹ is

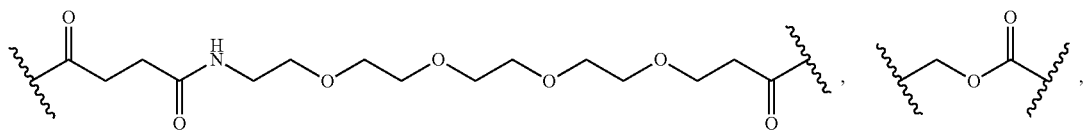 [SMILES: *C(=O)CCOCCOCCOCCOCCNC(=O)CCC(*)=O ; *COC(*)=O]

In some examples, SP¹ is

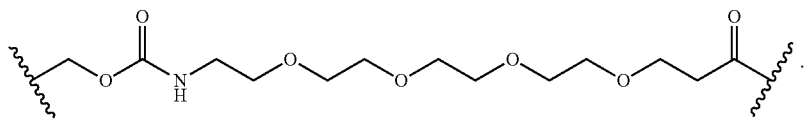 [SMILES: *COC(=O)NCCOCCOCCOCCOCCC(*)=O]

In some examples, SP¹ is

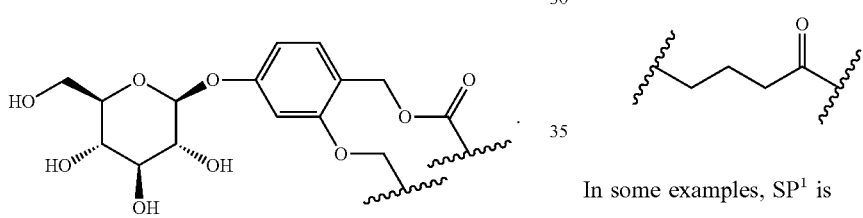

In some examples, SP¹ is

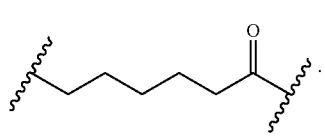 [SMILES: *CCCCCC(*)=O]

In some examples, SP¹ is

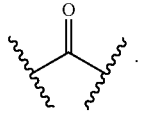 [SMILES: *C(*)=O]

In some examples, SP¹ is

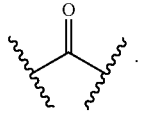 [SMILES: *C(*)=O]

In some examples, SP¹ is

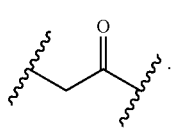 [SMILES: *CC(*)=O]

In some examples, SP¹ is

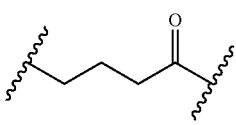

In some examples, SP¹ is (image of propanone linker)

In some examples, SP¹ is (image of pentanone linker)

In some examples, SP¹ is

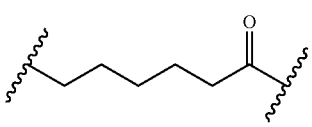

In some examples, SP¹ is (image of heptanone linker)

In some embodiments, RL-SP¹ may be selected from the group consisting of:

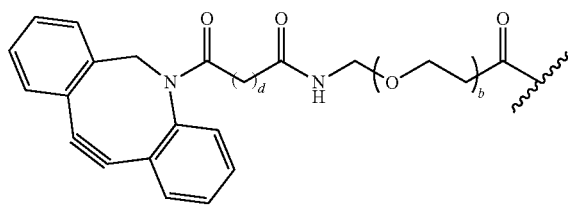

-continued
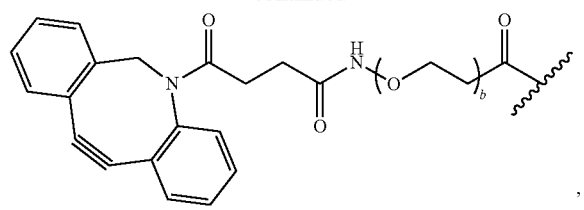
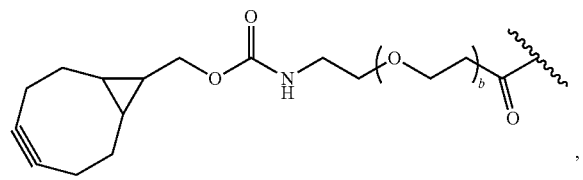
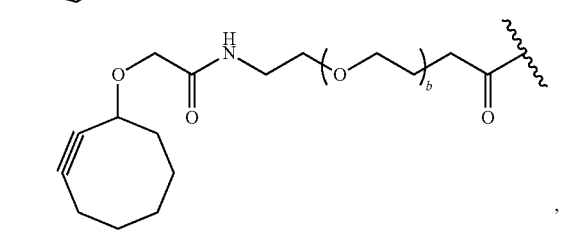
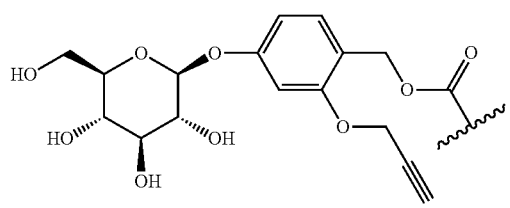
or
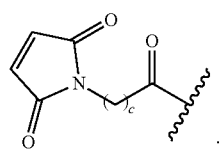
In some of these examples, subscripts b, c, and d are independently, in each instance, an integer from 1 to 20.
In some examples RL-SP$^1$- is
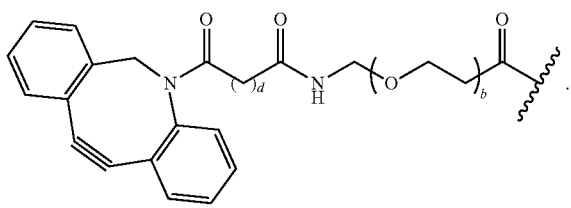
In some examples RL-SP$^1$ is
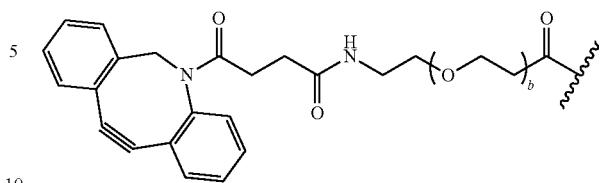
In some examples RL-SP$^1$ is
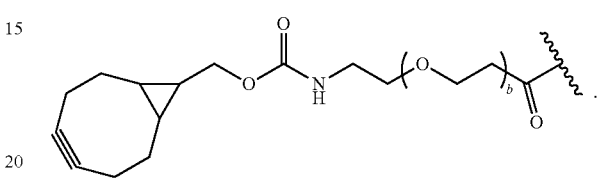
In some examples RL-SP$^1$ is
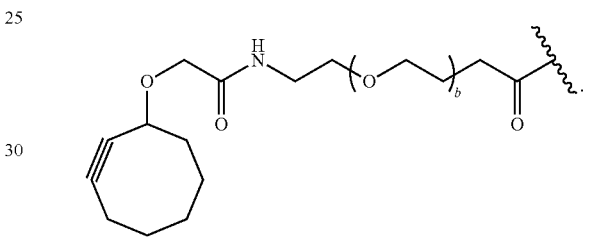
In some examples RL-SP$^1$ is
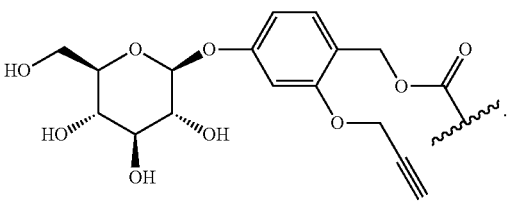 [SMILES: *C(=O)OCc1ccc(O[C@@H]2O[C@H](CO)[C@@H](O)[C@H](O)[C@H]2O)cc1OCC#C]
In some examples RL-SP$^1$ is
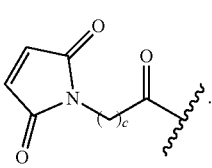
In any of the compounds of Formula (II), (IIa), (IIb), or (IIc), RL-SP$^1$ is selected from:
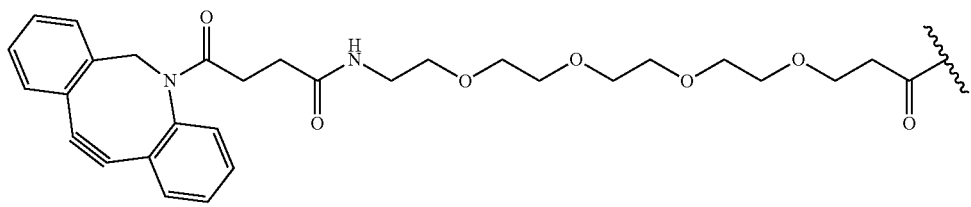

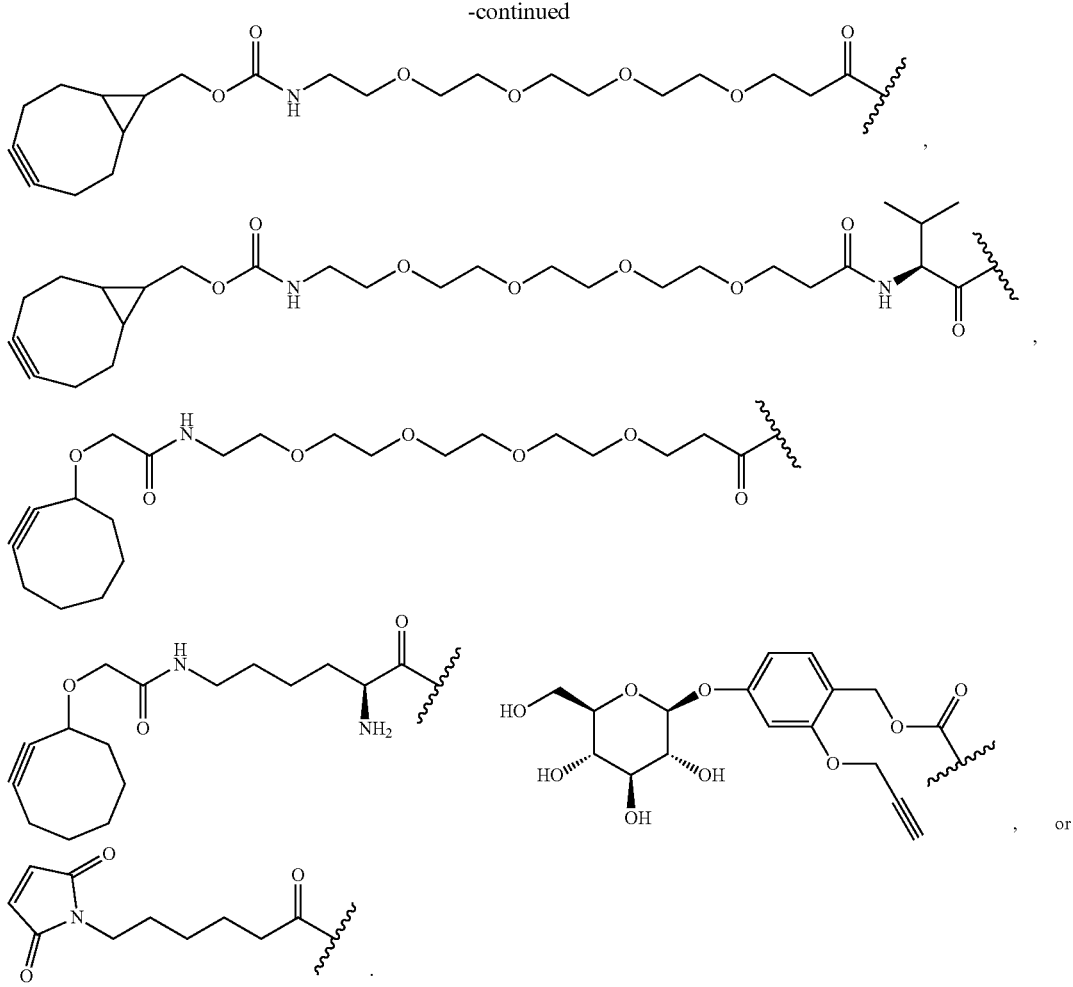

In some embodiments, A is a peptide selected from valine-citrulline, citrulline-valine, lysine-phenylalanine, phenylalanine-lysine, valine-asparagine, asparagine-valine, threonine-asparagine, asparagine-threonine, serine-asparagine, asparagine-serine, phenylalanine-asparagine, asparagine-phenylalanine, leucine-asparagine, asparagine-leucine, isoleucine-asparagine, asparagine-isoleucine, glycine-asparagine, asparagine-glycine, glutamic acid-asparagine, asparagine-glutamic acid, citrulline-asparagine, asparagine-citrulline, alanine-asparagine, or asparagine-alanine.

In some examples, A is valine-citrulline or citrulline-valine.

In some examples, A is valine-alanine or alanine-valine.
In some examples, A is valine.
In some examples, A is alanine.
In some examples, A is citrulline.
In some examples, A is

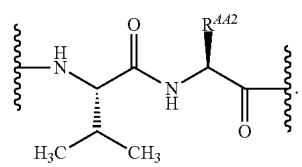

In some of these examples, $R^{AA1}$ is an amino acid side chain, and wherein $R^{AA2}$ is an amino acid side chain.

In some examples, A is

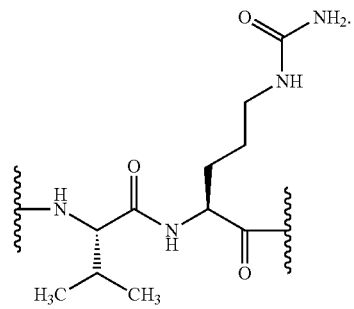 [SMILES: *N[C@H](C(=O)N[C@@H](CCCNC(N)=O)C(*)=O)C(C)C]

In some examples, A is

In some examples, $R^a$ is H

In some examples, $R^a$ is alkyl

In some examples, $R^a$ is methyl, ethyl, n-propyl, i-propyl, n-butyl, t-butyl, butyl, or pentyl.

In some embodiments, B is aryl.

In some examples, B is phenyl.

In some examples of compounds of Formula (II), (IIa), (IIb), or (IIc), B is phenyl or pyridinyl.

In some examples herein, B is:

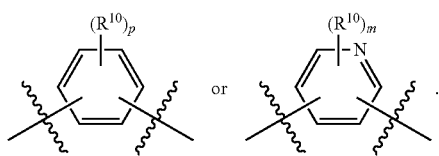

In these examples, $R^{10}$ is alkyl, alkenyl, alkynyl, alkoxy, aryl, alkylaryl, arylalkyl, halo, haloalkyl, haloalkoxy, heteroaryl, heterocycloalkyl, hydroxyl, cyano, nitro,

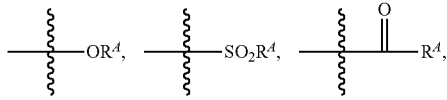

$NR^aR^b$, or azido. In these examples, subscripts p and m are independently, in each instance, selected from an integer from 0 to 4. In some examples herein, B is:

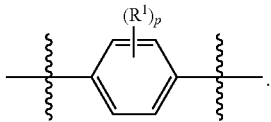

In these examples, p is 0, 1, 2, 3 or 4. In some of these examples, $R^1$ is, independently at each occurrence, alkyl, alkoxy, haloalkyl, or halo. In some examples, $R^1$ is alkyl. In some examples, $R^1$ is alkoxy. In some examples, $R^1$ is haloalkyl. In some examples, $R^1$ is halo.

In some embodiments of Formula ($RL^A$), the —$(NR^a)_s$—$(B)_t$—$(CH_2)_u$—$(O)_v$-$(SP^2)_w$ is:

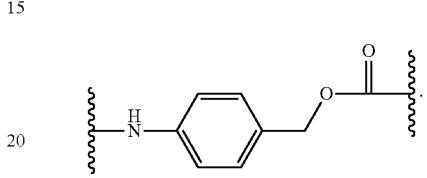

Provided herein are also linker-payloads of budesonide or diflorasone. In some embodiments, provided herein is a linker-payload having the following structure:

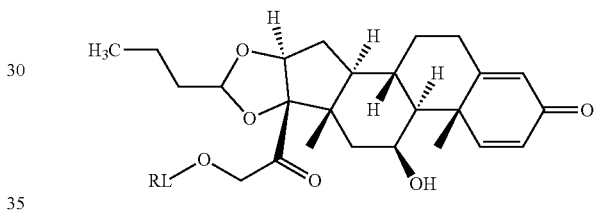

wherein RL is a reactive linker.

Examples of linker-payloads include, but are not limited to:

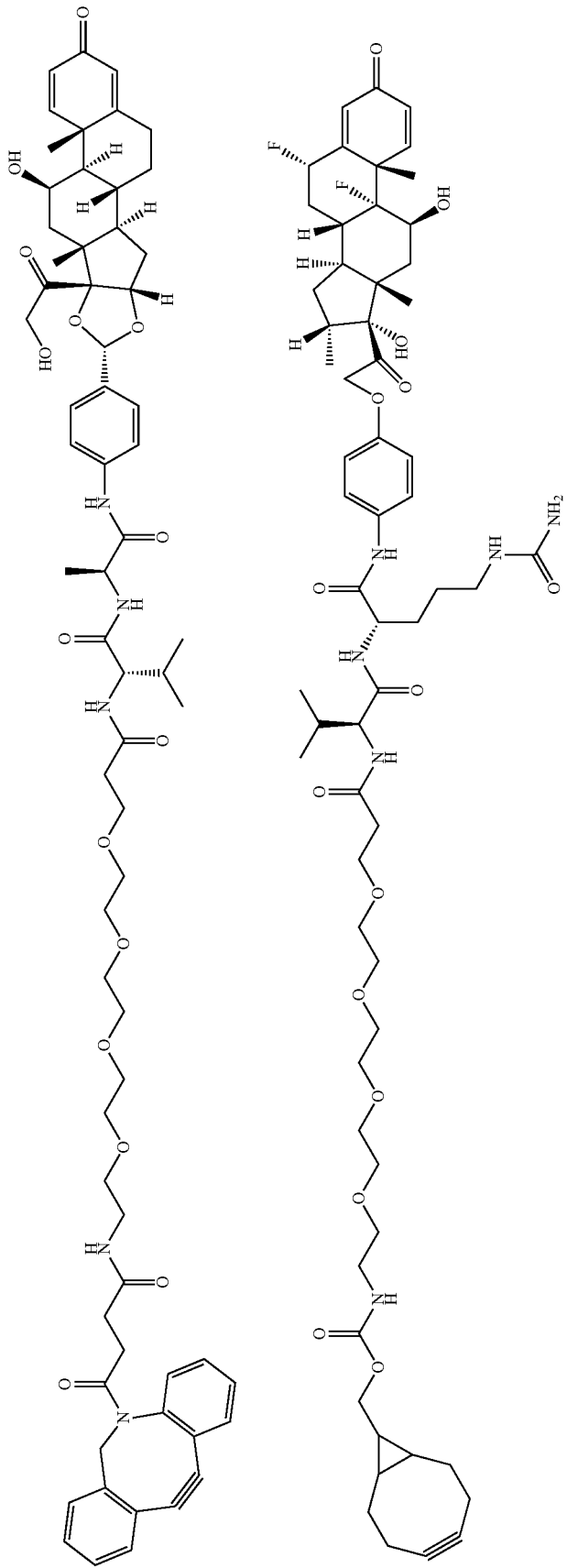

-continued
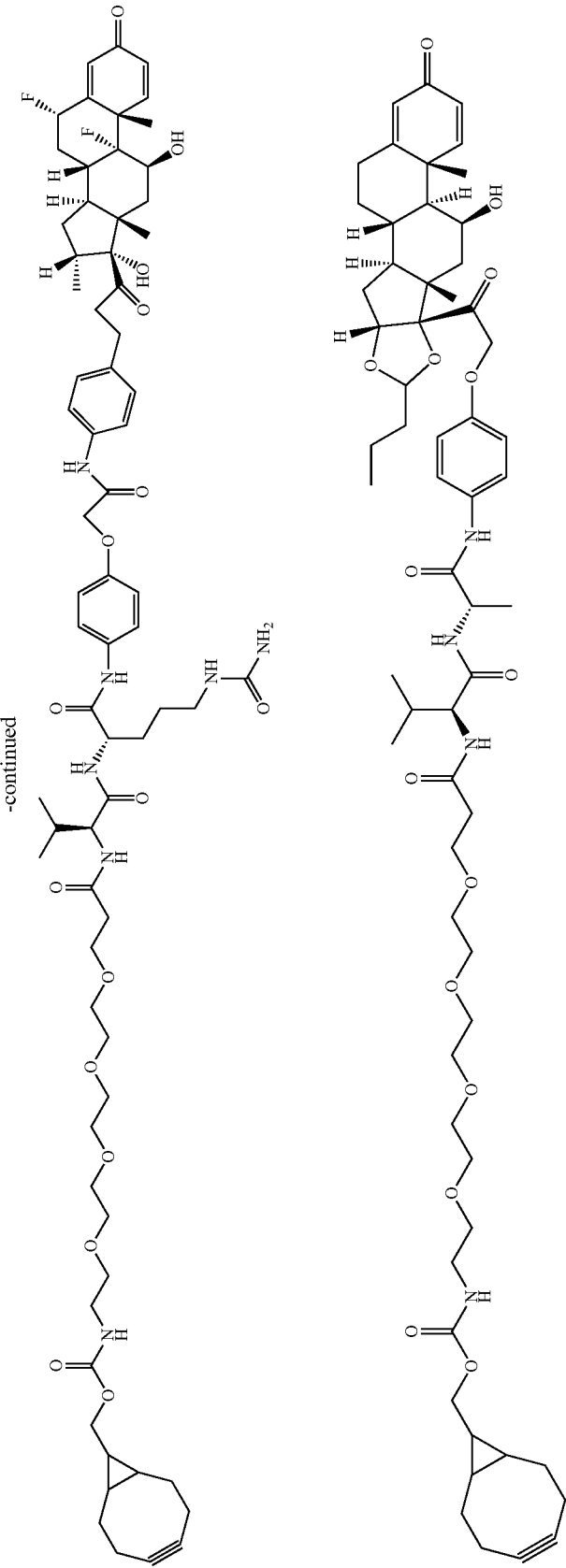

-continued
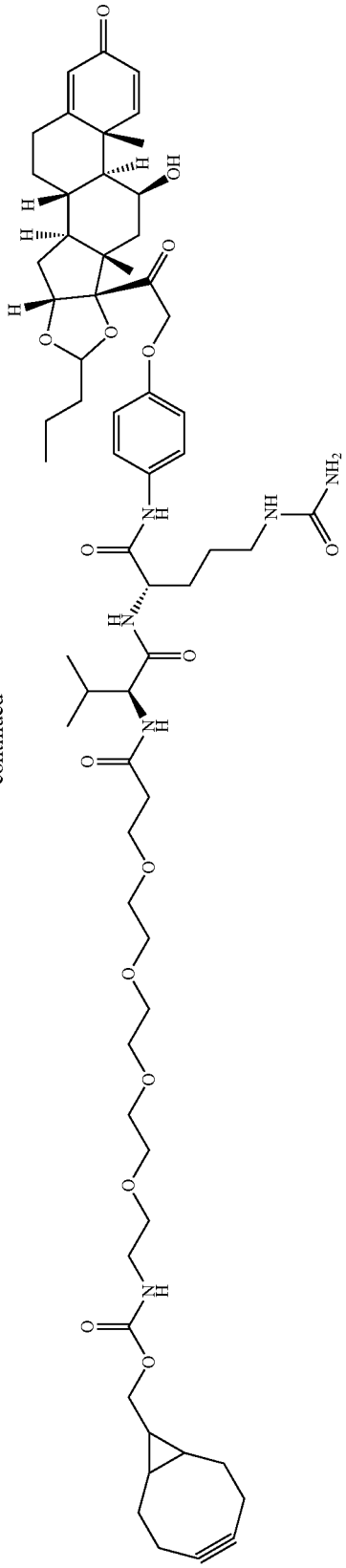
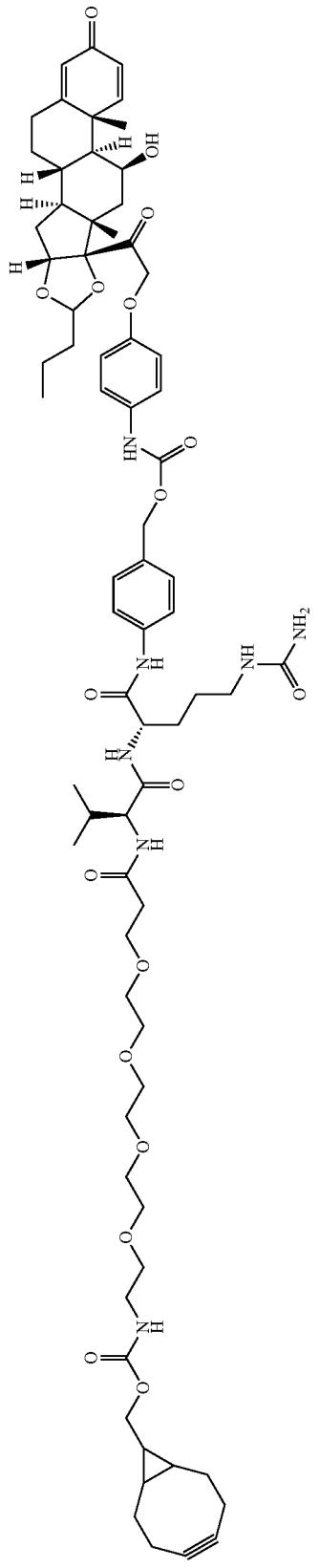

-continued
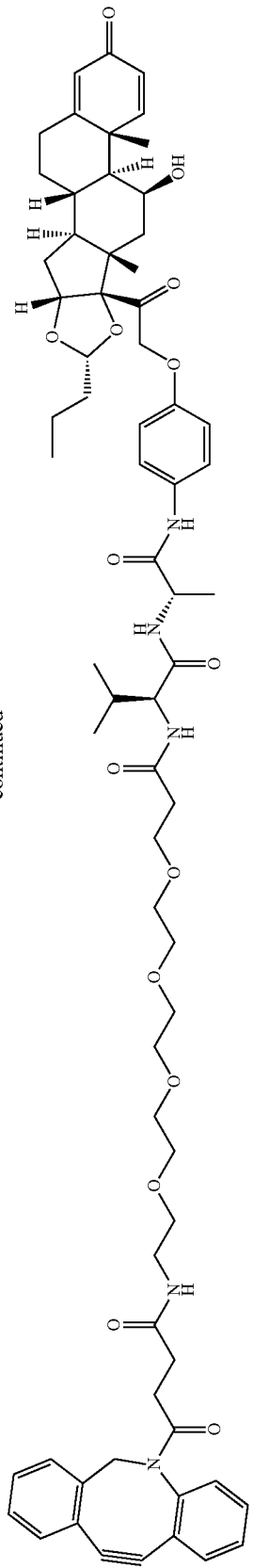
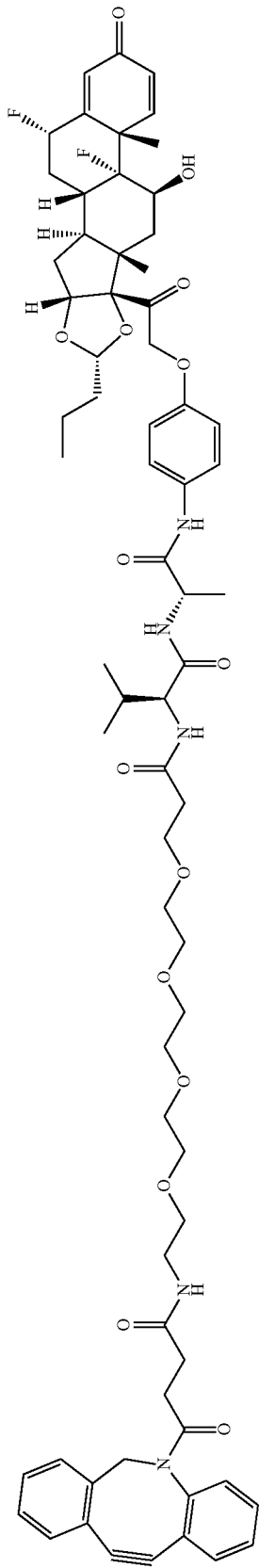

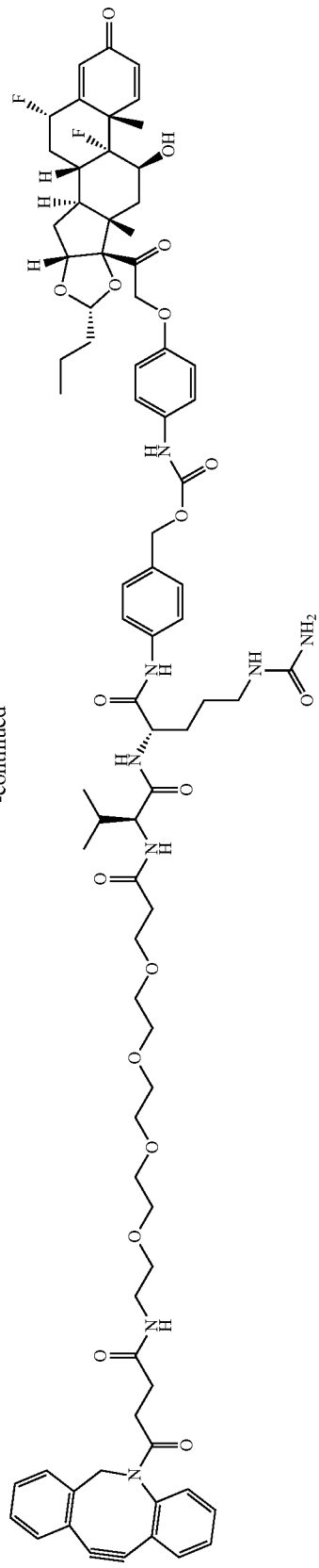
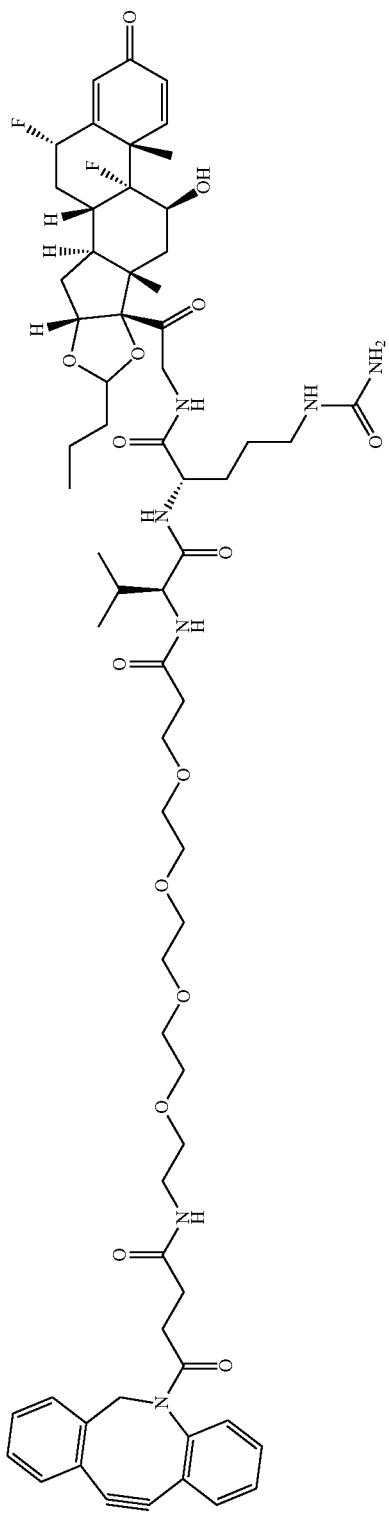

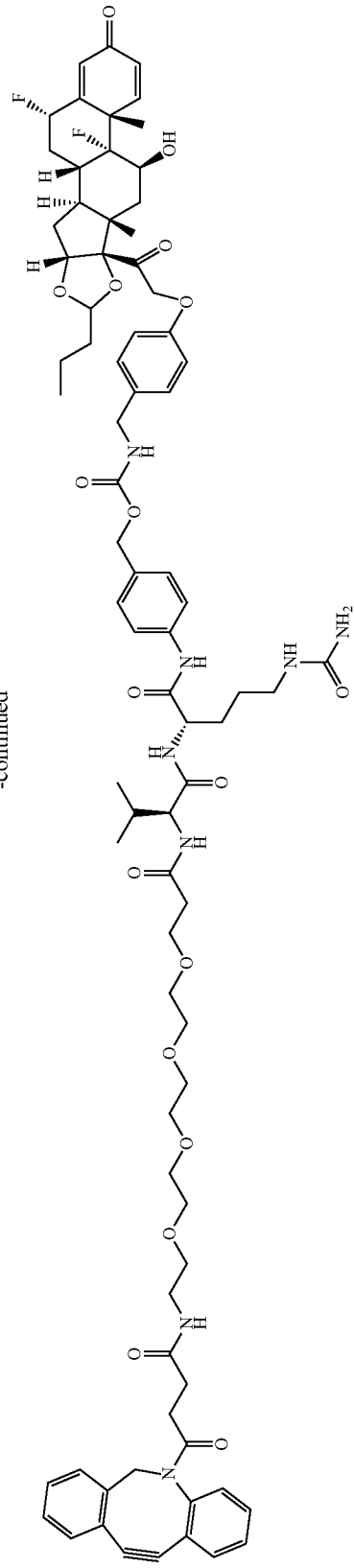
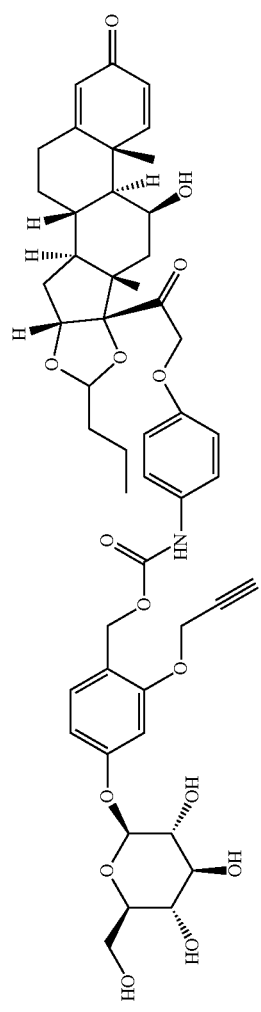

-continued
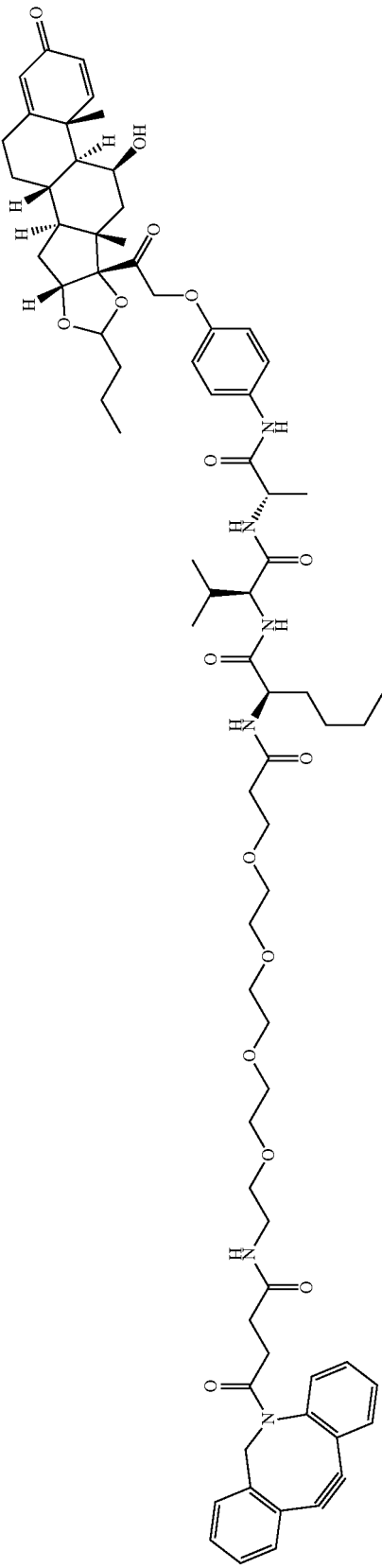
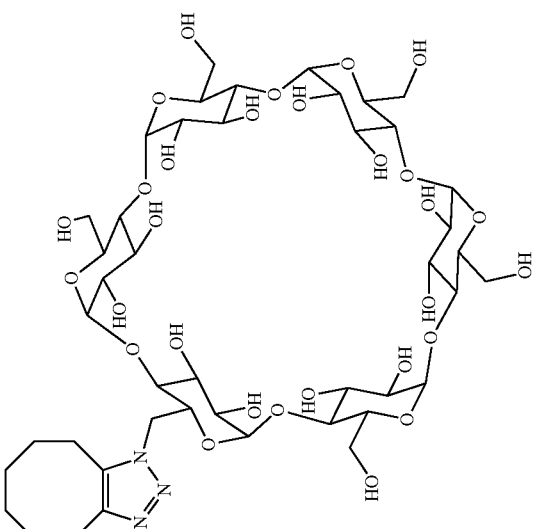

-continued
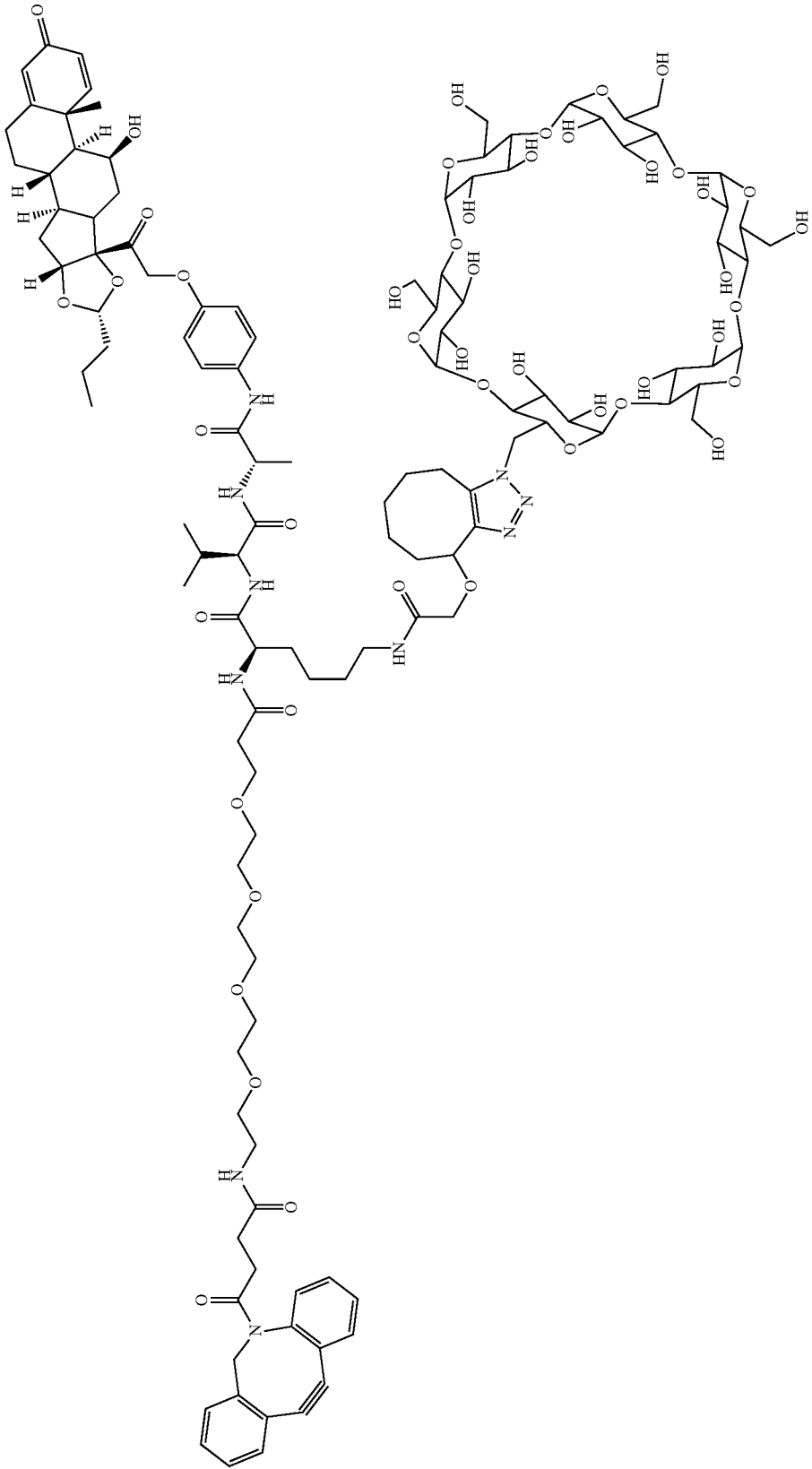

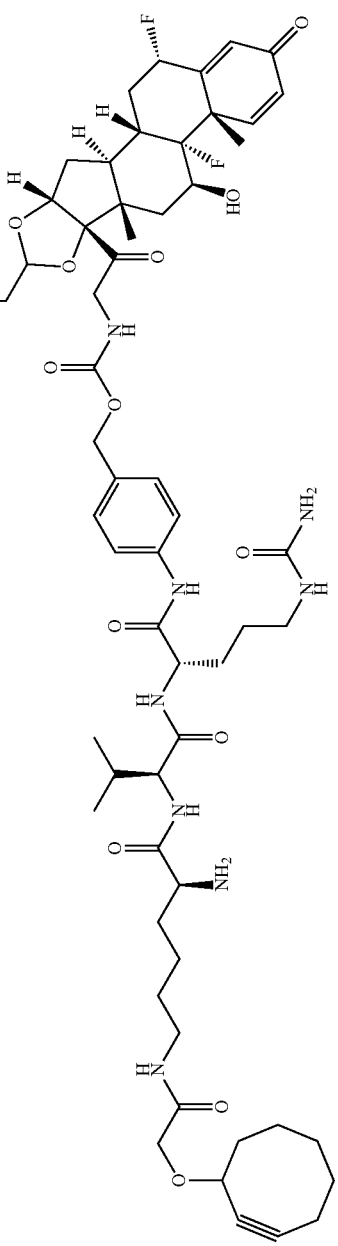
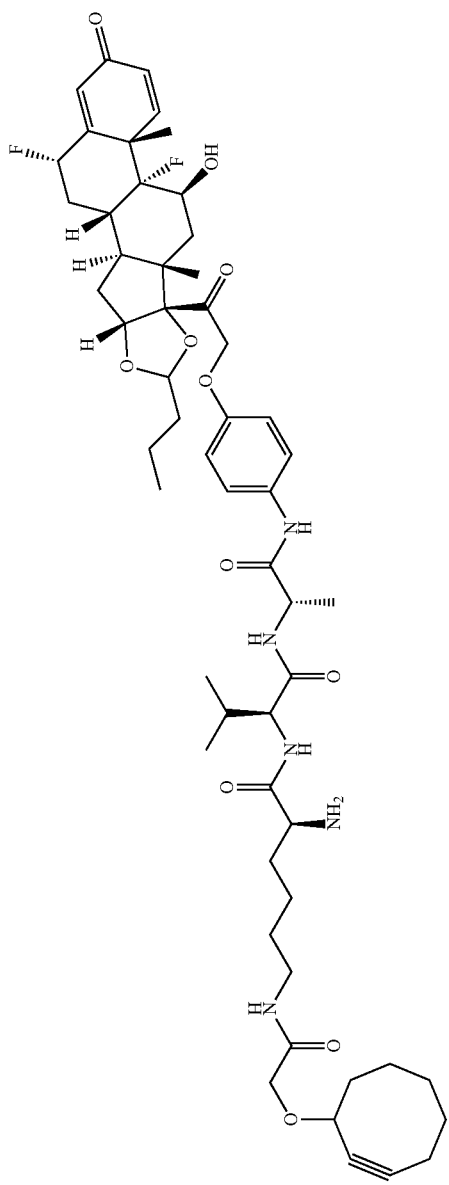

-continued
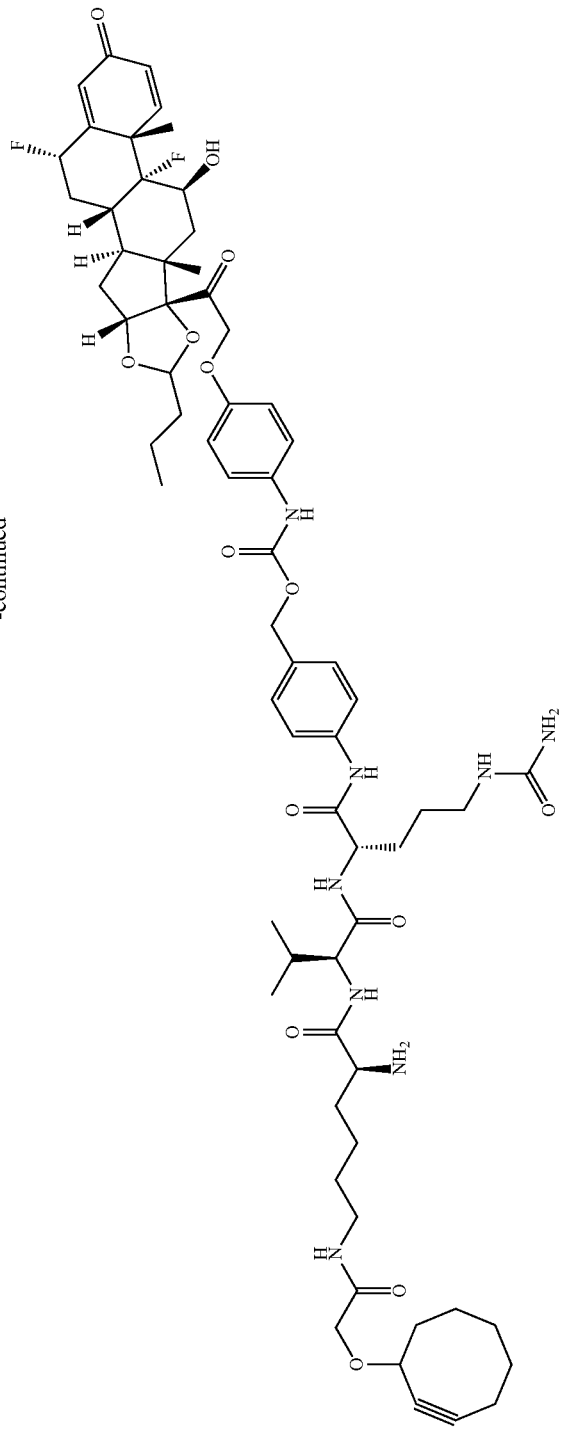

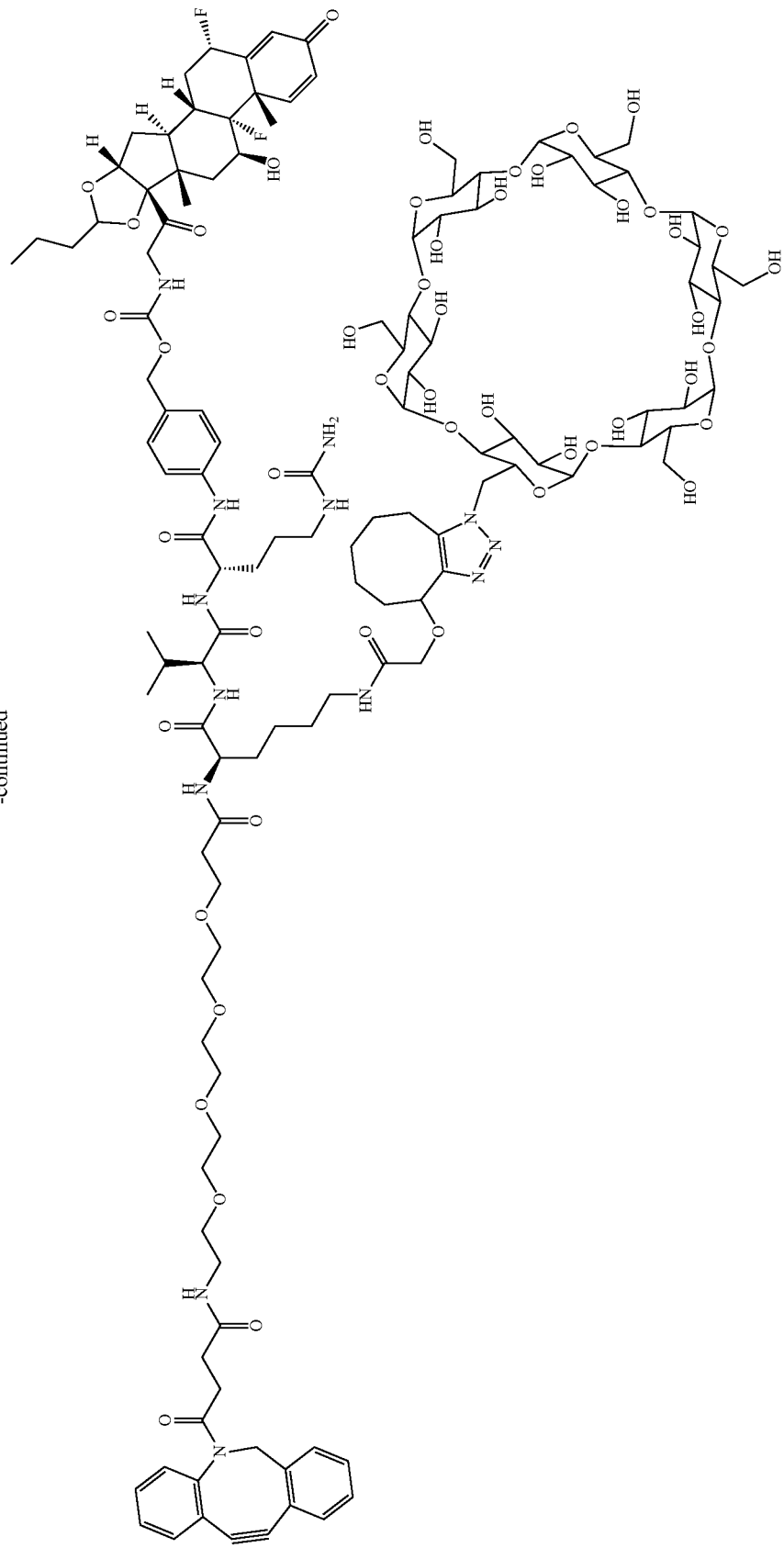

-continued
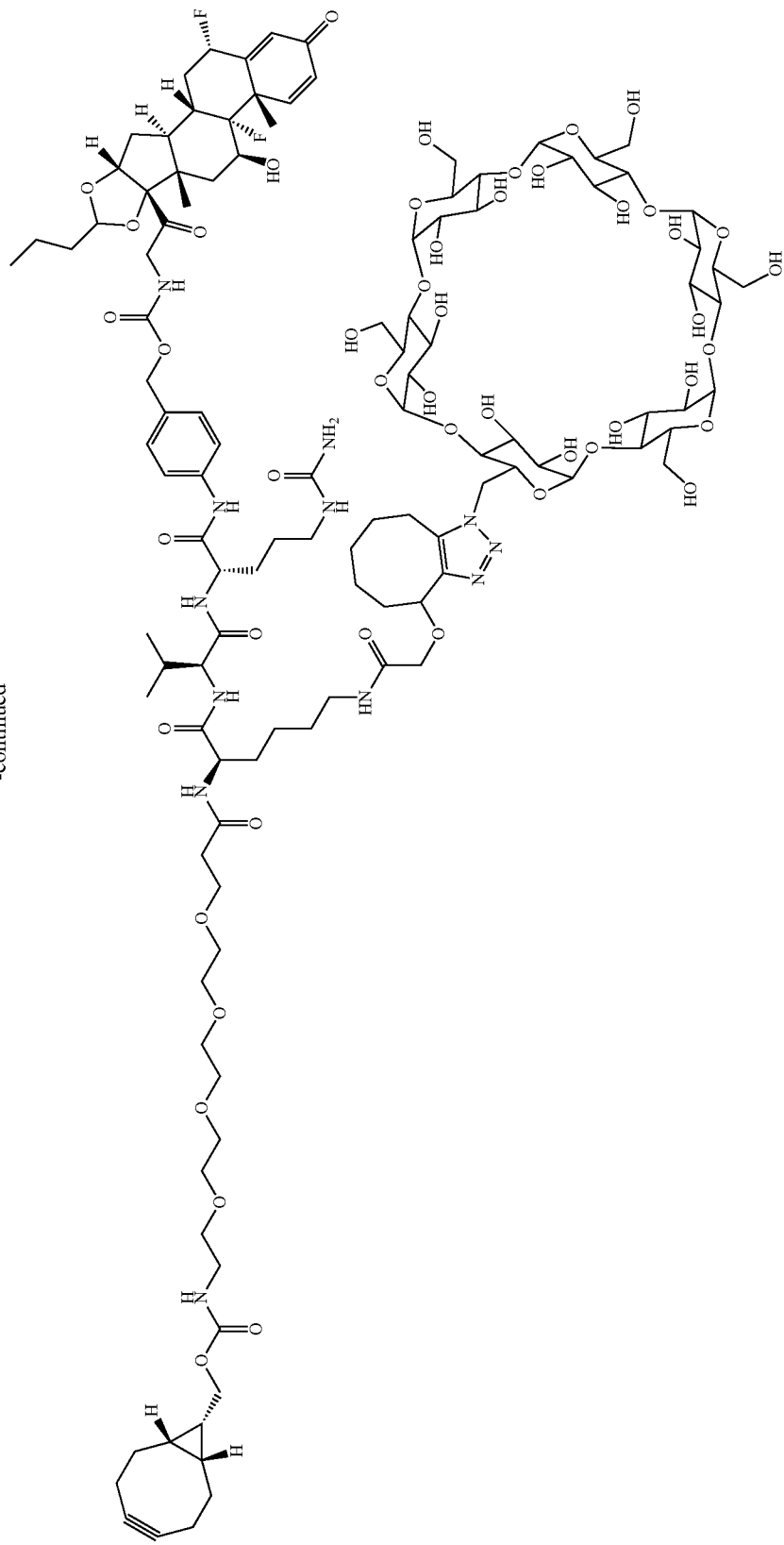

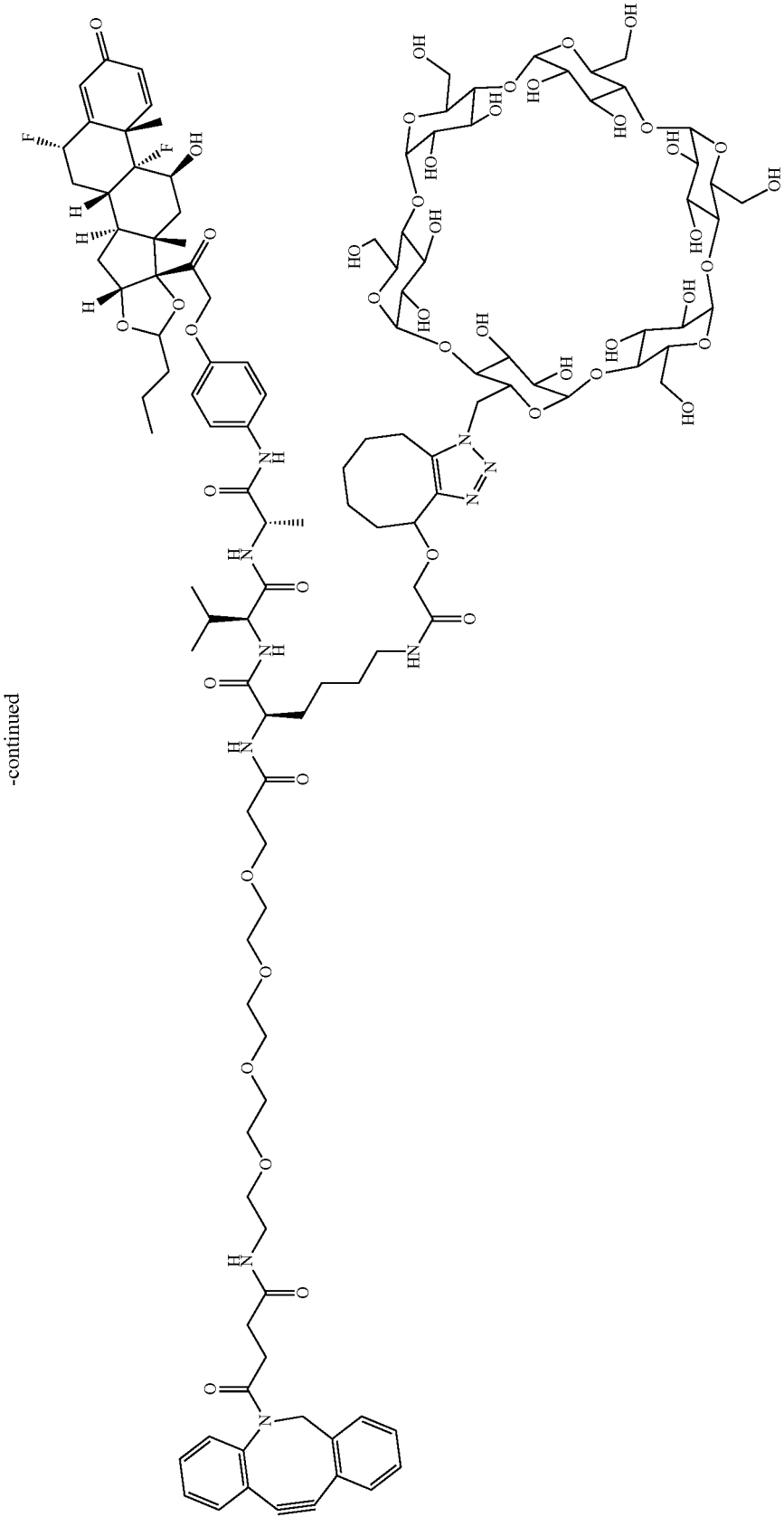

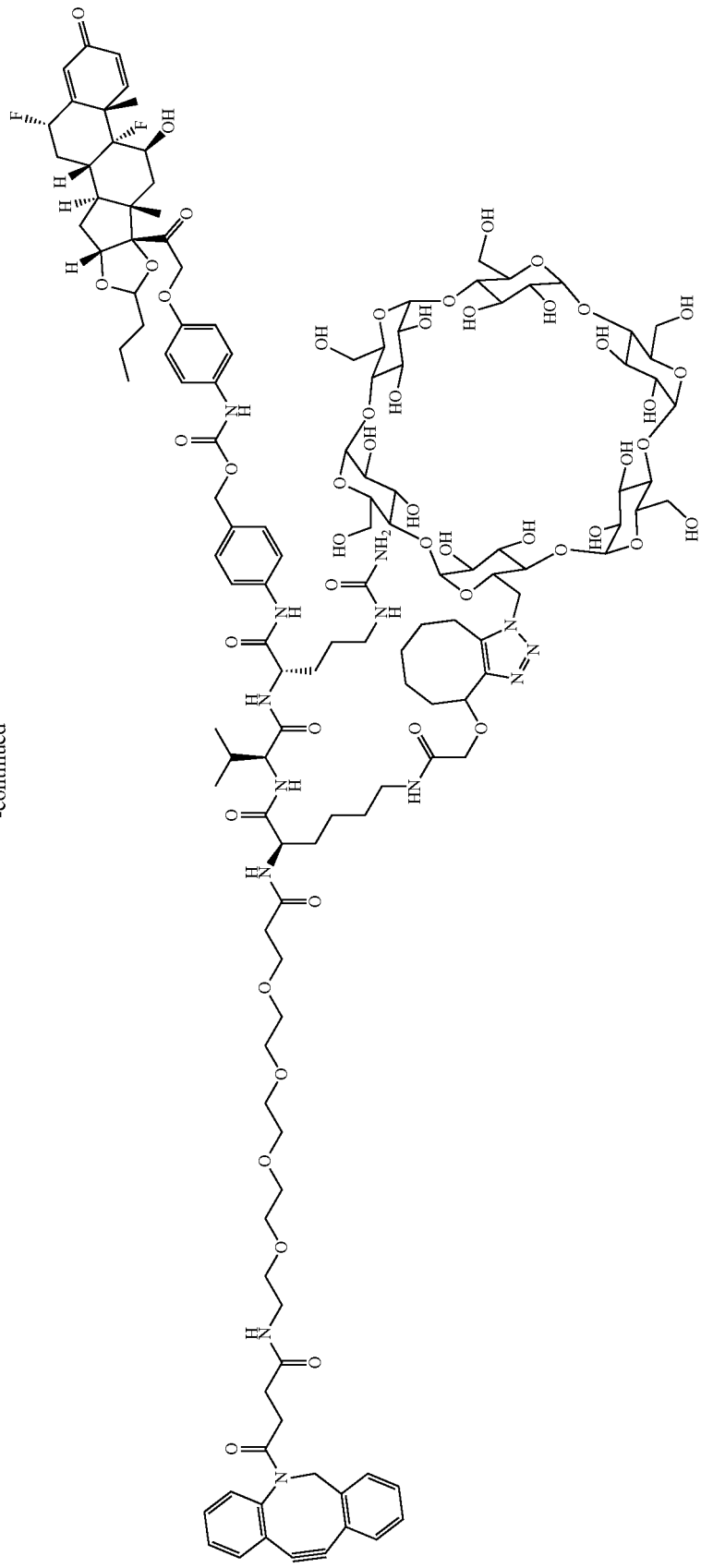

-continued
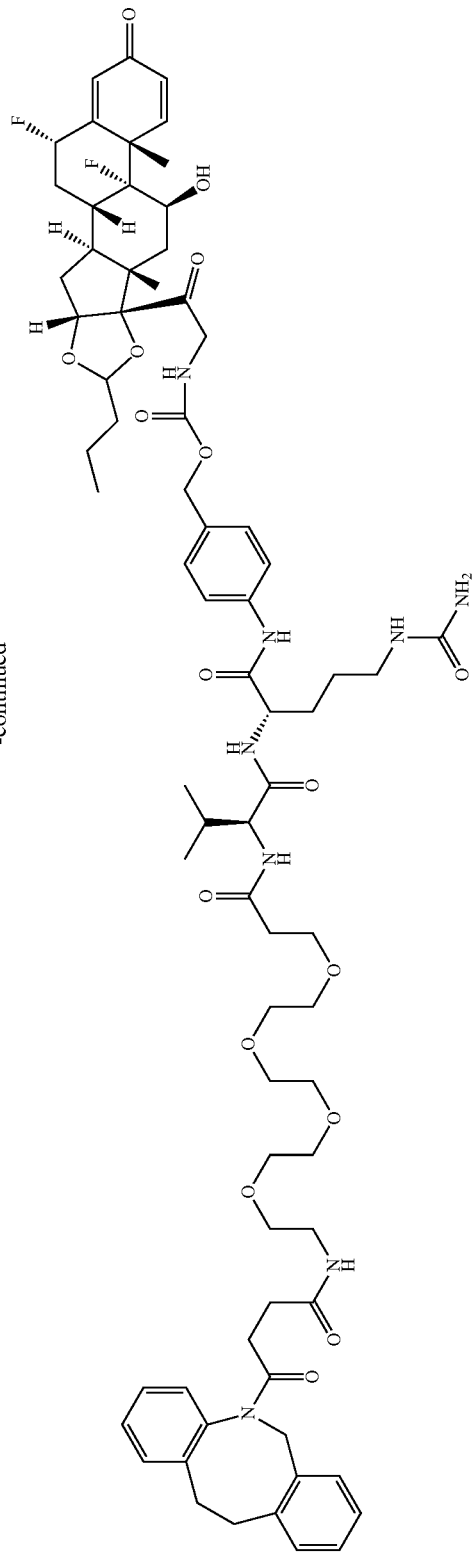
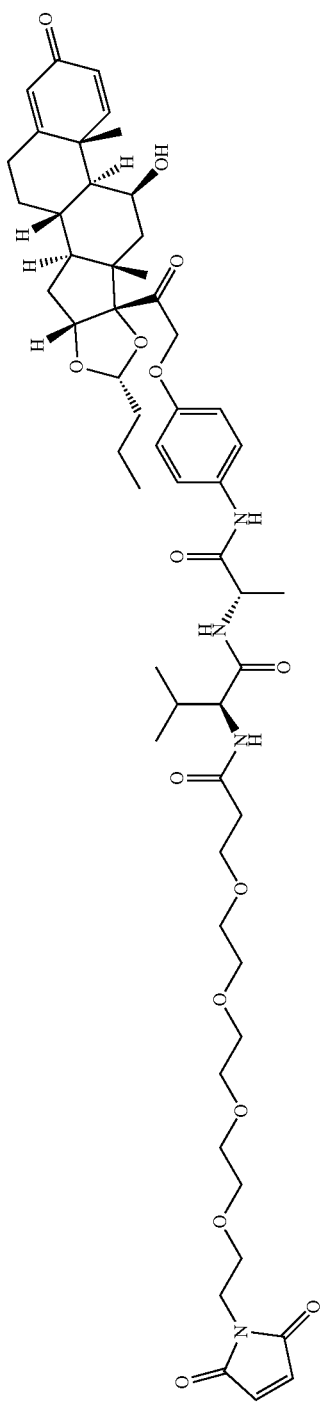

-continued
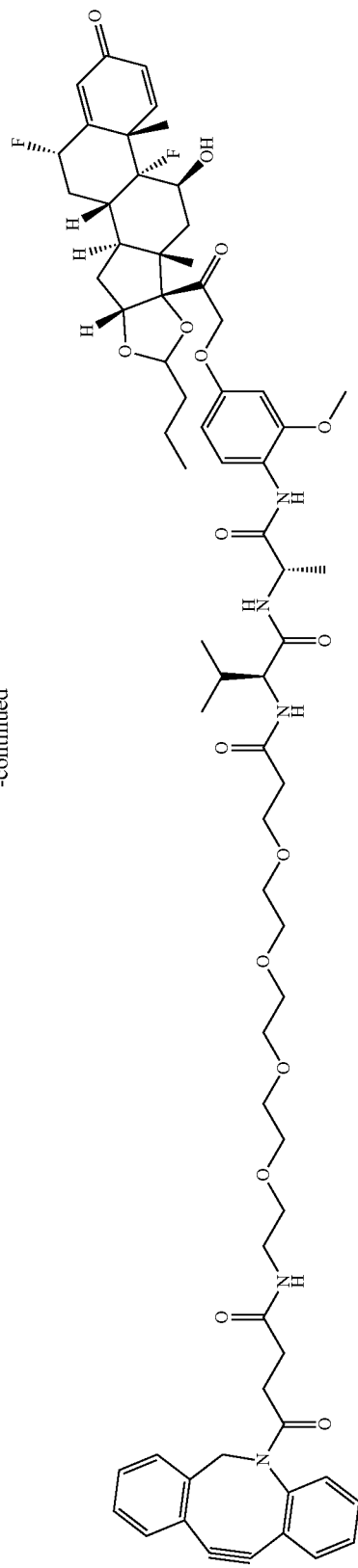
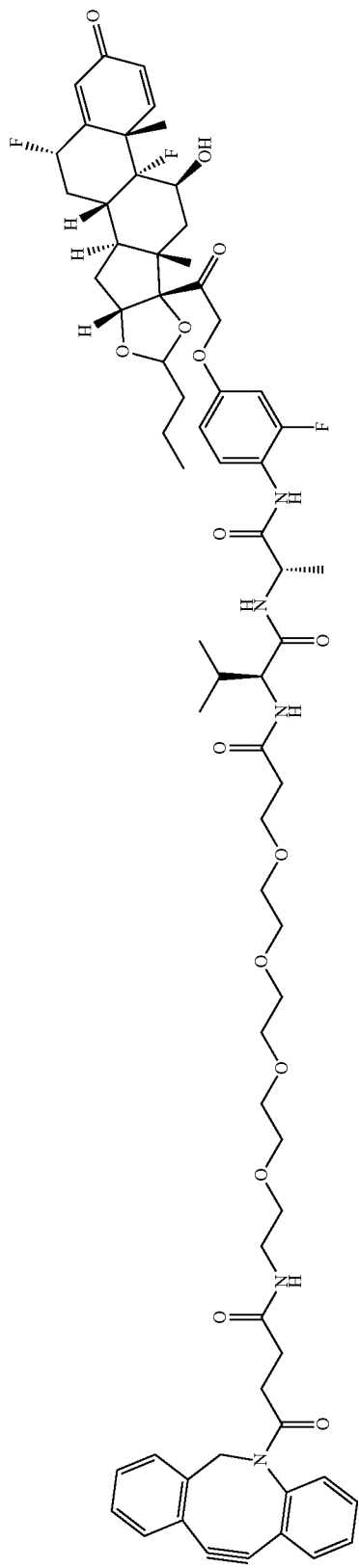

-continued
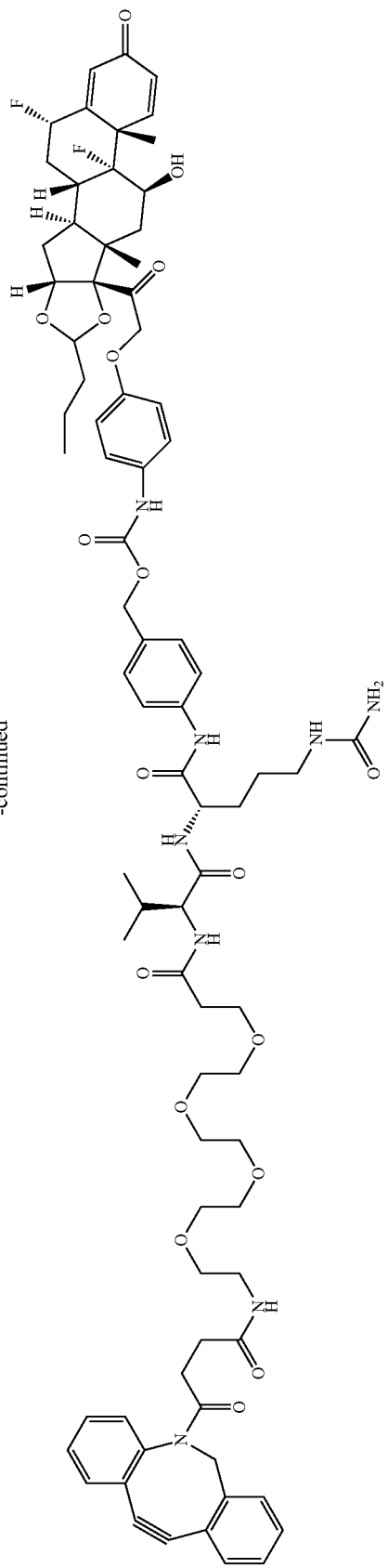
and
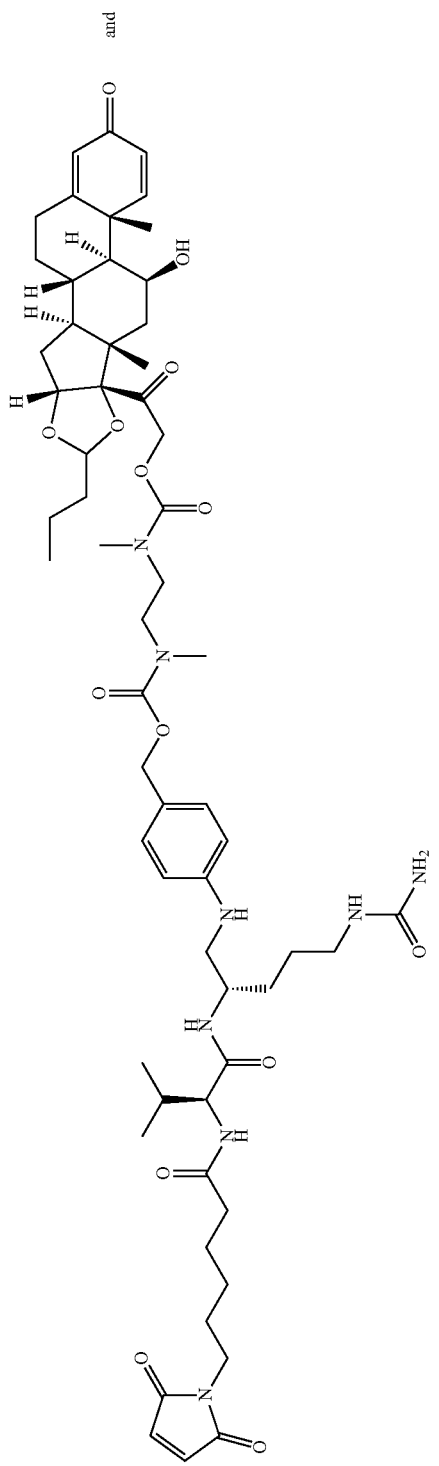

-continued
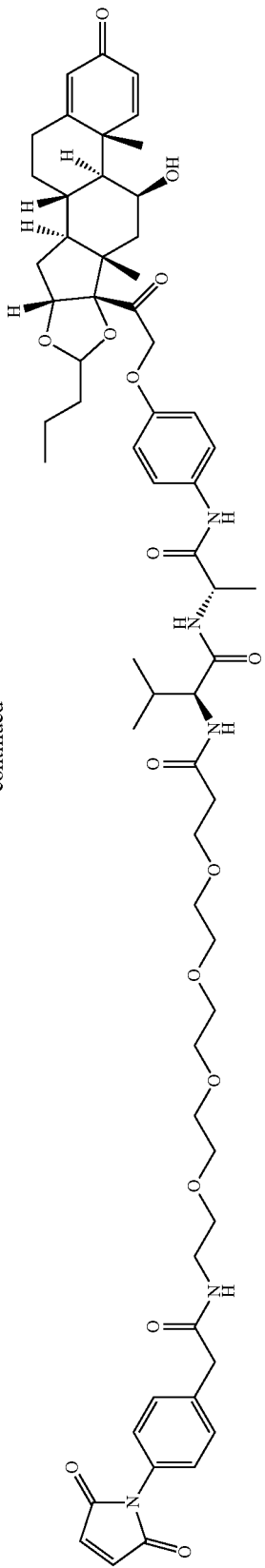

E. Pharmaceutical Compositions and Methods of Treatment

The present disclosure includes methods of treating diseases, conditions, or disorders e.g., inflammatory diseases and autoimmune disorders, or managing symptoms thereof, comprising administering a therapeutically effective amount of one or more of the compounds disclosed herein. Included are any diseases, disorders, or conditions associated with the glucocorticoid receptor, glucocorticoid binding, and/or glucocorticoid receptor signaling. Such methods comprise administering a steroid payload or protein conjugate thereof described herein to a patient. Thus, included in this disclosure are methods of treating a disease, disorder, or condition associated with the glucocorticoid receptor comprising administering a compound of Formula (I), (I)$^1$, or protein conjugate thereof, e.g., compound of Formula (III) to a patient having said disease, disorder, or condition. Set forth herein are methods of treating a disease, disorder, or condition associated with the glucocorticoid receptor comprising administering a protein conjugate of a compound of Formula selected from the group consisting of (A), (A$^1$), (A$^2$), (A$^3$), (A$^4$), (A$^5$), (A$^6$), (A$^7$), (I), (I$^1$), (PIa), (PIb-1), (PIb-2), PIc-1), (PIc-2), (PId-1), (PId-2), (PIe-1), (PIe-2), (PII), (PIIa), (PIIb), (PIII), (PIIIa), (PIIIb), (PIV), (PV), (PVa), (PVb), (PVI), (PVII), (PVIIa), (PVIIb), (PVIIb-1), (PVIIb-2), (PVIII), and combinations thereof.

In some embodiments, the disease, disorder, or condition is allergic state, including but not limited to asthma, atopic dermatitis, contact dermatitis, drug hypersensitivity reactions, perennial or seasonal allergic rhinitis, and serum sickness; dermatologic diseases, including but not limited to bullous dermatitis herpetiformis, exfoliative erythroderma, mycosis fungoides, pemphigus, and severe erythema multiforme (Stevens-Johnson syndrome); endocrine disorders, including but not limited to primary or secondary adrenocortical insufficiency, congenital adrenal hyperplasia, hypercalcemia associated with cancer, and nonsuppurative thyroiditis; gastrointestinal diseases; hematologic disorders, including but not limited to acquired (autoimmune) hemolytic anemia, congenital (erythroid) hypoplastic anemia (Diamond-Blackfan anemia), idiopathic thrombocytopenic purpura in adults, pure red cell aplasia, and secondary thrombocytopenia; trichinosis; tuberculous meningitis with subarachnoid block or impending block; neoplastic diseases, including but not limited to leukemias and lymphomas; nervous system disorders, including but not limited to acute exacerbations of multiple sclerosis, cerebral edema associated with primary or metastatic brain tumor, craniotomy, or head injury; ophthalmic diseases, including but not limited to sympathetic ophthalmia, temporal arteritis, uveitis, and ocular inflammatory conditions unresponsive to topical corticosteroids; renal diseases, including but not limited to for inducing a diuresis or remission of proteinuria in idiopathic nephrotic syndrome or that due to lupus erythematosus; respiratory diseases, including but not limited to berylliosis, fulminating or disseminated pulmonary tuberculosis when used concurrently with appropriate antituberculous chemotherapy, idiopathic eosinophilic pneumonias, symptomatic sarcoidosis; and Rheumatic disorders, including but not limited to use as adjunctive therapy for short-term administration (to tide the patient over an acute episode or exacerbation) in acute gouty arthritis, acute rheumatic carditis, ankylosing spondylitis, psoriaticarthritis, rheumatoid arthritis, including juvenile rheumatoid arthritis, and for use in dermatomyositis, polymyositis, and systemic lupus erythematosus.

In some examples, set forth herein is a method for treating a disease, disorder, or condition selected from an autoimmune disease, an allergy, arthritis, asthma, a breathing disorder, a blood disorder, a cancer, a collagen disease, a connective tissue disorders, a dermatological disease, an eye disease, an endocrine problem, an immunological disease, an inflammatory disease, an intestinal disorders, a gastrointestinal disease, a neurological disorder, an organ transplant condition, a rheumatoid disorder, a skin disorder, a swelling condition, a wound healing condition, and a combination thereof comprising administering a steroid payload or conjugate thereof described herein.

In some examples, the autoimmune disorder is selected from multiple sclerosis, autoimmune hepatitis, shingles, systemic lupus erythematosus (i.e., lupus), myasthenia gravis, Duchenne muscular dystrophy, and sarcoidosis. In some examples, the breathing disorder is selected from asthma, chronic obstructive pulmonary disease, bronchial inflammation, and acute bronchitis. In some examples, the cancer is selected from leukemia, lymphoblastic leukemia, acute lymphoblastic leukemia, chronic lymphoblastic leukemia, Hodgkin's lymphoma, Non-Hodgkin's lymphoma (NHL), and multiple myeloma. In some examples, the collagen disease is systemic lupus erythematosus. In some examples, the eye disease is keratitis. In some examples, the endocrine problem is selected from Addison's Disease, adrenal insufficiency, adrenocortical, and congenital adrenal hyperplasia. In some examples, the inflammatory disease is selected from joint inflammation, tendon inflammation, bursitis, epicondylitis, Crohn's disease, inflammatory bowels disease, lipid pneumonitis thyroiditis, urticaria (hives), pericarditis, nephrotic syndrome, and uveitis. In some examples, the intestinal disorder is selected from ulcerative colitis, Crohn's disease, and inflammatory bowels disease. In some examples, the rheumatoid disorder is selected from rheumatoid arthritis, polymyalgia rheumatica, psoriatic arthritis, ankylosing spondylitis, and systemic lupus erythematosus. In some examples, the skin disorder is selected from psoriasis, eczema, and poison ivy. In some examples, the neurological disorder is chronic inflammatory demyelinating polyradiculoneuropathy.

In some embodiments, the compounds described herein are administered to a patient to treat an acute inflammatory event, including but not limited to shock, brain edema, and graft-vs-host disease. In some embodiments, the compounds described herein are administered to treat lympholytic effects, including but not limited to those associated with hematological malignancies, e.g., leukemias, lymphomas, and myelomas.

In some examples, set forth herein is a method for reducing inflammation in a subject in need thereof, comprising administering to a subject in need thereof a therapeutically effective amount of a steroid or conjugate thereof described herein. In some examples, set forth herein is a method for modulating the immune system in a subject in need thereof, comprising administering to a subject in need thereof a therapeutically effective amount of a steroid or conjugate thereof described herein. In some examples, set forth herein is a method for modulating cortisol levels in a subject in need thereof, comprising administering to a subject in need thereof a therapeutically effective amount of a steroid or conjugate thereof described herein. In some examples, set forth herein is a method of reducing lymphocyte migration in a subject in need thereof, comprising administering to a subject in need thereof a therapeutically effective amount of a steroid or conjugate thereof described herein. In some examples, set forth herein is a method of treating hypercalcemia due to cancer, Meniere's disease, a migraine headache, a cluster headache, a severe aphthous ulcer, laryngitis, severe tuberculosis, a Herxheimer reaction to syphilis, a decompensated heart failure, allergic rhinitis or nasal polyps, comprising administering to a subject in need thereof a steroid payload or conjugate thereof described herein. In some examples, the compounds disclosed herein can be used for treating inflammatory bowel disease, Crohn's disease, or ulcerative colitis. In some examples, the disease, disorder, or condition is a chronic inflammatory condition, including but not limited to asthma, skin infections, and ocular infections. In some examples, compounds described herein are used for immunosuppression in patients undergoing organ transplantation.

In some embodiments, the steroid payloads and conjugates thereof described herein are administered to a patient to treat a nervous disorder associated with GR signaling, including but not limited to psychiatric disorders such as schizophrenia, drug addiction, post-traumatic stress disorder (PTSD), and mood disorders, substance abuse, stress, and anxiety. In some embodiments, the steroid payloads and conjugates thereof described herein are administered to a patient to treat a visual system disorder, including but not limited to ocular inflammation (e.g., conjunctivitis, keratitis, uveitis), macular edema, and macular degeneration. In some embodiments, the steroid payloads and conjugates thereof described herein are administered to a patient to treat a cardiovascular disorder. In some embodiments, the steroid payloads and conjugates thereof described herein are administered to a patient to treat a glucose and/or liver metabolism disorder. In some embodiments, the steroid payloads and conjugates thereof described herein are administered to a patient to treat a musculoskeletal system disorder. In some embodiments, the steroid payloads and conjugates thereof described herein are administered to a patient to treat a cutaneous inflammatory condition, such as eczema and psoriasis.

The protein conjugates described herein provide a means for targeted delivery of its steroid payload to particular cells or organ systems, thereby reducing or preventing side effects that result from administration of the free unconjugated steroid payload. Thus, provided herein are methods for treating a disease, disorder, or condition associated with the glucocorticoid receptor comprising administering a conjugate of Formula (I) or (I)$^1$, to a patient having said disease, disorder, or condition, wherein the side effects associated with administration of the free steroid payload of said conjugate is reduced. Furthermore, provided herein are methods of delivering a compound of Formula (I) or (I)$^1$ to a cell comprising contacting said cell with a protein conjugate the compound of Formula (I) or (I)$^1$, wherein the protein conjugate comprises an antibody or antigen binding fragment thereof that binds a surface antigen of said cell.

The compounds described herein can be administered alone or together with one or more additional therapeutic agents. The one or more additional therapeutic agents can be administered just prior to, concurrent with, or shortly after the administration of the compounds described herein. The present disclosure also includes pharmaceutical compositions comprising any of the compounds described herein in combination with one or more additional therapeutic agents, and methods of treatment comprising administering such combinations to subjects in need thereof.

Suitable additional therapeutic agents include, but are not limited to: a second glucocorticoid, an autoimmune therapeutic agent, a hormone, a biologic, or a monoclonal antibody. Suitable therapeutic agents also include, but are not limited to any pharmaceutically acceptable salts, acids or derivatives of a compound set forth herein.

The compounds described herein can also be administered and/or co-formulated in combination with antivirals, antibiotics, analgesics, corticosteroids, steroids, oxygen, antioxidants, COX inhibitors, cardioprotectants, metal chelators, IFN-gamma, and/or NSAIDs.

In some embodiments of the methods described herein, multiple doses of a compound described herein (or a pharmaceutical composition comprising a combination of an compound described herein and any of the additional therapeutic agents mentioned herein) may be administered to a subject over a defined time course. The methods according to this aspect of the disclosure comprise sequentially administering to a subject multiple doses of a compound described herein. As used herein, "sequentially administering" means that each dose of the compound is administered to the subject at a different point in time, e.g., on different days separated by a predetermined interval (e.g., hours, days, weeks or months). The present disclosure includes methods which comprise sequentially administering to the patient a single initial dose of a compound described herein, followed by one or more secondary doses of the compound, and optionally followed by one or more tertiary doses of the compound.

The terms "initial dose," "secondary doses," and "tertiary doses," refer to the temporal sequence of administration of the compounds described herein. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses can all contain the same amount the compound described herein, but generally can differ from one another in terms of frequency of administration. In certain embodiments, the amount of the compound contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present disclosure, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose the compound which is administered to a patient prior to the administration of the very next dose in the sequence with no intervening doses.

The methods according to this aspect of the disclosure may comprise administering to a patient any number of secondary and/or tertiary doses of the compound. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the disclosure, the frequency at which the secondary and/or tertiary doses are administered to a patient can vary over the course of the treatment regimen. The frequency of administration may also be adjusted during the course of treatment by a physician depending on the needs of the individual patient following clinical examination.

The present disclosure includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the disclosure, if the loading doses are administered at a frequency of once a month, then the maintenance doses may be administered to the patient once every six weeks, once every two months, once every three months, etc.

The present disclosure includes pharmaceutical compositions of the compounds and/or conjugates described herein, e.g., the compounds of Formula (I) and (II), e.g., compositions comprising a compound described herein, a salt, stereoisomer, polymorph thereof, and a pharmaceutically acceptable carrier, diluent, and/or excipient. Examples of suitable carriers, diluents and excipients include, but are not limited to: buffers for maintenance of proper composition pH (e.g., citrate buffers, succinate buffers, acetate buffers, phosphate buffers, lactate buffers, oxalate buffers and the like), carrier proteins (e.g., human serum albumin), nanoparticles, saline, polyols (e.g., trehalose, sucrose, xylitol, sorbitol, and the like), surfactants (e.g., polysorbate 20, polysorbate 80, polyoxolate, and the like), antimicrobials, and antioxidants.

In some examples, set forth herein is a method of treating a disease, disorder or condition including administering to a patient having said disorder a therapeutically effective amount of a compound of Formula I, III, or a pharmaceutical composition thereof.

In some examples, set forth herein is a method of treating a disease, disorder or condition including administering to a patient having said disorder a therapeutically effective amount of a compound set forth herein, or a pharmaceutical composition thereof.

In some examples, set forth herein is a method of treating a disease, disorder or condition selected from the group consisting of an immunological disease, autoimmune disease, inflammation, asthma, or an inflammatory bowel disorder, Crohn's disease, ulcerative colitis.

In some examples, set forth herein is a method of treating a disease, disorder or condition by targeting an antigen, e.g., cell-surface expressing antigen, to which steroid delivery can achieve a therapeutic benefit comprising administering the conjugates described herein. In some embodiments, the antigen is AXL, BAFFR, BCMA, BCR-list components, BDCA2, BDCA4, BTLA, BTNL2 BTNL3, BTNL8, BTNL9, C10orf54, CCR1, CCR3, CCR4, CCR5, CCR6, CCR7, CCR9, CCR10, CD11c, CD137, CD138, CD14, CD168, CD177, CD19, CD20, CD209, CD209L, CD22, CD226, CD248, CD25, CD27, CD274, CD276, CD28, CD30, CD300A, CD33, CD37, CD38, CD4, CD40, CD44, CD45, CD47, CD46, CD48, CD5, CD52, CD55, CD56, CD59, CD62E, CD68, CD69, CD70, CD74, CD79a, CD79b, CD8, CD80, CD86, CD90.2, CD96, CLEC12A, CLEC12B, CLEC7A, CLEC9A, CR1, CR3, CRTAM, CSF1R, CTLA4, CXCR1/2, CXCR4, CXCR5, DDR1, DDR2, DEC-205, DLL4, DR6, FAP, FCamR, FCMR, FcR's, Fire, GITR, HHLA2, HLA class II, HVEM, ICOSLG, IFNLR1, IL10R1, IL10R2, IL12R, IL13RA1, IL13RA2, IL15R, IL17RA, IL17RB, IL17RC, IL17RE, IL20R1, IL20R2, IL21R, IL22R1, IL22RA, IL23R, IL27R, IL29R, IL2Rg, IL31R, IL36R, IL3RA, IL4R, IL6R, IL5R, IL7R, IL9R, Integrins, LAG3, LIFR, MAG/Siglec-4, MMR, MSR1, NCR3LG1, NKG2D, NKp30, NKp46, PDCD1, PROKR1, PVR, PVRIG, PVRL2, PVRL3, RELT, SIGIRR, Siglec-1, Siglec-10, Siglec-5, Siglec-6, Siglec-7, Siglec-8, Siglec-9, SIRPA, SLAMF7, TACI, TCR-list components/assoc, PTCRA, TCRb, CD3z, CD3, TEK, TGFBR1, TGFBR2, TGFBR3, TIGIT, TLR2, TLR4, TROY, TSLPR, TYRO, VLDLR, VSIG4, or VTCN1. In some embodiments, the antigen is IL2R-γ.

In some examples, set forth herein is a method for treating a disease, disorder, or condition selected from an immunological disease, an autoimmune disease, an inflammatory disease, a dermatological disease, or a gastrointestinal disease.

In some examples, the disease is Crohn's disease, ulcerative colitis, Cushing's syndrome, adrenal insufficiency, or congenital adrenal hyperplasia.

In some examples, the disease is inflammation, asthma, or an inflammatory bowel disorder.

In some examples, the disease is an autoimmune diseases selected from multiple sclerosis, rheumatoid arthritis, inflammatory bowel disease, ulcerative colitis, psoriasis, or eczema.

In some examples, set forth herein is a method for reducing or ameliorating the side effects of chemotherapy, wherein the method includes administering to a patient having said disorder a therapeutically effective amount of a compound or a composition described herein.

In some examples, set forth herein is a method for reducing or ameliorating the side effects of immunosuppressive therapy, wherein the method includes administering to a patient having said disorder a therapeutically effective amount of a compound or a composition described herein.

In some examples, set forth herein is a method for treating cancer, wherein the method includes administering to a patient having said disorder a therapeutically effective amount of a compound or a composition described herein. In some examples, the cancer is selected from acute lymphoblastic leukemia, chronic lymphoblastic leukemia, Hodgkin's lymphoma, Non-Hodgkin's lymphoma (NHL), or multiple myeloma, as well as others.

F. Examples

Certain embodiments are illustrated by the following non-limiting examples.

Reagents and solvents were obtained from commercial sources such as Sinopharm Chemical Reagent Co. (SCRC), Sigma-Aldrich, Alfa, or other vendors, unless explicitly stated otherwise.

$^1$H NMR and other NMR spectra were recorded on a Bruker AVIII 400 or Bruker AVIII 500. The data were processed with Nuts software or MestReNova software, measuring proton shifts in parts per million (ppm) downfield from an internal standard tetramethyl silane.

HPLC-MS measurements were run on an Agilent 1200 HPLC/6100 SQ System using the follow conditions:

Method A for HPLC-MS measurement included, as the Mobile Phase: A: Water (0.01% trifluoroacetic acid TFA) and B: acetonitrile (0.01% TFA). The Gradient Phase was 5% of B that was increased to 95% of B over a time period of 15 minutes (min) and at a flow rate of 1.0 mL/min. The column used was a SunFire C18, 4.6×50 mm, 3.5 μm. The column temperature was 50° C. The detectors included an Analog to Digital Converter ELSD (Evaporative Light-scattering Detector, hereinafter "ADC ELSD"), DAD (Diode array detector, 214 nm and 254 nm), and Electrospray Ionization-Atmospheric Pressure Ionization (ES-API).

Method B for HPLC-MS measurement included, as the Mobile Phase: A: Water (10 mM $NH_4HCO_3$) and B: acetonitrile. The Gradient Phase was 5% of B that was increased to 95% of B over a time period of 15 min and a flow rate of 1.0 mL/min. The column used was a XBridge C18, 4.6×50 mm, 3.5 μm. The column temperature was 50° C. The detectors included an ADC ELSD, DAD (214 nm and 254 nm), and a mass-selcetive detector (MSD ES-API).

LC-MS measurement was run on an Agilent 1200 HPLC/6100 SQ System using the follow conditions:

Method A for LC-MS measurement was performed on a WATERS 2767 instrument. The column was a Shimadzu Shim-Pack, PRC-ODS, 20×250 mm, 15 μm, two connected in series. The Mobile Phase was A: Water (0.01% TFA) and B: acetonitrile (0.01% TFA). The Gradient Phase was 5% of B that was increased to 95% of B over a time period of 3 min and at a flow rate of 1.8-2.3 mL/min. The column used was a SunFire C18, 4.6×50 mm, 3.5 μm. The column temperature was 50° C. The detectors included an Analog to Digital Converter ELSD (Evaporative-Light Scattering Detector), DAD (Diode Array Detector) (214 nm and 254 nm), and ES-API.

Method B for LC-MS measurement was performed on a Gilson GX-281 instrument. The column was an Xbridge Prep C18 10 um OBD, 19×250 mm. The Mobile Phase was A: Water (10 mM $NH_4HCO_3$) and B: Acetonitrile. The Gradient Phase was 5% of B that was increased to 95% of B over a time period of 3 min and at a flow rate of 1.8-2.3 mL/min. The column used was an XBridge C18, 4.6×50 mm, 3.5 μm. The column temperature was 50° C. The detectors included ADC ELSD, DAD (214 nm and 254 nm), and Mass Selective Detector (MSD) (ES-API).

Preparative high-pressure liquid chromatography (Prep-HPLC) was performed on a Gilson GX-281 instrument. Two solvent systems were used, one acidic and one basic. The acidic solvent system included a Waters SunFire 10 μm C18 column (100 Å, 250×19 mm). Solvent A for prep-HPLC was 0.05% TFA in water and solvent B was acetonitrile. The elution condition was a linear gradient that increased solvent B from 5% to 100% over a time period of 20 minutes and at a flow rate of 30 mL/min. The basic solvent system included a Waters Xbridge 10 μm C18 column (100 Å, 250×19 mm). Solvent A for prep-HPLC was 10 mM ammonium bicarbonate ($NH_4HCO_3$) in water and solvent B was acetonitrile. The elution condition was a linear gradient that increased solvent B from 5% to 100% over a time period of 20 minutes and at a flow rate of 30 mL/min.

Flash chromatography was performed on a Biotage instrument, with Agela Flash Column silica-CS. Reversed phase flash chromatography was performed on Biotage instrument, with Boston ODS or Agela C18, unless explicitly indicated otherwise.

The following abbreviations are used in the Examples and throughout the specification:

| Abbreviation | Term |
| --- | --- |
| ADC | Antibody-drug conjugate |
| Aglycosylated antibody | Antibody that does not have any glycan residues |
| API | Atmospheric pressure ionization |
| aq | Aqueous |
| Boc | N-tert-butoxycarbonyl |
| BupH ™ | Thermo Scientific Prod#28372, containing 100 mM sodium phosphate and 150 mM sodium chloride, potassium free, pH was adjusted from 7.2 to 7.6-7.8 MQ, unless otherwise noted. |
| CD | Cyclodextrin |
| COT | Cyclooctynol |
| Da | Dalton |
| DAD | Diode array detector |
| DAR | Drug to antibody ratio |
| DCM | Dichloromethane |
| DIBAC | Dibenzocyclooctyne; or 11,12-didehydro-5,6-dihydro-Dibenz[b,f]azocine; or Dibenz[b,f]azocine-5(6H)-butanoic acid, 11,12-didehydro |
| DIBAC-Suc | 11,12-didehydro-5,6-dihydro-Dibenz[b,f]azocine succinamic acid |
| DIBAC-Suc-PEG$_4$-VC-pAB-PNP | {4-[(2S)-2-[(2S)-2-[1-(4-{2-azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl 4-nitrophenyl carbonate |
| DIBACT | 3H-Benzo[c]-1,2,3-triazolo[4,5-e][1]benzazocine, 8,9-dihydro-; or Dibenzocyclooctyne triazole |
| DIPEA | Diisopropylethylamine |
| DMF | N,N-dimethylformamide |
| DMSO | Dimethylsulfoxide |
| EC | Enzyme commission |
| ELSD | Evaporative light scattering detector |

-continued

| Abbreviation | Term |
|---|---|
| ESI | Electrospray ionization |
| Fmoc | Fluorenylmethyloxycarbonyl chloride |
| Fmoc-vcPAB-PNP | N-Fmoc-L-valine-L-citrulline-p-aminobenzyl alcohol p-nitrophenyl carbonate |
| g | Gram |
| HATU | 2-(7-Aza-1H-benzotriazole-1-yl)-1,1,3,3-tetramethyluronium hexafluorophosphate |
| HC | Heavy chain of immunoglobulin |
| HEK | Human embryonic kidney (cells) |
| HPLC | High performance liquid chromatography |
| hr or hrs | Hours |
| LC | Liquid chromatography |
| HPLC | High-pressure Liquid chromatography |
| MALDI | Matrix-assisted laser desorption/ionization |
| MC | Maleimidocaproyl |
| mg | milligrams |
| min | minutes |
| mL | milliliters |
| mmh | myc-myc-hexahistidine tag |
| μL | microliters |
| mM | millimolar |
| μM | micromolar |
| MMAE | Monomethyl auristatin E |
| MS | Mass spectrometry |
| MsCl | Methanesulfonyl chloride |
| MSD | Mass-selective detector |
| MTG | Microbial transglutaminase (MTG EC 2.3.2.13, Zedira, Darmstadt, Germany) |
| MW | Molecular weight |
| ncADC | Non-Cytotoxic antibody drug conjugation |
| NHS | N-hydroxy succinimide |
| nM | nanomolar |
| NMR | Nuclear magnetic resonance |
| NOESY | Nuclear Overhauser effect spectroscopy |
| PAB | Para-amino-benzyl alcohol |
| | [structure: H$_2$N-C$_6$H$_4$-CH$_2$OH] |
| PABC | Para-aminobenzyloxy(carbonyl) |
| | [structure: HN-C$_6$H$_4$-CH$_2$-O-C(=O)-] |
| PBS | 10 mM sodium phosphate buffer and 150 mM sodium chloride |
| PBSg | 10 mM phosphate, 150 mM sodium chloride, 5% glycerol |
| PEG | Polyethyleneglycol |
| PNP | p-nitrophenyl |
| MC-VC-PAB-PNP | [structure of maleimidocaproyl-valine-citrulline-PAB-PNP] |
| ppm | Parts per million (chemical shift) |
| RP | Reversed phase |
| RT | Room temperature |

-continued

| Abbreviation | Term |
| --- | --- |
| SDS-PAGE | Sodium dodecylsulfate polyacrylamide gel electrophoresis |
| SEC | Size exclusion chromatography |
| Suc | Succinic acid |
| TCEP | Tris(2-carboxyethyl)phosphine hydrochloride |
| TEA | Triethylamine |
| TFA | Trifluoroacetic acid |
| TG | Transglutaminase |
| THF | Tetrahydrofuran |
| TOF | Time-of-flight |
| UPLC | Ultra Performance Liquid Chromatography |
| UV | Ultraviolet |
| VA | Valine-alanine |
| VC | Valine-citrulline |
| VC-PABC | Valine-citrulline-para-aminobenzyloxy(carbonyl) |
| CD | Cyclodextrin |
| HATU | 2-(7-Aza-1H-benzotriazole-1-yl)-1,1,3,3-tetramethyluronium hexafluorophosphate |
| MC | Maleimidocaproyl |
| COT | Cyclooctynol |
| SFC | Supercritical fluid chromatography |

| Abbreviation | IUPAC name | Structure |
|---|---|---|
| Boc-vcPAB-PNP (L2a) | tert-butyl (S)-3-methyl-1-((S)-1-(4-(((4-nitrophenoxy)carbonyloxy)methyl)phenylamino)-1-oxo-5-ureidopentan-2-ylamino)-1-oxobutan-2-ylcarbamate | 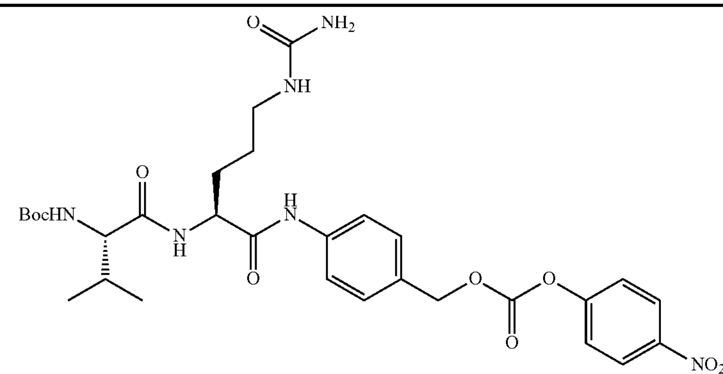 |
| Fmoc-vcPAB-PNP (L2b) | (9H-fluoren-9-yl)methyl (S)-3-methyl-1-((S)-1-(4-(((4-nitrophenoxy)carbonyloxy)methyl)phenylamino)-1-oxo-5-ureidopentan-2-ylamino)-1-oxobutan-2-ylcarbamate | 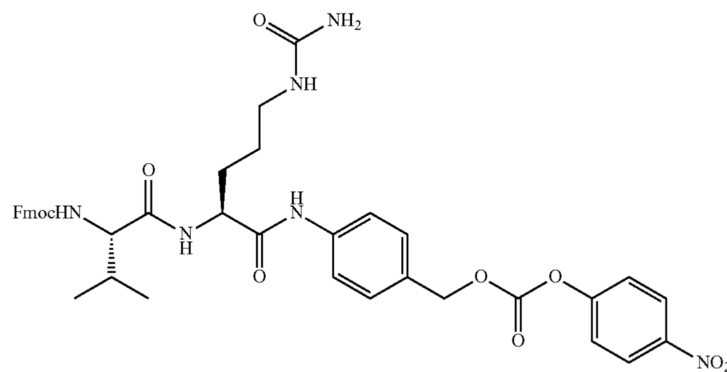 |
| Boc-Val-Ala-OH (L3a) | (S)-2-((S)-2-(tert-butoxycarbonylamino)-3-methylbutanamido)propanoic acid | 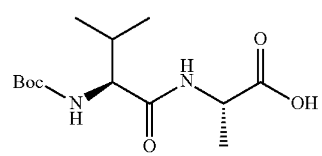 [SMILES: CC(C)[C@H](NC(=O)OC(C)(C)C)C(=O)N[C@@H](C)C(=O)O] |

-continued

| Abbreviation | IUPAC name | Structure |
|---|---|---|
| Fmoc-Val-Ala-OH (L3b) | (S)-2-((S)-2-(((9H-fluoren-9-yl)methoxy)carbonylamino)-3-methylbutanamido)propanoic acid | 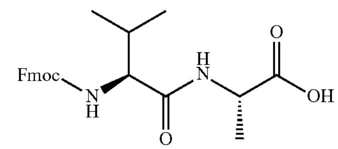 |
| Boc-Val-Cit-OH (L3c) | (6S,9S)-1-amino-9-isopropyl-13,13-dimethyl-1,8,11-trioxo-12-oxa-2,7,10-triazatetradecane-6-carboxylic acid | 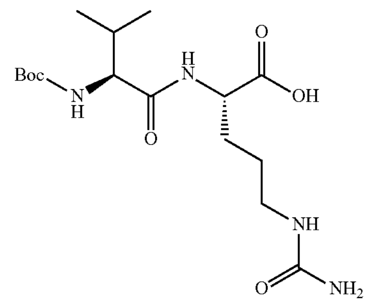 [SMILES: CC(C)[C@H](NC(=O)OC(C)(C)C)C(=O)N[C@@H](CCCNC(N)=O)C(=O)O] |
| Fmoc-D-Lys-COT (L5) | (2R)-2-(((9H-fluoren-9-yl)methoxy)carbonylamino)-6-(2-(cyclooct-2-ynyloxy)acetamido)hexanoic acid | 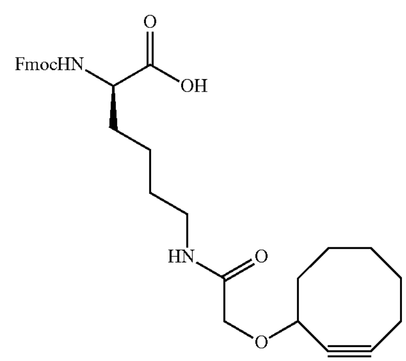 |

-continued
| Abbreviation | IUPAC name | Structure |
|---|---|---|
| CD-N₃ (L7a) | 5-(azidomethyl)-10,15,20,25,30-pentakis(hydroxymethyl)-2,4,7,9,12,14,17,19,22,24,27,29-dodecaoxaheptacyclo[26.2.2.2³,⁶.2⁸,¹¹.2¹³,¹⁶.2¹⁸,²¹.2²³,²⁶]dotetracontane-31,32,33,34,35,36,37,38,39,40,41,42-dodecol | 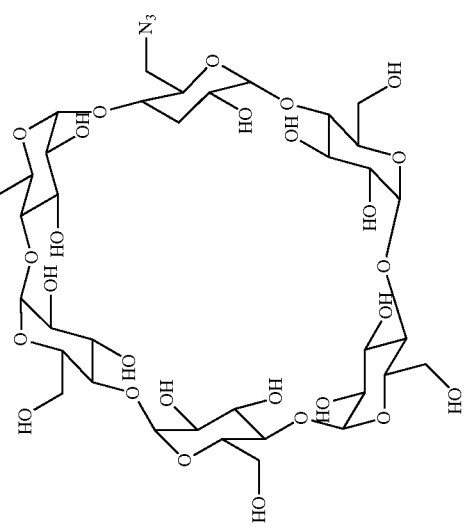 |
| N₃-PEG₄-CONHCH₂CH₂SO₃H (L7b) | 1-azido-15-oxo-3,6,9,12-tetraoxa-16-azaoctadecane-18-sulfonic acid | 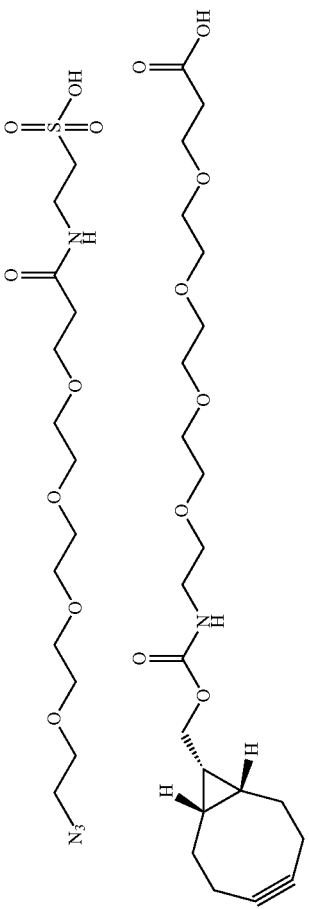 |
| BCN-PEG₄-acid (L9a) | (Endo)-1-(bicyclo[6.1.0]non-4-yn-9-yl)-3-oxo-2,7,10,13,16-pentaoxa-4-azanonadecan-19-oic acid |  |

-continued

| Abbreviation | IUPAC name | Structure |
|---|---|---|
| DIBAC-PEG$_4$-acid (L9b) | 1-(4-{2-azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-oic acid | 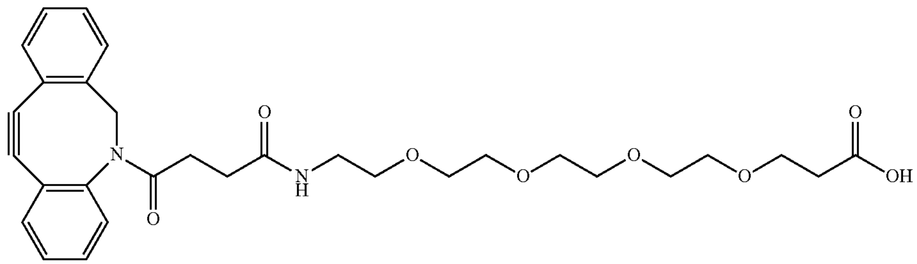 [SMILES: O=C(O)CCOCCOCCOCCOCCNC(=O)CCC(=O)N1Cc2ccccc2C#Cc2ccccc21] |
| BCN-PEG$_4$-NHS (L10a) | (Endo)-2,5-dioxopyrrolidin-1-yl 1-(bicyclo[6.1.0]non-4-yn-9-yl)-3-oxo-2,7,10,13,16-pentaoxa-4-azanonadecan-19-oate | 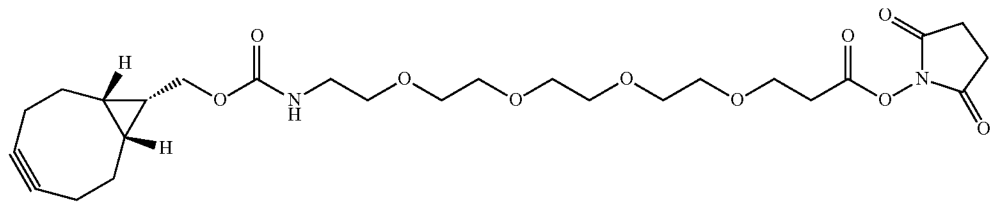 [SMILES: O=C(CCOCCOCCOCCOCCNC(=O)OC[C@@H]1[C@@H]2CCC#CCC[C@@H]21)ON1C(=O)CCC1=O] |
| DIBAC-PEG$_4$-NHS (L10b) | 2,5-dioxopyrrolidin-1-yl 1-(4-{2-azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-oate | 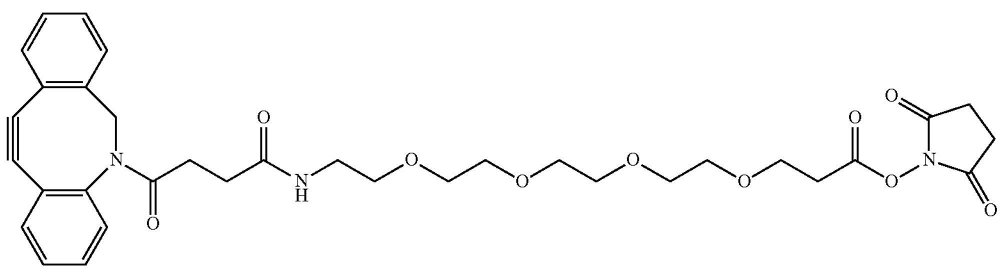 [SMILES: O=C(CCC(=O)N1Cc2ccccc2C#Cc2ccccc21)NCCOCCOCCOCCOCCC(=O)ON1C(=O)CCC1=O] |
| MAL-PEG$_4$-NHS (L10c) | 2,5-dioxopyrrolidin-1-yl 1-(2,5-dioxo-2,5-dihydro-1H-pyrrol-1-yl)-3,6,9,12-tetraoxapentadecan-15-oate | 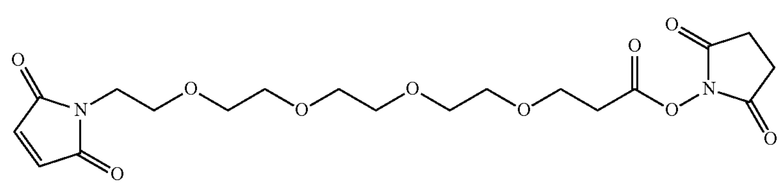 [SMILES: O=C(CCOCCOCCOCCOCCN1C(=O)C=CC1=O)ON1C(=O)CCC1=O] |

-continued

| Abbreviation | IUPAC name | Structure |
|---|---|---|
| DIBAC-PEG₄-vcPAB-PNP (L11) | {4-[(2S)-2-[(2S)-2-[1-(4-{2-azatricyclo[10.4.0.0⁴,⁹]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl 4-nitrophenyl carbonate | |
| Lk-DIBAC | — | 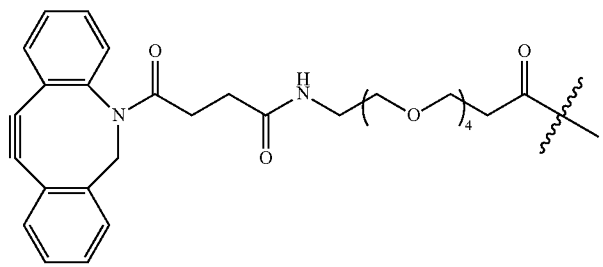 |
| Lk-BCN | — | 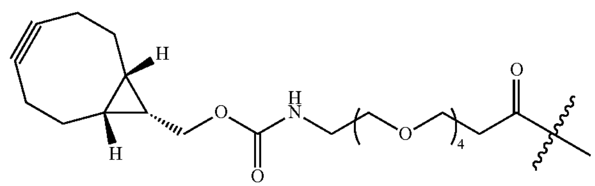 |
| Lk-MAL | — | 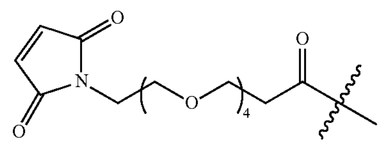 |

| Abbreviation | IUPAC name | Structure |
|---|---|---|
| Lk-CCK | — | 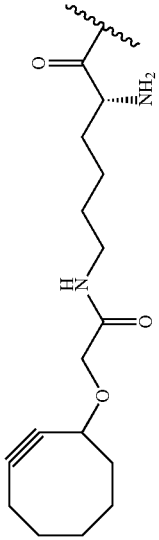 |
| aCDCCK | — | 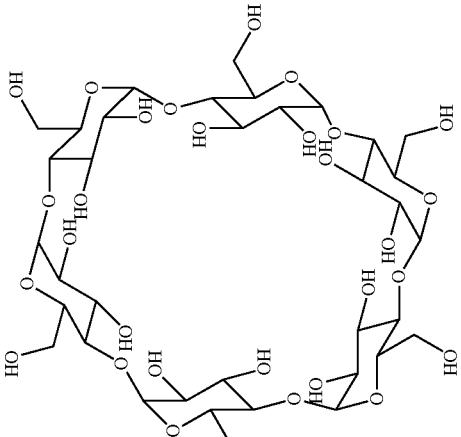 |

-continued
| Abbreviation | IUPAC name | Structure |
|---|---|---|
| SulCCK | — | 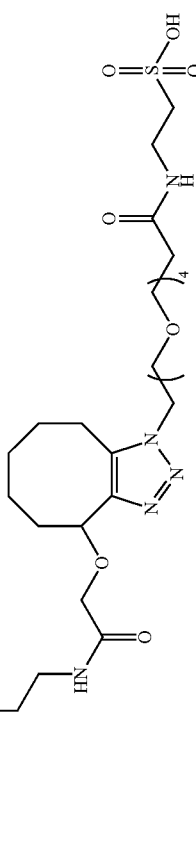 |
| dualSulCCK | — | 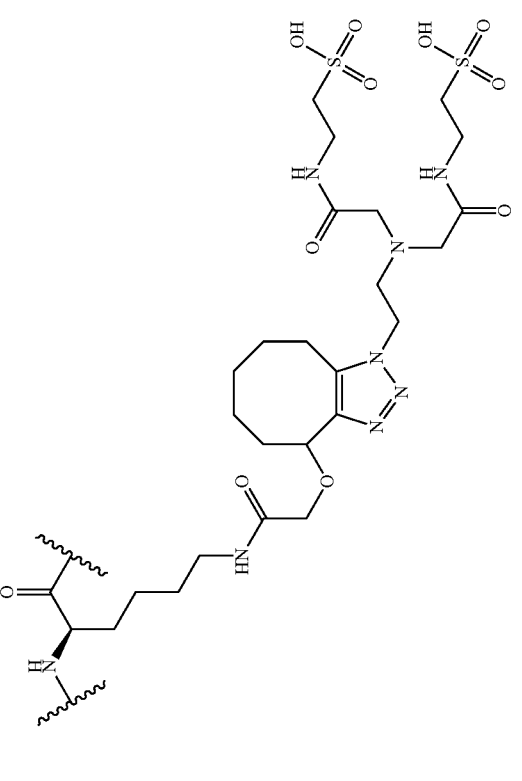 |

Preparation Methods

Example 1

Figure 2:
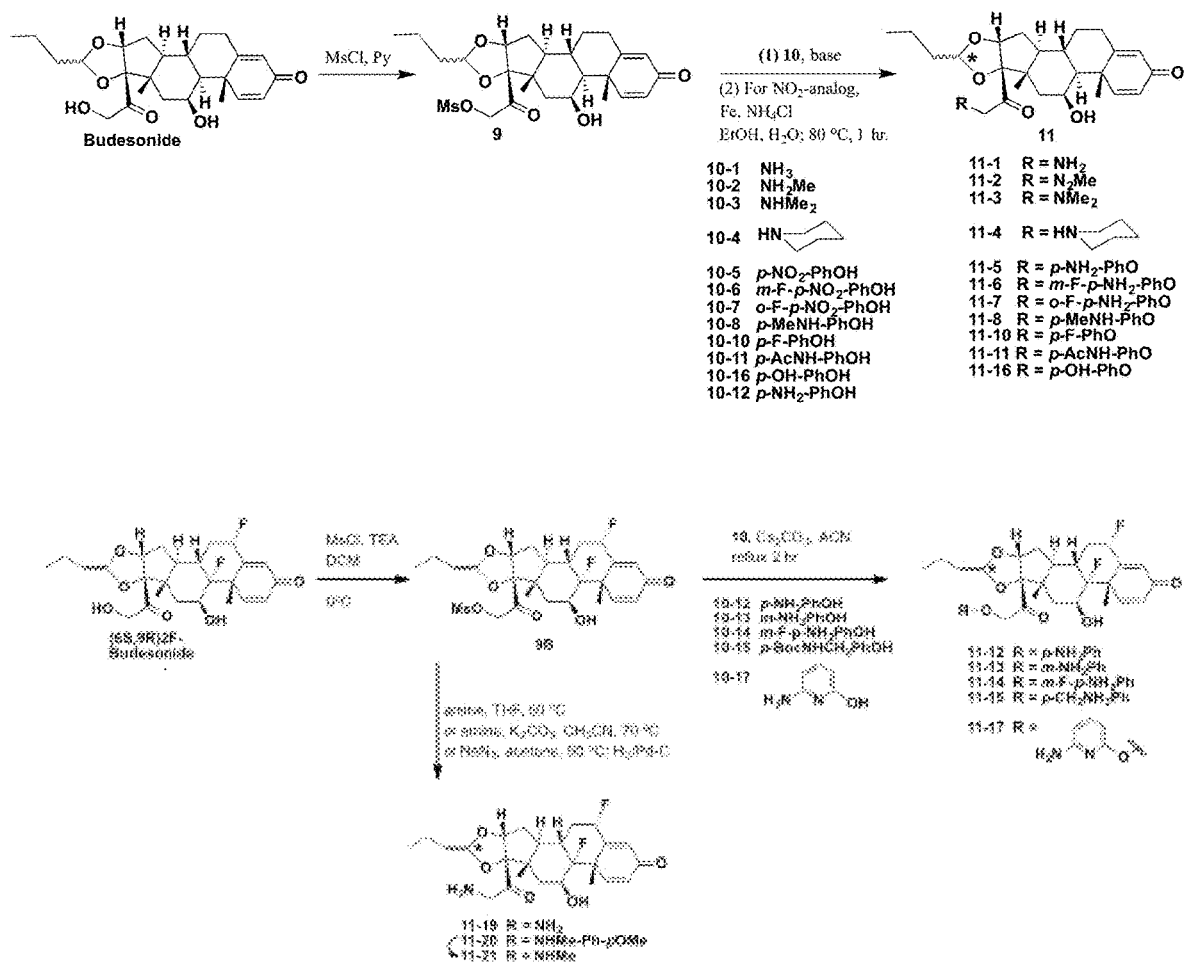

This example demonstrates one method for making chemical derivatives of Desonide with stereochemical control at the $C^{22}$-position. In FIGS. 1 and 2, the $C^{22}$ position is identified for compounds 7, 8 and 11 with an asterisk, i.e., *. The synthesis of steroids with stereochemical control at the $C^{22}$-position was performed following the synthetic route depicted in FIGS. 1 and 2.

Desonide (1), which is a generic name for (1S,2S,4R,8S,9S,11S,12S,13R)-11-hydroxy-8-(2-hydroxyacetyl)-6,6,9,13-tetramethyl-5,7-dioxapentacyclo[10.8.0.0$^{2,9}$.0$^{4,8}$.0$^{13,18}$]icosa-14,17-dien-16-one, was reacted with isobutyric anhydride (compound 2) to produce intermediate 3 by esterification at the primary alcohol position of compound 1. Compound 3 was reacted with a series of aldehydes (4-1; 4-2; 4-3; and 4-4, each differing with respect to the R—CHO group illustrated to the right of these numberical labels) by transacetalation under strong acid $HClO_4$ condition to produce alcohols 5 and esters 6. As indicated in FIG. 1, these aldehydes differed from each other with respect to the R group indicated in FIG. 1.

Alcohols 5 and ester 6 were separated by column chromatography.

Each alcohol 5 or ester 6 was individually, reacted with diethylamine to remove Fmoc-group or with $Fe/NH_4Cl$ to reduce nitro to provide epimer compounds 7 and 8 having both R/S stereochemistry at $C^{22}$, respectively.

As detailed below, R and S epimers were separated and their R- and S-configurations were identified. The R-epimers of, for example, compounds 7 and 8 in FIG. 1 were isolated and confirmed to be the majority stereoisomer by greater 90% by $^1$H NMR. The $C^{22}$ configuration of each epimer was determined by 2D-NOESY spectroscopic studies.

Table 1 below presents steroids made using the methods described herein.

TABLE 1

Structure and Chemical-Physical Properties of Compounds

| Cpd. No | $C^{22}$ | Structure | MF | MW (Cal.) | MS (M + H) | HPLC purity (%) | cLog P |
|---|---|---|---|---|---|---|---|
| 7-1 | S | | $C_{28}H_{33}NO_6$ | 479.6 | 480.2 | 96 | 2.53 |
| 7-1 | R | | $C_{28}H_{33}NO_6$ | 479.6 | 480.3 | 100 | 2.53 |
| 8-1 | R | 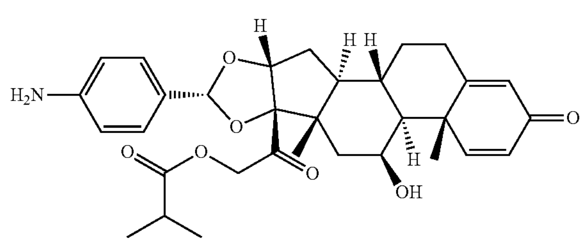 [SMILES: CC(C)C(=O)OCC(=O)[C@@]12O[C@H](c3ccc(N)cc3)O[C@@H]1C[C@H]1[C@@H]3CCC4=CC(=O)C=C[C@]4(C)[C@H]3[C@@H](O)C[C@@]12C] | $C_{32}H_{39}NO_7$ | 549.7 | 550.3 | 96 | 4.22 |
| 7-2 | R/S | 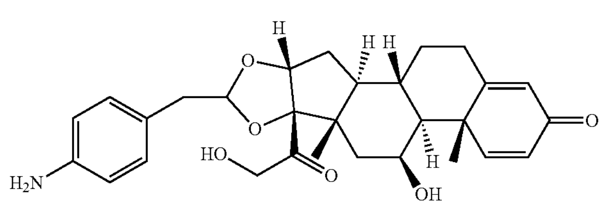 [SMILES: C[C@]12C=CC(=O)C=C1CC[C@@H]1[C@@H]2[C@@H](O)C[C@@]2(C)[C@H]1C[C@H]1OC(Cc3ccc(N)cc3)O[C@]12C(=O)CO] | $C_{29}H_{35}NO_6$ | 493.6 | 494.3 | 98 | 2.59 |

TABLE 1-continued
Structure and Chemical-Physical Properties of Compounds
| Cpd. No | C$^{22}$ | Structure | MF | MW (Cal.) | MS (M + H) | HPLC purity (%) | cLog P |
|---|---|---|---|---|---|---|---|
| 8-2 | R/S | 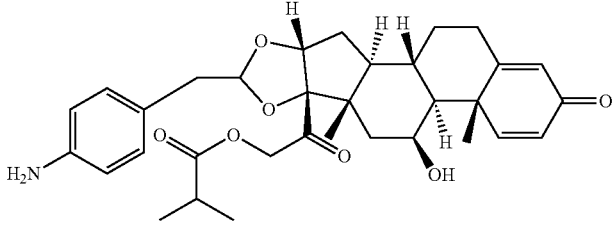 [SMILES: CC(C)C(=O)OCC(=O)[C@@]12OC(Cc3ccc(N)cc3)O[C@@H]1C[C@H]1[C@@H]3CCC4=CC(=O)C=C[C@]4(C)[C@H]3[C@@H](O)C[C@@]12C] | C$_{33}$H$_{41}$NO$_7$ | 563.7 | 564.3 | 98 | 4.28 |
| 8-3 | R/S | 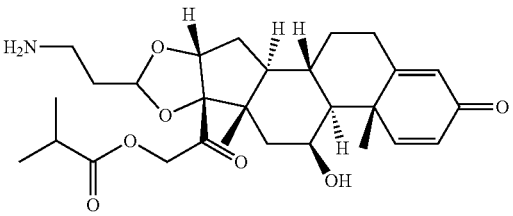 [SMILES: CC(C)C(=O)OCC(=O)[C@@]12OC(CCN)O[C@@H]1C[C@H]1[C@@H]3CCC4=CC(=O)C=C[C@]4(C)[C@H]3[C@@H](O)C[C@@]12C] | C$_{27}$H$_{37}$NO$_6$ | 471.6 | 472.2 | 96 | 1.63 |
| 7-4 | R | 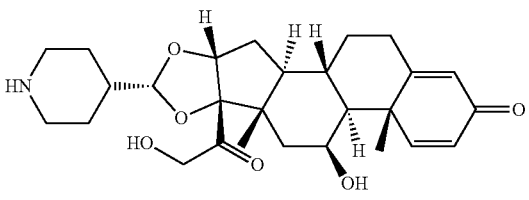 [SMILES: C[C@]12C=CC(=O)C=C1CC[C@@H]1[C@@H]2[C@@H](O)C[C@@]2(C)[C@H]1C[C@H]1O[C@@H](C3CCNCC3)O[C@]12C(=O)CO] | C$_{27}$H$_{37}$NO$_6$ | 471.6 | 472.2 | 96 | 1.63 |
| 11-1 | R/S | 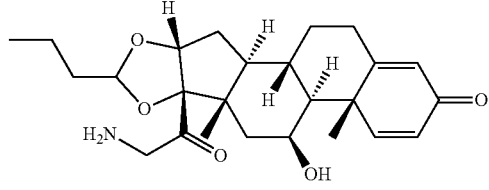 | C$_{25}$H$_{35}$NO$_5$ | 429.6 | 429.9 | 100 | 2.63 |
| 11-2 | R/S | 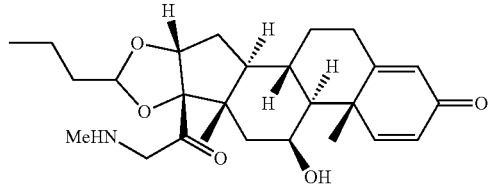 | C$_{26}$H$_{37}$NO$_5$ | 443.6 | 444.2 | 96 | 3.06 |
| 11-3 | R/S | 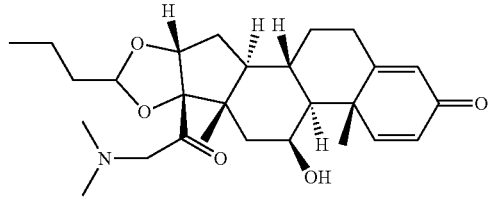 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CN(C)C)O1] | C$_{27}$H$_{39}$NO$_5$ | 457.6 | 458.2 | 100 | 3.44 |
| 11-4 | R/S | 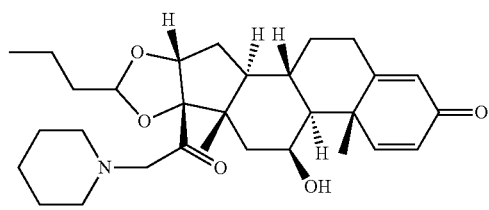 [SMILES: CCCC1O[C@@H]2C[C@H]3[C@@H]4CCC5=CC(=O)C=C[C@]5(C)[C@H]4[C@@H](O)C[C@]3(C)[C@]2(C(=O)CN2CCCCC2)O1] | C$_{30}$H$_{43}$NO$_5$ | 497.3 | 498.2 | 94 | 4.29 |

TABLE 1-continued

Structure and Chemical-Physical Properties of Compounds

| Cpd. No | C²² | Structure | MF | MW (Cal.) | MS (M + H) | HPLC purity (%) | cLog P |
|---|---|---|---|---|---|---|---|
| 11-5 | R/S | | $C_{31}H_{39}NO_6$ | 521.6 | 522.3 | 100 | 4.24 |
| 11-5 | S | | $C_{31}H_{39}NO_6$ | 521.6 | 522.2 | 99.8 | 4.24 |
| 11-5 | R | | $C_{31}H_{39}NO_6$ | 521.6 | 522.2 | 99.1 | 4.24 |
| 11-6 | S | | $C_{31}H_{38}FNO_6$ | 539.6 | 540.3 | 98 | 4.38 |
| 11-6 | R | | $C_{31}H_{38}FNO_6$ | 539.6 | 540.3 | 100 | 4.38 |
| 11-7 | R | 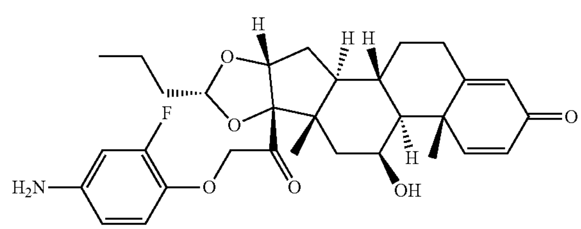 [SMILES: CCC[C@@H]1O[C@@H]2C[C@H]3[C@@H]4CCC5=CC(=O)C=C[C@]5(C)[C@H]4[C@@H](O)C[C@]3(C)[C@]2(C(=O)COc2ccc(N)cc2F)O1] | $C_{31}H_{38}FNO_6$ | 539.6 | 540.2 | 100 | 4.38 |
| 11-8 | R | 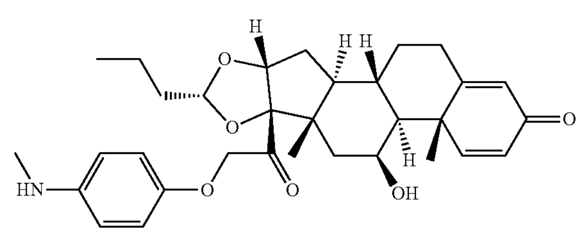 [SMILES: CCC[C@@H]1O[C@@H]2C[C@H]3[C@@H]4CCC5=CC(=O)C=C[C@]5(C)[C@H]4[C@@H](O)C[C@]3(C)[C@]2(C(=O)COc2ccc(NC)cc2)O1] | $C_{32}H_{41}NO_6$ | 535.7 | 518.2 (M + H − H₂O) | 100 | 4.54 |

TABLE 1-continued
Structure and Chemical-Physical Properties of Compounds
| Cpd. No | C22 | Structure | MF | MW (Cal.) | MS (M + H) | HPLC purity (%) | cLog P |
|---|---|---|---|---|---|---|---|
| 11-10 | R/S | 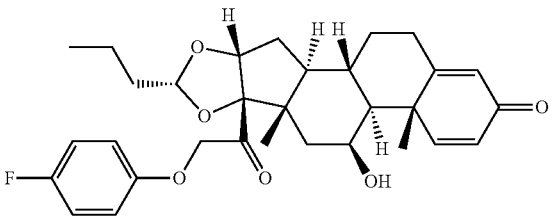 [SMILES: CCC[C@@H]1O[C@@H]2C[C@H]3[C@@H]4CCC5=CC(=O)C=C[C@]5(C)[C@H]4[C@@H](O)C[C@]3(C)[C@]2(C(=O)COc2ccc(F)cc2)O1] | C31H37FO6 | 524.3 | 525.3 | 100 | 5.21 |
| 11-11 | R/S | 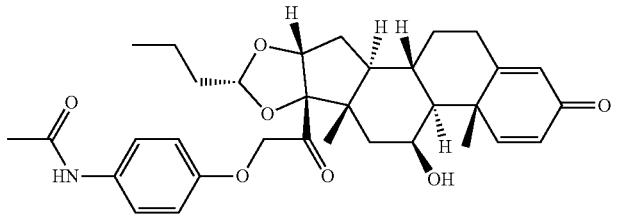 [SMILES: CCC[C@@H]1O[C@@H]2C[C@H]3[C@@H]4CCC5=CC(=O)C=C[C@]5(C)[C@H]4[C@@H](O)C[C@]3(C)[C@]2(C(=O)COc2ccc(NC(C)=O)cc2)O1] | C33H41NO7 | 563.7 | 564.4 | 100 | 4.31 |
| 11-12 11-12 | R/S R | 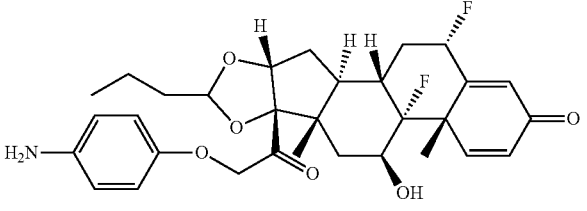 | C31H37F2NO6 C31H37F2NO6 | 557.6 557.6 | 558.3 558.2 | 97 100 | 3.94 |
| 11-13 | R | 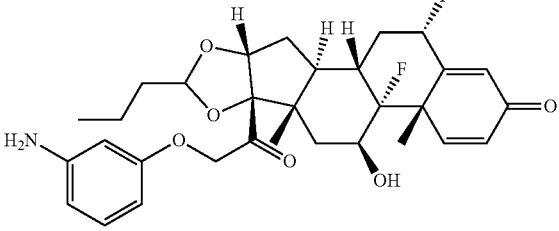 | C31H37F2NO6 | 557.6 | 558.2 | 100 | 3.94 |
| 11-14 | R/S | 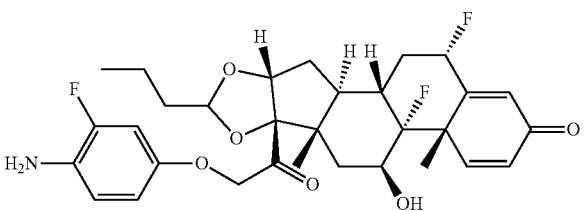 | C31H36F3NO6 | 575.6 | 576.2 | 100 | 4.09 |
| 11-15 | R/S | 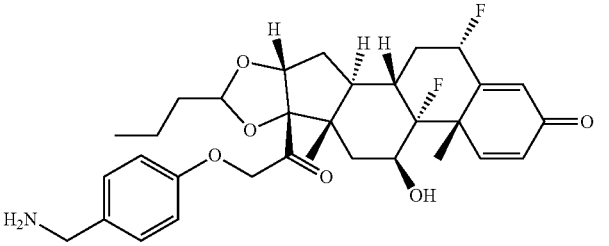 | C32H39F2NO6 | 554.2 | 555.2 | 100 | 3.90 |

TABLE 1-continued

Structure and Chemical-Physical Properties of Compounds

| Cpd. No | C$^{22}$ | Structure | MF | MW (Cal.) | MS (M + H) | HPLC purity (%) | cLog P |
|---|---|---|---|---|---|---|---|
| 11-16 | R/S | | C$_{31}$H$_{38}$O$_7$ | 522.3 | 523.5 | 100 | 4.76 |
| 11-17 | R/S | | C$_{30}$H$_{36}$F$_2$N$_2$O$_6$ | 558.6 | 559.2 | 100 | 3.91 |
| 11-19 | R/S | | C$_{25}$H$_{33}$F$_2$NO$_5$ | 465.2 | 466.2 | 98.5 | 2.33 |
| 11-19 | R | | | | | 100 | |
| 11-20 | R/S | | C$_{34}$H$_{43}$F$_2$NO$_6$ | 599.2 | 600.3 | 100 | 4.71 |
| 11-21 | R/S | | C$_{26}$H$_{35}$F$_2$NO$_5$ | 479.3 | 480.2 | 100 | 2.76 |
| 14-2 | | | C$_{26}$H$_{35}$F$_2$NO$_5$ | 479.6 | 480.2 | 98 | 2.81 |

TABLE 1-continued

Structure and Chemical-Physical Properties of Compounds

| Cpd. No | C[22] Structure | MF | MW (Cal.) | MS (M + H) | HPLC purity (%) | cLog P |
|---|---|---|---|---|---|---|
| 15-5 | (structure) | $C_{26}H_{35}F_2NO_5$ | 479.6 | 480.2 | 98 | 2.81 |
| 16-5 | (structure) | $C_{28}H_{33}F_2NO_5$ | 483.6 | 484 | 98 | 2.85 |

Table 2 below presents steroids made using the methods described herein.

TABLE 2

Structure and Chemical-Physical Properties of Compounds

| Cpd. No | Structure | MF | MS (m/z) 100% | Highest m/z peak | HPLC purity (%) |
|---|---|---|---|---|---|
| 4b | (structure) | $C_{25}H_{33}F_2NO_5 \cdot C_2HF_3O_2$ | 466.2 (M + H) | 466.2 (M + H) | 98.5 |
| 4c | (structure) | $C_{24}H_{31}F_4NO_6$ | 392.2 (M + H) | 392.2 (M + H) | >99 |

TABLE 2-continued

Structure and Chemical-Physical Properties of Compounds

| Cpd. No | Structure | MF | MS (m/z) 100% | Highest m/z peak | HPLC purity (%) |
|---|---|---|---|---|---|
| 4d | 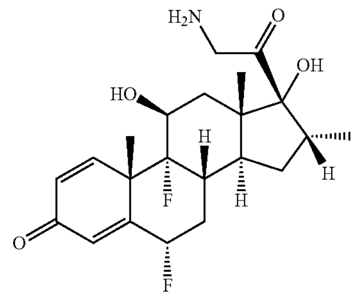 | $C_{24}H_{30}F_5NO_6$ | 410.2 (M + H) | 410.2 (M + H) | 98 |
| 4e | 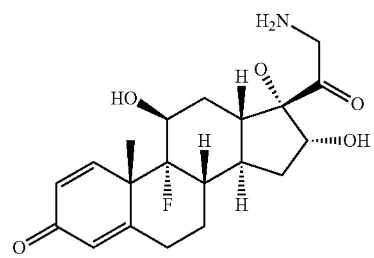 | $C_{21}H_{28}FNO_5 \cdot C_2HF_3O_2$ | 394.2 (M + H) | 394.2 (M + H) | >99 |
| 4f | 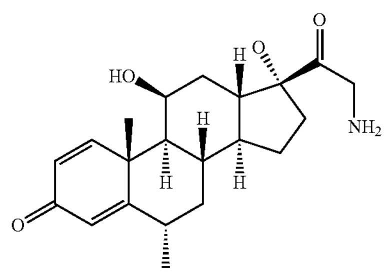 | $C_{22}H_{31}NO_4$ | 374.3 (M + H) | 374.3 (M + H) | >99 |
| 4h | 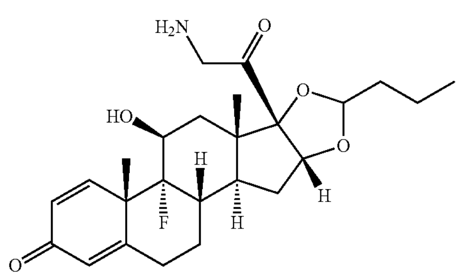 | $C_{25}H_{34}FNO_5 \cdot C_2HF_3O_2$ | 448.2 (M + H) | 448.2 (M + H) | >99 |
| 5-I | 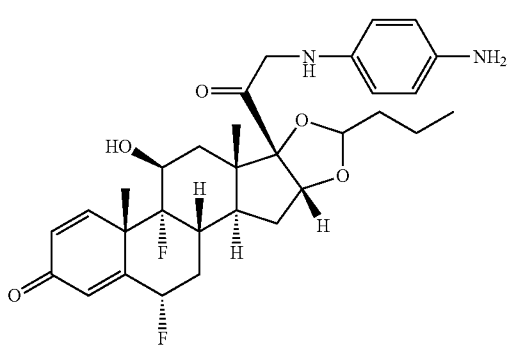 | $C_{31}H_{38}F_2N_2O_5 \cdot C_2HF_3O_2$ | 557.1 (M + H) | 557.1 (M + H) | >99 |

TABLE 2-continued

Structure and Chemical-Physical Properties of Compounds

| Cpd. No | Structure | MF | MS (m/z) 100% | Highest m/z peak | HPLC purity (%) |
|---|---|---|---|---|---|
| 6-I | 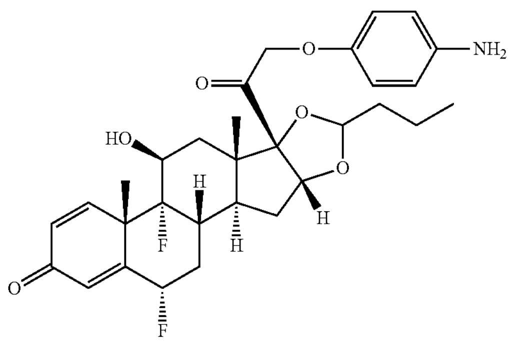 | $C_{31}H_{37}F_2NO_6$ | 522.3 (M + H) | 522.3 (M + H) | 97 |
| R-6-I | 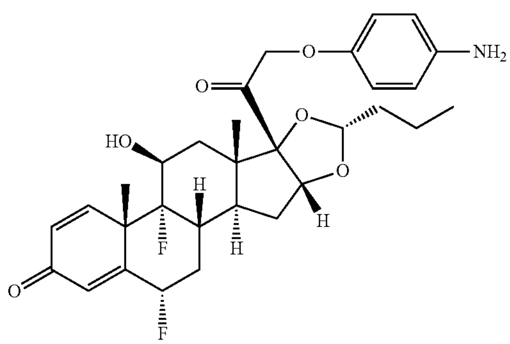 | $C_{31}H_{37}F_2NO_6$ | 522.2 (M + H) | 522.2 (M + H) | >99 |
| S-6-I | 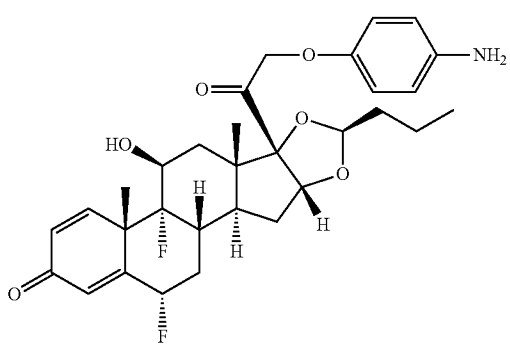 | $C_{31}H_{37}F_2NO_6$ | 522.2 (M + H) | 522.2 (M + H) | 97 |
| 6-I D | 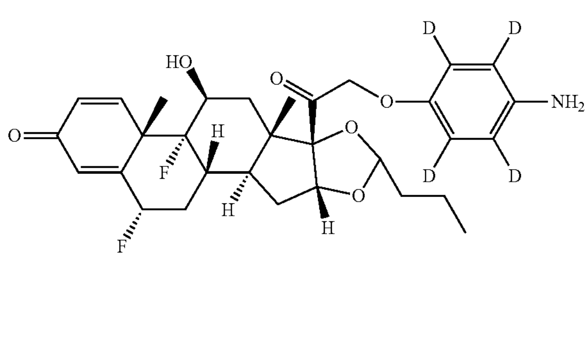 | $C_{31}H_{37}F_2NO_6$ | 297.6 (M/2 + H) | 558.2 (M + H) (10%) | 98.4 |

TABLE 2-continued

Structure and Chemical-Physical Properties of Compounds

| Cpd. No | Structure | MF | MS (m/z) 100% | Highest m/z peak | HPLC purity (%) |
|---|---|---|---|---|---|
| 6-II | 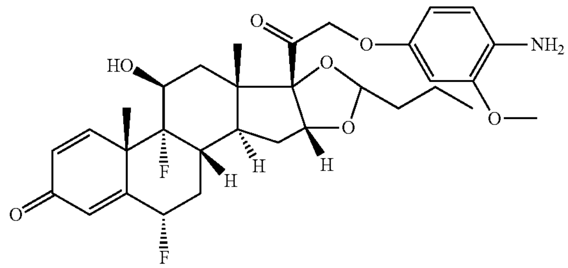 | $C_{32}H_{39}F_2NO_7 \cdot C_2HF_3O_2$ | 558.3 (M + H) | 558.3 (M + H) | >99 |
| 6-III | 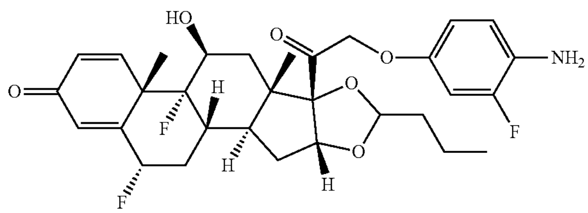 | $C_{31}H_{36}F_3NO_6$ | 558.3 (M + H) | 558.3 (M + H) | >99 |
| 6-VI | 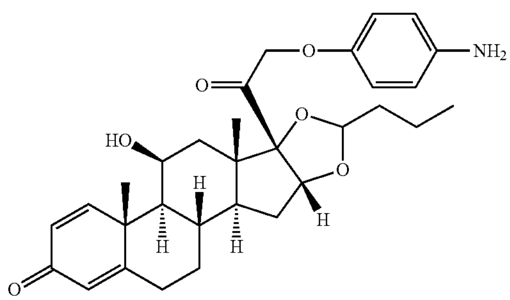 | $C_{31}H_{39}NO_6$ | 576.2 (M + H) | 576.2 (M + H) | >99 |
| R-6-VI | 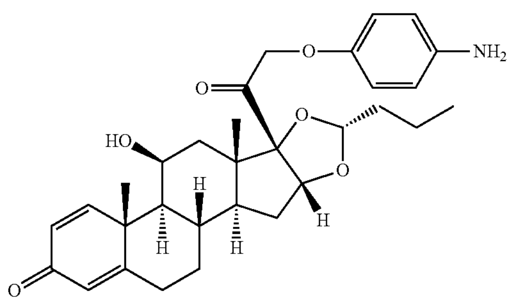 | $C_{31}H_{39}NO_6$ | 588.3 (M + H) | 588.3 (M + H) | >99 |
| S-6-VI | 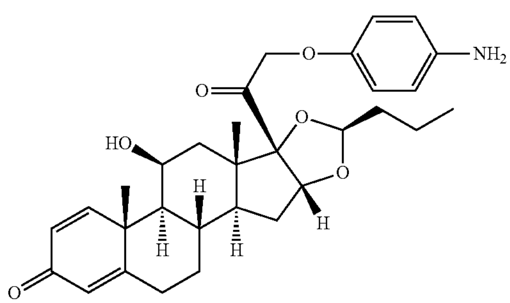 | $C_{31}H_{39}NO_6$ | 587.2 (M-55) | 665.2 (M + Na) (25%) | >99 |

TABLE 2-continued
Structure and Chemical-Physical Properties of Compounds
| Cpd. No | Structure | MF | MS (m/z) 100% | Highest m/z peak | HPLC purity (%) |
|---|---|---|---|---|---|
| 6-VII | 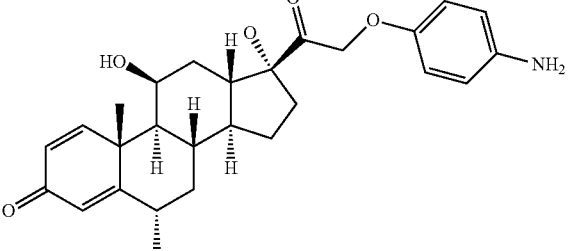 | $C_{28}H_{35}NO_5$ | 587.3 (M + H) | 587.3 (M + H) | >99 |
Table 3 below presents linker payloads made using the methods described herein.
TABLE 3
Examples of Linker-Payloads
| LP No. | Structures of Linker-Payloads |
|---|---|
| LP1 | 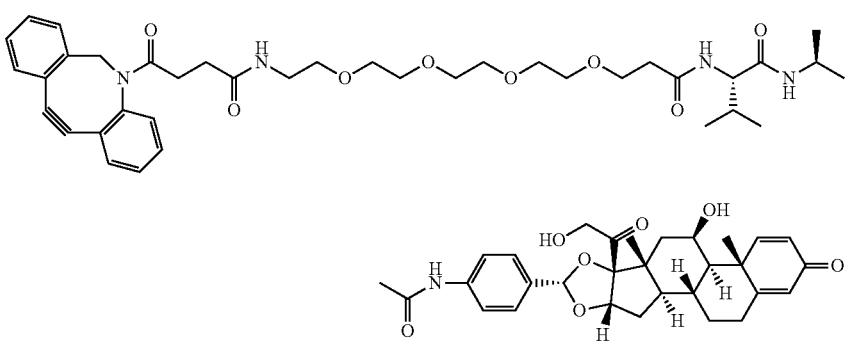 |
| LP2 | 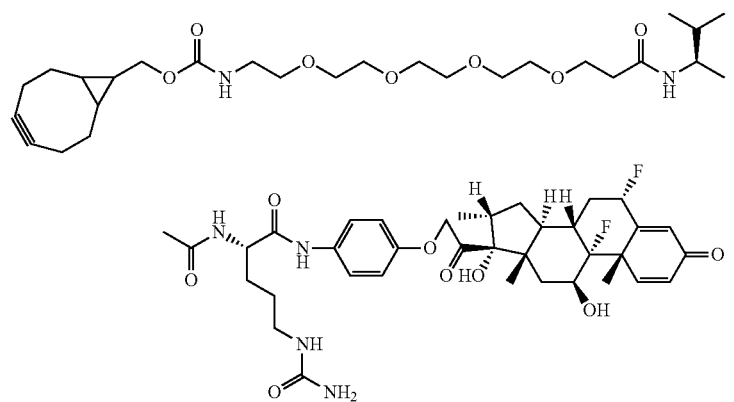 |

TABLE 3-continued

Examples of Linker-Payloads

| LP No. | Structures of Linker-Payloads |
| --- | --- |
| LP3 | |
| LP4 | |
| LP5 | |
| LP6 | |

TABLE 3-continued
Examples of Linker-Payloads
| LP No. | Structures of Linker-Payloads |
|---|---|
| LP7 | 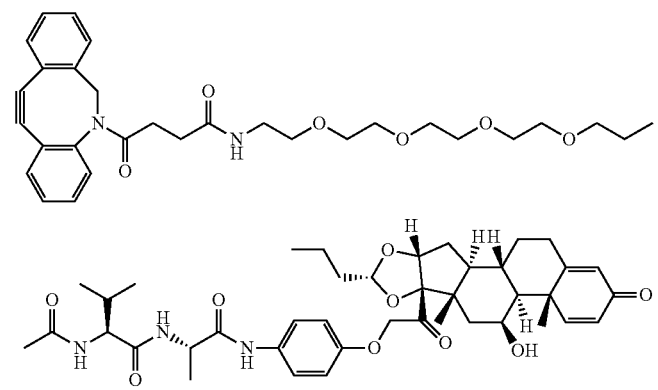 |
| LP8 | 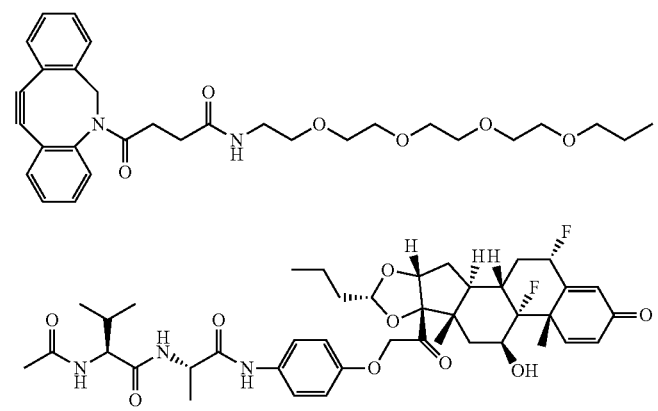 |
| LP9 | 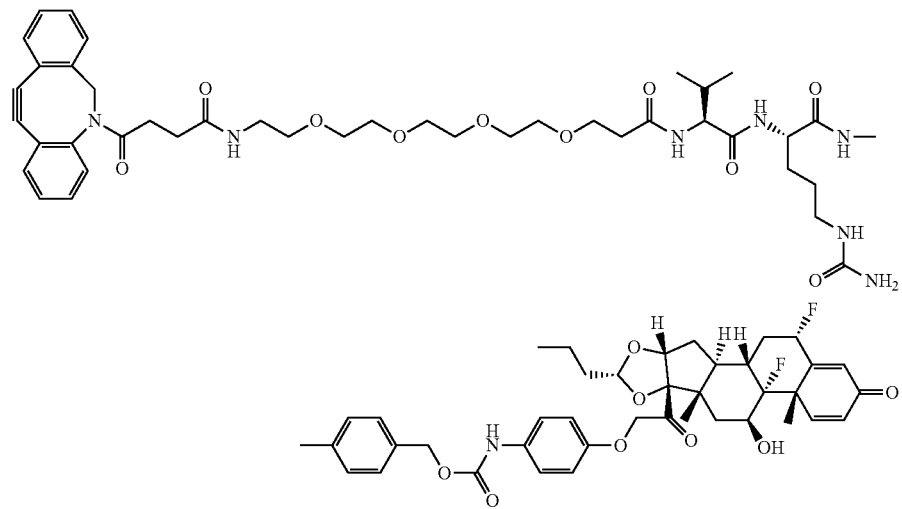 |

TABLE 3-continued
Examples of Linker-Payloads
| LP No. | Structures of Linker-Payloads |
| --- | --- |
| LP10 | 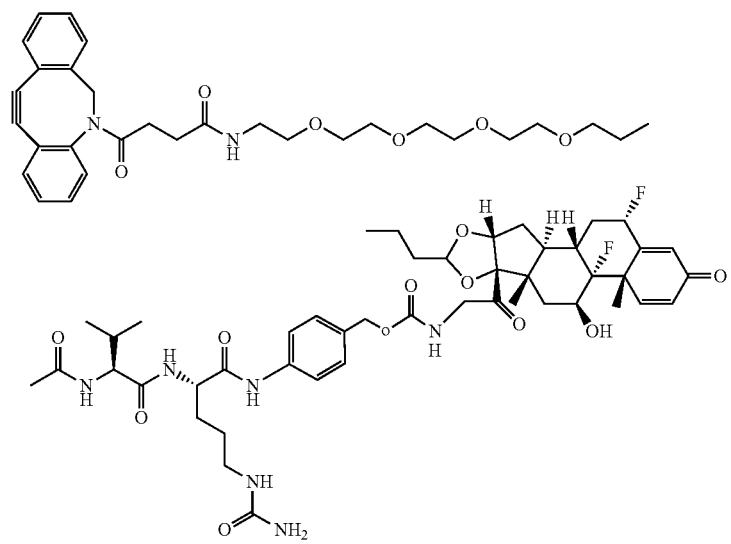 |
| LP11 | 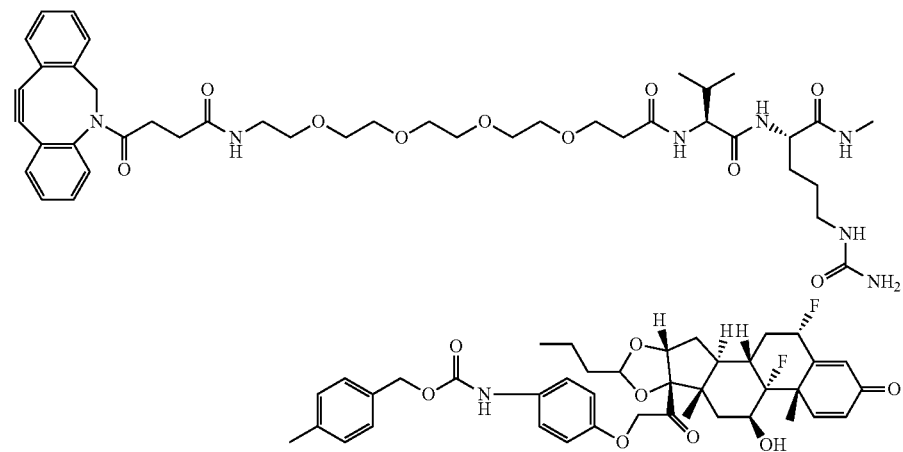 |
| LP12 | 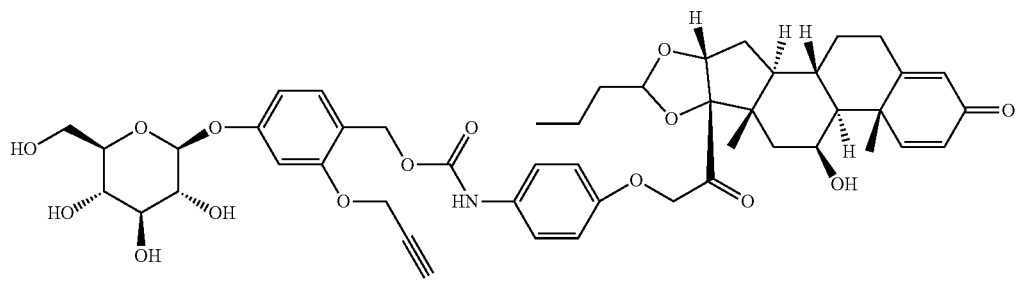 [SMILES: C#CCOc1cc(O[C@@H]2O[C@H](CO)[C@@H](O)[C@H](O)[C@H]2O)ccc1COC(=O)Nc1ccc(OCC(=O)[C@@]23OC(CCC)O[C@@H]2C[C@H]2[C@@H]4CCC5=CC(=O)C=C[C@]5(C)[C@H]4[C@@H](O)C[C@@]23C)cc1] |

TABLE 3-continued
Examples of Linker-Payloads
| LP No. | Structures of Linker-Payloads |
| --- | --- |
| LP13 | 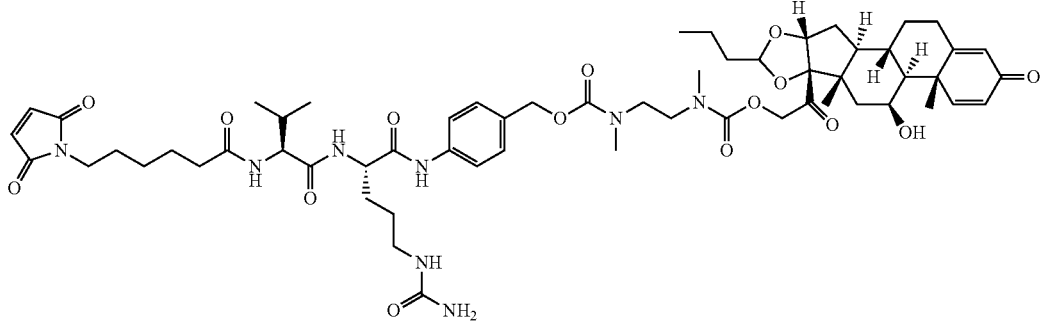 |
| LP14 | 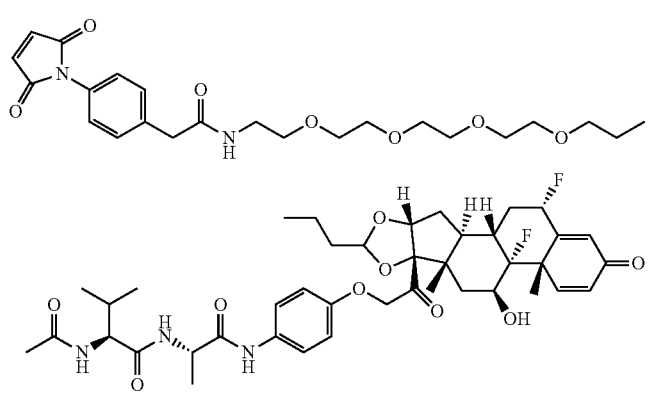 |
| LP15 | 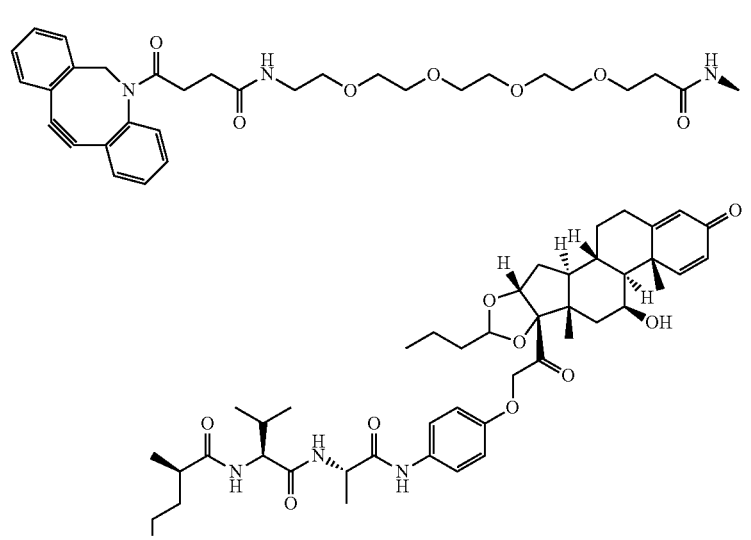 |

TABLE 3-continued
Examples of Linker-Payloads
| LP No. | Structures of Linker-Payloads |
|---|---|
| | 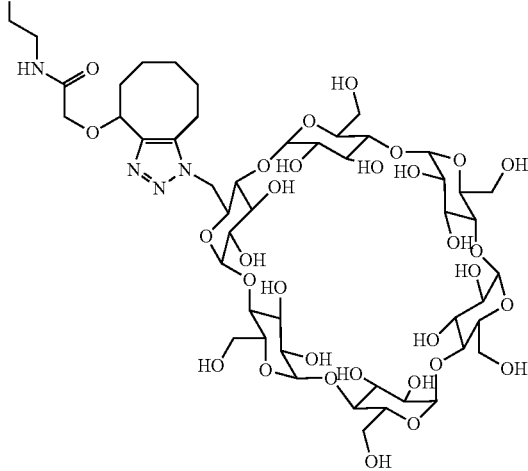 |
| LP16 | 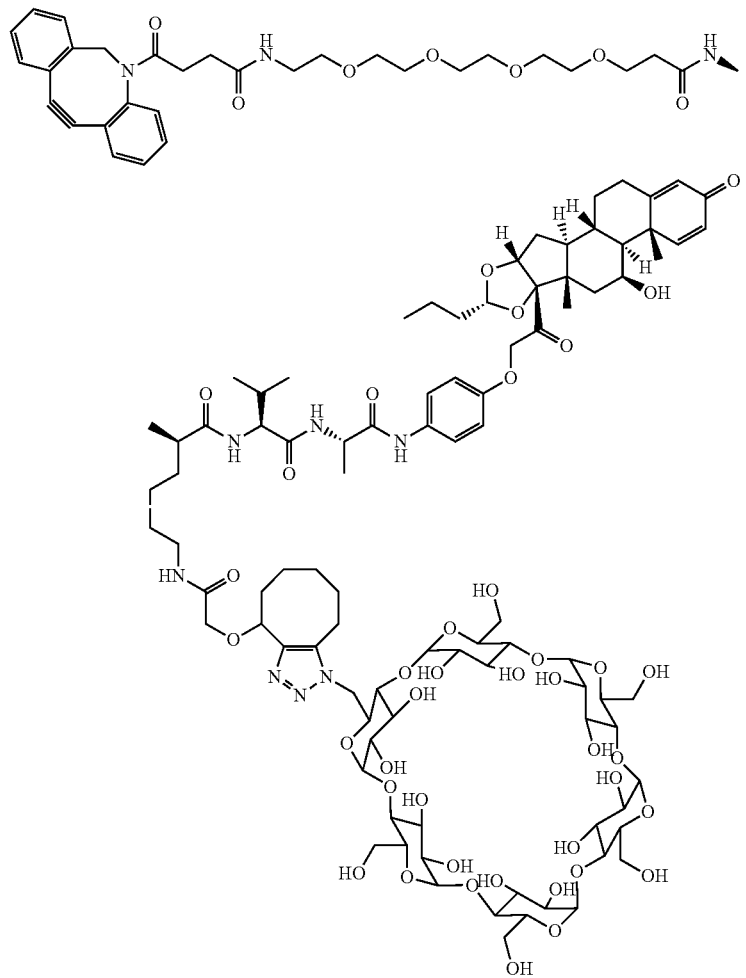 |
Table 4 below presents linker payloads made using the methods described herein.

TABLE 4
Examples of Linker-Payloads
| | Structure |
|---|---|
| LP101 | 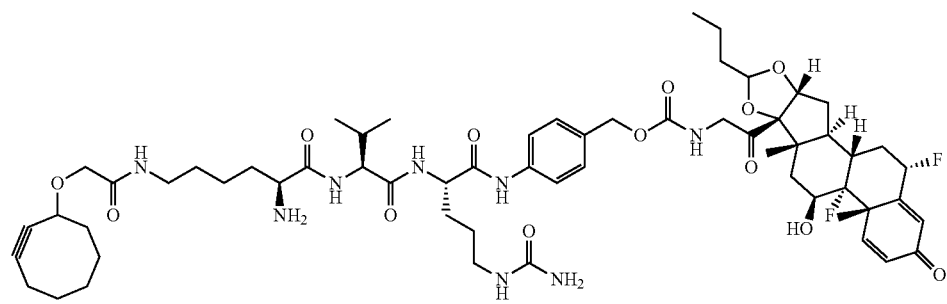 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@@H](N)CCCCNC(=O)COC3C#CCCCCC3)C(C)C)cc2)O1] |
| LP102 | 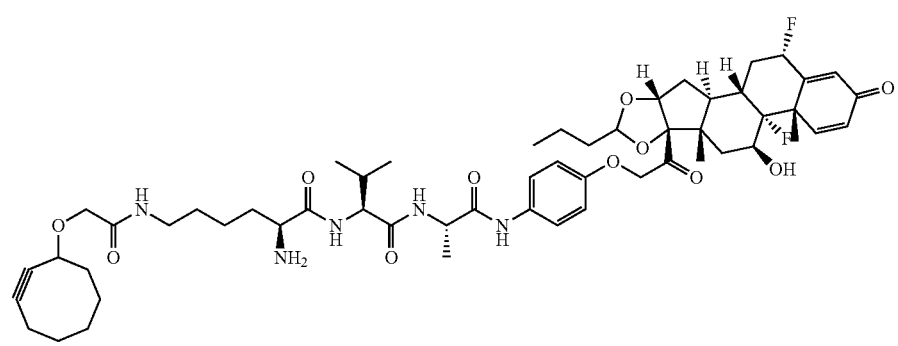 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](NC(=O)[C@@H](N)CCCCNC(=O)COC3C#CCCCCC3)C(C)C)cc2)O1] |
| LP103 | 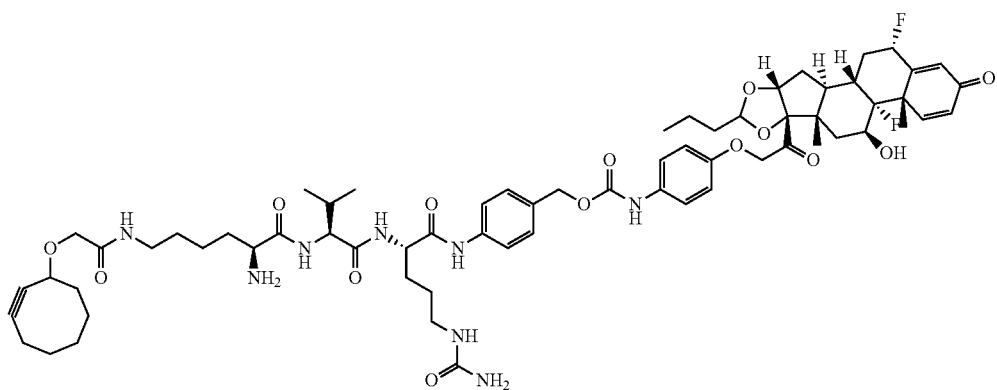 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](CCCNC(N)=O)NC(=O)[C@@H](NC(=O)[C@@H](N)CCCCNC(=O)COC4C#CCCCCC4)C(C)C)cc3)cc2)O1] |
| LP104 | 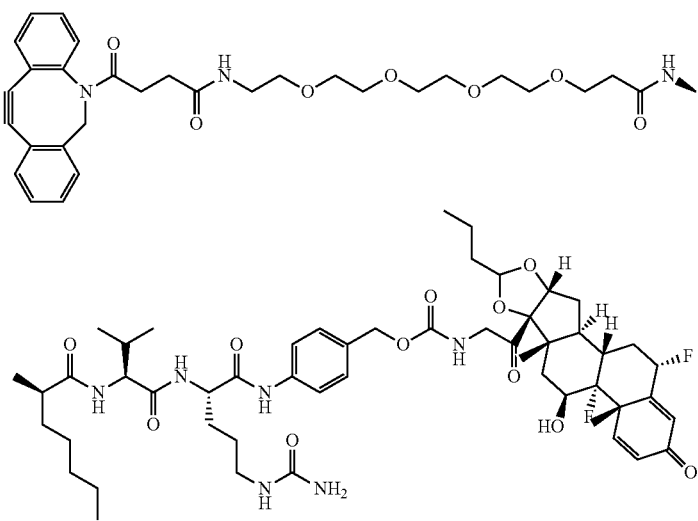 |

TABLE 4-continued
Examples of Linker-Payloads
Structure
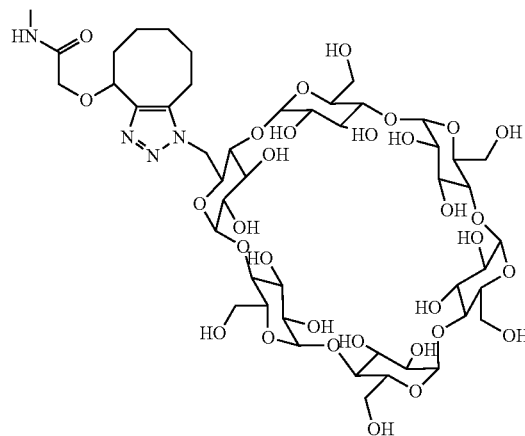
LP105
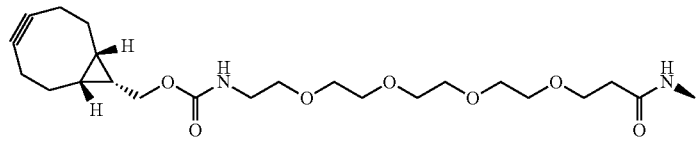
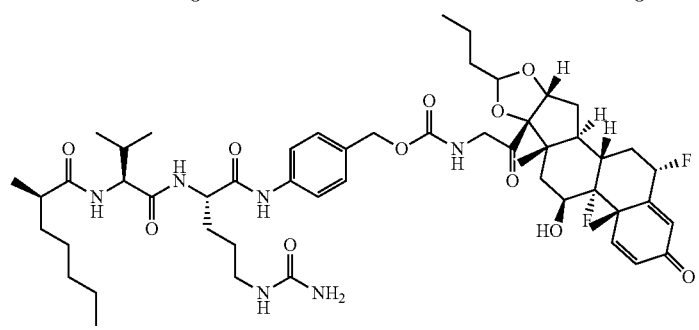
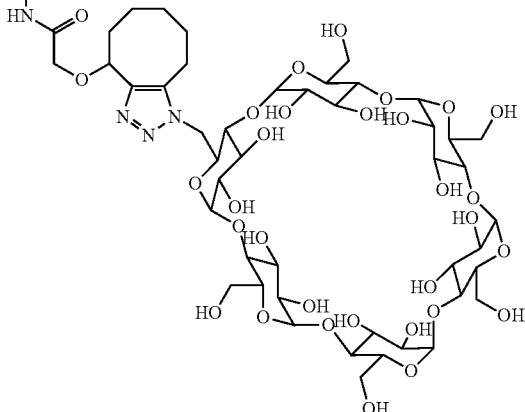
LP108
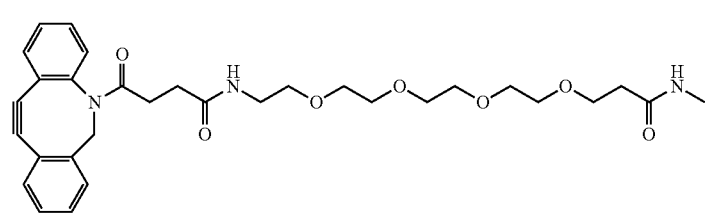

TABLE 4-continued
Examples of Linker-Payloads
Structure
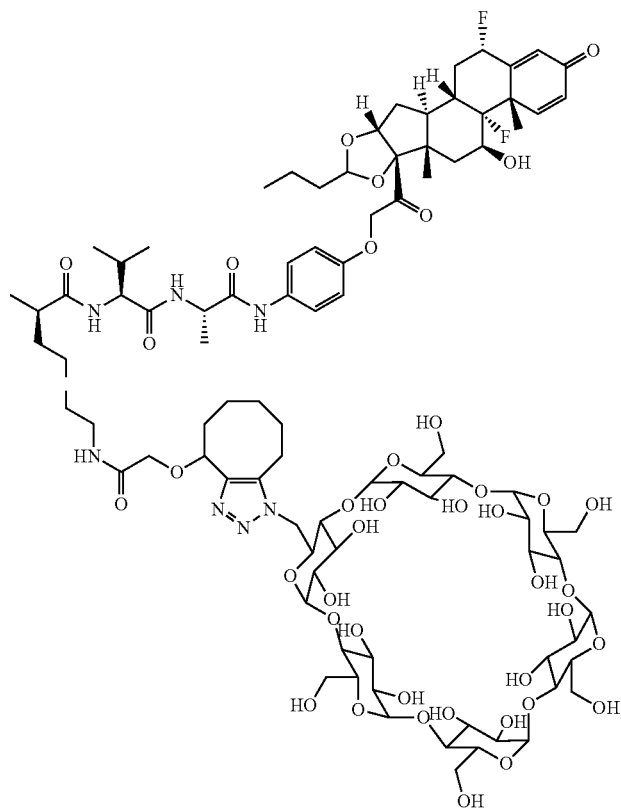
LP110
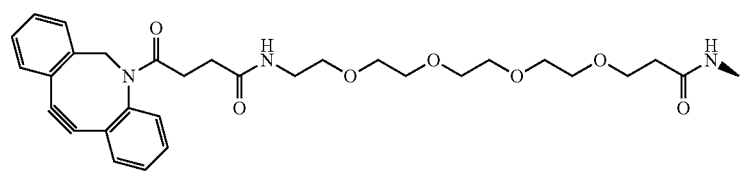
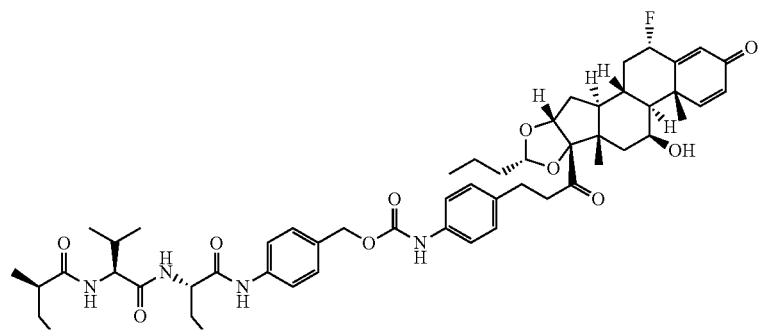

TABLE 4-continued
Examples of Linker-Payloads
Structure
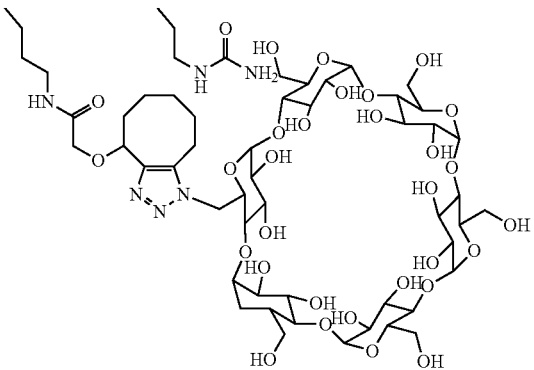
LP112
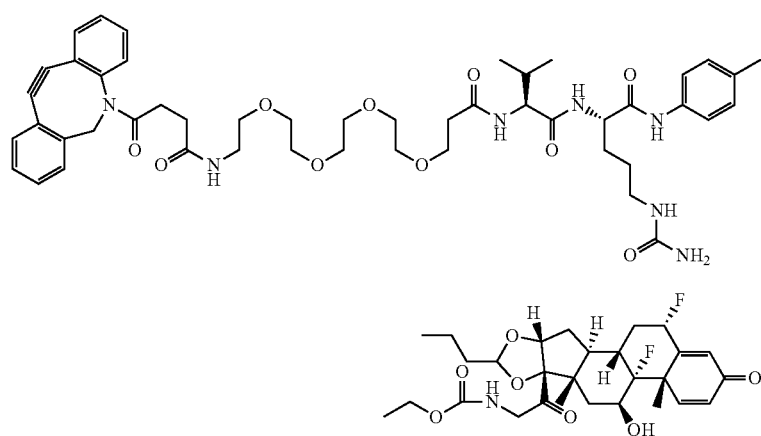
LP113
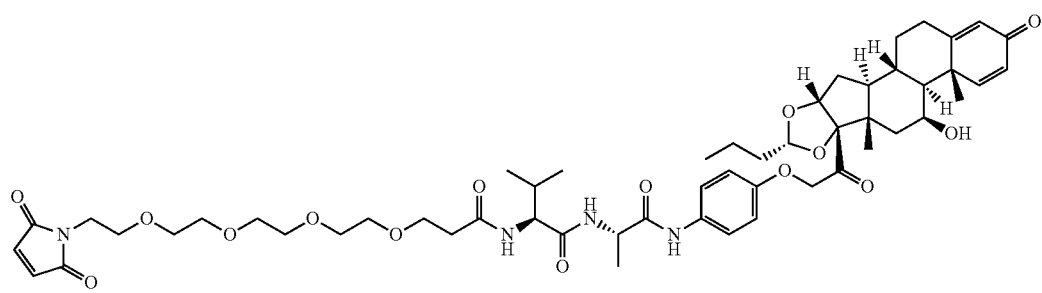 [SMILES: CCC[C@@H]1O[C@@H]2C[C@H]3[C@@H]4CCC5=CC(=O)C=C[C@]5(C)[C@H]4[C@@H](O)C[C@]3(C)[C@]2(C(=O)COc2ccc(NC(=O)[C@H](C)NC(=O)[C@@H](NC(=O)CCOCCOCCOCCOCCN3C(=O)C=CC3=O)C(C)C)cc2)O1]

TABLE 4-continued
Examples of Linker-Payloads
Structure
LP114
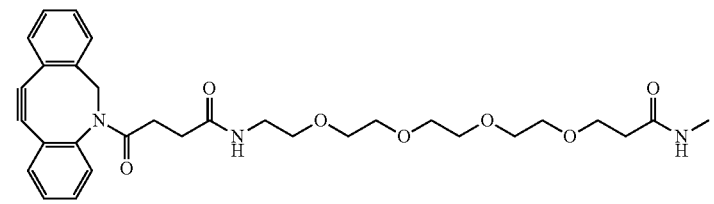
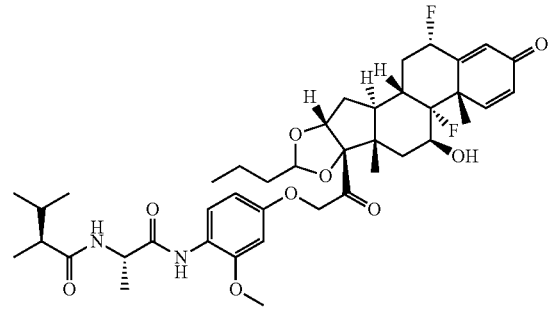
LP115
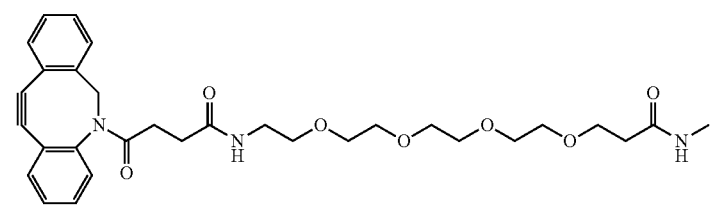
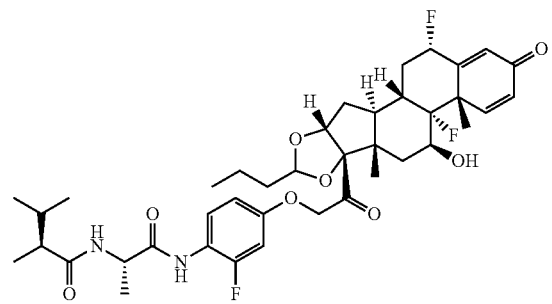
LP116
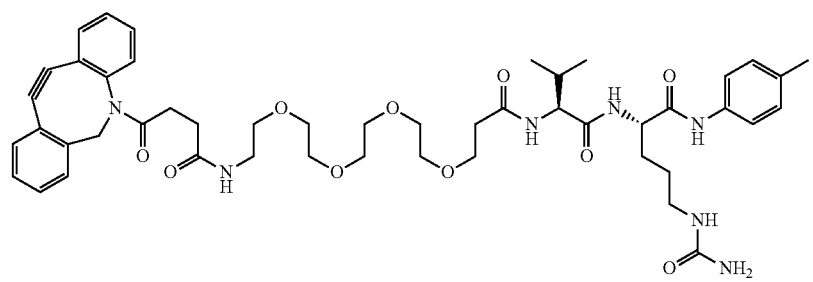
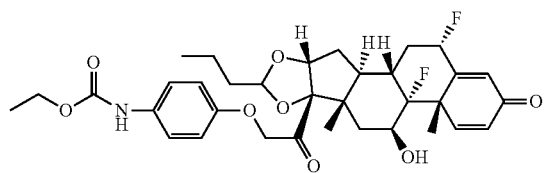

Example 2

This example demonstrates methods for making chemical derivatives of budesonide, dexamethasone, and flumethasone. These methods are illustrated, generally, as shown in FIGS. 2, 3, and 4.

As shown in FIG. 2, mesylate analogs of Budesonide (9) or its difluoro-analog (9B) were reacted with alkyl amines or substituted phenols (10) to yield aniline or amine including compounds (11), such as compounds 11-1 to 11-23 in FIG. 2.

Figure 3:
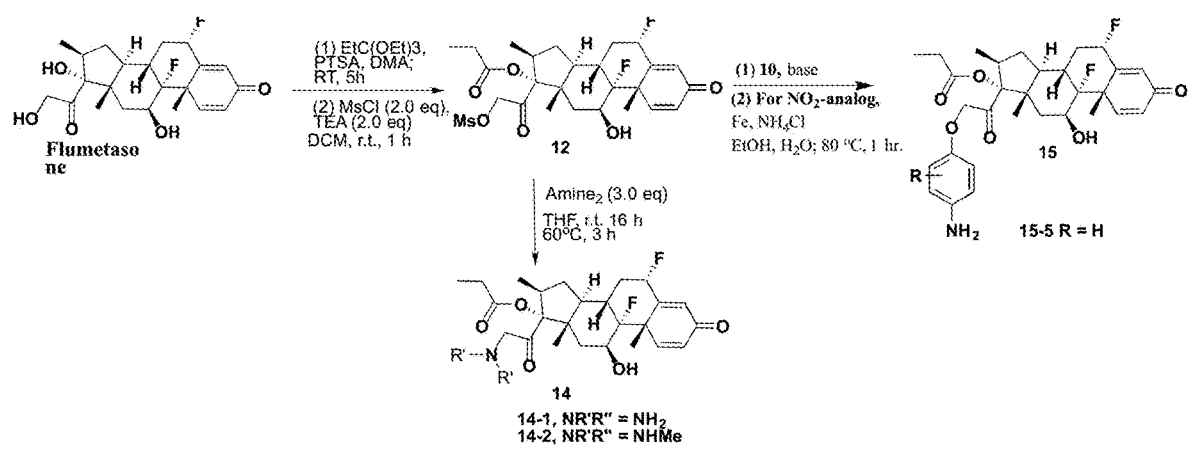

As shown in FIG. 3, mesylate analogs of Dexamethasone (12), were reacted with alkyl amines or substituted phenols (10) to yield aniline or amine-including compounds (14) or (15) in FIG. 3.

Figure 4:
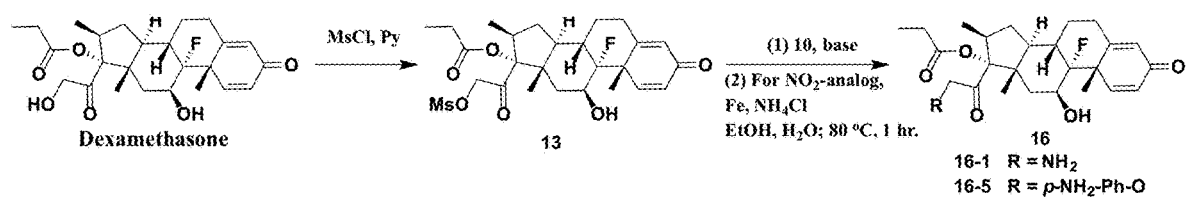

As shown in FIG. 4, mesylate analogs of Flumethasone (13), were reacted with alkyl amines or substituted phenols (10) to yield aniline- or amine-including compounds (16) in FIG. 4.

As detailed below, stereochemically pure epimers of 11-5S and 11-5R in Table 1 were obtained by chiral separation from a mixture of their corresponding R/S isomers. The absolute stereochemistry for each compound was determined by 2D-NOESY. The 2D-NOESY spectra showed that $H^{22}$ and $H^{18}$ were correlated in 11-5R, and that there was no correlation between $H^{22}$ and $H^{18}$ in 11-5S. Similarly, the chiral centers at $C^{22}$-position were identified for compounds 7-1S, 7-1R, 7-4R, 8-1R, 11-6S, 11-6R, 11-7R, 11-8R, 11-12R, 11-13R, and 11-19R in Table 1 by 2D-NOESY.

Example 3

This example demonstrates a method for making compounds 7-1S and 7-1R in Table 1. This example refers to the compounds numbered in FIG. 1.

2-[(1S,2S,4R,8S,9S,11S,12S,13R)-11-Hydroxy-9,13-dimethyl-6-(4-nitrophenyl)-16-oxo-5,7-dioxapentacyclo[10.8.0.0$^{2,9}$.0$^{4,8}$.0$^{13,18}$]icosa-14,17-dien-8-yl]-2-oxoethyl 2-methylpropanoate (5-1) and (1S,2S,4R,8S,9S,11S,12S,13R)-11-Hydroxy-8-(2-hydroxyacetyl)-9,13-dimethyl-6-(4-nitrophenyl)-5,7-dioxapentacyclo[10.8.0.0$^{2,9}$.0$^{4,8}$.0$^{13,18}$]icosa-14,17-dien-16-one (6-1)

Step 1: Compound 3 was synthesized according to the procedures in US2007/135398, the entire contents of which are herein incorporated by reference in its entirety for all purpose, by reacting desonide (1) with isobutyric acid in acetone.

Step 2: To a solution of compound 3 (320 mg, 0.657 mmol) in nitropropane (20 mL) was added aqueous perchloric acid (70%, 1.90 g, 1.33 mmol) dropwise at 0° C., followed by the addition of 4-nitrobenzaldehyde (4-1, 151 mg, 1.00 mmol). The resulting mixture was stirred at RT overnight, and was then diluted with ethyl acetate (80 mL). The resulting mixture was washed with saturated aqueous sodium bicarbonate solution (30 mL×3) and then brine (30 mL×2). The resulting solution was then dried over sodium sulfate and concentrated in vacuo. The residue was then purified by flash chromatography eluting with 0-35% ethyl acetate in petroleum-ether to yield compound (5-1) as a yellow solid (120 mg, yield 32%), which was a mixture of 5R/5S epimers in a ratio 3/1 based on $^1$H NMR, and further eluting with 60-70% ethyl acetate in petroleum ether to yield compound (6-1) as a yellow solid (150 mg, yield 36%), which was a mixture of 6R/6S epimers in a ratio 5/1 based on $^1$H NMR (R/S not determined).

Compound (5-1): ESI m/z: 580 (M+H)$^+$. $^1$H NMR (CDCl$_3$, 400 MHz, epimers A and B with ratio=3) δ 8.27 and 8.25 (d, J=8.8 Hz, 2H), 7.62 and 7.55 (d, J=8.8 Hz, 2H), 7.28-7.21 (m, 1H), 6.33-6.23 (m, 1H), 6.03 and 6.05 (s, 1H), 5.62 and 6.16 (s, 1H), 5.12 and 5.43 (d, J=5.4 Hz, 1H), 4.97 and 4.77 (d, J=17.6 Hz, 1H), 4.88 and 4.33 (d, J=17.6 Hz, 1H), 4.52 (br s, 1H), 2.80-2.50 (m, 2H), 2.44-2.29 (m, 1H), 2.29-2.05 (m, 3H), 2.01-1.84 (m, 2H), 1.80-1.67 (m, 2H), 1.51 and 1.59 (br s, 1H), 1.46 and 1.48 (s, 3H), 1.29-1.07 (m, 7H), 1.03 and 1.05 (s, 3H) ppm.

Compound 6-1: ESI m/z: 510 (M+H)$^+$. $^1$H NMR (DMSO$_{d6}$, 400 MHz, epimers A and B with ratio=5) δ 8.26 and 8.24 (d, J=8.8 Hz, 2H), 7.77 and 7.57 (d, J=8.8 Hz, 2H), 7.32 (d, J=10.0 Hz, 1H), 6.17 and 6.18 (dd, J=10.0 Hz, 1.8 Hz, 1H), 5.93 and 5.95 (s, 1H), 5.63 and 6.28 (s, 1H), 5.14 and 5.03 (t, J=6.0 Hz, 1H), 4.99 and 5.35 (d, J=6.3 Hz, 1H), 4.82 (d, J=3.2 Hz, 1H), 4.64-4.13 (m, 3H), 2.64-2.51 (m, 1H), 2.37-2.24 (m, 1H), 2.20-1.99 (m, 2H), 1.94-1.57 (m, 5H), 1.40 (s, 3H), 1.14-0.98 (m, 2H), 0.88 (s, 3H) ppm.

Step 3: Making (1S,2S,4R,6R,8S,9S,11S,12S,13R)-6-(4-Aminophenyl)-11-hydroxy-8-(2-hydroxyacetyl)-9,13-dimethyl-5,7-dioxapentacyclo[10.8.0.0$^{2,9}$.0$^{4,8}$.0$^{13,18}$]icosa-14,17-dien-16-one (7-1R) in Table 1) and (1S,2S,4R,6S,8S,9S,11S,12S,13R)-6-(4-Aminophenyl)-11-hydroxy-8-(2-hydroxyacetyl)-9,13-dimethyl-5,7-dioxapentacyclo[10.8.0.0$^{2,9}$.0$^{4,8}$.0$^{13,18}$]icosa-14,17-dien-16-one (7-1S) in Table 1)

Iron powder (56.0 mg, 1.00 mmol) and ammonium chloride (53.5 mg, 1.00 mmol) were simultaneously added to a solution of compound 5-1 (51.0 mg, 0.100 mmol) in a combined solution of ethanol (3 mL) and water (0.5 mL). The suspension was stirred at 80° C. for an hour and was filtered through Celite to remove the solid. The filtrate was concentrated in vacuo and the residue was purified by prep-HPLC (method B) to yield compound 7-1R (30 mg, yield 63%) as a white solid and compound 7-1S (8 mg, yield 17%) as a white solid.

Figure 5:
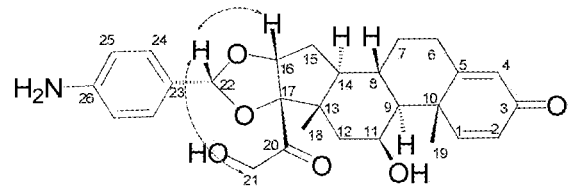
FIG. 5 shows a two-dimensional nuclear Overhauser effect (NOE) magnetic resonance spectrum (hereinafter "2D-NOESY") for compound 7-1R in Table 1.
Figure 5:
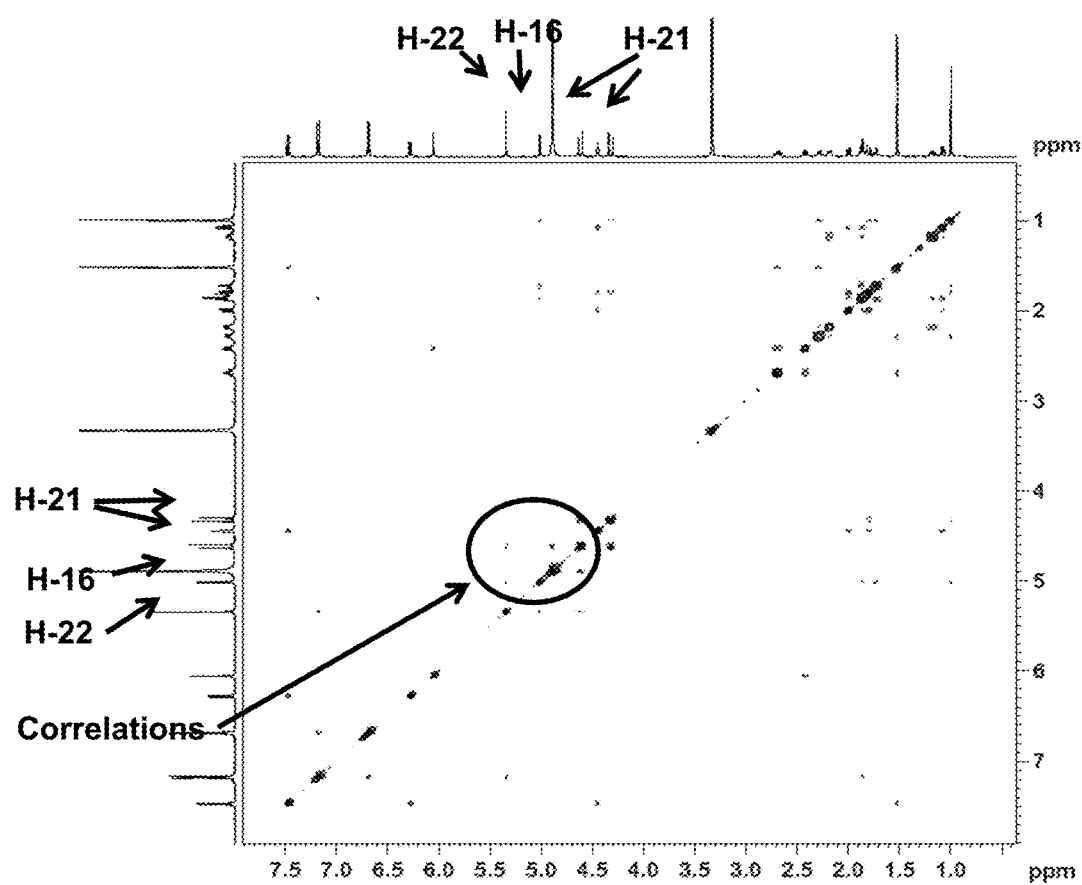
Figure 6:
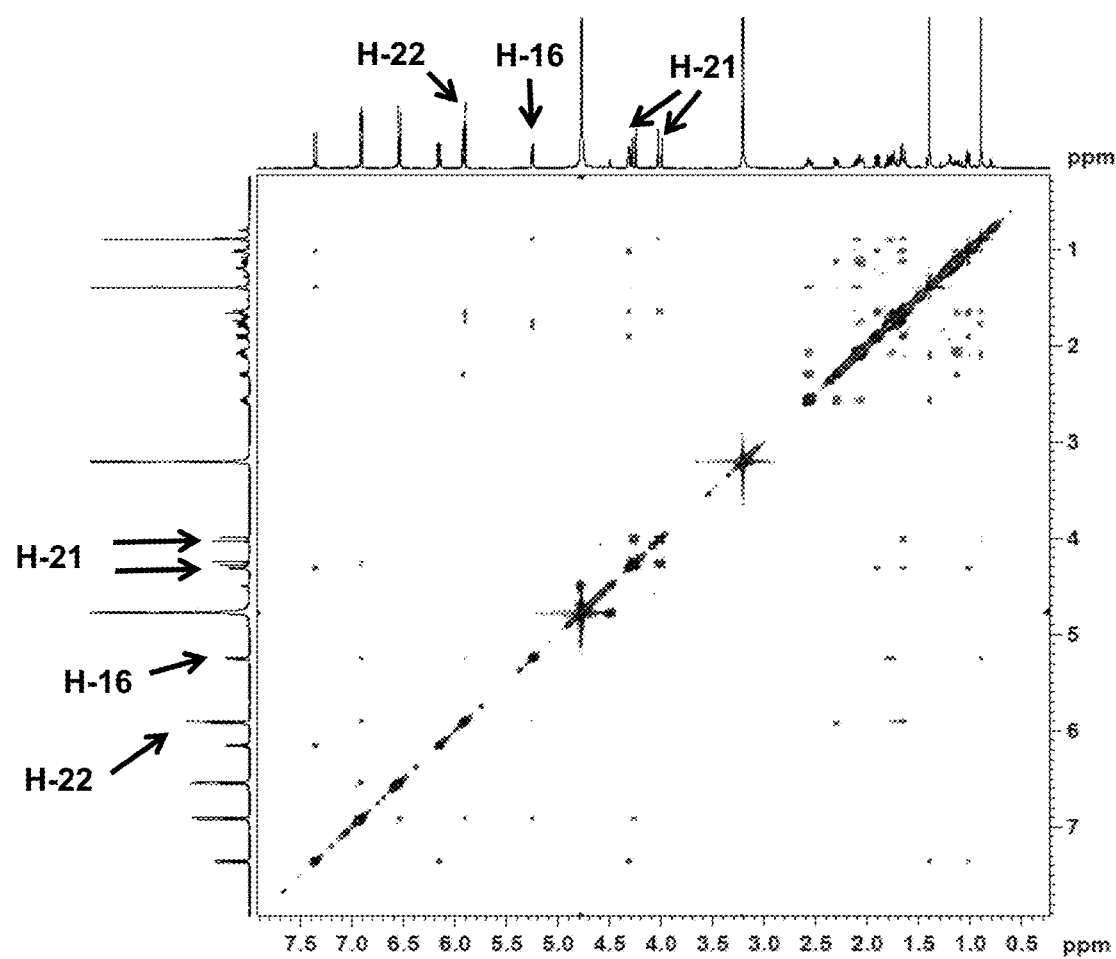
FIG. 6 shows a 2D-NOESY for compound 7-1S in Table 1.

2D-NOESY spectroscopy was used to determine the stereochemical configurations of the chiral centers of compound 7-1R and compound 7-1S. The 2D-NOESY spectra confirmed that there is a correlation between $H^{22}$ and $H^{21}$ in compound 7-1R, which indicates that it has an R configuration chiral center. No correlation was observed between $H^{22}$ and $H^{21}$ in compound 7-1S, indicating it has an S configuration chiral center. The NMR study also showed that the shift of $H^{22}$ in compound 7-1R (5.33 ppm) was much higher than that of compound 7-1S (6.01 ppm), indicating $H^{22}$ of compound 7-1R was more hindered. The 2D-NOESY spectra of compound 7-1-22R and compound 7-1-22S are shown in FIGS. 5 and 6.

Compound 7-1R in Table 1: ESI m/z: 480 (M+H)$^+$. $^1$H NMR (MeOD$_{d4}$, 400 MHz) δ 7.46 (d, J=10.1 Hz, 1H), 7.17 (d, J=8.4 Hz, 2H), 6.67 (d, J=8.4 Hz, 2H), 6.27 (dd, J=10.1, 1.8 Hz, 1H), 6.04 (s, 1H), 5.33 (s, 1H), 5.00 (d, J=5.4 Hz, 1H), 4.61 (d, J=19.4 Hz, 1H), 4.50-4.39 (m, 1H), 4.31 (d, J=19.4 Hz, 1H), 2.78-2.61 (m, 1H), 2.47-2.35 (m, 1H), 2.35-2.22 (m, 1H), 2.22-2.10 (m, 1H), 2.04-1.94 (m, 1H), 1.91-1.66 (m, 4H), 1.51 (s, 3H), 1.25-1.11 (m, 1H), 1.07 (dd, J=11.2 Hz, 3.5 Hz, 1H), 0.99 (s, 3H) ppm.

Compound 7-1S in Table 1: ESI m/z: 480 (M+H)$^+$. $^1$H NMR (MeOD$_{d4}$, 400 MHz) δ 7.47 (d, J=10.1 Hz, 1H), 7.02 (d, J=8.4 Hz, 2H), 6.65 (d, J=8.5 Hz, 2H), 6.27 (dd, J=10.1, 1.8 Hz, 1H), 6.03 (s, 1H), 6.01 (s, 1H), 5.36 (d, J=6.2 Hz, 1H), 4.46-4.31 (m, 2H), 4.12 (d, J=19.2 Hz, 1H), 2.75-2.61 (m, 1H), 2.47-2.35 (m, 1H), 2.27-2.11 (m, 2H), 2.08-1.97 (m, 1H), 1.96-1.73 (m, 4H), 1.51 (s, 3H), 1.33-1.17 (m, 2H), 1.17-1.09 (m, 1H), 1.01 (s, 3H) ppm.

Example 4

This example demonstrates a method for making compounds (8-1R/S) and compound (8-1R) in Table 1. This example refers to the compound numbering in FIG. 1.

2-[(1S,2S,4R,8S,9S,11S,12S,13R)-6-(4-Aminophenyl)-11-hydroxy-9,13-dimethyl-16-oxo-5,7-dioxapentacyclo[10.8.0.0$^{2,9}$.0$^{4,8}$.0$^{13,18}$]icosa-14,17-dien-8-yl]-2-oxoethyl 2-methylpropanoate (8-1R)

Iron powder (56.0 mg, 1.00 mmol) and ammonium chloride (53.5 mg, 1.00 mmol) were simultaneously added to a solution of compound (6-1) (58.0 mg, 0.100 mmol) in a combined solution of ethanol (3 mL) and water (1 mL). The resulting suspension was stirred at 80° C. for an hour and was filtered through Celite to remove the solid. The filtrate was concentrated in vacuo and the residue was purified by prep-HPLC (method B) to yield compound (8-1R) and its enantiomer (i.e., S stereochemistry at $C^{22}$) (26 mg, yield 45%) as a white solid. The ratio of the R epimer to the S-epimer is 4:1 by HPLC and $^1$H NMR. ESI m/z: 550 (M+H)$^+$.

The R-epimer was further isolated and the configuration was determined by 2D NMR.

Compound (8-1R): ESI m/z: 550 (M+H)$^+$. $^1$H NMR (MeOD$_{d4}$, 500 MHz) δ 7.46 (d, J=10.0 Hz, 1H), 7.19 (d, J=8.5 Hz, 2H), 6.69 (d, J=8.4 Hz, 2H), 6.27 (dd, J=10.0 Hz, 2.0 Hz, 1H), 6.05 (s, 1H), 5.44 (s, 1H), 5.07 (d, J=17.5 Hz, 1H), 4.96 (d, J=5.5 Hz, 1H), 4.88 (d, J=17.5 Hz, 1H), 4.48-4.44 (m, 1H), 2.73-2.64 (m, 2H), 2.42-2.39 (m, 1H), 2.32-2.24 (m, 1H), 2.19-2.15 (m, 1H), 2.03-1.99 (m, 1H), 1.95-1.92 (m, 1H), 1.90-1.83 (m, 2H), 1.76-1.69 (m, 1H), 1.52 (s, 3H), 1.27-1.12 (m, 7H), 1.09-1.05 (m, 1H), 1.02 (s, 3H) ppm.

Example 5

This example demonstrates a method for making compound (7-2R/S) in Table 1. This example refers to the compound numbering in FIG. 1.

Step 1: 1S,2S,4R,8S,9S,11S,12S,13R)-11-Hydroxy-8-(2-hydroxyacetyl)-9,13-dimethyl-6-[(4-nitrophenyl)methyl]-5,7-dioxapentacyclo[10.8.0.0$^{2,9}$.0$^{4,8}$.0$^{13,18}$]icosa-14,17-dien-16-one (5-2)

To a solution of compound (3) (226 mg, 0.464 mmol) in nitropropane (10 mL) was added aqueous perchloric acid (70%, 985 mg, 6.90 mmol) dropwise at 0° C., followed by the addition of 2-(4-nitrophenyl)acetaldehyde (4-2, 115 mg, 0.696 mmol) according to the synthesis in *Synthesis*, 2011, 18, 2935-2940, the entire contents of which are herein incorporated by reference in their entirety for all purposes. The resulting mixture was stirred at RT overnight, and was then diluted with ethyl acetate (60 mL). The mixture was washed with saturated aqueous sodium bicarbonate solution (50 mL×3), then brine (50 mL×3), and then dried over sodium sulfate and concentrated in vacuo. The residue was purified by flash chromatography eluting with 0-35% ethyl acetate in petroleum ether to yield compound (6-2) as a brown solid (95 mg, yield 34%, including 22R/S epimers in a ratio >10/1 by $^1$H NMR), and further eluting with 60-70% ethyl acetate in petroleum ether to yield compound (5-2) (145 mg, yield 60%) as a brown solid.

Compound (5-2): ESI m/z: 524 (M+H)$^+$. $^1$H NMR (CDCl$_3$, 400 MHz) δ 8.09 (d, J=8.7 Hz, 2H), 7.39 (d, J=8.7 Hz, 2H), 7.17 (d, J=10.1 Hz, 1H), 6.31 (dd, J=10.1 Hz, 1.8 Hz, 1H), 6.02 (s, 1H), 4.92 (d, J=5.3 Hz, 1H), 4.86 (t, J=3.6 Hz, 1H), 4.52-4.39 (m, 2H), 4.28-4.17 (m, 1H), 3.08 (d, J=3.5 Hz, 2H), 2.96 (t, J=4.9 Hz, 1H), 2.53-2.40 (m, 1H), 2.32-2.19 (m, 1H), 2.04-1.95 (m, 1H), 1.95-1.82 (m, 2H), 1.60-1.46 (m, 3H), 1.38 (s, 3H), 1.34 (br s, 1H), 0.91-0.77 (m, 4H), 0.76-0.62 (m, 2H) ppm.

Step 2: (1S,2S,4R,8S,9S,11S,12S,13R)-6-[(4-Aminophenyl)methyl]-11-hydroxy-8-(2-hydroxyacetyl)-9,13-dimethyl-5,7-dioxapentacyclo[10.8.0.0$^{2,9}$.0$^{4,8}$.0$^{13,18}$]icosa-14,17-dien-16-one (7-2R/S)

Iron powder (78.0 mg, 1.40 mmol) and ammonium chloride (75.0 mg, 1.40 mmol) were simultaneously added to a solution of compound (5-2) (75.0 mg, 0.143 mmol) in a combined solution of ethanol (4 mL) and water (0.5 mL). The suspension was stirred at 80° C. for 1.5 hours and was filtered through Celite to remove the solid. The filtrate was concentrated in vacuo and the residue was purified by prep-HPLC (method B) to yield compound (7-2R/S) (26 mg, yield 37%) as a white solid. ESI m/z: 494 (M+H)$^+$. $^1$H NMR (MeOD$_{d4}$, 400 MHz) δ 7.44 (d, J=10.1 Hz, 1H), 6.93 (d, J=8.3 Hz, 2H), 6.48 (d, J=8.3 Hz, 2H), 6.30 (dd, J=10.1 Hz, 1.9 Hz, 1H), 6.07 (s, 1H), 4.85-4.77 (m, 2H), 4.51 (d, J=19.4 Hz, 1H), 4.35-4.29 (m, 1H), 4.24 (d, J=19.4 Hz, 1H), 2.87-2.72 (m, 2H), 2.62-2.47 (m, 1H), 2.38-2.28 (m, 1H), 2.08-1.93 (m, 1H), 1.90-1.78 (m, 2H), 1.67-1.58 (m, 1H), 1.53-1.37 (m, 5H), 0.91-0.77 (m, 5H), 0.74 (dd, J=11.2 Hz, 3.4 Hz, 1H) ppm.

Example 6

This example demonstrates a method for making compound (8-2R/S) in Table 1. This example refers to the compound numbering in FIG. 1.

Step 1: 2-[(1S,2S,4R,8S,9S,11S,12S,13R)-11-Hydroxy-9,13-dimethyl-6-[(4-nitrophenyl)methyl]-16-oxo-5,7-dioxapentacyclo[10.8.0.0$^{2,9}$.0$^{4,8}$.0$^{13,18}$]icosa-14,17-dien-8-yl]-2-oxoethyl 2-methylpropanoate (6-2)

The synthesis of compound 6-2 was described in EXAMPLE 5, above. Compound 6-2: ESI m/z: 594 (M+H)$^+$. $^1$H NMR (CDCl$_3$, 400 MHz) δ 8.15 (d, J=8.7 Hz, 0.1H) and 8.09 (d, J=8.7 Hz, 1.9H), 7.40 (d, J=8.6 Hz, 2H), 7.20 (d, J=10.1 Hz, 1H), 6.31 (dd, J=10.1 Hz, 1.8 Hz, 1H), 6.02 (s, 1H), 4.94 (t, J=3.6 Hz, 1H), 4.87 (d, J=5.1 Hz, 1H), 4.81 (d, J=17.6 Hz, 1H), 4.71 (d, J=17.6 Hz, 1H), 4.46 (s, 1H), 3.09 (d, J=3.5 Hz, 2H), 2.73-2.61 (m, 1H), 2.53-2.41 (m, 1H), 2.31-2.21 (m, 1H), 2.07-1.96 (m, 1H), 1.94-1.84 (m, 2H), 1.84-1.76 (m, 1H), 1.63-1.43 (m, 3H), 1.39 (s, 3H), 1.22 (t, J=7.0 Hz, 6H), 0.92-0.82 (m, 4H), 0.76-0.61 (m, 2H) ppm.

Step 2: 2-[(1S,2S,4R,8S,9S,11S,12S,13R)-6-[(4-Aminophenyl)methyl]-11-hydroxy-9,13-dimethyl-16-oxo-5,7-dioxapentacyclo[10.8.0.0$^{2,9}$.0$^{4,8}$.0$^{13,18}$]icosa-14,17-dien-8-yl]-2-oxoethyl 2-methylpropanoate (8-2R/S)

To a solution of compound 6-2 (65.0 mg, 0.109 mmol) in a combined solution of ethanol (5 mL) and water (1 mL)

were simultaneously added iron powder (61.0 mg, 1.09 mmol) and ammonium chloride (58.4 mg, 1.09 mmol). The suspension was stirred at 80° C. for an hour and was filtered through Celite to remove the solid. The filtrate was concentrated in vacuo and the residue was purified by prep-HPLC (method B) to yield compound (8-2R/S) (30 mg, yield 49%) as a white solid. ESI m/z: 564 (M+H)$^+$. $^1$H NMR (CDCl$_3$, 400 MHz) δ 7.25 (d, J=10.2 Hz, 1H), 6.95 (d, J=8.3 Hz, 2H), 6.44 (d, J=8.3 Hz, 2H), 6.31 (dd, J=10.1, 1.8 Hz, 1H), 6.05 (s, 1H), 4.92-4.84 (m, 2H), 4.80 (d, J=5.2 Hz, 1H), 4.73 (d, J=17.7 Hz, 1H), 4.41 (s, 1H), 3.48 (br s, 1H), 2.85 (d, J=2.7 Hz, 2H), 2.75-2.62 (m, 1H), 2.56-2.41 (m, 1H), 2.31-2.19 (m, 1H), 2.05-1.91 (m, 2H), 1.88-1.80 (m, 1H), 1.77-1.70 (m, 1H), 1.55-1.41 (m, 3H), 1.39 (s, 3H), 1.29-1.18 (m, 8H), 0.91-0.74 (m, 5H) ppm.

Example 7

This example demonstrates a method for making compound (8-3R/S) in Table 1. This example refers to the compound numbering in FIG. 1.

Step 1: 2-[(1S,2S,4R,8S,9S,11S,12S,13R)-6-(2-{[(9H-Fluoren-9-ylmethoxy)carbonyl]amino}ethyl)-11-hydroxy-9,13-dimethyl-16-oxo-5,7-dioxapentacyclo[10.8.0.0$^{2,9}$.0$^{4,8}$.0$^{13,18}$]icosa-14,17-dien-8-yl]-2-oxoethyl 2-methylpropanoate (6-3)

To a solution of compound 3 (240 mg, 0.493 mmol) in nitropropane (5 mL) was added aqueous perchloric acid (70%, 214 mg, 1.49 mmol) dropwise at 0° C., followed by the addition of Fmoc-3-amino-1-propanal (4-3, 236 mg, 0.799 mmol) according to the synthesis in *J Am. Chem. Soc.*, 2006, 128 (12), 4023-4034, the entire contents of which are herein incorporated by reference in their entirety for all purposes. The resulting mixture was stirred at RT overnight, and was then diluted with ethyl acetate (80 mL). The mixture was washed with saturated aqueous sodium bicarbonate solution (50 mL×3), then water (50 mL×2) then brine (50 mL), and then dried over sodium sulfate and concentrated in vacuo. The residue was purified by prep-TLC (silica gel, methanol/methylene chloride, v/v=1/25) to yield compound (6-3) (200 mg, yield 56%, 6R/6S epimers) as an off-white solid. ESI m/z: 724 (M+H)$^+$. $^1$H NMR (CDCl$_3$, 400 MHz) δ 7.76 (d, J=7.6 Hz, 2H), 7.56 (d, J=7.2 Hz, 2H), 7.40 (d, J=7.2 Hz, 1H), 7.32-7.20 (m, 3H), 6.28-6.25 (m, 2H), 6.00 (s, 1H), 5.28-5.04 (m, 2H), 4.87-4.76 (m, 1H), 4.46-4.35 (m, 3H), 4.18 (t, J=6.8 Hz, 1H), 3.49 (s, 1H), 3.39-3.24 (m, 2H), 2.77-2.49 (m, 2H), 2.37-2.26 (m, 1H), 2.23-1.96 (m, 3H), 1.96-1.47 (m, 6H), 1.45-1.41 (m, 3H), 1.28-1.06 (m, 10H), 1.02-0.94 (m, 3H) ppm.

Step 2: 2-[(1S,2S,4R,8S,9S,11S,12S,13R)-6-(2-Aminoethyl)-11-hydroxy-9,13-dimethyl-16-oxo-5,7-dioxapentacyclo[10.8.0.0$^{2,9}$.0$^{4,8}$.0$^{13,18}$]icosa-14,17-dien-8-yl]-2-oxoethyl 2-methylpropanoate (8-3R/S)

A solution of compound (6-3) (40.0 mg, 55.3 µmol) in diethylamine (1 mL) and methylene chloride (1 mL) was stirred at RT overnight. The volatiles were removed in vacuo and the residue was purified by prep-HPLC (method B) followed by prep-TLC (thin layer chromatography) (silica gel, methylene chloride/methanol, v/v=75/10) to yield compound (8-3R/S) (3 mg, yield 11%) as an off-white solid. ESI m/z: 502 (M+H)$^+$. $^1$H NMR (MeOD$_{d4}$, 400 MHz) δ 7.36 (d, J=10.1 Hz, 1H), 6.16 (dd, J=10.1 Hz, 1.8 Hz, 1H), 5.91 (s, 1H), 5.23 (t, J=4.4 Hz, 1H), 5.08-4.90 (m, 1H), 4.75-4.65 (m, 1H), 4.38-4.28 (m, 1H), 2.83-2.50 (m, 2H), 2.33-2.23 (m, 1H), 2.13-2.00 (m, 2H), 1.90-1.46 (m, 6H), 1.39 (s, 3H), 1.24-1.12 (m, 2H), 1.23-0.78 (m, 11H) ppm.

Example 8

This example demonstrates a method for making compound 7-4R in Table 1. This example refers to the compound numbering in FIG. 1.

(1S,2S,4R,6R,8S,9S,11S,12S,13R)-11-Hydroxy-8-(2-hydroxyacetyl)-9,13-dimethyl-6-(piperidin-4-yl)-5,7-dioxapentacyclo[10.8.0.0$^{2,9}$.0$^{4,8}$.0$^{13,18}$]icosa-14,17-dien-16-one (7-4R)

To a solution of desonide (1, 0.10 g, 0.25 mmol) in nitropropane (5 mL) was added aqueous perchloric acid (70%, 0.11 g, 0.75 mmol) dropwise at 0° C., followed by the addition of 1-Boc-4-piperidinecarboxaldehyde (4-4, 64 mg, 0.30 mmol). After being stirred at RT overnight, the suspension was concentrated in vacuo. The residue was basified by the addition of ammonia solution in methanol (7 M, 10 mL). The resulting mixture was concentrated in vacuo and the crude product was purified by prep-HPLC twice (method B) to yield compound 7-4R (15 mg, yield 13%) as a white solid. ESI m/z: 472 (M+H)$^+$. $^1$H NMR (MeOD$_{d4}$, 500 MHz) δ 7.47 (d, J=10.0 Hz, 1H), 6.27 (dd, J=10.0 Hz, 2.0 Hz, 1H), 6.03 (s, 1H), 4.90 (d, J=4.0 Hz, 1H), 4.50 (d, J=19.0 Hz, 1H), 4.46-4.43 (m, 1H), 4.41 (d, J=4.0 Hz, 1H), 4.29 (d, J=19.0 Hz, 1H), 3.13-3.09 (m, 2H), 2.71-2.60 (m, 3H), 2.42-2.38 (m, 1H), 2.27-2.13 (m, 2H), 1.99-1.96 (m, 1H), 1.85-1.64 (m, 7H), 1.52 (s, 3H), 1.51-1.38 (m, 2H), 1.14-0.99 (m, 2H), 0.96 (s, 3H) ppm. The stereochemical R-configuration for compound 7-4R was determined by 2D NMR.

Example 9

This example demonstrates a method for making compound (11-1R/S) in Table 1. The method is illustrated, generally, as shown in FIG. 2.

Step 1: 2-[(1S,2S,4R,8S,9S,11S,12S,13R)-11-Hydroxy-9,13-dimethyl-16-oxo-6-propyl-5,7-dioxapentacyclo[10.8.00$^{2,9}$.0$^{4,8}$.0$^{13,18}$]icosa-14,17-dien-8-yl]-2-oxoethyl methanesulfonate (9)

General procedure A for the synthesis of mesylates from its alcohol: To a solution of the alcohol (1.0 equiv.) in DCM (10 mL per gram of the starting material) were added triethylamine or 4-dimethylaminopyridine (2 equiv.) and methanesulfonyl chloride (1.2 equiv.). After stirred at 0° C. for half an hour or until the starting material was consumed according to TLC, the reaction mixture was added silica gel (100-200 mesh) and concentrated in vacuo. The residue with silica gel was purified by silica gel column chromatography (0-50% ethyl acetate in petroleum ether) to give the mesylate product. Alternatively, the mixture was washed with diluted aq. hydrochloride (1 N) and brine, dried over sodium sulfate and concentrated. The crude product was purified by flash chromatography (0-2% MeOH in DCM) to give the corresponding mesylate product.

Alternative method to make compound 9: to a solution of Budesonide (0.28 mg, 0.65 mmol) in pyridine (5 mL) was added 4-dimethylaminopyridine (0.16 g, 1.3 mmol) and then methanesulfonyl chloride (0.11 g, 0.97 mmol) was added dropwise at 0° C. After being stirred at RT for 2 hours, the resulting mixture was poured into ethyl acetate (100 mL).

The mixture was washed with diluted aq. hydrochloride (1N) and then brine, dried over sodium sulfate and concentrated. The crude product was purified by flash chromatography (0-1% methanol in methylene chloride) to yield compound (9) (0.26 g, yield 85%) as a white solid. ESI m/z: 509 (M+H)+. $^1$H NMR (CDCl$_3$, 400 MHz) (which epimers) δ 7.25 and 7.22 (d, J=2.0 Hz, 1H), 6.30-6.27 (m, 1H), 6.03-6.02 (m, 1H), 5.17-5.11 (m, 1.5H), 5.06-4.96 (m, 1.5H), 4.87-4.86 (m, 0.5H), 4.59 (d, J=4.5 Hz, 0.5H), 4.52-4.50 (m, 1H), 3.24 (s, 3H), 2.60-2.53 (m, 1H), 2.36-2.33 (m, 1H), 2.24-2.00 (m, 3H), 1.86-1.62 (m, 4H), 1.53-1.33 (m, 8H), 1.21-1.09 (m, 2H), 1.02-0.96 (m, 3H), 0.94-0.91 (m, 3H) ppm.

Step 2: (1S,2S,4R,8S,9S,11S,12S,13R)-8-(2-Amino-acetyl)-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (11-1R/S)

To a solution of ammonia in MeOH (7 M, 15 mL) at RT was added compound 9 (0.10 g, 0.20 mmol). The solution was sealed and stirred at 40° C. overnight. The volatiles were removed in vacuo and the crude product was purified by prep-HPLC (method B) to yield compound (11-1R/S) (8.0 mg, 9% yield) as an off-white solid. ESI m/z: 429.9 (M+H)+. $^1$H NMR (MeOD$_{d4}$, 400 MHz) δ 7.46 (d, J=10.0 Hz, 1H), 6.26 (d, J=10.0 Hz, 1H), 6.02 (s, 1H), 5.22-5.15 (m, 1.5H), 4.88 (m, 0.6H), 4.58 (m, 0.5H), 4.42 (m, 1H), 3.96-3.81 (m, 0.7H), 3.50-3.41 (m, 0.7H), 2.70-2.63 (m, 1H), 2.40-2.37 (m, 1H), 2.22-1.94 (m, 3H), 1.87-1.25 (m, 11H), 1.17-0.80 (8H) ppm. Anal. HPLC: >95%, Retention time: 7.63 min (method B).

Example 10

This example demonstrates a method for making compound 11-2R/S in Table 1. This example refers to the compound numbering in FIG. 2.

(1S,2S,4R,8S,9S,11S,12S,13R)-11-hydroxy-9,13-dimethyl-8-[2-(methylamino)acetyl]-6-propyl-5,7-dioxapentacyclo[10.8.0.0$^{2,9}$.0$^{4,8}$.0$^{13,18}$]icosa-14,17-dien-16-one (11-2R/S)

A solution of compound 9 (51 mg, 0.10 mmol) in methylamine (2 M solution in THF, 0.5 mL) in a sealed tube was stirred at 20-25° C. for 4 hours, and was then stirred at 40° C. overnight. The volatiles were removed in vacuo and the residue was purified by prep-HPLC (method A) and then prep-HPLC (method B) to yield compound (11-2R/S) (15 mg, 33% yield) as a white solid. ESI m/z: 444.3 (M+H)+. $^1$H NMR (CDCl$_3$, 400 MHz) δ 7.26-7.23 (d, J=10.8 Hz, 1H), 6.30-6.26 (m, 1H), 6.03-6.02 (m, 1H), 5.20-5.16 (m, 1H), 4.90-4.89 (d, J=4.8 Hz, 0.5H), 4.69-4.66 (t, J=4.8 Hz, 0.5H), 4.49-4.51 (m, 1H), 3.50-3.29 (m, 2H), 2.61-2.52 (m, 1H), 2.37-2.32 (m, 1H), 2.17-2.16 (d, J=3.6 Hz, 3H), 2.14-2.08 (m, 3H), 1.86-1.74 (m, 3H), 1.59-1.48 (m, 2H), 1.45 (s, 3H), 1.42-0.89 (m, 12H) ppm.

Example 11

This example demonstrates a method for making compound 11-3R/S in Table 1. This example refers to the compound numbering in FIG. 2.

(1S,2S,4R,8S,9S,11S,12S,13R)-8-[2-(Dimethylamino)acetyl]-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (11-3R/S)

To a solution of compound 9 (51 mg, 0.10 mmol) in THF (3 mL) was added dropwise a solution of dimethylamine in THF (2 M, 0.75 mL, 1.5 mmol) at RT. The reaction mixture was stirred at 50° C. overnight. The reaction mixture was concentrated, and the crude product was purified by prep-HPLC (method B) to yield compound 11-3R/S (15 mg, 33% yield) as a white solid. ESI m/z: 458.2 (M+H)+. $^1$H NMR (MeOD$_{d4}$, 400 MHz) δ 7.46 (d, J=10.4 Hz, 1H), 6.26 (d, J=10.0 Hz, 1H), 6.02 (s, 1H), 5.21 (t, J=4.8 Hz, 0.6H), 5.17 (d, J=7.2 Hz, 0.6H), 4.58 (d, J=4.4 Hz, 0.4H), 4.44-4.41 (m, 1H), 3.80-3.57 (m, 1H), 3.26 (d, J=18.8 Hz, 0.7H), 3.08-2.91 (m, 0.7H), 2.70-2.61 (m, 1H), 2.49-2.33 (m, 7H), 2.26-2.11 (m, 2H), 2.02-1.95 (m, 1H), 1.85-1.55 (m, 5H), 1.49 (s, 3H), 1.49-1.30 (m, 3H), 1.09-1.00 (m, 2H), 0.98-0.90 (m, 6H) ppm. Anal. HPLC: >95%, Retention time: 8.34 min (method B).

Example 12

This example demonstrates a method for making compound 11-5R/S in Table 1. This example refers to the compound numbering in FIG. 2.

(1S,2S,4R,8S,9S,11S,12S,13R)-8-[2-(4-Aminophenoxy)acetyl]-11-hydroxy-9,13-dimethyl-6-propyl-5,7-dioxapentacyclo[10.8.00$^{2,9}$.0$^{4,8}$.0$^{13,18}$]icosa-14,17-dien-16-one (11-5R/S)

General procedure B for making substituted phenol ether from its mesylate precursor: To hot acetonitrile or acetone (60-65° C.) were added mesylate precursor (1 equiv.), substituted phenol (2.0-2.5 equiv.), and potassium carbonate or cesium carbonate (2.0-3.0 equiv.). The resulting suspension was refluxed for 2-3 hours, and the reaction was monitored by LC-MS and/or TLC. After the reaction was cooled to RT, the volatiles were removed in vacuo and to the residue was added water. The aqueous mixture was extracted with ethyl acetate. The combined organic solution was washed with water and brine, dried over sodium sulfate and concentrated in vacuo. The crude product was used for the next step directly or purified by flash chromatography or prep-HPLC.

Step 1: A mixture of compound 9 (0.13 g, 0.26 mmol), 4-nitrophenol (10-5, 72 mg, 0.52 mmol) and potassium carbonate (72 mg, 0.52 mmol) in acetone (10 mL) was refluxed (60° C.) overnight. After filtration to remove the solids, the filtrate was concentrated in vacuo. The crude product was purified by flash chromatography (0-1% methanol in methylene chloride) to yield a nitro-intermediate (0.11 g, yield 77%) as brown oil. ESI m/z: 552 (M+H)+. $^1$H NMR (CDCl$_3$, 500 MHz) (with epimers) δ 8.23-8.15 (m, 2.4H), 7.26-7.23 (m, 1H), 6.97-6.91 (m, 2.4H), 6.31-6.28 (m, 1H), 6.05-6.04 (m, 1H), 5.22-5.18 (m, 1.4H), 5.10-5.07 (m, 0.6H), 4.93 (d, J=5.0 Hz, 0.6H), 4.83-4.77 (m, 1H), 4.67 (d, J=5.0 Hz, 0.6H), 4.56-4.53 (m, 1H), 2.62-2.55 (m, 1H), 2.38-2.5 (m, 1H), 2.24-2.07 (m, 3H), 1.88-1.56 (m, 5H), 1.46-1.40 (m, 6H), 1.20-1.13 (m, 2H), 1.05-0.99 (m, 3H), 0.97-0.94 (m, 3H) ppm.

Step 2: Iron powder (0.10 g, 1.9 mmol) and ammonium chloride (0.10 g, 1.9 mmol) were simultaneously added to a solution of the nitro-intermediate (0.10 g, 0.19 mmol) in a combined solution of ethanol (20 mL) and water (2 mL). The suspension was stirred at 80° C. for 2 hours and was filtered through Celite to remove inorganic salts. The filtrate was concentrated in vacuo and the residue was purified by prep-HPLC (method B) to yield compound (11-5R/S) (50 mg, yield 50%) as a white solid. ESI m/z: 522 (M+H)$^+$. $^1$H NMR (MeOD$_{d4}$, 500 MHz) (with epimers) δ 7.47 (d, J=10.0 Hz, 1H), 6.78-6.70 (m, 4H), 6.29-6.26 (m, 1H), 6.04 (br s, 1H), 5.25 (t, J=5.0 Hz, 0.4H), 5.20 (d, J=7.0 Hz, 0.4H), 5.06 (d, J=18.0 Hz, 0.4H), 4.98 (d, J=18.0 Hz, 0.6H), 4.90-4.87 (m, 0.6H), 4.75-4.66 (m, 1.6H), 4.46-4.44 (m, 1H), 2.71-2.64 (m, 1H), 2.42-2.38 (m, 1H), 2.28-2.18 (m, 2H), 2.06-2.00 (m, 1H), 1.87-1.83 (m, 1H), 1.76-1.73 (m, 1H), 1.69-1.61 (m, 3H), 1.55-1.38 (m, 3H), 1.51 (s, 3H), 1.20-1.02 (m, 3H), 0.98-0.92 (m, 5H) ppm.

A mixture of two epimers of compound 11-5R and compound 11-5S from Table 1 (0.30 g, 0.58 mmol) were isolated by chiral HPLC (Instrument: Gilson-281, Column: OZ-H 20*250 mm, 10 um (Dacel), using mobile phase: hexane (0.1% DEA)/Ethanol (0.1% DEA)=70/30 at flow rate of 60 mL/min, detected at 214 nm. The resultant solution was concentrated to afford compound 11-5S (30 mg, 10% yield) and compound 11-5R (50 mg, 17% yield) as white solids, separately. The structures of compound 11-5S and compound 11-5R were determined by 2D-NOESY.

(1S,2S,4R,8S,9S,11S,12S,13R)-8-[2-(4-Aminophenoxy) acetyl]-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (11-5S): First peak on HPLC; ESI m/z: 522 (M+H)$^+$. Retention time in HPLC (method A): 7.54 min; chiral SFC (CC4): Retention time 4.71 min, 99.5 d.e. %; $^1$H NMR (400 MHz, CDCl$_3$) δ 7.21 (d, J=10.1 Hz, 1H), 6.77 (d, J=8.8 Hz, 2H), 6.63 (d, J=8.8 Hz, 2H), 6.24 (dd, J=10.1, 1.6 Hz, 1H), 6.02 (s, 1H), 5.20 (d, J=6.8 Hz, 1H), 5.18 (t, J=4.8 Hz, 1H), 4.99 (d, J=17.9 Hz, 1H), 4.61 (d, J=17.9 Hz, 1H), 4.43 (s, 1H), 3.46 (s, 2H), 2.57 (td, J=13.2, 4.4 Hz, 1H), 2.34 (dd, J=13.4, 3.2 Hz, 1H), 2.16-2.01 (m, 4H), 1.85-1.68 (m, 3H), 1.59-1.49 (m, 3H), 1.44 (s, 3H), 1.44-1.26 (m, 2H), 1.18-1.09 (2H), 1.00 (s, 3H), 0.91 (t, J=7.3 Hz, 3H) ppm. $^{13}$C NMR (100 MHz, CDCl$_3$) δ 204.0, 186.7, 170.0, 156.3, 151.4, 141.0, 127.9, 122.6, 116.5, 116.4, 108.4, 98.6, 83.2, 72.6, 69.8, 55.3, 53.0, 47.2, 44.2, 41.5, 37.3, 34.1, 33.0, 32.0, 31.1, 21.2, 17.9, 17.7, 14.1 ppm.

(1S,2S,4R,8S,9S,11S,12S,13R)-8-[2-(4-Aminophenoxy) acetyl]-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (11-5R): Second peak on HPLC; ESI m/z: 522 (M+H)$^+$; Retention time in HPLC (method A): 7.58 min; chiral SFC (CC4): Retention time 3.80 min, 98.1 d.e. %; $^1$H NMR (400 MHz, CDCl$_3$) δ 7.23 (d, J=10.1 Hz, 1H), 6.79 (dd, J=8.8 Hz, 2H), 6.65 (d, J=8.8 Hz, 2H), 6.27 (dd, J=10.1, 1.7 Hz, 1H), 6.04 (s, 1H), 4.94 (d, J=4.4 Hz, 1H), 4.89 (d, J=18.0 Hz, 1H), 4.65 (d, J=18.0 Hz, 1H), 4.61 (t, J=4.4 Hz, 1H), 4.48 (d, J=2.1 Hz, 1H), 3.51 (s, 2H), 2.58 (td, J=13.3, 4.9 Hz, 1H), 2.35 (dd, J=13.4, 2.8 Hz, 1H), 2.23-1.99 (m, 4H), 1.79-1.61 (m, 6H), 1.46-1.38 (m, 2H), 1.44 (s, 3H), 1.23-1.09 (m, 2H), 0.95 (s, 3H), 0.93 (t, J=7.3 Hz, 3H) ppm. $^{13}$C NMR (101 MHz, CDCl$_3$) δ 204.9, 186.6, 170.0, 156.2, 151.2, 141.0, 127.9, 122.5, 116.3, 116.3, 104.5, 97.6, 81.9, 72.6, 69.9, 55.1, 49.8, 45.7, 44.0, 41.1, 35.0, 34.0, 33.3, 31.9, 30.3, 21.1, 17.5, 17.1, 14.0 ppm.

Example 13

This example demonstrates a method for making compounds 11-5S and (11-5R) in Table 1. This example refers to the compound numbering in FIG. 2.

Figure 7:
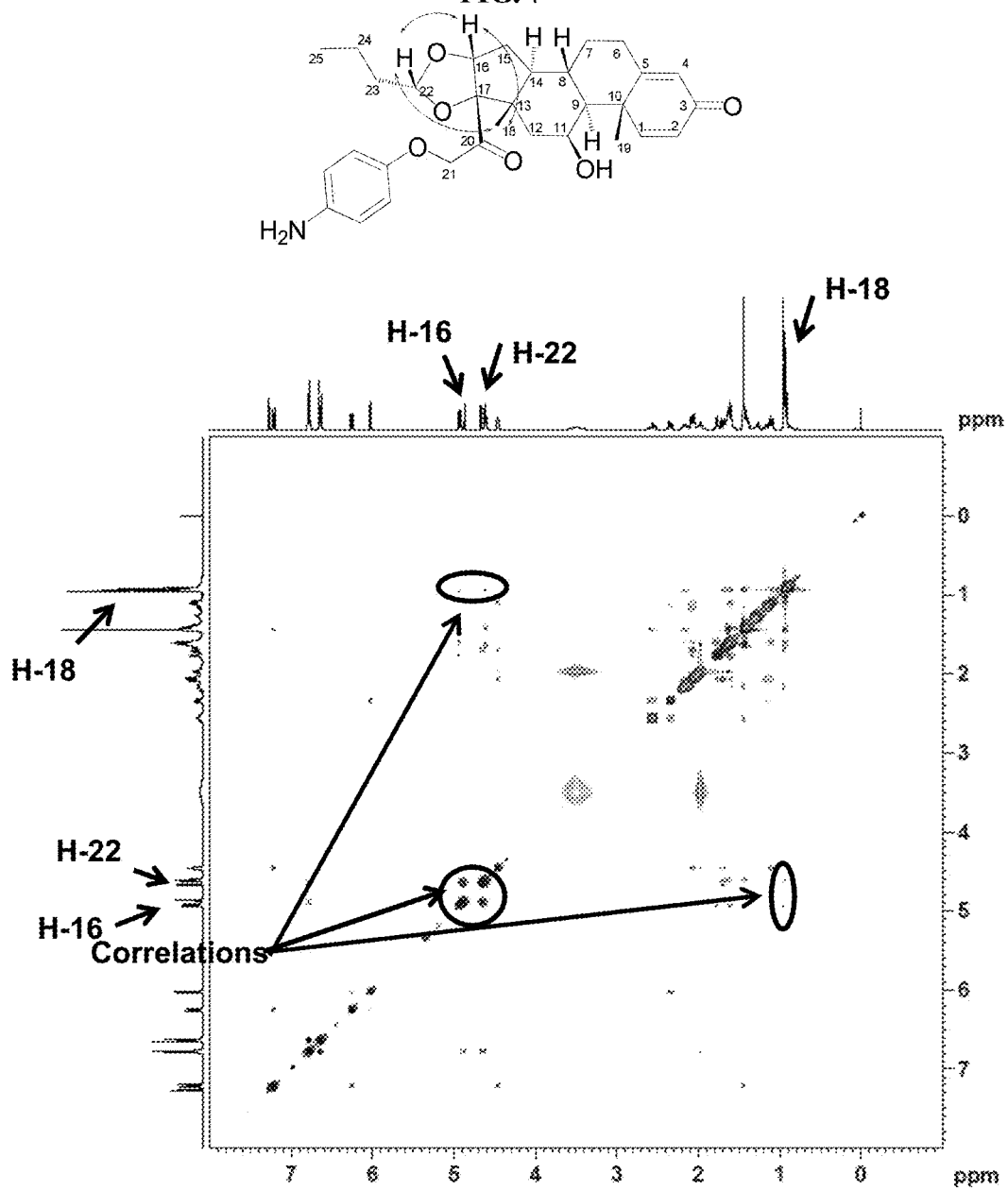
FIG. 7 shows a 2D-NOESY spectrum for 11-5R in Table 1.
Figure 8:
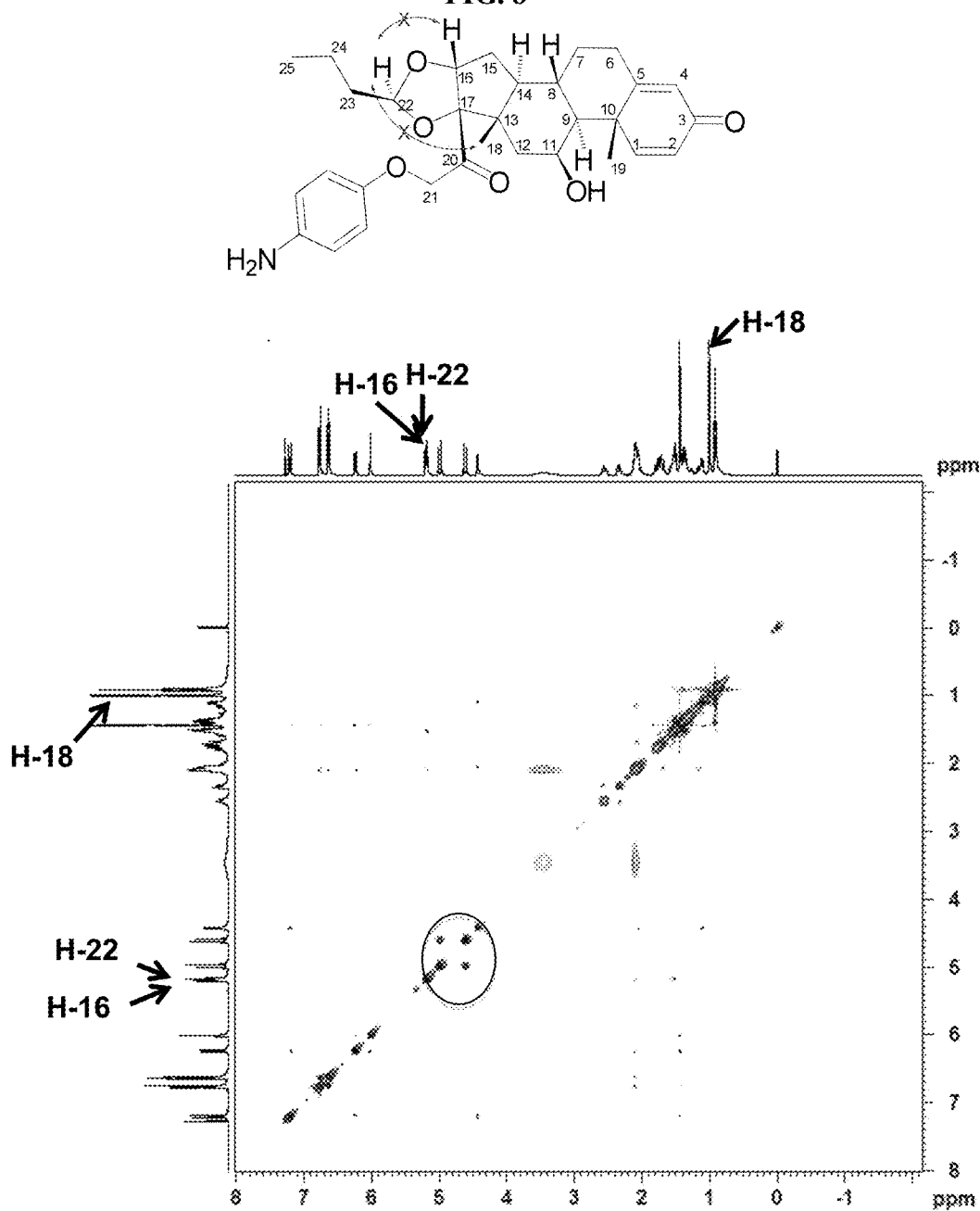
FIG. 8 shows a 2D-NOESY spectrum for compound 11-5S in Table 1.

Compound 9R was prepared from (R)-budesonide and compound 9S was prepared from (S)-Budesonide, respectively, according to the General procedure A in Example 9. Using the same method described in EXAMPLE 12, compound (11-5S) was obtained from the reaction of compound (9S) with compound (10-12), and compound (11-5R) was obtained from the reaction of compound (9R) with compound (10-9), respectively. A representative procedure is following. To a solution of compound (9R) or compound (9S) (100 mg) in acetone (10 mL) was simultaneously added compound 10-9 (2 eq.) and Cs$_2$CO$_3$ (2 eq.). The mixture was refluxed for 2 hours, and the crude was worked up by removing the acetone in vacuo, extracting the crude with ethyl acetate, washing the inorganic salts with water, and purifying the resulting product by chromatography (0-50% ethyl acetate in petroleum ether) to provide compound 11-5R or compound 11-5S (25-60% yield) as a pale yellow solid. ESI m/z: 522 (M+H)$^+$. Anal. HPLC: 98%. The 2D-NOESY spectra of compound 11-5R and compound 11-5S were shown in FIGS. 7 and 8.

Example 14

This example demonstrates a method for making compound 11-6S and 11-6R from Table 1. This example refers to the compound numbering in FIG. 2.

(1S,2S,4R,6S,8S,9S,11S,12S,13R)-8-[2-(4-Amino-3-fluorophenoxy)acetyl]-11-hydroxyl-9,13-dimethyl-6-propyl-5,7-dioxapentacyclo[10.8.0.0$^{2,9}$.0$^{4,8}$.0$^{13,18}$] icosa-14,17-dien-16-one (11-6S) and (1S,2S,4R,6R,8S,9S,11S,12S,13R)-8-[2-(4-Amino-3-fluorophenoxy)acetyl]-11-hydroxyl-9,13-dimethyl-6-propyl-5,7-dioxapentacyclo[10.8.0.0$^{2,9}$.0$^{4,8}$.0$^{13,18}$] icosa-14,17-dien-16-one (11-6R)

A racemic mixture of compounds 11-6R/S were prepared according to the method set forth in Example 12. The racemic products were separated by chiral SFC (see details in Section 2.3) to yield compound 11-6S (second peak) and compound 11-6R (first peak) as off-white solids.

Compound 11-6S (30 mg, 7.9% yield). ESI m/z: 540.2 (M+H)$^+$. $^1$H NMR (500 MHz, DMSO$_{d6}$) δ 7.32 (d, J=10.1 Hz, 1H), 6.71-6.62 (m, 2H), 6.49 (dd, J=8.5, 2.0 Hz, 1H), 6.19-6.16 (m, 1H), 5.93 (s, 1H), 5.21 (t, J=4.8 Hz, 1H), 5.10 (d, J=7.3 Hz, 1H), 5.02 (d, J=18.1 Hz, 1H), 4.69 (dd, J=58.9, 28.6 Hz, 4H), 4.31 (s, 1H), 2.56-2.51 (m, 1H), 2.29 (d, J=10.6 Hz, 1H), 2.06-1.97 (m, 3H), 1.89 (s, 2H), 1.79-1.72 (m, 1H), 1.30 (m, 10H), 0.88-0.85 (m, 6H) ppm. Retention time: 2.94 min, 98% in chiral SFC (AD). Anal. HPLC: >96.94%, Retention time: 7.94 min (method B).

Compound 11-6R (28 mg, 7.4% yield). ESI m/z: 540.3 (M+H)$^+$. $^1$H NMR (500 MHz, DMSO$_{d6}$) δ 7.32 (d, J=10.1 Hz, 1H), 6.72-6.68 (m, 2H), 6.52 (dd, J=8.6, 2.1 Hz, 1H), 6.18 (d, J=10.1 Hz, 1H), 5.93 (s, 1H), 5.01 (d, J=18.3 Hz, 1H), 4.77 (dd, J=12.9, 3.3 Hz, 2H), 4.71 (s, 2H), 4.65 (t, J=4.3 Hz, 1H), 4.32 (s, 1H), 3.17 (d, J=5.2 Hz, 1H), 2.57-2.51 (m, 1H), 2.30 (d, J=10.5 Hz, 1H), 2.10 (d, J=7.2 Hz, 1H), 2.01-1.99 (m, 1H), 1.84 (s, 2H), 1.62-1.52 (m, 5H), 1.39-1.33 (m, 5H), 1.23 (s, 1H), 1.02-0.95 (m, 2H), 0.87 (t, J=7.4 Hz, 3H), 0.83 (s, 3H) ppm. Retention time: 2.25 min, 100% in chiral SFC (AD). Anal. HPLC: >98.50%, Retention time: 8.01 min (method B).

Example 15

This example demonstrates a method for making compound 11-7R in Table 1. This example refers to the compound numbering in FIG. 2.

(1S,2S,4R,8S,9S,11S,12S,13R)-8-[2-(4-Amino-3-fluorophenoxy)acetyl]-11-hydroxyl-9,13-dimethyl-6-propyl-5,7-dioxapentacyclo[10.8.0.0$^{2,9}$.0$^{4,8}$.0$^{13,18}$] icosa-14,17-dien-16-one (11-7S and 11-7R)

A racemic mixture of steroids 11-7-22R/S were prepared according to the method set forth in Example 12. The racemic products were separated by chiral SFC (see details in Section 2.3) to yield compound 11-7S (second peak) and compound 11-7R (first peak).

Compound 11-7R: ESI m/z: 540.2 (M+H)$^+$. $^1$H NMR (500 MHz, CDCl$_3$) δ 7.25 (d, J=10.1 Hz, 1H), 6.87 (dt, J=15.5, 7.7 Hz, 1H), 6.47 (dd, J=12.8, 2.4 Hz, 1H), 6.37 (d, J=8.7 Hz, 1H), 6.29 (dd, J=9.9, 4.4 Hz, 1H), 6.04 (s, 1H), 5.22-4.49 (m, 5H), 3.61 (s, 2H), 2.58 (td, J=13.5, 4.9 Hz, 1H), 2.36 (d, J=10.3 Hz, 1H), 2.19-2.03 (m, 3H), 1.87-1.72 (m, 2H), 1.67-1.55 (m, 3H), 1.51-1.33 (m, 7H), 1.21-1.11 (m, 2H), 1.00-0.90 (m, 6H). Anal. HPLC: >62.24%, 36.49%, Retention time: 7.78, 7.86 min (method B).

Example 16

This example demonstrates a method for making compound 11-8R in Table 1. This example refers to the compound numbering in FIG. 2.

(1S,2S,4R,6R,8S,9S,11S,12S,13R)-11-Hydroxyl-9,13-dimethyl-8-{2-[4-(methylamino)phenoxy]acetyl}-6-propyl-5,7-dioxapentacyclo[10.8.0.0$^{2,9}$.0$^{4,8}$.0$^{13,18}$]icosa-14,17-dien-16-one (11-8R)

Steroid 11-8 was prepared according to the method set forth in Example 13.

Compound (11-8R) was obtained as a white solid (14 mg, 54% yield). ESI m/z: 525.3 (M+H)$^+$. $^1$H NMR (500 MHz, MeOD$_{d4}$) δ 7.47 (d, J=10.1 Hz, 1H), 6.83-6.80 (m, 2H), 6.65-6.62 (m, 2H), 6.28 (dd, J=10.1, 1.9 Hz, 1H), 6.04 (s, 1H), 4.99 (d, J=18.2 Hz, 1H), 4.90 (d, J=4.8 Hz, 1H), 4.74 (d, J=18.1 Hz, 1H), 4.66 (t, J=4.5 Hz, 1H), 4.46 (d, J=3.0 Hz, 1H), 2.75 (s, 3H), 2.67 (td, J=13.6, 5.2 Hz, 1H), 2.40 (dd, J=13.5, 2.7 Hz, 1H), 2.30-2.22 (m, 1H), 2.16-2.12 (m, 1H), 2.02 (dd, J=13.7, 3.3 Hz, 1H), 1.85 (dd, J=13.7, 2.6 Hz, 1H), 1.76 (d, J=6.9 Hz, 1H), 1.67-1.63 (m, 4H), 1.51 (s, 3H), 1.48-1.44 (m, 2H), 1.17-1.08 (m, 1H), 1.05 (dd, J=11.2, 3.5 Hz, 1H), 0.98-0.94 (m, 6H) ppm. Anal. HPLC: 100%, Retention time: 7.56 min (method A).

Example 17

This Example demonstrates a method for making compound (11-10R/S), in Table 1. This example refers to the compound numbering in FIG. 2.

(1S,2S,4R,6R,8S,9S,11S,12S,13R)-8-[2-(4-Fluorophenoxy)acetyl]-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (11-10R/S)

Steroids 11-10R/S were prepared according to the method set forth in Example 13.

Compound 11-10R/S was obtained as a white solid (14 mg, 54% yield). ESI m/z: 525.2 (M+H)$^+$. $^1$H NMR (400 MHz, MeOD$_{d4}$) δ 7.47 (d, J=10.1 Hz, 1H), 7.02 (t, J=8.7 Hz, 2H), 6.94-6.90 (m, 2H), 6.27 (dd, J=10.1, 1.8 Hz, 1H), 6.03 (s, 1H), 5.06 (d, J=18.1 Hz, 1H), 4.90-4.88 (m, 1H), 4.82 (d, J=18.1 Hz, 1H), 4.69 (t, J=4.4 Hz, 1H), 4.46 (d, J=2.8 Hz, 1H), 2.71-2.63 (m, 1H), 2.42-2.38 (m, 1H), 2.30-2.11 (m, 2H), 2.05-2.01 (m, 1H), 1.89-1.84 (m, 1H), 1.77-1.63 (m, 5H), 1.51-1.41 (m, 5H), 1.18-1.02 (m, 2H), 0.97-0.93 (m, 6H) ppm. Anal. HPLC: 100%, Retention time: 9.94 min (method A).

Example 18

This Example demonstrates a method for making compound 11-11R/S in Table 1. This example refers to the compound numbering in FIG. 2.

N-(4-{2-[(1S,2S,4R,6R,8S,9S,11S,12S,13R)-11-Hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)acetamide (11-11R/S)

Steroids 11-11R/S were prepared according to the method set forth in Example 13.

Compounds 11-11R/S were obtained as a white solid (25 mg, 46% yield). ESI m/z: 564.3 (M+H)$^+$. $^1$H NMR (500 MHz, MeOD$_{d4}$) δ 7.49-7.45 (m, 3H), 6.89 (d, J=9.0 Hz, 2H), 6.28 (d, J=10.2 Hz, 1H), 6.04 (s, 1H), 5.09 (d, J=18.1 Hz, 1H), 4.91-4.89 (m, 1H), 4.83 (d, J=18.1 Hz, 1H), 4.70 (t, J=4.3 Hz, 1H), 4.47 (d, J=3 Hz, 1H), 2.72-2.65 (m, 1H), 2.43-2.39 (m, 1H), 2.30-2.22 (m, 1H), 2.18-2.12 (n, 4H), 2.06-2.03 (m, 1H), 1.90-1.86 (m, 1H), 1.77-1.65 (m, 5H), 1.48 (m, 5H), 1.18-1.09 (m, 1H), 1.07-1.04 (m, 1H), 0.99-0.95 (m, 6H) ppm. Anal. HPLC: 100%, Retention time: 7.33 min (method B).

Example 19

This Example demonstrates a method for making compounds 11-12R/S in Table 1. This example refers to the compound numbering in FIG. 2.

(1S,2S,4R,8S,9S,11S,12R,13S,19S)-8-[2-(4-Aminophenoxy)acetyl]-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (11-12R/S)

Step 1: Compound (9B) was prepared according to the General procedure A in Example 9. To a solution of (6S, 9R)2F-budesonide (80 mg, 0.17 mmol) in DCM (1 mL) were added dropwise triethylamine (34 mg, 0.34 mmol) and methanesulfonyl chloride (30 mg, 0.26 mmol) at 0° C. The mixture was stirred at this temperature for half an hour until (6S,9R)2F-Budesonide was consumed, which was monitored by TLC. The reaction mixture was then diluted with DCM (100 mL) and quenched with sat. aq. ammonium chloride (30 mL). The organic solution was washed with sat. aq. ammonium chloride and brine, dried over sodium sulfate and concentrated in vacuo. The crude product was purified by flash chromatography (0-2% MeOH in DCM) to give the corresponding mesylate product (9B).

Step 2: Compound 9B was dissolved in acetone (0.5 mL). To the solution were added 4-aminophenol (10-9, 37 mg, 0.34 mmol) and cesium carbonate (0.11 g, 0.34 mmol). The reaction mixture was refluxed for 1.5 hours or until (9B) was totally consumed according to TLC and LC-MS. The mixture was then diluted with ethyl acetate and filtered. The filtrate was concentrated in vacuo and the residue was purified by prep-HPLC (method B) to give compounds 11-12R/S (6.0 mg, 6.3% yield from (6S,9R)2F-Budesonide) as a white solid. ESI m/z: 558 (M+H)$^+$. $^1$H NMR (500 MHz, MeOD$_{d4}$) δ 7.34 (d, J=10.0 Hz, 1H), 6.78-6.71 (m, 4H), 6.37-6.33 (m, 2H), 5.63-5.49 (m, 1H), 5.10-4.99 (m, 1H), 4.77-4.63 (m, 2H), 4.33 (d, J=9.1 Hz, 1H), 2.74-2.57 (m, 1H), 2.39-2.13 (m, 3H), 1.98-1.31 (m, 12H), 1.03-0.93 (m, 6H) ppm. Anal. HPLC: purity 97.4%, Retention time: 7.55 min (method B).

(1S,2S,4R,6R,8S,9S,11S,12R,13S,19S)-8-[2-(4-Aminophenoxy)acetyl]-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (11-12R)

Compound 9BR was prepared according to the General procedure A in Example 9. A reaction of compound 9BR (0.90 g, 1.7 mmol) with 4-aminophenol (0.20 g, 1.8 mmol) and cesium carbonate (1.1 g, 3.4 mmol) in acetonitrile (20 mL) provided (11-12R) (0.20 g, 54% yield) as yellow oil after purification by silica gel column chromatography (50-80% ethyl acetate in petroleum ether). ESI m/z: 558 (M/+H)$^+$. $^1$H NMR (500 MHz, DMSO$_{d6}$) δ 7.26 (d, J=10.5 Hz, 1H), 6.64 (d, J=5.0 Hz, 2H), 6.50 (d, J=5.0 Hz, 2H), 6.30 (dd, J=10 Hz, 2 Hz, 1H), 6.11 (s, 1H), 5.72-5.65 (m, 0.5H), 5.62-5.55 (m, 0.5H), 5.52-5.48 (m, 1H), 5.0 (s, 0.5H), 4.95 (s, 0.5H), 4.80-4.78 (m, 1H), 4.75-4.65 (m, 1H), 4.24-4.16 (m, 1H), 2.70-2.52 (m, 1H), 2.30-2.21 (m, 1H), 2.11-2.00 (m, 2H), 1.77 (d, J=13.0 Hz, 1H), 1.61-1.54 (m, 4H), 1.49 (s, 3H), 1.36 (q, J=7.5 Hz, 3H), 1.23 (s, 1H), 0.87 (d, J=7.5 Hz, 3H), 0.83 (s, 3H) ppm. Anal. HPLC: 100%, Retention time: 8.44 min (method B).

Example 20

This Example demonstrates a method for making compound 11-13R in Table 1. This example refers to the compound numbering in FIG. 2.

(1S,2S,4R,6R,8S,9S,11S,12R,13S,19S)-8-[2-(3-Aminophenoxy)acetyl]-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (11-13R)

Steroid 11-13R was prepared according to the method set forth in Example 19.

Compound (11-13R) was obtained as a light orange solid (9.0 mg, 44% yield) after purification by prep-HPLC (method A). ESI m/z: 558 (M+H)$^+$. $^1$H NMR (500 MHz, MeOD$_{d4}$) δ 7.35 (dd, J=10.1, 1.3 Hz, 1H), 7.29 (t, J=8.1 Hz, 1H), 6.76-6.70 (m, 3H), 6.40-6.29 (m, 2H), 5.66-5.48 (m, 1H), 5.14 (d, J=18.1 Hz, 1H), 4.93-4.91 (m, 1H), 4.90-4.87 (m, 1H), 4.77 (t, J=4.3 Hz, 1H), 4.35 (d, J=9.3 Hz, 1H), 2.76-2.62 (m, 1H), 2.41-2.18 (m, 3H), 1.83-1.56 (m, 9H), 1.50 (dt, J=15.4, 7.6 Hz, 2H), 0.99-0.96 (m, 6H) ppm. Anal. HPLC: 100%, Retention time: 7.77 min (method A).

Example 21

This Example demonstrates a method for making compounds 11-14R/S in Table 1. This example refers to the compound numbering in FIG. 2.

(1S,2S,4R,8S,9S,11S,12R,13S,19S)-8-[2-(4-Amino-3-fluorophenoxy)acetyl]-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (11-14R/S)

To a solution of (9B) (0.20 g, 0.37 mmol) in DMSO (3 mL) were added 4-amino-3-fluorophenol (10-14, 0.25 g, 2.0 mmol) and potassium hydroxide (0.11 g, 2.0 mmol) at RT. The resulting mixture was stirred at 60° C. for an hour under nitrogen protection until the reaction was completed, which was monitored by TLC and LC-MS. After cooled to RT and filtered through membrane, the reaction solution was directly purified by prep-HPLC (method A) to give compound 11-14R/S (40 mg, 19% yield) as an off-white solid. ESI m/z: 576 (M+H)$^+$. $^1$H NMR (500 MHz, MeOD$_{d4}$) δ 7.40-7.31 (m, 1H), 7.20 (td, J=9.1, 1.9 Hz, 1H), 6.91-6.84 (m, 1H), 6.80-6.76 (m, 1H), 6.40-6.30 (m, 2H), 5.57 (ddd, J=48.6, 9.7, 6.8 Hz, 1H), 5.15 (d, J=18.1 Hz, 1H), 4.90-4.79 (m, 2H), 4.75 (t, J=4.3 Hz, 1H), 4.41-4.28 (m, 1H), 2.78-2.57 (m, 1H), 2.40-2.12 (m, 3H), 1.98-1.39 (m, 11H), 1.07-0.92 (m, 6H) ppm. Anal. HPLC: 100%, Retention time: 8.10 min (method A).

Example 22

This Example demonstrates a method for making compounds 11-15R/S in Table 1. This example refers to the compound numbering in FIG. 2.

tert-Butyl N-[(4-{2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)methyl]carbamate (N-Boc-11-15R/S)

Step 1: To a solution of 4-(aminomethyl)phenol (1.2 g, 10 mmol) in methanol (70 mL) and water (5 mL) was added Boc$_2$O (2.4 g, 11 mmol) dropwise by syringe at RT. The resulting mixture was stirred at RT for an hour until 4-(aminomethyl)phenol was totally consumed, which was monitored by LC-MS and TLC. The volatiles were removed in vacuo and the residue was dissolved in ethyl acetate (150 mL). The solution was washed with sat. aq. citric acid (50 mL×2) and brine, dried over sodium sulfate and concentrated in vacuo to give N-Boc-4-aminomethylphenol (2.1 g, 94% yield) as brown oil. ESI m/z: 246 (M+Na)$^+$. $^1$H NMR (500 MHz, CDCl$_3$) δ 7.12 (d, J=7.8 Hz, 2H), 6.82-6.71 (m, 2H), 4.84 (s, 1H), 4.23 (d, J=5.3 Hz, 2H), 1.46 (s, 9H) ppm.

Step 2: Compound (N-Boc-11-15R/S) was prepared according to the method set forth in Example 19.

(1S,2S,4R,8S,9S,11S,12R,13S,19S)-8-{2-[4-(Aminomethyl)phenoxy]acetyl}-12,19-difluoro-11-hydroxy-9,13-dimethyl-6-propyl-5,7-dioxapentacyclo[10.8.0.0$^{2,9}$.0$^{4,8}$.0$^{13,8}$]icosa-14,17-dien-16-one (11-15R/S)

To a solution of (N-Boc-11-15R/S) (30 mg, 45 μmol) in DCM (2 mL) was added dropwise TFA (0.4 mL) by syringe at 0° C. The resulting mixture was stirred at RT for an hour until Boc was totally removed, which was monitored by LC-MS. The volatiles were removed in vacuo and the residue was purified by prep-HPLC (method A) to give compound (11-15R/S) (15 mg, 49% yield) as a white solid. ESI m/z: 572 (M+H)$^+$. $^1$H NMR (500 MHz, MeOD$_{d4}$) δ 7.45-7.32 (m, 3H), 7.01-6.96 (m, 2H), 6.41-6.30 (m, 2H), 5.57 (ddd, J=18.2, 10.4, 7.3 Hz, 1H), 5.21 (dd, J=19.7 Hz, 1H), 4.93-4.91 (m, 1H), 4.85 (d, J=18.0 Hz, 1H), 4.77 (t, J=4.3 Hz, 1H), 4.37-4.32 (m, 1H), 4.07 (s, 2H), 2.75-2.58 (m, 1H), 2.40-2.15 (m, 3H), 1.86-1.40 (m, 11H), 1.08-0.92 (m, 6H) ppm. Anal. HPLC: 100%, Retention time: 7.47 min (method A).

Example 23

This Example demonstrates a method for making compounds 11-16R/S in Table 1. This example refers to the compound numbering in FIG. 2.

(1S,2S,4R,6R,8S,9S,11S,12S,13R)-11-Hydroxy-8-[2-(4-hydroxyphenoxy)acetyl]-9,13-dimethyl-6-propyl-5,7-dioxapentacyclo[10.8.0.0$^{2,9}$.0$^{4,8}$.0$^{13,18}$]icosa-14,17-dien-16-one (11-16R/S)

Compounds 11-16R/S were prepared according to the method set forth in Example 12.

Compounds 11-16R/S (20 mg, 38% yield) were obtained as a tan solid after purification by prep-HPLC (method A). ESI m/z: 523.2 (M+H)$^+$. $^1$H NMR (500 MHz, MeOD$_{d4}$) δ 7.47 (d, J=10.1 Hz, 1H), 6.82-6.77 (m, 2H), 6.75-6.70 (m, 2H), 6.28 (dd, J=10.1, 1.8 Hz, 1H), 6.04 (s, 1H), 5.00 (d, J=18.1 Hz, 1H), 4.91-4.89 (m, 1H), 4.75 (d, J=18.1 Hz, 1H), 4.67 (t, J=4.5 Hz, 1H), 4.46 (d, J=3.1 Hz, 1H), 2.68 (td, J=13.6, 5.8 Hz, 1H), 2.40 (dd, J=13.5, 2.8 Hz, 1H), 2.31-2.21 (m, 1H), 2.17-2.13 (m, 1H), 2.02 (dd, J=13.7, 3.3 Hz, 1H), 1.86 (dd, J=13.7, 2.6 Hz, 1H), 1.80-1.58 (m, 5H), 1.53-1.40 (m, 5H), 1.18-0.93 (m, 8H) ppm. Anal. HPLC: 100%, Retention time: 8.92 min (method A).

Example 24

This Example demonstrates a method for making compounds 11-17R/S in Table 1. This example refers to the compound numbering in FIG. 2.

(1S,2S,4R,8S,9S,11S,12R,13S,19S)-8-{2-[(6-Aminopyridin-2-yl)oxy]acetyl}-12,19-difluoro-11-hydroxy-9,13-dimethyl-6-propyl-5,7-dioxapentacyclo[10.8.0.0$^{2,9}$0.$^{4,8}$.0$^{13,18}$]icosa-14,17-dien-16-one (11-17R/S)

Compounds 11-17R/S were prepared according to the method set forth in Example 19.

Compounds 11-17R/S (50 mg, 24% yield) were obtained as a white solid after purification by flash chromatography (10-50% ethyl acetate in petroleum ether). ESI: 559 (M+H)$^+$. $^1$H NMR (500 MHz, DMSO$_{d6}$) δ 7.35-7.31 (m, 2H), 6.31 (d, J=11.5 Hz, 1H), 6.13 (s, 1H), 6.03 (d, J=8.0 Hz, 1H), 5.98 (d, J=7.5 Hz, 1H), 5.84-5.82 (m, 1H), 5.68-5.56 (m, 3H), 5.25-4.72 (m, 4H), 4.29 (br s, 1H), 2.66-2.57 (m, 1H), 2.28-2.05 (m, 4H), 1.63-1.58 (m, 4H), 1.50-1.30 (m, 6H), 0.95-0.87 (m, 6H) ppm. Anal. HPLC: 100%, Retention time: 8.65 min (method A).

Example 25

This Example demonstrates a method for making compound 11-19 in Table 1. This example refers to the compound numbering in FIG. 2.

(1S,2S,4R,8S,9S,11S,12R,13S,19S)-8-(2-Azido-acetyl)-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (11-19)

Step 1: A suspension of compound 9B (1.0 g, 1.8 mmol), sodium azide (1.2 g, 18 mmol) in acetone (15 mL) was stirred at 50° C. overnight, when the reaction was completed according to LC-MS. After cooled, the reaction mixture was poured into cold water (80 mL). The aqueous mixture was extracted with ethyl acetate (50 mL×3). The combined organic solution was washed by brine (30 mL), dried over sodium sulfate and concentrated in vacuo to afford crude compound azido precursor of (11-19R/S) (0.90 g, >99% yield) as a yellow solid, which was used for the next step without further purification. ESI m/z: 492 (M+H)$^+$.

(1S,2S,4R,6R,8S,9S,11S,12R,13S,19S)-8-(2-Amino-acetyl)-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one; trifluoroacetic acid salt (11-19R/S)

Step 2: To a solution of the precursor of compounds 11-19R/S (0.85 g, 1.7 mmol) in THF (20 mL) was added aq. hydrochloride (1 N, 10 mL). The mixture was stirred at 28-32° C. until it turned clear, to which was then added triphenylphosphine (0.68 g, 2.6 mmol) at this temperature. The resulting yellow clear solution was stirred at 28-32° C. for 18 hours, when the reaction was completed according to TLC and LC-MS. The mixture was concentrated under vacuum and the residue was purified by reversed phase flash chromatography (0-50% acetonitrile in aq. TFA (0.05%)) to give compounds 11-19R/S (0.56 g, 57% yield, TFA salt) as an off-white solid. ESI m/z: 466 (M+H)$^+$. $^1$H NMR (400 MHz, MeOD$_{d4}$) δ 7.33 (d, J=9.9 Hz, 1H), 6.40-6.29 (m, 2H), 5.69-5.45 (m, 1H), 4.93-4.92 (m, 1H), 4.71 (t, J=4.3 Hz, 1H), 4.35-4.27 (m, 2H), 3.90-3.84 (m, 1H), 2.81-2.54 (m, 1H), 2.42-2.06 (m, 3H), 1.82-1.32 (m, 11H), 1.09-0.87 (m, 6H) ppm. $^{19}$F NMR (376 MHz, MeOD$_{d4}$) δ −77.01, −166.24, −166.92, −188.81, −188.83 ppm. Anal. HPLC: 100%, Retention time: 6.86 min (method A).

(1S,2S,4R,6R,8S,9S,11S,12R,13S,19S)-8-(2-Amino-acetyl)-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one; trifluoroacetic acid salt (11-19R)

Step 1: Using the same procedure described above, the azido precursor of (11-19R) (0.12 g, 87% yield) was obtained from compound (9BR) as a white solid after purification by flash chromatography (0-50% ethyl acetate in petroleum ether). ESI m/z: 492 (M+H)$^+$. $^1$H NMR (500 MHz, CDCl$_3$) δ 7.10 (dd, J=10.2, 1.3 Hz, 1H), 6.44 (s, 1H), 6.38 (dd, J=10.2, 1.8 Hz, 1H), 5.48-5.31 (m, 1H), 4.92 (d, J=5.4 Hz, 1H), 4.62 (t, J=4.4 Hz, 1H), 4.43 (dd, J=5.6, 2.7 Hz, 1H), 4.22 (d, J=18.7 Hz, 1H), 3.94 (d, J=18.7 Hz, 1H), 2.56-2.39 (m, 2H), 2.32-2.18 (m, 2H), 1.85-1.71 (m, 3H), 1.67-1.54 (m, 7H), 1.46-1.37 (m, 2H), 0.97-0.90 (m, 6H) ppm.

Step 2: Using the same procedure described above, compound 11-19R (30 mg, 66% yield) was obtained as a white solid after purification by prep-HPLC (method A). ESI m/z: 466 (M+H)$^+$. $^1$H NMR (500 MHz, MeOD$_{d4}$) δ 7.34 (d, J=10.0 Hz, 1H), 6.40-6.30 (m, 2H), 5.65-5.46 (m, 1H), 4.94-4.91 (m, 1H), 4.72 (t, J=4.3 Hz, 1H), 4.34-4.28 (m, 2H), 3.88 (d, J=18.8 Hz, 1H), 2.78-2.60 (m, 1H), 2.39-2.34 (m, 1H), 2.33-2.18 (m, 2H), 1.77-1.54 (m, 9H), 1.53-1.40 (m, 2H), 0.99-0.95 (m, 6H) ppm. Anal. HPLC: 100%, Retention time: 6.85 min (method A).

Example 26

This Example demonstrates a method for making compound 11-20R/S in Table 1. This example refers to the compound numbering in FIG. 2.

(1S,2S,4R,8S,9S,11S,12R,13S,19S)-12,19-Difluoro-11-hydroxy-8-(2-{[(4-methoxyphenyl)methyl](methyl)amino}acetyl)-9,13-dimethyl-6-propyl-5,7-dioxapentacyclo[10.8.0.0$^{2,9}$.0$^{4,8}$.0$^{13,18}$]icosa-14,17-dien-16-one; trifluoroacetic acid (11-20R/S)

To a solution of compound 9B (0.54 g, 1.0 mmol) in acetonitrile (10 mL) were added N-PMB-methylamine (0.30 g, 2.0 mmol) and potassium carbonate (0.28 g, 2.0 mmol) at RT successively. The reaction mixture was stirred at 70° C. overnight. After cooled, the mixture was diluted with DCM and filtered. The filtrate was concentrated in vacuo and the residue was purified by flash chromatography (10-90% ethyl acetate in petroleum ether) to afford crude compound (11-20R/S) (0.20 g, 33% yield) as a white solid. The crude product (30 mg) was further purified by prep-HPLC (method A) to afford pure compound (11-20R/S) as a white solid (12 mg, 13% yield). ESI m/z: 600 (M+H)$^+$. $^1$H NMR (500 MHz, MeOD$_{d4}$) δ 7.50-7.43 (m, 2H), 7.34 (d, J=10.1 Hz, 1H), 7.07 (d, J=8.5 Hz, 2H), 6.39-6.30 (m, 2H), 5.56 (ddd, J=48.5, 10.7, 6.5 Hz, 1H), 5.24-5.21 (m, 1H), 4.94-4.92 (m, 1H), 4.64-4.53 (m, 1H), 4.38-4.16 (m, 4H), 3.86 (s, 3H), 2.92-2.91 (m, 3H), 2.76-2.56 (m, 1H), 2.39-2.31 (m, 1H), 2.28-2.09 (m, 2H), 1.97 (td, J=13.2, 7.8 Hz, 1H), 1.78-1.23 (m, 10H), 1.08-0.88 (m, 6H) ppm. Anal. HPLC: 100%, Retention time: 7.81 min (method A).

Example 27

This Example demonstrates a method for making compounds 11-21R/S in Table 1. This example refers to the compound numbering in FIG. 2.

(1S,2S,4R,8S,9S,11S,12R,13S,19S)-12,19-Difluoro-11-hydroxy-9,13-dimethyl-8-[2-(methylamino)acetyl]-6-propyl-5,7-dioxapentacyclo[10.8.0.0$^{2,9}$.0$^{4,8}$.0$^{13,18}$]icosa-14,17-dien-16-one; trifluoroacetic acid (11-21R/S)

To compounds 11-20R/S (30 mg, 0.053 mmol) in 4 mL-screw-capped vial were added 1-chloroethyl carbonochloridate (1 drop) and chloroform (0.4 mL). The mixture was stirred at 70° C. for 2 hours until the starting material was consumed by TLC. After cooled to RT, the mixture was added methanol (1.5 mL). The mixture was stirred at 70° C. for 1 h until the reaction was completed, which was monitored by TLC and LC-MS. The volatiles were removed in vacuo and the residue was purified by prep-HPLC (method A) to afford compounds 11-21R/S (8.0 mg, 28% yield) as a white solid. ESI m/z: 480 (M+H)$^+$. $^1$H NMR (400 MHz, MeOD$_{d4}$) δ 7.34 (d, J=10.1 Hz, 1H), 6.41-6.26 (m, 2H), 5.56 (ddd, J=48.7, 10.0, 6.8 Hz, 1H), 5.28 (t, J=4.9 Hz, 1H), 5.23 (d, J=7.4 Hz, 1H), 4.47-4.41 (m, 1H), 4.34-4.30 (m, 1H), 4.07-4.00 (m, 1H), 2.82-2.54 (m, 4H), 2.43-2.09 (m, 3H), 1.96 (td, J=13.6, 7.9 Hz, 1H), 1.81-1.34 (m, 10H), 1.10-0.85 (m, 6H) ppm. $^{19}$F NMR (376 MHz, MeOD$_{d4}$) δ −76.96, −166.28, −166.95, −188.80, −188.83 ppm. Anal. HPLC: 99%, Retention time: 6.97 min (method A).

Example 28

This example demonstrates a method for making compound 14-2 in Table 1. This example refers to the compound numbering in FIG. 3.

(1R,2S,8S,10S,11S,13S,14R,15S,17S)-1,8-difluoro-17-hydroxy-2,13,15-trimethyl-14-[2-(methylamino)acetyl]-5-oxotetracyclo[8.7.0.0$^{2,7}$.0$^{11,15}$]heptadeca-3,6-dien-14-yl propanoate (14-2)

The synthesis of mesylate flumethasone (12) was reported in *Bioorg. Med. Chem. Lett.*, 2015, 25, 2837-2843, the entire contents of which are herein incorporated by reference in their entirety for all purposes.

A solution of 12 (82 mg crude) in methylamine (2M solution in THF, 1.5 mL, 3.000 mmol) in a sealed tube was stirred at RT for overnight, and then heated at 60° C. for 3 hours until the reaction was completed. The solution was concentrated in vacuo and the residue was purified by prep. HPLC (0-80% acetonitrile in water with 10 mM NH$_4$HCO$_3$) to get compound 14-2 (8 mg, yield 11% for two steps) as a white solid. ESI m/z: 480.2 (M+H). 1H NMR (DMSO$_{d6}$, 400 MHz) δ 7.27-7.25 (d, J=10.4 Hz, 1H), 6.30-6.27 (dd, J=10.4, 2.0 Hz, 1H), 6.10 (s, 1H), 5.73-5.56 (m, 1H), 5.43-5.32 (m, 2H), 4.62-4.42 (m, 1H), 4.25-4.18 (m, 2H), 4.15 (brs, 1H), 2.87 (s, 2H), 2.70 (s, 1H), 2.60-2.56 (m, 1H), 2.36-1.90 (m, 7H), 1.49-1.35 (m, 5H), 1.10-0.91 (m, 10H).

Example 29

This example demonstrates a method for making compound 15-5 Table 1. This example refers to the compound numbering in FIG. 3.

(1R,2S,8S,10S,11S,13R,14R,15S,17S)-14-[2-(4-Aminophenoxy)acetyl]-1,8-difluoro-14,17-dihydroxy-2,13,15-trimethyltetracyclo[8.7.0.0$^{2,7}$.0$^{11,15}$]heptadeca-3,6-dien-5-one (15-5)

Step 1: A mixture of compound (12) (0.16 g, 0.33 mmol), 4-nitrophenol (10-5, 92 mg, 0.67 mmol) and potassium carbonate (92 mg, 0.67 mmol) in acetone (15 mL) was refluxed (60° C.) for 18 hours. After cooled down to RT, the volatiles were removed in vacuo. The residue was purified by flash chromatography (0-1% ethyl acetate in petroleum ether) to yield a nitro-intermediate (0.14 g, yield 79%) as a white solid. ESI m/z: 532 (M+H)$^+$. $^1$H NMR (CDCl$_3$, 400 MHz) δ 8.20 (d, J=9.0 Hz, 2H), 7.10 (d, J=10.5 Hz, 1H), 6.94 (d, J=9.0 Hz, 2H), 6.43 (br s, 1H), 6.39-6.37 (m, 1H), 5.45-5.32 (m, 1H), 5.26 (d, J=18.0 Hz, 1H), 4.85 (d, J=18.0 Hz, 1H), 4.43-4.40 (m, 1H), 3.21-3.16 (m, 1H), 2.60 (s, 1H), 2.52-2.40 (m, 2H), 2.30-2.20 (m, 2H), 2.06-1.99 (m, 1H), 1.86-1.68 (m, 3H), 1.53-1.48 (m, 2H), 1.09 (s, 3H), 0.99 (d, J=7.0 Hz, 3H) ppm.

Step 2: To a solution of the nitro-intermediate (0.13 g, 0.25 mmol) in a combined solution of ethanol (20 mL) and water (2 mL) was added iron powder (0.14 g, 2.5 mmol) and then ammonium chloride (0.14 g, 2.5 mmol). After stirring at 80° C. for 2 hours, the suspension was cooled down to RT and filtered through Celite to remove the inorganic salts. The filtrate was concentrated in vacuo and the residue was purified by prep-HPLC (method B) to yield compound 15-5 (90 mg, yield 70%) as a white solid. ESI m/z: 502 (M+H)$^+$. $^1$H NMR (DMSO$_{d6}$, 500 MHz) δ 7.27 (d, J=10.0 Hz, 1H), 6.59 (d, J=8.5 Hz, 2H), 6.49 (d, J=8.5 Hz, 2H), 6.31-6.28 (m, 1H), 6.11 (s, 1H), 5.77-5.57 (m, 1H), 5.42-5.39 (m, 1H), 5.22 (s, 1H), 5.07 (d, J=18.5 Hz, 1H), 4.63 (s, 1H), 4.59 (d, J=18.5 Hz, 1H), 4.29-4.10 (m, 1H), 2.99-2.91 (m, 1H), 2.55-2.43 (m, 3H), 2.25-2.19 (m, 3H), 1.71-1.64 (m, 1H), 1.56-1.43 (m, 5H), 1.15-1.10 (m, 1H), 0.88 (s, 3H), 0.83 (d, J=6.0 Hz, 3H) ppm.

Example 30

This example demonstrates a method for making compound 16-5 in Table 1. This example refers to the compound numbering in FIG. 4.

(1R,2S,10S,11S,13R,14R,15S,17S)-14-[2-(4-Amino-phenoxy)acetyl]-1-fluoro-14,17-dihydroxy-2,13,15-trimethyltetracyclo[8.7.0.0$^{2,7}$.0$^{11,15}$]heptadeca-3,6-dien-5-one (16-5)

The synthesis of mesylate dexamethasone (13) was reported in *J. Pharmacol.*, 172, 1360 (2015), the entire contents of which are herein incorporated by reference in their entirety for all purposes.

A mixture of mesylate dexamethasone (13, 94 mg, 0.20 mmol), 4-nitrophenol (10-5, 42 mg, 0.30 mmol) and potassium carbonate (55 mg, 0.40 mmol) in acetone (10 mL) was refluxed (60° C.) for 3 hours and was then concentrated. The crude product was concentrated in vacuo, and then directly purified by flash chromatography (0-50% ethyl acetate in petroleum ether) to yield a nitro-intermediate (0.10 g, yield 97%) as a white solid. ESI m/z: 514 (M+H)$^+$. $^1$H NMR (MeOD$_{d4}$, 400 MHz) δ 8.23 (d, J=9.0 Hz, 2H), 7.43 (d, J=10.5 Hz, 1H), 7.04 (d, J=9.0 Hz, 2H), 6.31 (dd, J=10.0 Hz, 2.0 Hz, 1H), 6.11 (br s, 1H), 5.41 (d, J=18.0 Hz, 1H), 4.96 (d, J=18.0 Hz, 1H), 4.34-4.30 (m, 1H), 3.13-3.06 (m, 1H), 2.79-2.72 (m, 1H), 2.57-2.41 (m, 3H), 2.32-2.26 (m, 1H), 1.94-1.90 (m, 1H), 1.82-1.75 (m, 1H), 1.62 (s, 3H), 1.62-1.53 (m, 2H), 1.28-1.23 (m, 1H), 1.07 (s, 3H), 0.92 (d, J=7.0 Hz, 3H) ppm.

To a solution of the nitro-intermediate (i.e., NO$_2$-analog in FIG. 4, 60 mg, 0.12 mmol) in a combined solution of ethanol (3 mL) and water (0.5 mL) were added iron powder (67 mg, 1.2 mmol) and then ammonium chloride (64 mg, 1.2 mmol). After stirring at 80° C. for 1.5 hours, the suspension was cooled down to RT and filtered through Celite to remove the inorganic salts. The filtrate was concentrated in vacuo and the residue was purified by prep-HPLC (method B) to yield compound 16-5 (20 mg, yield 35%) as a white solid. ESI m/z: 484 (M+H)$^+$. $^1$H NMR (MeOD$_{d4}$, 500 MHz) δ 7.42 (d, J=10.5 Hz, 1H), 6.78-6.74 (m, 2H), 6.73-6.70 (m, 2H), 6.31 (dd, J=10.0 Hz, 2.0 Hz, 1H), 6.10 (br s, 1H), 5.08 (d, J=18.0 Hz, 1H), 4.71 (d, J=18.0 Hz, 1H), 4.30-4.27 (m, 1H), 3.14-3.09 (m, 1H), 2.78-2.71 (m, 1H), 2.54-2.37 (m, 3H), 2.30-2.24 (m, 1H), 1.94-1.89 (m, 1H), 1.81-1.74 (m, 1H), 1.62 (s, 3H), 1.59-1.52 (m, 2H), 1.26-1.21 (m, 1H), 1.06 (s, 3H), 0.91 (d, J=7.5 Hz, 3H) ppm.

Example 31

This example demonstrates methods for separating stereoisomers of certain compounds disclosed herein.

SFC (Supercritical fluid chromatography) technology was used for the purification of small molecular compounds, which are thermally labile, including chiral compounds. SFC used supercritical fluid carbon dioxide as a mobile phase and organic polymer bonded solid adsorbent as a stationary phase. Based on different partition coefficient of the epimers in the two phases, the mixed epimers could be separated by adjusting the mobile phase's density. The instrument and column conditions are described as follows: Instrument: SFC-80 (Thar, Waters), Column: AD 20*250 mm, Sum (Decial), Column temperature: 35° C., Mobile phase: CO$_2$/EtOH (1% Methanol Ammonia)=65/35, Flow rate: 80 g/min, Back pressure: 100 bar, Detection wavelength: 214 nm, Cycle time: 4.5 min, Sample solution: 130 mg dissolved in 30 ml Methanol, Injection volume: 1.5 ml). By using a chiral ADH column, 20 grams of 22R/S-budesonide were separated to yield 8.9 grams of R-budesonide and 8.9 grams of S-budesonide in a total of 89% recovery yield. Similarly, two epimers of compound 11-5R/S were also separated by SFC. The detail separation conditions were described below in Table 5.

TABLE 5

Conditions of chiral separation of Budesonide and Compound (11-5) in Table 1.

| Compound | Budesonide | 11-5R/S |
| --- | --- | --- |
| Instrument | SFC-200 (Thar, Waters) | SFC-200 (Thar, Waters) |
| Column | AD-H 20*250 mm, 5 um (Dacel) | SC 20*250 mm, 5 um |
| Column temperature | 35° C. | 35° C. |
| Mobile phase | CO$_2$/methanol (0.5% NH$_4$OH) = 70/30 | CO$_2$/methanol (0.5% NH$_4$OH) = 60/40 |
| Flow rate | 120 g/min | 140 g/min |
| Back pressure | 100 bar | 100 bar |
| Detection wavelength | 214 nm | 214 nm |
| Cycle time | 4.0 min | 5.0 min |
| Sample solution | 20 g dissolved in 130 ml Methanol | 10 g dissolved in 130 ml Methanol |
| Injection volume | 1.0 ml | 0.5 ml |

The structures of 22R/S-Budesonide were determined stereospecifically by 2D-NOESY. Compared with reported proton NMR data of 22R/S-Budesonide, the first compound from the chiral SFC was determined to be the R-epimer, while the second was determined to be the S epimer. The configuration at C$^{22}$ influences the magnetic resonances of the neighboring protons. A double doublet with $J_{16\beta H-15\beta H}$=5.0 Hz and $J_{16\beta H-15\alpha H}$=2.5 Hz were observed in the S-spectrum, which resulted from a steric repulsion from the 22-propyl substituent deshielding the C$^{16}$ proton in the S-epimer. This effect is not observed in the R-epimer. The C$^{22}$ proton in the S-epimer also moved downfield compared to that of the R-epimer, indicating deshielding of the C$^{22}$ proton in the S-epimer due to a steric repulsion between the 17β-ketol substituent and the 22β-propyl chain in the S-epimer. Similarly, the C$^{22}$ proton in the R-epimer was shielded by anisotropy effect from the C20-carbonyl group in the 22R-epimer. The detail chemical shifts are described below in Table 6.

TABLE 6

Chemical shifts (ppm) in D-chloroform

| Protons at | R-epimer reported | 1st compound from chiral SFC | S-epimer reported | 2nd compound from chiral SFC |
|---|---|---|---|---|
| C-1 | 7.26 (d, $J_{1,2}$ = 10.1) | 7.26 (d, $J_{1,2}$ = 10.1) | 7.23 (d, $J_{1,2}$ = 10.1) | 7.26 (d, $J_{1,2}$ = 10.0) |
| C-2 | 6.27 (dd, $J_{1,2}$ = 10.1, $J_{2,4}$ = 1.8) | 6.28 (dd, $J_{1,2}$ = 10.1, $J_{2,4}$ = 1.7) | 6.27 (dd, $J_{1,2}$ =10.1, $J_{2,4}$ = 1.8) | 6.27 (dd, $J_{1,2}$ = 10.1, $J_{2,4}$ = 1.7) |
| C-4 | 6.03 (m) | 6.03 (s) | 6.02 (m) | 6.02 (s) |
| C-11 | 4.4-4.6 (m) | 4.42-4.60 (m) | 4.50 (m) | 4.50 (br s) |
| C-16 | 4.90 (dd, $J_{16\beta H\text{-}15\beta H}$ = 4.2) | 4.90 (d, $J_{16\beta H\text{-}15\beta H}$ = 4.4) | 5.16 (dd, $J_{16\beta H\text{-}15\beta H}$ = 5.0, $J_{16\beta H\text{-}15\beta H}$ = 2.5) | 5.23-5.11 (m) |
| C-18 | 0.92 (s) | 0.92 (s) | 0.99 (s) | 0.99 (s) |
| C-19 | 1.45 (s) | 1.44 (s) | 1.45 (s) | 1.46 (s) |
| C-21 | 4.50 (dd), 4.25 (dd) ($J_{21H, H'}$ = −20.2, $J_{21H\text{-}21OH}$ = 4.8) | 4.50 (m), 4.26 (dd, $J_{21H, HH'}$ = 20.1, $J_{21H\text{-}21OH}$ = 4.3) | 4.60 (dd), 4.20 (dd) ($J_{21H,HH'}$ = −20.2, $J_{21H\text{-}21OH}$ = 4.8) | 4.62 (d), 4.21 (d) ($J_{21H, HH'}$ = 19.9) |
| C-22 | 4.55 (t, $J_{22,23}$ = 4.2) | 4.55 (t, $J_{22,23}$ = 4.6) | 5.16 (t, $J_{22,23}$ = 4.6) | 5.23-5.11 (m) |
| C-25 | 0.92 (t, $J_{24,25}$ = 6.7) | 0.92 (t, $J_{24,25}$ = 7.3) | 0.91 (t, $J_{24,25}$ = 7.3) | 0.91 (t, $J_{24,25}$ = 7.3) |

Example 32

This example demonstrates methods for making linkers and linker-payloads, generally.

Figure 9:
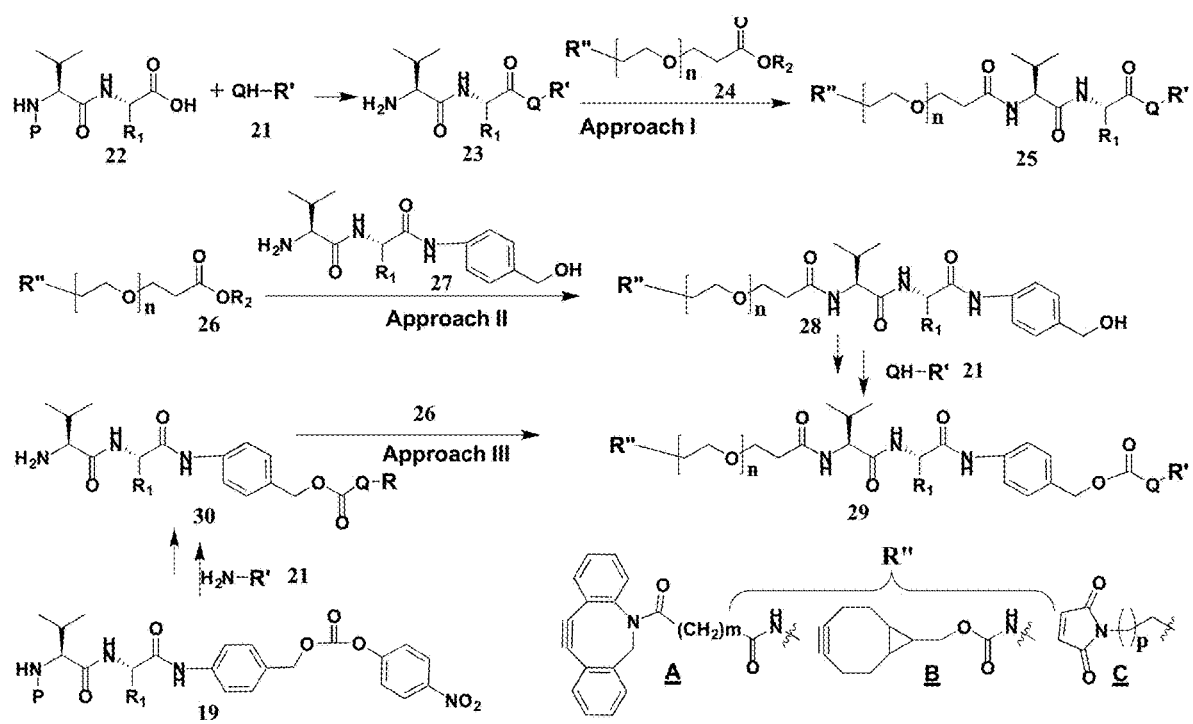
FIG. 9 shows a general approaches for synthesizing certain Linker-Payloads.
Figure 10:
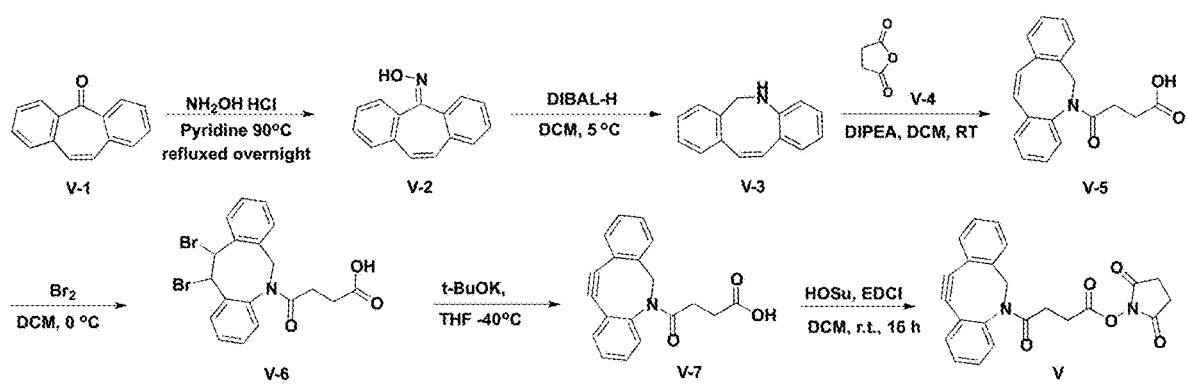
FIG. 10 shows a sequence for synthesizing DIBAC-Suc-NHS (Compound (V)).
Figure 11:
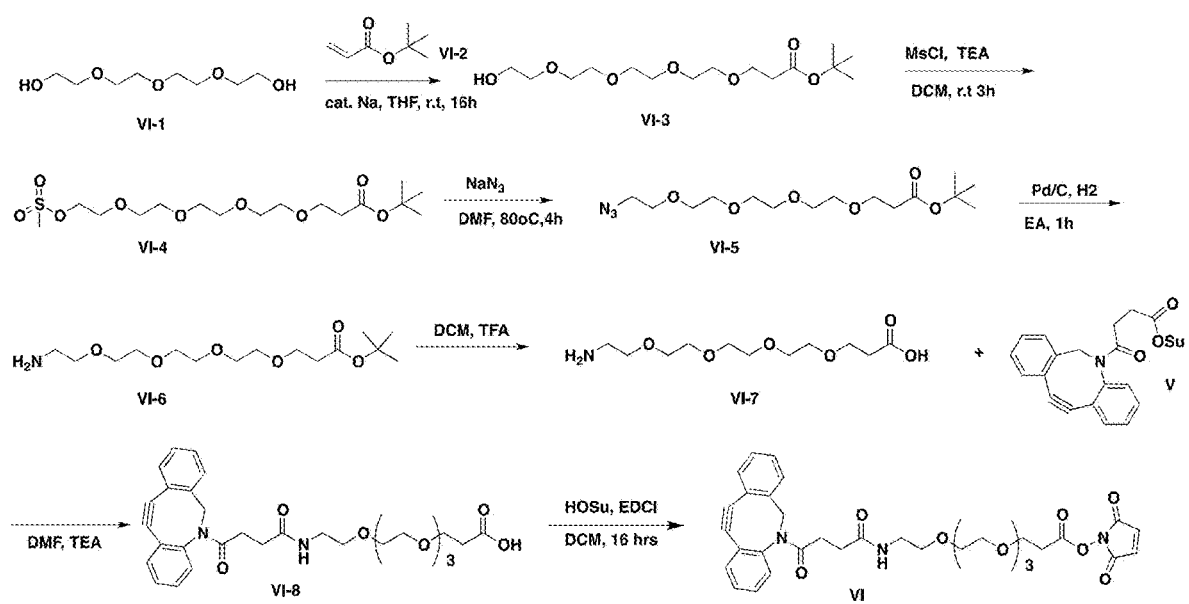
FIG. 11 shows a sequence for synthesizing DIBAC-Suc-PEG$_4$-acid/NHS (Compound (VI)).
Figure 12:
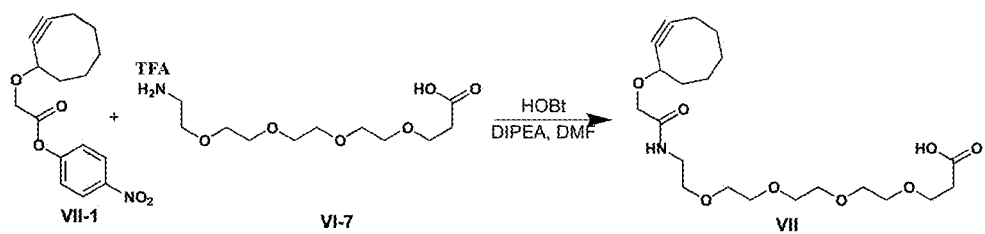
FIG. 12 shows a sequence for synthesizing BCN-PEG$_4$-Acid (Compound (VII)).

Three generic approaches for making linker-payloads are shown in FIG. 9. In FIG. 9, R' is a steroid amine or aniline; R" is an alkyne containing moiety, such as fragment A or B, or a maleimide moiety, such as C; $R_1$ is an amino-acid residue; P is a protective group, such as Fmoc or Boc; n is an integer from 0-11; m is an integer from 2-4; p is an integer from 0-5. Approach I forms an amide (23) from a coupling reaction between the steroid amine or aniline (21, Q=NH or NR) and a dipeptide (22) followed by N-deprotection. The amine (23) was then coupled with an acid or its active ester (24), such as V-5, V-7, V in FIG. 10, VI-8 and VI in FIG. 11, and VII in FIG. 12, to generate the linker-payloads (25). Approach II forms an amide (28) from a coupling reaction between an acid or its active ester (26) and VC-pAB (27) followed by N-deprotection. Compound 28 was then converted to its PNP derivative that further reacted with 21 to generate the linker-payload carbamate (29). Approach III forms a carbamate (30) from N-protected-dipeptide-pAB-PNP (19) and the steroid amine or aniline (21), followed by N-deprotection; the amine moiety in 30 was then coupled with an acid or its active ester (26) to generate 29.

Example 33

This example demonstrates methods for making linker DIBAC-Suc-NHS (V). The following Example refers to FIG. 10.

See methods in *J. Org. Chem.*, 2010, 75, 627-636 which are incorporated by reference herein in their entirety for all purposes.

Step 1: N-[Tricyclo[9.4.0.0$^{3,8}$]pentadeca-1(11),3,5,7,9,12,14-heptaen-2-ylidene]hydroxylamine (V-2): A mixture of dibenzosuberenone (V-1) (21 g, 0.10 mol) and hydroxylamine hydrochloride (9.3 g, 0.14 mol) in a combined solution of absolute ethanol (100 mL) and pyridine (200 mL) was stirred and refluxed for 15 hours. TLC showed the starting material was consumed (TLC: 5% methanol in methylene chloride). After cooling to below 25° C., the reaction mixture was diluted with methylene chloride (500 mL) and the resulting solution was washed with aqueous (aq.) HCl (1N, 3×200 mL) and then brine (200 mL). The organic solution was dried over sodium sulfate and concentrated in vacuo to yield crude V-2 (22 g, 98% crude yield) as a light brown solid. ESI m/z: 222.1 (M+H)$^+$.

Step 2: 2-Azatricyclo[10.4.0.0$^{4\text{-}9}$]hexadeca-1(16),4(9),5,7,10,12,14-heptene (V-3): To a solution of the oxime (V-2) (5.5 g, 25 mmol) in dry methylene chloride (herein also dichloromethane or DCM) (150 mL) at 5° C. was added DIBAL-H (1 M in toluene, 250 mL) dropwise while maintaining the temperature below 5° C. The reaction was then stirred at RT overnight and was subsequently quenched with a solution of sodium fluoride solid (38 g, 0.90 mol) in water (12 mL) at 0° C. The slurry was stirred at 0° C. for another 30 minutes and filtered through Celite. The Celite was thoroughly washed with methylene chloride and the combined organic solution was concentrated in vacuo to yield V-3 (4.6 g, 89% yield) as a yellow solid. ESI m/z: 222.1 (M+H)$^+$.

Step 3: 4-[2-Azatricyclo[10.4.0.0$^{4,9}$]hexadeca-1(16),4(9),5,7,10,12,14-heptaen-2-yl]-4-oxobutanoic acid (V-5): To a solution of (V-3) (5.0 g, 24 mmol) in methylene chloride (50 mL) were added DIPEA (3.1 g, 24 mmol) and then succinic anhydride (V-4, 2.9 g, 29 mmol). The mixture was then stirred at RT for 4 hours, quenched with aq. sodium bisulfate (1N, 100 mL), and extracted with methylene chloride (3×100 mL). The combined organic solution was washed with water (100 mL) and then brine (100 mL), dried over sodium sulfate and concentrated in vacuo to afford (V-5) (7.7 g, 95% yield) as a white solid, which was used without further purification. ESI m/z: 308.2 (M+H)$^+$.

Step 4: 4-{10,11-dibromo-2-azatricyclo[10.4.0.0^{4,9}]hexadeca-1(16),4(9),5,7,12,14-hexaen-2-yl}-4-oxobutanoic acid (V-6): A solution of (V-5) (15 g, 49 mmol) in methylene chloride (200 mL) was flushed with nitrogen and cooled to 0° C. To the solution was added liquid bromine (23 g, 0.14 mol) dropwise at 0° C. via a syringe. The reaction was stirred at this temperature for 2 hours and TLC showed the reaction was completed (TLC: 10% methanol in methylene chloride). The reaction mixture was diluted with methylene chloride (50 mL) and was allowed to warm to RT. The organic solution was washed with saturated (sat.) aq. sodium sulfite (3×50 mL), water (50 mL) and then brine (50 mL), dried over sodium sulfate and concentrated in vacuo to yield (V-6) (13 g, 99% crude yield) as an off-white solid. ESI m/z: 467.9 (M+H)$^+$. $^1$H NMR (CDCl$_3$, 400 MHz): δ 7.71 (d, J=6.8 Hz, 1H), 7.25-7.01 (m, 6H), 6.94-6.88 (m, 1H), 5.90 (d, J=9.6 Hz, 1H), 5.84-5.79 (m, 1H), 5.25-5.25 (m, 1H), 4.24-4.10 (m, 1H), 2.87-2.80 (m, 1H), 2.68-2.47 (m, 3H) ppm.

Step 5: 4-{2-Azatricyclo[10.4.0.0$^{4,9}$]hexadeca-1(16),4(9),5,7,12,14-hexaen-10-yn-2-yl}-4-oxobutanoic acid (V-7): A solution of (V-6) (5.0 g, 11 mmol) in anhydrous THF (50 mL) was cooled to 40° C. with a dry-ice/acetonitrile bath and to the solution was added a solution of potassium tert-butanolate in tetrahydrofuran (1N, 37 mL, 37 mmol) dropwise under argon atmosphere. The reaction mixture was stirred at this temperature for half an hour after the addition. TLC showed that the reaction was completed (TLC: 10% methanol in methylene chloride). The reaction mixture was allowed to warm to RT and was quenched with aq. sodium bisulfate (1N) to pH 1. The mixture was extracted with methylene chloride (3×50 mL). The combined organic solution was washed with water (50 mL) and then brine (50 mL), dried over sodium sulfate and concentrated in vacuo to yield compound (V-7) (2.7 g, 95% yield) as an off-white solid. ESI m/z: 306.1 (M+H)$^+$. $^1$H NMR (DMSO$_{d6}$, 500 MHz): δ 11.98 (s, 1H), 7.67-7.29 (m, 8H), 5.02 (d, J=13.5 Hz, 1H), 3.61 (d, J=14.5 Hz, 1H), 2.61-2.56 (m, 1H), 2.32-2.27 (m, 1H), 2.21-2.16 (m, 1H), 1.80-1.76 (m, 1H) ppm.

Step 6: 4-{2-Azatricyclo[10.4.0.0$^{4,9}$]hexadeca-1(12),4(9),5,7,13,15-hexaen-10-yn-2-yl}-4-oxobutanoic acid (V): To a solution of acid (V-7) (50 mg, 0.16 mmol) in methylene chloride (10 mL) were subsequently added N-hydroxysuccinimide (HOSu, 28 mg, 0.24 mmol) and N-(3-dimethylaminopropyl)-N'-ethylcarbodiimide hydrochloride (EDCI, 47 mg, 0.24 mmol). After stirring at RT overnight, the mixture was washed with water and then brine, dried over sodium sulfate and concentrated in vacuo to yield intermediate V, which was used for next step directly. ESI m/z: 403.0 (M+H)$^+$.

Example 34

This example demonstrates methods for making linker DIBAC-Suc-PEG$_4$-acid/NHS (VI). The following Example refers to FIG. 11.

Step 1: Tert-butyl-1-hydroxy-3,6,9,12-tetraoxapentadecan-15-oate (VI-3): To a solution of tetraethylene glycol (VI-1, 58 g, 0.30 mol) in dry THF (200 mL) was added sodium (0.12 g), and the mixture was stirred until the sodium was consumed. To the resulting solution was then added tert-butyl acrylate (VI-2, 13 g, 0.10 mol) in dry THF (50 mL) dropwise, and the resulting mixture was stirred at RT overnight. The reaction was quenched with acetic acid (0.1 mL) first and then water (0.5 mL), and the resulting mixture was stirred at RT for half an hour, and subsequently was extracted with ethyl acetate (3×200 mL). The combined organic solution was washed with water (30 mL) and then brine (3×100 mL), dried over sodium sulfate, filtered and concentrated to yield product (VI-3, 26 g, 81% yield) as colorless oil. ESI m/z: 340 (M+18)$^+$.

Step 2: tert-Butyl 1-(methanesulfonyloxy)-3,6,9,12-tetraoxapentadecan-15-oate (VI-4): To a solution of (VI-3) (26 g, 81 mmol), triethylamine (12 mL, 89 mmol) in methylene chloride (150 mL) in an ice-water bath was added a solution of methanesulfonyl chloride (10 g, 89 mmol) in DCM (50 mL) dropwise. The mixture was stirred at RT for 14 hours, and was then concentrated in vacuo. The residue was mixed with water (30 mL), and was then extracted with ethyl acetate (3×200 mL). The combined organic layer was washed with brine (3×100 mL), dried over sodium sulfate, filtered, and concentrated in vacuo to yield the desired product (VI-4) (31 g, 95% yield) as light yellow oil. ESI m/z: 418 (M+18)$^+$.

Step 3: tert-Butyl 1-azido-3,6,9,12-tetraoxapentadecan-15-oate (VI-5): To a solution of (VI-4) (27 g, 67 mmol) in DMF (70 mL) was added sodium azide (6.6 g, 0.10 mol), which was then stirred at 80° C. for 4-16 hours. After cooled to RT, the mixture was diluted with ethyl acetate (3×150 mL). The combined solution was washed with water (30 mL) and then brine (3×100 mL), dried over sodium sulfate, filtered, and concentrated in vacuo. The crude product was purified by silica gel column chromatography (petroleum ether/ethyl acetate (with 1% to 2% methanol)=4/1) to yield (VI-5) (18 g, 67% yield) as colorless oil. ESI m/z: 365 (M+18)$^+$.

Step 4: tert-Butyl 1-amino-3,6,9,12-tetraoxapentadecan-15-oate (VI-6): To a solution of (VI-5) (1.5 g, 4.3 mmol) in ethyl acetate (20 mL) was added wet Pd/C (10%, 0.15 g) under nitrogen. The mixture was then flushed with hydrogen and stirred at RT under a hydrogen balloon overnight. The mixture was then filtered through Celite. The Celite was washed with ethyl acetate (10 mL). The combined filtrate was concentrated in vacuo to yield crude (VI-6) (1.4 g) as light a yellow oil, which was used on the next step without further purification. ESI m/z: 322 (M+H)$^+$.

Step 5: 1-Amino-3,6,9,12-tetraoxapentadecan-15-oic acid (VI-7): To a solution of (VI-6), obtained above (1.4 g) in methylene chloride (10 mL) was added TFA (5 mL). The mixture was stirred at RT for an hour. The volatiles were removed in vacuo to yield crude product (VI-7) as its TFA salt (1.6 g) as yellow oil, which was used for the next step without further purification. ESI m/z: 266 (M+H)$^+$.

Step 6: 1-(4{-2-Azatricyclo[10.4.0.0$^{4-9}$]hexadeca-1(12),4(9),5,7,13,15-hexane-10-yn-2-yl}-4-oxobutanamido)-3,6,9,12-tetraoxapentadecan-15-oic acid (VI-8): A mixture of 4{-2-Azatricyclo[10.4.0.0$^{4,9}$]hexadeca-1(12),4(9),5,7,13,15-hexaen-10-yn-2-yl}-4-oxobutanoic acid (V in FIG. 11, 1.0 g, 2.5 mmol) and (VI-7) (0.91 g, 2.5 mmol) in DMF (10 mL) was added triethylamine (0.50 g, 5.0 mmol). The mixture was stirred at RT overnight. The mixture was directly purified by reversed phase flash chromatography (0-100% acetonitrile in water (NH$_4$HCO$_3$, 10 mM)) to yield the (VI-8) (1.0 g, 74% yield in 3 steps from VI-5) as brown oil. ESI m/z: 553.3 (M+H)$^+$. $^1$H NMR (MeOD$_{d4}$, 400 MHz): δ 7.65 (d, J=7.2 Hz, 1H), 7.64-7.58 (m, 1H), 7.49-7.42 (m, 3H), 7.40-7.30 (m, 2H), 7.28-7.22 (m, 1H), 5.12 (d, J=13.6 Hz, 1H), 3.75-3.68 (m, 3H), 3.63-3.50 (m, 12H), 3.50-3.39 (m, 2H), 3.25 (t, J=5.6 Hz, 2H), 2.76-2.66 (m, 1H), 2.52 (t, J=6.0 Hz, 2H), 2.41-2.30 (m, 1H), 2.21-2.14 (m, 1H), 2.03-1.93 (m, 1H) ppm.

Step 7: 2,5-Dioxopyrrolidin-1-yl 1-(4-{2-azatricyclo[10.4.0.0$^{4-9}$]hexadeca-1(12),4(9),5,7,13,15-hexane-10-yn-2-yl}-4-oxobutanamido)-3,6,9,12-tetraoxapentadecan-15- oate (VI): To a solution of (VI-8) (40 mg, 72 µmol) in methylene chloride (10 mL) was subsequently added HOSu (1-hydroxypyrrolidine-2,5-dione, 12 mg, 0.11 mmol) and EDCI (21 mg, 0.11 mmol). The mixture was stirred at RT overnight and was then diluted with methylene chloride (50 mL). The organic solution was washed with water (50 mL) and then brine (50 mL), dried over sodium sulfate, filtered, and concentrated in vacuo to generate intermediate (VI), which was used in next step without further purification. ESI m/z: 650 (M+H)$^+$. $^1$H NMR (CDCl$_3$, 400 MHz): δ 7.70 (m, 1H), 7.66 (m, 1H), 7.55-7.47 (m, 3H), 7.38-7.24 (m, 4H), 6.33 (br s, 1H), 5.13 (d, J=13.6 Hz, 1H), 3.83-3.78 (m, 1H), 3.66-3.60 (m, 13H), 3.47-3.35 (m, 2H), 2.99-2.82 (m, 6H), 2.51-2.43 (m, 2H), 2.20-1.89 (m, 4H) ppm.

Example 35

This example demonstrates methods for making 1-((1R,8S,9s)-Bicyclo[6.1.0]non-4-yn-9-yl)-3-oxo-2,7,10,13,16-pentaoxa-4-azanonadecan-19-oic acid (BCN-PEG$_4$-Acid, VII). The following Example refers to FIG. 12.

To a solution of intermediate VII-1 (0.10 g, 0.33 mmol) in tetrahydrofuran (THF) (5 mL) were subsequently added diisopropylethylamine (0.17 g, 1.3 mmol), intermediate (VI-7) (89 mg, 0.33 mmol), and 1-hydroxybenzotriazole (HOBt, 43 mg, 0.33 mmol). The mixture was stirred at RT overnight. After filtered to remove the insoluble solid and concentrated in vacuo, the reaction mixture was directly purified by prep-HPLC (method B) to yield BCN-PEG$_4$-acid (VII) (25 mg, 17% yield) as colorless oil. $^1$H NMR (CDCl$_3$, 400 MHz): δ 5.07 (br s, 1H), 4.14 (d, J=7.6 Hz, 2H), 3.77 (t, J=6.4 Hz, 2H), 3.70-3.55 (m, 14H), 3.40-3.31 (m, 2H), 2.58 (t, J=6.0 Hz, 2H), 2.30-2.19 (m, 6H), 1.61-1.52 (m, 2H), 1.43-1.32 (m, 1H), 1.0-0.92 (m, 2H) ppm.

Example 36

Figure 13:
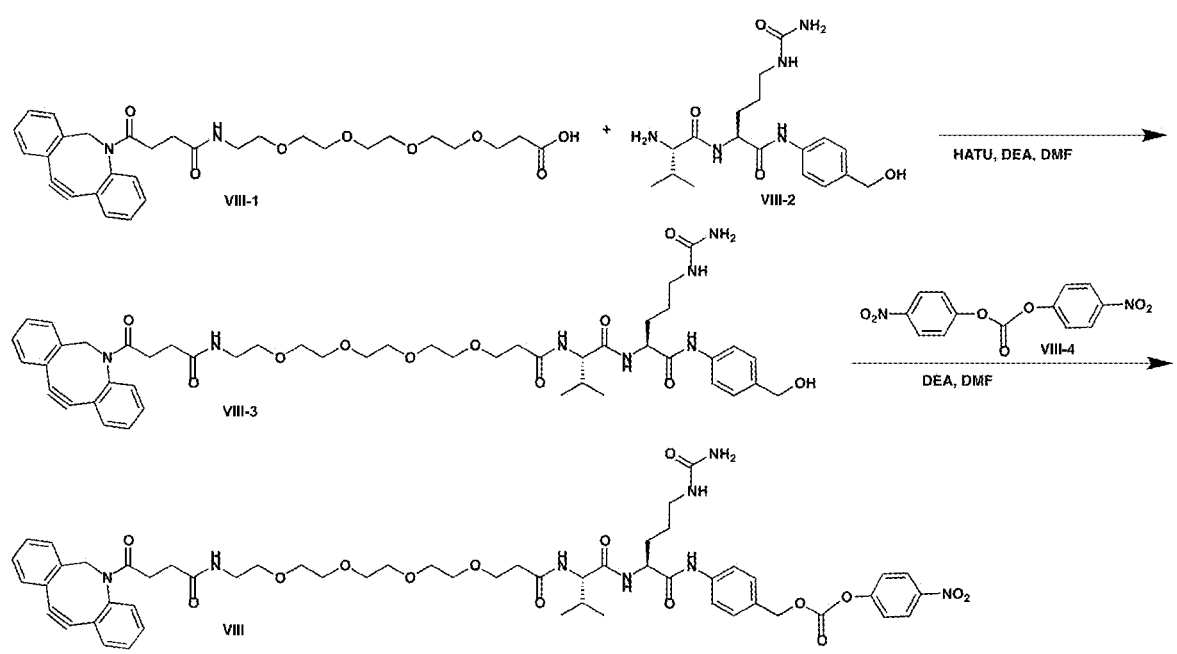
FIG. 13 shows a sequence for synthesizing DIBAC-Suc-PEG$_4$-VC-pAB-PNP (Compound (VIII)).

This example demonstrates methods for making {4-[(2S)-2-[(2S)-2-[1-(4-{2-azatricyclo[10.4.0.0$^{4,9}$]hexadeca-1(12),4(9),5,7,13,15-hexaen-10-yn-2-yl}-4-oxobutanamido]-3,6,9,12-tetraoxapentadecan-15-amido]-3-methylbutanamido]-5-(carbamoylamino)pentanamido]phenyl}methyl 4-nitrophenyl carbonate (DIBAC-Suc-PEG$_4$-VC-pAB-PNP, VIII). The following Example refers to FIG. 13.

1-(4-{2-azatricyclo[10.4.0.0$^{4-9}$]hexadeca-1(12),4(9),5,7,13,15-hexane-10-yn-2-yl}-4-oxobutanamido)-N-[(1S)-1-{[(1S)-4-(carbamoylamino)-1-{[4-(hydroxymethyl)phenyl]carbamoyl}butyl]carbamoyl}-2-methylpropyl]-3,6,9,12-tetraoxapentadecan-15-amide (VIII-3)

Step 1: To a solution of compound (VIII-1) (300 mg, 0.54 mmol) and compound (VIII-2, 205 mg, 0.54 mmol) in DMF (10 ml) were added HATU (309 mg, 0.81 mmol) and then DIEA (140 mg, 1.08 mmol). The mixture was stirred at RT for 3 hours. After filtering to remove the insoluble solid and concentrated in vacuo, the reaction mixture was directly purified by reverse flash (NH$_4$HCO$_3$ as buffer), and a white solid (VIII-3) (300 mg, 60%) was obtained. ESI m/z: 617 (M+1).

{4-[(2S)-2-[(2S)-2-[1-(4-{2-azatricyclo[10.4.0.0$^{4-9}$]hexadeca-1(12),4(9),5,7,13,15-hexane-10-yn-2-yl}-4-oxobutanamido)-3,6,9,12-tetraoxapentadecan-15-amido]-3-methylbutanamido]-5-(carbamoylamino)pentanamido]phenyl}methyl 4-nitrophenyl carbonate (VIII)

Step 2: To a solution of (VIII-3) (150 mg, 0.16 mmol) and (VIII-4) (150 mg, 0.49 mmol) in DMF (10 mL) was added DIEA (63 mg, 0.49 mmol). The mixture was stirred at RT for 3 hours. After filtered to remove the insoluble solid and concentrated in vacuo, the reaction mixture was directly purified by reverse flash chromatography (NH$_4$HCO$_3$ as buffer), and (VIII) as a yellow solid (50 mg, 28%) was obtained. ESI m/z: 1079 (M+1).

Example 37

Figure 14:
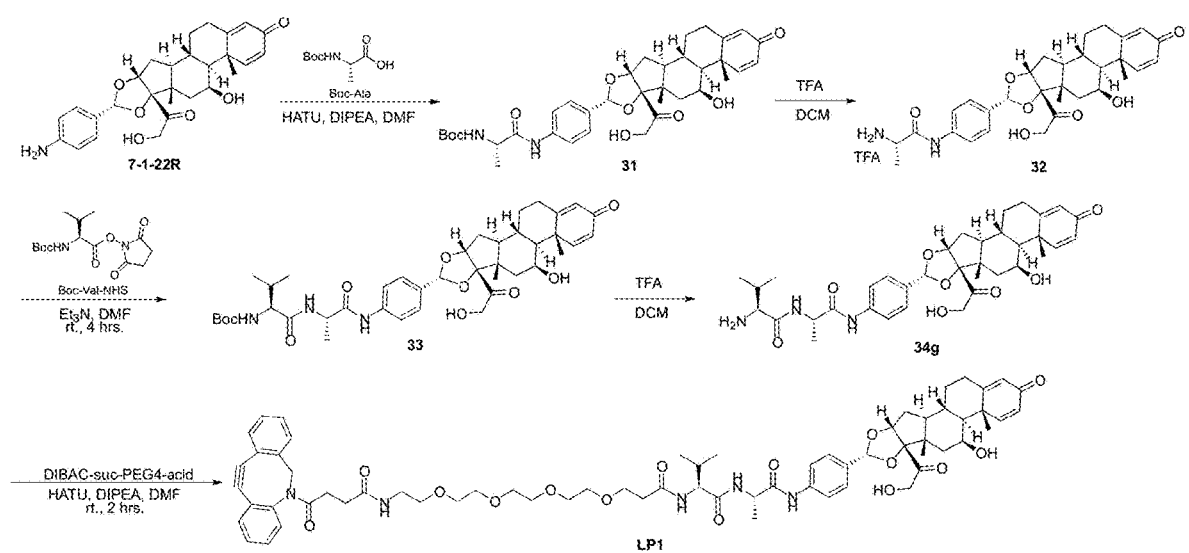
FIG. 14 shows a sequence for synthesizing Linker-Payload 1 (LP1).

This example demonstrates methods for making Linker-Payload (LP1). The following Example refers to FIG. 14.

Tert-Butyl N-[(1S)-1-({4-[(1S,2S,4R,6R,8S,9S,11S,12S,13R)-11-hydroxy-8-(2-hydroxyacetyl)-9,13-dimethyl-16-oxo-5,7-dioxapentacyclo[10.8.00$^{2,9}$.0$^{4,8}$.0$^{13,18}$]icosa-14,17-dien-6-yl]phenyl}carbamoyl)ethyl]carbamate (31)

Step 1: A mixture of Boc-Ala-OH (0.20 g, 0.42 mmol), DIPEA (0.12 g, 0.84 mmol) and HATU (0.24 g, 0.63 mmol) in DMF (5 mL) was stirred at 23° C. for 30 minutes. To the solution was then added compound 7-1R (87 mg, 0.46 mmol). After stirring at 23° C. for another 2 hours, the mixture was directly purified by prep-HPLC (method B) to yield compound 31 (0.11 g, 40% yield) as a white solid. ESI m/z: 651 (M+H)$^+$.

(2S)-2-Amino-N-{4-[(1S,2S,4R,6R,8S,9S,11S,12S,13R)-11-hydroxy-8-(2-hydroxyacetyl)-9,13-dimethyl-16-oxo-5,7-dioxapentacyclo[10.8.00$^{2,9}$.0$^{4,8}$.0$^{13,18}$]icosa-14,17-dien-6-yl]phenyl}propanamide (32)

Step 2: To a solution of compound 31 (0.10 g, 0.15 mmol) in methylene chloride (3 mL) was added TFA (0.3 mL) dropwise. The mixture was stirred at 23° C. for an hour, and the volatiles were removed in vacuo to yield crude (32) (83 mg) as an oil, which was used next step without further purification. ESI m/z: 551 (M+H)$^+$.

Tert-Butyl N-[(1S)-1-{[(1S)-1-({4-[(1S,2S,4R,6R,8S,9S,11S,12S,13R)-11-hydroxy-8-(2-hydroxyacetyl)-9,13-dimethyl-16-oxo-5,7-dioxapentacyclo[10.8.00$^{2,9}$.0$^{4,8}$.0$^{13,18}$]icosa-14,17-dien-6-yl]phenyl}carbamoyl)ethyl]carbamoyl}-2-methylpropyl]carbamate (33)

Step 3: A mixture of (32) (83 mg, 0.15 mmol), triethylamine (31 mg, 0.31 mmol) and Boc-Val-NHS (58 mg, 0.19 mmol) in DMF (5 mL) was stirred 23° C. for 4 hours and the reaction mixture was directly purified by prep-HPLC (method B) to yield (33) (52 mg, 20% yield in 2 steps) as a white solid. ESI m/z: 750 (M+H)$^+$. $^1$H NMR (500 MHz, DMSO$_{d6}$) δ 10.00 (s, 1H), 8.07 (d, J=7.0 Hz, 1H), 7.58 (d, J=8.5 Hz, 2H), 7.40 (d, J=8.0 Hz, 2H), 7.31 (d, J=10.0 Hz, 1H), 6.72 (d, J=9.0 Hz, 1H), 6.16 (dd, J=1.5, 10.0 Hz, 1H), 5.91 (s, 1H), 5.38 (s, 1H), 5.08 (t, J=6.5 Hz, 1H), 4.92 (d, J=5.1 Hz, 1H), 4.78 (d, J=3.0 Hz, 1H), 4.55-4.46 (m, 1H), 4.42 (t, J=7.0 Hz, 1H), 4.29 (s, 1H), 4.21-4.14 (m, 1H), 3.82 (t, J=8.5 Hz, 1H), 2.65-2.52 (m, 1H), 2.37-2.25 (m, 1H), 2.18-2.06 (m, 1H), 2.04-1.88 (m, 2H), 1.85-1.57 (m, 5H), 1.40 (s, 3H), 1.37 (s, 9H), 1.29 (d, J=7.0 Hz, 3H), 1.15-0.98 (m, 2H), 0.96-0.76 (m, 9H) ppm.

(2S)-2-Amino-N-[(1S)-1-({4-[(1S,2S,4R,6R,8S,9S,11S,12S,13R)-11-hydroxy-8-(2-hydroxyacetyl)-9,13-dimethyl-16-oxo-5,7-dioxapentacyclo[10.8.00$^{2,9}$.0$^{4,8}$.0$^{13,18}$]icosa-14,17-dien-6-yl]phenyl}carbamoyl)ethyl]-3-methylbutanamide (34g)

Step 4: To a solution of compound 33 (50 mg, 67 µmol) in methylene chloride (3 mL) was added TFA (0.3 mL)

dropwise, which was then stirred at 23° C. for an hour. The volatiles were removed in vacuo to yield crude compound 34 g (42 mg) as an oil, which was used the next step without further purification. ESI m/z: 650 (M+H)+.

1-(4-{2-Azatricyclo[10.4.0.0^{4,9}]hexadeca-1(12),4(9), 5,7,13,15-hexane-10-yn-2-yl}-4-oxobutanamido)-N-[(1S)-1-{[(1S)-1-({4-[(1S,2S,4R,6R,8S,9S,11S,12S, 13R)-11-hydroxy-8-(2-hydroxyacetyl)-9,13-dimethyl-16-oxo-5,7-dioxapentacyclo[10.8.00^{2,9}.0^{4,8}.0^{13,18}]icosa-14,17-dien-6-yl]phenyl}carbamoyl) ethyl]carbamoyl}-2-methylpropyl]-3,6,9,12-tetraoxapentadecan-15-amide (LP1)

Step 5: A solution of DIBAC-suc-PEG$_4$-OH (VI-8, 41 mg, 74 μmol), DIPEA (24 mg, 0.19 mmol) and HATU (47 mg, 0.12 mmol) in DMF (5 mL) was stirred at 23° C. for 30 minutes, and then (34g) (40 mg, 62 μmol) was added. After being stirred at 23° C. for another 2 hours, the reaction mixture was directly purified by prep-HPLC (method B) to yield LP1 (33 mg, 44% yield in 2 steps) as a white solid. ESI m/z: 1185 (M+H)+. NMR (500 MHz, DMSO$_{d6}$) δ 9.97 (s, 1H), 8.18 (d, J=6.5 Hz, 1H), 7.87 (d, J=8.5 Hz, 1H), 7.75 (t, J=5.5 Hz, 1H), 7.67 (d, J=6.5 Hz, 1H), 7.63-7.56 (m, 3H), 7.53-7.41 (m, 3H), 7.42-7.27 (m, 6H), 6.19-6.14 (m, 1H), 5.93 (s, 1H), 5.38 (s, 1H), 5.08 (t, J=6.5 Hz, 1H), 5.03 (d, J=14.0 Hz, 1H), 4.92 (d, J=5.1 Hz, 1H), 4.78 (d, J=3.0 Hz, 1H), 4.55-4.46 (m, 1H), 4.42 (t, J=7.0 Hz, 1H), 4.29 (s, 1H), 4.21-4.14 (m, 2H), 3.63-3.55 (m, 3H), 3.50-3.40 (m, 12H), 3.32-3.26 (m, 2H), 3.10-3.05 (m, 2H), 2.65-2.52 (m, 2H), 2.48-2.48 (m, 2H), 2.40-2.25 (m, 3H), 2.18-2.06 (m, 1H), 2.04-1.88 (m, 3H), 1.85-1.57 (m, 5H), 1.40 (s, 3H), 1.28 (d, J=7.0 Hz, 3H), 1.15-0.98 (m, 2H), 0.96-0.84 (m, 6H), 0.84-0.80 (d, J=7.0 Hz, 3H) ppm.

Example 38

Figure 15:
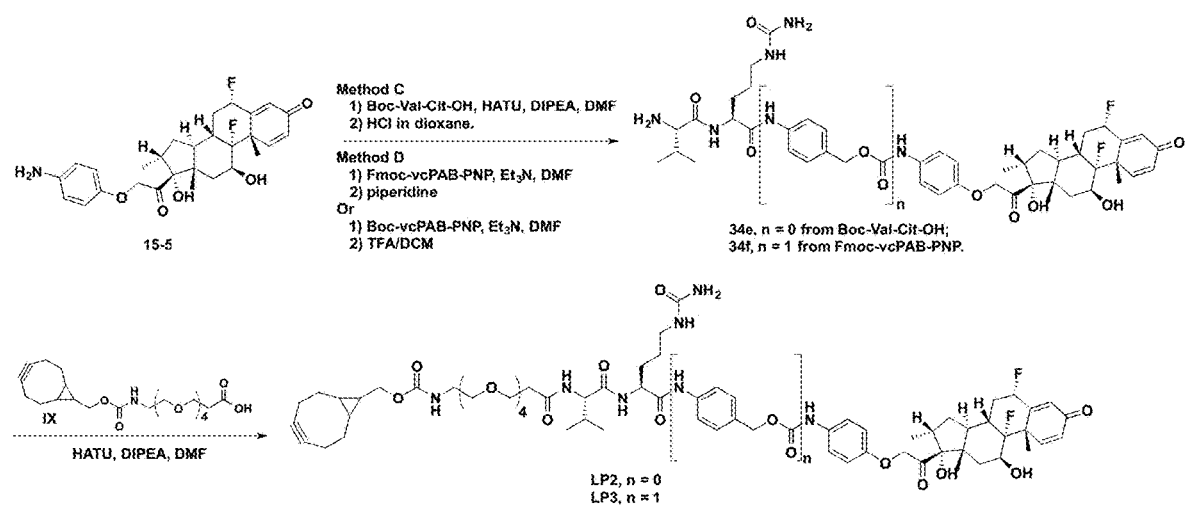
FIG. 15 shows a sequence for synthesizing Linker-Payload 2 (LP2) and Linker-Payload 3 (LP3).

The example demonstrates a method for making Linker-Payload (LP2). The following Example refers to FIG. 15.

Tert-Butyl N-[(1S)-1-{[(1S)-4-(carbamoylamino)-1-[(4-{2-[(1R,2S,8S,10S,11S,13R,14R,15S,17S)-1,8-difluoro-14,17-dihydroxy-2,13,15-trimethyl-5-oxo-tetracyclo[8.7.0.0^{2,7}.0^{11,15}]heptadeca-3,6-dien-14-yl]-2-oxoethoxy}phenyl)carbamoyl]butyl] carbamoyl}-2-methylpropyl]carbamate (34e)

General Procedure C: To a solution of Boc-Val-Ala-OH or Boc-Val-Cit-OH (1.0 equiv.) in an organic solvent (such as DCM or DMF) were added a base (such as DIPEA) (2.0 equiv.) and HATU (1.2 equiv.) at 20-25° C. The mixture was stirred at 20-25° C. for 30 minutes followed with the addition of an aniline (1.1 equiv.). The mixture was further stirred for 16 hours until the peptide was consumed according to LC-MS. To the reaction mixture was then added TFA (0.05 mL per 10 mg of peptide). The mixture was stirred at 20-25° C. for another hour. The volatiles were removed under reduced pressure and the residue was directly purified by prep-HPLC (method B).

Step 1: To a solution of Boc-VC (VC is Val-Cit) (67 mg, 0.18 mmol) in DMF (3 mL) were added HATU (68 mg, 0.18 mmol) and NMM (30 mg, 0.30 mmol), and the resulting solution was stirred at 23° C. for 10 minutes. To the reaction mixture was then added compound 15-5 (75 mg, 0.15 mmol). After stirring at 23° C. overnight, the reaction mixture was poured into ethyl acetate (80 mL), washed with brine, and then dried over anhydrous sodium sulfate. The combined organic solution was concentrated in vacuo and the residue was purified by flash chromatography (0-10% methanol in methylene chloride) to yield (34e) (0.12 g, yield 89%) as a white solid. ESI m/z: 858 (M+H)+. $^1$H NMR (MeOD$_{d4}$, 500 MHz) δ 7.54-7.47 (m, 2H), 7.36 (d, J=10.0 Hz, 1H), 6.90-6.87 (m, 2H), 6.34 (dd, J=10.0, 1.5 Hz, 1H), 6.31 (s, 1H), 5.63-5.50 (m, 1H), 5.20 (d, J=18.0 Hz, 1H), 4.80 (d, J=18.0 Hz, 1H), 4.54-4.47 (m, 1H), 4.32-4.30 (m, 1H), 3.92-3.81 (m, 1H), 3.23-3.11 (m, 3H), 2.65-2.52 (m, 1H), 2.43-2.32 (m, 3H), 2.11-1.99 (m, 1H), 1.79-1.58 (m, 9H), 1.46-1.24 (m, 11H), 1.06 (s, 3H), 1.00-0.92 (m, 9H) ppm.

Bicyclo[6.1.0]non-4-yn-9-ylmethyl N-(14-{[(1S)-1-{[(1S)-4-(carbamoylamino)-1-[(4-{2-[(1R,2S,8S, 10S,11S,13R,14R,15S,17S)-1,8-difluoro-14,17-dihydroxy-2,13,15-trimethyl-5-oxotetracyclo [8.7.0.0^{2,7}.0^{11,15}]heptadeca-3,6-dien-14-yl]-2-oxoethoxy}phenyl)carbamoyl]butyl]carbamoyl}-2-methylpropyl]carbamoyl}-3,6,9,12-tetraoxatetradecan-1-yl)carbamate (LP2)

Step 2: To a solution of intermediate compound 34e (25 mg, 29 μmol) in methylene chloride (2 mL) was added TFA (1 mL), and the resulting mixture was stirred at 23° C. for an hour. The volatiles were removed in vacuo to yield a residue (25 mg, ESI m/z: 758.3 (M+H)+) as brown oil residue.

To a solution of BCN-PEG$_4$-acid (VII in FIG. 12, 18 mg, 41 μmol) in DMF (2 mL) were added HATU (15 mg, 41 μmol) and NMM (6.9 mg, 41 μmol), and the resulting solution was stirred at 23° C. for a half hour. To the reaction solution was then added a solution of the brown oil residue obtained above in DMF (1 mL). After stirring at 23° C. overnight, the mixture was worked up and purified directly by prep-HPLC (method B) to yield LP2 (15 mg, 37% yield) as a white solid. ESI m/z: 1181.4 (M+H)+. $^1$H NMR (DMSO$_{d6}$, 400 MHz) (rotamer) δ 9.82 and 9.37 (s, 1H), 8.39 (d, J=8.0 Hz, 0.4H), 8.09 (d, J=7.2 Hz, 0.6H), 8.00 (d, J=8.0 Hz, 0.4H), 7.88 (d, J=8.8 Hz, 0.6H), 7.55 (d, J=8.8 Hz, 1H), 7.49 (d, J=8.8 Hz, 1H), 7.27 (d, J=10.0 Hz, 1H), 7.10 (br s, 1H), 6.80 (m, 2H), 6.29 (dd, J=10.0, 1.0 Hz, 1H), 6.11 (s, 1H), 5.99-5.94 (m, 1H), 5.72-5.56 (m, 1H), 5.43-5.41 (m, 3H), 5.31 (s, 1H), 5.22 (d, J=18.0 Hz, 1H), 4.71 (d, J=18.0 Hz, 1H), 4.37-4.31 (m, 1H), 4.24-4.14 (m, 2H), 4.04 (s, 1H), 4.02 (s, 1H), 3.62-3.56 (m, 2H), 3.50-3.45 (m, 12H), 3.40-3.37 (m, 2H), 3.13-3.08 (m, 2H), 3.00-2.92 (m, 3H), 2.54-2.33 (m, 2H), 2.25-2.08 (m, 8H), 2.09-1.90 (m, 1H), 1.78-1.23 (m, 15H), 1.14-1.09 (m, 1H), 0.89-0.82 (m, 14H) ppm.

Example 39

The example demonstrates a method for making Linker-Payload (LP3). The following Example refers to FIG. 15.

{4-[(2S)-2-[(2S)-2-Amino-3-methylbutanamido]-5-(carbamoylamino)pentanamido]phenyl}methyl N-(4-{2-[(1R,2S,8S,10S,11S,13R,14R,15S,17S)-1,8-difluoro-14,17-dihydroxy-2,13,15-trimethyl-5-oxotetracyclo[8.7.0.0^{2,7}.0^{11,15}]heptadeca-3,6-dien-14-yl]-2-oxoethoxy}phenyl) carbamate (34f)

General procedure D: Step 1: To a solution of payload an aniline (1.0 equiv.) in DMF were added Fmoc-vcPAB-PNP (1.1 equiv.), HOBt (1.5 equiv.) and DIPEA (2.0 equiv.) at RT. The mixture was stirred at RT (18-30° C.) until the starting material was consumed according to LC-MS. Step 2: To the reaction mixture was added piperidine (0.03 mL per 10 mg of payload) and the mixture was stirred at RT (18-30° C.) for an hour until Fmoc was removed monitored by LC-MS. After filtered through membrane, the reaction solution was directly purified by reversed phase flash chromatography or prep-HPLC to generate the vcPAB carbonate.

When N-Boc-vcPAB-PNP was used to replace Fmoc-vcPAB-PNP in the Step 1 reaction, the N-Boc vcPAB carbonate was obtained from Step 1. After purification, the N-Boc vcPAB carbonate was redissolved in DCM, and was treated with TFA (TFA concentration <25%) at 0° C. until the Boc was removed monitored by LC-MS. The reaction mixture was concentrated to remove the volatiles and the resulting residue was purified by chromatography or prep-HPLC to generate the vcPAB carbonate.

To a solution of Fmoc-vcPAB-PNP (73 mg, 96 μmol) in DMF (1 mL) were added compound 15-5 (40 mg, 80 μmol), DMAP (20 mg, 0.16 mmol), HOBt (23 mg, 0.16 mmol) and DIPEA (55 mg, 0.40 mmol) successively at RT. The reaction mixture was stirred at RT for half an hour until (15-5) was totally consumed according to LC-MS. (ESI: 565.3 (M+H)$^+$). To the resulting mixture was then added piperidine (34 mg, 0.40 mmol) at RT. After stirring at RT for further 30 minutes, which was monitored by LCMS, the resulting mixture was directly purified by reversed phase flash chromatography (0-30% acetonitrile in water) to (34f) (50 mg, yield 69%) as a pale yellow solid. ESI: 907 (M+H)$^+$ Bicyclo[6.1.0]non-4-yn-9-ylmethyl N-(14-{[(1S)-1-{[(1S)-4-(carbamoylamino)-1-{[4-({[4-{2-[(1R,2S,8S,10S,11S,13R,14R,15S,17S)-1,8-difluoro-14,17-dihydroxy-2,13,15-trimethyl-5-oxotetracyclo[8.7.0.0$^{2,7}$0.$^{11,15}$]heptadeca-3,6-dien-14-yl]-2-oxoethoxy}phenyl)carbamoyl]oxy}methyl)phenyl]carbamoyl}butyl]carbamoyl}-2-methylpropyl]carbamoyl}-3,6,9,12-tetraoxatetradecan-1-yl)carbamate (LP3)

Step 3: To a solution of BCN-PEG$_4$-acid (60 mg, 67 μmol) in DMF (3.6 mL) were added HATU (27 mg, 70 μmol) and DIPEA (20 mg, 0.15 mmol) successively at RT. The reaction mixture was stirred at RT for half an hour followed by the addition of compound (34f) (50 mg, 60 μmol) portionwise. The reaction mixture was then stirred at RT for 2 hours until compound 34f was totally consumed according to LCMS. The reaction mixture was then directly purified by prep-HPLC (method B) to yield compound LP3 (36 mg, yield 54%) as a white solid. ESI: 1330 (M+H)$^+$. $^1$H NMR (400 MHz, DMSO$_{d6}$) δ 10.02 (s, 1H), 9.56 (s, 1H), 8.14 (d, J=7.2 Hz, 1H), 7.89 (d, J=8.8 Hz, 1H), 7.62 (d, J=8.4 Hz, 2H), 7.35 (d, J=8.4 Hz, 4H), 7.27 (d, J=10.4 Hz, 1H), 7.11 (t, J=4.4 Hz, 1H), 6.78 (d, J=8.8 Hz, 2H), 6.33-6.26 (m, 1H), 6.10 (s, 1H), 5.98 (t, J=5.4 Hz, 1H), 5.75-5.52 (m, 1H), 5.42 (s, 3H), 5.30 (s, 1H), 5.20 (d, J=18.4 Hz, 1H), 5.05 (s, 2H), 4.70 (d, J=18.4 Hz, 1H), 4.43-4.35 (m, 1H), 4.26-4.15 (m, 2H), 4.02 (d, J=7.6 Hz, 2H), 3.64-3.55 (m, 2H), 3.49 (s, 11H), 3.38 (t, J=6.0 Hz, 2H), 3.11 (dd, J=11.8, 5.9 Hz, 2H), 3.05-2.88 (m, 3H), 2.44-2.31 (m, 2H), 2.28-2.08 (m, 9H), 2.02-1.90 (m, 1H), 1.76-1.10 (m, 16H), 0.91-0.77 (m, 14H) ppm. HPLC purity: >99%, retention time: 7.03 min.

Example 40

Figure 16:
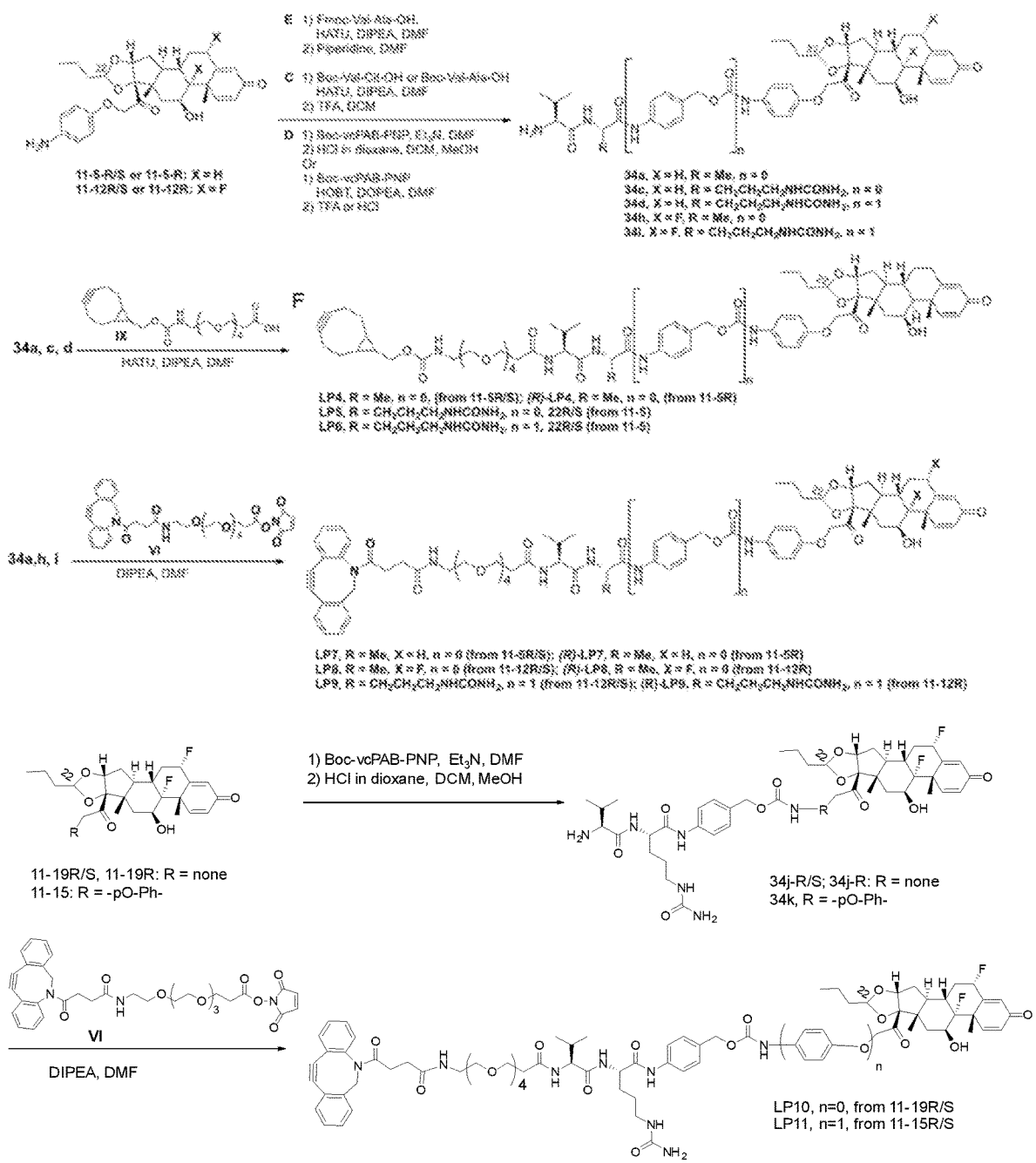
FIG. 16 shows a sequence for synthesizing Linker-Payloads 4-11 (LP4-LP11).

The example demonstrates a method for making Linker-Payload (LP4). The following Example refers to FIG. 16.

(2S)-2-Amino-N-[(1S)-1-[(4-{2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]-3-methylbutanamide (34a)

General procedure E: To a solution of Fmoc-Val-Ala-OH (1.2 equiv.) in DMF (0.2 mL per 10 mg of peptide) were added DIPEA (3.0 equiv.) and HATU (1.4 equiv.) at 20-25° C. The mixture was stirred at 20-25° C. for 5 minutes followed with the addition of aniline (1.0 equiv.). The mixture was stirred for additional 2 hours until the peptide was totally consumed, according to LCMS. To the reaction mixture was then added piperidine (5.0 equiv.). The mixture was stirred at 20-25° C. for 2 hour. After filtering through membrane, the reaction solution was directly purified by reversed phase flash chromatography (0-100% acetonitrile in aq. ammonium bicarbonate (10 mM)) or prep-HPLC (method B). Compound (34a) was obtained following this General procedure.

Alternatively compound (34a) was obtained according to General Procedure C. To a solution of Boc-Val-Ala-OH (0.29 g, 1.0 mmol) in methylene chloride (5 mL) were added DIPEA (0.26 g, 2.0 mmol) and HATU (0.46 g, 1.2 mmol), and the mixture was stirred at 23° C. for 30 minutes and to the reaction mixture was then added compound (11-5) (0.57 g, 1.1 mmol). After stirring at 23° C. for additional 16 hours, to the reaction mixture was added TFA (1.5 mL) and the resulting mixture was stirred at 23° C. for another hour. The volatiles were removed under reduced pressure and the residue was directly purified by prep-HPLC (method B) to yield 34a (0.17 g, 25% yield in 2 steps) as a white solid. ESI m/z: 692 (M+H)$^+$. NMR (500 MHz, DMSO$_{d6}$) δ 10.00 (s, 1H), 8.47 (d, J=6.5 Hz, 1H), 7.57-7.47 (m, 2H), 7.33 (d, J=10 Hz, 1H), 6.87-6.82 (m, 2H), 6.18 (d, J=10 Hz, 1H), 5.93 (s, 3H), 5.25-5.11 (m, 1H), 5.09 (d, J=6.5 Hz, 1H), 4.92-4.65 (m, 3H), 4.55-4.40 (m, 1H), 4.40-4.30 (m, 1H), 2.32-2.22 (m, 1H), 2.18-1.80 (m, 5H), 1.65-1.45 (m, 5H), 1.45-1.25 (m, 9H), 1.25-0.98 (m, 2H), 0.96-0.76 (m, 13H) ppm.

Bicyclo[6.1.0]non-4-yn-9-ylmethyl N-(14-{[(1S)-1-{[(1S)-1-[(4-{2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]carbamoyl}-3,6,9,12-tetraoxatetradecan-1-yl)carbamate (LP4)

General procedure F: To a solution of an BCN-PEG$_4$-acid or its NHS-ester in DMF were added HATU (1 eq.) and DIPEA (2.5 eq.). The mixture was stirred at 25° C. for 30 minutes followed by the addition of a solution of an amine. After stirring at 25° C. for 2 hours monitored by LC-MS, the starting materials were consumed and the mixture was purified directly by prep-HPLC to yield the desired amide.

To a solution of BCN-PEG$_4$-acid (IX, 70 mg, 0.16 mmol) in DMF (8 mL) were added HATU (66 mg, 0.17 mmol) and DIPEA (56 mg, 0.43 mmol) successively. The mixture was stirred at 25° C. for 30 minutes followed by the addition of a solution of 34a (0.10 g, 0.15 mmol). After stirring at 25° C. for 2 hours, the mixture was purified directly by prep-HPLC (method B) to yield LP4 (25 mg, 16% yield) as a white solid. ESI m/z=1116 (M+H)$^+$.

Using chiral compound 11-5R as the starting material, chiral (R)-LP4 was obtained as a white solid (24 mg, 31% yield) according to General procedure F. ESI m/z: 1115

(M+H)+. 1H NMR (500 MHz, DMSO$_{d6}$) (rotamers) δ 9.78 (s, 0.5H), 9.69 (s, 0.5H), 8.40 (d, J=7.5 Hz, 0.5H), 8.15 (d, J=7.0 Hz, 0.5H), 8.01 (d, J=8.0 Hz, 0.5H), 7.89 (d, J=9.0 Hz, 0.5H), 7.57 (d, J=9.0 Hz, 1H), 7.51 (d, J=9.0 Hz, 1H), 7.32 (d, J=10.1 Hz, 1H), 7.09 (s, 1H), 6.85 (d, J=9.1 Hz, 2H), 6.18 (d, J=11.4 Hz, 1H), 5.93 (s, 1H), 5.10 (d, J=18.5 Hz, 1H), 4.86-4.67 (m, 4H), 4.45-4.36 (m, 1H), 4.33 (s, 1H), 4.20 (t, J=7.5 Hz, 0.5H), 4.10 (t, J=7.8 Hz, 0.5H), 4.03 (d, J=8.0 Hz, 2H), 3.59 (d, J=6.6 Hz, 2H), 3.49-3.45 (m, 11H), 3.39 (s, 2H), 3.30 (s, 2H), 3.11 (dd, J=11.4, 5.9 Hz, 2H), 2.47-2.43 (m, 1H), 2.38-2.12 (m, 8H), 2.03-1.83 (s, 5H), 1.62-1.51 (m, 6H), 1.42-1.24 (m, 10H), 1.02-0.94 (m, 2H), 0.90-0.82 (m, 14H) ppm. Anal. HPLC: 100%, Retention time: 9.49 min (method A).

Example 41

The example demonstrates a method for making Linker-Payload (LP5). The following Example refers to FIG. 16.

(2S)-2-[(2S)-2-Amino-3-methylbutanamido]-5-(carbamoylamino)-N-(4-{2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)pentanamide (34c)

Compound 34c was obtained following the General Procedure C. A mixture of Boc-vc (0.26 g, 0.50 mmol), DIPEA (0.19 g, 0.60 mmol) and HATU (0.23 g, 0.60 mmol) in DMF (10 mL) was stirred at 23° C. for 30 minutes and to the mixture was then added 11-5 (0.28 g, 0.55 mmol). After stirring at 23° C. for 16 hours, the reaction mixture was directly purified by reversed phase flash chromatography (0-50% acetonitrile in water) to yield a crude (ESI m/z 878 (M+H)+), which was dissolved in methylene chloride (8 mL) and treated with TFA (3 mL). The resulting mixture was stirred at 23° C. for one hour. The volatiles were removed under reduced pressure and the residue was directly purified by prep-HPLC (method B) to yield compound 34c (0.12 g, 31% yield in 2 steps) as a white solid. ESI m/z: 778 (M+H)+. 1H NMR (500 MHz, DMSO$_{d6}$) δ 9.97 (d, J=12.0 Hz, 1H), 8.10 (m, 1H), 7.51 (d, J=6.5 Hz, 2H), 7.32 (dd, J=10.1, 2.5 Hz, 1H), 6.83 (dd, J=15.9, 9.0 Hz, 2H), 6.17 (d, J=10.0 Hz, 1H), 5.97 (t, J=5.0 Hz, 1H), 5.93 (s, 1H), 5.40 (s, 2H), 5.22 (t, J=4.8 Hz, 1H), 5.12 (d, J=6.0 Hz, 1H), 5.09 (d, J=6.5 Hz, 1H), 4.83-4.67 (m, 3H), 4.47-4.37 (m, 1H), 4.35-4.29 (m, 1H), 3.05-2.90 (m, 3H), 2.57-2.51 (m, 1H), 2.30 (d, J=12.0 Hz, 1H), 2.13-1.74 (m, 7H), 1.70-1.46 (m, 7H), 1.45-1.29 (m, 7H), 1.17-0.93 (m, 2H), 0.91-0.82 (m, 9H), 0.77 (dd, J=6.7, 2.7 Hz, 3H) ppm.

Bicyclo[6.1.0]non-4-yn-9-ylmethyl N-(14-{[(1S)-1-{[(1S)-4-(carbamoylamino)-1-[(4-{2-[(1 S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]butyl]carbamoyl}-2-methylpropyl]carbamoyl}-3,6,9,12-tetraoxatetradecan-1-yl)carbamate (LP5)

LP5 was obtained following the General procedure F. A solution of BCN-PEG4-acid (IX in FIG. 15, 0.28 g) in methylene chloride (6 mL) was added to a mixture of HATU (59 mg, 0.15 mmol) and DIPEA (50 mg, 0.39 mmol) in DMF (5 mL). The reaction mixture was stirred at 25° C. for 30 minutes and to it was added compound 34c (0.10 g, 0.13 mmol) in one portion. The resulting mixture was stirred at 25° C. overnight and was directly purified by prep-HPLC (method B) to yield LP5 (35 mg, 23% yield) as a pale yellow solid. ESI m/z=1202 (M+H)+. 1H NMR (400 MHz, MeOD$_{d4}$) δ 7.61-7.43 (m, 3H), 6.87 (t, J=8.6 Hz, 2H), 6.26 (d, J=10.0 Hz, 1H), 6.02 (s, 1H), 5.29-5.02 (m, 2H), 4.84-4.65 (m, 2H), 4.51-4.44 (s, 2H), 4.22-4.05 (m, 3H), 3.80-3.68 (m, 2H), 3.67-3.45 (m, 14H), 3.22-3.08 (m, 2H), 2.72-2.50 (m, 3H), 2.45-2.33 (m, 1H), 2.30-2.02 (m, 10H), 1.99-1.82 (m, 2H), 1.81-1.32 (m, 17H), 1.26-0.85 (m, 17H) ppm.

Example 42

The example demonstrates a method for making Linker-Payload (LP6). The following Example refers to FIG. 16.

{4-[(2S)-2-[(2S)-2-Amino-3-methylbutanamido]-5-(carbamoylamino)pentanamido]phenyl}methyl N-(4-{2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamate (34d)

Compound 34d was prepared according to General procedure D.

Step 1: To a solution of compound (11-5) from Table 1 (66 mg, 0.10 mmol) in DMF (3.5 mL) were added successively Boc-vcPAB-PNP (64 mg, 0.12 mmol), HOBt (14 mg, 0.10 mmol) and DIPEA (13.0 mg, 0.10 mmol). The reaction mixture was stirred at 13° C. overnight and was purified directly by prep-HPLC (method B) to yield intermediate Boc-34d (61 mg, yield 58%) as a white solid. ESI m/z: 1027.3 (M+H)+. 1H NMR (MeOD$_{d4}$, 400 MHz) δ 7.60 (d, J=8.4 Hz, 2H), 7.46 (d, J=10.4 Hz, 1H), 7.38-7.33 (m, 4H), 6.87-6.83 (m, 2H), 6.26 (dt, J=10.0, 2.0 Hz, 1H), 6.02 (s, 1H), 5.26-5.03 (m, 4.2H), 4.82-4.67 (m, 1.8H), 4.54-4.51 (m, 1H), 4.48-4.43 (m, 1H), 3.91 (d, J=6.4 Hz, 1H), 3.31-3.18 (m, 1H), 3.14-3.08 (m, 1H), 2.70-2.63 (m, 1H), 2.40-2.37 (m, 1H), 2.26-2.00 (m, 4H), 1.94-1.72 (m, 4H), 1.68-1.35 (m, 20H), 1.22-0.92 (m, 14H) ppm.

Step 2: To a solution of Boc-34d (59 mg, 58 μmol) in DCM (2 mL) and MeOH (1 mL) was added dropwise HCl in dioxane (4 N, 1.5 mL) at 0° C. The mixture was then stirred at RT (14° C.) for 4 hours. The volatiles were removed in vacuo to yield 34d (60 mg, crude) as brown oil, which was used directly for the next step. ESI m/z: 927 (M+H)+.

Bicyclo[6.1.0]non-4-yn-9-ylmethyl N-(14-{[(1S)-1-{[(1S)-4-(carbamoylamino)-1-{[4-({[(4-{2-[(1S,2S,4R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]oxy}methyl)phenyl]carbamoyl}butyl]carbamoyl}-2-methylpropyl]carbamoyl}-3,6,9,12-tetraoxatetradecan-1-yl)carbamate (LP6)

LP6 was obtained as a white solid (24 mg, 31% yield) following the General procedure F. ESI m/z: 1350.5 (M+H)+. 1H NMR (DMSO$_{d6}$, 400 MHz) δ 10.02 (s, 1H), 9.58 (s, 1H), 8.13 (d, J=7.6 Hz, 1H), 7.88 (d, J=8.4 Hz, 1H), 7.61 (d, J=8.4 Hz, 2H), 7.36-7.30 (m, 5H), 7.11 (t, J=4.8 Hz, 1H), 6.84-6.78 (m, 2H), 6.19-6.16 (m, 1H), 5.98 (t, J=5.2 Hz, 1H), 5.93 (s, 1H), 5.42 (s, 2H), 5.23-5.06 (m, 4H), 4.80-4.67 (m, 3H), 4.39-4.31 (m, 2H), 4.23 (t, J=7.2 Hz, 1H), 4.02 (d, J=8.0 Hz, 2H), 3.64-3.55 (m, 2H), 3.49 (m, 12H), 3.42-3.27 (m, 3H), 3.13-2.89 (m, 4H), 2.41-2.12 (m, 9H), 2.03-1.95 (m, 2H), 1.91-1.82 (m, 2H), 1.75-1.68 (m, 1H), 1.61-1.20 (m, 16H), 1.15-0.95 (m, 2H), 0.92-0.81 (m, 15H) ppm. Anal. HPLC: 69%+31%=100%, Retention time: 8.86 min and 8.92 min (method B).

Example 43

The example demonstrates a method for making Linker-Payload LP7. The following Example refers to FIG. 16.

(Bicyclo[6.1.0]non-4-yn-9-ylmethyl N-(14-{[(1S)-1-{[(1S)-1-[(4-{2-[(1S,2S,4R,6R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]carbamoyl}-3,6,9,12-tetraoxatetradecan-1-yl)carbamate (LP7)

LP7 (24 mg, 31% yield in 3 steps from 34a) was obtained as a white solid according to General procedure F. ESI m/z: 1115 (M+H)$^+$. $^1$H NMR (500 MHz, DMSO$_{d6}$) (rotamers) δ 9.78 (s, 0.5H), 9.69 (s, 0.5H), 8.40 (d, J=7.5 Hz, 0.5H), 8.15 (d, J=7.0 Hz, 0.5H), 8.01 (d, J=8.0 Hz, 0.5H), 7.89 (d, J=9.0 Hz, 0.5H), 7.57 (d, J=9.0 Hz, 1H), 7.51 (d, J=9.0 Hz, 1H), 7.32 (d, J=10.1 Hz, 1H), 7.09 (s, 1H), 6.85 (d, J=9.1 Hz, 2H), 6.18 (d, J=11.4 Hz, 1H), 5.93 (s, 1H), 5.10 (d, J=18.5 Hz, 1H), 4.86-4.67 (m, 4H), 4.45-4.36 (m, 1H), 4.33 (s, 1H), 4.20 (t, J=7.5 Hz, 0.5H), 4.10 (t, J=7.8 Hz, 0.5H), 4.03 (d, J=8.0 Hz, 2H), 3.59 (d, J=6.6 Hz, 2H), 3.49-3.45 (m, 11H), 3.39 (s, 2H), 3.30 (s, 2H), 3.11 (dd, J=11.4, 5.9 Hz, 2H), 2.47-2.43 (m, 1H), 2.38-2.12 (m, 8H), 2.03-1.83 (s, 5H), 1.62-1.51 (m, 6H), 1.42-1.24 (m, 10H), 1.02-0.94 (m, 2H), 0.90-0.82 (m, 14H) ppm. Anal. HPLC: 100%, Retention time: 9.47 min (method A).

Example 44

Figure 26:
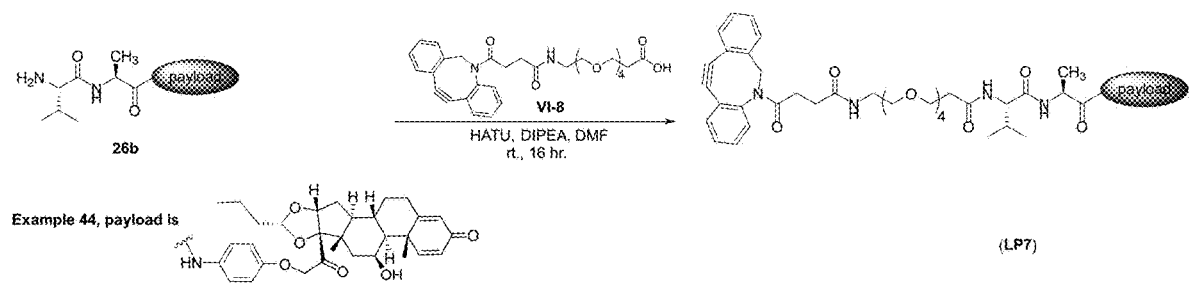
FIG. 26 shows a sequence for synthesizing Linker-Payload (LP7).

The example also demonstrates a method for making Linker-Payload (LP7). The following Example refers to FIG. 26. The following reaction conditions were used:

To a solution of acid (VI-8) (1.0-2.5 equiv.) in DMF (or DCM/DMF) were added DIPEA (1.5-10 equiv.) and HATU (2.5-4.0 equiv.) at room temperature successively. The resulting mixture was stirred at this temperature for 0.5-1 hour before the amine (26b) (1.0 equiv.) was added. The reaction mixture was stirred at room temperature for 2-16 hours until the amine was totally consumed, as monitored by LC-MS. The reaction mixture was filtered through a membrane and the filtrate was concentrated then separated by prep-HPLC (method B) to give the example compound LP7 (20-69% yield) as a white solid.

1-(4-{2-azatricyclo[10.4.0.0$^{4,9}$]hexadeca-1(12),4(9),5,7,13,15-hexaen-10-yn-2-yl}-4-oxobutanamido)-N-[(1S)-1-{[(1S)-1-[(4-{2-[(1S,2S,4R,6R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]-3,6,9,12-tetraoxapentadecan-15-amide (LP7)

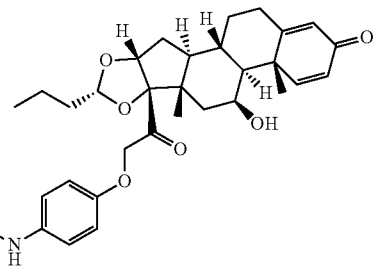
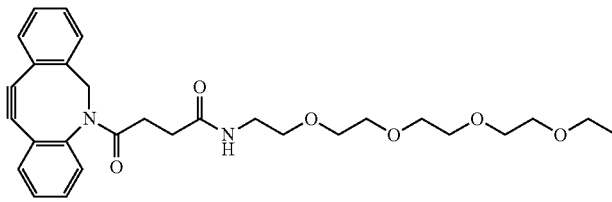

ESI m/z: 1227.6 (M+H)$^+$.

$^1$H NMR (500 MHz, DMSO$_{d6}$) (rotamers) δ 9.79 (s, 0.5H), 9.70 (s, 0.5H), 8.41 (d, J=7.5 Hz, 0.5H), 8.17 (d, J=7.0 Hz, 0.5H), 8.02 (d, J=8.0 Hz, 0.5H), 7.89 (d, J=8.6 Hz, 0.5H), 7.77 (t, J=4.8 Hz, 1H), 7.68 (d, J=7.3 Hz, 1H), 7.62 (d, J=7.3 Hz, 1H), 7.58 (d, J=9.0 Hz, 1H), 7.53-7.43 (m, 4H), 7.40-7.28 (m, 4H), 6.88-6.82 (m, 2H), 6.18 (d, J=9.1 Hz, 1H), 5.93 (s, 1H), 5.10 (d, J=18.4 Hz, 1H), 5.03 (d, J=14.0 Hz, 1H), 4.83-4.67 (m, 4H), 4.45-4.29 (m, 2H), 4.23-4.17 (m, 0.5H), 4.11 (t, J=7.7 Hz, 0.5H), 3.64-3.40 (m, 15H), 3.31-3.26 (m, 2H), 3.13-3.03 (m, 2H), 2.65-2.52 (m, 2H), 2.47-1.26 (m, 24H), 1.06-0.93 (m, 2H), 0.90-0.80 (m, 12H) ppm.

Anal. HPLC: 99%, Retention time: 8.55 min (method B).

Solubility: <0.1 mg/mL water; 0.06 mg/mL 20% DMSO in water; 0.07 mg/mL 30% DMSO in water.

| | | | | Step 1 | | | | | |
|---|---|---|---|---|---|---|---|---|---|
| Amine mg (μmol) | Acid mg (μmol) | HATU mg (μmol) | DIPEA mg (μmol) | DMF (mL) | Temp. (° C.) | Time (hr) | mg % Yield | MS m/z | |
| 26b 30 (43) | VI-8 48 (87) | 40 (105) | 17 (132) | 1 | 25 | 16 | 30 56% | 1227.6 (M + H)$^+$ | |

Example 45

This example demonstrates a method for making Linker-Payload (LP15). The following Example refers to FIGS. 27-28. Note that in FIG. 27, compound 11b is identical to compound 11-5 in FIG. 2.

Step 1: Making Compound (13b), with Reference to FIG. 27.

To a solution of acid Fmoc-Val-Ala-OH (12b) in DMF were added HATU (1.0-2.8 equiv.) and TEA (2.0-5.0 equiv.) at 25° C. After the mixture was stirred at 25° C. for 30 minutes, a solution of amine (11b, i.e., payload, 1.0 equiv.) in DMF (1 mL) was added by syringe. The resulting mixture was stirred at 25° C. for 2-24 hours until the amine was mostly consumed according to LC-MS. To the mixture was then added piperidine or diethylamine (excess), and the mixture was stirred at 25° C. for 1-16 hours until Fmoc was totally removed, as monitored by LCMS. The reaction mixture was filtered through a membrane and the filtrate was concentrated and directly purified by prep-HPLC (method B) or reversed phase flash chromatography to give compound 13b (23-64% yield) as a white solid. Specifically, the following conditions were used:

| Amine mg (mmoL) | Acid mg (mmoL) | Step 1 HATU mg (mmol) | DIPEA mg (mmol) | DMF (mL) | Time (hr) | Step 2 Et$_2$NH (mL) | Time (hr) | Purification* | Yield mg | % m/z (M + H)$^+$ |
|---|---|---|---|---|---|---|---|---|---|---|
| 11b 85 (0.076) | 12b 69 (0.088) | 69 (0.18) | TEA 18 (0.18) | 3 | 2 | 0.5 | 16 | RP | 17, 43% | 832.2 (M/2 + H)$^+$ |

Step 2: Making Compound (17a), with Reference to FIG. 27.

To a solution of compound 13b in DMF were added HATU (1.0-2.8 equiv.) and DIPEA or TEA (2.0-5.0 equiv.) at 25° C. After the mixture was stirred at 25° C. for 30 minutes, a solution of Fmoc-Lys-(PEG)4-COT (13c, 1.0 equiv.) in DMF (1 mL) was added by syringe. The resulting mixture was stirred at 25° C. for 2-24 hours until the amine (13b) was mostly consumed according to LC-MS. To the mixture was then added piperidine or diethylamine (excess), and the mixture was stirred at 25° C. for 1-16 hours until Fmoc was totally removed, as monitored by LC-MS. The reaction mixture was filtered through a membrane and the filtrate was concentrated and directly purified by prep-HPLC (method B) or reversed phase flash chromatography to give compound (17a) (23-64% yield) as a white solid.

Step 3: Making Compound (27b), with Reference to FIG. 27.

To a solution of alkyne (17a) (1.0 equiv.) in DMF or DMSO was added α-cyclodextrin-azide (16a) (See *Synth. Commun.*, 2002, 32(21), 3367-3372; *J. Am. Chem. Soc.*, 2012, 134(46), 19108-19117; *J. Med. Chem.*, 1997, 40(17), 2755-2761; *J. Am. Chem. Soc.*, 1993, the entire contents of each of these publications is herein incorporated by reference in their entirety for all purposes, 115(12), 5035-5040) (1.5-3.0 equiv.). The resulting mixture was then stirred at 20-30° C. for 16 hours to 3 days until the compound 16a was mostly consumed and the desired intermediate mass was detected, as monitored by LC-MS. After filtration, the resulting mixture was directly purified by prep-HPLC (or used directly) to give compound 27b (25-58% yield) as a white solid (with triazole regioisomers). Specifically, the following conditions were used.

| Alkyne mg (mmol) | 16a mg (mmol) | Solvent (mL) | Temp. (° C.) | Time (hr) | Purification | Yield | m/z |
|---|---|---|---|---|---|---|---|
| 50 (0.030) | 60 (0.06) | DMSO (2) | 25 | 48 | RP-B | 46 mg, 58% | 887.9 (M/3 + H)$^+$ |

Step 4: Making Compound (LP15), with Reference to FIG. 28.

The following reaction conditions were used:

| Amine mg (μmol) | Acid mg (μmol) | HATU mg (μmol) | DIPEA mg (μmol) | DMF (mL) | Temp. (° C.) | Time (hr) | mg % Yield | MS m/z |
|---|---|---|---|---|---|---|---|---|
| 27b 13 (6.0) | VI-8 20 (36) | 15 (39) | 4.0 (31) | 2 | 25 | 2 | 6.0 36% | 1259.1 (M/2 + H)$^+$ |

To a solution of acid (VI-8) (1.0-2.5 equiv.) in DMF (or DCM/DMF) were added DIPEA (1.5-10 equiv.) and HATU (2.5-4.0 equiv.) at room temperature successively. The resulting mixture was stirred at this temperature for 0.5-1 hour before the amine (27b) (1.0 equiv.) was added. The reaction mixture was stirred at room temperature for 2-16 hours until the amine (27b) was totally consumed, as monitored by LC-MS. The reaction mixture was filtered through a membrane, the filtrate was concentrated, and then separated by prep-HPLC (method B) to give the example compound (20-69% yield) as a white solid.

1-(4-{2-Azatricyclo[10.4.0.0$^{4,9}$]hexadeca-1(12),4(9), 5,7,13,15-hexaen-10-yn-2-yl}-4-oxobutanamido)-N-[(1R)-5-{2-[(1-{[31,32,33,34,35,36,37,38,39,40,41, 42-dodecahydroxy-10,15,20,25,30-pentakis (hydroxymethyl)-2,4,7,9,12,14,17,19,22,24,27,29-dodecaoxaheptacyclo[26.2.2.2$^{3,6}$.2$^{8,11}$.2$^{13,16}$. 2$^{18,21}$.2$^{23,26}$]dotetracontan-5-yl]methyl}-1H,4H,5H, 6H,7H,8H,9H-cycloocta[d][1,2,3]triazol-4-yl)oxy] acetamido}-1-{[(1S)-1-{[(1S)-1-[(4-{2-[(1S,2S,4R, 8S,9S,11S,12S,13R)-11-hydroxy-9,13-dimethyl-16-oxo-6-propyl-5,7-dioxapentacyclo[10.8.0.0$^{2,9}$. 0$^{4,8}$.0$^{13,18}$]icosa-14,17-dien-8-yl]-2-oxoethoxy}phenyl)carbamoyl]ethyl]carbamoyl}-2-methylpropyl]carbamoyl}pentyl]-3,6,9,12-tetraoxa-pentadecan-15-amide (LP15)

ESI m/z: 1259.1 (M/2+H)$^+$.

$^1$H NMR (500 MHz, DMSO$_{d6}$) (rotamers) δ 9.84 (s, 1H), 8.34 (s, 0.5H), 8.15 (d, J=7.3 Hz, 1H), 8.04 (d, J=6.6 Hz, 1H), 7.90-7.84 (m, 1H), 7.81-7.74 (m, 1.5H), 7.72-7.56 (m, 4H), 7.56-7.27 (m, 11H), 6.89-6.79 (m, 2H), 6.17 (d, J=10.0 Hz, 1H), 5.93 (s, 1H), 5.64-5.44 (m, 12H), 5.24-5.00 (m, 5H), 4.86-4.51 (m, 16H), 4.40-4.16 (m, 5H), 4.05-3.96 (m, 1H), 3.86-3.73 (m, 10H), 3.67-2.88 (m, 35H), 2.80-2.69 (m, 1H), 2.62-2.55 (m, 1H), 2.41-2.20 (m, 6H), 2.10-1.71 (m, 10H), 1.66-1.07 (m, 26H), 1.05-0.79 (m, 17H) ppm. Anal. HPLC: 97%, Retention time: 6.62 and 6.67 min (method B). Retention times are from two triazole-regioisomers.

Example 46

Figure 27:
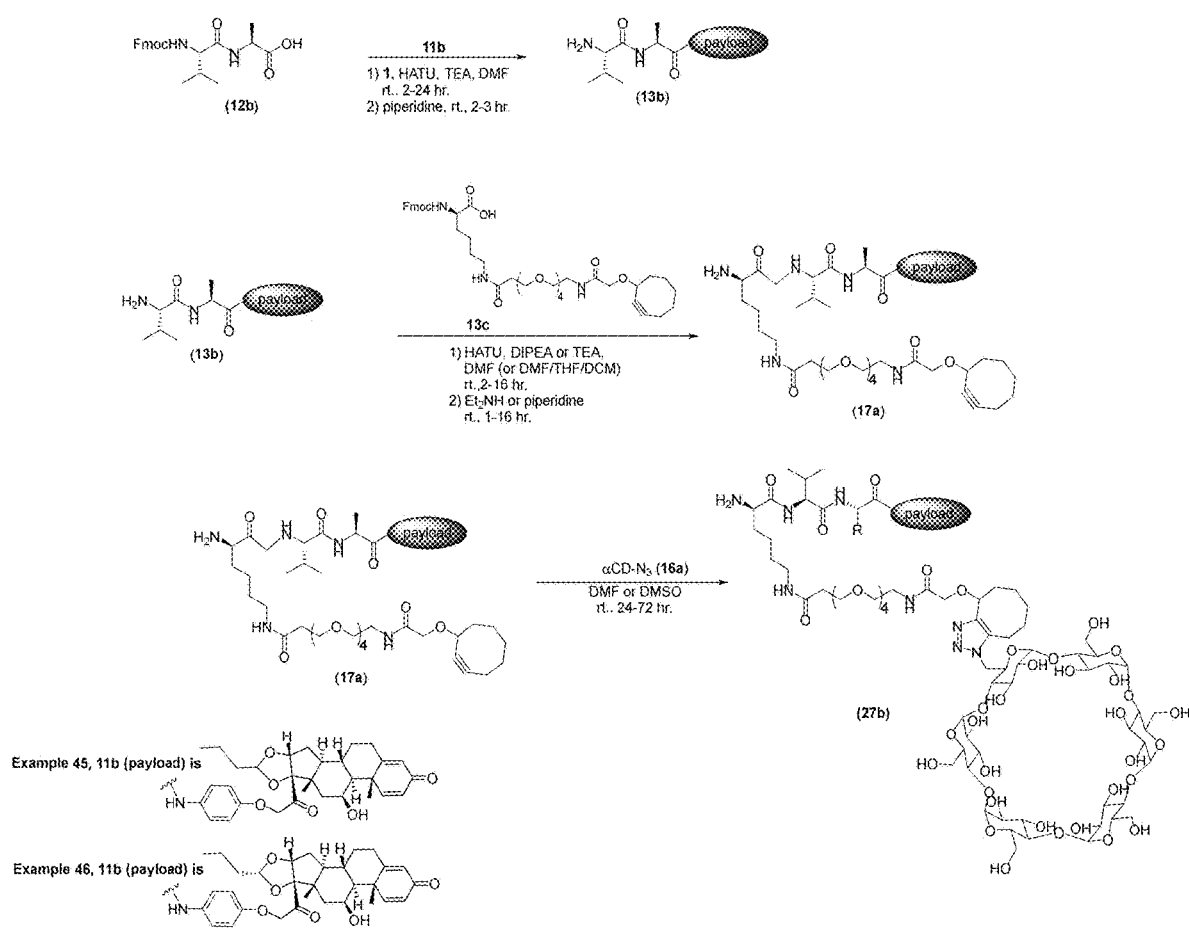
FIG. 27 shows a synthetic process for preparing compound (27b).
Figure 28:
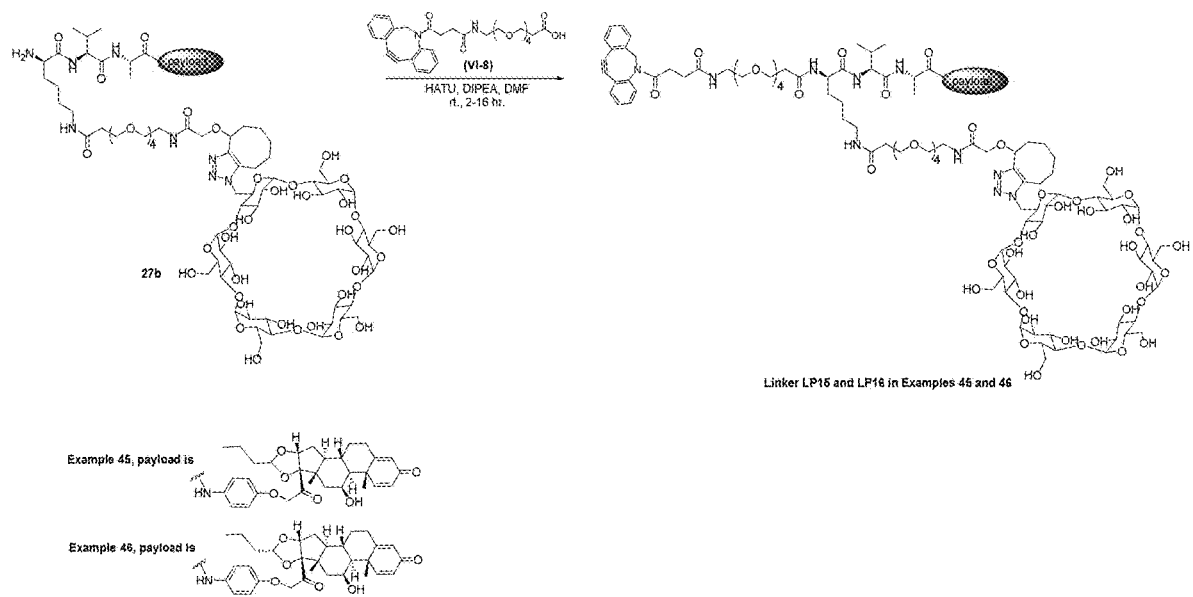
FIG. 28 shows a sequence for synthesizing Linker-Payloads (LP15 and LP16).

This example demonstrates a method for making Linker-Payload (LP16). The following Example refers to FIGS. 27-28. The method for making LP16 was the same as the method for making LP15, in Example 45 herein, except that a different payload was used, as shown in FIGS. 27-28. The following reaction conditions were used:

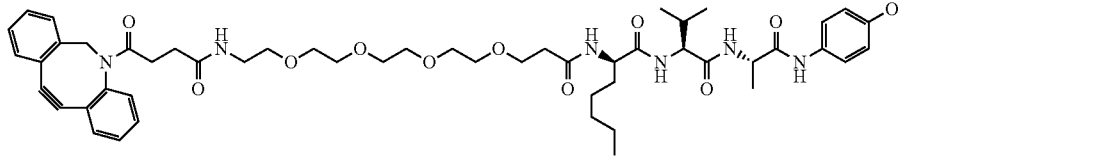

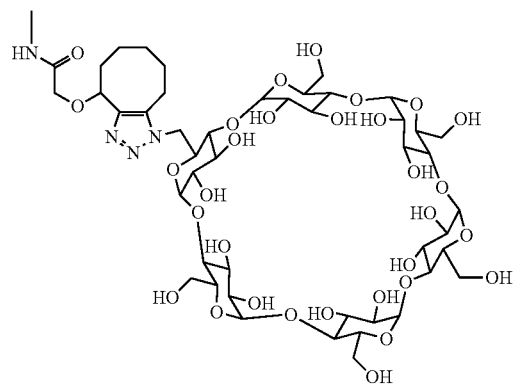

| Step 1 | | | | | | | | | |
|---|---|---|---|---|---|---|---|---|---|
| Amine mg (μmol) | Acid mg (μmol) | HATU mg (μmol) | DIPEA mg (μmol) | DMF (mL) | Temp. (° C.) | Time (hr) | purification | mg % Yield | MS m/z |
| 27b 30 (15) | VI-8 10 (18) | 8.0 (21) | 6.0 (47) | 1 | 15-20 | 16 | B | 18 47% | 1259.1 (M/2 + H)+ |

To a solution of acid VI-8 (1.0-2.5 equiv.) in DMF (or DCM/DMF) were added DIPEA (1.5-10 equiv.) and HATU (2.5-4.0 equiv.) at room temperature successively. The resulting mixture was stirred at this temperature for 0.5-1 hour before the amine (27b) (1.0 equiv.) was added. The reaction mixture was stirred at room temperature for 2-16 hours until the amine (27b) was totally consumed, as monitored by LC-MS. The reaction mixture was filtered through a membrane and the filtrate was concentrated and then separated by prep-HPLC (method B) to give the example compound (20-69% yield) as a white solid.

1-(4-{2-Azatricyclo[10.4.0.0⁴,⁹]hexadeca-1(12),4(9),5,7,13,15-hexaen-10-yn-2-yl}-4-oxobutanamido)-N-[(1R)-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2³,⁶.2⁸,¹¹.2¹³,¹⁶.2¹⁸,²¹.2²³,²⁶]dotetracontan-5-yl]methyl}-1H,4H,5H,6H,7H,8H,9H-cycloocta[d][1,2,3]triazol-4-yl)oxy]acetamido}-1-{[(1S)-1-{[(1S)-1-[(4-{2-[(1S,2S,4R,6R,8S,9S,11S,12S,13R)-11-hydroxy-9,13-dimethyl-16-oxo-6-propyl-5,7-dioxapentacyclo[10.8.0.0²,⁹.0⁴,⁸.0¹³,¹⁸]icosa-14,17-dien-8-yl]-2-oxoethoxy}phenyl)carbamoyl]ethyl]carbamoyl}-2-methylpropyl]carbamoyl}pentyl]-3,6,9,12-tetraoxapentadecan-15-amide (LP16)

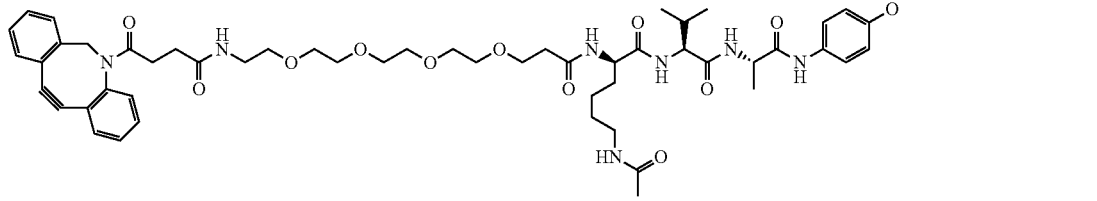

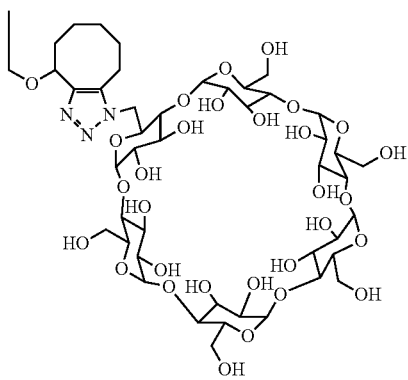

ESI m/z: 839.5 (M/3+H)$^+$, 1259.1 (M/2+H)$^+$ (60%).

$^1$H NMR (500 MHz, DMSO$_{d6}$) (with triazole regioisomer) δ 9.77-9.42 (m, 1H), 8.27-8.20 (m, 0.5H), 8.17-8.01 (m, 2H), 7.86-7.74 (m, 2.5H), 7.70-7.60 (m, 4H), 7.57-7.43 (m, 7H), 7.39-7.28 (m, 6H), 6.88-6.81 (m, 2H), 6.21-6.14 (m, 1H), 5.93 (s, 1H), 5.61-5.42 (m, 10H), 5.16-4.97 (m, 4H), 4.89-4.48 (m, 17H), 4.40-4.28 (m, 4H), 4.16-4.10 (m, 1H), 4.04-3.94 (m, 1H), 3.83-3.74 (m, 7H), 3.65-3.56 (m, 9H), 3.48-3.21 (m, 23H), 3.15-3.06 (m, 4H), 2.97-2.89 (m, 1H), 2.81-2.69 (m, 1H), 2.61-2.53 (m, 2H), 2.40-2.20 (m, 6H), 2.14-2.06 (m, 2H), 2.03-1.95 (m, 4H), 1.91-1.70 (m, 5H), 1.64-1.52 (m, 9H), 1.49-1.25 (m, 14H), 1.13-0.81 (m, 19H) ppm. Anal. HPLC: 98%, Retention time: 6.61 (59%) and 6.73 (39%) min (method B). Retention times are from two triazole-regioisomers.

Solubility: 0.1 mg/mL 10% DMSO in water.

Example 47

The example demonstrates a method for making Linker-Payload (LP8). The following Example refers to FIG. 16.

(2S)-2-[(2S)-2-Amino-3-methylbutanamido]-5-(carbamoylamino)-N-(4-{2-[(1S,2S,4R,8S,9S,11S,12S, 13R)-11-hydroxy-9,13-dimethyl-16-oxo-6-propyl-5, 7-dioxapentacyclo[10.8.0.0$^{2,9}$.0$^{4,8}$.0$^{13,18}$]icosa-14, 17-dien-8-yl]-2-oxoethoxy}phenyl)pentanamide (34h)

Compound (34h) as a white solid was prepared according to General procedure C after purification by prep-HPLC (method B). ESI m/z: 778 (M+H)$^+$. $^1$H NMR (500 MHz, DMSO$_{d6}$) δ 9.97 (d, J=12.0 Hz, 1H), 8.10 (m, 1H), 7.51 (d, J=6.5 Hz, 2H), 7.32 (dd, J=10.1, 2.5 Hz, 1H), 6.83 (dd, J=15.9, 9.0 Hz, 2H), 6.17 (d, J=10.0 Hz, 1H), 5.97 (t, J=5.0 Hz, 1H), 5.93 (s, 1H), 5.40 (s, 2H), 5.22 (t, J=4.8 Hz, 1H), 5.12 (d, J=6.0 Hz, 1H), 5.09 (d, J=6.5 Hz, 1H), 4.83-4.67 (m, 3H), 4.47-4.37 (m, 1H), 4.35-4.29 (m, 1H), 3.05-2.90 (m, 3H), 2.57-2.51 (m, 1H), 2.30 (d, J=12.0 Hz, 1H), 2.13-1.74 (m, 7H), 1.70-1.46 (m, 7H), 1.45-1.29 (m, 7H), 1.17-0.93 (m, 2H), 0.91-0.82 (m, 9H), 0.77 (dd, J=6.7, 2.7 Hz, 3H) ppm.

1-(4-{2-Azatricyclo[10.4.0.0$^{4,9}$]hexadeca-1(12),4(9), 5,7,13,15-hexaen-10-yn-2-yl}-4-oxobutanamido)-N-[(1S)-1-{[(1S)-1-[(4-{2-[(1S,2S,4R,6R,8S,9S,11S, 12R,13S,19S)-12,19-difluoro-11-hydroxy-9,13-dimethyl-16-oxo-6-propyl-5,7-dioxapentacyclo [10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]-3,6,9,12-tetraoxapentadecan-15-amide (LP8)

Compound LP8 (25 mg, 20% yield) was obtained as a white solid according to General procedure F. ESI m/z: 1263 (M/+H)$^+$. $^1$H NMR (400 MHz, DMSO$_{d6}$) δ 9.79 (s, 0.7H), 9.69 (s, 0.3H),8.41 (d, J=8.0 Hz, 0.3H), 8.16 (d, J=8.0 Hz, 0.7H), 8.01 (d, J=7.6 Hz, 0.3H), 7.89 (d, J=7.6 Hz, 0.7H), 7.77 (t, J=5.2 Hz, 1H), 7.70-7.66 (m, 1H), 7.64-7.60 (m, 1H), 7.60-7.54 (m, 1H), 7.54-7.44 (m, 4H), 7.40-7.24 (m, 4H), 6.90-6.82 (m, 2H), 6.30 (dd, J=10 Hz, 1.2 Hz, 1H), 6.11 (s, 1H), 5.72-5.55 (m, 1H), 5.52-5.48 (m, 1H), 5.16-5.08 (m, 1H), 5.06-5.00 (m, 1H), 4.88-4.80 (m, 1H), 4.80-4.76 (m, 1H), 4.74 (t, J=4.0 Hz, 1H), 4.42-4.33 (m, 1H), 4.26-4.06 (m, 2H), 3.64-3.54 (m, 3H), 3.50-3.40 (m, 12H), 3.12-3.02 (m, 2H), 2.70-2.55 (m, 2H), 2.40-2.20 (m, 4H), 2.12-1.90 (m, 2H), 1.86-1.70 (m, 2H), 1.64-1.54 (m, 4H), 1.49 (s, 4H), 1.46-1.34 (m, 3H), 1.29 (d, J=6.8 Hz, 3H), 0.90-0.80 (m, 13H) ppm. Anal. HPLC: 100%, Retention time: 8.26 min (method B).

Example 48

The example demonstrates a method for making Linker-Payload (LP9). The following Example refers to FIG. 16.

{4-[(2S)-2-[(2S)-2-[1-(4-{2-Azatricyclo[10.4.0.0$^{4,9}$] hexadeca-1(12),4(9),5,7,13,15-hexaen-10-yn-2-yl}-4-oxobutanamido)-3,6,9,12-tetraoxapentadecan-15-amido]-3-methyl butanamido]-5-(carbamoylamino) pentanamido]phenyl}methyl N-(4-{2-[(1S,2S,4R, 8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamate (LP9)

Compound (34i) as a white solid was prepared according to General procedure D.

Compound LP9 (20 mg, 22% yield) was obtained according to General procedure F. ESI m/z: 1499 (M+H)$^+$. $^1$H NMR (400 MHz, DMSO$_{d6}$) δ 10.02 (s, 1H), 9.59 (s, 1H),8.14 (d, J=7.6 Hz, 1H), 7.88 (d, J=8.8 Hz, 1H), 7.80-7.75 (m, 1H), 7.70-7.66 (m, 1H), 7.65-7.60 (m, 3H), 7.53-7.45 (m, 3H), 7.40-7.28 (m, 7H), 6.84 (d, J=9.2 Hz, 2H), 6.30 (dd, J=10.4 Hz, J=1.6 Hz, 1H), 6.11 (s, 1H), 6.10-6.0 (m, 1H), 5.72-5.55 (m, 1H), 5.52 (s, 1H), 5.43 (s, 2H), 5.16-5.05 (m, 4H), 4.88-4.70 (m, 3H), 4.43-4.33 (m, 1H), 4.25-4.20 (m, 2H), 3.65-3.55 (m, 3H), 3.50-3.40 (m, 12H), 3.30-3.25 (m, 2H), 3.12-2.90 (m, 4H), 2.70-2.55 (m, 2H), 2.48-2.43 (m, 1H), 2.40-2.35 (m, 1H), 2.30-2.20 (m, 2H), 2.15-1.95 (m, 4H), 1.86-1.75 (m, 2H), 1.64-1.54 (m, 5H), 1.49 (s, 4H), 1.46-1.34 (m, 4H), 1.23 (s, 2H), 0.90-0.80 (m, 12H) ppm. Anal. HPLC: 100%, Retention time: 7.83 min (method B).

Example 49

The example demonstrates a method for making Linker-Payload (LP10). The following Example refers to FIG. 16.

(1S,2S,4R,6R,8S,9S,11S,12R,13S,19S)-8-(2-Aminoacetyl)-12,19-difluoro-11-hydroxy-9,13-dimethyl-6-propyl-5,7-dioxapentacyclo[10.8.0.0$^{2,9}$.0$^{4,8}$.0$^{13,18}$] icosa-14,17-dien-16-one (34j)

Compound 34j (80 mg, 64% yield) was obtained from compound 1-19 according to the General procedure D. ESI m/z: 871 (M+H)$^+$.

{4-[(2S)-2-[(2S)-2-[1-(4-{2-Azatricyclo[10.4.0.0$^{4,9}$] hexadeca-1(12),4(9),5,7,13,15-hexaen-10-yn-2-yl}-4-oxobutanamido)-3,6,9,12-tetraoxapentadecan-15-amido]-3-methyl butanamido]-5-(carbamoylamino) pentanamido]phenyl}methyl N-(4-{2-[(1S,2S,4R, 8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamate (LP10)

Following the General procedure F, compound (LP10) (20 mg, 22% yield) was obtained from the reaction of 34j (43 mg, 50 µmol) with DIBAC-suc-PEG$_4$-NHS ester (VI), after purification by prep-HPLC (method B). ESI m/z: 1406 (M+H)$^+$. $^1$H NMR (DMSO$_{d6}$, 500 MHz) δ 9.99 (s, 1H), 8.11

(d, J=7.5 Hz, 1H), 7.88 (d, J=8.5 Hz, 1H), 7.80-7.75 (m, 1H), 7.70-7.66 (m, 1H), 7.65-7.60 (m, 3H), 7.53-7.33 (m, 6H), 7.33-7.28 (m, 3H), 6.30 (dd, J=10.0 Hz and 1.5 Hz, 1H), 6.11 (s, 1H), 6.10-6.00 (m, 1H), 5.72-5.55 (m, 2H), 5.41 (s, 2H), 5.05-5.01 (m, 1H), 4.97 (s, 2H), 4.80-4.72 (m, 1H), 4.60-4.58 (m, 1H), 4.43-4.33 (m, 1H), 4.25-4.10 (m, 3H), 3.88-3.80 (m, 1H), 3.65-3.55 (m, 3H), 3.50-3.40 (m, 12H), 3.30-3.25 (m, 2H), 3.12-2.90 (m, 4H), 2.70-2.55 (m, 2H), 2.48-2.35 (m, 2H), 2.30-2.20 (m, 2H), 2.15-1.95 (m, 4H), 1.86-1.65 (m, 3H), 1.64-1.54 (m, 5H), 1.49 (s, 4H), 1.46-1.34 (m, 5H), 0.90-0.80 (m, 12H) ppm. Anal. HPLC: 100%, Retention time: 7.40 min (method B).

Example 50

The example demonstrates a method for making Linker-Payload LP11. The following Example refers to FIG. 16.

{4-[(2S)-2-[(2S)-2-[1-(4-{2-Azatricyclo[10.4.0.0$^{4,9}$]
hexadeca-1(12),4(9),5,7,13,15-hexaen-10-yn-2-yl}-
4-oxobutanamido)-3,6,9,12-tetraoxapentadecan-15-
amido]-3-methylbutanamido]-5-(carbamoylamino)
pentanamido]phenyl}methyl N-[(4-{2-[(1S,2S,4R,
6R,8S,9S,11S,12R,13S,19S)-12,19-difluoro-11-
hydroxy-9,13-dimethyl-16-oxo-6-propyl-5,7-
dioxapentacyclo[10.8.0.0$^{2,9}$.0$^{4,8}$.0$^{13,18}$]icosa-14,17-
dien-8-yl]-2-oxoethoxy}phenyl)methyl]carbamate
(LP11)

Compound 34k (80 mg, 64% yield) was obtained from (11-19) according to the General procedure D.

Following the General procedure C, compound (LP11) (18 mg, 31% yield) as a white solid was obtained from the reaction of compound (34k). ESI m/z: 756.5 (M/2+H)$^+$.

$^1$H NMR (500 MHz, DMSO$_{d6}$) δ 10.02 (s, 1H), 8.14 (d, J=8.0 Hz, 1H), 7.88 (d, J=8.0 Hz, 1H), 7.76 (t, J=5.5 Hz, 1H), 7.72 (t, J=5.5 Hz, 1H), 7.70-7.66 (m, 1H), 7.65-7.60 (m, 3H), 7.53-7.45 (m, 3H), 7.40-7.31 (m, 2H), 7.31-7.25 (m, 4H), 7.20-7.15 (m, 2H), 6.86-6.80 (m, 2H), 6.30 (dd, J=10.4 Hz, 1.6 Hz, 1H), 6.11 (s, 1H), 6.10-6.00 (m, 1H), 5.72-5.55 (m, 1H), 5.52 (s, 1H), 5.43 (s, 2H), 5.16-5.10 (m, 1H), 5.06-5.00 (m, 1H), 5.00-4.93 (m, 2H), 4.90-4.76 (m, 2H), 4.75 (t, J=4.0 Hz, 1H), 4.43-4.33 (m, 1H), 4.25-4.20 (m, 2H), 4.12 (d, J=6.0 Hz, 2H), 3.65-3.55 (m, 3H), 3.50-3.40 (m, 12H), 3.30-3.25 (m, 2H), 3.12-2.90 (m, 4H), 2.70-2.55 (m, 2H), 2.48-2.43 (m, 1H), 2.40-2.35 (m, 1H), 2.30-2.20 (m, 2H), 2.15-1.95 (m, 4H), 1.86-1.70 (m, 3H), 1.64-1.54 (m, 5H), 1.49 (s, 4H), 1.46-1.34 (m, 4H), 0.90-0.80 (m, 12H) ppm. Anal. HPLC: 99%, Retention time: 7.89 min (method B).

Example 51

Figure 17:
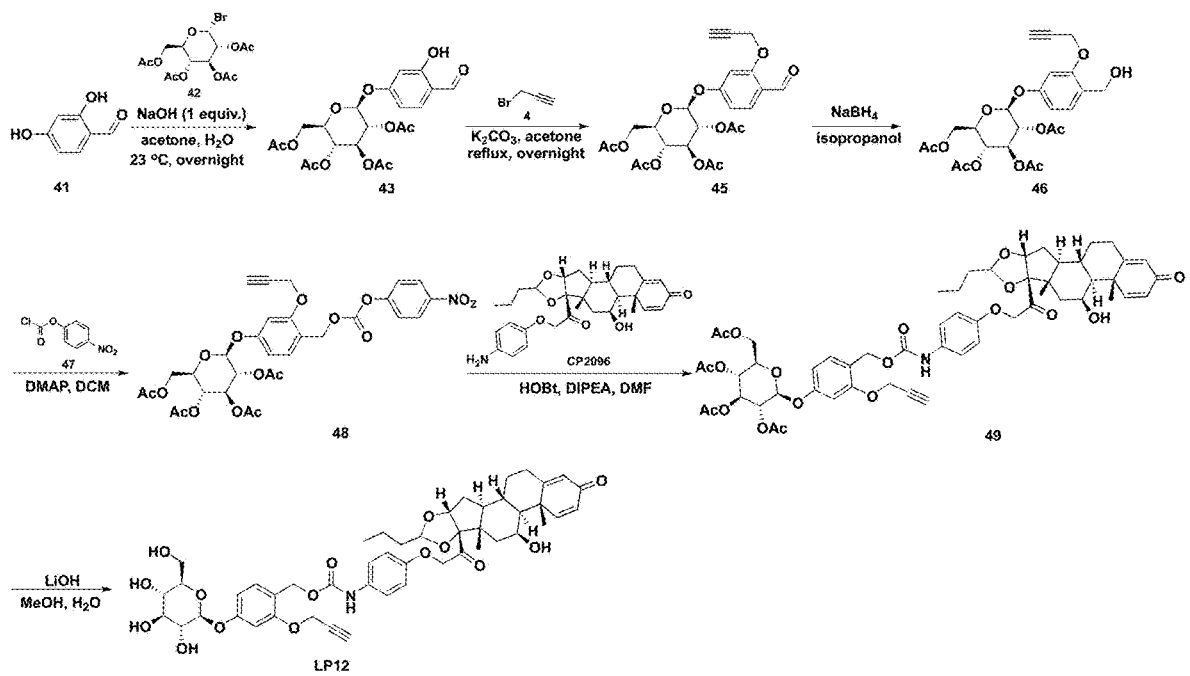
FIG. 17 shows a sequence for synthesizing Linker-Payload 12 (LP12).

The example demonstrates a method for making Linker-Payload LP12. The following Example refers to FIG. 17.

[(2R,3R,4S,5R,6S)-3,4,5-Tris(acetyloxy)-6-[4-
formyl-3-(prop-2-yn-1-yloxy)phenoxy]oxan-2-yl]
methyl acetate (45)

Step 1: The synthesis of [(2R,3R,4S,5R,6S)-3,4,5-Tris(acetyloxy)-6-(4-formyl-3-hydroxyphenoxy)oxan-2-yl]methyl acetate (43) was reported in *Carbohydrate Research*, 1986, 146, 241-249, the entire contents of which are herein incorporated by reference in its entirety. To a solution of intermediate compound 43 (2.8 g, 6.0 mmol) in acetone (40 mL) was simultaneously added potassium carbonate (1.7 g, 12 mmol) and 3-bromoprop-1-yne (44, 3.5 g, 30 mmol), and the resulting mixture was refluxed overnight. The mixture was then concentrated in vacuo and the residue was purified by flash chromatography (0-33% ethyl acetate in petroleum ether) to yield compound 45 (1.9 g, yield 63%) as a brown solid. ESI m/z: 507 (M+H)$^+$. $^1$H NMR (MeOD$_{d4}$, 500 MHz) δ 10.26 (s, 1H), 7.78 (d, J=8.5 Hz, 1H), 6.87 (d, J=2.0 Hz, 1H), 6.77 (dd, J=8.5, 2.0 Hz, 1H), 5.51 (d, J=8.0 Hz, 1H), 5.41 (t, J=9.5 Hz, 1H), 4.93 (t, J=2.5 Hz, 2H), 5.23-5.19 (m, 1H), 5.14 (t, J=9.5 Hz, 1H), 4.34-4.30 (m, 1H), 4.22-4.15 (m, 2H), 3.11 (t, J=2.0 Hz, 1H), 2.05-1.99 (m, 12H) ppm.

[(2R,3R,4S,5R,6S)-3,4,5-Tris(acetyloxy)-6-[4-(hydroxym-
ethyl)-3-(prop-2-yn-1-yloxy)phenoxy]oxan-2-yl]methyl
acetate (46)

Step 2: To a solution of compound 45 (0.83 g, 1.6 mmol) in isopropanol (50 mL) was added sodium borohydride (31 mg, 0.82 mmol). The mixture was stirred at 23° C. for 2 hours and was then concentrated in vacuo. The residue was diluted with ethyl acetate and washed with brine. The organic solution was dried over sodium sulfate and concentrated to afford compound 46 (0.70 g, yield 84%) as brown oil. ESI m/z: 526.1 (M+H$_2$O)$^+$. $^1$H NMR (MeOD$_{d4}$, 500 MHz) δ 7.32 (d, J=8.0 Hz, 1H), 6.78 (d, J=2.0 Hz, 1H), 6.67 (dd, J=8.0, 2.0 Hz, 1H), 5.40 (t, J=9.0 Hz, 1H), 5.33 (dd, J=7.5 Hz, 1H), 5.20-5.11 (m, 2H), 4.78 (t, J=2.5 Hz, 2H), 4.59 (s, 2H), 4.32 (d, J=12.5, 5.0 Hz, 1H), 4.21 (dd, J=12.5, 2.5 Hz, 1H), 4.12-4.08 (m, 1H), 3.02 (t, J=2.0 Hz, 1H), 2.07-2.0.

[(2R,3R,4S,5R,6S)-3,4,5-Tris(acetyloxy)-6-(4-{[(4-
nitrophenoxycarbonyl)oxy]methyl}-3-(prop-2-yn-1-
yloxy)phenoxy)oxan-2-yl]methyl acetate (48)

Step 3: To a solution of compound 46 (0.40 g, 0.79 mmol) in methylene chloride (30 mL) were added 4-nitrophenyl carbonochloridate (47, 0.24 g, 1.2 mmol), 4-dimethylamin-opyridine (0.19 g, 1.6 mmol) and diisopropylethylamine (0.20 g, 1.6 mmol). The mixture was stirred at 23° C. overnight and diluted with methylene chloride (50 mL). The organic solution was washed with saturated aqueous ammonium chloride solution (50 mL) and then brine (50 mL), dried over sodium sulfate and concentrated. The residue was purified by flash chromatography (0-33% ethyl acetate in petroleum ether) to afford compound 48 (0.30 g, yield 57%) as an off-white solid. ESI m/z: 691.0 (M+H$_2$O)$^+$. $^1$H NMR (CDCl$_3$, 500 MHz) δ 8.27 (d, J=9.0 Hz, 2H), 7.38 (d, J=9.0 Hz, 2H), 7.35 (d, J=8.5 Hz, 1H), 6.75 (d, J=2.5 Hz, 1H), 6.64 (dd, J=9.0, 2.5 Hz, 1H), 5.33-5.26 (m, 4H), 5.21-5.17 (m, 1H), 4.76 (t, J=2.0 Hz, 2H), 4.28 (dd, J=12.5, 5.0 Hz, 1H), 4.20 (dd, J=12.5, 2.5 Hz, 1H), 3.89-3.88 (m, 1H), 2.56 (t, J=7.0 Hz, 1H), 2.08-2.04 (m, 12H) ppm.

[(2R,3R,4S,5R,6S)-3,4,5-Tris(acetyloxy)-6-[4-({[(4-
{2-[(1S,2S,4R,8S,9S,11S,12S,13R)-11-hydroxy-9,
13-dimethyl-16-oxo-6-propyl-5,7-dioxapentacyclo
[10.8.002,9.04,8.013,18]icosa-14,17-dien-8-yl]-2-
oxoethoxy}phenyl)carbamoyl]oxy}methyl)-3-(prop-
2-yn-1-yloxy)phenoxy]oxan-2-yl]methyl acetate
(49)

Step 4: To a solution of compound 48 (0.15 g, 0.22 mmol) in DMF (5 mL) were added 11-5 (0.14 g, 0.26 mmol), HOBt (59 mg, 0.44 mmol) and diisopropylethylamine (57 mg, 0.44 mmol) successively. The mixture was stirred at 23° C. overnight and was then purified by prep-HPLC (method B) to yield compound 49 (0.14 g, 62% yield) as a white solid. ESI m/z: 1056.3 (M+H)+. 1H NMR (MeODd4, 400 MHz)

δ 7.46 (d, J=10.4 Hz, 1H), 7.35-7.26 (m, 3H), 6.87-6.80 (m, 3H), 6.67 (dd, J=8.0, 2.4 Hz, 1H), 6.26 (dt, J=10.0, 2.4 Hz, 1H), 6.03 (br s, 1H), 5.42-5.34 (m, 2.5H), 5.26-5.03 (m, 5.5H), 4.88-4.64 (m, 4H), 4.46-4.43 (m, 1H), 4.34-4.30 (m, 1H), 4.21-4.18 (m, 1H), 4.12-4.08 (m, 1H), 3.03 (t, J=2.0 Hz, 1H), 2.71-2.62 (m, 1H), 2.41-2.38 (m, 1H), 2.28-2.15 (m, 2H), 2.06-2.04 (m, 12H), 1.90-1.39 (m, 12H), 1.20-0.89 (m, 8H) ppm.

[2-(Prop-2-yn-1-yloxy)-4-{[(2S,3R,4S,5S,6R)-3,4,5-trihydroxy-6-(hydroxymethyl)oxan-2-yl]oxy}phenyl]methyl N-(4-{2-[(1S,2S,4S,8R,9S,11S,12S,13R)-11-hydroxy-4,9,13-trimethyl-16-oxo-6-propyl-7-oxapentacyclo[10.8.0$0^{2,9}$.0$^{4,8}$.0$^{13,18}$]icosa-14,17-dien-8-yl]-2-oxoethoxy}phenyl)carbamate (LP12)

Step 5: To a solution of compound 49 (35 mg, 33 μmop in methanol (3 mL) was added another solution of LiOH in H$_2$O (14 mg, 0.33 mmol) in water (1 mL). The mixture was stirred at 23° C. for 1.5 hours and was quenched with HOAc (20 mg). The mixture was concentrated in vacuo and the residue was purified by prep-HPLC (method B) to yield linker-payload LP12 (26 mg, 88% yield) as a white solid. ESI m/z: 888 (M+H)+. 1H NMR (MeODd4, 400 MHz) δ 7.46 (d, J=10.0 Hz, 1H), 7.35-7.30 (m, 3H), 6.91 (d, J=2.0 Hz, 1H), 6.87-6.83 (m, 2H), 6.74 (dd, J=8.0, 2.0 Hz, 1H), 6.27 (dt, J=10.0, 2.0 Hz, 1H), 6.03 (s, 1H), 5.25 (t, J=4.8 Hz, 0.5H), 5.19 (d, J=7.2 Hz, 0.5H), 5.13-5.03 (m, 3H), 4.94-4.91 (m, 1H), 4.82-4.75 (m, 3H), 4.71-4.67 (m, 1H), 4.46-4.43 (m, 1H), 3.91 (dd, J=12.0, 2.0 Hz, 1H), 3.70 (dd, J=12.0, 5.2 Hz, 1H), 3.48-3.36 (m, 4H), 2.99 (t, J=2.4 Hz, 1H), 2.71-2.62 (m, 1H), 2.40-2.37 (m, 1H), 2.26-2.12 (m, 2H), 2.07-2.00 (m, 1H), 1.88-1.61 (m, 5H), 1.56-1.35 (m, 6H), 1.20-0.92 (m, 8H) ppm.

Example 52

Figure 18:
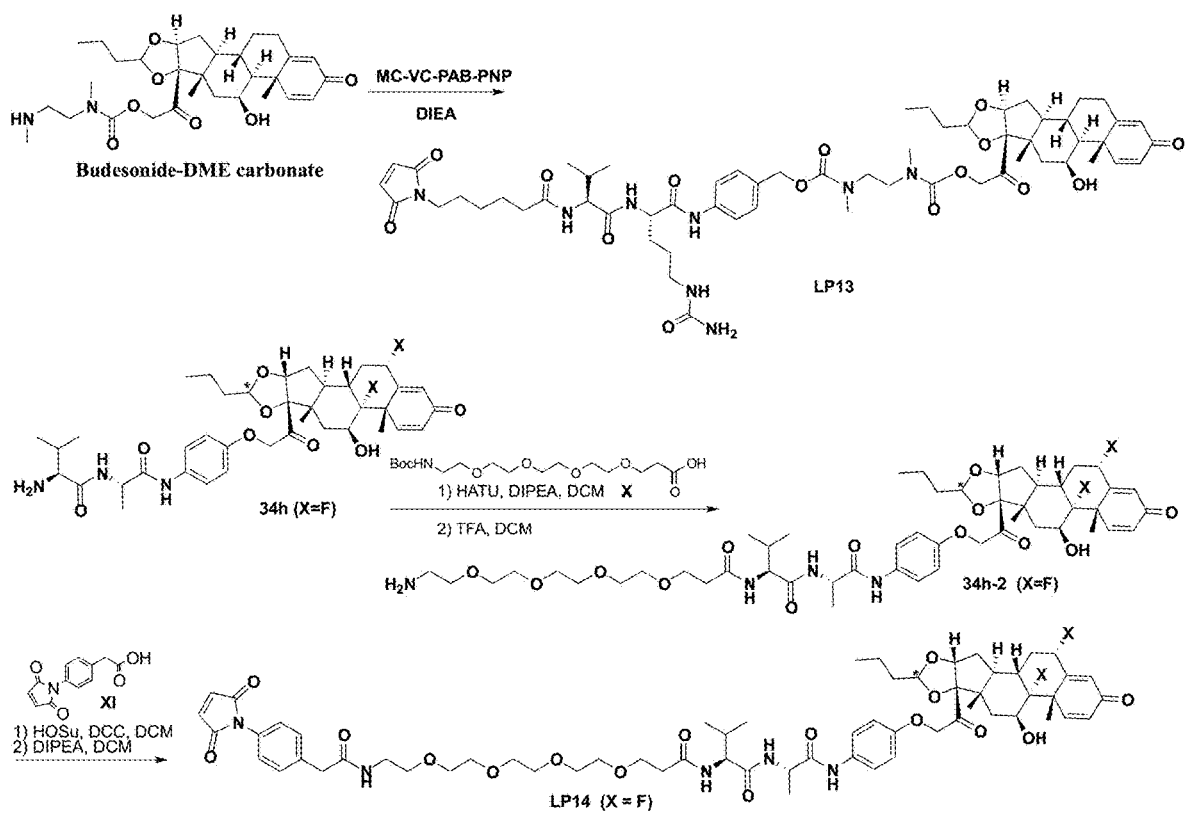
FIG. 18 shows a synthesis sequence for making Linker-Payload 12 (LP13) and Linker-Payload 14 (LP14).

The example demonstrates a method for making Linker-Payload LP13. The following Example refers to FIG. 18.

2-[(1S,2S,4S,8S,9S,11S,12S,13S)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxo-ethyl N-(2-{[({4-[(2S)-5-(carbamoylamino)-2-[(2S)-2-[6-(2,5-dioxo-2,5-dihydro-1H-pyrrol-1-yl)hexanamido]-3-methylbutanamido]pentanamido]phenyl}methoxy)carbonyl](methyl)amino}ethyl)-N-methylcarbamate (LP13)

To a solution of Budesonide-DME carbonate (20 mg, 0.037 mmol) in DMF (1 ml) was subsequently added MC-VC-PAB-PNP (22 mg, 0.03 mmol), DIPEA (12 mg, 0.09 mmol), and HOBt (6 mg, 0.05 mmol). This mixture was stirred at RT for 12 hours, then prep-HPLC was performed to get two epimers: Epimer 1: 3.3 mg (yield 10%) and Epimer 2: 4.1 mg (yield 12%).

Epimer 1: ESI m/z: 1143.4 (M+1). 1H NMR (400 MHz, MeOD) δ 7.63-7.62 (m, 2H), 7.50-7.49 (m, 1H), 7.37-7.35 (m, 2H), 6.81 (s, 1H), 6.29-6.27 (m, 1H), 6.03 (brs, 1H), 5.37-5.08 (m, 5H), 4.83-4.79 (m, 3H), 4.53-4.46 (m, 2H), 4.18-4.15 (m, 1H), 3.69-3.37 (m, 6H), 3.25-3.13 (m, 3H), 3.12-2.96 (m, 5H), 2.90-2.86 (m, 2H), 2.68-2.64 (m, 1H), 2.41-2.40 (m, 1H), 2.31-2.28 (m, 2H), 2.26-1.95 (m, 7H), 1.93-1.77 (m, 11H), 1.51 (s, 3H), 1.42-1.30 (m, 10H), 1.25-0.89 (m, 15H)

Epimer 2: ESI ink: 1143.4 (M+1). 1H NMR (400 MHz, MeOD) δ 7.62-7.34 (m, 5H), 6.81 (brs, 1H), 6.29-6.23 (m, 1H), 6.05-6.00 (m, 1H), 5.27-5.17 (m, 4H), 4.92-4.79 (m, 2H), 3.75-3.37 (m, 7H), 3.03-2.86 (m, 5H), 2.72-2.63 (m, 1H), 2.41-2.28 (m, 3H), 2.23-2.04 (m, 7H), 1.91-1.32 (m, 31H), 1.19-0.90 (m, 14H).

Example 53

The example demonstrates a method for making Linker-Payload LP14. The following Example refers to FIG. 18.

N-[(1S)-1-{[(1S)-1-[(4-{2-[(1S,2S,4R,6R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]-1-{2-[4-(2,5-dioxo-2,5-dihydro-1H-pyrrol-1-yl)phenyl]acetamido}-3,6,9,12-tetraoxapentadecan-15-amide (LP14)

Compound 34h-2 (0.18 g, 74% yield in 2 steps) was obtained according to the General procedure F. ESI m/z: 728 (M+H)$^+$.

Compound LP14 (20 mg, 14% yield in 3 steps from 34h) was obtained as a white solid. ESI: 1189 (M+H)$^+$. 1H NMR (500 MHz, DMSO$_{d6}$) δ 9.81-9.67 (m, 1H), 8.43-8.13 (m, 2H), 8.03-7.84 (m, 1H), 7.61-7.47 (m, 2H), 7.35 (d, J=8.4 Hz, 2H), 7.29-7.21 (m, 3H), 7.17 (s, 2H), 6.88-6.81 (m, 2H), 6.33-6.28 (dd, J=10.1, 1.8 Hz, 1H), 6.11 (s, 1H), 5.71-5.56 (m, 1H), 5.51 (s, 1H), 5.12 (d, J=18.5 Hz, 1H), 4.84 (d, J=18.5 Hz, 1H), 4.79-4.76 (m, 1H), 4.74 (t, J=4.3 Hz, 2H), 4.38-4.33 (m, 1H), 4.25-4.17 (m, 2H), 3.63-3.55 (m, 2H), 3.52-3.44 (m, 14H), 3.42 (t, J=5.8 Hz, 2H), 3.21 (q, J=5.7 Hz, 1H), 2.69-2.55 (m, 1H), 2.47-2.41 (m, 1H), 2.41-2.34 (m, 1H), 2.29-2.23 (m, 1H), 2.14-2.02 (m, 2H), 1.99-1.90 (m, 1H), 1.82 (d, J=13.0 Hz, 1H), 1.65-1.53 (m, 4H), 1.49 (s, 3H), 1.47-1.41 (m, 1H), 1.40-1.33 (m, 2H), 1.29 (d, J=7.1 Hz, 3H), 0.90-0.80 (m, 12H) ppm. Anal. HPLC: 100%, Retention time: 8.45 min (method A).

Table 7 below summarizes certain physical properties of LP1-LP16.

TABLE 7

Physical Properties of Certain Linker-Payloads

| LP No. | MF | MW | Purity (%) | MS m/z (100%) | Highest m/z | HPLC RT (min) |
|---|---|---|---|---|---|---|
| LP1 | C$_{66}$H$_{81}$N$_5$O$_{15}$ | 1184.4 | 98 | 593 (M/2 + H) | 1185 (M + H, 20%) | 6.53 (B) |
| LP2 | C$_{61}$H$_{86}$F$_2$N6O$_{15}$ | 1181.4 | 100 | 1181.4 (M + H) | 1181.4 (M + H) | 7.83 (B) |

TABLE 7-continued

Physical Properties of Certain Linker-Payloads

| LP No. | MF | MW | Purity (%) | MS m/z (100%) | Highest m/z | HPLC RT (min) |
|---|---|---|---|---|---|---|
| LP3 | $C_{70}H_{94}F_2N_6O_{17}$ | 1329.5 | 100 | 1330.4 (M + H) | 1330.4 (M + H) | 7.03 (B) |
| LP4 | $C_{61}H_{86}N_4O_{15}$ | 1115.4 | 100 | 1115 [M + H] | 1115 [M + H] | 8.17 (A) 8.24 (B) |
| LP5 | $C_{64}H_{92}N_6O_{16}$ | 1201.5 | 100 | 1201 [M + H] | 1201 [M + H] | 7.34 (A) 7.44 (B) |
| LP6 | $C_{72}H_{99}N_7O_{18}$ | 1350.6 | 100 | 1350.5 (M + H) | 1350.5 (M + H) | 8.87 (A) |
| LP7 | $C_{61}H_{86}N_4O_{15}$ | 1226.5 | 100 | 1227.8 (M + H) | 1227.8 (M + H) | 9.47 (A) |
| LP8 | $C_{69}H_{85}F_2N_5O_{15}$ | 1262.4 | 100 | 1262.4 (M + H) | 1262.4 (M + H) | 8.26 (B) |
| LP9 | $C_{80}H_{98}F_2N_8O_{18}$ | 1497.7 | 100 | 749.5 (M/2 + H) | 1497.7 (M + H) | 7.99 (B) |
| LP10 | $C_{74}H_{94}F_2N_8O_{17}$ | 1405.6 | 100 | 703.5 (M/2 + H) | 1405.7 (M + H) (5%) | 7.40 (B) |
| LP11 | $C_{81}H_{100}F_2N_8O_{18}$ | 1511.7 | 99.3 | 756.5 (M/2 + H) | 756.5 (M/2 + H) | 7.89 (B) |
| LP12 | $C_{48}H_{57}NO_{15}$ | 888.0 | 100 | 566.2 (M-glucose-PAB) | 889.1 (M + H, 25%) | 8.02 (A) 8.08 (B) |
| LP13 | $C_{72}H_{99}N_7O_{18}$ | 1350.6 | 100 | 1350.5 (M + H) | 1350.5 (M + H) | 8.87 (A) |
| LP14 | $C_{62}H_{79}F_2N_5O_{16}$ | 1188.31 | 100 | 594.8 (M/2 + H) | 1188.5 (M + H, 40%) | 7.99 (B) |
| LP15 | $C_{121}H_{170}N_{10}O_{47}$ | 2516.71 | 97 | 1259 (M/2 + H) | 1259.1 (M/2 +H)$^+$. | 6.62 and 6.67 (B) |
| LP16 | $C_{121}H_{170}N_{10}O_{47}$ | 2516.71 | 98 | 1258 (M/2 + H) | 1259.1 (M/2 + H, 60%) | 6.61 (59%) and 6.73 (39%) (B) |

Example 54

Figure 19:
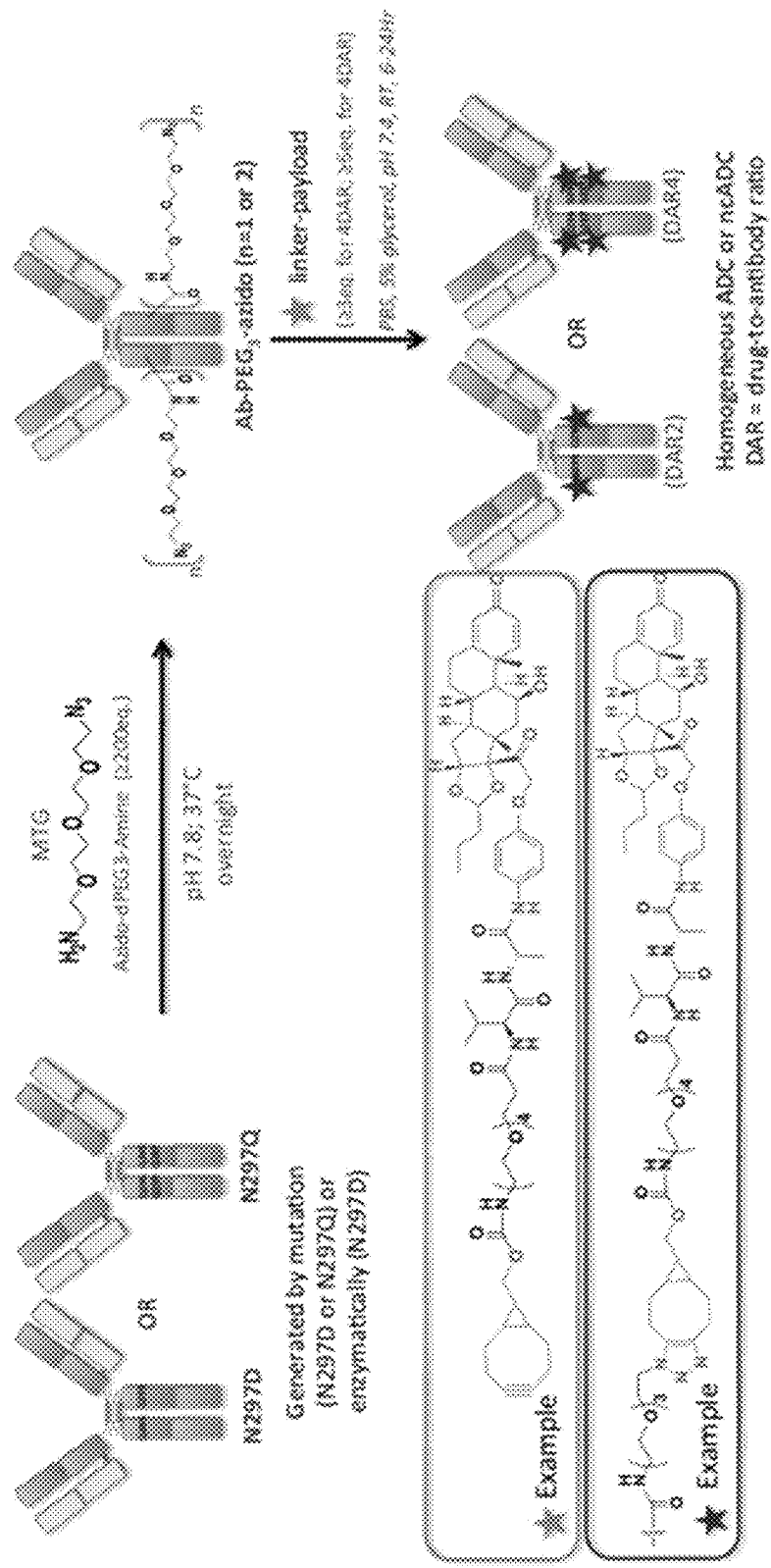
FIG. 19 shows a general synthetic process for an ADC conjugation via a [2+3] click reaction with LP4.

This example demonstrates a method for site-specific conjugation, generally, of a payload to an antibody or antigen-binding fragment thereof. This example refers to FIG. 19.

In one example, site-specific conjugates were produced via Microbial transglutaminase (MTG EC 2.3.2.13, Zedira, Darmstadt, Germany) (herein "MTG-based") two-step conjugation of an N297Q or N297D mutated antibody. In the first step, the mutated antibody was functionalized with azido-PEG$_3$-amine via MTG based enzymatic reaction. See, e.g., International PCT Patent Application No. PCT/US17/19537, filed Feb. 24, 2017, entitled OPTIMIZED TRANSGLUTAMINASE SITE-SPECIFIC ANTIBODY CONJUGATION, incorporated herein by reference in its entirety for all purposes. In the second step, an alkyne-functionalized linker-payload was attached to the azido-functionalized antibody via [2+3] 1,3-dipolar cycloaddition reaction (see, e.g., FIG. 19, which depicts a DIBAC-functionalized linker-payload conjugated with an azido-functionalized antibody derived via [2+3] cyclization). This process provided site-specific and stoichiometric conjugates in about 50-80% isolated yield.

Example 55

This Example demonstrates specific procedures for site-specific conjugation of an alkyne-linker-payload to antibody.

Figure 29:
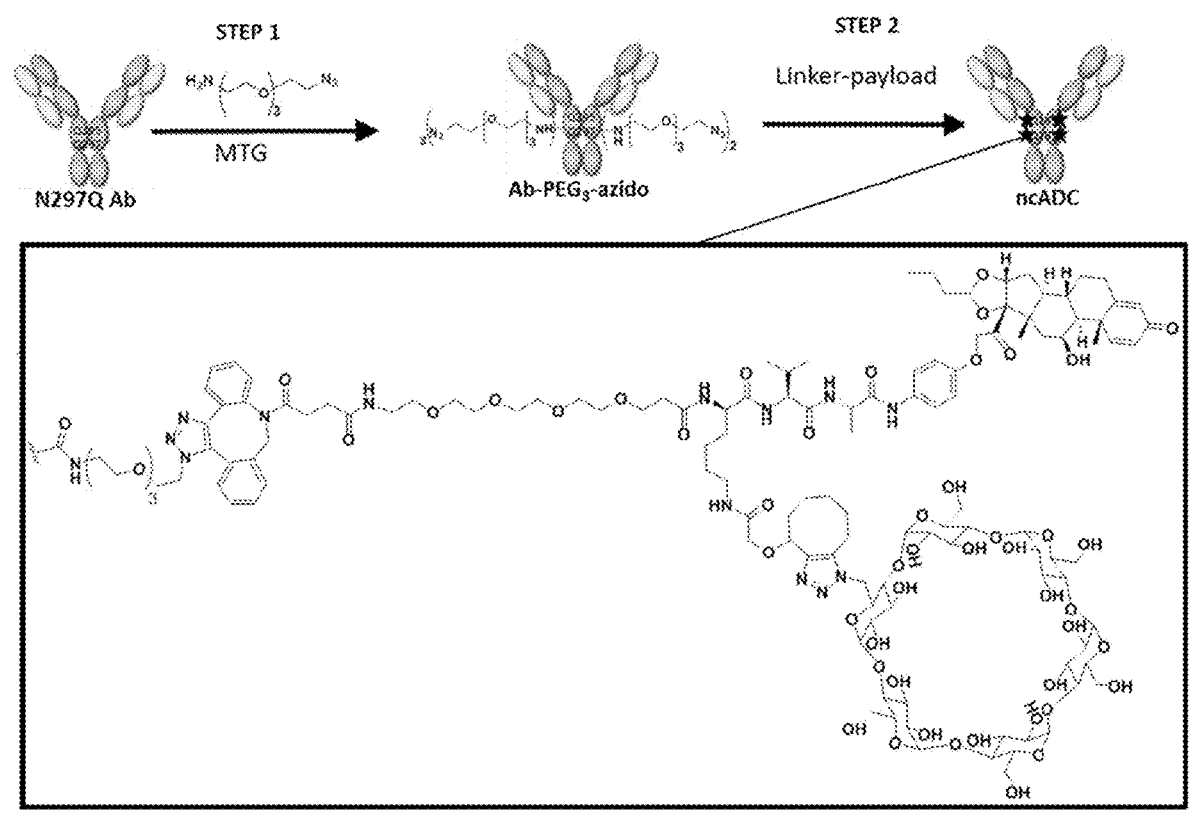
FIG. 29 shows a general synthetic process for an ADC conjugation via a [2+3] click reaction with Cyclodextrin-Linker-Payloads.

This example refers to the compounds depicted in FIG. 29.

In this example, the site-specific conjugates were produced in two steps. The first step is Microbial transglutaminase (MTG)-based enzymatic attachment of a small molecule, such as azide-PEG$_3$-amine (supra), to the antibody having a Q-tag (references for the Qtag) (hereinafter "MTG-based" conjugation). The second step employed the attachment of a linker-payload to the azido-functionalized antibody via a [2+3] cycloaddition, for example, the 1,3-dipolar cycloaddition between the azides and the cyclooctynes (aka copper-free click chemistry). See, Baskin, J. M.; Prescher, J. A.; Laughlin, S. T.; Agard, N. J.; Chang, P. V.; Miller, I. A.; Lo, A.; Codelli, J. A.; Bertozzi, C. R. PNAS 2007, 104 (43), 16793-7, the entire contents of which are herein incorporated by reference in its entirety for all purposes. Shown in FIG. 28 is an example of a linker-payload having a DIBAC moiety conjugated with an azido-functionalized antibody via a [2+3] cycloaddition. This process provided the site specific and stoichiometric conjugates in about 50-80% isolated yield.

ADC conjugation via [2+3] click reaction.

Step 1: Preparation of an Azido-Functionalized Antibody.

Aglycosylated human antibody IgG (IgG1, IgG4, etc.) or a human IgG1 isotype with N297Q mutation, in PBS (pH 6.5-8.0) was mixed with ≥200 molar equivalents of azido dPEG$_3$-amine (MW=218.26 g/mol). The resulting solution was mixed with MTG (EC 2.3.2.13 from Zedira, Darmstadt, Germany, or Modernist Pantry [L #210115A]—ACTIVA TI contains Maltodextrin from Ajinomoto, Japan) (25 U/mL; 5 U MTG per mg of antibody) resulting in a final concentration of the antibody at 0.5-5 mg/mL, and the solution was then incubated at 37° C. for 4-24 h while gently shaking. The reaction was monitored by ESI-MS. Upon reaction completion, the excess amine and MTG were removed by SEC or protein A column chromatography, to generate the azido-functionalized antibody. This product was characterized by SDS-PAGE and ESI-MS. The azido-dPEG$_3$-amine added to two sites of the antibody resulting in a 204 Da increase for the 2DAR antibody-PEG$_3$-azide conjugate.

In a specific experimental, the N-terminal Q tag antibody (24 mg) in 7 mL potassium-free PBS buffer (pH 7.3) was incubated with >200 molar equivalent of the azido-PEG$_3$-amine (MW 218.26) in the presence of MTG (0.350 mL, 35 U, mTGase, Zedira, Darmstadt, Germany). The reaction was incubated at 37° C. overnight while gently mixing. Excess azido-PEG$_3$-amine and mTGase were removed by size exclusion chromatography (SEC, Superdex 200 PG, GE Healthcare).

Step 2: Preparation of Site-Specific Conjugates of a Drug to an Antibody Using Click Chemistry Reactions.

The site-specific antibody drug conjugates with a human IgG (IgG1, IgG4, etc.) in Table 10 were prepared by a [2+3] click reaction between azido-functionalized antibodies and an alkyne containing linker-payload. The detailed conjugation procedure follows. A site-specific antibody conjugate with linker-payload (LP) was prepared by incubating mAb-PEG$_3$-N$_3$ (1-3 mg/mL) in an aqueous medium (e.g., PBS, PBS containing 5% glycerol, HBS) with ≥6 molar equivalents of an LP dissolved in a suitable organic solvent, such as DMSO, DMF or DMA (i.e., the reaction mixture contains 5-20% organic solvent, v/v) at 24° C. to 37° C. for over 6 h. The progress of the reaction was monitored by ESI-MS and the absence of mAb-PEG$_3$-N$_3$ indicated the completion of the conjugation. The excess amount of the LP and organic solvent were removed by SEC via elution with PBS, or via protein A column chromatography via elution with acidic buffer followed by neutralization with Tris (pH 8.0).

In a specific example, the azido-functionalized antibody (1 mg) in 0.800 mL PBSg (PBS, 5% glycerol, pH 7.4) was treated with six molar equivalents of DIBAC-PEG$_4$-D-Lys (COT-∝-CD)-VC-PABC-payload (conc. 10 mg/mL in DMSO) for 6-12 hours at room temperature and the excess linker payload (LP) was removed by size exclusion chromatography (SEC, Superdex 200 HR, GE Healthcare).

The final product was concentrated by ultra centrifugation and characterized by UV, SEC, SDS-PAGE and ESI-MS.

Example 56

This example demonstrates a method for making an azido-functionalized antibody drug conjugate.

Aglycosylated antibody with a human IgG1 isotype in BupH™ (pH 7.6-7.8) was mixed with ≥200 molar equivalents of azido-dPEG$_3$-amine (MW. 218.26 g/mol). The resulting solution was mixed with transglutaminase (25 U/mL; 5 U MTG per mg of antibody, Zedira, Darmstadt, Germany) resulting in a final concentration of the antibody at 0.5-3 mg/mL, and the solution was then incubated at 37° C. for 4-24 hours while gently shaking. The reaction was monitored by SDS-PAGE or ESI-MS. Upon the completion, the excess amine and MTG were removed by Size Exclusion Chromatography (see FIG. 21) to generate the azido-functionalized antibody. This product was analyzed on SDS-PAGE (see FIG. 20) and ESI-MS (see FIG. 22). The azido-dPEG$_3$-amine added to two sites—Q295 and Q297—of the antibody resulting in an 804 Da increase for the 4 DAR aglycosylated antibody-PEG$_3$-azide conjugate. The conjugation sites were identified and confirmed at EEQ$^{Linker}$YQ$^{Linker}$STYR for the 4 DAR azido-functionalized antibody via peptide sequence mapping of trypsin digested heavy chains.

Example 57

This example demonstrates a method for making a site-specific conjugations of a drug to an antibody using click chemistry reactions.

The site-specific aglycosylated antibody drug conjugates with an human IgG1 containing an N297Q mutation in Table 8 described below were prepared by a [2+3] click reaction between azido-functionalized antibodies with an alkyne containing linker-payload. As shown in Table 8, Anti Her2-PEG$_3$-N$_3$ was conjugated to compounds LP1, LP2, LP3, LP4, LP5, LP6, LP7, LP8, LP9, LP10, and LP11. As shown in Table 8, Anti PRLR-PEG$_3$-N$_3$ was conjugated to LP1 LP2, LP3, LP4, LP5, LP6, LP7, LP8, LP9, LP10, LP11, LP15, and LP16. As shown in Table 8, Anti-IL2Rg-PEG$_3$-N$_3$ was conjugated to LP4 and LP7. As shown in Table 8, Anti-Fel d1-PEG$_3$-N$_3$ was conjugated to LP4.

For the conjugation, an azido-functionalized aglycosylated human IgG1 antibody (mAb-PEG$_3$-N$_3$) and linker-payload (LP) conjugate was prepared by incubating mAb-PEG$_3$-N$_3$ (1-3 mg/mL) in an aqueous medium (e.g., PBS, PBS containing 5% glycerol, HBS) with ≥6 molar equivalent of an LP dissolved in a suitable organic solvent, such as DMSO, DMF or DMA (reaction mixture contains 10-20% organic solvent, v/v) at 24° C. to 37° C. for over 6 hours. The progress of the reaction was monitored by ESI-MS. The reaction was monitored by ESI-MS, and the absence of mAb-PEG$_3$-N$_3$ indicated the completion of the conjugation. The excess amount of the LP and organic solvent were removed by SEC eluting with PBS. The purified conjugates were analyzed by SEC, SDS-PAGE, and ESI-MS. Shown in Table 8 is a list of nontoxic steroid antibody conjugates (ncADCs) from the corresponding LPs, their molecular weights and ESI-DAR values. In Table 8, Ab refers to an antibody, Ab-N$_3$ refers to the azide functionalized antibody, and ncADC refers to a non-cytotoxic antibody drug conjugate.

TABLE 8

| | Ab, Ab-N$_3$, or ncADC | MS m/z (ncADC) | LP # | M.W. (LP) | DAR (ESI-MS) |
|---|---|---|---|---|---|
| 1 | Anti Her2 mAb | 145126 | | | |
| 2 | Anti Her2-PEG$_3$-N$_3$ | 145930 | NH$_2$-PEG$_3$-N$_3$ | 218.3 | 4 |
| 3 | Anti Her2-LP1 | 150683 | LP1 | 1184.4 | 4 |
| 4 | Anti Her2-LP2 | 150671 | LP2 | 1181.4 | 4 |
| 5 | Anti Her2-LP3 | 151274 | LP3 | 1330.5 | 4 |
| 6 | Anti Her2-LP4 | 150406 | LP4 | 1115.4 | 4 |
| 7 | Anti Her2-LP5 | 150726 | LP5 | 1201.5 | 4 |
| 8 | Anti Her2-LP6 | 151358 | LP6 | 1350.6 | 4 |
| 9 | Anti Her2-LP7 | 151297 | LP7 | 1226.5 | 4 |
| 10 | Anti Her2-LP8 | 152239 | LP8 | 1262.4 | 4 |
| 11 | Anti Her2-LP9 | 151868 | LP9 | 1497.7 | 4 |
| 12 | Anti Her2-LP10 | 152293 | LP10 | 1405.6 | 4 |
| 13 | Anti Her2-LP11 | 145430 | LP11 | 1511.7 | 4 |
| 14 | Anti PRLR mAb | 144579 | | | |

TABLE 8-continued

| Ab, Ab-N$_3$, or ncADC | MS m/z (ncADC) | LP # | M.W. (LP) | DAR (ESI-MS) |
|---|---|---|---|---|
| 15 Anti PRLR- PEG$_3$-N$_3$ | 145373 | NH$_2$-PEG$_3$-N$_3$ | 218.3 | 4 |
| 16 Anti PRLR-LP1 | 150110 | LP1 | 1184.4 | 4 |
| 17 Anti PRLR-LP2 | 150101 | LP2 | 1181.4 | 4 |
| 18 Anti PRLR-LP3 | 150721 | LP3 | 1330.5 | 4 |
| 19 Anti PRLR-LP4 | 149836 | LP4 | 1115.4 | 4 |
| 20 Anti PRLR-LP5 | 150181 | LP5 | 1201.5 | 4 |
| 21 Anti PRLR-LP6 | 150795 | LP6 | 1350.6 | 4 |
| 22 Anti PRLR-LP7 | 150311 | LP7 | 1226.5 | 4 |
| 23 Anti PRLR-LP8 | 150444 | LP8 | 1262.4 | 4 |
| 24 Anti PRLR-LP9 | 151386 | LP9 | 1497.7 | 4 |
| 25 Anti PRLR-LP10 | 151015 | LP10 | 1405.6 | 4 |
| 26 Anti PRLR-LP11 | 151447 | LP11 | 1511.7 | 4 |
| 27 Anti-IL2Rg mAb | 144960 | | | |
| 28 Anti-IL2Rg-PEG$_3$-N$_3$ | 145768 | NH$_2$-PEG$_3$-N$_3$ | 218.26 | 4 |
| 29A Anti-IL2Rg-LP4 | 150237 | LP4 | 1115.37 | 4 |
| 29B Anti-IL2Rg-LP7 | 150670 | LP7 | 1226.5 | 4 |
| 30 Anti-Fel d 1 mAb | 145430 | | | |
| 31 Anti-Fel d 1-PEG$_3$-N$_3$ | 146235 | NH$_2$-PEG$_3$-N$_3$ | 218.26 | 4 |
| 32 Anti Fel d 1-LP4 | 150705 | LP4 | 1115.37 | 4 |
| 33 Anti-PRLR-LP15 | 155460 | LP15 | 2515.1 | 4 |
| 34 Anti-PRLR-LP16 | 155486 | LP16 | 2515.1 | 4 |

Example 58

This example demonstrates a method for making a non-site-specific conjugation of a drug to an antibody using a thiol-maleimide reaction.

Conjugation through antibody cysteines was performed in two steps using the methods described similar to those described in *Mol Pharm.* 2015 Jun. 1; 12(6):1863-71.

A monoclonal antibody (mAb, 10 mg/ml in 50 mM HEPES, 150 mM NaCl) at pH 7.5 was reduced with 1 mM dithiothreitol (0.006 mg per mg of antibody) or TCEP (2.5 molar equivalent to antibody) at 37° C. for 30 minutes. After gel filtration (G-25, pH 4.5 sodium acetate), compound LP13 in DMSO (10 mg/mL) was added to the reduced antibody, and the mixture was adjusted to pH 7.0 with 1 M HEPES (pH 7.4). The reaction was allowed to react for 3-14 hours. The resulting conjugate was purified by SEC. The DAR (UV) values were determined using the measured absorbances of the ncADC and the extinction coefficients of the antibody and LP13.

Example 59

This example demonstrates methods for characterizing antibody and non-cytotoxic antibody drug conjugates (ncADC).

The antibody and ncADC were characterized by SDS-PAGE, SEC, and MS (ESI). The anti-PRLR-LP4 conjugate in Table 8 generated from anti-PRLR antibody via its azido-functionalized antibody (anti-PRLR-PEG$_3$-N$_3$) was characterized by SDS-PAGE performed under non-reducing and reducing conditions (FIG. 20), SEC (FIG. 21) and ESI-MS (FIG. 22), and demonstrated completion of the ncADC formation.

SDS-PAGE was used to analyze the integrity and purity of the ADCs.

In one method, SDS-PAGE running conditions included non-reduced and reduced samples (2-4 μg) along with BenchMark Pre-Stained Protein Ladder (Invitrogen, cat #10748-010; L #1671922.) were loaded per lane in (1.0 mm×10 well) Novex 4-20% Tris-Glycine Gel and was ran at 180 V, 300 mA, for 80 minutes. An analytic sample was prepared using Novex Tris-Glycine SDS buffer (2×) (Invitrogen, Cat # LC2676) and the reducing sample was prepared with SDS sample buffer (2×) containing 10% 2-mercaptoethanol.

Figure 20:
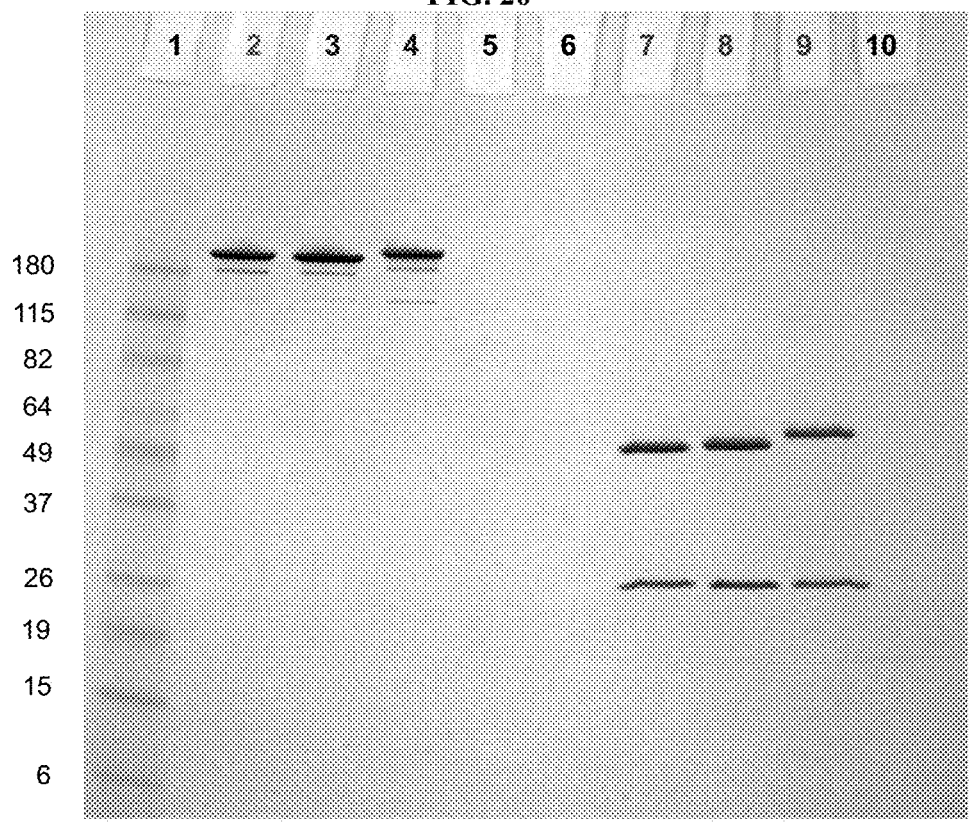
FIG. 20 shows a Coomassie-stained SDS-PAGE Gel of an anti-PRLR antibody, azido-functionalized anti-PRLR antibody, and anti-PRLR antibody-LP4 conjugate as described in Example 59.
Figure 21:
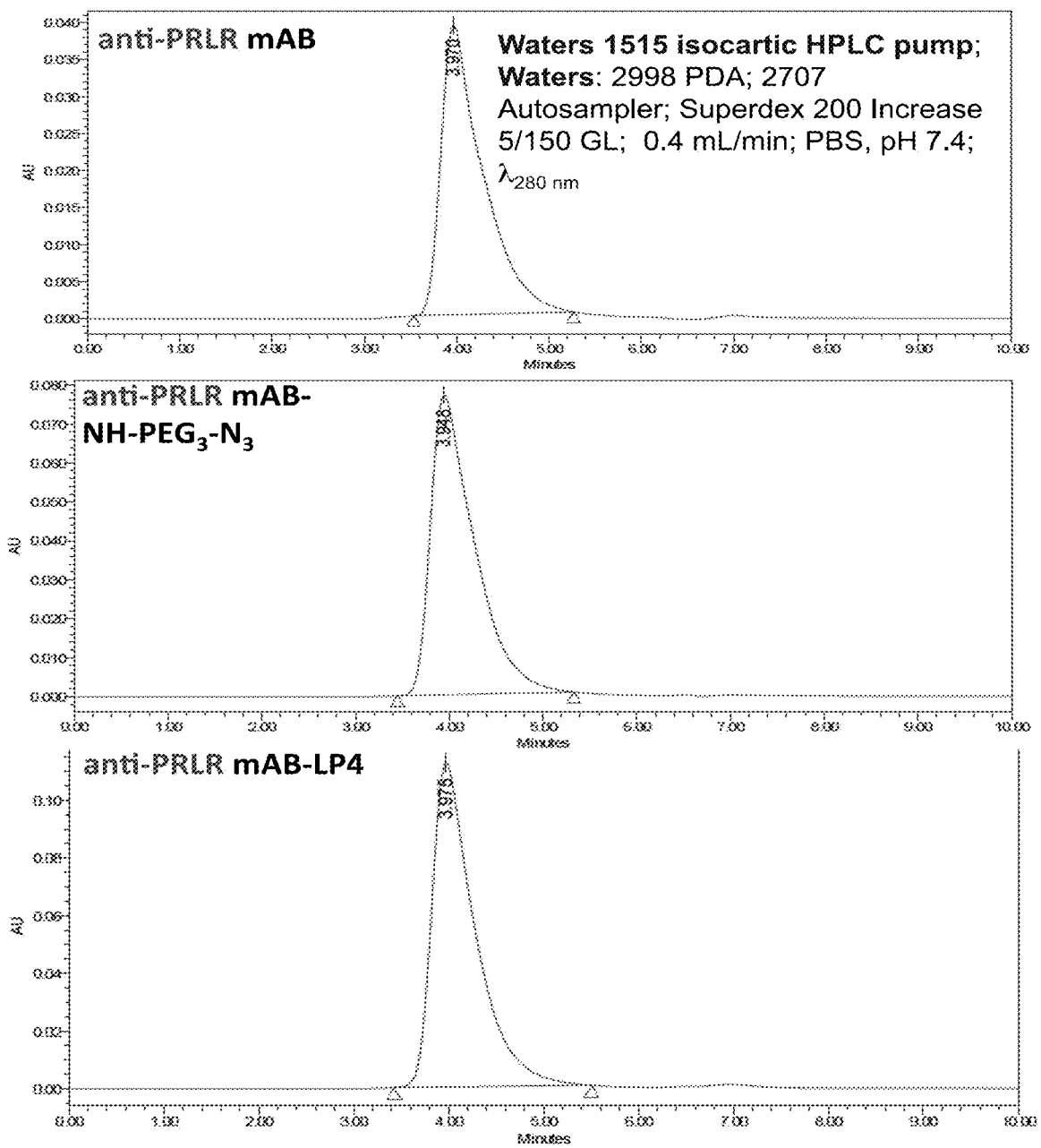
FIG. 21 shows size exclusion chromatography (SEC) of an anti-PRLR antibody, azido-functionalized antibody, and 4 DAR anti-PRLR-LP4 Conjugate as described in Example 59.

In FIG. 20 are shown the molecular weights of the antibodies and ncADCs on SDS-PAGE performed under non-reducing and reducing conditions. The mass shifts were not obvious under non-reducing conditions due to relatively small percentages of mass changes. However, the masses of the heavy chains were increased from the naked antibodies to the azido-functionalized antibodies, and further to the ncADC conjugate. There was no detectable cross-linked material.

As shown in FIG. 20, the SDS-PAGE lanes included the following species based on the following lane labels in Table 9.

TABLE 9

| Lane | Sample |
|---|---|
| 1 | Standards (Bench Mark 10 μL) |
| 2 | anti-PRLR antibody |
| 3 | anti-PRLR antibody-NH-PEG$_3$-N$_3$ |
| 4 | anti-PRLR antibody-LP4 |
| 8 | anti-PRLR antibody (reduced) |
| 9 | anti-PRLR antibody NH-PEG$_3$-N$_3$ (reduced) |
| 10 | anti-PRLR antibody-LP4 (reduced) |

~2 μg of non-reduced/reduced sample/lane.

ADC were analyzed for purity by Size Exclusion Chromatography (SEC)

To determine the purity of antibody drug conjugates, size exclusion chromatography was performed. Analytical SEC experiments were run using a Waters 600 instrument, on a Superdex 200 (1.0×30 cm) HR column, at flow rate of 0.80 mL/min using PBS pH 7.4, and monitored at λ280 nm using a Waters 2998 PDA. An analytic sample was composed of 200 μL PBS (pH 7.4) with 30-100 μL of test sample. Preparative SEC purifications were performed using an AKTA instrument from GE Healthcare, on Superdex 200 PG (2.6×60 cm) column, at a flow rate 2 mL/min eluting with PBSg at pH 7.4, and monitored at λ280 nm. The SEC results in FIG. 21 indicated typical retention time for monomeric mAb and its conjugates and there was no detectable aggregation or degradation.

Antibody and ADC were analyzed by intact mass analysis by LC-ESI-MS.

Measurement of intact mass of the ncADC samples by LC-ESI-MS was performed to determine drug-payload distribution profile and to calculate the average DAR of intact ADC forms. Each testing sample (20-50 ng, 5 uL) was loaded onto an Acquity UPLC Protein BEH C4 column (10 K psi, 300 Å, 1.7 µm, 75 µm×100 mm; Cat No. 186003810). After 3 min desalting, the protein was eluted and mass spectra were acquired by a Waters Synapt G2-Si mass spectrometer (Waters).

Figure 22:
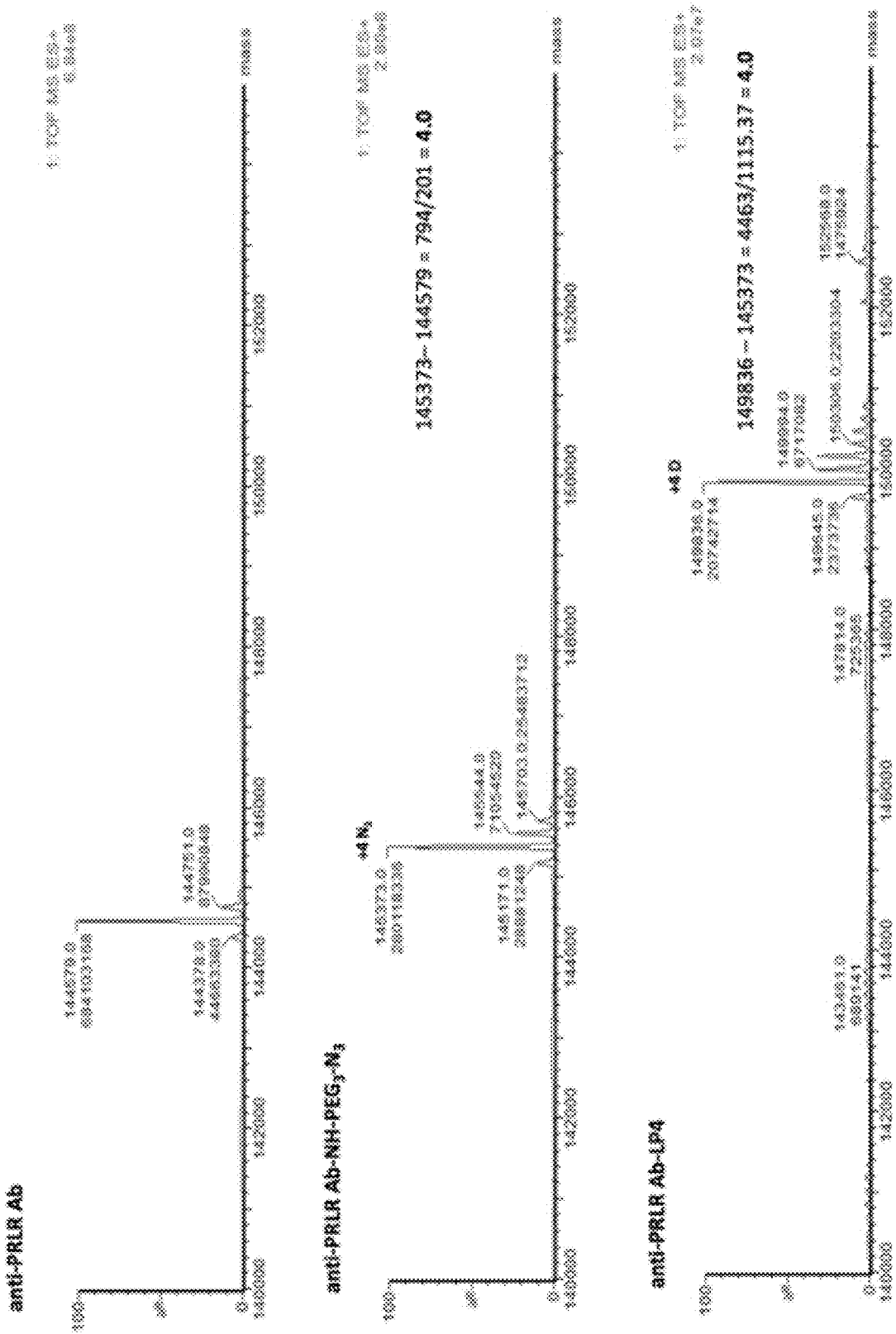
FIG. 22 shows an ESI-MS of anti-PRLR antibody, azido-functionalized anti-PRLR antibody and anti-PRLR antibody-LP4 conjugate as described in Example 59.

As shown in FIG. 22, the deconvoluted mass spectra exhibited a predominant peak for the aglycosylated anti-PRLR antibody with molecular weight of 144579.0 Da, and a predominant peak for its azido functionalized anti-PRLR antibody with molecular weight of 145373.0 Da, indicating a 794.0 Da increase compared to its aglycosylated parent antibody (corresponding to 4 amino-PEG$_3$-azide conjugation to each aglycosylated antibody). Also, the predominant peak for anti-PRLR-LP4 conjugate had a molecular weight of 149836.0 Da, indicating a 4463 Da increase compared to its aglycosylated parent antibody (corresponding to 4 LP4 conjugation to each aglycosylated antibody). As summarized in Table 8, most site-specific ADCs in this document have 4 DAR.

For non-site specific antibody drug conjugates, the DAR values were determined based on the ESI Q-TOF mass analysis. The ESI Q-TOF mass spectra were deconvoluted to zero charge mass spectra using a Maximum Entropy algorithm (MassLynx). The resulting mass spectra demonstrated the distribution of each drug(s) conjugated antibody. The area percentage of a peak represents the relative distribution of the particular drug-loaded antibody species. The average DAR was calculated using the percentage peak area information and the drug load numbers on the antibody.

Example 60

This example demonstrates, using the LanthaScreen TR-FRET GR Competitive Binding Assay, that the payload steroids set forth herein bind to the Glucocorticoid Receptor (GR).

To evaluate the ability of novel steroids to bind to the Glucocorticoid Receptor (GR), a cell-free binding assay was performed using a LanthaScreen TR-FRET GR Competitive Binding Assay kit (Life Technologies, Cat # A15901). The assay was performed according to the manufacturer's instruction. Budesonide is a commercial GR steroid and was used as a reference control in the binding assay and other cell based assays described later in the document. Briefly, a three-fold serial dilution of budesonide and the derivative compounds noted below were prepared in 100% DMSO starting at 100 nM (100× of final). Serial dilutions were further diluted 50-fold in nuclear receptor buffer F with 5 mM DTT and 0.1 mM stabilizing peptide, and transferred to a 384-well assay plate. Next, Fluormone GS1 Green, GR-LBD (GST) and Tb anti-GST antibody was sequentially added to 384-well assay plate. The plate was then incubated at room temperature for 2.5 hours while being protected from light. The plate was analyzed on an Envision Multi-label Plate Reader (PerkinElmer) with excitation set at 340 nm and emission filters at 520 nm and 486 nm. The FRET ratio was calculated as 520 nm/486 nm. The IC$_{50}$ values were determined using a four parameter logistic equation over a 12-point response curve (GraphPad Prism).

As shown in Table 10, Budesonide competed binding of Fluormone GS1 Green in the GR assay with an IC$_{50}$ value between 10 to 100 nM. The N-analogs of Budesonide similarly competed binding with IC$_{50}$ values ranging from less than 10 nM to greater than 100 nM. The novel steroids tested herein demonstrated comparable or better (lower IC$_{50}$ values) in this assay and similar displacement for GR ligand compared to Budesonide. The 22R-isomers in general are more potent than the 22S-isomers or at least identical to the 22S-isomers.

TABLE 10

Cell free binding and cell based functional activity

| Compounds' numbers | | HEK293/9xUAS-Luc2P/ pBind-GR/PRLR-HA high cells EC$_{50}$ (nM) | | GR Competitive Binding Assay IC50 (nM) |
|---|---|---|---|---|
| 1 | Budesonide | +++ | Full activation | ++ |
| 2 | Diflorasone | +++ | Full activation | ++ |
| 3 | 7-1 S | + | Partial activation | +++ |
| 4 | 7-1 R | +++ | Full activation | ++ |
| 5 | 7-2S/R | +++ | No activation | +++ |
| 6 | 7-4 S/R | + | No activation | +++ |
| 7 | 8-1 R | ++ | full activation | NT |
| 8 | 8-2 S/R | + | No activation | +++ |
| 9 | 8-3 S/R | + | No activation | +++ |
| 10 | 11-1 S/R | +++ | Full activation | ++ |
| 11 | 11-2 S/R | + | Full activation | ++ |
| 12 | 11-3 S/R | ++ | Partial activation | +++ |
| 13 | 11-5 S/R | +++ | Full activation | ++ |
| 14 | 11-5 S | +++ | Full activation | ++ |
| 15 | 11-5 R | +++ | Full activation | ++ |
| 16 | 11-6 S | +++ | Full activation | ++ |
| 17 | 11-6 S/R | ++ | Full activation | ++ |
| 18 | 11-7 R | ++ | Full activation | ++ |
| 19 | 11-8 R | +++ | Full activation | ++ |
| 20 | 11-10 S/R | + | No activation | +++ |
| 21 | 11-11 S/R | + | No activation | +++ |
| 22 | 11-12 S/R | +++ | Full activation | ++ |
| 23 | 11-13 R | +++ | Full activation | +++ |
| 24 | 11-14 S/R | +++ | Full activation | +++ |
| 25 | 11-15 S/R | ++ | Partial activation | +++ |
| 26 | 11-17 S/R | ++ | Full activation | +++ |
| 27 | 11-19 S/R | +++ | Full activation | +++ |
| 28 | 11-20 S/R | + | no activation | +++ |
| 29 | 11-21 S/R | ++ | Partial activation | +++ |
| 30 | 14-2 | + | No activation | +++ |
| 31 | 15-5 | ++ | Full activation | ++ |
| 32 | 16-5 | ++ | Full activation | ++ |

+++: ≤10 nM;
++: ≤100 nM > 10 nM;
+: >100 nM; NT: Not tested.

Full activation: >75% of fold activation induced by Budesonide. Partial activation: (20%, 75%) of fold activation induced by Budesonide. No activation: <20% of fold activation induced by Budesonide. Cell free assay is used to assess the direct binding of compounds to recombinant GR LBD regardless of their permeability. Cell based assay is used to measure how compounds activate intracellular GR mediated transcription after passing through the plasma membrane, thus membrane permeability of compound is prerequisite for activity.

Example 61

This example demonstrates that the PRLR-ncADC is internalized into HEK293/PRLR cells.

The internalization of an anti-PRLR antibody and an isotype control antibody were evaluated in HEK293 cells engineered to express full length human PRLR (amino acids 1 through 622 of accession number NP_000940.1 with a K2E mutation; HEK293/PRLR). HEK293 parental cells were also evaluated as a negative control. Cells were plated at 20,000 cells/well in complete medium and incubated overnight at 37° C. The following day, the wells were washed with PBS, and placed on ice. Antibody serial dilutions from 0.1-100 nM were added to appropriate wells in 2% FBS in PBS and incubated on ice for 30 minutes. Cells were washed twice with PBS, and then incubated on ice for 30 minutes with Alexa 488 conjugated Fab fragment goat anti-hIgG (Jackson Immunoresearch, Cat #109-547-003). Cells were washed twice with PBS and then either fixed in 3.7% formaldehyde in PBS (4° C. control condition) or incubated at 37° C. for 3 hours to allow for internalization. After the 3-hour incubation, the cells were fixed in 3.7% formaldehyde in PBS for 15 minutes, washed with PBS, and imaged on a Molecular Devices ImagExpress MicroXL.

The anti-PRLR-ncADC and the parental PRLR antibody internalized into HEK293/PRLR cells, while the isotype control ncADC and the isotype control parental antibody were not internalized since they do not bind to a protein found on the cell lines tested. No internalization was observed in HEK293 parental cells for any samples tested.

Example 62

Bioassays described herein were used to assess the efficacy of free steroids and anti-PRLR-ncADCs. In one example, the bioassay assessed the activity of steroids, after internalization of a site-specific anti-PRLR-GC steroid ADC into cells, to bind to pBIND-GR and subsequent luciferase reporter activation. For this assay, a 293 cell line was engineered to express human full length PRLR. Then such stable cell line was further transfected with a chimeric receptor consisting of a GR ligand binding domain fused to the yeast Gal4 DNA binding domain (pBind-GR, Promega Cat # E1581), and a Gal4 upstream activator sequence (9×Gal4UAS-Luc2P) that drives luciferase gene expression. Such assay format offers high sensitivity and low cross-reactivity with other nuclear receptors. Since the two vectors together as a whole is used to monitor GR ligand binding and transactivation, the resulting stable cell line is referred to herein as 293/PRLR/GRE-Luc for simplicity (see Improved Dual-Luciferase Reporter Assays for Nuclear Receptors, *Current Chem Genomics*, 2010; 4: 43-49; Aileen Paguio, Pete Stecha, Keith V Wood, and Frank Fan).

In a second example, a bioassay assessed both the efficacy of free steroids as well as any non-specific activity by anti-PRLR-ncADCs. For this assay a 293 cell line was transfected with pGL4.36[Luc2P/MMTV/Hygro] vector (Cat # E1360, Promega). The resulting cell line is referred to herein as 293/MMTV-Luc.

Example 63

A Glucocorticoid Receptor (GR) co-activator luciferase reporter cell based assay was used to analyze the GR activation by Budesonide and the steroids described herein as a function of time.

The activity of steroids in the 293/PRLR/GRE-Luc cells was studied at 72 hours of incubation. For this assay, 20,000 cells were seeded in 96-well plates in media containing DMEM supplemented with 10% FBS and penicillin/streptomycin (complete media) and grown overnight at 37° C. in 5% $CO_2$. For the free drug or ncADC dose response curves, serially diluted reagents ranging from 100 nM to 5.1 pM was added to the cells and incubated for 72 hours at 37° C. Luciferase activity was determined by addition of One-Glo™ reagent (Promega, Cat # E6130) and relative light units (RLUs) were measured on a Victor luminometer (Perkin Elmer). The $EC_{50}$ values were determined from a four-parameter logistic equation over a 10-point response curve using GraphPad Prism. Delivery of the steroids will result in an activation of the Luc reporter in 293/PRLR/GRE-Luc cells.

As shown in Table 11, at the 72 hour time point, Budesonide activated 293/PRLR/GRE-Luc cells with an $IC_{50}$ value between 10 to 100 nM. The N-analogs of Budesonide activated 293/PRLR/GRE-Luc cells with similar fold activation and $IC_{50}$ values ranging from less than 10 nM to greater than 100 nM.

Example 64

Selective GR Activation by ADCs in Targeted Cell Lines

The activity of the steroids and the steroid ncADCs, after internalization in the 293/PRLR/GRE-Luc cell line as well as in 293/MMTV-Luc cells, which do not express PRLR as described in Example 61, and 293/PRLR cells, which do not express luciferase reporter described in Example 62, were studied at concentrations 100 nM to 5.1 pM using the assay procedures outlined in Example 63 at 72 hours of incubation.

The PRLR-LP4 conjugate (in Table 8) and its isotype control conjugate, as well as the free payloads and unconjugated antibodies were studied in two types of cell lines. The PRLR-LP4 conjugate (Anti PRLR-LP4 in Table 8) demonstrated selective activation of the 293/PRLR/GRE-Luc cell line (FIG. 23A), and no GR activation (FIG. 23B) in 293/MMTV-Luc cells, which do not express PRLR.

As shown in FIG. 23A, in 293/PRLR/GRE-Luc cells, the anti-PRLR antibody site-specifically conjugated with LP4 (Anti PRLR-LP4 in Table 8) induced a full GRE-Luc activation with an $EC_{50}$ value<10 nM. The isotype control antibody conjugated with LP4 (Anti Her2-LP4 in Table 8) did not induce significant GRE-Luc activation. The unconjugated isotype control antibody did not induce significant GRE-Luc activation. The free payload 11-5 in Table 1 (payload of LP4) induced a full GRE-Luc activation with an $EC_{50}$<10 nM. The reference control, Budesonide, induced a full GRE-Luc activation with an $EC_{50}$<10 nM. As shown in FIG. 23B, in 293/MMTV-Luc cells, only the free payload 11-5 in Table 1 (payload of LP4) and the reference control, Budesonide, induced GRE-Luc activation: 11-5 in Table 1 (payload of LP4) induced a full GRE-Luc activation with an $EC_{50}$ value between 10 to 100 nM, and Budesonide induced a full GRE-Luc activation with an $EC_{50}$ value between 10 to 100 nM.

The Examples herein demonstrate that Anti PRLR-LP4 in Table 8 specifically activates 293/PRLR/GRE-Luc cells that express both target PRLR and steroid induced GRE luciferase reporter, but has no effect on steroid responsive 293-MMTV-Luc cell line or target expressing 293-PRLR cell line.

Example 65

Linker and payload contribution to the GR activation of ncADCs was examined in this example.

The activity of free steroids and their corresponding ncADCs after internalization in the 293/PRLR/GRE-Luc cell line were studied at concentrations of 100 nM to 5.1 pM using the assay procedures outlined in Example 63 at 72 hours of incubation.

Figure 24:
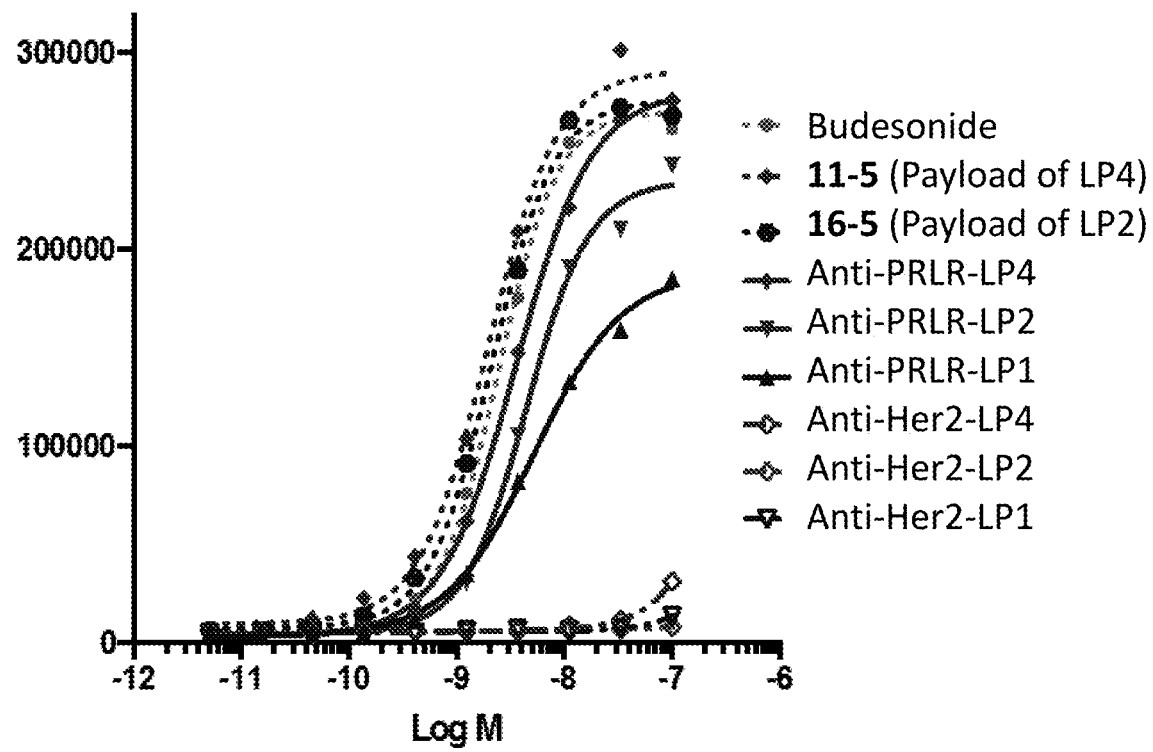
FIG. 24 shows the linker-payload contribution to GR activation by steroid ADC and budesonide control as tested in 293/PRLR/GRE-Luc cells as described in Example 65.

As shown in Table 11 and also shown in FIG. 24, in 293/PRLR/GRE-Luc cells, the anti-PRLR antibody site-specifically conjugated with LP4 (Anti PRLR-LP4 in Table 8) induced a full GRE-Luc activation with an $EC_{50}$<10 nM at 72 hours. The isotype control antibody conjugated with LP4 (Anti Her2-LP4 in Table 8) did not induce significant GRE-Luc activation. The free payload, 11-5 in Table 1 (payload of LP4), induced a full GRE-Luc activation with an $EC_{50}$<10 nM.

The anti-PRLR antibody site-specifically conjugated with LP2 (Anti PRLR-LP2 in Table 8) induced a full GRE-Luc activation with an $EC_{50}$<10 nM. The isotype control antibody conjugated with LP2 (Anti Her2-LP2 in Table 8) did not induce significant GRE-Luc activation. The free payload 16-5 in Table 1 (payload of LP2) induced a full GRE-Luc activation with an $EC_{50}$<10 nM. Finally, the anti-PRLR antibody site-specifically conjugated with LP1 (Anti PRLR-LP1 in Table 8) induced a full GRE-Luc activation with an $EC_{50}$ between 10-100 nM. The isotype control antibody conjugated with LP1 (Anti Her2-LP1 in Table 8) did not induce significant GRE-Luc activation. The free payload 7-1R in Table 1 (payload of LP1) induced a full GRE-Luc activation with an $EC_{50}$ between 10-100 nM.

This example demonstrates that with the same antibody and linker, the potency of payload 11-5 in Table 1 (payload of LP4) is greater than payload 16-5 in Table 1 (payload of LP2) which is greater than 7-1R in Table 1 (payload of LP1). Anti PRLR-LP4 in Table 8 had a higher potency than Anti PRLR-LP2 in Table 8, which had a higher potency than Anti PRLR-LP1 in Table 8.

TABLE 11

Linker-Payload Contribution in GR activation of steroid ncADC as tested in 293/PRLR/GRE-Luc cells

| Sample tested | Fold Activation | $EC_{50}$ (nM) |
|---|---|---|
| Anti PRLR-LP1 | Full | ++ |
| Anti PRLR-LP2 | Full | +++ |
| Anti PRLR-LP4 | Full | +++ |
| Anti Her2-LP1 | NA | NA |
| Anti Her2-LP2 | NA | NA |
| Anti Her2-LP4 | NA | NA |
| 7-2 (LP1 payload) | Full | ++ |
| 16-5 (LP2 payload) | Full | +++ |
| 11-5 (LP4 payload) | Full | +++ |
| Budesonide | Full | +++ |

NA = not applicable;
+++: ≤10 nM;
++: 10-100 nM,
+: >100 nM.

Example 66

IL2Rγ-ncADC Bioassay with HEK293/MMTV-Luc/IL2Rγ/IL7R Cells.

Common cytokine receptor γ-chain, also known as IL2Rγ and CD132, is a type I cytokine receptor that is common to the signaling pathways for interleukin-2 (IL-2), IL-4, IL-7, IL-9, IL-15, and IL-21 and plays an important role in the formation and regulation of immune systems (Rochman et al. 2009). IL2Rγ is expressed primarily on immune cells and therefore can be a useful target for delivering immunosuppressive drugs such as steroids via non-cytotoxic antibody-drug conjugate (ncADC) and suppress immune cell activity while avoiding off-target side effects associated with systemic administration of steroids.

The cell-based assay described herein was used to detect transcriptional activation of the glucocorticoid receptor (GR) by ncADC with murine mammary tumor virus long terminal repeat (MMTV LTR) region that has been used to study GR activation (Deroo et al. 2001). HEK293 cell line was first generated to stably express a luciferase reporter pGL4.36[luc2P/MMTV/Hygro] (Promega, # E136A), referred to herein as HEK293/MMTV-luc, and maintained in DMEM containing 10% FBS, NEAA, penicillin/streptomycin/L-glutamine, and 100 µg/mL hygromycin (complete media). The parental HEK293/MMTV-luc stable cell line was then transfected with a plasmid encoding full-length human IL2Rγ (expressing amino acids 1-369 of accession number NP_000197.1) and transduced with a plasmid encoding full-length IL7Rα (expressing amino acids 1-459 of accession number NP_002176.2) and sorted for high expression of IL2Rγ and IL7Rα by flow cytometry. The resulting cell line referred to herein as, HEK293/MMTV-luc/IL-2Rγ/IL7R, was maintained in complete media supplemented with 1 µg/mL puromycin, and 500 µg/mL G418 sulfate.

For the bioassay, HEK293/MMTV-luc or HEK293/MMTV-luc/IL2Rγ/IL7R cells were seeded onto 96-well assay plates at 10,000 cells/well in complete media and incubated at 37° C. in 5% $CO_2$ overnight. The next morning, to test GR activation, budesonide, compound 11-5 in Table 1 (LP4 payload) and compound 16-5 in Table 1 (LP2 payload), anti-IL2Rg-LP4 conjugate (in Table 8), control antibody (isotype control in Table 8) and naked antibodies were serially diluted at 1:3 from 200 nM-1 µM to 0.002-0.01 nM, and added to cells. The concentrations were adjusted according to drug-to-antibody ratio for ncADCs and other techniques known to those of skill in the art. One well without any test article was also included as a control.

Luciferase activity was measured after 6, 24, 48, and 72 hours of incubation in 37° C. at 5% $CO_2$ on a Victor X instrument (Perkin Elmer). The results were analyzed using nonlinear regression (4-parameter logistics) with Prism 6 software (GraphPad) to obtain $EC_{50}$ values. Fold activation was calculated by determining the ratio of the luciferase activity of each sample to that observed without any test article added As shown in Table 12, after 6, 24, and 48 hours of incubation, budesonide demonstrated the highest GR activation with full activations; 16-5 in Table 1 (LP2 payload) and 11-5 in Table 1 (LP4 payload) showed partial activation. At longer incubation times of 72 hours, 16-5 in Table 1 (LP2 payload) and 11-5 in Table 1 (LP4 payload) showed similar level of GR activation to Budesonide with full activations. These results demonstrate that Budesonide, 16-5 (LP2 payload), and 11-5 (LP4 payload) in Table 1 activate GR with $EC_{50}$s between 10-100 nM.

TABLE 12

Activation of glucocorticoid receptor in HEK293/MMTV-luc/IL-2Rγ/IL7R cells by budesonide, 11-5 in Table 1 or 16-5 in Table 1 at 6, 24, 48 or 72-hours

| | Time points | | | | | | | |
|---|---|---|---|---|---|---|---|---|
| | 6 hours | | 24 hours | | 48 hours | | 72 hours | |
| Drug | Fold Activation | EC$_{50}$ [nM] | Fold Activation | EC$_{50}$ [nM] | Fold Activation | EC$_{50}$ [nM] | Fold Activation | EC$_{50}$ [nM] |
| Budesonide | Full activation | ++ | Full activation | ++ | Full activation | ++ | Full activation | ++ |
| Compound 11-5 in Table 1 | Partial activation | + | Partial activation | + | Partial activation | ++ | Full activation | ++ |
| Compound 16-5 in Table 1 | Partial activation | + | Partial activation | + | Partial activation | ++ | Full activation | ++ |

+++: ≤10 nM;
++: 10-100 nM,
+: >100 nM.

Budesonide, linker-payload LP4 (payload 11-5) and linker-payload LP7 (payload R-11-5), anti-IL2Rγ, anti-IL2Rγ mAbs-ncADCs with LP4 and LP7 (referred to as anti-IL2Rγ-LP4 and anti-IL2Rγ-LP7), as well as a Control mAb-LP7 and the unconjugated anti-IL2Rγ mAb were added to either HEK293/MMTV-Luc/IL2Rγ/IL7R cells and incubated for 24 hrs (A), for 48 hrs (B), for 72 hrs (C) or HEK293/MMTV-Luc cells for 72 hrs (D) with max concentration at 200 nM (RLU, relative light unit) in FIG. 25 and Table 13.

Figure 25C:
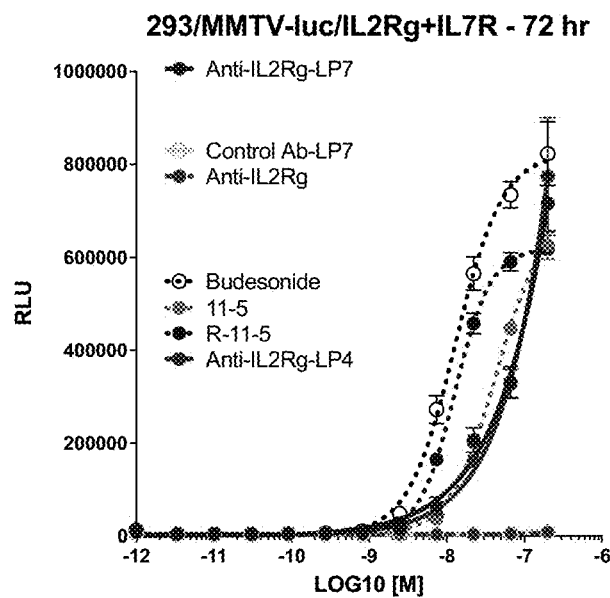
FIG. 25 shows activation of glucocorticoid receptor in a HEK293/MMTV-luc/IL-2Rγ/IL7R cell line by Budesonide, 11-5 in Table 1, and anti-IL2Rγ ncADC at twenty-four (24) (FIG. 25A), forty-eight (48) (FIG. 25B), or seventy-two (72) hours (FIG. 25C and FIG. 25D) as described in Example 66.

As shown in Table 13.1 and FIG. 25, after 24 hrs of incubation, budesonide showed the highest maximum fold activation in HEK293/MMTV-Luc/IL2Rγ/IL7R cells, and 11-5 and R-11-5 showed relatively lower levels of activation compared to budesonide (FIG. 25A). With longer incubation times of 48 and 72 hrs, 11-5 and R-11-5 showed similar level of activation to budesonide (FIG. 25B and FIG. 25C).

Figure 25D:
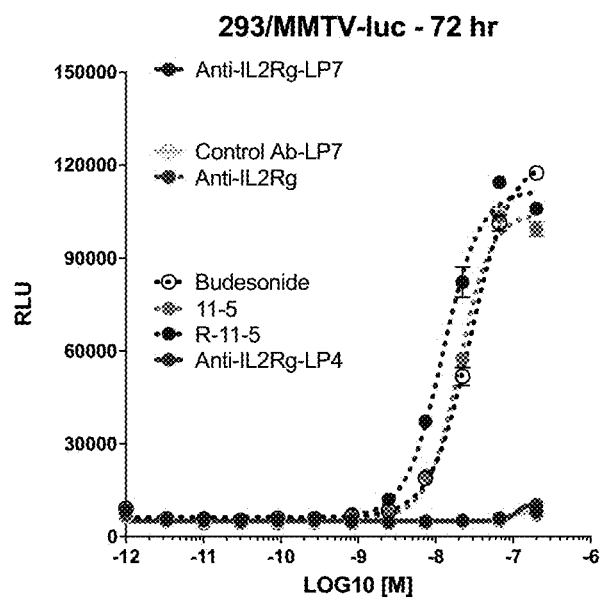

Anti-IL2Rγ-LP4 and anti-IL2Rγ-LP7 showed little to no activation in HEK293/MMTV-Luc/IL2Rγ/IL7R cells after 24 hrs of incubation (FIG. 25A), but showed greater levels of activation with longer incubation period of 48 hours and 72 hours (FIGS. 25B and 25C). The anti-IL2Rγ-ncADCs, anti-IL2Rγ-LP4 and anti-IL2Rγ-LP7, did not demonstrate any activation in HEK293/MMTV-Luc cells (FIG. 25D) indicating the ncADC delivery of steroids is dependent on binding to IL2Rγ antigen on the cell surface and subsequent internalization. In contrast, the unconjugated anti-IL2Rγ antibody, the unconjugated and conjugated isotype control antibodies did not show any significant activation in any conditions. Budesonide, 11-5 and R-11-5 showed activation in HEK293/MMTV-Luc at 72 hrs of incubation, indicating the GR activation by the free drugs (FIG. 25D).

TABLE 13.1

Activation of Glucocorticoid Receptor in HEK293/MMTV-Luc/IL-2Rγ/IL7R by Steroid Payloads and Anti-IL2Rγ-Steroid ADCs and Control ADC

| | Max Fold Activation | | |
|---|---|---|---|
| Treatment | at 24 hours | at 48 hours | at 72 hours |
| Anti-IL2Rγ-LP4 | NA | + | ++ |
| Anti-IL2Rγ-LP7 | NA | + | ++ |
| Payload LP4 (11-5) | + | ++ | +++ |

TABLE 13.1-continued

Activation of Glucocorticoid Receptor in HEK293/MMTV-Luc/IL-2Rγ/IL7R by Steroid Payloads and Anti-IL2Rγ-Steroid ADCs and Control ADC

| | Max Fold Activation | | |
|---|---|---|---|
| Treatment | at 24 hours | at 48 hours | at 72 hours |
| Payload LP7 (R-11-5) | + | ++ | +++ |
| Budesonide | +++ | +++ | +++ |
| Control Ab-LP7 | NA | NA | NA |

+++: ≤10 nM;
++: 10-100 nM;
+: >100 nM.

Example 67

Figure 30:
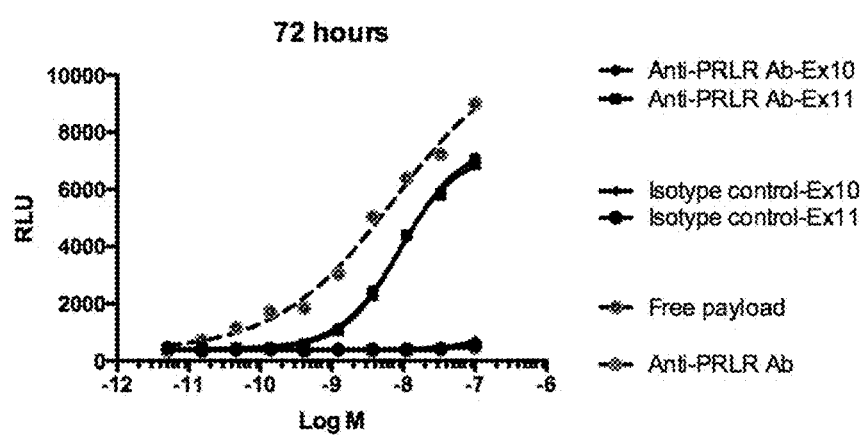
FIG. 30 shows bioactivity of steroid ADCs with and without cyclodextrin linkers in a plot of relative light units (RLU) vs. Log$_{10}$ [M].

This Example shows bioactivity of cytotoxic ADCs with and without Cyclodextrin linkers (FIG. 30).

To assess the comparability of ADCs with and without CDs containing cytotoxic payloads, a cytotoxicity assay using SKBR3 cells was performed. SKBR3 cells have been commonly used to assess anti-Her2 ADC activity. An anti-PRLR ADC has been used as a control mAb ADC in the SKBR3 cytotoxicity assay. For the assay, in vitro cytotoxicity of anti-PRLR ADCs were evaluated using the CellTiter-Glo Assay Kit (Promega, Cat # G7573), in which the quantity of ATP present is used to determine the number of viable cells in culture. For the assay, SKBR3 cells were seeded at 6000 cells/well on Nunclon white 96-well plates in complete growth medium and grown overnight at 37° C. in 5% $CO_2$. For cell viability curves, 1:4 serially diluted ADCs or free payload were added to the cells at concentrations starting at 100 nM including a no treatment control and were then incubated for 5 days. After the 5-day incubation, cells were incubated at room temperature with 100 μL of Cell-Titer-Glo reagents for 5 minutes. Relative luminescence units (RLU) were determined on a Victor plate reader (PerkinElmer). The $IC_{50}$ values were determined from a four-parameter logistic equation over a 10-point response curve (GraphPad Prism). All curves and $EC_{50}$ values were corrected for payload equivalents. All $IC_{50}$s are expressed in nM concentration and percentage of cells killed (% kill) is reported for the highest concentration tested.

Bioactivity of steroid ADCs with and without Cyclodextrin linkers is shown in FIG. 30.

To test the comparability of ADCs with and without CDs containing steroid payloads, their activity in the 293/PRLR/GRE-Luc cells was studied at 72 hours of incubation. For this assay, 20,000 cells were seeded in 96-well plates in media containing DMEM supplemented with 10% FBS and penicillin/streptomycin (complete media) and grown overnight at 37° C. in 5% $CO_2$. For the free drug or ADC dose response curves, serially diluted reagents ranging from 100 nM to 5.1 pM were added to the cells and incubated for 72 hours at 37° C. Luciferase activity was determined by addition of One-Glo™ reagent (Promega, Cat # E6130) and relative light units (RLUs) were measured on a Victor luminometer (Perkin Elmer). The $EC_{50}$ values were determined from a four-parameter logistic equation over a 10-point response curve using GraphPad Prism. Delivery of the steroids will result in an activation of the Luc reporter in 293/PRLR/GRE-Luc cells. Full activation in this assay is defined between 90 and 100% of the maximal activation measured with the free payload. Partial activation in this assay is defined as activation that is between 10% and 90% of the maximal activation measured with the free payload. Minimal activation in this assay is defined as less than 10% of the maximal activation measured with the free payload.

As shown in Table 13.2 and FIG. 30, anti-PRLR Ab ADCs containing CD (Anti-PRLR Ab-Ex46) have similar efficacy and potency in activating GRE-Luc reporter in 293/PRLR/GRE-Luc cells as anti-PRLR Ab ADC that do not contain CD (Anti-PRLR Ab-Ex44). In this assay, isotype control ADCs, regardless of whether they contain CD or not, as well as the unconjugated antibody did not demonstrate any significant effects in this assay.

TABLE 13.2

GR ACTIVATION OF STEROID ADCS WITH OR WITHOUT CYCLODEXTRIN LINKERS IN 293/PRLR/GRE-LUC CELLS

| Molecule tested | Maximal Activation | $EC_{50}$ (nM) | Molecule tested | Maximal Activation | $EC_{50}$ (nM) |
|---|---|---|---|---|---|
| Anti-PRLR Ab-Ex46 | Partial | 8.6 | Isotype control Ab-Ex46 | Minimal | NA |
| Anti-PRLR Ab-Ex45 | Partial | 9.5 | Isotype control Ab-Ex45 | Minimal | NA |
| Free payload (compound 1c) | Full | 8.4 | Anti-PRLR Ab | Minimal | NA |

NA = not-applicable

TABLE 14

CHEMICAL-PHYSICAL PROPERTY OF LINKER-STEROIDS

| Entry | MF | MW | cLog P | HPLC purity (%) | HPLC RT (min) | MS (m/z) 100% | Highest m/z peak |
|---|---|---|---|---|---|---|---|
| LP101 | $C_{60}H_{84}F_2N_8O_{13}$ | 1163.35 | 4.04 | 100 | 7.07 (B) | 1163.6 (M + H) | 1163.6 (M + H) |
| LP102 | $C_{55}H_{75}F_2N_5O_{11}$ | 1020.21 | 5.41 | >99 | 8.44 (A) 8.47 (B) | 510.8 (M/2 + H) | 1020.3 (M + H) (33%) |
| LP103 | $C_{66}H_{88}F_2N_8O_{14}$ | 1255.45 | 5.9 | >99 | 8.46 (A) | 1255.5 (M + H) | 1255.5 (M + H) |
| LP104 | $C_{126}H_{177}F_2N_{13}O_{49}$ | 2695.81 | −5.09 | >99 | 6.23 (B) | 899.2 (M/3 + H) | 1348.6 (M/2 + H) (40%) |
| LP105 | $C_{118}H_{176}F_2N_{12}O_{49}$ | 2584.71 | −5.21 | >99 | 7.37 (A) 7.41 (B) | 1293.6 (M/2 + H) | 1293.6 (M/2 + H) |
| LP108 | $C_{121}H_{168}F_2N_{10}O_{47}$ | 2552.66 | −3.72 | >99 | 7.76 (B) | 851.4 (M/3 + H) | 1276.8 (M/2 + H) (83%) |
| LP110 | $C_{132}H_{181}F_2N_{13}O_{50}$ | 2787.9 | −3.23 | >99 | 7.94 (A) 8.02 (B) | 930.3 (M/3 + H) | 1394.2 (M/2 + H) (33%) |
| LP112 | $C_{74}H_{94}F_2N_8O_{17}$ | 1405.60 | 4.39 | >99 | 7.40 (B) | 703.5 (M/2 + H) | 703.5 (M/2 + H) |
| LP113 | $C_{54}H_{74}N_4O_{15}$ | 1019.18 | 3.46 | 100 | 7.46 (B) | 510.3 (M/2 + H) | 1041.3 (M + Na) (10%) |
| LP114 | $C_{70}H_{87}F_2N_5O_{16}$ | 1292.46 | 5.61 | 99 | 9.18 (A) 9.22 (B) | 1292.1 (M + H) | 1292.1 (M + H) |
| LP115 | $C_{69}H_{84}F_3N_5O_{15}$ | 1280.42 | 5.91 | 100 | 8.34 (B) | 1279.6 (M + H) | 1279.6 (M + H) |
| LP116 | $C_{80}H_{98}F_2N_8O_{18}$ | 1497.70 | 6.25 | 99 | 7.99 (B) | 1498.7 (M/2 + H) | 1498.7 (M + H) (10%) |

TABLE 15
PHYSICAL PROPERTY OF LINKER-STEROIDS
| | structure | | Linker | | | | |
|---|---|---|---|---|---|---|---|
| LP # | Payload structure | | Cleavage piece L3 | Hydrophilic piece L2 | Conjugation linker L1 | cLogP | MW |
| LP112 | 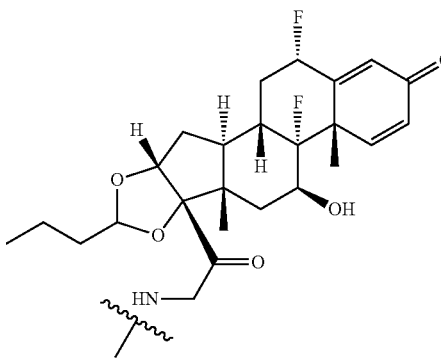 | | vcPAB | / | Lk-DIBAC | 4.39 | 1405.58 |
| LP101 | | | vcPAB | / | LkCCK | 4.04 | 1163.35 |
| LP104 | | | vcPAB | aCDCCK | Lk-DIBAC | −5.09 | 2695.81 |
| LP105 | | | vcPAB | aCDCCK | Lk-BCN | −5.21 | 2584.71 |
| LP102 | 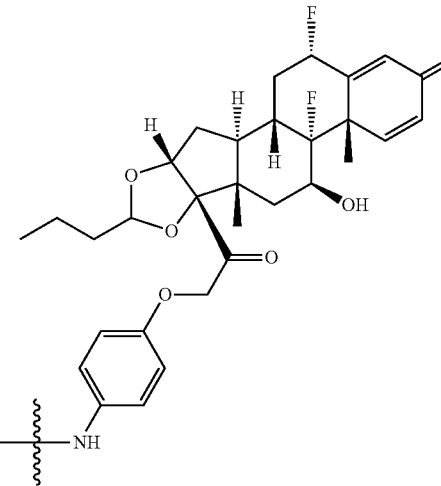 | | VA | / | Lk-CCK | 5.41 | 1020.2 |
| LP108 | | | VA | aCDCCK | Lk-DIBAC | −3.72 | 2552.66 |
| LP116 | | | vcPAB | / | Lk-DIBAC | 6.25 | 1497.67 |
| LP103 | | | vcPAB | / | LkCCK | 5.90 | 1255.5 |
| LP110 | | | vcPAB | aCDCCK | Lk-DIBAC | −3.23 | 2787.9 |
| LP113 | 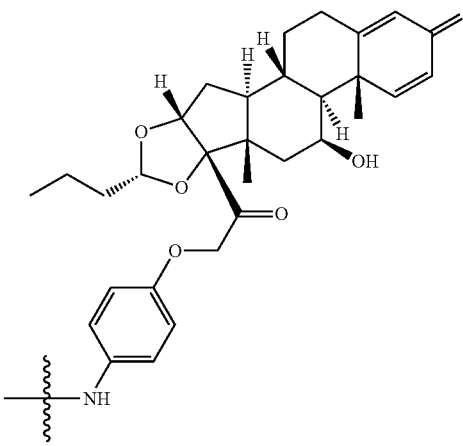 | | VA | / | Lk-MAL | 3.46 | 1019.18 |

TABLE 15-continued

PHYSICAL PROPERTY OF LINKER-STEROIDS

| LP # | Payload structure | Cleavage piece L3 | Hydrophilic piece L2 | Conjugation linker L1 | cLogP | MW |
|---|---|---|---|---|---|---|
| LP114 | 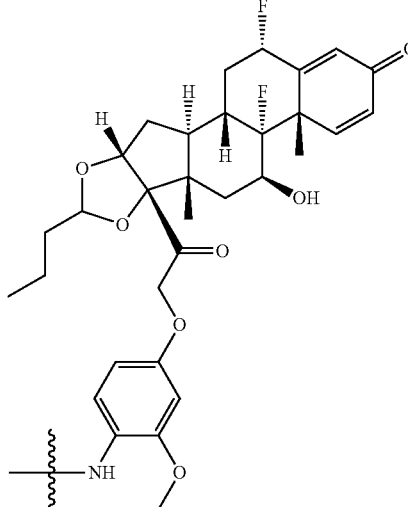 | VA | / | Lk-DIBAC | 5.61 | 1292.46 |
| LP115 | 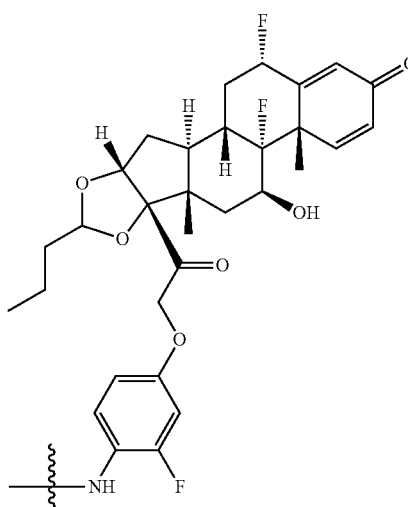 | VA | / | Lk-DIBAC | 5.91 | 1280.42 |

TABLE 16

LIST OF SITE-SPECIFIC STEROID-ANTIBODY CONJUGATES

| EX | LP MS m/z | Ab, Ab-N3, or Ab-Steroid conjugates Name | MW (Da) | DAR |
|---|---|---|---|---|
| | | Anti-PRLR Ab | 144602 | 4.0 |
| PEG$_3$-N$_3$ | 218.3 | Anti PRLR-Ab-N$_3$ | 145385 | 3.9 |
| LP112 | 1405.6 | Anti-PRLR Ab-LP12z | 151015 | 4.0 |
| LP104 | 2695.9 | Anti-PRLR Ab-LP4z | 156198 | 4.0 |
| LP116 | 1497.7 | Anti-PRLR Ab-LP16z | 151015 | 4.0 |
| | | Anti-Fel D1 Ab | | |
| PEG$_3$-N$_3$ | 218.3 | Anti-Fel D1 Ab-N3z | 146251 | 4 |
| LP112 | 1405.6 | Anti-Fel D1 Ab-LP12z | 151871 | 3.9 |
| LP116 | 1497.7 | Anti-Fel D1 Ab-LP16z | 152235 | 3.9 |

Example 68

Figure 31:
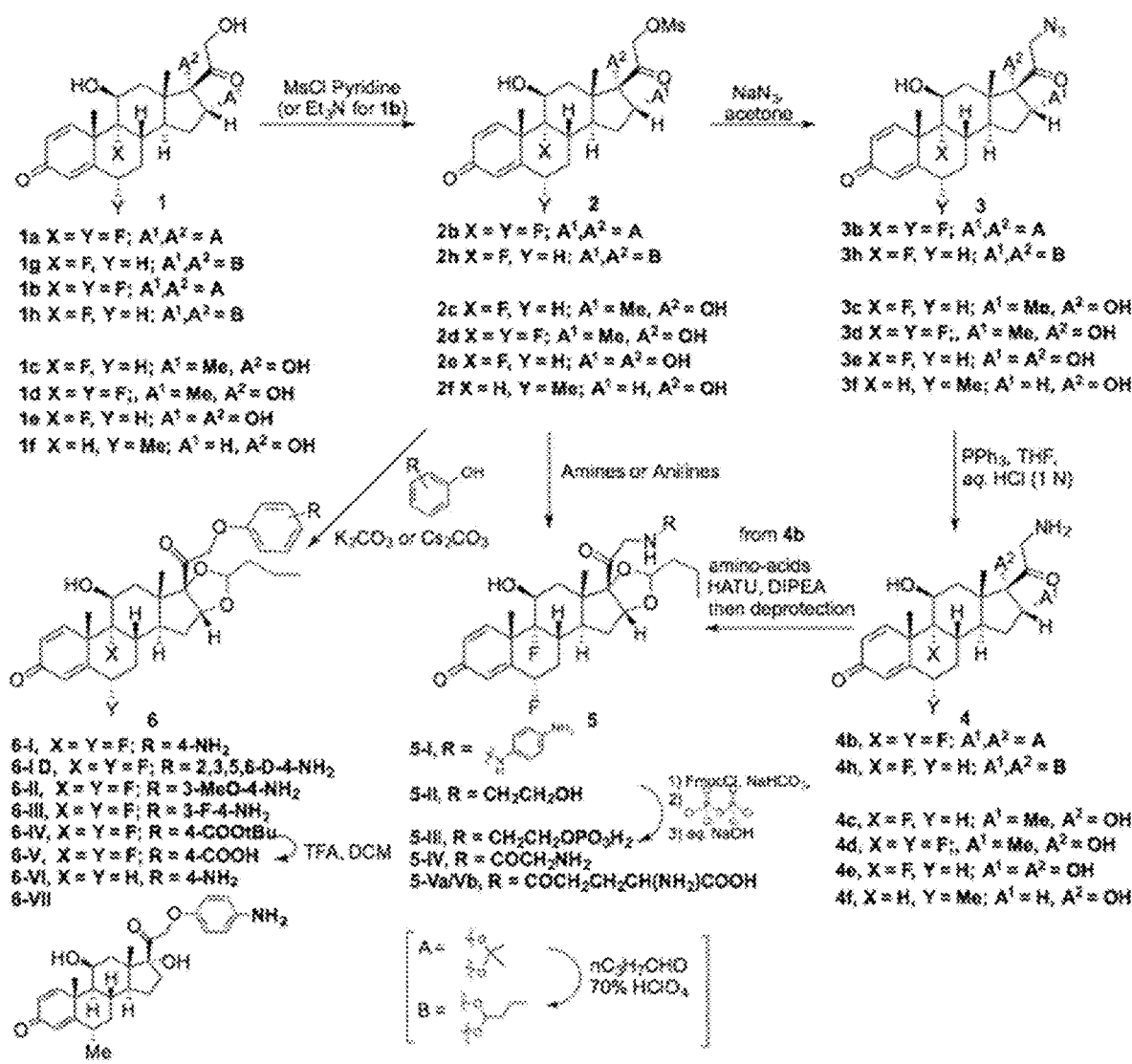
FIG. 31 shows a sequence for synthesizing certain steroids (payloads 1-6) described herein.
Figure 32:
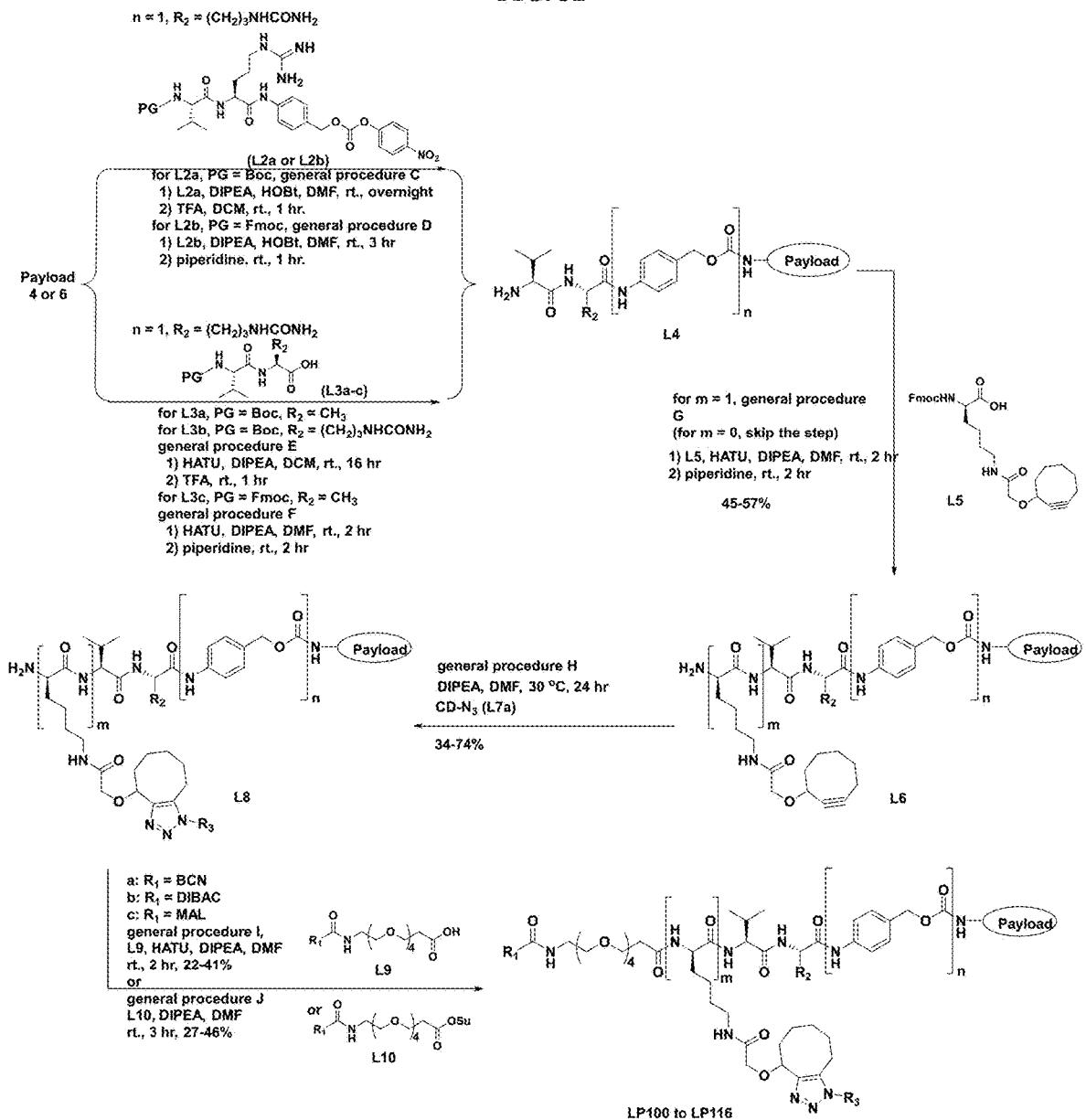
FIG. 32 shows a sequence for synthesizing certain linker-steroids (LP101 to LP116).

This example refers to the compounds in Table 2 and FIG. 31.

Commercial steroids including fluocinolone acetonide (1a), dexamethasone (1c), flumethasone (1d), triamcinolone (1e), and methylprednisolone (1f), and triamcinolone acetonide (1g) where used as staring materials. Compound 1b was obtained from 1a by ketal-exchange with butyraldehyde in the presence of perchloric acid, and its two chiral isomers were obtained from chiral SFC separation. Taking the same approach, compound 1h was obtained from 1g. Compounds 1b-f and 1h were converted to the corresponding mesylate derivatives (2b-f, 2h), followed by replacement of the mesylate group with an azide moiety to form compounds 3b-f and 3h that were further reduced to the amines (4b-f, 4h). The mesylate moiety in compound 2b was also replaced by an anilines to afford 5-Iz, replaced by an alkylamine to provide 5-II, and replaced by phenols to provide 6-I to 6-III. Compound 6-VI was obtained from replacement of the mesylate of budesonide with a 4-aminophenol, and 6-VII was obtained from replacement of the mesylate in 2f with 4-amino-phenol.

Example 69

Synthesis of Compound 1b, R-1b, S-1b, and 1h.

This example refers to the compounds in Table 2 and FIG. 31.

(1S,2S,4R,8S,9S,11S,12R,13S,19S)-12,19-Difluoro-11-hydroxy-8-(2-hydroxyacetyl)-9,13-dimethyl-6-propyl-5,7-dioxapentacyclo[10.8.0.0$^{2,9}$.0$^{4,8}$.0$^{13,18}$]icosa-14,17-dien-16-one (1b)

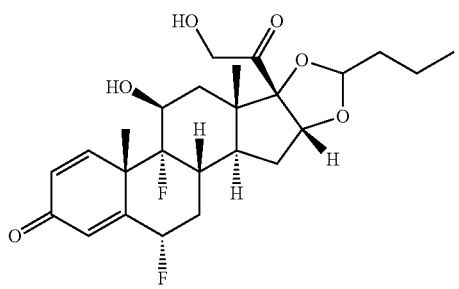

To a mixture of fluocinolone acetonide (1a, 0.90 g, 2.0 mmol) and silica gel (18 g) in heptanes (90 mL) was added butyraldehyde (0.27 mL, 3.0 mmol) at 10° C. and the suspension was stirred at 10-20° C. for 10 minutes. To the mixture was added perchloric acid (70%, 0.68 mL, 8.3 mmol) dropwise at 0° C. The reaction mixture was then stirred at 10-20° C. overnight. Most of compound 1a was consumed according to TLC and LC-MS. The reaction mixture was diluted with petroleum ether and quenched with sat. aq. sodium carbonate. The suspension was filtered and the solid was washed with DCM/methanol (v/v=1). The combined filtrate was concentrated in vacuo. The residue was purified by flash chromatography (0-100% ethyl acetate in petroleum ether) to give compound 1b (0.15 g, 16% yield) as a white solid. ESI m/z: 467.1 (M+H)$^+$. Compound 1b was further purification by prep-HPLC (method B) gave compound R-1b (40 mg, 39% yield) and S-1b (10 mg, 9% yield) as white solids. ESI m/z: 467 (M+H)$^+$.

(1S,2S,4R,6R,8S,9S,11S,12R,13S,19S)-12,19-Difluoro-11-hydroxy-8-(2-hydroxyacetyl)-9,13-dimethyl-6-propyl-5,7-dioxapentacyclo[10.8.0.0$^{2,9}$.0$^{4,8}$.0$^{13,18}$]icosa-14,17-dien-16-one (R-1b)

Certain methods and/or intermediates in EP0262108A1 were employed, the entire contents of which are herein incorporated by reference in their entirety for all purposes:

Compound R-1b is

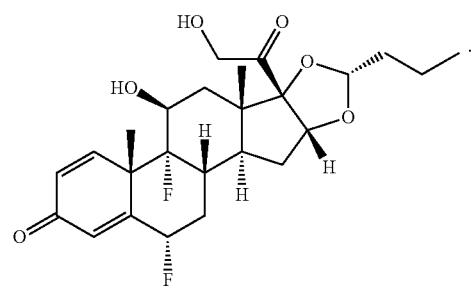

$^1$H NMR (400 MHz, MeOD$_{d4}$) δ 7.34 (dd, J=10.1, 1.3 Hz, 1H), 6.37-6.32 (m, 2H), 5.65-5.48 (m, 1H), 4.63 (t, J=4.3 Hz, 1H), 4.55 (d, J=19.4 Hz, 1H), 4.33-4.28 (m, 2H), 2.74-2.59 (m, 1H), 2.38-2.32 (m, 1H), 2.26-2.16 (m, 2H), 1.70-1.41 (m, 12H), 0.97-0.93 (m, 6H) ppm. Anal. HPLC: >99.9%, Retention time: 8.05 min (method A).

(1S,2S,4R,8S,9S,11S,12R,13S)-12-Fluoro-11-hydroxy-8-(2-hydroxyacetyl)-9,13-dimethyl-6-propyl-5,7-dioxapentacyclo[10.8.0.0$^{2,9}$.0$^{4,8}$.0$^{13,18}$]icosa-14,17-dien-16-one (1h)

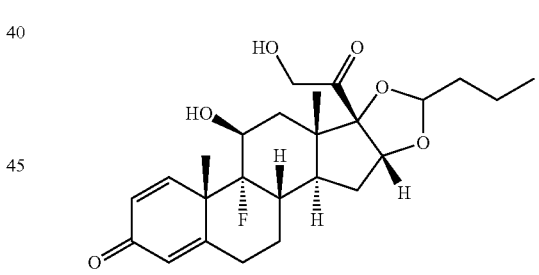

Following the procedure for making compound 1b, compound 1g (1.3 g, 3.0 mmol) was converted to compound 1h (1.1 g, 85% yield) as a white solid. ESI m/z: 449 (M+1)$^+$.

Example 70

General Procedure A for the Synthesis of Mesylates (Ms) 2 in FIG. 31:

This example refers to the compounds in Table 2 and FIG. 31.

To a solution of compound 1 (1c, 1d, 1e, 1f, or 1h, 1 eq.) in pyridine (10 mL per gram of 1) were added 4-dimethylaminopyridine (2 eq.) and methanesulfonyl chloride (1.5 eq.) dropwise at 0° C. After stirring at RT for 2 hours and monitoring the reaction by LC-MS until the compound 1 (1c, 1d, 1e, 1f, or 1h, 1 eq.) was totally consumed, the resulting mixture was poured into ethyl acetate (100 mL).

The mixture was washed with diluted aq. hydrochloride (1N) to pH=7 and brine, dried over sodium sulfate and concentrated. The crude product was purified by flash chromatography (0-2% MeOH in DCM) to give compound 2 (2c, 2d, 2e, 2f, or 2h, 1 eq.).

Example 71

This example refers to the compounds in Table 2 and FIG. 31.

2-[(1S,2S,4R,8S,9S,11S,12R,13S,19S)-12,19-Difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl methanesulfonate (2b)

This example refers to the compounds in Table 2 and FIG. 31.

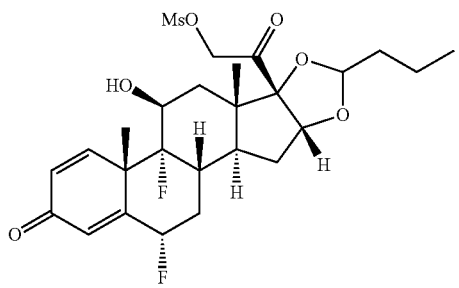

To a solution of compound 1b (0.28 g, 0.65 mmol)) in DCM (3 mL) was added triethylamine (0.13 g, 1.3 mmol) and methanesulfonyl chloride (89 mg, 0.78 mmol). After stirring at 0° C. for half an hour until compound 1b was consumed according to TLC, the reaction mixture was concentrated in vacuo. The residue on silica gel was purified by silica gel column chromatography (0-50% ethyl acetate in petroleum ether) to give compound 2b (0.26 g, >99% yield) as a white solid. ESI m/z: 545 (M+H)$^+$.

Example 72

This example refers to the compounds in Table 2 and FIG. 31.

2-[(1R,2S,10S,11S,13R,14R,15S,17S)-1-Fluoro-14,17-dihydroxy-2,13,15-trimethyl-5-oxotetracyclo[8.7.0.0$^{2,7}$.0$^{11,15}$]heptadeca-3,6-dien-14-yl]-2-oxoethyl methanesulfonate (2c)

Certain methods and/or intermediates in WO2015/71657 A1 were employed, the entire contents of which are herein incorporated by reference in their entirety for all purposes:

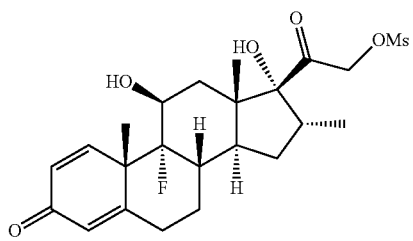

Following the general procedure A, compound 2c (0.32 g, 50% yield) was obtained as a white solid from dexamethasone (1c, 0.53 g, 1.4 mmol). ESI m/z: 471 (M+H)$^+$. $^1$H NMR (MeOD$_{d4}$, 500 MHz) δ 7.42 (d, J=10.0 Hz, 1H), 6.31 (dd, J=10.0, 2.0 Hz, 1H), 6.10 (s, 1H), 5.27 (d, J=18.0 Hz, 1H), 5.04 (d, J=18.0 Hz, 1H), 4.30-4.27 (m, 1H), 3.21 (s, 3H), 3.10-3.05 (m, 1H), 2.78-2.71 (m, 1H), 2.55-2.40 (m, 1H), 2.36-2.32 (m, 1H), 2.27-2.21 (m, 1H), 1.93-1.88 (m, 1H), 1.82-1.74 (m, 1H), 1.61 (s, 3H), 1.58-1.51 (m, 2H), 1.25-1.20 (m, 1H), 1.06 (s, 3H), 0.89 (d, J=7.5 Hz, 3H) ppm.

Example 73

This example refers to the compounds in Table 2 and FIG. 31.

2-[(1R,2S,8S,10S,11S,13R,14R,15S,17S)-1,8-Difluoro-14,17-dihydroxy-2,13,15-trimethyl-5-oxotetracyclo[8.7.0.0$^{2,7}$.0$^{11,15}$]heptadeca-3,6-dien-14-yl]-2-oxoethyl methanesulfonate (2d)

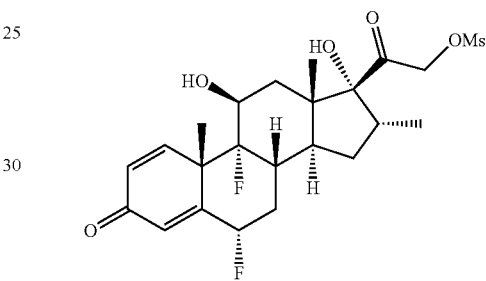

Certain methods and/or intermediates in *Bioorg. Med. Chem. Lett.*, 2015, 25, 2837-2843 were employed, the entire contents of which are herein incorporated by reference in their entirety for all purposes:

Following the general procedure A, compound 2d (0.17 g, 71% yield) was obtained as a white solid from flumethasone (1d, 0.20 g, 0.49 mmol). ESI m/z: 489 (M+H)$^+$.

Example 74

This example refers to the compounds in Table 2 and FIG. 31.

2-((8S,9R,10S,11S,13S,14S,16R,17S)-9-Fluoro-11,16,17-trihydroxy-10,13-dimethyl-3-oxo-6,7,8,9,10,11,12,13,14,15,16,17-dodecahydro-3H-cyclopenta[a]phenanthren-17-yl)-2-oxoethyl methanesulfonate (2e)

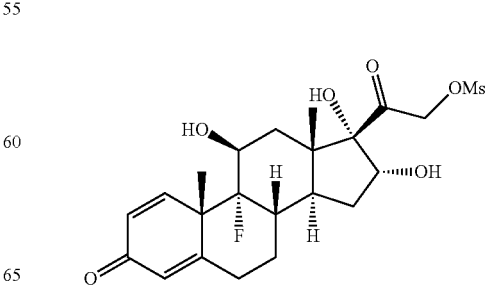

Following the general procedure A, compound 2e (0.38 g, 81% yield) was obtained as a white solid from triamcinolone (1e, 0.39 g, 1.0 mmol). ESI m/z: 473 (M+H)+.

Example 75

This example refers to the compounds in Table 2 and FIG. 31.

2-((6S,8S,9S,10R,11S,13S,14S,17R)-11,17-Dihydroxy-6,10,13-trimethyl-3-oxo-6,7,8,9,10,11,12,13,14,15,16,17-dodecahydro-3H-cyclopenta[a]phenanthren-17-yl)-2-oxoethyl methanesulfonate (2f)

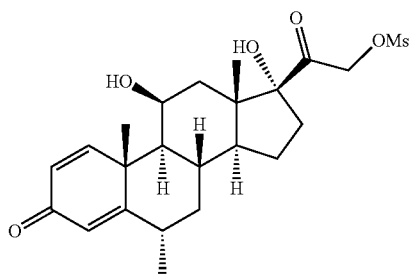

Following the general procedure A, compound 2f (0.16 g, 35% yield) was obtained as a white solid from methylprednisolone (1f, 0.38 g, 1.0 mmol). ESI m/z: 453 (M+H)+.

Example 76

This example refers to the compounds in Table 2 and FIG. 31.

2-[(1S,2S,4R,8S,9S,11S,12R,13S)-12-Fluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl methanesulfonate (2h)

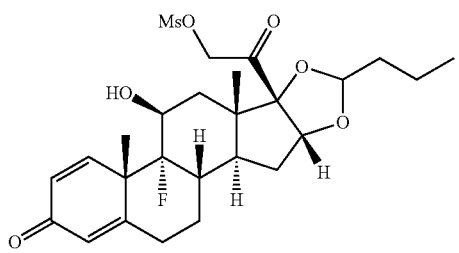

This example refers to the compounds in Table 2 and FIG. 31.

Following the general procedure A, compound 2h (0.45 g, 85% yield) was obtained as a white solid from methylprednisolone (1h, 0.39 g, 1.0 mmol). ESI m/z: 528 (M+H)+.

Example 77

This example refers to the compounds in Table 2 and FIG. 31.

Synthesis of Steroidal Payload 4b.

(1S,2S,4R,8S,9S,11S,12R,13S,19S)-8-(2-Azidoacetyl)-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (3b)

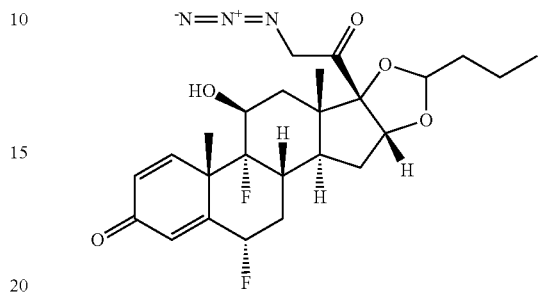

A suspension of compound 2b (1.0 g, 1.8 mmol) and sodium azide (1.2 g, 18 mmol) in acetone (15 mL) was stirred at 50° C. overnight, at which time the reaction was complete according to LC-MS analysis. After cooling the suspension, the reaction mixture was poured into cold water (80 mL). The aqueous mixture was extracted with ethyl acetate (50 mL×3). The combined organic solution was washed by brine (30 mL), dried over sodium sulfate and concentrated in vacuo to afford crude compound 3b (0.90 g, >99% yield) as a yellow solid, which was used for the next step without further purification. ESI m/z: 492 (M+H)+.

(1S,2S,4R,6R,8S,9S,11S,12R,13S,19S)-8-(2-Aminoacetyl)-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one; trifluoroacetic acid salt (4b)

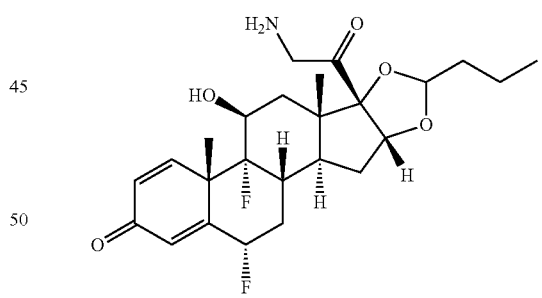

To a 100 mL round bottom flask was added compound 3b (0.85 g, 1.7 mmol), followed by the addition of THF (20 mL) and aq. hydrochloride (1 N, 10 mL). The mixture was stirred at 28-32° C. until it turned clear, to which was then added triphenylphosphine (0.68 g, 2.6 mmol) at this temperature. The resulting yellow clear solution was stirred at 28-32° C. for 18 hours, when the reaction was completed according to TLC and LC-MS. The mixture was concentrated under vacuum and the residue was purified by reversed phase flash chromatography (0-50% acetonitrile in aq. TFA (0.05%)) to give the title compound 4b (0.56 g, 57% yield, TFA salt) as an off-white solid. ESI m/z: 466 (M+H)+.
$^1$H NMR (400 MHz, MeOD$_{d4}$) δ 7.33 (d, J=9.9 Hz, 1H), 6.40-6.29 (m, 2H), 5.69-5.45 (m, 1H), 4.93-4.92 (m, 1H), 4.71 (t, J=4.3 Hz, 1H), 4.35-4.27 (m, 2H), 3.90-3.84 (m, 1H), 2.81-2.54 (m, 1H), 2.42-2.06 (m, 3H), 1.82-1.32 (m, 11H), 1.09-0.87 (m, 6H) ppm. $^{19}$F NMR (376 MHz, MeOD$_{d4}$) δ −77.01, −166.24, −166.92, −188.81, −188.83 ppm. Anal. HPLC: 100%, Retention time: 6.86 min (method A).

Example 78

This example refers to the compounds in Table 2 and FIG. 31.

(1R,2S,10S,11S,13R,14R,15S,17S)-14-(2-Aminoacetyl)-1-fluoro-14,17-dihydroxy-2,13,15-trimethyltetracyclo[8.7.0.0$^{2,7}$.0$^{11,15}$]heptadeca-3,6-dien-5-one trifluoroacetate (4c)

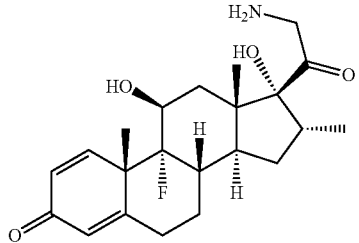

Following the in procedure in Example 77 for making compound 4b, except substituting compound 2c for compound 2d, compound 4c as the TFA salt was obtained (0.50 g, 53% yield in 2 steps) as a white solid. ESI m/z: 392 (M+H)$^+$. $^1$H NMR (400 MHz, DMSO$_{d6}$) δ 8.22 (s, 3H), 7.35 (d, J=10.0 Hz, 1H), 6.19 (d, J=10.0 Hz, 1H), 5.98 (s, 1H), 5.60 (d, J=4.0 Hz, 1H), 5.38 (s, 1H), 4.30-4.10 (m, 2H), 3.62 (d, J=18.8 Hz, 1H), 2.98-2.83 (m, 1H), 2.65-2.50 (m, 1H), 2.50-2.22 (m, 2H), 2.20-2.01 (m, 2H), 1.80-1.72 (m, 1H), 1.72-1.58 (m, 1H), 1.46 (s, 3H), 1.46-1.25 (m, 2H), 1.13-1.01 (m, 1H), 0.89 (s, 3H), 0.78 (d, J=6.8 Hz, 3H) ppm. $^{19}$F NMR (376 MHz, DMSO$_{d6}$) δ −73.79, −164.32. Anal. HPLC: >99%, Retention time: 6.34 min (method A).

Example 79

This example refers to the compounds in Table 2 and FIG. 31.

(1R,2S,8S,10S,11S,13R,14R,15S,17S)-14-(2-Aminoacetyl)-1,8-difluoro-14,17-dihydroxy-2,13,15-trimethyltetracyclo[8.7.0.0$^{2,7}$.0$^{11,15}$]heptadeca-3,6-dien-5-one trifluoroacetate (4d)

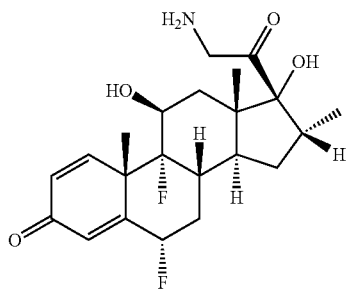

Following the procedure in Example 77 for making compound 4b, except substituting compound 2d for compound 2b, compound 4d as TFA salt was obtained (0.18 g, 21% yield in 2 steps) as a white solid. ESI m/z: 410 (M+H)$^+$. $^1$H NMR (400 MHz, DMSO$_{d6}$) δ 8.17 (s, 3H), 7.36 (d, J=10.3 Hz, 1H), 6.29 (dd, J=10.2, 1.7 Hz, 1H), 6.11 (s, 1H), 5.74-5.54 (m, 2H), 5.42 (s, 1H), 4.28-4.10 (m, 2H), 3.70-3.59 (m, 1H), 3.02-2.89 (m, 1H), 2.58-2.40 (m, 1H), 2.31-2.12 (m, 3H), 2.08 (s, 1H), 1.77-1.64 (m, 1H), 1.51-1.44 (m, 4H), 1.16-1.06 (m, 1H), 0.91 (s, 3H), 0.82 (d, J=7.2 Hz, 3H) ppm. $^{19}$F NMR (376 MHz, DMSO$_{d6}$) δ −73.65, −163.75, −186.04 ppm. Anal. HPLC: >99%, Retention time: 6.36 min (method A).

Example 80

This example refers to the compounds in Table 2 and FIG. 31.

(8S,9R,10S,11S,13S,14S,16R,17S)-17-(2-Aminoacetyl)-9-fluoro-11,16,17-trihydroxy-10,13-dimethyl-7,8,11,12,13,15,16,17-octahydro-6H-cyclopenta[a]phenanthren-3(9H,10H,14H)-one trifluoroacetate (4e)

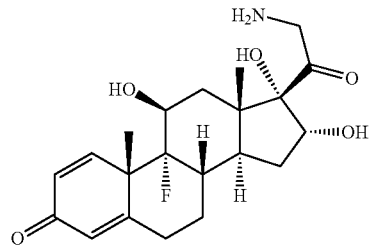

Following the procedure in Example 77 for making compound 4b, except substituting compound 2e for compound 2b, compound 4e as TFA salt was obtained (28 mg, 21% yield in 2 steps) as a white solid. ESI m/z: 394 (M+H)$^+$. $^1$H NMR (500 MHz, DMSO$_{d6}$) δ 8.04 (s, 3H), 7.33 (d, J=10 Hz, 1H), 6.24 (dd, J=10 Hz, 1.0 Hz, 1H), 6.02 (s, 1H), 5.53 (d, J=5.5 Hz, 1H), 5.50-5.45 (m, 1H), 5.04 (s, 1H), 4.76-4.70 (m, 1H), 4.20-4.12 (m, 2H), 3.68 (d, J=20 Hz, 1H), 2.66-2.57 (m, 1H), 2.40-2.20 (m, 3H), 2.20-2.10 (m, 1H), 1.90-1.70 (m, 2H), 1.50-1.20 (m, 6H), 0.89 (s, 3H) ppm. Anal. HPLC: >99%, Retention time: 5.79 min (method A).

Example 81

This example refers to the compounds in Table 2 and FIG. 31.

435

(6S,8S,9S,10R,11S,13S,14S,17R)-17-(2-Amino-acetyl)-11,17-dihydroxy-6,10,13-trimethyl-6,7,8,9,10,11,12,13,14,15,16,17-dodecahydro-3H-cyclopenta[a]phenanthren-3-one (4f)

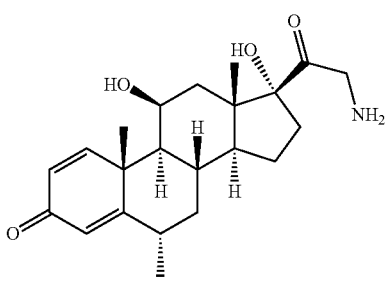

Following the procedure in Example 77 for making compound 4b, except replacing 2b with 2f and stirring at 60° C., not 28~32° C., in $2^{nd}$ step, compound 4f was obtained (10 mg, 14% yield in 2 steps) as a yellow solid after purification by prep-HPLC (method B). ESI m/z: 466 (M+H)$^+$. $^1$H NMR (400 MHz, MeOD$_{d4}$) δ 8.50 (s, 1H), 7.50 (d, J=10.0 Hz, 1H), 6.27 (dd, J=1.6 Hz, 10.0 Hz, 1H), 6.02 (s, 1H), 4.43-4.42 (m, 1H), 4.32-4.27 (m, 1H), 3.80-3.76 (m, 1H), 2.79-2.73 (m, 2H), 2.29-2.15 (m, 3H), 1.83-1.50 (m, 7H), 1.10-0.80 (m, 8H) ppm.

Example 82

This example refers to the compounds in Table 2 and FIG. 31.

(1S,2S,4R,8S,9S,11S,12R,13S)-8-(2-Aminoacetyl)-12-fluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (4h) with 22R/S isomers (ratio 2:1)

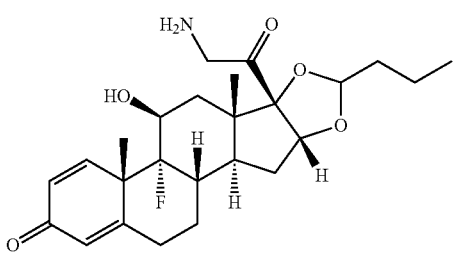

Following the procedure in Example 77 for making compound 4b, except substituting compound 2h (0.26 g, 0.5 mmol) for compound 2b, compound 4h was obtained (5 mg, 6% yield in 2 steps) as a yellow solid after purification by prep-HPLC (method A) twice. ESI m/z: 448 (M+H)$^+$. $^1$H NMR (500 MHz, DMSO$_{d6}$) δ 8.04 (s, 3H), 7.95-7.70 (m, 1H), 7.32 (d, J=10 Hz, 1H), 6.24 (d, J=9.0 Hz, 1H), 6.02 (s, 1H), 5.65-5.55 (m, 1H), 5.18 (t, J=4 Hz, 0.24H), 5.12 (d, J=5 Hz, 0.24H), 4.77 (d, J=5.0 Hz, 0.76H), 4.66 (t, J=4 Hz, 0.76H), 4.25-4.10 (m, 2H), 3.80-3.70 (m, 1H), 2.65-2.55 (m, 1H), 2.36-2.30 (m, 1H), 2.05-1.95 (m, 2H), 1.85-1.75 (m, 1H), 1.70-1.55 (m, 4H), 1.48 (s, 3H), 1.40-1.30 (m, 3H), 1.25-1.20 (m, 1H), 0.90-0.80 (m, 6H) ppm. $^{19}$F NMR (376 MHz, DMSO$_{d6}$) δ -73.51 (3F), -164.50 (0.3F), -165.27 (0.7F) ppm.

Example 83

This example refers to the compounds in Table 2 and FIG. 31.

(1S,2S,4R,8S,9S,11S,12R,13S,19S)-8-{2-[(4-Aminophenyl)amino]acetyl}-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one trifluoroacetate (5-I)

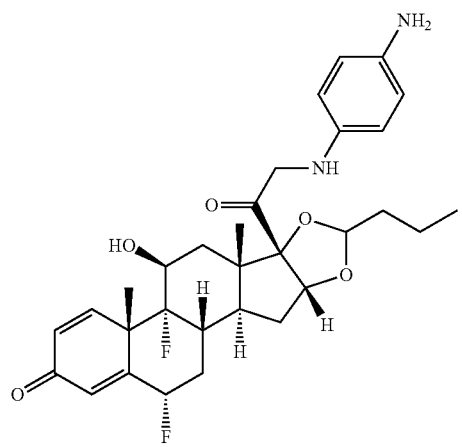

To compound 2b (0.10 g, 0.18 mmol) in DMF (2 mL) in a screw-capped tube were added 4-hydroxyaniline (0.10 mg, 0.92 mmol), triethylamine (0.20 g, 2.0 mmol) and sodium iodide (0.10 g, 0.67 mmol). The mixture was stirred at 70° C. for 5 hours, which was monitored by LC-MS. The reaction mixture was directly purified twice by prep-HPLC (method A) to give compound 5-I (10 mg, 8% yield) as a white solid. ESI m/z: 557 (M+H)$^+$. $^1$H NMR (500 MHz, DMSO$_{d6}$) δ 9.59 (br s, 3H), 7.50-5.96 (m, 8H), 5.76-3.81 (m, 7H), 2.73-2.55 (m, 1H), 2.28 (s, 1H), 2.20-1.99 (m, 2H), 1.86-1.79 (m, 1H), 1.70-1.27 (m, 10H), 0.93-0.76 (m, 6H) ppm. $^{19}$F NMR (376 MHz, DMSO$_{d6}$) δ -73.90, -164.22, -165.02, -186.37 ppm. Anal. HPLC: >99%, Retention time: 7.55 min (method A).

Example 84

This example refers to the compounds in Table 2 and FIG. 31.

General Procedure B for Making Compound 6 by Substituting Compound 2 with Phenol:

To hot acetonitrile or acetone (60-65° C.) were added compound 2 (1 eq.), corresponding phenol (2.0-2.5 eq.) and potassium carbonate or cesium carbonate (2.0-3.0 eq.). The resulting suspension was refluxed for 2-3 hours, monitored by LC-MS and TLC. After cooled to RT, the volatiles were removed in vacuo and to the residue was added water. The aqueous mixture was extracted with ethyl acetate. The combined organic solution was washed with water and brine, dried over sodium sulfate and concentrated in vacuo. The crude product was used for the next step directly or purified by flash chromatography or prep-HPLC to give pure aryl ester 6.

Example 85

This example refers to the compounds in Table 2 and FIG. 31.

(1S,2S,4R,8S,9S,11S,12R,13S,19S)-8-[2-(4-Aminophenoxy)acetyl]-12,19-difluoro-11-hydroxy-9,13-dimethyl-6-propyl-5,7-dioxapentacyclo[10.8.0.0²,⁹.0⁴,⁸.0¹³,¹⁸]icosa-14,17-dien-16-one (6-I)

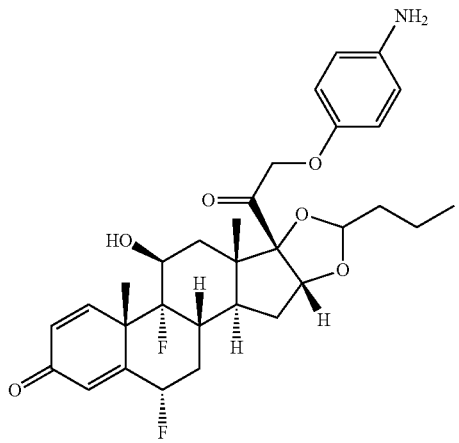

Following the general procedure B in a reaction of 2b (calc. as 0.17 mmol) with 4-aminophenol (37 mg, 0.34 mmol) and cesium carbonate (0.11 g, 0.34 mmol) in acetone (0.5 mL), the title compound 6-I (6.0 mg, 6.3% yield from 1b) was obtained as a white solid after purification by prep-HPLC (method B). ESI m/z: 298 (M/2+H)⁺, 558 (M+H)⁺ (10%). ¹H NMR (500 MHz, MeOD$_{d4}$) δ 7.34 (d, J=10.0 Hz, 1H), 6.78-6.71 (m, 4H), 6.37-6.33 (m, 2H), 5.63-5.49 (m, 1H), 5.10-4.99 (m, 1H), 4.77-4.63 (m, 2H), 4.33 (d, J=9.1 Hz, 1H), 2.74-2.57 (m, 1H), 2.39-2.13 (m, 3H), 1.98-1.31 (m, 12H), 1.03-0.93 (m, 6H) ppm. Anal. HPLC: purity 97.4%, Retention time: 7.55 min (method B).

Example 86

This example refers to the compounds in Table 2 and FIG. 31.

(1S,2S,4R,6S,8S,9S,11S,12R,13S,19S)-8-[2-(4-Aminophenoxy)acetyl]-12,19-difluoro-11-hydroxy-9,13-dimethyl-6-propyl-5,7-dioxapentacyclo[10.8.0.0²,⁹.0⁴,⁸.0¹³,¹⁸]icosa-14,17-dien-16-one (S-6-I)

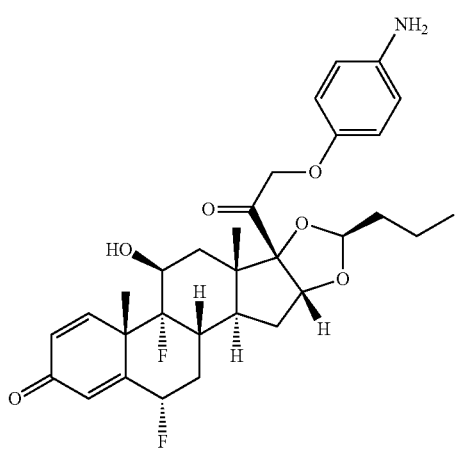

Following the general procedure B except replacing 2b with S-2b, compound S-6-I (19 mg, 19% yield in 2 steps from S-2b) was obtained as a white solid. ESI m/z: 558 (M+H)⁺. ¹H NMR (400 MHz, DMSO$_{d6}$) δ 7.26 (dd, J=10.2, 1.0 Hz, 1H), 6.65-6.55 (m, 2H), 6.51-6.44 (m, 2H), 6.30 (dd, J=10.2, 1.9 Hz, 1H), 6.11 (s, 1H), 5.74-5.46 (m, 2H), 5.23 (t, J=4.9 Hz, 1H), 5.14 (d, J=7.2 Hz, 1H), 4.99 (d, J=18.2 Hz, 1H), 4.74-4.55 (m, 3H), 4.26-4.12 (m, 1H), 2.65-2.53 (m, 1H), 2.29-2.19 (m, 1H), 2.13-1.94 (m, 2H), 1.86-1.22 (m, 11H), 0.92-0.78 (m, 6H) ppm. ¹⁹F NMR (376 MHz, DMSO$_{d6}$) δ −164.26, −186.38 ppm. Anal. HPLC: >99%, Retention time: 7.34 min (method B).

Example 87

This example refers to the compounds in Table 2 and FIG. 31.

Certain methods in *Org. Biomol. Chem.*, 2014, 12, 7551-7560 where employed, the entire contents of which are herein incorporated by reference in their entirety for all purposes.

Step one: 4-Amino(²H₄)phenol:

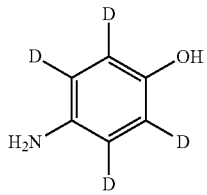

A 20 mL microwave tube was charged 4-hydroxyaniline (0.97 g, 8.9 mmol), deuterium oxide (D₂O, 10 mL) and conc. deuterium chloride (DCl, 125 uL) to give a suspension. The tube was fulfilled with nitrogen atmosphere, sealed and irradiated with microwave (CEM Discover SP) at 180° C. for 2.5 hours, which was monitored by LC-MS. The mixture was then cooled to RT (28-32° C.) and was kept at this temperature for 18 hours. The volatiles were removed in vacuo to give brown residue, which was suspended in deuterium oxide (10 mL) in a 20 mL-microwave tube. The tube was fulfilled with nitrogen, sealed and irradiated with microwave at 180° C. for 5.5 hours. After cooled to RT (28-32° C.), the mixture was kept at this temperature for 16 hours. The volatiles were removed in vacuo and the residue was purified by flash chromatography (10-60% ethyl acetate in petroleum ether) to afford 4-Amino(²H₄)phenol (0.50 g, 50% yield) as a brown solid. ¹H NMR (500 MHz, DMSO$_{d6}$) δ 8.31 (s, 1H), 4.36 (s, 2H) ppm.

439

(1S,2S,4R,8S,9S,11S,12R,13S,19S)-8-{2-[4-Amino (2,3,5,6-$^2$H$_4$)phenoxy]acetyl}-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (6-I D)

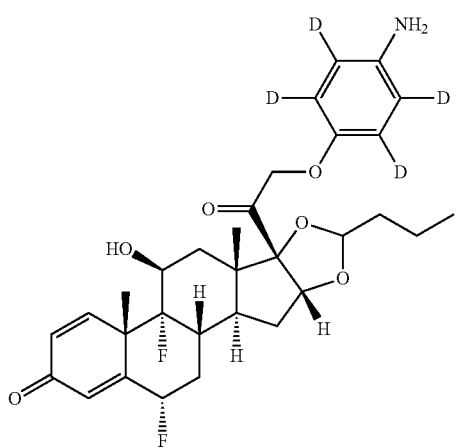

Step two: To a mixture of 4-Amino($^2$H$_4$)phenol (0.10 g, 0.88 mmol) in DMSO (3 mL) was added potassium hydroxide (45 mg, 0.80 mmol). After stirring at 28-32° C. for 2 minutes and then stirring at 60° C., to the mixture was added compound 2b (0.20 g, 0.40 mmol) in one portion and stirred under nitrogen protection at 60° C. for an hour. After cooling to RT, the mixture was directly purified by prep-HPLC (method A) and then prep-HPLC (method B) to afford 6-II (10 mg, 4.4% yield) as an off-white solid. ESI m/z: 562 (M+H)$^+$. $^1$H NMR (400 MHz, DMSO$_{d6}$) δ 7.27 (d, J=10.1 Hz, 1H), 6.30 (dd, J=10.1, 1.7 Hz, 1H), 6.12 (s, 1H), 5.74-5.45 (m, 2H), 5.03-4.93 (m, 1H), 4.82-4.58 (m, 4H), 4.27-4.14 (m, 1H), 3.33 (s, 1H), 2.70-2.53 (m, 1H), 2.31-2.20 (m, 1H), 2.14-1.93 (m, 2H), 1.86-1.70 (m, 1H), 1.67-1.24 (m, 10H), 0.92-0.73 (m, 6H) ppm. $^{19}$F NMR (376 MHz, DMSO$_{d6}$) δ −164.24, −165.05, −186.35 ppm. Anal. HPLC: 98.41%, Retention time: 7.34 min (method B)

Compound 6-I D is useful, for example, for analytical methods.

Example 88

This example refers to the compounds in Table 2 and FIG. 31.

440

(1S,2S,4R,8S,9S,11S,12R,13S,19S)-8-[2-(4-Amino-3-methoxyphenoxy)acetyl]-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one trifluoroacetate (6-II)

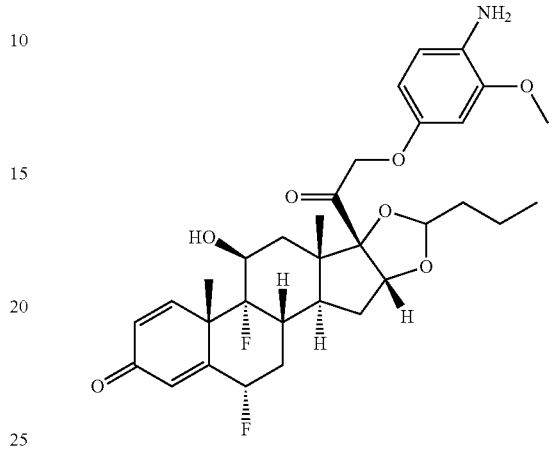

Following the general procedure B, by reacting compound 2b (0.50 g, 0.92 mmol) with 4-amino-3-methoxyphenol (0.32 g, 2.3 mmol) and cesium carbonate (0.60 g, 1.8 mmol) in acetonitrile (20 mL), compound 6-II (0.25 g, 47% yield) was obtained as a white solid. ESI m/z: 588 (M+H)$^+$. $^1$H NMR (400 MHz, DMSO$_{d6}$) δ 9.00 (s, 2H), 7.33-7.23 (m, 1H), 7.16-7.08 (m, 1H), 6.77-6.68 (m, 1H), 6.52-6.41 (m, 1H), 6.35-6.27 (m, 1H), 6.12 (s, 1H), 5.74-5.51 (m, 2H), 5.31-5.11 (m, 2H), 4.98-4.68 (m, 3H), 4.28-4.15 (m, 1H), 3.90-3.83 (m, 3H), 2.74-2.55 (m, 1H), 2.35-2.21 (m, 1H), 2.17-1.97 (m, 2H), 1.88-1.75 (m, 1H), 1.67-1.28 (m, 10H), 0.93-0.78 (m, 6H) ppm. Anal. HPLC: >99%, Retention time: 7.68 and 7.72 min (method A).

Example 89

This example refers to the compounds in Table 2 and FIG. 31.

Making Compound 6-III (1S,2S,4R,8S,9S,11S,12R,13S,19S)-8-[2-(4-Amino-3-fluorophenoxy)acetyl]-12,19-difluoro-11-hydroxy-9,13-dimethyl-6-propyl-5,7-dioxapentacyclo[10.8.0.0$^{2,9}$.0$^{4,8}$.0$^{13,18}$]icosa-14,17-dien-16-one (6-III)

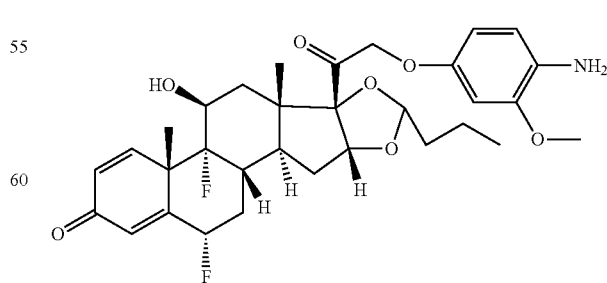

To a round-bottom-bottle were added compound 2e (0.20 g, 0.37 mmol), 4-amino-3-fluorophenol (0.25 g, 2.0 mmol), potassium hydroxide (0.11 g, 2.0 mmol) and DMSO (3 mL) at room temperature. The resulting mixture was stirred at 60° C. for an hour under nitrogen protection until the reaction was completed, which was monitored by TLC and LC-MS. After cooling to room temperature and filtering through membrane, the reaction solution was directly purified by prep-HPLC (method A) to give the title compound 6-III (40 mg, 19% yield) as an off-white solid. ESI m/z: 576 (M+H)$^+$. $^1$H NMR (500 MHz, MeOD$_{d4}$) δ 7.40-7.31 (m, 1H), 7.20 (td, J=9.1, 1.9 Hz, 1H), 6.91-6.84 (m, 1H), 6.80-6.76 (m, 1H), 6.40-6.30 (m, 2H), 5.57 (ddd, J=48.6, 9.7, 6.8 Hz, 1H), 5.15 (d, J=18.1 Hz, 1H), 4.90-4.79 (m, 2H), 4.75 (t, J=4.3 Hz, 1H), 4.41-4.28 (m, 1H), 2.78-2.57 (m, 1H), 2.40-2.12 (m, 3H), 1.98-1.39 (m, 11H), 1.07-0.92 (m, 6H) ppm. Anal. HPLC: 100%, Retention time: 8.10 min (method A).

Example 90

This example refers to the compounds in Table 2 and FIG. 31.

(6S,8S,9S,10R,11S,13S,14S,17R)-17-(2-(4-Aminophenoxy)acetyl)-11,17-dihydroxy-6,10,13-trimethyl-6,7,8,9,10,11,12,13,14,15,16,17-dodecahydro-3H-cyclopenta[a]phenanthren-3-one (6-VI)

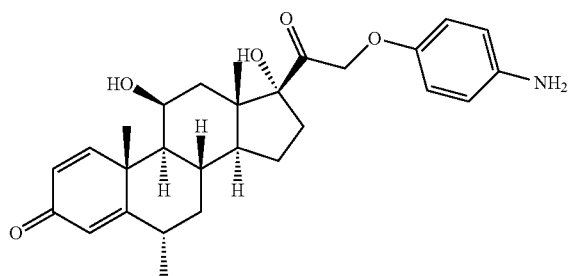

To a solution of compound 2f (60 mg, 0.13 mmol) in DMF (3 mL) were added cesium carbonate (86 mg, 0.26 mmol) and N-Boc-4-aminophenol (28 mg, 0.13 mmol). The reaction mixture was stirred at RT for 18 hours, which was monitored by LC-MS. The mixture was diluted with ethyl acetate (10 mL). The organic solution was washed with water (10 mL), dried over sodium sulfate and concentrated. The white residue (50 mg, ESI m/z: 566 (M+H)$^+$) was dissolved in DCM (5 mL) and to the solution was added TFA (0.5 mL). The reaction mixture was stirred at RT for 2 hours until Boc was totally removed according to LC-MS. The volatiles were removed in vacuo. And the residue was purified by reversed phase flash chromatography (0-25% acetonitrile in water) to give 6-VI (10 mg, 7.5% yield) as a white solid. ESI m/z: 466 (M+H)$^+$. $^1$H NMR (400 MHz, DMSO$_{d6}$) δ 7.32 (d, J=10.0 Hz, 1H), 6.61-6.58 (m, 2H), 6.51-6.47 (m, 2H), 6.19 (dd, J=10.0, 1.6 Hz, 1H), 5.82 (t, J=1.6 Hz, 1H), 5.39 (s, 1H), 5.04-5.01 (m, 3H), 4.66 (d, J=3.2 Hz, 1H), 4.58 (d, J=18.0 Hz, 1H), 4.30 (d, J=2.4 Hz, 1H), 2.67-2.50 (m, 2H), 2.13-2.01 (m, 2H), 1.93-1.89 (m, 1H), 1.67-1.61 (m, 3H), 1.45-1.30 (m, 5H), 1.01 (d, J=3.2 Hz, 3H), 0.95-0.71 (m, 5H) ppm.

Example 91

This Example demonstrates the general synthetic procedures for making intermediates of Linker-Payloads in Table 4.

Figure 33:
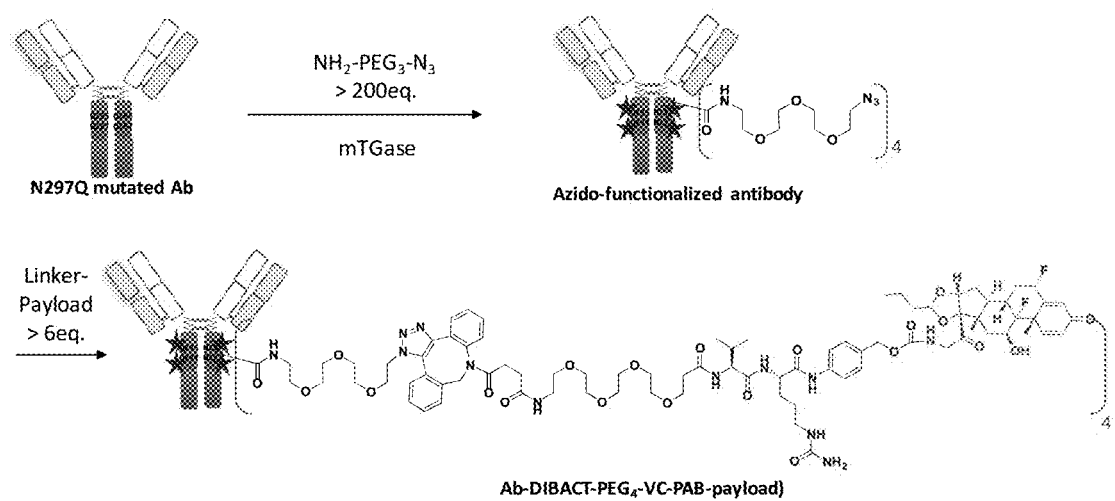
FIG. 33 shows a general synthetic process for an ADC conjugation via [2+3] click reaction.

This example refers to the compounds in Table 4 and FIGS. 31 and 33.

The synthesis of Linker-Payloads (LP1-LP16) started by making carbonates L4 from the reactions of amines (4) or anilines (6) with protected Val-Cit-PAB-PNP (L2a or L2b) followed by N-deprotection, or from the generation of the amides L4 between anilines (6) with Boc or Fmoc protected Val-Cit-OH or Fmoc-Val-Ala-OH (L3a-c) followed by N-deprotection. Compounds L4 were then directly coupled with L9 or L10 to generate the final linker-steroids LP1, LP2, LP3, LP13, LP14, LP15 and LP16. Compounds L4 were also coupled with Fmoc-D-Lys-COT L5 followed by de-Fmoc to afford L6, which were underwent [3+2] cycloadditions with azido-cyclodextrin (7a) or azido sulfonates (7b or 7c) to generate L8. Finally, coupling reactions of L8 with PEG$_4$ acid or NHS ester (L9 or L10) were used to produce linker-payload LP5, LP8, LP10, and LP12.

General Procedure C for synthesis of intermediate L4:

To a solution of payload 4 or 6 (1.0 eq.) and Boc-vcPAB-PNP (1.1 eq.) in DMF (1 mL per 10 mg of payload) were added HOBt (1.0 eq.) and DIPEA (2.0 eq.) at RT. The resulting mixture was stirred at RT (18-30° C.) overnight until the payload was consumed, which was monitored by LC-MS. After filtering through a membrane, the reaction solution was directly purified by prep-HPLC to give Boc-L4 (52% yield) as a white solid, which was dissolved in DCM (0.6 mL per mg of Boc-L4). To this solution was added dropwise TFA (0.2 mL per mg of Boc-L4) at 0° C. The mixture was stirred at RT (18-30° C.) for an hour until Boc was removed, which was monitored by LC-MS. The volatiles were removed in vacuo to give compound L4, which was used for the next step without further purification.

General Procedure D for synthesis of intermediate L4:

To a solution of payload 4 or 6 (1.0 eq.) in DMF (0.3 mL per 10 mg of payload) were added Fmoc-vcPAB-PNP (1.1 eq.), HOBt (1.5 eq.) and DIPEA (2.0 eq.) at RT. The mixture was stirred at RT (18-30° C.) for 3 hours until payload was totally consumed, which was monitored by LC-MS. To the reaction mixture was added piperidine (0.03 mL per 10 mg of payload) and the mixture was stirred at RT (18-30° C.) for an hour until Fmoc was removed, which was monitored by LC-MS. After filtering through membrane, the reaction solution was directly purified by reversed phase flash chromatography or prep-HPLC to give compound L4.

General Procedure E for synthesis of intermediate L4:

To a solution of Boc-Val-Ala-OH or Boc-Val-Cit-OH (1.0 eq.) in DCM (0.2 mL per 10 mg of peptide) were added DIPEA (2.0 eq.) and HATU (1.2 eq.) at 20-25° C. The mixture was stirred at 20-25° C. for 30 minutes followed with the addition of aniline (1.1 eq.) and was further stirred for 16 hours until the peptide was totally consumed, which was monitored by LC-MS. To the reaction mixture was then added TFA (0.05 mL per 10 mg of peptide). The mixture was stirred at 20-25° C. ° C. for another hour. The volatiles were removed under reduced pressure and the residue was directly purified by prep-HPLC (method B) to give compound L4.

General Procedure F for synthesis of intermediate L4:

To a solution of Fmoc-Val-Ala-OH (1.2 eq.) in DMF (0.2 mL per 10 mg of peptide) were added DIPEA (3.0 eq.) and HATU (1.4 eq.) at 20-25° C. The mixture was stirred at 20-25° C. ° C. for 5 minutes followed with the addition of aniline (1.0 eq.) and the resulting mixture was further stirred for 2 hours until the peptide was totally consumed, which was monitored by LC-MS. To the reaction mixture was then added piperidine (5.0 eq.). The mixture was stirred at 20-25° C. for 2 hour. After filtering through membrane, the reaction solution was directly purified by reversed phase flash chromatography (0-100% acetonitrile in aq. ammonium bicarbonate (10 mM)) or prep-HPLC (method B) to give compound L4.

Example 92

This example refers to the compounds in Table 4 and FIG. 33.

Making Compound L4a, VA-R-6-VI (2S)-2-Amino-N-[(1S)-1-[(4-{2-[(1S,2S,4R,6R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]-3-methylbutanamide

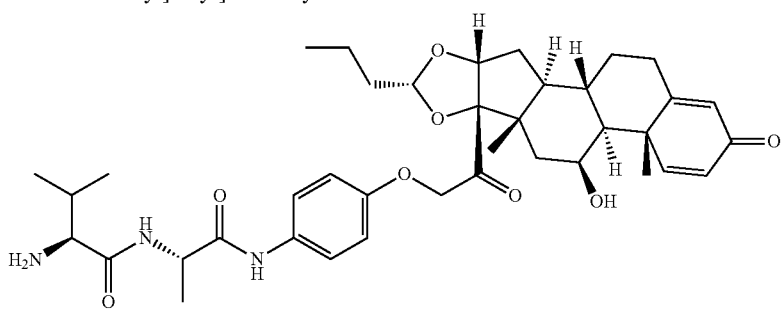

Following the General Procedure E (65% yield) or F (53% yield) from R-6-VI, compound L4a was obtained as a white solid. ESI m/z: 692 (M+H)$^+$. $^1$H NMR (500 MHz, DMSO$_{d6}$) δ 9.95 (d, J=8.2 Hz, 1H), 8.19-8.09 (m, 1H), 7.54-7.47 (m, 2H), 7.33 (d, J=10.1 Hz, 1H), 6.85 (d, J=9.0 Hz, 2H), 6.22-6.13 (m, 1H), 5.93 (s, 1H), 5.14-5.04 (m, 1H), 4.86-4.77 (m, 2H), 4.75 (d, J=4.2 Hz, 1H), 4.70 (t, J=4.3 Hz, 1H), 4.48-4.38 (m, 1H), 4.34 (s, 1H), 3.01 (t, J=5.0 Hz, 1H), 2.58-2.52 (m, 1H), 2.33-2.25 (m, 1H), 2.13-2.06 (m, 1H), 2.03-2.00 (m, 1H), 1.95-1.89 (m, 1H), 1.88-1.84 (m, 2H), 1.63-1.53 (m, 5H), 1.45-1.33 (m, 6H), 1.32-1.26 (m, 3H), 1.06-0.93 (m, 2H), 0.92-0.82 (m, 10H), 0.80-0.75 (m, 3H) ppm.

Example 93

This example refers to the compounds in Table 4 and FIG. 33.

Making Compound L4b, vcPAB-4b

{4-[(2S)-2-[(2S)-2-Amino-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamate

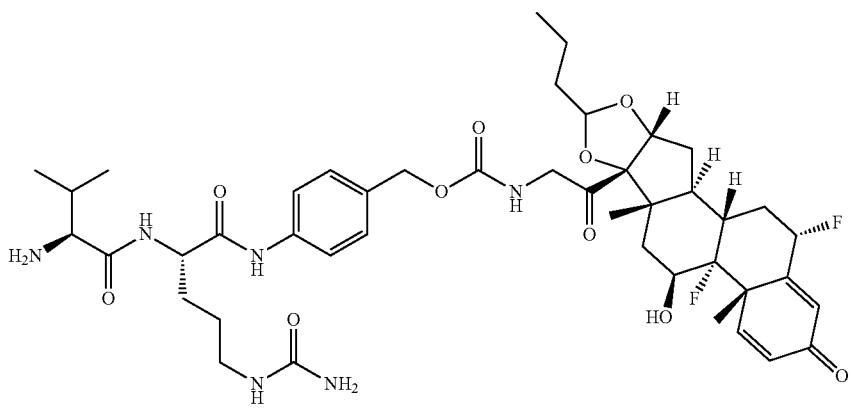 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](N)C(C)C)cc2)O1]

Following the General Procedure D from compound 4b, (93 mg, 0.20 mmol), compound vcPAB-4b (0.13 g, 73% yield) was obtained after purification by reversed phase flash chromatography (50-80% acetonitrile in aq. ammonium bicarbonate (10 mM)) as a white solid. ESI m/z: 871 (M+H)+.

Example 94

This example refers to the compounds in Table 4 and FIG. 33.

Making Compound L4c, VA-6-I (2S)-2-Amino-N-[(1S)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]-3-methylbutanamide

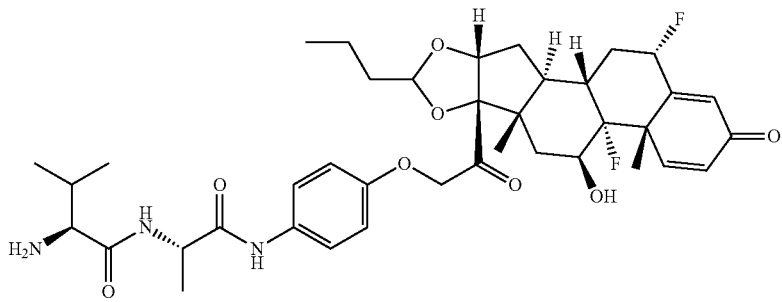 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](N)C(C)C)cc2)O1]

Following the General Procedure E from compound 6-I, (0.50 g, 0.90 mmol) with Boc-Val-Ala-OH, the crude compound L4c (0.69 g, 72% yield in 2 steps) was obtained without purification as yellow oil, which was used directly for the next step. ESI m/z: 728 (M+H)+.

Example 95

This example refers to the compounds in Table 4 and FIG. 33.

Making Compound L4d, VC-PAB-6-I

{4-[(2S)-2-[(2S)-2-Amino-3-methylbutanamido]-5-(carbamoylamino)pentanamido]phenyl}methyl N-(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamate

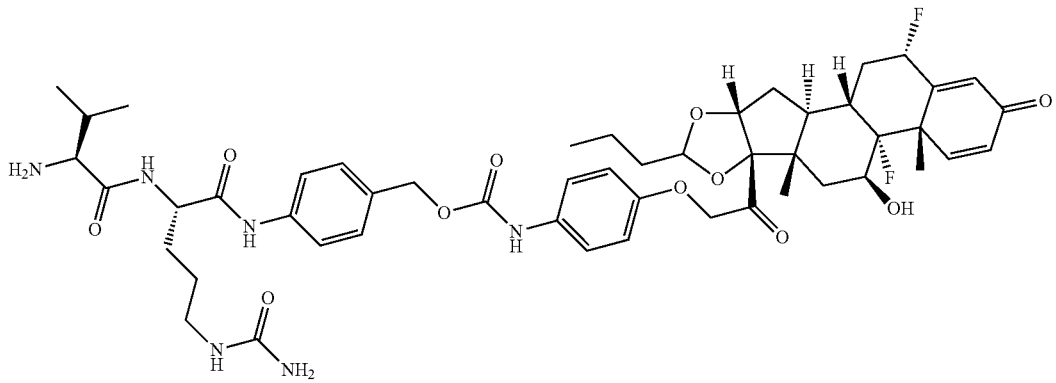 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](CCCNC(N)=O)NC(=O)[C@@H](N)C(C)C)cc3)cc2)O1]

Following the General Procedure E from compound 6-I, (87 mg, 0.15 mmol), compound L4d (80 mg, 64% yield) was obtained as a white solid after purification by prep-HPLC (method B). ESI m/z: 963 (M+H)$^+$. $^1$H NMR (500 MHz, DMSO$_{d6}$) δ 10.22 (s, 1H), 9.57 (s, 1H), 8.69 (d, J=7.5 Hz, 1H), 8.08 (s, 3H), 7.61 (d, J=6.8 Hz, 2H), 7.36 (d, J=6.8 Hz, 3H),7.27 (d, J=8.0 Hz, 1H), 7.22-7.0 (m, 1H), 6.84 (d, J=7.2 Hz, 2H), 6.30 (dd, J=8.0 Hz, J=1.6 Hz, 1H), 6.11 (s, 1H), 6.10-6.0 (m, 1H), 5.72-5.55 (m, 1H), 5.52 (s, 1H), 5.48 (s, 1H), 5.16-5.05 (m, 3H), 4.88-4.80 (m, 1H), 4.80-4.76 (m, 1H), 4.75-4.70 (m, 1H), 4.55-4.48 (m, 1H), 4.25-4.20 (m, 1H), 3.70-3.60 (m, 1H), 3.12-2.90 (m, 2H), 2.70-2.55 (m, 1H), 2.40-2.20 (m, 1H), 2.15-2.0 (m, 3H), 1.86-1.75 (m, 1H), 1.75-1.65 (m, 1H), 1.64-1.54 (m, 5H), 1.49 (s, 4H), 1.46-1.34 (m, 4H), 0.97-0.91 (m, 5H), 0.90-0.85 (m, 4H), 0.85-0.80 (m, 3H) ppm.

Example 96

This example refers to the compounds in Table 4 and FIG. 33.

Making Compound L4e, VA-6-II (2S)-2-Amino-N-[(1S)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}-2-methoxyphenyl)carbamoyl]ethyl]-3-methylbutanamide

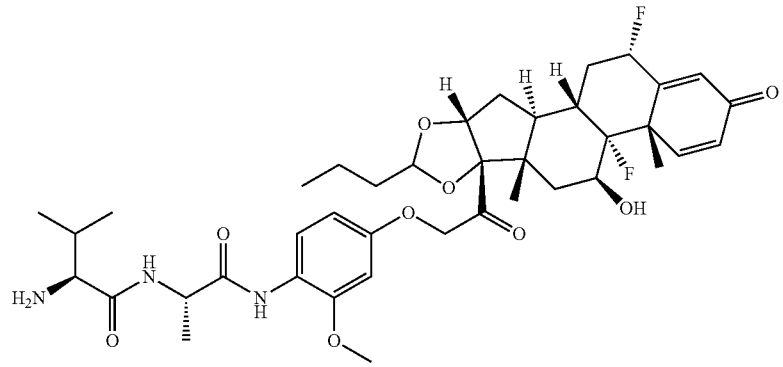 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](N)C(C)C)c(OC)c2)O1]

Following the general procedure F from compound 6-III, (0.10 g, 0.17 mmol), the crude compound L4e (0.12 g, 82% yield in 2 steps) was obtained which was used for the next step without further purification. ESI m/z: 758 (M+H)$^+$.

Example 97

This example refers to the compounds in Table 4 and FIG. 33.

Making Compound L4f, VA-6-III (2S)-2-Amino-N-[(1S)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}-2-fluorophenyl)carbamoyl]ethyl]-3-methylbutanamide

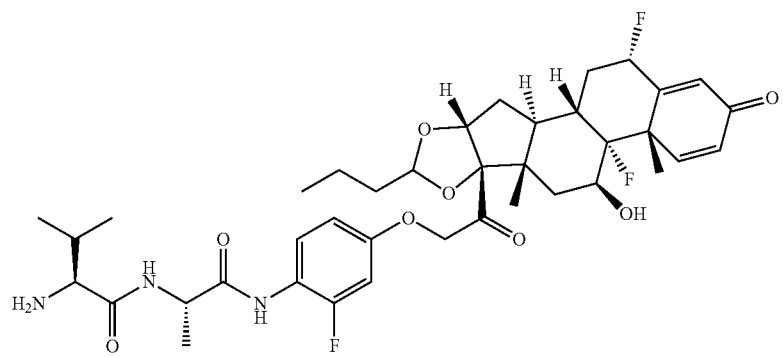 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](N)C(C)C)c(F)c2)O1]

Following the general procedure F from compound L4f, (95 mg, 0.17 mmol), the crude title compound L4f (0.10 g, 66% yield in 2 steps) was obtained which was used for the next step without further purification. ESI m/z: 746 (M+H)+.

Example 98

This example refers to the compounds in Table 4 and FIG. 33.

Synthesis of Intermediates of Linker-Payloads L6

General Procedure: To a solution of compound L5 (1.2 eq.) in DMF (0.2 mL per 10 mg of L5) were added HATU (1.4 eq.) and DIPEA (3 eq.) at RT. The mixture was stirred at RT for 5 minutes before the addition of compound L4 (1.0 eq.). The reaction mixture was then stirred at RT for 2 hours until compound L4 was totally consumed, which was monitored by LC-MS. After filtered through membrance, the reaction solution was directly purified by prep-HPLC to give the cyclooctyne L6.

Example 99

General Procedure H for Making Intermediates 8

To a solution of L6 in DMF (0.5 mL per 10 mg of L6) were added azido compound (L7a (CD-$N_3$), L7b ($N_3$-$PEG_4$-sulfonate) or L7c ($N_3$-dualsulfonate), 1.5 eq. vs L6) and DIPEA (0.1 mL per 10 mg of L6) at RT. After stirring at 30° C. for 24 hours, most of the starting materials were consumed, which was monitored by LC-MS. The reaction mixture was directly purified by prep-HPLC to give compound L8 as a white solid.

Example 100

Making Compound L8a, aCDCCK-vcPAB-4b

{4-[(2S)-2-[(2S)-2-[(2R)-2-Amino-6-{2-[(1-{[31,32,
33,34,35,36,37,38,39,40,41,42-dodecahydroxy-10,
15,20,25,30-pentakis(hydroxymethyl)-2,4,7,9,12,14,
17,19,22,24,27,29-dodecaoxaheptacyclo
[26.2.2.2$^{3,6}$.2$^{8,11}$.2$^{13,16}$.2$^{18,31}$.2$^{23,26}$]dotetracontan-5-
yl]methyl}-1H,4H,5H,6H,7H,8H,9H-cycloocta[d][1,
2,3]triazol-4-yl)oxy]acetamido}hexanamido]-3-
methylbutanamido]-5-(carbamoylamino)
pentanamido]phenyl}methyl N-{2-[(1S,2S,4R,8S,
9S,11S,12R,13S,19S)-12,19-difluoro-11-hydroxy-9,
13-dimethyl-16-oxo-6-propyl-5,7-dioxapentacyclo
[10.8.0.0$^{2,9}$.0$^{4,8}$.0$^{13,18}$]icosa-14,17-dien-8-yl]-2-
oxoethyl}carbamate (L8a)

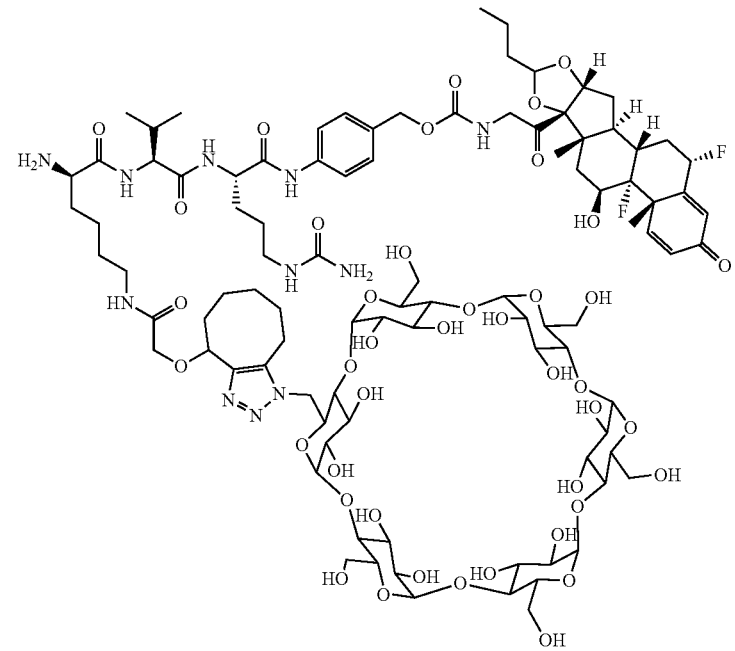 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)CNC(=O)OCc2ccc(NC(=O)[C@H](CCCNC(N)=O)NC(=O)[C@@H](NC(=O)[C@H](N)CCCCNC(=O)COC3CCCCCc4c3nnn4CC3OC4OC5C(CO)OC(OC6C(CO)OC(OC7C(CO)OC(OC8C(CO)OC(OC9C(CO)OC(OC3C(O)C4O)C(O)C9O)C(O)C8O)C(O)C7O)C(O)C6O)C(O)C5O)C(C)C)cc2)O1]

Following the general procedure H for making compound L6a (0.12 g, 0.10 mmol) with L7a, compound L8a (0.11 g, 51% yield) was obtained as a white solid. ESI m/z: 1081 (M/2+H)+. 1H NMR (400 MHz, DMSO$_{d6}$) δ 10.05 (s, 1H), 8.30-7.80 (m, 3H), 7.80-7.55 (m, 2H), 7.50-7.40 (m, 1H), 7.40-7.25 (m, 3H), 6.30 (d, J=12.5 Hz, 1H), 6.11 (s, 1H), 6.0 (s, 1H), 5.80-5.35 (m, 16H), 5.25-5.05 (m, 1H), 4.97 (s, 2H), 4.90-4.50 (m, 13H), 4.50-4.00 (m, 5H), 3.95-3.55 (m, 22H), 3.30-3.20 (m, 8H), 3.20-3.00 (m, 4H), 3.00-2.85 (m, 5H), 2.25-2.20 (m, 2H), 2.10-1.95 (m, 4H), 1.80-1.00 (m, 30H), 1.00-0.90 (m, 4H), 0.90-0.80 (m, 14H) ppm.

Example 101

Making Compound L8d, aCDCCK-VA-2168

(2R)-2-Amino-N-[(1S)-1-{[(1S)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamide (L8d)

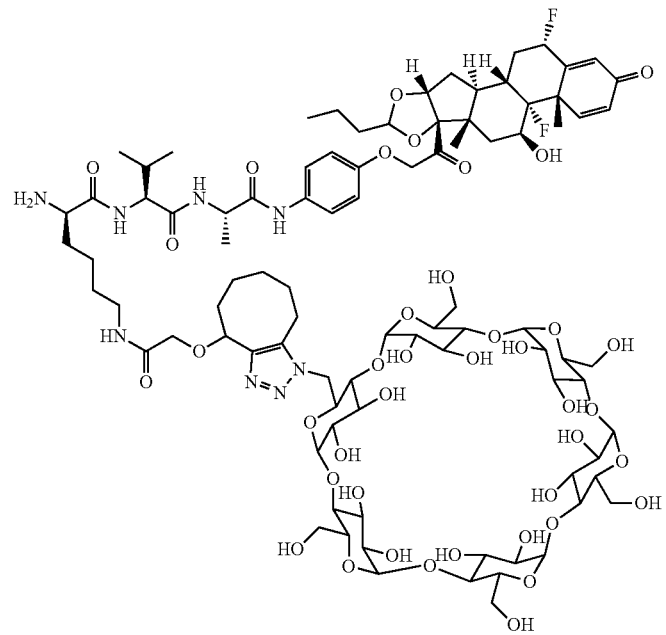 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](NC(=O)[C@H](N)CCCCNC(=O)COC3CCCCCc4c3nnn4CC3OC4OC5C(CO)OC(OC6C(CO)OC(OC7C(CO)OC(OC8C(CO)OC(OC9C(CO)OC(OC3C(O)C4O)C(O)C9O)C(O)C8O)C(O)C7O)C(O)C6O)C(O)C5O)C(C)C)cc2)O1]

Following the general procedure H from L6b (60 mg, 59 μmop with L7a, compound L8d (40 mg, 34% yield) was obtained as a white solid. ESI m/z: 1009.5 (M/2+H)+.

Example 102

Making Compound L8f, aCDCCK-vcPAB-6-I

{4-[(2S)-2-[(2S)-2-[(2R)-2-Amino-6-{2-[(1-{[31,32,
33,34,35,36,37,38,39,40,41,42-dodecahydroxy-10,
15,20,25,30-pentakis(hydroxymethyl)-2,4,7,9,12,14,
17,19,22,24,27,29-dodecaoxaheptacyclo
[26.2.2.2$^{3,6}$.2$^{8,11}$.2$^{13,16}$.2$^{18,21}$.2$^{23,26}$]dotetracontan-5-
yl]methyl}-1H,4H,5H,6H,7H,8H,9H-cycloocta[d][1,
2,3]triazol-4-yl)oxy]acetamido}hexanamido]-3-
methylbutanamido]-5-(carbamoylamino)
pentanamido]phenyl}methyl N-(4-{2-[(1S,2S,4R,
8S,9S,11S,12R,13S,19S)-12,19-difluoro-11-
hydroxy-9,13-dimethyl-16-oxo-6-propyl-5,7-
dioxapentacyclo[10.8.0.0$^{2,9}$.0$^{4,8}$.0$^{13,18}$]icosa-14,17-
dien-8-yl]-2-oxoethoxy}phenyl)carbamate

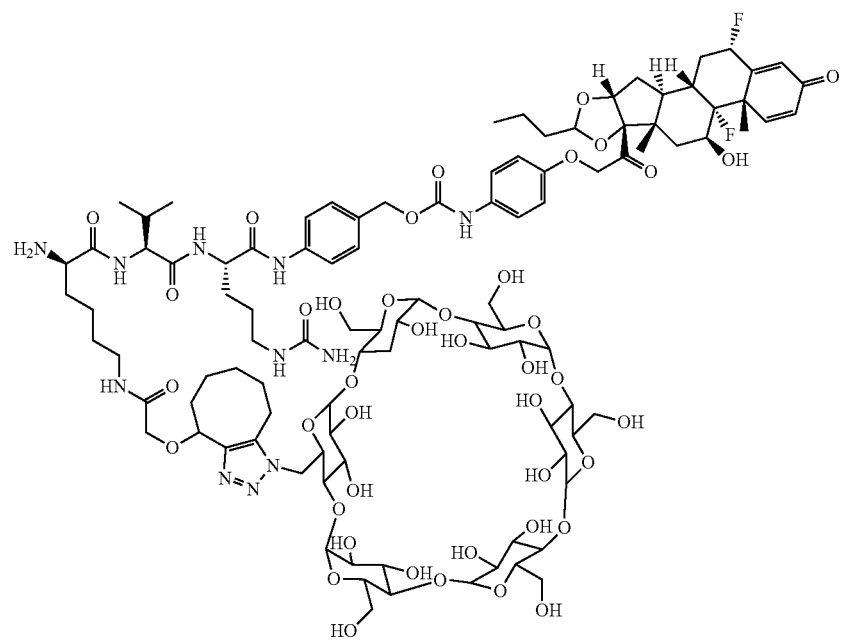 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](CCCNC(N)=O)NC(=O)[C@@H](NC(=O)[C@H](N)CCCCNC(=O)COC4CCCCCc5c4nnn5CC4OC5OC6CC(O)C(OC6CO)OC6C(CO)OC(OC7C(CO)OC(OC8C(CO)OC(OC9C(CO)OC(OC4C(O)C5O)C(O)C9O)C(O)C8O)C(O)C7O)C(O)C6O)C(C)C)cc3)cc2)O1]

Following the general procedure H from L6c (0.10 g, 80 μmol) with L7a, compound L8f (0.11 g, 58% yield) was obtained as a white solid. ESI m/z: 751 (M/3+H)$^+$.

Example 103

Making Linker-Payloads LP101 to LP116
Making Compound LP1:L6a (COT-dLys-vcPAB-4b)

{4-[(2S)-2-[(2S)-2-[(2R)-2-Amino-6-[2-(cyclooct-2-yn-1-yloxy)acetamido]hexanamido]-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$-12$^{,8}$-12,$^{18}$]icosa-14,17-dien-8-yl]-2-oxoethyl}carbamate

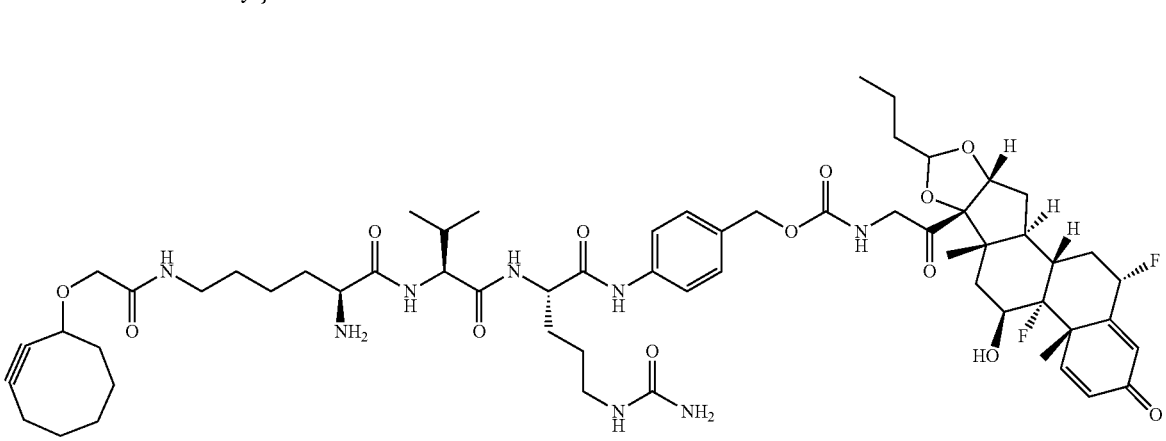

Following the General Procedure G for making compound L4b (0.20 g, 0.23 mmol), compound L6a (0.12 g, 45% yield) was obtained as a white solid after prep-HPLC (method B). ESI m/z: 1385 (M+H)$^+$. $^1$H NMR (400 MHz, MeOD$_{d4}$) δ 7.65-7.55 (m, 2H), 7.40-7.26 (m, 3H), 6.39-6.27 (m, 2H), 5.65-5.45 (m, 1H), 5.13-5.01 (m, 2H), 4.71-4.50 (m, 2H), 4.40-4.14 (m, 4H), 4.11-3.82 (m, 3H), 3.46-3.39 (m, 1H), 3.29-3.09 (m, 4H), 2.76-2.54 (m, 1H), 2.41-2.10 (m, 7H), 2.09-1.99 (m, 1H), 1.96-1.80 (m, 5H), 1.78-1.21 (m, 23H), 1.06-0.82 (m, 12H) ppm.

Example 104

Making Compound LP102: L6b (COT-dLys-VA-6-I)

(2R)-2-Amino-6-[2-(cyclooct-2-yn-1-yloxy)acetamido]-N-[(1S)-1-{[(1S)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]hexanamide

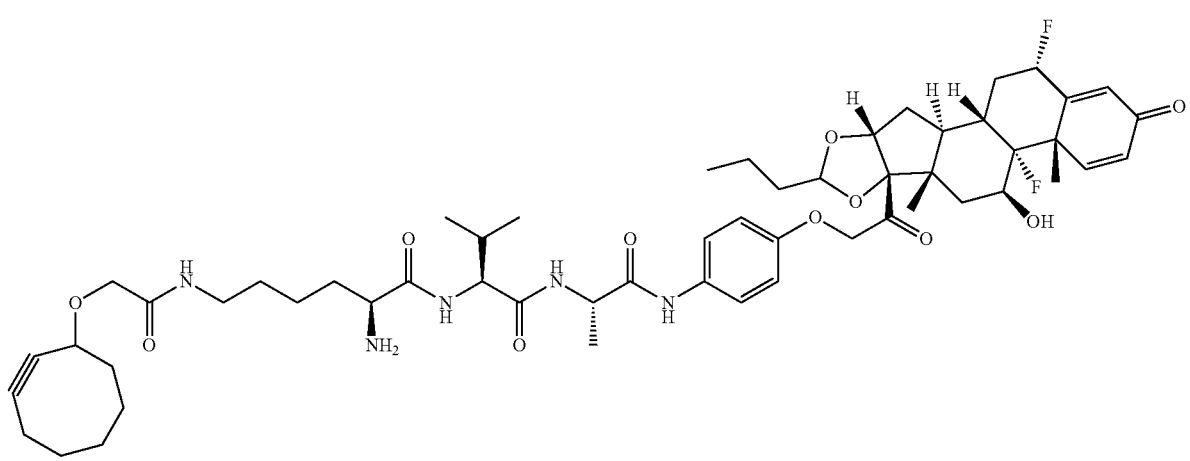 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](NC(=O)[C@@H](N)CCCCNC(=O)COC3C#CCCCCC3)C(C)C)cc2)O1]

Following the general procedure G for making L4c (0.28 g, 0.38 mmol), compound L6b (0.21 g, 46% yield) was obtained as a white solid after prep-HPLC (method B). ESI m/z: 1021.5 (M+H)+. $^1$H NMR (400 MHz, MeOD$_{d4}$) δ 7.33-7.60 (m, 3H), 6.87-6.91 (m, 2H), 6.32-6.37 (m, 2H), 5.47-5.65 (m, 1H), 5.07-5.30 (m, 1H), 4.72-4.86 (m, 3H), 4.34-4.51 (m, 3H), 3.83-4.20 (m, 3H), 3.33-3.49 (m, 1H), 3.14-3.27 (m, 3H), 2.59-2.75 (m, 1H), 1.31-2.39 (m, 33H), 0.93-1.05 (m, 12H) ppm.

Example 105

Making Compound LP103: L6c (COT-dLys-vcPAB-6-I)

{4-[(2S)-2-[(2S)-2-[(2R)-2-Amino-6-[2-(cycloct-2-yn-1-yloxy)acetamido]hexanamido]-3-methylbutanamido]-5-(carbamoylamino)pentanamido]phenyl}methyl N-(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamate

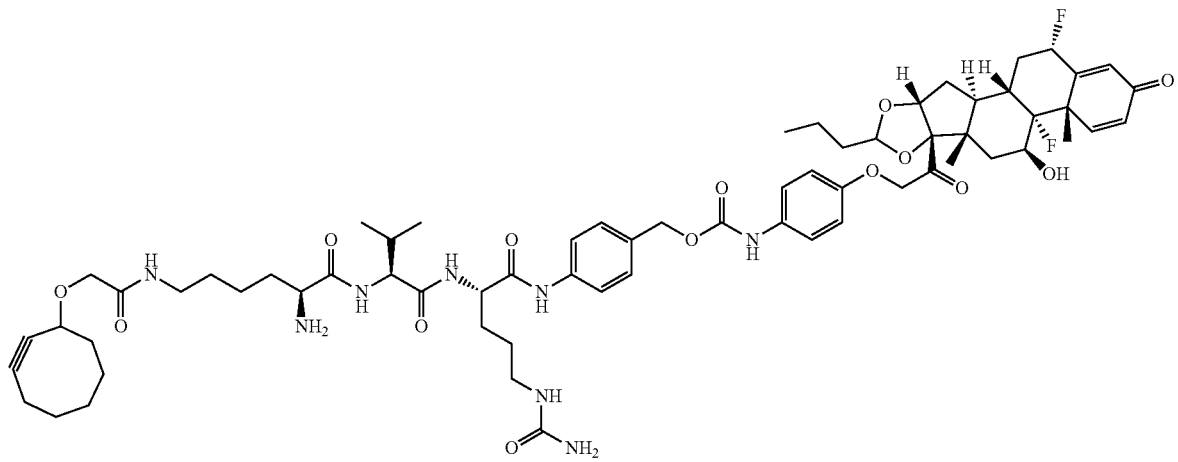 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)OCc3ccc(NC(=O)[C@H](CCCNC(N)=O)NC(=O)[C@@H](NC(=O)[C@@H](N)CCCCNC(=O)COC4C#CCCCCC4)C(C)C)cc3)cc2)O1]

Following the general procedure G for making compound L4d (0.14 g, 0.15 mmol), compound L6c (0.10 g, 57% yield) was obtained as a white solid after prep-HPLC (method B). ESI m/z: 1255.5 (M+H)+. $^1$H NMR (400 MHz, MeOD$_{d4}$) δ 7.61 (d, J=8.4 Hz, 1H), 7.32-7.39 (m, 4H), 6.84-6.88 (m, 2H), 6.31-6.36 (m, 2H), 5.43-5.63 (m, 1H), 5.05-5.16 (m, 3H), 4.71-4.83 (m, 1H), 4.50-4.54 (m, 1H), 4.18-4.33 (m 3H), 3.00-2.85 (m, 2H), 3.40-3.51 (m, 1H), 3.00-3.29 (m, 6H), 1.31-2.35 (m, 34H), 1.29 (t, J=7.2 Hz, 2H), 0.93-1.02 (m, 12H) ppm.

Example 106

General Procedure I for LP104 to LP116:

To a solution of PEG$_4$-acid L9 (1.2-1.3 eq.) in DMF (1 mL per 10 mg of L9) were added HATU (1.3 eq.) and DIPEA (5.0 eq.) at RT. The mixture was stirred at RT (19° C.) for half an hour followed by the addition of a solution of compound L4 or L8 (1.0 eq.) in DMF (0.6 mg per 10 mg of L4 or L8). The resulting mixture was stirred at RT for 2 hours until compound L4 or L8 was consumed, which was monitored by LC-MS. After filtered through membrance, the filtrate was directly purified by prep-HPLC to give compound L1. (L9a: BCN-PEG$_4$-acid, L9b: DIBAC-PEG$_4$-acid, L9c: MAL-PEG$_4$-acid)

General Procedure J for LP104 to LP116

To a solution of compound L4 or L8 (1.0 eq.) in DMF (1 mL per 50 mg) were added compound DIBAC-PEG$_4$-NHS L10b (1.1-1.2 eq.) and DIPEA (5.0 eq.) at RT. The reaction mixture was stirred at RT for 3 hours, which was monitored by LC-MS. The reaction mixture was directly purified by prep-HPLC (method B) to give compound L1.

Example 107

Making Compound LP104: L11a (DIBAC-PEG4-aCD-CCK-vcPAB-4b

{4-[(2S)-2-[(2S)-2-[(2R)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamate

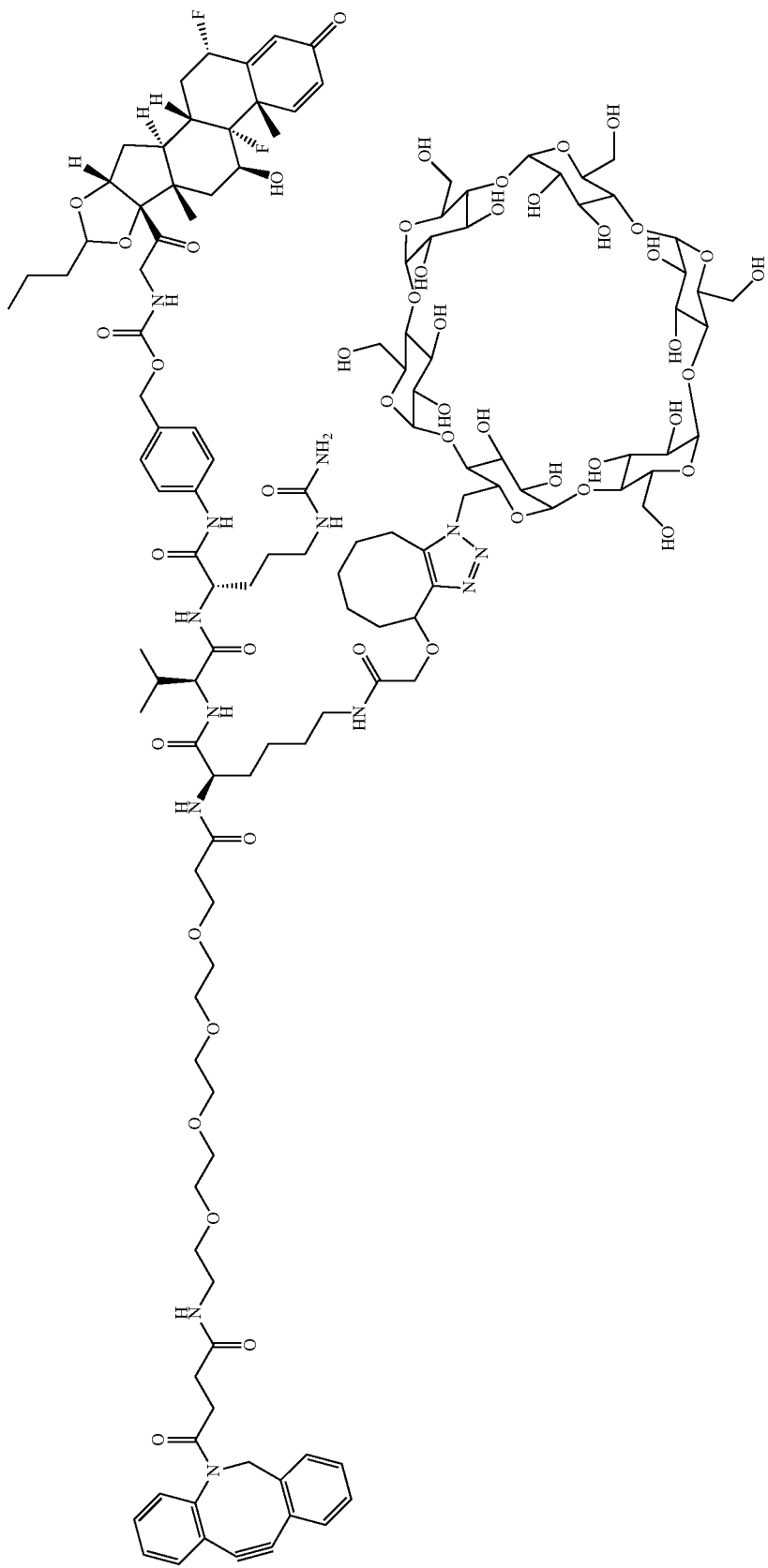

Following the general procedure I from compound L8a (0.10 g, 46 µmol) with L9b, compound L1a (26 mg, 22% yield) was obtained as a white solid. ESI m/z: 1349 (M/2+ H)$^+$. $^1$H NMR (500 MHz, DMSO$_{d6}$) δ 9.71 (s, 1H), 8.30-8.00 (m, 3H), 8.00-7.74 (m, 2H), 7.70-7.58 (m, 5H), 7.52-7.20 (m, 12H), 6.35-6.20 (m, 2H), 6.15-5.85 (m, 3H), 5.80-5.35 (m, 18H), 5.25-4.90 (m, 6H), 4.90-4.50 (m, 14H), 4.40-4.25 (m, 4H), 4.25-4.10 (m, 3H), 4.10-3.95 (m, 2H), 3.95-3.55 (m, 22H), 3.55-3.40 (m, 22H), 3.20-3.00 (m, 6H), 3.00-2.85 (m, 3H), 2.65-2.55 (m, 1H), 2.25-2.20 (m, 4H), 2.10-1.95 (m, 6H), 1.80-1.70 (m, 5H), 1.70-1.50 (m, 10H), 1.50-1.45 (m, 9H), 0.90-0.80 (m, 14H) ppm. Anal. HPLC: >99%, Retention time: 6.23 min (method B).

Example 108

Making Compound LP105: L11b (BCN-PEG4-aCD-CCK-vcPAB-4b (1R,8S,9S)-Bicyclo[6.1.0]non-4-yn-9-ylmethyl N-(14-{[(1R)-1-{[(1S)-1-{[(1S)-4-(carbamoylamino)-1-[(4-{[({2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethyl}carbamoyl)oxy]methyl}phenyl)carbamoyl]butyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]carbamoyl}-3,6,9,12-tetraoxatetradecan-1-yl)carbamate

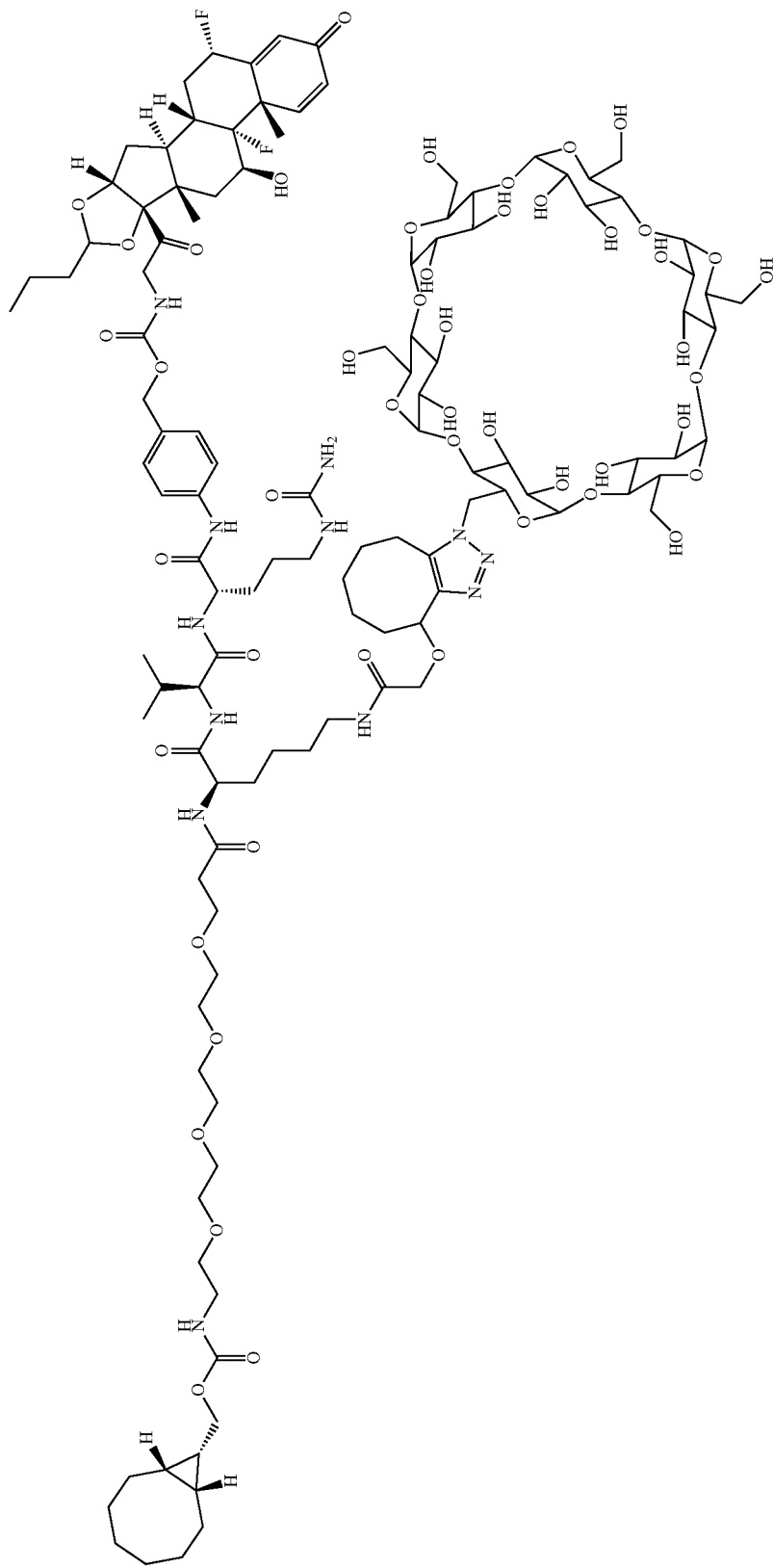

Following the General Procedure I from compound L8a (22 mg, 10 μmol) with BCN-PEG$_4$-acid L9a, compound L1b (10 mg, 38% yield) was obtained as a white solid. ESI m/z: 1293 (M/2+H)$^+$. $^1$H NMR (500 MHz, DMSO$_{d6}$) δ 9.68 (s, 1H), 8.14-7.08 (m, 11H), 6.30 (d, J=10.0 Hz, 1H), 6.11 (s, 1H), 5.99 (s, 1H), 5.67-5.31 (m, 15H), 5.21-3.33 (m, 61H), 3.13-2.60 (m, 22H), 2.30-1.96 (m, 46H), 0.95-0.80 (m, 17H) ppm. Anal. HPLC: Retention time: 7.31 min (48%) and 7.41 (52%) (method B).

Example 109

Making Compound LP108: L11e (DIBAC-PEG4-aCD-CCK-VA-6-I 1-(4-{2-Azatricyclo[10.4.0.0$^{4,9}$]hexadeca-1(12),4(9),5,7,13,15-hexaen-10-yn-2-yl}-4-oxobutanamido)-N-[(1R)-1-{[(1S)-1-{[(1S)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]carbamoyl}-5-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}pentyl]-3,6,9,12-tetraoxapentadecan-15-amide

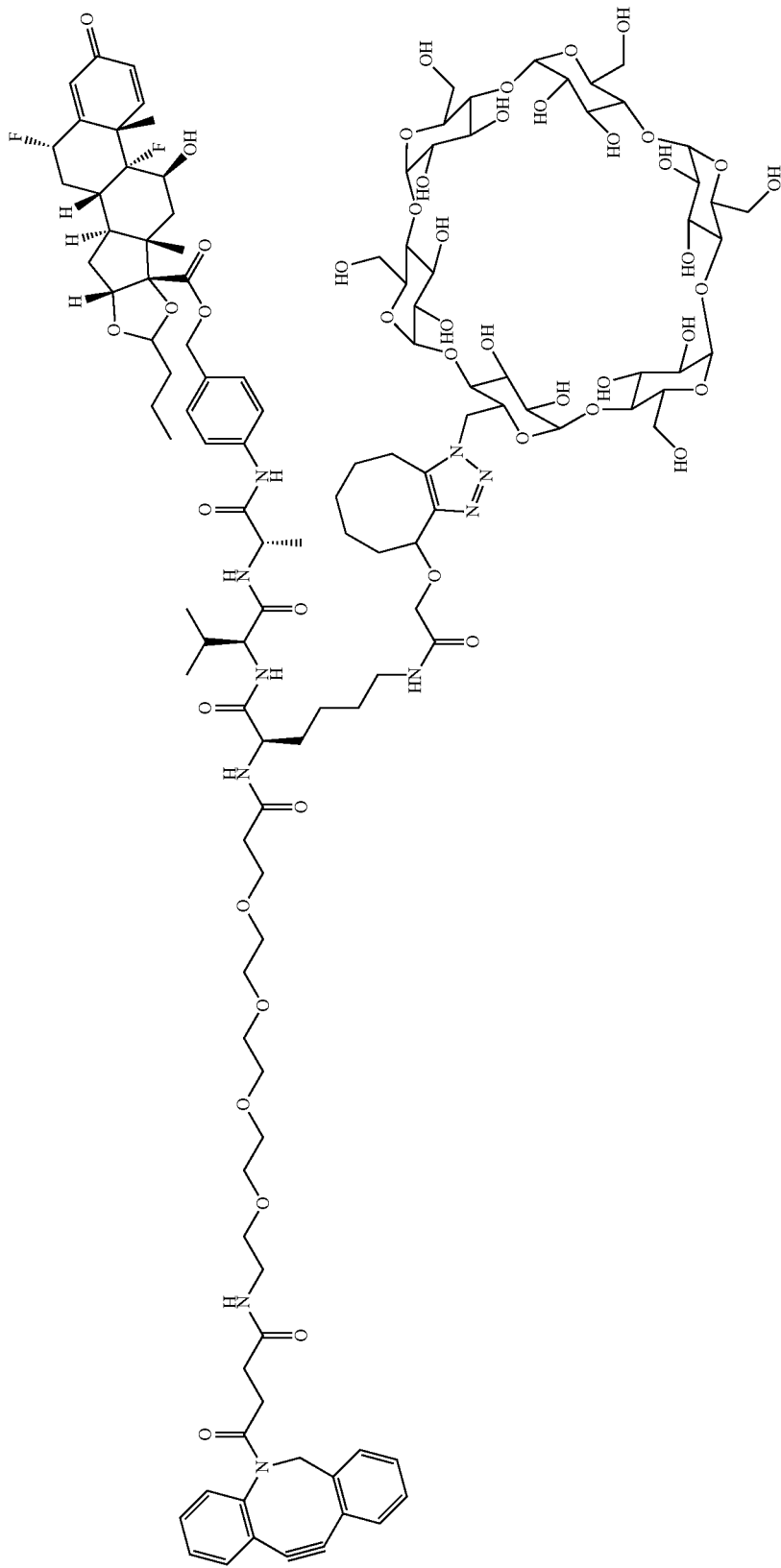

Following the General Procedure J from compound L8d (19 mg, 9.4 μmol) with DIBAC-PEG$_4$-NHS L10b, compound L1e (7.0 mg, 29% yield) was obtained as a white solid. ESI m/z: 1276.8 (M/2+H)$^+$. $^1$H NMR (400 MHz, DMSO$_{d6}$) δ 9.80-9.47 (m, 1H), 8.23-7.91 (m, 3H), 7.83-7.11 (m, 13H), 6.87-6.66 (m, 2H), 6.32-6.11 (m, 2H), 5.85-5.23 (m, 14H), 5.14-5.01 (m, 3H), 4.86-3.99 (m, 19H), 3.85-3.40 (m, 38H), 3.27-2.87 (m, 13H), 2.76-2.55 (m, 3H), 2.33-2.20 (m, 4H), 2.12-1.91 (m, 6H), 1.83-1.72 (m, 4H), 1.59-0.98 (m, 31H), 0.89-0.84 (m, 12H) ppm. Anal. HPLC: 100%, Retention time: 7.76 min (method B).

Example 110

Making Compound LP110: L11g (DIBAC-PEG4-aCD-CCK-vcPAB-6-I

{4-[(2S)-2-[(2S)-2-[(2R)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-6-{2-[(1-{[31,32,33,34,35,36,37,38,39,40,41,42-dodecahydroxy-10,15,20,25,30-pentakis(hydroxymethyl)-2,4,7,9,12,14,17,19,22,24,27,29-dodecaoxaheptacyclo[26.2.2.2$^{3,6}$.2$^{8,11}$.2$^{13,16}$.2$^{18,21}$.2$^{23,26}$]dotetracontan-5-yl]methyl}-1H,4H,5H,6H,7H,8H,9H-cycloocta[d][1,2,3]triazol-4-yl)oxy]acetamido}hexanamido]-3-methylbutanamido]-5-(carbamoylamino)pentanamido]phenyl}methyl N-(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamate

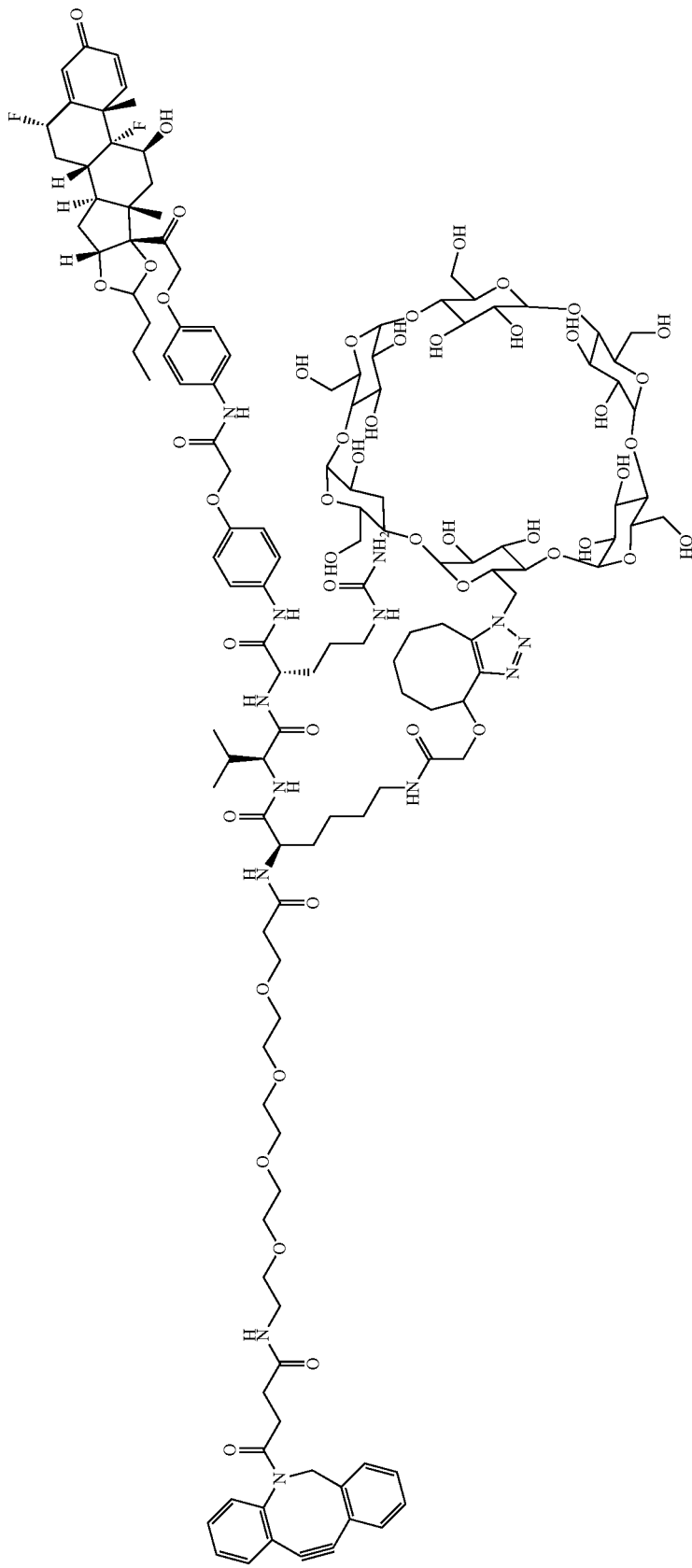

Following the General Procedure I from compound L8d (0.10 g, 44 μmol) with DIBAC-PEG$_4$-acid L9b, compound L1g (29 mg, 24% yield) was obtained as a white solid. ESI m/z: 1394 (M/2+H)$^+$. $^1$H NMR (500 MHz, DMSO$_{d4}$) δ 9.67 (s, 1H), 9.56 (s, 1H), 8.20-8.05 (m, 2H), 7.85-7.70 (m, 2H), 7.70-7.60 (m, 4H), 7.50-7.25 (m, 12H), 6.90-6.80 (m, 2H), 6.30 (d, J=12.5 Hz, 1H), 6.11 (s, 1H), 6.0 (s, 1H), 5.80-5.35 (m, 16H), 5.25-5.00 (m, 6H), 4.90-4.65 (m, 10H), 4.65-4.45 (m, 4H), 4.40-4.00 (m, 6H), 3.95-3.55 (m, 22H), 3.50-3.30 (m, 22H), 3.20-2.85 (m, 12H), 2.65-2.55 (m, 2H), 2.45-2.35 (m, 2H), 2.35-2.20 (m, 3H), 2.15-1.95 (m, 5H), 1.90-1.70 (m, 4H), 1.70-1.50 (m, 10H),1.50-1.00 (m, 18H), 0.90-0.80 (m, 12H) ppm. Anal. HPLC: Retention time: 7.93 (82%) and 8.02 (18%) min (method B).

Example 111

Making Compound LP112: (DIBAC-PEG$_4$-aCDCCK-vc-PAB-4b

{4-[(2S)-2-[(2S)-2-[1-(4-{2-Azatricyclo[10.4.0.0$^{4,9}$] hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino) pentanamido]phenyl}methyl N-{2-[(1S,2S,4R,8S,9S,11S,12R,13S,19S)-12,19-difluoro-11-hydroxy-9,13-dimethyl-16-oxo-6-propyl-5,7-dioxapentacyclo [10.8.0.0$^{2,9}$.0$^{4,8}$.0$^{13,18}$]icosa-14,17-dien-8-yl]-2-oxoethyl}carbamate

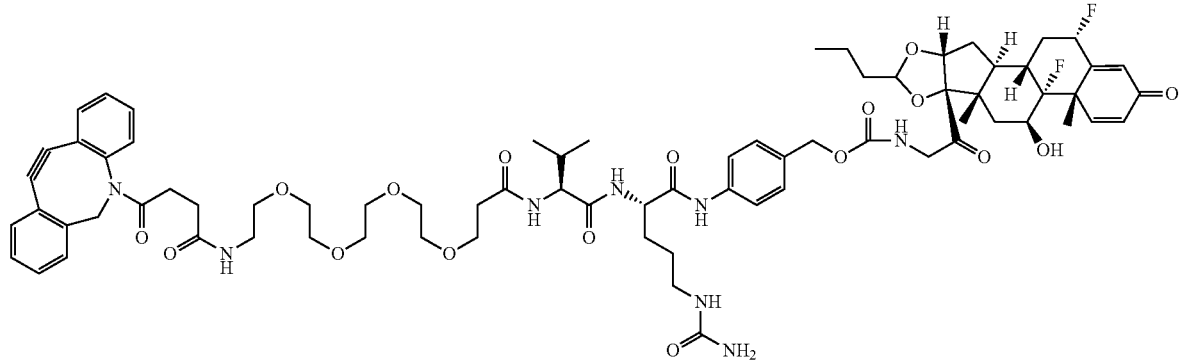

Following the General Procedure J from compound L4b (43 mg, 50 μmol) with DIBAC-suc-PEG$_4$-acid (L9b), the title compound L12 (16 mg, 23% yield) was obtained after purification by prep-HPLC (method B) as a white solid. ESI m/z: 1406 (M+H)$^+$. $^1$H NMR (DMSO$_{d6}$, 500 MHz) δ 9.99 (s, 1H), 8.11 (d, J=7.5 Hz, 1H), 7.88 (d, J=8.5 Hz, 1H), 7.80-7.75 (m, 1H), 7.70-7.66 (m, 1H), 7.65-7.60 (m, 3H), 7.53-7.33 (m, 6H), 7.33-7.28 (m, 3H), 6.30 (dd, J=10.0 Hz and 1.5 Hz, 1H), 6.11 (s, 1H), 6.10-6.00 (m, 1H), 5.72-5.55 (m, 2H), 5.41 (s, 2H), 5.05-5.01 (m, 1H), 4.97 (s, 2H), 4.80-4.72 (m, 1H), 4.60-4.58 (m, 1H), 4.43-4.33 (m, 1H), 4.25-4.10 (m, 3H), 3.88-3.80 (m, 1H), 3.65-3.55 (m, 3H), 3.50-3.40 (m, 12H), 3.30-3.25 (m, 2H), 3.12-2.90 (m, 4H), 2.70-2.55 (m, 2H), 2.48-2.35 (m, 2H), 2.30-2.20 (m, 2H), 2.15-1.95 (m, 4H), 1.86-1.65 (m, 3H), 1.64-1.54 (m, 5H), 1.49 (s, 4H), 1.46-1.34 (m, 5H), 0.90-0.80 (m, 12H) ppm. Anal. HPLC: 100%, Retention time: 7.40 min (method B).

Example 112

Making Compound LP113: MAL-PEG4-VA-R-11-5

1-(2,5-Dioxo-2,5-dihydro-1H-pyrrol-1-yl)-N-[(1S)-1-{[(1S)-1-[(4-{2-[(1S,2S,4R,6R,8S,9S,11S,12S,13R)-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamoyl]ethyl]carbamoyl}-2-methylpropyl]-3,6,9,12-tetraoxapentadecan-15-amide

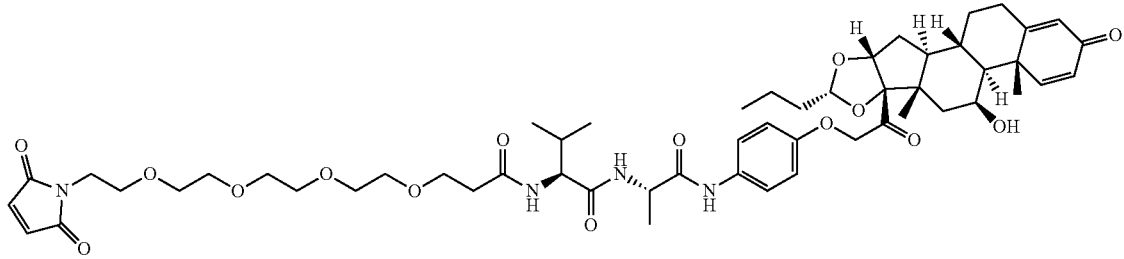 [SMILES: CCC[C@@H]1O[C@@H]2C[C@H]3[C@@H]4CCC5=CC(=O)C=C[C@]5(C)[C@H]4[C@@H](O)C[C@]3(C)[C@]2(C(=O)COc2ccc(NC(=O)[C@H](C)NC(=O)[C@@H](NC(=O)CCOCCOCCOCCOCCN3C(=O)C=CC3=O)C(C)C)cc2)O1]

Following the general procedure J from compound L4a (20 mg, 25 μmol) with MAL-PEG$_4$-NHS L10c, compound LP113 (7 mg, 27% yield) was obtained as a white solid. ESI m/z: 1119 (M+H)$^+$. $^1$H NMR (400 MHz, DMSO$_{d6}$) δ 9.89-9.60 (m, 1H), 8.51-6.73 (m, 10H), 6.18 (dd, J=10.1, 1.7 Hz, 1H), 5.93 (s, 1H), 5.17-4.05 (m, 9H), 4.02-3.52 (m, 13H), 2.71-2.54 (m, 1H), 2.46-2.20 (m, 5H), 2.15-1.77 (m, 5H), 1.63-1.53 (m, 5H), 1.47-1.20 (m, 9H), 1.10-0.94 (m, 2H), 0.95-0.65 (m, 12H) ppm. Anal. HPLC: 100%, Retention time: 7.46 min (method B).

Example 113

Making Compound LP114: L11j (DIBAC-PEG4-VA-6-II 1-(4-{2-Azatricyclo[10.4.0.0$^{4,9}$]hexadeca-1(16),4(9),5,7,12,14-hexaen-10-yn-2-yl}-4-oxobutanamido)-N-[(1S)-1-{[(1S)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}-2-methoxyphenyl)carbamoyl]ethyl]carbamoyl}-2-methylpropyl]-3,6,9,12-tetraoxapentadecan-15-amide

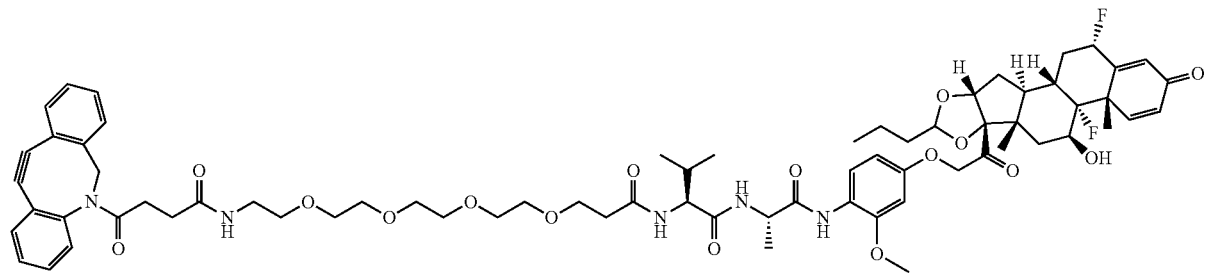 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](NC(=O)CCOCCOCCOCCOCCNC(=O)CCC(=O)N3Cc4ccccc4C#Cc4ccccc43)C(C)C)c(OC)c2)O1]

Following the General Procedure I from L4e (40 mg, 47 µmol) with DIBAC-suc-PEG$_4$-acid L9b, compound L1j (25 mg, 41% yield) as a white solid. ESI m/z: 1293 (M+H)$^+$. $^1$H NMR (400 MHz, DMSO$_{d6}$) δ 8.98-8.86 (m, 1H), 8.37-8.30 (m, 1H), 7.94-7.88 (m, 1H), 7.87-7.72 (m, 2H), 7.70-7.57 (m, 2H), 7.52-7.42 (m, 3H), 7.41-7.22 (m, 4H), 6.65-6.59 (m, 1H), 6.44-6.34 (m, 1H), 6.33-6.27 (m, 1H), 6.12 (s, 1H), 5.77-5.49 (m, 2H), 5.18-5.11 (m, 1H), 5.07-4.98 (m, 1H), 4.91-4.70 (m, 3H), 4.54-4.43 (m, 1H), 4.29-4.16 (m, 2H), 3.79 (s, 3H), 3.65-3.53 (m, 3H), 3.51-3.38 (m, 12H), 3.30-3.22 (m, 2H), 3.13-3.03 (m, 2H), 2.72-2.54 (m, 2H), 2.47-2.18 (m, 4H), 2.13-1.91 (m, 4H), 1.85-1.72 (m, 2H), 1.64-1.55 (m, 3H), 1.52-1.33 (m, 6H), 1.31-1.23 (m, 3H), 0.99-0.77 (m, 13H) ppm. Anal. HPLC: 99%, Retention time: 9.18 and 9.22 min (method B).

Example 114

Making Compound LP115: L11k-(DIBAC-PEG4-VA-6-III 1-(4-{2-Azatricyclo[10.4.0.0$^{4,9}$]hexadeca-1(12),4(9),5,7,13,15-hexaen-10-yn-2-yl}-4-oxobutanamido)-N-[(1S)-1-{[(1S)-1-[(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}-2-fluorophenyl)carbamoyl]ethyl]carbamoyl}-2-methylpropyl]-3,6,9,12-tetraoxapentadecan-15-amide

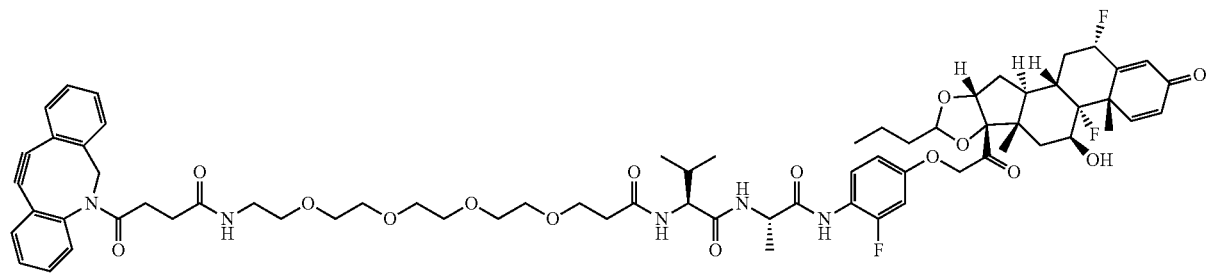 [SMILES: CCCC1O[C@@H]2C[C@H]3[C@@H]4C[C@H](F)C5=CC(=O)C=C[C@]5(C)[C@@]4(F)[C@@H](O)C[C@]3(C)[C@]2(C(=O)COc2ccc(NC(=O)[C@H](C)NC(=O)[C@@H](NC(=O)CCOCCOCCOCCOCCNC(=O)CCC(=O)N3Cc4ccccc4C#Cc4ccccc43)C(C)C)c(F)c2)O1]

Following the General Procedure I from L4f (82 mg, 0.11 mmol) with DIBAC-suc-PEG$_4$-acid L9b, compound L1k (50 mg, 35% yield) as a white solid. ESI m/z: 1280 (M+H. $^1$H NMR (500 MHz, DMSO$_{d6}$) δ 9.54 (s, 1H), 8.41-8.15 (m, 1H), 8.01-7.17 (m, 12H), 6.90 (d, J=10.8 Hz, 1H), 6.73 (s, 1H), 6.31 (d, J=9.9 Hz, 1H), 6.12 (s, 1H), 5.77-5.46 (m, 2H), 5.28-4.65 (m, 5H), 4.58-4.42 (m, 1H), 4.29-4.11 (m, 2H), 3.71-3.43 (m, 15H), 3.29 (s, 2H), 3.08 (s, 2H), 2.71-2.54 (m, 2H), 2.47-2.17 (m, 4H), 2.16-1.88 (m, 4H), 1.88-1.69 (m, 2H), 1.69-1.19 (m, 13H), 0.95-0.80 (m, 12H) ppm. $^{19}$F NMR (376 MHz, DMSO) δ −121.11 and −121.92, −165.13 and −165.14, −186.38 and −186.40 ppm. Anal. HPLC: >99%, Retention time: 8.32 min (method B).

Example 115

Making Compound LP116: L11k-(DIBAC-PEG4-VC-PAB-4b)

{4-[(2S)-2-[(2S)-2-[1-(4-{2-Azatricyclo[10.4.0.0$^{4,9}$]hexadeca-1(12),4(9),5,7,13,15-hexaen-10-yn-2-yl}-4-oxobutanamido)-3,6,9,12-tetraoxapentadecan-15-amido]-3-methylbutanamido]-5-(carbamoylamino)pentanamido]phenyl}methyl N-(4-{2-[(1S,2S,4R,8S,9S,11S,12R,13S,19S)-12,19-difluoro-11-hydroxy-9,13-dimethyl-16-oxo-6-propyl-5,7-dioxapentacyclo[10.8.0.0$^{2,9}$.0$^{4,8}$.0$^{13,18}$]icosa-14,17-dien-8-yl]-2-oxoethoxy}phenyl)carbamate

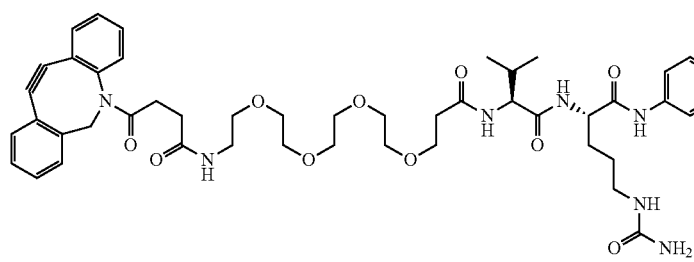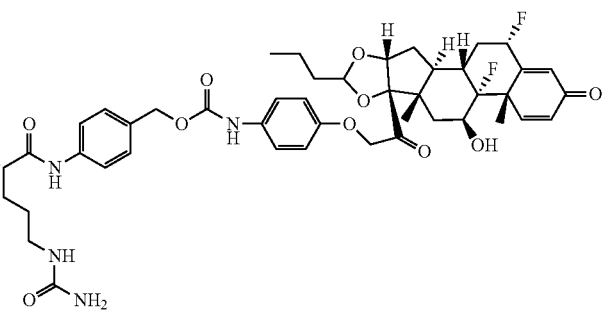

Following the General Procedure I from compound L4k (58 mg, 60 μmop with DIBAC-suc-PEG$_4$-acid L9b, the title compound L1v (20 mg, 22% yield) was obtained as a white solid. ESI m/z: 1499 (M+H)$^+$. $^1$H NMR (400 MHz, DMSO$_{d6}$) δ 10.02 (s, 1H), 9.59 (s, 1H), 8.14 (d, J=7.6 Hz, 1H), 7.88 (d, J=8.8 Hz, 1H), 7.80-7.75 (m, 1H), 7.70-7.66 (m, 1H), 7.65-7.60 (m, 3H), 7.53-7.45 (m, 3H), 7.40-7.28 (m, 7H), 6.84 (d, J=9.2 Hz, 2H), 6.30 (dd, J=10.4 Hz, J=1.6 Hz, 1H), 6.11 (s, 1H), 6.10-6.0 (m, 1H), 5.72-5.55 (m, 1H), 5.52 (s, 1H), 5.43 (s, 2H), 5.16-5.05 (m, 4H), 4.88-4.70 (m, 3H), 4.43-4.33 (m, 1H), 4.25-4.20 (m, 2H), 3.65-3.55 (m, 3H), 3.50-3.40 (m, 12H), 3.30-3.25 (m, 2H), 3.12-2.90 (m, 4H), 2.70-2.55 (m, 2H), 2.48-2.43 (m, 1H), 2.40-2.35 (m, 1H), 2.30-2.20 (m, 2H), 2.15-1.95 (m, 4H), 1.86-1.75 (m, 2H), 1.64-1.54 (m, 5H), 1.49 (s, 4H), 1.46-1.34 (m, 4H), 1.23 (s, 2H), 0.90-0.80 (m, 12H) ppm. Anal. HPLC: 100%, Retention time: 7.83 min (method B).

Example 116

ADC Conjugation

The steroid antibody conjugations were outlined in FIG. 33. In one example, site-specific conjugates were produced via Microbial transglutaminase (MTG EC 2.3.2.13, Zedira, Darmstadt, Germany) (herein "MTG-based") two-step conjugation of an N297Q or N297D mutated antibody. In the first step, the N297Q-mutated antibody was functionalized with azdio-PEG$_3$-amine via MTG based enzymatic reaction. See, e.g., International PCT Patent Application No. PCT/US17/19537 filed on Feb. 24, 2017, incorporated herein by reference in its entirety for all purposes. In the second step, an alkyne-functionalized linker payload was attached to the azido-functionalized antibody via [2+3] 1,3-dipolar cycloaddition reaction (FIG. 33 depicts a DIBAC-functionalized linker-payload (LP112) conjugated with an azido-functionalized antibody derived via [2+3] cyclization). This process provided site specific and stoichiometric conjugates in about 50-80% isolated yield.

Steroid-Antibody Conjugates Prepared in FIG. 33

This example demonstrates a method for site-specific conjugation, generally, of a payload to an antibody or antigen-binding fragment thereof. This example refers to FIG. 33.

The following example demonstrates a method for making an azido functionalized antibody drug conjugate listed in Table 16.

Aglycosylated antibody with a human IgG1 isotype in BupH™ (pH 7.6 lated antibody with a human IgG1 isotype in BupHonalized $_3$-amine (MW. 218.26 g/mol). The resulting solution was mixed with transglutaminase (25 U/mL; 5 U MTG per mg of antibody) resulting in a final concentration of the antibody at 0.5-3 mg/mL, and the solution was then incubated at 37° C. for 4-24 hours while gently shaking. The reaction was monitored by SDS-PAGE or ESI-MS. Upon the completion, the excess amine and MTG were removed by Size Exclusion Chromatography (SEC) to generate the azido-functionalized antibody. This product was analyzed on SDS-PAGE and ESI-MS. The azido-dPEG$_3$-amine added to two sites—Q295 and Q297—of the antibody resulting in an 804 Da increase for the 4 DAR aglycosylated antibody-PEG$_3$-azide conjugate. The conjugation sites were identified and confirmed at EEQ$^{Linker}$YQ$^{Linker}$STYR for the 4 DAR azido-functionalized antibody via peptide sequence mapping of trypsin digested heavy chains.

The following example demonstrates a method for making a site-specific conjugations of a drug to an antibody using click chemistry reactions.

The site-specific aglycosylated antibody drug conjugates with a human IgG1 containing an N297Q mutation in Table 16 described below were prepared by a [2+3] click reaction between azido-functionalized antibodies with an alkyne containing linker-payload. As shown in Table 16, anti PRLR Ab-PEG$_3$-N$_3$ was conjugated to LP112, LP104, and LP116; and anti Fel D1 Ab-PEG$_3$-N$_3$ was conjugated to LP112, and LP116.

The detailed conjugation procedure follows. A site-specific antibody conjugate with linker-payload (LP) was prepared by incubating mAb-PEG$_3$-N$_3$ (1-3 mg/mL) in an aqueous medium (e.g., PBS, PBS containing 5% glycerol, HBS) with ≥6 molar equivalents of an LP dissolved in a suitable organic solvent, such as DMSO, DMF or DMA (i.e., the reaction mixture contains 5-20% organic solvent, v/v) at 24° C. to 37° C. for over 6 h. The progress of the reaction was monitored by ESI-MS and the absence of mAb-PEG$_3$-N$_3$ indicated the completion of the conjugation. The excess amount of the LP and organic solvent were removed by SEC via elution with PBS, or via protein A column chromatography via elution with acidic buffer followed by neutralization with Tris (pH 8.0). The purified conjugates were analyzed by SEC, SDS-PAGE, and ESI-MS. Shown in Table 16 is a list of the steroid antibody conjugates from the corresponding LPs, their molecular weights and ESI-DAR values In a specific example, the azido-functionalized antibody (1 mg) in 0.800 mL PBSg (PBS, 5% glycerol, pH 7.4) was treated with six molar equivalents of DIBAC-PEG$_4$-D-Lys (COT-α-CD)-VC-PABC-payload (conc. 10 mg/mL in DMSO) for 6-12 hours at room temperature and the excess linker payload (LP) was removed by size exclusion chromatography (SEC, Superdex 200 HR, GE Healthcare). The final product was concentrated by ultra-centrifugation and characterized by UV, SEC, SDS-PAGE and ESI-MS.

Example 117

Characterization of ADC by LC-ESI-MS

Measurement of intact mass for the ADC samples by LC-ESI-MS was performed to determine drug-payload distribution profile and to calculate the average DAR. Each testing sample (20-50 ng, 5 uL) was loaded onto an Acquity UPLC Protein BEH C4 column (10 K psi, 300 Å, 1.7 μm, 75 μm×100 mm; Cat No. 186003810). After 3 min desalting, the protein was eluted and mass spectra were acquired by a Waters Synapt G2-Si mass spectrometer.

Figure 34:
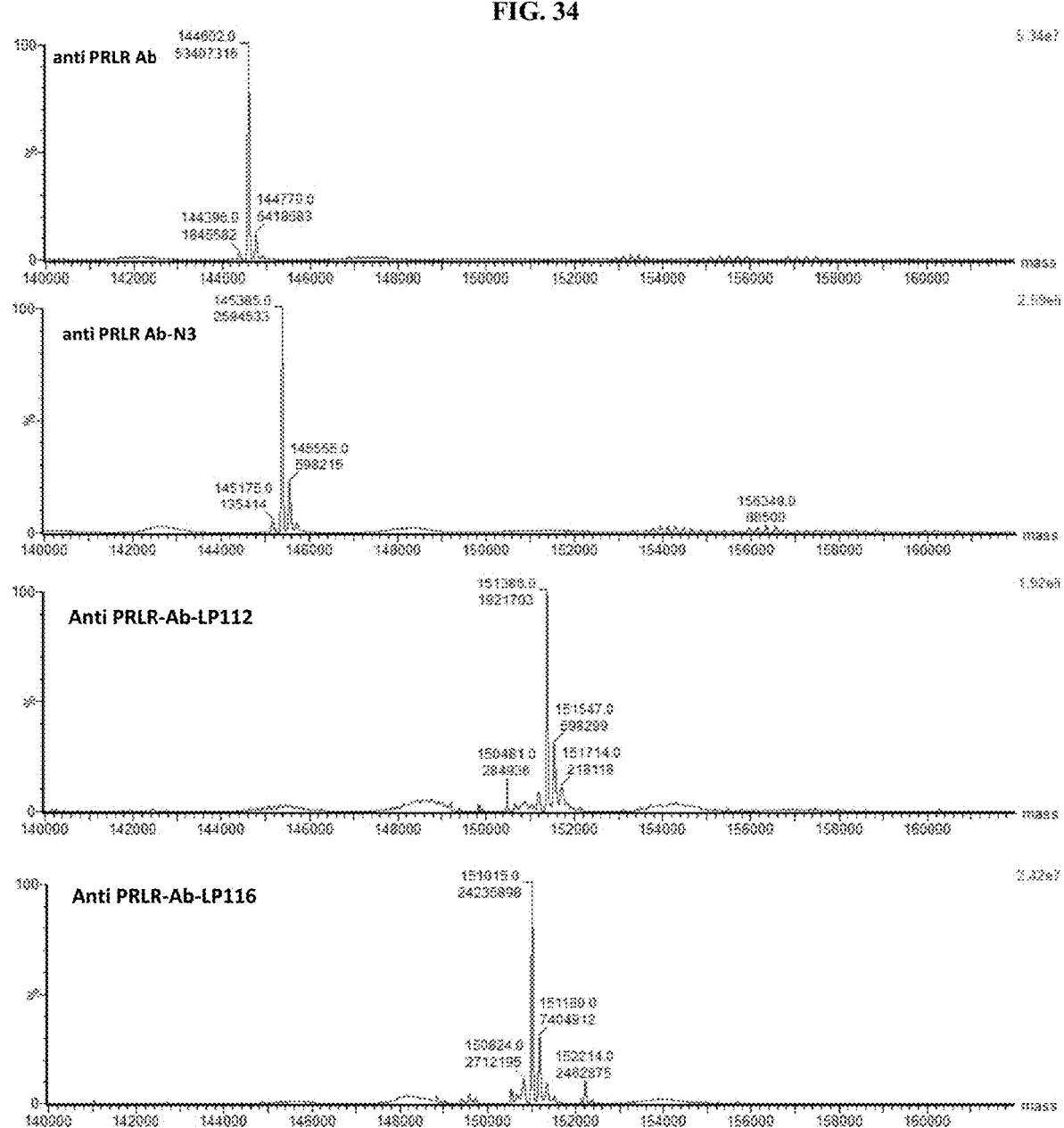
FIG. 34 shows ESI-MS of anti-PRLR Ab, anti-PRLR Ab-N$_3$, and anti-PRLR-LPs.

As shown in following FIG. 34, the deconvoluted mass spectra exhibited a predominant peak for the aglycosylated anti-PRLR antibody with a molecular weight of 144602 Da, and a predominant peak for the azido functionalized anti-PRLR antibody with a molecular weight of 145385 Da, indicating a 783 Da increase compared to its aglycosylated parent antibody (i.e., corresponding to 4 amino-PEG$_3$-azide conjugations to each aglycosylated antibody). Also, the predominant peak for anti-PRLR-LP12 conjugate had a molecular weight of 151015 Da, indicating a 5630 Da increase compared to its azido-functionalized antibody (i.e., corresponding to 4 LPs (MW=1405.6 Da) conjugations to each aglycosylated antibody). Similarly, other site-specific anti-PRLR-ADCs had 3.9-4 DAR.

Figure 35:
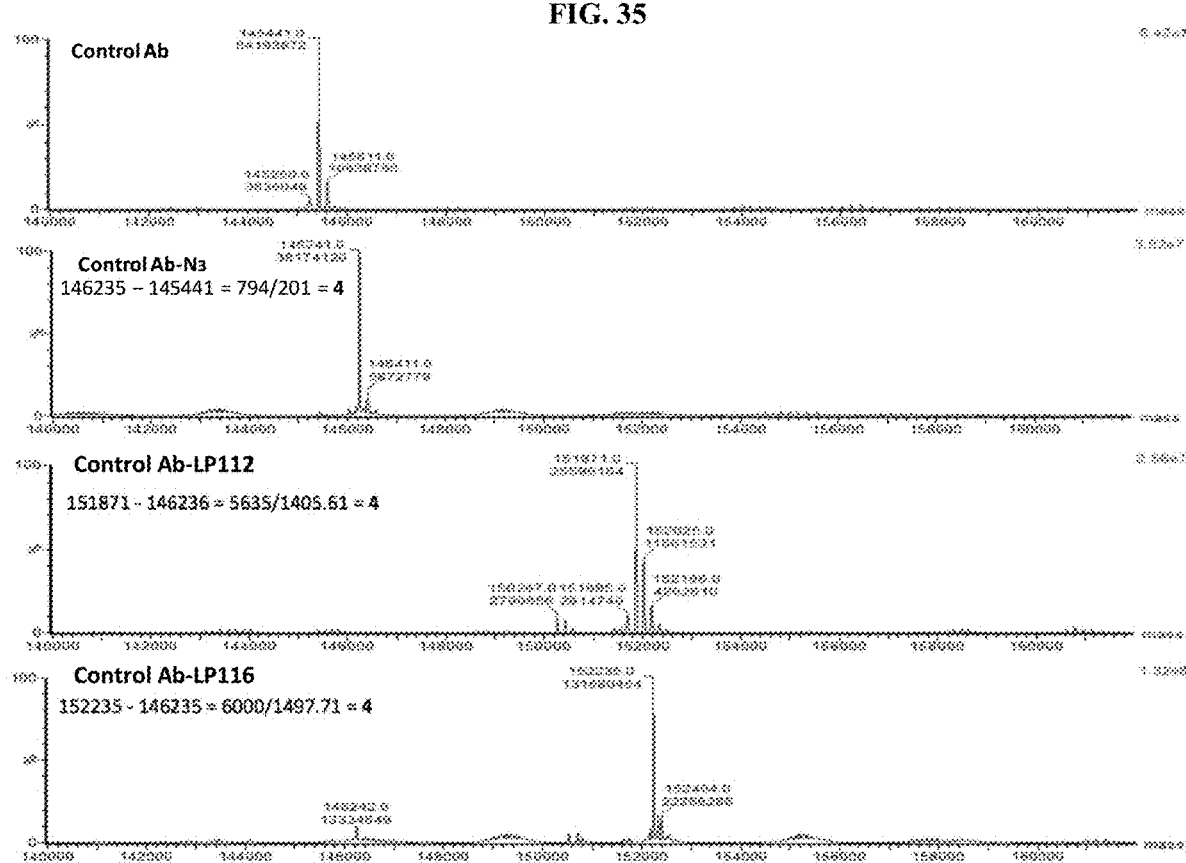
FIG. 35 shows ESI-MS of anti-Fel d1 Ab, anti-Fel d1 Ab-PEG$_3$-N$_3$, and anti-Fel d1 Ab-LPs.

As shown in following FIG. 35, the deconvoluted mass spectra exhibited a predominant peak for the aglycosylated anti-Fel D1 antibody with a molecular weight of 145441 Da, and a predominant peak for the azido functionalized anti-Fel d1 antibody with a molecular weight of 146235 Da, indicating a 794 Da increase compared to its aglycosylated parent antibody (i.e., corresponding to 4 amino-PEG$_3$-azide conjugations to each aglycosylated antibody). Also, the predominant peak for anti-Fel d1-LP12 conjugate had a molecular weight of 151871.0 Da, indicating a 5635 Da increase compared to its azido-functionalized antibody (i.e., corresponding to 4 LPs (MW=1405.6 Da) conjugations to each aglycosylated antibody). Similarly, other site-specific anti-Fel d1-ADCs had 3.9-4 DAR.

Shown in Table 16 is a list of non-cytotoxic steroid antibody conjugates (ncADCs) from the corresponding LPs, their molecular weights of the naked antibodies, the azido-functionalized antibodies, the LPs, and the steroid ADCs, as well as the ESI-DAR values. In the table, Ab refers to an antibody, Ab-N$_3$ refers to an azido-functionalized antibody, and ncADC refers to a non-cytotoxic steroid antibody conjugate.

Example 118

In Vitro Enzymatic Assay
Linker-Payload Cleavage in Cathepsin B Assay

The linker-payloads were tested in a Cathepsin B assay. After 4 hr incubation in Cathepsin B (CapB) with and without CapB inhibitor (VA074), both linker-payloads and free payload were evaluated using LC-MS/MS. The results indicated that the hydrophilic linker-payloads (LP104) could be cleaved by CapB and released more payload (4b) compared to non-hydrophilic linker-payloads (LP12).

The CapB assay procedure follows: Linker-payload stock solution (10 mM in DMSO) was spiked into incubation buffer (100 mM NaOAc, 10 mM dithiothreitol, pH 5) to obtain a 50 μM substrate solution. 4 μL of 0.47 μg/μL human liver cathepsin B (Athens Research & Technology, Athens, Ga.) in 50 mM NaOAc, 1 mM EDTA, pH 5 was added into 196 μL of 50 μM substrate solution. The reaction mixture was incubated at 37° C. for 4 hr. Then 5 μL of acetic acid and 150 μL of acetonitrile (containing osalmid as internal standard) were added to 50 μL of reaction mixture aliquots. After vortexing, the quenched samples were frozen in a −70° C. deep freezer, followed by thawing and centrifugation at 14,000 rpm. 50 μL aliquots of the resultant supernatants were then diluted with equal volume of water and analyzed by LC-ESI-MS/MS for released payload.

TABLE 17

CATHEPSIN B CLEAVAGE RESULTS

| | | Linker | | | | | Conversion |
|---|---|---|---|---|---|---|---|
| Cpd | Payload | Cleaved piece | Hydrophilic linker | Conjugated piece | With or without CA074 | | rate (%) |
| LP101 | 4b | vcPAB | / | Lk-CCK | Without | Mean RSD | 48.20 |
| | | | | | With | Mean RSD | <1.00 |
| LP112 | 4b | vcPAB | / | Lk-DIBAC | Without | Mean RSD | 20.8 |
| | | | | | With | Mean RSD | <1.00 |
| LP104 | 4b | vcPAB | aCDCCK | Lk-DIBAC | Without | Mean RSD | 29.0 |
| | | | | | With | Mean RSD | <1.00 |
| LP102 | 6-I | Val-Ala | / | Lk-CCK | Without | Mean RSD | 22.72 |
| | | | | | With | Mean RSD | <1.00 |

TABLE 17-continued

CATHEPSIN B CLEAVAGE RESULTS

| Cpd | Payload | Linker Cleaved piece | Linker Hydrophilic linker | Linker Conjugated piece | With or without CA074 | | Conversion rate (%) |
|---|---|---|---|---|---|---|---|
| LP108 | 6-I | Val-Ala | aCDCCK | Lk-DIBAC | Without | Mean | |
| | | | | | | RSD | |
| | | | | | With | Mean | |
| | | | | | | RSD | |
| LP116 | 6-I | vcPAB | / | Lk-DIBAC | Without | Mean | |
| | | | | | | RSD | |
| | | | | | With | Mean | <1.00 |
| | | | | | | RSD | |
| LP103 | 6-I | vcPAB | / | Lk-CCK | Without | Mean | 29.0 |
| | | | | | | RSD | |
| | | | | | With | Mean | <1.00 |
| | | | | | | RSD | |

The CapB assay experiment included the following procedure.
1. Preheat assay buffer: 0.1 M NaOAc/0.01 M DTT (pH 5.0)
2. Spiking solutions for test compounds: 25 μM Spiking solutions for test compounds: Add 2 μL of 5 mM stock solution into 398 μL of 0.1 M NaOAc/0.01 M DTT buffer (pH 5.0).
3. Prepare 0.47 μg/μL Cathepsin B in 50 mM NaOAc/1 mM EDTA (pH 5.0). Put on ice.
4. Without CA074 samples: Add 4 μL of 0.47 μg/μL Cathepsin B into 196 μL of 25 μM Spiking solutions (from step 2), incubate the tubes at 37° C.
5. With CA074 samples: Add 4 μL of 0.47 μg/μL Cathepsin B with 4 μL of 10 mM Inhibitor (CA074) into 196 μL of 25 μM Spiking solutions (from step 2), incubate the tubes at 37° C.
6. After 4 hours, Aliquots of 5 μL (with CA074 and without CA074) were taken for enzyme activity test (step 15-17). Meanwhile, Aliquots of 50 μL were taken at the time point (4 h), adding 5 μL of acetic acid, and then add 150 μL of ACN (IS) to stop the reaction.
7. After quenching, shake the plate and centrifuge them at 14000 rpm.
8. Transfer 50 μL of the supernatant from each well into a 96-well sample plate containing 50 μL of ultra pure water (Millipore, ZMQS50F01) for LC/MS analysis.

The CapB assay experiment included the reference compounds and the following procedure.
9. Preheat assay buffer: 100 mM Na/K phosphate, pH 6.0, with 1.33 mM EDTA and 2 mM DTT.
10. Prepare 0.024 μg/μL Cathepsin B: Add 1 μL of 0.47 μg/μL Cathepsin B stock into 19 μL of assay buffer (from step 11).
11. Add 2 μL of 0.024 μg/μL Cathepsin B (from step 12) to a opaque 96-well plate.
12. Add 96 μL of assay buffer to each sample.
13. Add 2 μL of the 10 mM substrate Z-RR-MNA (200 μM final concentration).
   For negative control (with inhibitor), add 4 μL of 10 mM Inhibitor (CA074).
14. Immediately read the samples in a kinetic mode at excitation of 340 nm/emission of 425 nm (Read the plate every 30 Second for 3 min).
   Stability of Cathepsin B in incubation samples:
15. Take 5 μL of incubation samples into 93 μL of assay buffer (from step 11), and then add 2 μL of 10 mM substrate (Z-RR-MNA).
16. Incubate the samples at 37° C. for 2 min.
17. Read the samples at excitation of 340 nm/emission of 425 nm.

Example 119

In Vitro Cell Free and Cell Based Activity

Cell Free Binding to the Glucocorticoid Receptor (GR) in LanthaScreen TR-FRET GR Competitive Binding Assay To evaluate the ability of novel steroids to bind to the Glucocorticoid Receptor (GR), a cell-free binding assay was performed using a LanthaScreen TR-FRET GR Competitive Binding Assay kit (Life Technologies, Cat # A15901). The assay was performed according to the manufacturer's instruction. Budesonide is a commercial GR steroid and was used as a reference control in the binding assay and other cell based assays described later in the document. Briefly, a three-fold serial dilution of budesonide and the derivative compounds noted below were prepared in 100% DMSO starting at 100 nM (100× of final). Serial dilutions were further diluted 50-fold in nuclear receptor buffer F with 5 mM DTT and 0.1 mM stabilizing peptide, and transferred to a 384-well assay plate. Next, Fluormone GS1 Green, GR-LBD (GST) and Tb anti-GST antibody were sequentially added to the 384-well assay plate. The plate was analyzed on an Envision Multilabel Plate Reader (PerkinElmer) with excitation set at 340 nm and emission filters at 520 nm and 486 nm. The FRET ratio was calculated as 520 nm/486 nm. The $IC_{50}$ values were determined using a four-parameter logistic equation over a 12-point response curve (GraphPad Prism).

As shown in Table 18, Budesonide competed binding of Fluormone GS1 Green in the GR assay with an $IC_{50}$ value between 10 to 100 nM. The N-analogs of Budesonide similarly competed binding with $IC_{50}$ values ranging from less than 10 nM to greater than 100 nM. The novel steroids tested herein demonstrated comparable or better (lower $IC_{50}$ values) in this assay and similar displacement for GR ligand compared to Budesonide.

TABLE 18

CELL FREE BINDING AND CELL BASED FUNCTIONAL ACTIVITY

| Cpd # | HEK293/9xUAS-Luc2P/pBind-GR/PRLR-HA high cells EC$_{50}$ (nM) | | GR Competitive Binding Assay IC50 (nM) |
|---|---|---|---|
| Budesonide | +++ | Full activation | ++ |
| 4b | +++ | Full activation | +++ |
| 4d | ++ | Partial activation | ++ |
| 4h | +++ | Full activation | ++ |
| 5-I | +++ | Full activation | NT |
| 6-I | +++ | Full activation | NT |
| R-6-I | +++ | Full activation | +++ |
| S-6-1 | +++ | Full activation | +++ |
| 6-I D | +++ | Full activation | +++ |
| 6-II | +++ | Full activation | +++ |
| 6-III | +++ | Full activation | NT |
| 6-VI | +++ | Full activation | NT |
| 6-VII | NA | No activation | +++ |

In Table 18:
+++ <10 nM;
10 nM ≤ ++ < 50 nM;
50 nM ≤ +;
NT = not tested;
NA = no activation.
Full activation: >75% of fold activation induced by Budesonide. Partial activation: (20%, 75%) of fold activation induced by Budesonide. No activation: <20% of fold activation induced by Budesonide. Cell free assay is used to assess the direct binding of compounds to recombinant GR LBD regardless of their permeability. Cell based assay is used to measure how compounds activate intracellular GR mediated transcription after passing through the plasma membrane, thus membrane permeability of compound is prerequisite for activity.

Example 120

Glucocorticoid Receptor (GR) Co-Activator Luciferase Reporter Cell Based Assay

Glucocorticoid Activation Assay

The activity of steroid payloads and anti-PRLR steroid ncADCs were studied using a luciferase reporter cell based assay using either the 293/PRLR/GRE-luc cell line described in Example 62 as well as an antigen negative 293 cell line that contains a chimeric receptor consisting of a GR ligand binding domain fused to the yeast CAL4 DNA binding domain (pBind-GR, Promega catalog no. E1581), and a Gal4 upstream activator sequence (9xGal4 UAS-Luc) that drives luciferase expression. The resulting cell line is referred to as 293/GRE-Luc.

The bioassay was conducted using these two cell lines, tesgin anti-PRLR-LP112, dexamethasone, budesonide, compound 4b, control Ab-LP112, as well as anti-PRLR Ab alone, using an assay set up as described in Example 63.

Figure 36A:
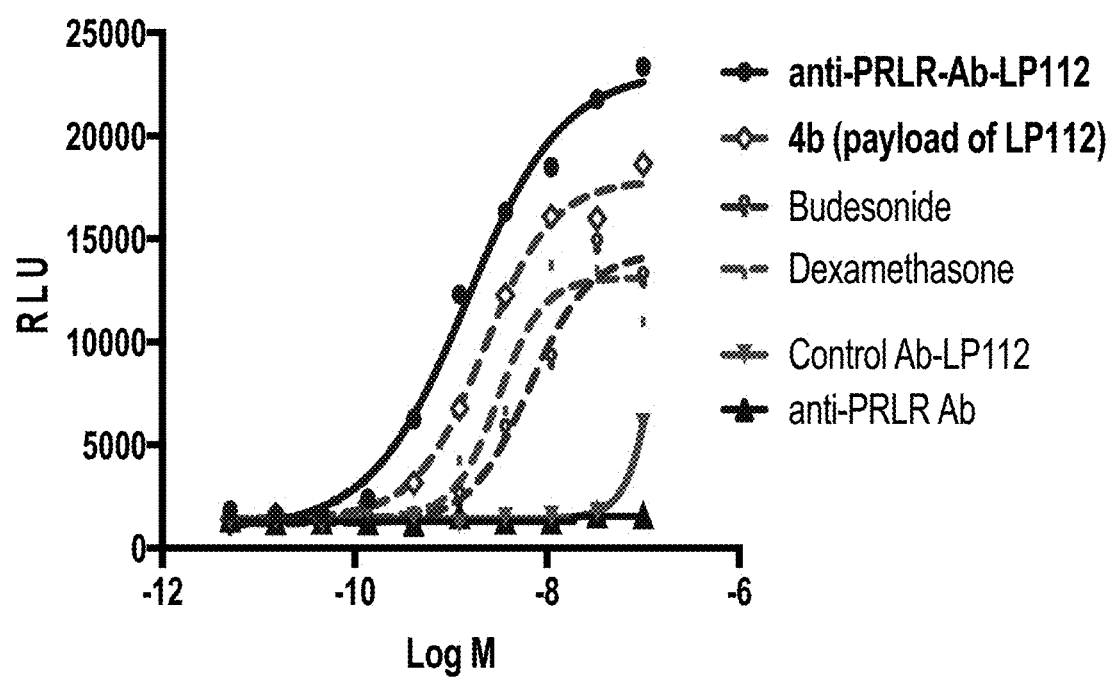
FIG. 36 shows bioactivity of steroid ADCs in antigen positive cells (293_PRLR_PBind GR/UAS-Luc cells, FIG. 36A) vs in antigen negative cells (293_PBind GR/UAS-Luc cells, FIG. 36B) in a plot of relative light units (RLU) vs. Log 10 [M].

As shown in FIG. 36A and the Table below, after 72 hrs of incubation, anti-PRLR-LP112 showed the highest fold in the 293/PRLR/GRE-luc cell line while the payload of LP112 (4b) showed a better IC$_{50}$ value than Budesonide and Dexamethasone. The Control Ab-LP112 and unconjugated anti-PRLR mAb demonstrated no activity in this cell line.

Figure 36B:
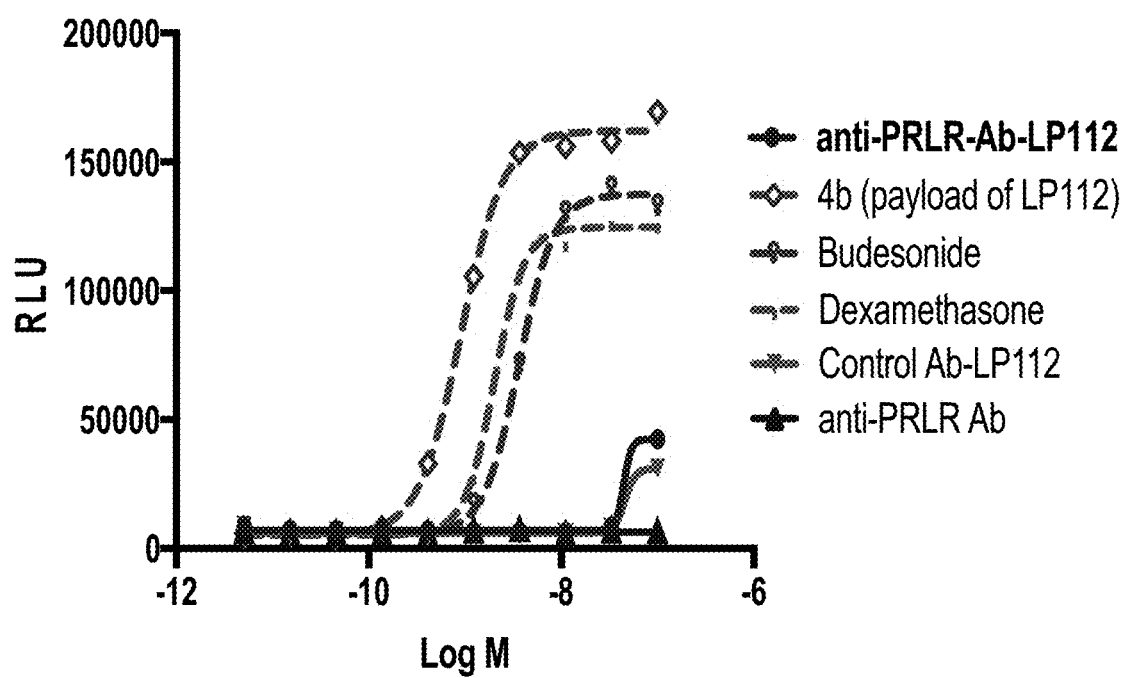

As shown in FIG. 36B and the Table below, after 72 hrs of incubation, anti-PRLR-LP112 showed no activation in the 293/PRLR/GRE-luc cell line that does not express PRLR, indicating the delivery of steroids by anti-PRLR-ncADCs is antigen-dependent. The payload LP112 (4b) again showed a better IC$_{50}$ value than Budesonide and Dexamethasone. The Control Ab-LP112 and unconjugated anti-PRLR Ab did not demonstrate any activity in this cell line.

The following table refers to FIGS. 36A and 36B.

| | EC$_{50}$ in 293/PRLR/GRE-Luc (M) | EC$_{50}$ in 293/GRE-Luc (M) |
|---|---|---|
| Anti-PRLR Ab-LP112 | +++ | + |
| Control Ab-LP112 | + | + |
| Anti-PRLR Ab | NA | NA |
| 4b (payload of LP112) | +++ | +++ |
| Budesonide | ++ | +++ |
| Dexamethasone | +++ | +++ |

In the table,
+++ < 5 nM,
5 nM < ++ < 10 nM,
10 nM < +.

Example 121

This example describes a mouse model of LPS induced cytokine release.

The aim of this study is to evaluate the test compounds, 4b and 6-I, on inhibition of LPS-induced cytokine release in mice. Test compounds were administered 48 hr, 24 hr and 2 hr before LPS challenge, cytokine levels in blood samples including TNF-α and IL6 were measured at 2 hr and 4 hr time-points after LPS challenge.

Materials and Reagents

Lipopolysaccharide (LPS) derived from E. Coli K12 was purchased from Invivogen (San Diego, Calif., USA, cat # Tlrl-eklps), Dexamethasone was purchased from ADAMAS (Emeryville, Calif., USA, Cat #50-02-2). Mouse TNF-α ELISA kit was from ebioscience (ThermoFisher Scientific, Cat #88-7324). Mouse IL6 ELISA kit was from ebioscience (ThermoFisher Scientific, Cat #88-7064).

Experimental Methods

Animal Husbandry:

A total of 18 naive C57BL/6j mice were used in this study. The animals were male, with body weight of 18-20 g at the initiation of the study. Animals were purchased from Shanghai Laboratory Animal Center, CAS (SLAC), and housed in ChemPartner's animal vivarium in a SPF environment. After arrival, animals were checked for health conditions including coat, extremities, orifices and abnormal signs in posture or movements, and acclimated to the environment for more than 7 days.

Animals were housed 3 mice per cage in IVC polycarbonate shoebox cages in SPF environment; the environment controls for the animal room were set to maintain a temperature of 20-26° C., humidity of 40-70%, and a 12-hour light/12-hour dark cycle.

Standard chow (SLAC-M01, from Shanghai Laboratories Animal Center) and purified water (filtered, municipal water quality) were provided ad libitum throughout the study period.

Experimental Procedures

Grouping: Animals were randomly allocated into 6 groups (A-F) before study initiation. Each group included 3 mice. Group A served as naive control; Group B received dexamethasone and served as positive control; Group C was treated with 4b and Group D-F was treated with 6-I.

Experimental Procedure

All mice received LPS dissolved in PBS at a dose of 0.5 mpk by i.p injection. Mice in group A received PBS, mice in group B received Dex (5 mpk) and mice in group C received 4b (5 mpk) by ip injection, 2 hr prior to LPS challenge; Mice in group D, E and F received at a dose of 5 mpk by ip injection, 2 hr, 24 hr and 48 hr prior to LPS challenge, respectively.

Blood samples were collected at 2 hr and 4 hr time points post LPS challenge, into heparin containing tubes. Blood samples were centrifuged, and plasma samples were collected and stored at −80° C. before analysis.

The levels of TNFα in plasma were measured with ELISA kits following the standard procedures recommended by the manufacturer.

Figure 37A:
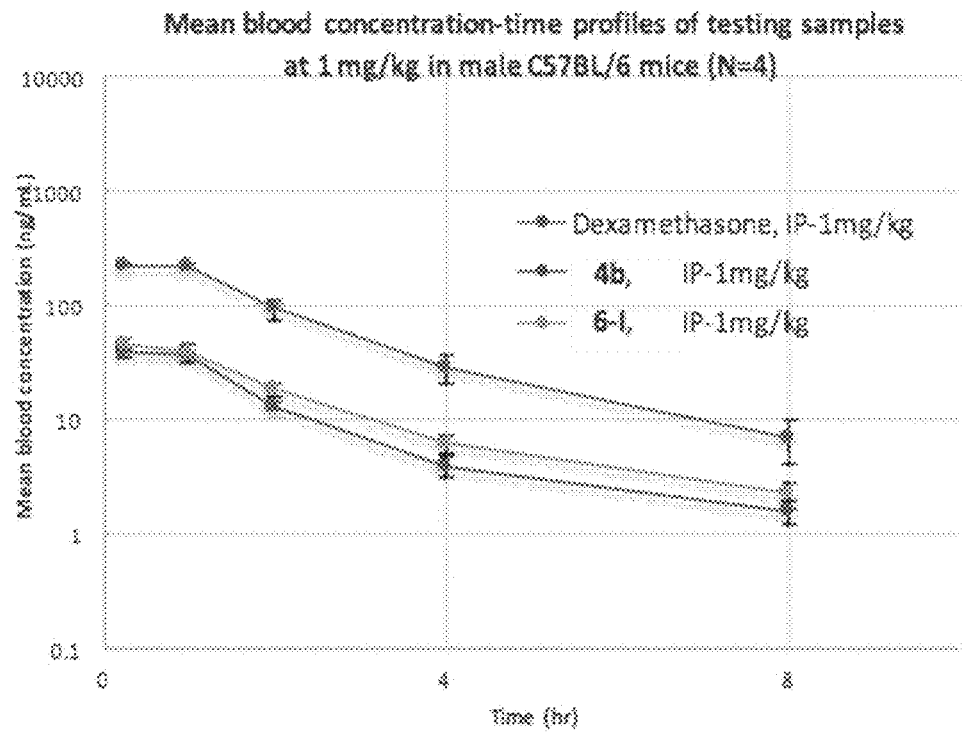
FIG. 37A shows mean blood concentration-time provides for compounds 4b and 6-I.

PK Results are provided in FIG. 37A and Table 20

TABLE 20

SUMMARY PK PARAMETERS OF 4B AND 6-I

| PK parameters | Unit | Dexamethasone (IP, 1 mg/Kg in male C57BL/6 mice) | | | 4b (IP, 1 mg/Kg in male C57BL/6 mice) | | | 6-I (IP, 1 mg/Kg in male C57BL/6 mice) | | |
|---|---|---|---|---|---|---|---|---|---|---|
| | | Mean | SD | CV(%) | Mean | SD | CV(%) | Mean | SD | CV(%) |
| $T_{max}$ | hr | 0.625 | 0.433 | 69.3 | 0.438 | 0.375 | 85.7 | 0.250 | 0.00 | 0.00 |
| $C_{max}$ | ng/mL | 231 | 7.97 | 3.45 | 39.4 | 1.75 | 4.43 | 44.8 | 4.77 | 10.6 |
| Terminal $t_{1/2}$ | hr | 1.64 | 0.187 | 11.4 | 1.69 | 0.620 | 36.7 | 1.91 | 0.210 | 11.0 |
| $AUC_{last}$ | hr*ng/mL | 545 | 60.6 | 11.1 | 84.6 | 7.71 | 9.12 | 107 | 13.6 | 12.7 |
| $AUC_{INF}$ | hr*ng/mL | 562 | 67.2 | 11.9 | 89.2 | 8.20 | 9.19 | 113 | 14.1 | 12.5 |

PD Results

LPS challenge induced TNF-α release in this pharmacodynamic model observed at the 2 hr sampling time-point. The results were consistent with the reported kinetics of cytokine release in LPS challenge model in mice, the levels of TNF-α declined at 4 hr time-point. Therefore, the effect of test compounds will not be able to be measured, in congruent with of this, no significances between groups at 4 hr time point were observed.

Blood samples were collected at 2 hr and 4 hr post LPS challenge; TNF-α levels in plasma were measured. Data were expressed as mean±SEM, *p<0.05, **p<0.01 vs Group A, by Oneway Shown in FIG. 37A, at 2 hr time point, 4b at a dose of 5 mpk significantly inhibited TNF-α production; 6-I demonstrated time dependent inhibition, and significant TNF-α production was inhibited when dosed 2 hr prior to LPS challenge. DEX was able to significantly inhibit TNF-α at the 2 hr sampling time-point.

Blood samples were collected at 2 hr and 4 hr post LPS challenge; TNF-α levels in plasma were measured. Data were expressed as mean±SEM, *p<0.05, **p<0.01 vs Group A, by Oneway ANOVA analysis.

Figure 37B:
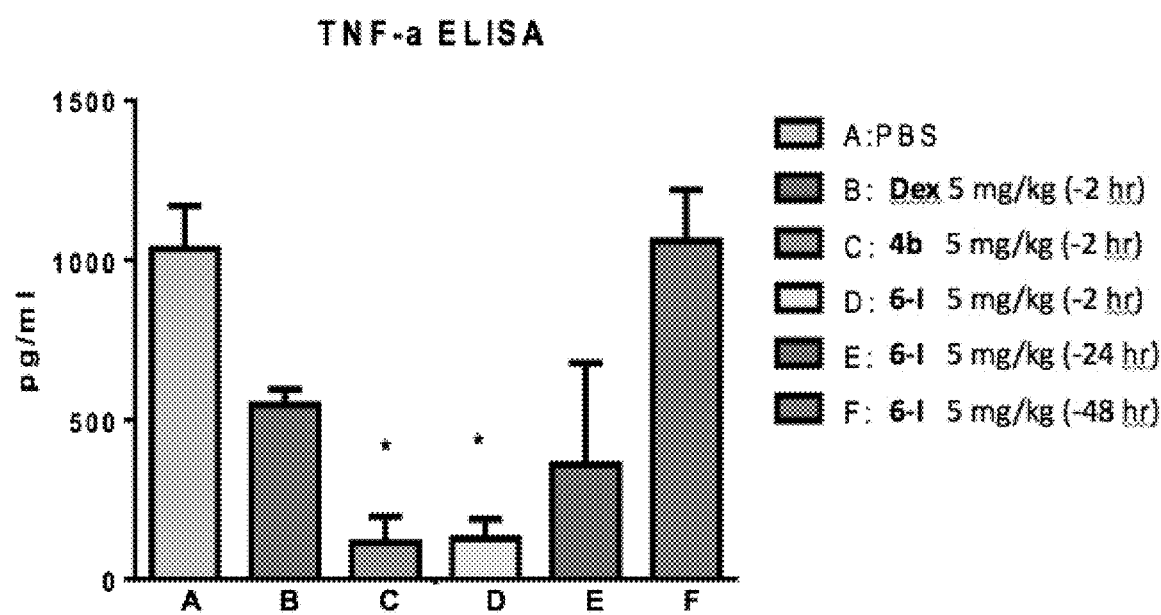
FIG. 37B shows TNF-α level in blood samples of payloads 4b and 6-I as described in Examples 120-121.

ANOVA analysis is provided in FIG. 37B and Table 21

TABLE 21

RAW DATA OF TNF-α

| TNF-a (pg/ml) | A: PBS | B: DEX 5MPK (−2 h) | C: 4b 5MPK (−2 h) | D: 6-I 5MPK (−2 h) | E) 6-I 5MPK (−24 h) | F) 6-I 5MPK (−48 h) |
|---|---|---|---|---|---|---|
| 2 hr | 840.2 | 644.3 | 56.5 | 110.6 | 23.1 | 1280.1 |
| | 1293.6 | 508.5 | 10.4 | 30.8 | 997.3 | 1149.4 |
| | 968.6 | 487.1 | 274.8 | 240.8 | 55.4 | 750.0 |

Example 122

Mouse Dendritic Cells

To determine the effect of Compound 4b on ex-vivo LPS-induced inflammatory immune responses, CD11c+ dendritic cells (DC) were isolated from the spleens of wildtype C57Bl/6 mice (Jackon Labs, Protocol #426.0). Splenic DCs were isolated using a Collagenase D digestion (400 U/mL collagenase D (Roche Cat #11088858001), 20 µg/mL DNase I (Roche Cat #10104159001), 2% FCS in HEPES-buffered RPMI-1640) and incubated at 37° C. for 25 minutes. Post incubation, the splenic tissue was washed with RPMI-1640 and filtered through a 70 µm filter, then red blood cell lysis was performed using ACK lysing buffer (Gibco Cat # A1049201) for 1 minute. The cell suspension was subsequently washed twice using RPMI-1640. Classical DCs were isolated from the mononuclear cell suspension using CD11 c magnetic MicroBeads (Milteny Biotec Cat #130108338). In brief, the cell suspension was washed twice with autoMACS running buffer (Milteny Biotec Cat #130091221) prior to a 30-minute incubation at 4° C. with CD11c' MicroBeads, as per Milteny Biotec established protocols. CD11c' cells were isolated by positive selection, washed, suspended in complete-RPMI [RPMI-1640 (ThermoFisher Scientific, Cat #15140122) containing 10% of FBS (ThermoFisher Scientific, Cat #10082147) and 1% of penicillin-streptomycin (ThermoFisher Scientific, Cat #11875093)], and counted prior to culture at $2×10^5$ cells per well. Control complete-RPMI, Compound 4b treated complete-RMPI (at 10 nM and 100 nM) or Dexamethasone (Sigma, Cat # D4902-25MG) treated complete-RMPI (at 10 nM and 100 nM) was added to the cells in a 96-well-culture dish. DC/Control, Compound 4b or Dexamethasone treated cells were incubated for 24 hours at 37° C. prior to stimulation with 10 ng/mL of LPS for 24 hours.

Human Dendritic Cells:

To determine the effect of Compound 4b on ex-vivo LPS-induced inflammatory immune responses in human innate immune cells, CD14$^+$ monocytes (Lonza Cat #2W-400C) were isolated and cultured in the presence of complete-RPMI [RPMI-1640 (ThermoFisher Scientific, Cat #15140122) containing 10% of FBS (ThermoFisher Scientific, Cat #10082147) and 1% of penicillin-streptomycin (ThermoFisher Scientific, Cat #11875093)] supplemented with human IL4 (50 ng/mL) (Milteny Biotec, Cat #130-093-922) and human GM-CSF (100 ng/mL) (Milteny Biotec, Cat #130093866) for 7 days. The complete-RPMI with IL4 and GM-CSF was changed every three days. Two specific culture conditions were developed: Condition 1: Incubation of CD14$^+$ monocytes with control complete-RPMI, Compound 4b treated complete-RMPI (at 10 nM and 100 nM) or Dexamethasone (Sigma) treated complete-RMPI (at 10 nM and 100 nM) for the entire 7 day culture or Condition 2: Incubation of CD14$^+$ monocytes with control complete-RPMI for 5 days prior to incubation with Control complete-RMPI, Compound 4b treated complete-RMPI (at 10 nM and 100 nM) or Dexamethasone (Sigma, Cat # D4902-25MG) treated complete-RMPI (at 10 nM and 100 nM) until day 7. On day 7 the various experimental groups were stimulated with 10 ng/mL of LPS for 24 hours.

In brief, 50 µL/well of calibrators and samples (diluted in Diluent 1:2) were added to the plates pre-coated with capture antibodies and incubated at room temperature while shaking at 700 rpm for 2 hours. The plates were then washed 3 times with 1×PBS containing 0.05% (w/v) Tween-20, followed by the addition of 25 µL of Detection Antibody Solution diluted in Diluent 45. After 2-hour incubation at room temperature while shaking, the plates were washed 3 times, and 150 µL of 2× Read Buffer was added to each well. Electrochemiluminescence was immediately read on a MSD Spector® instrument. Data analysis was performed using GraphPad Prism™ software. Statistical significance within the groups was determined by one-way Anova with Turkey's multiple comparison post-test and standard error of mean (SEM±) calculated.

RESULTS SUMMARY AND CONCLUSIONS

As shown in Table 22, ex vivo LPS challenge induced robust production of IL12p70, IL1β, IL6, KC-GRO and TNF-α by splenic CD11c$^+$ DCs. On the contrary, in vitro administration of Dexamethasone and Compound 4b at escalating doses for 24 hours significantly decreased LPS-induced cytokine responses in CD11c$^+$ DCs.

TABLE 22

Compound 4b and Dexamethasone (Sigma) inhibit LPS-induced cytokine production in CD11c$^+$ splenic DCs.

| Cytokine | Control | Control + LPS | Dexamethasone (10 nM) | Dexamethasone (10 nM) + LPS | Dexamethasone (100 nM) | Dexamethasone (100 nM) + LPS |
|---|---|---|---|---|---|---|
| IL-12p70 | 17.43 ± 2.72 | 77.02 ± 4.40 | 8.55 ± 1.08 | 30.41 ± 3.22 | 6.05 ± 1.13 | 9.29 ± 3.28 |
| IL-1b | 9.53 ± 0.26 | 162.48 ± 5.69 | 6.299 ± 0.33 | 34.76 ± 4.33 | 5.25 ± 0.12 | 10.58 ± 0.88 |
| IL-6 | 144.49 ± 16.69 | 1492.12 ± 66.47 | 98.93 ± 8.98 | 714.89 ± 77.13 | 55.07 ± 1.76 | 303.48 ± 11.37 |
| KC-GRO | 111.69 ± 10.96 | 536.47 ± 49.90 | 75.75 ± 8.03 | 399.40 ± 49.75 | 65.99 ± 2.75 | 233.49 ± 18.48 |
| TNF-a | 0 ± 0 | 8644.14 ± 74.73 | 0 ± 0 | 2496.27 ± 415.75 | 0 ± 0 | 405.49 ± 70.23 |

| Cytokine | 4b (10 nM) | 4b (10 nM) + LPS | 4b (100 nM) | 4b (100 nM) + LPS |
|---|---|---|---|---|
| IL-12p70 | 5.24 ± 1.12 | 3.84 ± 2.88 | 6.43 ± 0.67 | 8.21 ± 2.79 |
| IL-1b | 5.22 ± 0.11 | 6.32 ± 0.83 | 5.65 ± 0.18 | 4.80 ± 0.99 |
| IL-6 | 47.90 ± 4.55 | 184.54 ± 21.59 | 63.87 ± 4.78 | 201.10 ± 20.96 |
| KC-GRO | 62.85 ± 6.51 | 186.57 ± 15.71 | 84.30 ± 6.06 | 211.96 ± 25.23 |
| TNF-a | 0 ± 0 | 146.46 ± 18.66 | 0 ± 0 | 193.29 ± 25.56 |

Measurement of Cytokines in the Supernatants 24 Hours Post-LPS Ex Vivo Challenge:

Supernatants were collected into 96-well round bottom tissue culture plates 24 hours post-LPS challenge and stored at −20° C. until further analysis. Cytokine concentrations in the supernatants were measured using a Pro-inflammatory Panel 1 (mouse) multiplex immunoassay kit (MesoScale Discovery, Cat # K15048D) according to manufacturer's instructions or Pro-inflammatory Panel 1 (human) multiplex immunoassay kit (MesoScale Discovery, Cat # K15049D).

As shown in Table 23, ex vivo LPS challenge induced robust expression of IL12p70, IL1β, IL6, and TNF-α by human monocyte-derived DCs. In contrast, monocytes cultured for the entire 7-day conditioning period (Condition 1) with Compound 4b and Dexamethasone (Sigma) resulted in significantly reduced pro-inflammatory cytokine production. Moreover, conditioning of mature monocyte-derived DCs with Compound 4b and Dexamethasone (Sigma) also significantly decreased the production of IL12p70, IL6 and TNF-α compared to control DC LPS stimulation

TABLE 23

Compound 4b and Dexamethasone (Sigma) inhibit LPS-induced cytokine production in human monocyte derived-DC.

| | Condition 1 | | | |
|---|---|---|---|---|
| Cytokine | Control | Control + LPS | Dexamethasone (10 nM) | Dexamethasone (10 nM) + LPS |
| IL-12p70 | 0.79 ± 0.04 | 994.23 ± 19.89 | 0.65 ± 0.02 | 4.83 ± 0.05 |
| IL-1b | 0.80 ± 0.001 | 12.97 ± 0.186 | 0.625 ± 0.006 | 1.77 ± 0.11 |

TABLE 23-continued

Compound 4b and Dexamethasone (Sigma) inhibit LPS-induced cytokine production in human monocyte derived-DC.

| | | | | |
|---|---|---|---|---|
| IL-6 | 8.71 ± 0.23 | 5669.2 ± 266.12 | 2.68 ± 0.03 | 687.45 ± 2.17 |
| IL-8 | 850.50 ± 0.89 | 1677.86 ± 20.06 | 174.59 ± 0.68 | 8789.98 ± 126.98 |
| TNF-a | 44.20 ± 1.08 | 7476.12 ± 177.0 | 2.32 ± 0.098 | 242.34 ± 10.75 |

| | 4b (10 nM) | 4b (10 nM) + LPS | 4b (100 nM) | 4b (100 nM) + LPS |
|---|---|---|---|---|
| IL-12p70 | 0.58 ± 0.002 | 1.05 ± 0.08 | 0.66 ± 0.03 | 0.50 ± 0.19 |
| IL-1b | 0.61 ± 0.007 | 1.18 ± 0.11 | 0.641 ± 0.15 | 1.01 ± 0.07 |
| IL-6 | 2.23 ± 0.002 | 325.46 ± 2.12 | 3.45 ± 0.13 | 159.32 ± 7.31 |
| IL-8 | 166.99 ± 2.01 | 8670.27 ± 268.97 | 136.50 ± 0.87 | 8461.59 ± 522.77 |
| TNF-a | 1.28 ± 0.087 | 117.75 ± 6.63 | 1.46 ± 0.10 | 123.31 ± 0.11 |

Condition 2

| Cytokine | Control | Control + LPS | Dexamethasone (10 nM) | Dexamethasone (10 nM) + LPS |
|---|---|---|---|---|
| IL-12p70 | 5.83 ± 2.55 | 49.64 ± 2.05 | 0.64 ± 0.03 | 6.32 ± 1.69 |
| IL-1b | 3.13 ± 0.05 | 13.03 ± 1.26 | 0.611 ± 0.003 | 37.88 ± 1.90 |
| IL-6 | 37.74 ± 1.50 | 6679.97 ± 173.8 | 14.76 ± 0.267 | 5747.37 ± 234.08 |
| IL-8 | 1541.04 ± 82.6 | 1958.27 ± 5.35 | 288.23 ± 6.02 | 3314.0 ± 37.86 |
| TNF-a | 61.49 ± 4.82 | 2690.61 ± 164.5 | 1.73 ± 0.02 | 994.92 ± 73.66 |

| | 4b (10 nM) | 4b (10 nM) + LPS | 4b (100 nM) | 4b (100 nM) + LPS |
|---|---|---|---|---|
| IL-12p70 | 0.60 ± 0.01 | 4.81 ± 0.63 | 0.61 ± 0.02 | 2.03 ± 0.16 |
| IL-1b | 0.59 ± 0.005 | 30.10 ± 0.93 | 0.59 ± 0.03 | 18.20 ± 1.04 |
| IL-6 | 12.87 ± 0.312 | 5124.75 ± 114.8 | 11.25 ± 0.82 | 4680.03 ± 104.90 |
| IL-8 | 274.75 ± 1.75 | 3003.52 ± 212.16 | 317.46 ± 14.83 | 2735.36 ± 87.88 |
| TNF-a | 2.03 ± 0.14 | 874.18 ± 30.46 | 1.37 ± 0.251 | 696.26 ± 75.10 |

The embodiments and examples described above are intended to be merely illustrative and non-limiting. Those skilled in the art will recognize or will be able to ascertain using no more than routine experimentation, numerous equivalents of specific compounds, materials and procedures. All such equivalents are considered to be within the scope and are encompassed by the appended claims.

What is claimed is:

1. A compound of Formula (A):

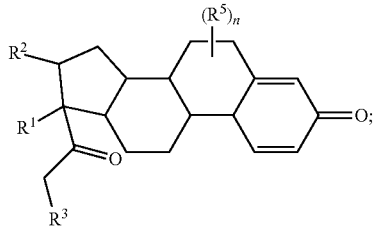

or a pharmaceutically acceptable salt, solvate, or stereoisomer thereof,
wherein:
$R^1$ and $R^2$ together form

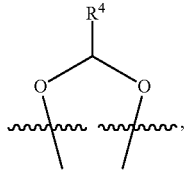

wherein $R^4$ is alkyl, aryl, arylalkyl, or an N-containing heterocycloalkyl, wherein the alkyl, aryl, arylalkyl, and N-containing heterocycloalkyl are, independently in each instance, optionally substituted with —$NR^aR^b$;

$R^3$ is

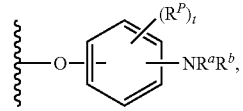

wherein $R^P$ is halo, t is an integer from 0 to 2;
$R^5$ is, independently in each instance, —OH, halo, alkyl, or arylalkyl;
$R^a$ and $R^b$ are, independently in each instance, —H or alkyl
n is an integer from 0-19.

2. The compound of claim 1, wherein the compound of Formula (A) has the structure of Formula ($A^1$):

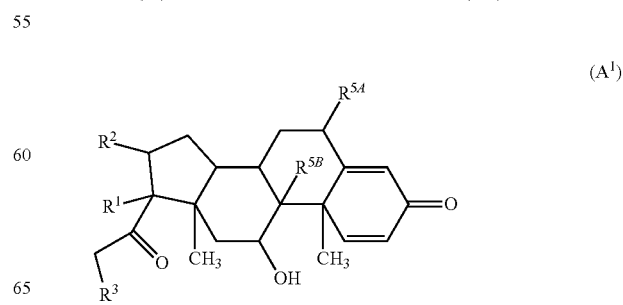

wherein $R^{5A}$ and $R^{5B}$ are each, independently, halo or a hydrogen atom.

3. The compound of claim 2, wherein $R^4$ is aryl, arylalkyl, or alkyl, wherein the aryl, arylalkyl, and alkyl are optionally substituted with —$NR^aR^b$.

4. The compound of claim 1 according to Formula ($A^2$):

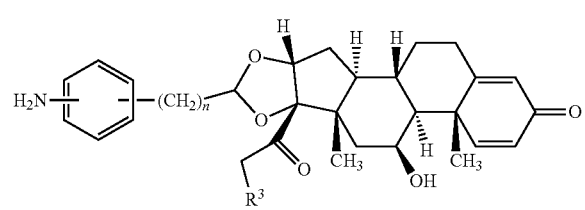

wherein n is an integer from 0 to 4.

5. The compound of claim 1 according to Formula ($A^3$):

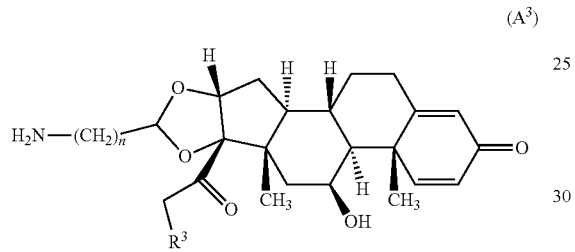

wherein n is an integer from 1-4.

6. The compound of claim 1 according to Formula ($A^4$):

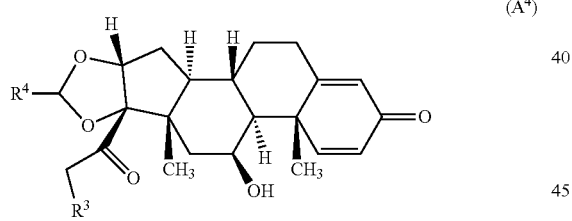

wherein $R^4$ is alkyl.

7. The compound of claim 6, wherein $R^4$ is $C_{1-4}$ alkyl.

8. The compound of claim 1 according to Formula ($A^5$):

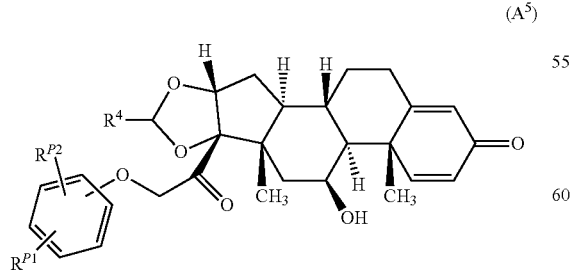

wherein $R^4$ is alkyl, $R^{P1}$ is halo or a hydrogen atom, and $R^{P2}$ is —$NR^aR^b$, wherein $R^a$ and $R^b$ are each, independently, a hydrogen atom or alkyl.

9. The compound of claim 1 according to Formula ($A^6$):

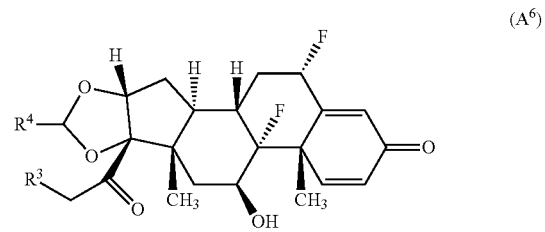

wherein $R^4$ is alkyl.

10. The compound of claim 1 according to Formula 1000:

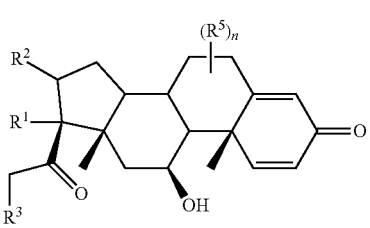

or a pharmaceutically acceptable salt, solvate, or stereoisomer thereof, wherein:

$R^1$ and $R^2$ together form

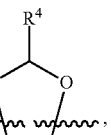

$R^3$ is

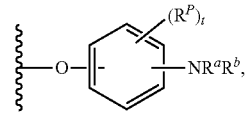

wherein $R^P$ is halo, t is an integer from 0 to 2;

$R^4$ is selected from the group consisting of alkyl, aryl, arylalkyl, -alkylene-$NR^aR^b$, —X-arylene-Y—$NR^aR^b$, and N-containing heterocycloalkyl; wherein X is absent or —$CH_2$—; wherein Y is absent;

$R^5$ is, independently in each instance, selected from a substituent in the group consisting of —OH, halo, and alkyl; n is an integer from 0-17; and each $R^5$ is positioned on any ring atom;

$R^a$ and $R^b$ are, independently in each instance, selected from the group consisting of —H and alkyl.

11. The compound of claim 10 according to Formula 1110, 1120, 1130, or 1140:

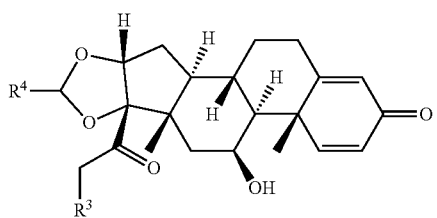

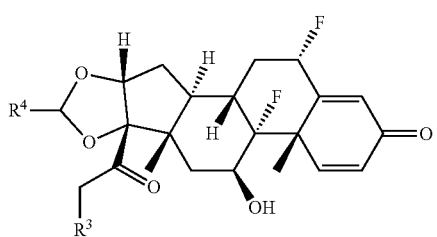

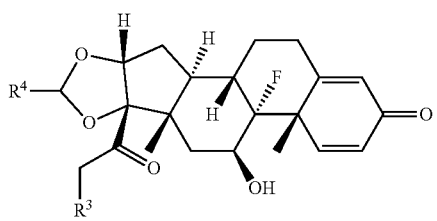

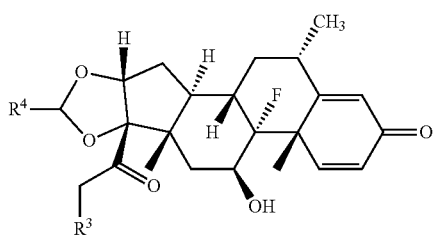

or a pharmaceutically acceptable salt, solvate, or stereoisomer thereof.

12. The compound of claim 11 wherein R⁴ is n-propyl.

13. The compound of claim 11 according to formula 1120.

14. The compound of claim 11 wherein R⁴ is H₂NCH₂CH₂— or

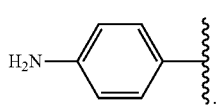

15. The compound of claim 11 wherein R⁴ is alkyl, aryl, or arylalkyl.

16. The compound of claim 15 wherein R³ is

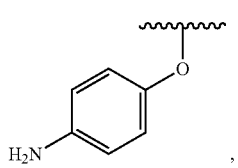

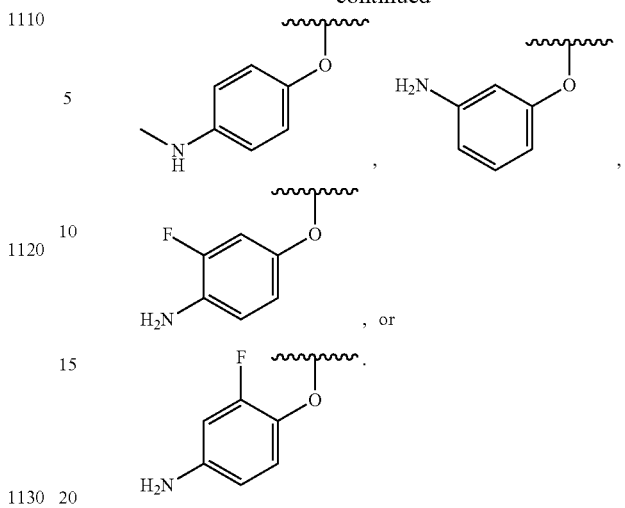

17. The compound of claim 15, wherein R⁴ is n-propyl.

18. The compound of claim 1, wherein the compound is:

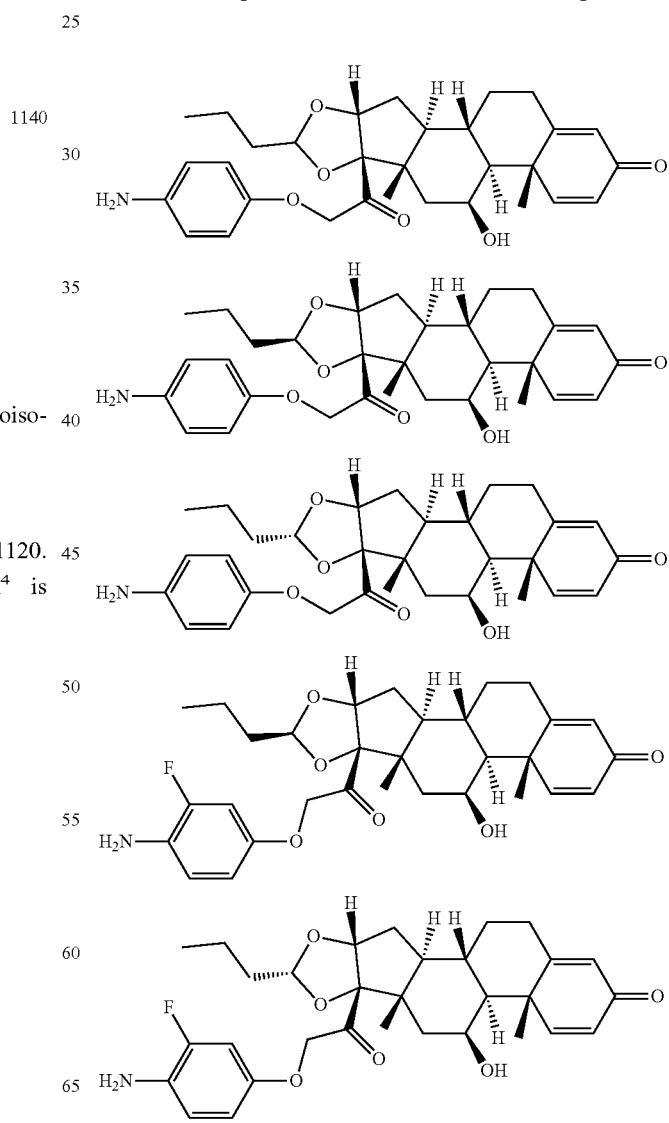

499
-continued
500
-continued
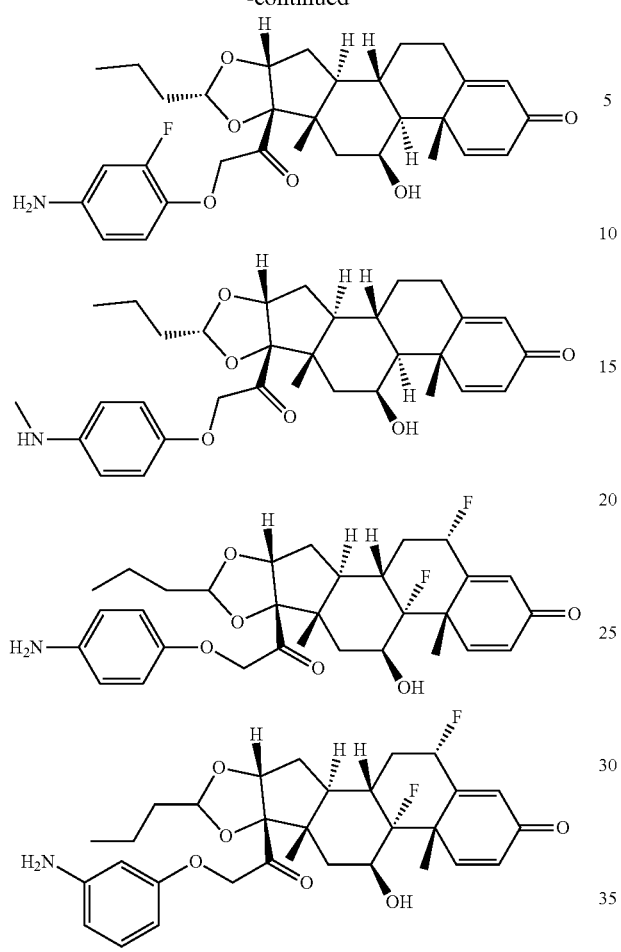
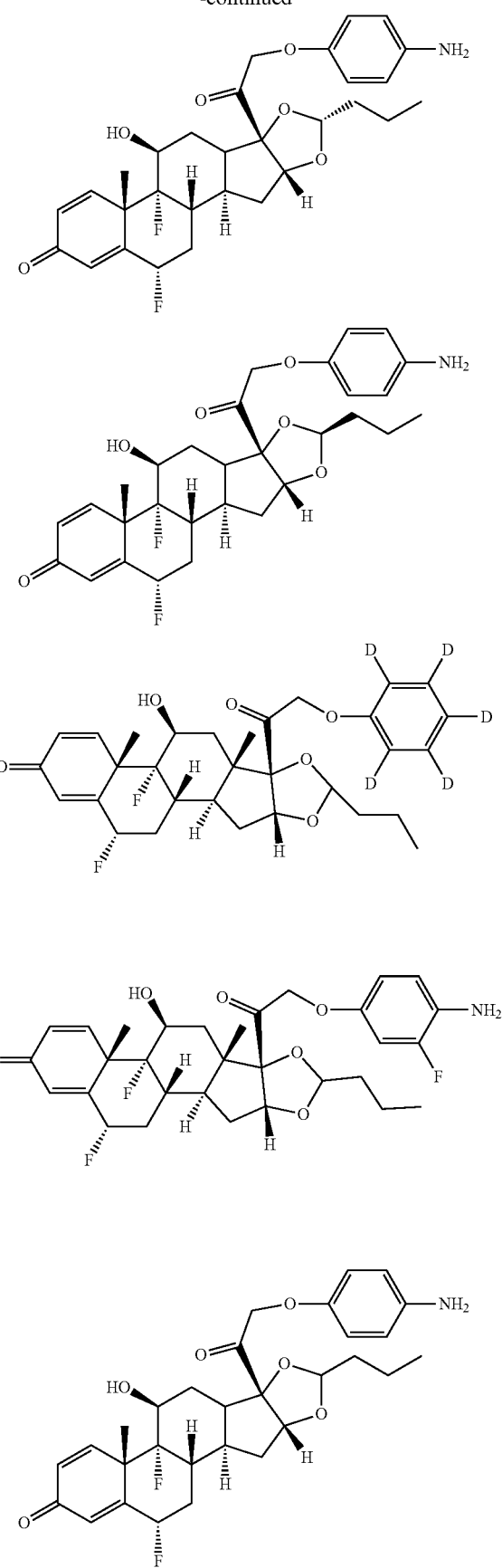

-continued

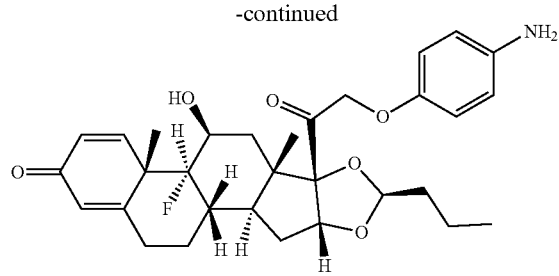

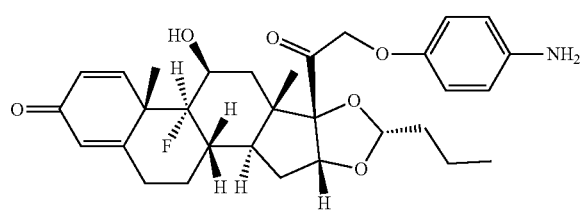

or a pharmaceutically acceptable salt, solvate, or stereoisomer thereof.

19. The compound of claim 18, wherein the compound is:

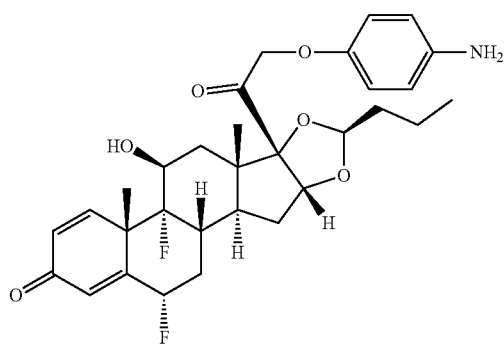

or a pharmaceutically acceptable salt, solvate, or stereoisomer thereof.

20. The compound of claim 18, wherein the compound is:

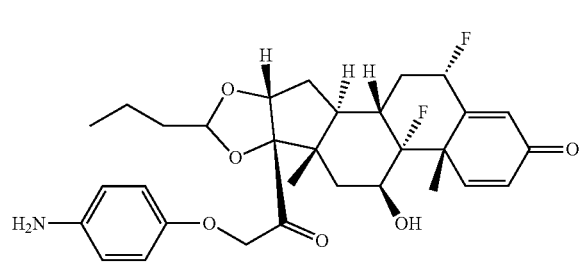

or a pharmaceutically acceptable salt, solvate, or stereoisomer thereof.

21. The compound of claim 18, wherein the compound is:

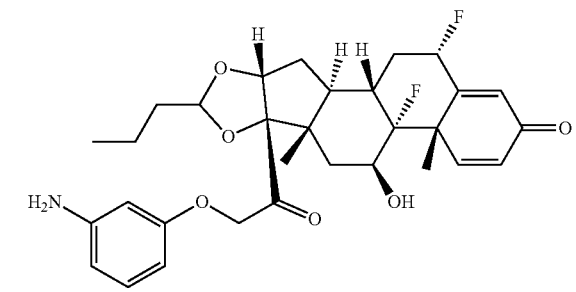

or a pharmaceutically acceptable salt, solvate, or stereoisomer thereof.

22. The compound of claim 18, wherein the compound is:

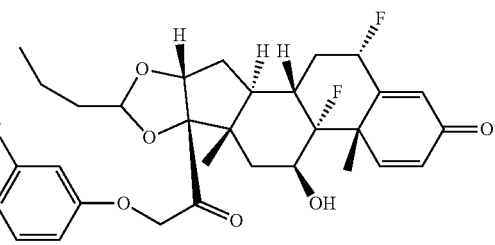

or a pharmaceutically acceptable salt, solvate, or stereoisomer thereof.

23. The compound of claim 18, wherein the compound is:

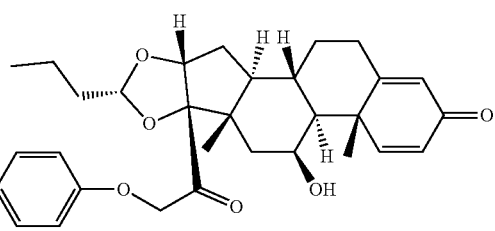

or a pharmaceutically acceptable salt, solvate, or stereoisomer thereof.

24. The compound of claim 18, wherein the compound is:

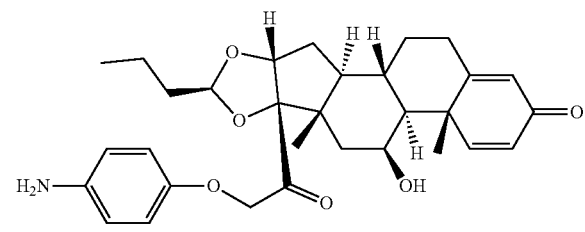 [SMILES: CCC[C@H]1O[C@@H]2C[C@H]3[C@@H]4CCC5=CC(=O)C=C[C@]5(C)[C@H]4[C@@H](O)C[C@]3(C)[C@]2(C(=O)COc2ccc(N)cc2)O1]

or a pharmaceutically acceptable salt, solvate, or stereoisomer thereof.

25. The compound of claim 18, wherein the compound is:

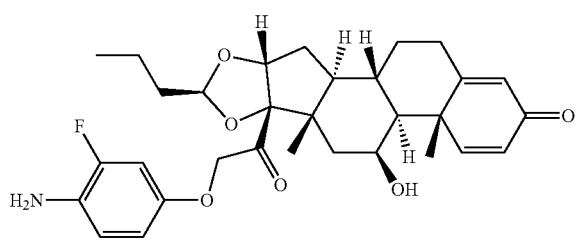 [SMILES: CCC[C@H]1O[C@@H]2C[C@H]3[C@@H]4CCC5=CC(=O)C=C[C@]5(C)[C@H]4[C@@H](O)C[C@]3(C)[C@]2(C(=O)COc2ccc(N)c(F)c2)O1]

or a pharmaceutically acceptable salt, solvate, or stereoisomer thereof.

26. The compound of claim 18, wherein the compound is:

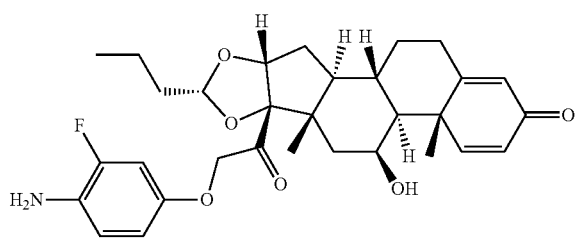 [SMILES: CCC[C@@H]1O[C@@H]2C[C@H]3[C@@H]4CCC5=CC(=O)C=C[C@]5(C)[C@H]4[C@@H](O)C[C@]3(C)[C@]2(C(=O)COc2ccc(N)c(F)c2)O1]

or a pharmaceutically acceptable salt, solvate, or stereoisomer thereof.

27. The compound of claim 18, wherein the compound is:

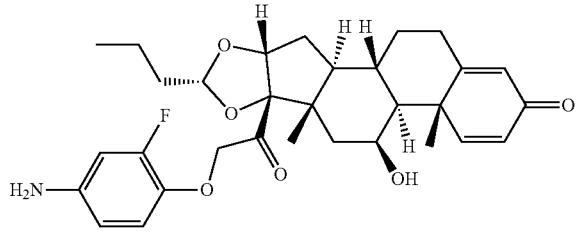 [SMILES: CCC[C@@H]1O[C@@H]2C[C@H]3[C@@H]4CCC5=CC(=O)C=C[C@]5(C)[C@H]4[C@@H](O)C[C@]3(C)[C@]2(C(=O)COc2ccc(N)cc2F)O1]

or a pharmaceutically acceptable salt, solvate, or stereoisomer thereof.

28. The compound of claim 18, wherein the compound is:

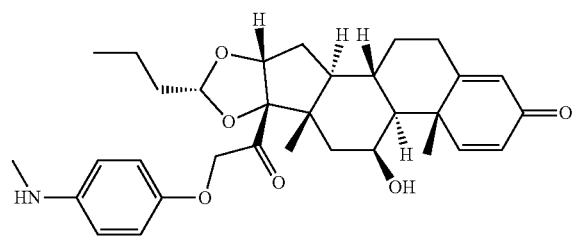 [SMILES: CCC[C@@H]1O[C@@H]2C[C@H]3[C@@H]4CCC5=CC(=O)C=C[C@]5(C)[C@H]4[C@@H](O)C[C@]3(C)[C@]2(C(=O)COc2ccc(NC)cc2)O1]

or a pharmaceutically acceptable salt, solvate, or stereoisomer thereof.

29. The compound of claim 20, wherein the compound is:

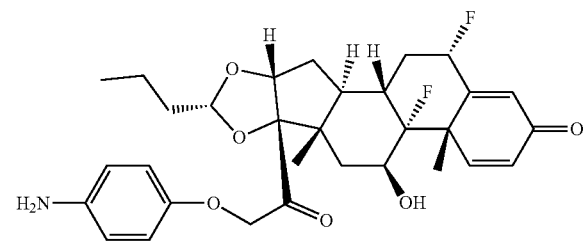

or a pharmaceutically acceptable salt, solvate, or stereoisomer thereof.

30. The compound of claim 18, wherein the compound is:

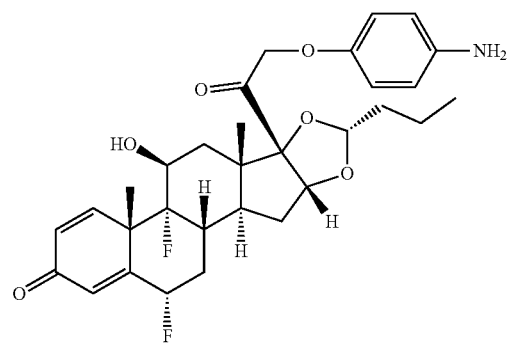

or a pharmaceutically acceptable salt, solvate, or stereoisomer thereof.

31. The compound of claim 18, wherein the compound is:

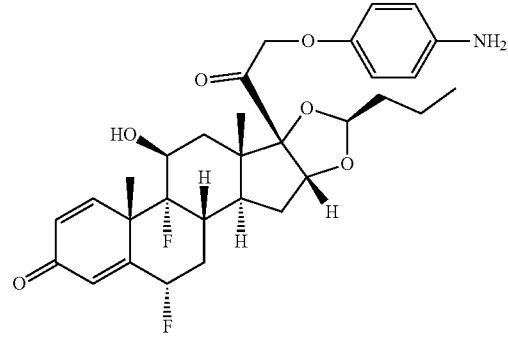

or a pharmaceutically acceptable salt, solvate, or stereoisomer thereof.

32. The compound of claim 18, wherein the compound is:

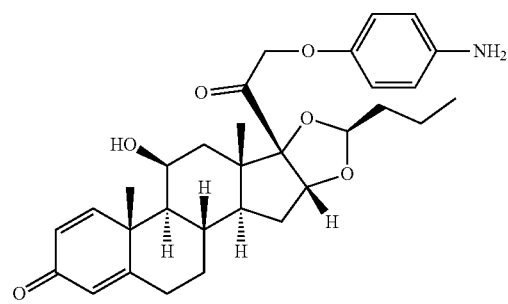

or a pharmaceutically acceptable salt, solvate, or stereoisomer thereof.
33. The compound of claim 18, wherein the compound is:
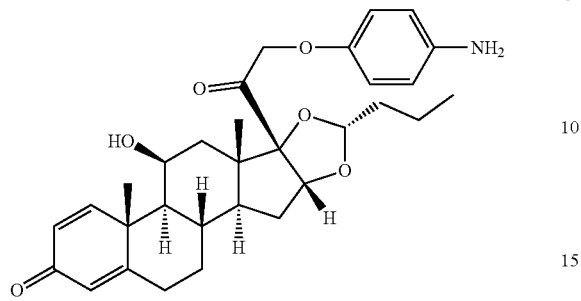
or a pharmaceutically acceptable salt, solvate, or stereoisomer thereof.
* * * * *